US009238815B2

(12) United States Patent
Shaw et al.

(10) Patent No.: US 9,238,815 B2
(45) Date of Patent: Jan. 19, 2016

(54) COMPOSITIONS AND METHODS FOR INHIBITING HUMAN HOST FACTORS REQUIRED FOR INFLUENZA VIRUS REPLICATION

(75) Inventors: Megan Shaw, New York, NY (US); Peter Palese, Leonia, NJ (US); Adolfo Garcia-Sastre, New York, NY (US); Silke Stertz, Zurich (CH); John Young, San Diego, CA (US); Renate König, San Diego, CA (US); Sumit Chanda, La Jolla, CA (US)

(73) Assignees: Icahn School of Medicine at Mounta Sinai, New York, NY (US); Salk Institute for Biological Studies, La Jolla, CA (US); Sanford-Burnham Medical Research Institute, La Jolla, CA (US)

( * ) Notice: Subject to any disclaimer, the term of this patent is extended or adjusted under 35 U.S.C. 154(b) by 36 days.

(21) Appl. No.: 13/514,783

(22) PCT Filed: Dec. 10, 2010

(86) PCT No.: PCT/US2010/003138
§ 371 (c)(1),
(2), (4) Date: Dec. 20, 2012

(87) PCT Pub. No.: WO2011/071535
PCT Pub. Date: Jun. 16, 2011

(65) Prior Publication Data
US 2013/0090367 A1    Apr. 11, 2013

Related U.S. Application Data

(60) Provisional application No. 61/285,951, filed on Dec. 11, 2009.

(51) Int. Cl.
*A61K 31/18*    (2006.01)
*C12N 15/113*   (2010.01)
*A61K 31/365*   (2006.01)

(52) U.S. Cl.
CPC ............ *C12N 15/1131* (2013.01); *A61K 31/18* (2013.01); *A61K 31/365* (2013.01)

(58) Field of Classification Search
CPC ...... A61K 31/18; A61K 31/436; A61K 31/09
USPC .................................. 514/604, 183, 291, 557
See application file for complete search history.

(56) References Cited

U.S. PATENT DOCUMENTS 6,063,383 A * 5/2000 Hsu et al. ....................... 424/764
2004/0086580 A1* 5/2004 Tripp et al. .................... 424/745

(Continued)

FOREIGN PATENT DOCUMENTS

WO    WO 2008/043561    4/2008
WO    WO 2009/136979    11/2009

(Continued)

OTHER PUBLICATIONS

Yun et al. "Immunomodulatory Activity of betulinic acid by producing Pro-inflammatory cytokines and activation of macrophages," Arch. Pharm. Res.. 2003, vol. 26, No. 12, pp. 1087-1095.*

(Continued)

*Primary Examiner* — Shengjun Wang
(74) *Attorney, Agent, or Firm* — Jones Day

(57) ABSTRACT

This application relates to the modulation of host cell factors required for influenza virus replication. The application relates to compounds, including nucleic acid compounds (such as, e.g., small interfering RNAs (siRNAs)) and small molecules, that target human host cell factors involved in influenza virus replication, and the use of such compounds for modulating influenza virus replication and as antiviral agents. The application also relates to methods of treating an influenza virus infection and methods of treating or preventing a symptom or disease associated with influenza virus infection, comprising administering to a subject a composition comprising a compound, such as a nucleic acid compound (e.g., an siRNA) or small molecule, that targets a human host cell factor involved in influenza virus replication.

5 Claims, 12 Drawing Sheets

(56) References Cited

U.S. PATENT DOCUMENTS

Figure 1:
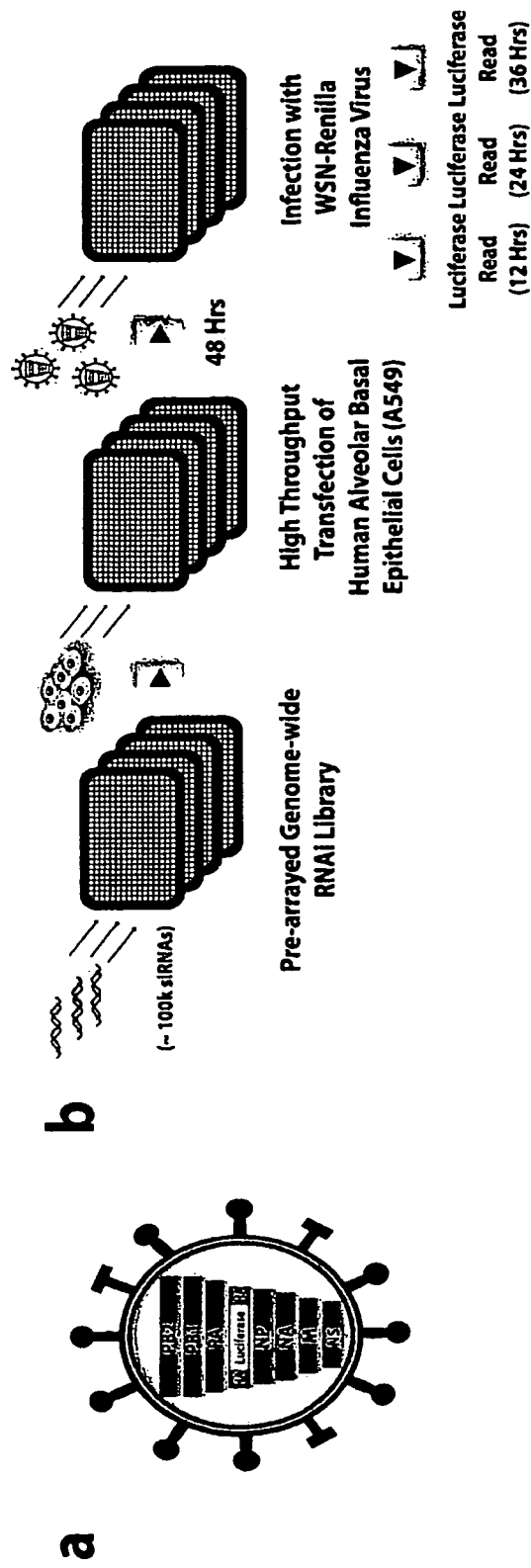

| | | |
|---|---|---|
| 2007/0265294 A1* | 11/2007 | Kleinman et al. ............ 514/291 |
| 2009/0068257 A1 | 3/2009 | Leunis et al. |
| 2011/0105423 A1 | 5/2011 | Shaw et al. |
| 2013/0137678 A1 | 5/2013 | Shaw et al. |

FOREIGN PATENT DOCUMENTS

| | | |
|---|---|---|
| WO | WO 2011/071535 | 6/2011 |
| WO | WO 2011/150413 | 12/2011 |

OTHER PUBLICATIONS

Bermejo-Martin et al. "Macrolides for the treatment of severe respiratory illness caused by novel H1N1 swine influenza viral strains," J. Infect. developing Countries, Apr. 2009, vol. 3, No. 3, pp. 159-161.*

Anieto et al., "An endosomal beta COP is involved in the pH-dependent formation of transport vesicles destined for late endosomes", J Cell Biol 133:29-41 (1996).

Apweiler et al., "The InterPro database, an integrated document resource for protein families, domains and functional sites", Nucl Acids Res 29:37-40 (2001).

Ashburner et al., "Gene ontology: tool for the unification of biology. The Gene Oncology Consortium", Nat Genetics 25:25-29 (2000).

Aza-Blanc et al., "Identification of Modulators of TRAIL-induced apoptosis via RNAi-based phenotypic screening", Mol Cell 12:627-637 (2003).

Bader and Hogue, "An automated method for finding molecular complexes in large protein interaction networks", BMC Bioinformatics 4:2 (2003).

Beer et al., "Caveola-dependent endocytic entry of amphoropic murine leukemia virus", J Virol 79:10776-10787 (2005).

Brass et al., "Identification of host proteins required for HIV infection through a functional genomic screen", Science 319:921-926 (2008).

Brass et al., "The IFITM proteins mediate cellular resistance to influenza a H1N1 virus, West Nile virus, and Dengue virus", Cell 139:1243-1254 (2009).

Bright et al., "Adamantane resistance among influenza a viruses isolated early during the 2005-2006 influenza season in the United States", JAMA 295:891-894 (2006).

Chanda et al., "Genome-scale functional profiling of the mammalian AP-1 signaling pathway", Proc Natl Acad Sci USA 100:12153-12158 (2003).

Cheung et al., "Distribution of amantadine-resistant H5N1 avian influenza variant in Asia", J Infect Dis 193:1626-1629 (2006).

Chung et al., "Rapamycin-FKBP specifically blocks growth-dependent activation of and signaling by the 70 kd S6 protein kinases", Cell 69:1227-1236 (1992).

Colbran, "Targeting of calcium/calmodulin-dependent protein kinase II", Biochem J 378:1-16 (2004).

De Clercq, "Antiviral agents active against influenza a viruses", Nat Rev Drug Discov 5:1015-1025 (2006).

Desbene et al., "Drugs that inhibit tubulin polymerization: the particular case of podophyllotoxin and analogues", Curr Med Chem Anticancer Agents 2:71-90 (2002).

Donelan et al., "A recombinant influenza a virus expressing an RNA-binding-defective NS1 protein induces high levels of beta interferon and is attenuated in mice", J Virol 77:13257-13266 (2003).

Garman and Laver, "Controlling influenza by inhibiting the virus's neuraminidase", Curr Drug Targets 5:119-136 (2004).

Goto and Kawaoka, "A novel mechanism for the acquisition of virulence by a human influenza a virus", Proc Natl Acad Sci USA 95:10224-10228 (1998).

Hao et al., "Drosophila RNAi screen identifies host genes important for influenza virus replication", Nature 454:890-893 (2008).

Hardcastle et al., "Solid-phase immunoassays in mechanism-based drug discovery: their application in the development of inhibitors of the molecular chaperone heat-shock protein 90", Assay Drug Dev Technol 3:273-285 (2005).

Hoffmann et al., "Modulation of influenza virus replication by alteration of sodium ion transport and protein kinase C activity", Antiviral Res 80:124-134 (2008).

Huang et al., "Systematic and integrative analysis of large gene lists using David bioinformatics resources", Nat Protoc 4:44-57 (2009).

Karlas et al., "Genome-wide RNAi screen identifies human host factors crucial for influenza virus replication", Nature 463:818-822 (2010).

Konig et al., "A probability-based approach for the analysis of large-scale RNAi screens", Nat Meth 4:847-849 (2007).

Konig et al., "Global analysis of host-pathogen interactions that regulate early-stage HIV-1 replication", Cell 135:49-60 (2008).

Konig et al., "Human host factors required for influenza virus replication", Nature 463:813-817 (2010).

Krishnan et al., "RNA interference screen for human genes associated with West Nile virus infection", Nature 455:242-245 (2008).

Kutay et al., "Export of importin alpha from the nucleous is mediated by a specific nuclear transport factor", Cell 90:1061-1071 (1997).

Layne et al., "Pandemic influenza: an inconvenient mutation", Science 323:1560-1561 (2009).

Li et al., "A genome-wide genetic screen for host factors required for hepatitis C virus propagation", Proc Natl Acad Sci USA 106:16410-16415 (2009).

Marsh et al., "Specific residues of the influenza a virus hemagglutinin viral RNA are important for efficient packaging into budding virions", J Virol 81:9727-9736 (2007).

McClure et al., "The pH independence of mammalian retrovirus infection", J Gen Virol 71:767-773 (1990).

Meijer et al, "Inhibition of cyclin-dependent kinases, GSK-3beta and CK1 by hymenialdisine, a marine sponge constituent", Chem Biol 7:51-63 (2000).

Melzig and Bormann, "Betulinic acid inhibits aminopeptidase N activity", Planta Medica 64:655-657 (1998).

O'Neill et al., "The influenza virus NEP (NS2 protein) mediates the nuclear export of viral ribonucleoproteins", EMBO J 17:288-296 (1998).

Palese and Shaw, "Orthomixoviridae: The Viruses and Their Replication" in: Fields Virology, 5$^{th}$ ed., vol. 2 (D.M. Knipe & P.M. Howley, eds.), Lippincott Williams & Wilkins, Philadelphia, pp. 1647-1689 (2007).

Park et al., "Newcastle disease virus (NDV)-based assay demonstrates interferon-antagonist activity for the NDV V protein and the Nipah virus V, W, and C proteins", J Virol 77:1501-1511 (2003).

Pinto and Lamb, "Understanding the mechanism of action of the anti-influenza virus drug amantadine", Trends Microbiol. 3:271 (1995).

Price et al., "Rapamycin-induced inhibition of the 70-kilodalton S6 protein kinase", Science 257:973-977 (1992).

Renhowe et al., "Design, structure-activity relationships and in vivo characterization of 4-amino-3-benzimidazol-2-ylhydroquinoline-2-ones: a novel class of receptor tyrosine kinase inhibitors", J Med Chem 52:278-292 (2009).

Rines et al., "Whole genome functional analysis identifies novel components required for mitotic spindle integrity in human cells", Genome Biol 9:R44 (2008).

Sarbassov et al., "Phosphorylation and regulation of Akt/PKB by the rictor-mTOR complex", Science 307:1098-1101 (2005).

Sato et al., "Modulation of Akt kinase activity by binding to Hsp 90", Proc Natl Acad. Sci USA 97:10832-10837 (2000).

Sessions et al., "Discovery of insect and human dengue virus host factors", Nature 458:1047-1050 (2009).

Shapira et al., "A physical and regulatory map of host-influenza interactions reveals pathways in H1N1 infection", Cell 139:1255-1267 (2009).

Sharp et al., "In vitro biological characterization of a novel, synthetic diaryl pyrazole resorcinol class of heat shock protein 90 inhibitors", Cancer Res 67:2206-2216 (2007).

Smith et al., "Preclinical pharmacokinetics and metabolism of a novel diaryl pyrazole resorcinol series of heat shock protein 90 inhibitors", Mol Cancer Ther 5:1628-1637 (2006).

Sorensen et al., "Diphyllin, a novel and naturally potent V-ATPase inhibitor, abrogates acidification of the osteoclastic resorption lacunae and bone resorption", J Bone Miner Res 22:1640-1648 (2007).

(56) References Cited

OTHER PUBLICATIONS

Stertz et al., "The antiviral potential of interferon-induced cotton rat Mx proteins against orthomyxovirus (influenza), rhabdovirus and bunyavirus", J Interferon Cytokine Res 27:847-855 (2007).

Su et al., "Pooled RNAi screen identifies ubiquitin ligase itch as crucial for influenza a virus release from the endosome during virus entry", Proc Natl Acad Sci USA 110:17516-17521 (2013).

Sui et al., "The use of Random Homozygous Gene Perturbation to identify novel host-oriented targets for influenza", Virology 387:473-481 (2009).

Sumi et al., "The newly synthesized selective $Ca^{2+}$/calmodulin dependent protein kinase II inhibitor KN-93 reduces dopamine contents in PC12h cells", Biochem Biophys Res Comm 181:968-975 (1991).

Supriyono et al., "Bioactive alkaloids from the tropical marine sponge *Axinella carteri*", Z Naturforsch C 50:669-674 (1995).

Tai et al., "A functional genomic screen identifies cellular cofactors of hepatitis C virus replication", Cell Host Microbe 5:298-307 (2009).

Terada et al., "Rapamycin inhibits the phosphorylation of p70 S6 kinase in IL-2 and mitogen-activated human T cells", Biochem Biophys Res Comm 186:1315-1321 (1992).

Tscherne et al., "An enzymatic virus-like particle assay for sensitive detection of virus entry", J Virol Meth 163:336-343 (2010).

Venkatesan et al., "An empirical framework for binary interactome mapping", Nat Meth 6:83-90 (2009).

Wang and Palese, "Unraveling the mystery of swine influenza virus", Cell 137:983-985 (2009).

Ward et al., "Host modulators of H1N1 cytopathogenicity", PLOS One 7:e39284 (2012).

Wharton et al., "Role of virion M2 protein in influenza virus uncoating: specific reduction in the rate of membrane fusion between virus and liposomes by amantidine", J Gen Virol 75:945-948 (1994).

Whitney et al., "Cytoplasmic coat proteins involved in endosome function", Cell 83:703-713 (1995).

Young et al., "The *Plasmodium falciparum* sexual development transcriptome: a microarray analysis using ontology-based pattern identification", Mol Biochem Parasitol 143:67-79 (2005).

Zhou et al., "In silico gene function prediction using ontology-based pattern identification", Bioinformatics 21:1237-1245 (2005).

Zhou et al., "Genome-scale RNAi screen for host factors required for HIV replication", Cell Host Microbe 4:495-504 (2008).

\* cited by examiner

Fig. 4

COMPOSITIONS AND METHODS FOR INHIBITING HUMAN HOST FACTORS REQUIRED FOR INFLUENZA VIRUS REPLICATION

This application is a national stage application under 35 U.S.C. §371 of International Patent Application No. PCT/US2010/003138, filed Dec. 10, 2010, which claims the benefit under 35 U.S.C., §119(e) of LS. Provisional Application No. 61/285,951, filed Dec. 11, 2009, each of which is incorporated by reference herein in its entirety.

This invention was made with government support under Grant Nos. AI057158, AI058113, AI074539, AI083673, HHSN266200700010C, and HHSN272200900032C awarded by the National Institutes of Health. The government has certain rights in the invention.

1. INTRODUCTION

This application relates to the modulation of host cell factors required for influenza virus replication. The application relates to compounds, including nucleic acid compounds (such as, e.g., small interfering RNAs (siRNAs)) and small molecules, that target human host cell factors involved in influenza virus replication, and the use of such compounds for modulating influenza virus replication and as antiviral agents. The application also relates to methods of treating an influenza virus infection and methods of treating or preventing a symptom or disease associated with influenza virus infection, comprising administering to a subject a composition comprising a compound, such as a nucleic acid compound (e.g., an siRNA) or small molecule, that targets a human host cell factor involved in influenza virus replication.

2. BACKGROUND

Influenza viruses are enveloped RNA viruses that belong to the family of Orthomyxoviridae (Palese and Shaw, 2007). Influenza A and B viruses are considered to be major human pathogens and in a normal season they can cause between 3-5 million cases of severe illness and up to 500,000 deaths worldwide (World Health Organization, 2003). Influenza A viruses can also cause pandemics such as those that occurred in 1918, 1957 and 1968. These outbreaks resulted in high mortality rates because of the lack of pre-existing immunity against the new virus strain. The current pandemic outbreak, beginning in 2009, of the swine-origin H1N1 influenza virus (Wang & Palese, 2009), and the emergence of the highly pathogenic avian H5N1 influenza virus in the late 1990s (Claas et al., 1998), have sparked renewed interest in the development of anti-influenza virus drugs.

Strategies for identifying targets for antiviral intervention typically focus on compounds that attack the virus itself, i.e., viral proteins—the structural components of the virion, as well as viral genome-encoded enzymes which are necessary for propagation of the virus. The approach of targeting viral proteins has several limitations: i) the limited number of viral targets; ii) viral targets tend to be highly specific to a particular virus or even strain of virus; and iii) viruses are able to rapidly alter their genetic composition to develop resistance to antiviral drugs. Another approach in antiviral drug development is to design drugs to strengthen the host's immune system to fight the viral infection, rather than to fight the viral infection itself. Using this strategy, drugs are designed to boost the host's immune system to allow the host to better fight off infection by the virus.

Cellular targets have traditionally been considered less desirable candidates for antiviral therapy. Relatively few antiviral drugs have been directed at host enzymes for several reasons, the most prominent being the high risk of toxicity to the host itself. Although host cell factors play a key role in facilitating viral growth and propagation, strategies for attacking such host factors remain elusive.

Currently there are only four U.S. Food and Drug Administration (FDA)—approved drugs available for the treatment of influenza, amantadine, rimantadine, oseltamivir, and zanamivir (DeClercq, 2006). The adamantanes (amantadine and rimantadine) block the M2 ion channel of the virus and prevent the release of the viral genome into the host cell (Pinto and Lamb, 1995; Wharton et al., 1994). These drugs are effective if used prophylactically and if administered within 48 hours of infection but are not effective against influenza B viruses. However, the development of widespread resistance has precluded the use of adamantanes in recent influenza seasons (Bright et al., 2006) and isolates of the H5N1 influenza virus have been shown to be resistant to these drugs due to mutations in M2 (Cheung et al., 2006).

The preferred treatment for influenza virus infection is now the use of the neuraminidase (NA) inhibitors, oseltamivir and zanamivir (Garman and Laver, 2004). By targeting NA, these compounds prevent the release of the virus from the infected cell and halt the spread of the virus. As part of its pandemic preparedness plan, the World Health Organization (WHO) has advised that supplies of the NA inhibitors be stockpiled, but it is always advantageous to have at least two antiviral drugs (aimed at different targets) available due to the possible emergence of resistant virus strains. In fact the 2007-2008 influenza season in the Northern hemisphere has shown a marked increase in the number of H1N1 isolates that are resistant to oseltamivir (World Health Organization, 2008) and concerns have also been raised regarding oseltamivir-resistant H5N1 influenza viruses isolated from patients in Southeast Asia (Le et al., 2005). There is now widespread resistance to both of these drug classes (Layne et al., 2009).

Thus, a major challenge to anti-influenza drug development is finding new strategies for combating influenza virus infection.

3. SUMMARY

The present application is based, in part, on the discovery that influenza virus replication can be reduced by pharmacologically targeting human host cell factors required for viral replication. Targeting host cell factors, rather than the viral factors required for influenza virus replication, may greatly reduce the emergence of viral resistance and expands the number of targets for antiviral intervention.

Provided herein are compounds, including but not limited to nucleic acid compounds (e.g., siRNAs) and small molecules, that target human host cell factors involved in influenza virus replication. Provided herein are compositions, including pharmaceutical compositions, comprising such compounds, and methods of using such compounds and compositions for modulating influenza virus replication. In some embodiments, the compounds and compositions comprising them reduce or inhibit influenza virus replication. Provided herein are methods of using such compounds and compositions for reducing or inhibiting influenza virus replication. In some embodiments, the compounds modulate influenza virus replication by altering the expression (e.g., mRNA or protein) and/or activity of the human host cell factor involved in influenza virus replication. In some embodiments, the compounds reduce or inhibit influenza virus replication by reducing or inhibiting the expression (e.g., mRNA or protein) and/or activity of the human host cell factor involved in influenza virus replication. In some embodiments, the human host cell factor interacts with a component of the influenza virus. In some embodiments, the human host cell factor is required for influenza virus replication.

The compounds provided herein, and for use in the compositions and methods provided herein, target human host cell factors involved in influenza virus replication and modulate influenza virus replication. In some embodiments, the compounds provided herein, and for use in the compositions and methods provided herein, target human host cell factors involved in influenza virus replication and reduce or inhibit influenza virus replication. The targeted human host cell factor may be required for influenza virus replication. The targeted human host cell factor may be involved in or required for one or more of the following events of the influenza virus life cycle: entry; uncoating; nuclear import; viral RNA transcription; or viral RNA translation. The targeted human host cell factor may be involved in or required for replication of more than one strain or sub-type of influenza. For example, the human host cell factor may be involved in or required for replication of an influenza A virus, an influenza B virus, and/or an influenza C virus. In some embodiments, the human host cell factor is involved in or required for replication of a human-origin, an avian-origin (e.g., H5N1), and/or a swine-origin (e.g., H1N1) influenza virus.

In some embodiments, a compound provided herein, and for use in the compositions and methods provided herein, targets a component or regulator of, or factor that interacts with, one or more of the following categories of human host cell factors: cytoskeleton; ribonucleoprotein; spliceosome; ubiquitin/proteasome system; ribosome or other translation machinery; kinase; phosphatase; signaling (e.g., G-protein coupled receptors; signaling at the plasma membrane); mitochondrion or mitochondrial ribosome; plasminogen; stress response; v-ATPase; ion channel or other ion transport; nucleus; sumoylation; nuclear transport; nucleotide binding; cell cycle; vesicular transport (e.g., COPI vesicle); chromosome; or carboxylic acid metabolism. In some embodiments, a compound provided herein, and for use in the compositions and methods provided herein, targets a component or regulator of, or a factor that interacts with, one or more of the following categories of human host cell factors: IP3-PKC pathway; COPI vesicles; endosomal uptake, maturation, acidification, and fusion; actin organization and function; PI3K-AKT pathway; endosomal recycling pathway; MAPK pathway; proteases; calcium/calmodulin system; nuclear trafficking; trafficking; sumoylation; microtubule organization (including assembly) and function; autophagy; or ubiquitination. Exemplary, non-limiting, components or regulators of, or factors that interact with, these categories of human host cell factors that may be targeted in accordance with these embodiments are provided in Table 5 infra (see, e.g., the column labeled "Gene names"). In particular embodiments, the compound reduces or inhibits the expression and/or activity of the human host cell factor.

In some embodiments, the compounds provided herein, and for use in the compositions and methods provided herein, reduce or inhibit influenza virus replication. In some embodiments, the compound is an agent that reduces or inhibits the expression (e.g., mRNA or protein) and/or activity of a human host cell factor involved in influenza virus replication. In some embodiments, the human host cell factor is required for influenza virus replication. In some embodiments, the compound reduces or inhibits the interaction of a human host cell factor with a component of the influenza virus. In some embodiments, the compound reduces or inhibits one or more of the following events of the influenza viral life cycle: entry; uncoating; nuclear import; viral RNA transcription; or viral RNA translation. In some embodiments, the compound reduces or inhibits replication of more than one strain or sub-type of influenza. For example, the compound may reduce or inhibit replication of influenza virus A, an influenza B virus, and/or an influenza C virus. In some embodiments, the compound reduces or inhibits replication of a human-origin, an avian-origin (e.g., H5N1), and/or a swine-origin (e.g., H1N1) influenza virus. In some embodiments, the compound reduces or inhibits replication of an influenza virus and one or more other viruses.

In some embodiments, the compound modulates the expression and/or activity of one or more of the human host cell factors listed in Table 3. In specific embodiments, the compound reduces or inhibits the expression and/or activity of one or more of the human host cell factors listed in Table 3.

In some embodiments, the compound modulates the expression and/or activity of one or more of the human host cell factors listed in Table 7. In specific embodiments, the compound reduces or inhibits the expression and/or activity of one or more of the human host cell factors listed in Table 7.

In some embodiments, the compound modulates the expression and/or activity of one or more of the human host cell factors listed in Table 9. In specific embodiments, the compound reduces or inhibits the expression and/or activity of one or more of the human host cell factors listed in Table 9.

In some embodiments, the compound modulates the expression (e.g., mRNA or protein) and/or activity of one or more of the following human host cell factors: ACRC; AKAP13; AKT1; ANAPC2; ANPEP; ARCN1; BRWD3; CAD; CAMK2B; CANT1; CBLL1; CD81; CHAF1A; CLK1; CLOCK; COPA; COPB1; COPB2; COPG; CSE1L; CTSW; DTX2; DUSP3; EPHB2; EPS8L3; F13A1; FAM135A; FGFR2; FGFR4; FPR1, FRAP1 (mTOR); GABBR1; GRK6; GSK3B; HAND2; HIST3H3; HSP90AA1; IL1F9; ITGA3; JAK2; KCNJ11; KPNB1; MAP2K3; MAP3K11; MAP3K12; MC1R; MID1IP1; NEK6; NUP153; NUP214; OSBPL6; PHF2; PLK4; PPP1R12C; PPP1R14D; PRPH2; PRSS35; PSMD1; RAB11B; RBM5; RP11-45B20.2; RPS10; RPS20; SF3A1; SNRPA1; STK31; STK39; STX10; SUMO2; SUMO4; TBK1; TEAD3; TNPO3; TRPV2; TUBB; UBXD3; USE1; VEGFB (GeneID 7423); WDR18; WDR34; or one or more v-ATPase subunits, e.g., ATP6V0B, ATP6V0C, ATP6V1A, ATP6V1B2, or ATP6AP1 (gene ID numbers for representative human host cell factors are provided in Tables 3 and 9). In specific embodiments, the compound reduces or inhibits the expression and/or activity of one or more of the aforementioned human host cell factors.

In certain embodiments, the compound modulates the expression (e.g., mRNA or protein) and/or activity of one or more of the following human host cell factors: AKAP13; ARCN; BRWD3; CD81; COPG; CTSW; DUSP3; EPHB2; FAM135A; FGFR2; FGFR4; GABBR1; GSK3B; ITGA3; JAK2; MAP2K3; NEK6; RAB11B; or one or more of the v-ATPase subunits, ATP6V0B, ATP6V0C, ATP6V1A, ATP6V1B2, or ATP6AP1. In certain embodiments, the compound modulates the expression (e.g., mRNA or protein) and/or activity of one or more of the following human host cell factors: CAMK2B; CSE1L; F13A1; KPNB1; MAP3K12; PP1R14D; PRSS35; RPS10; SF3A1; or SUMO4. In certain embodiments, the compound modulates the expression (e.g., mRNA or protein) and/or activity of one or more of the following human host cell factors: ACRC; DTX2; EPS8L3; FPR1; MAP3K11; NUP214; PRPH2;

RP11-45B20.2; STX10; SUMO2; TRPV2; or TUBB. In certain embodiments, the compound modulates the expression (e.g., mRNA or protein) and/or activity of one or more of the following human host cell factors: ANPEP; CAM2 KB; FGFR4; FRAP1 (mTOR); GSK3B/CSNK1G2; HSP90AA1; or TUBB. In specific embodiments, the compound reduces or inhibits the expression and/or activity of one or more of the aforementioned human host cell factors.

The compound may be any compound described herein, known in the art, or yet to be discovered that targets one or more of the aforementioned categories of human host cell factors, a specific factor(s) in such a category, and/or one of the aforementioned human host cell factors. In certain embodiments, the compound is not toxic to the human host cell.

In certain embodiments, the compound does not target AKT1, ARCN1, COPG, GRK6, HAND2, HIST3H3, an HSP90 (e.g., HSP90AA1), NUP153, RBM5, RPS10, RPS20, or a v-ATPase subunit. In certain embodiments, the compound does not reduce or inhibit the expression and/or activity of AKT1, ARCN1, COPG, GRK6, HAND2, HIST3H3, an HSP90 (e.g., HSP90AA1), NUP153, RBM5, RPS10, RPS20, or a v-ATPase subunit. In certain embodiments, the compound does not target AKAP13, CD81, CAMK2B, CSE1L, DUSP3, FGFR2, FGFR4, GSK3B, ITGA3, KPNB1, MAP2K3, or RAB11B. In certain embodiments, the compound does not reduce or inhibit the expression and/or activity of AKAP13, CD81, CAMK2B, CSE1L, DUSP3, FGFR2, FGFR4, GSK3B, ITGA3, KPNB1, MAP2K3, or RAB11B.

In some embodiments, the compound is a nucleic acid compound. In some embodiments, the nucleic acid compound is an siRNA. In some embodiments, the nucleic acid compound has a sequence optimized for use as an siRNA, according to methods known in the art. In some embodiments, the nucleic acid compound is an antisense compound. In certain embodiments, the nucleic acid compound is a modified oligonucleotide. In some embodiments, the nucleic acid compound is contained within a larger nucleic acid compound, such as a plasmid. In some embodiments, the nucleic acid compound comprises an oligonucleotide of 12 to 30 linked nucleosides, for example, 12 to 15, 15 to 20, 20 to 25, e.g., 21 or 25 nucleosides, or 26 to 30 linked nucleosides, which may be targeted to a nucleic acid encoding a human host cell factor involved in influenza virus replication. In some embodiments, the human host cell factor involved in influenza virus replication is a human host cell factor described supra. Any region of the human host cell factor gene or mRNA may be targeted as provided for herein and known to one of skill in the art.

In some embodiments, the compound targets a nucleotide sequence selected from Table 1 (see also Table 9) (Section 7 below). In certain embodiments, e.g., when targeting of a deoxyribonucleic acid (DNA) sequence is desired, the nucleobases represented by a "U" (uracil) in a sequence in Table 1 may be replaced with thymine nucleobases (represented by a "T"). In certain embodiments, e.g., when targeting a ribonucleic acid (RNA) sequence is desired, the nucleobases represented by a "T" (thymine) in a sequence in Table 1 may be replaced with uracil nucleobases (represented by a "U"). For example, the nucleotide sequence "AAGTAGG-GATAAATTACTCTA" (SEQ ID NO: 90) in Table 1 may be replaced with the nucleotide sequence "AAGUAGG-GAUAAAUUACUCUA" (SEQ ID NO: 724)

In certain embodiments, the nucleic acid compound targeting a sequence in Table 1 is an antisense compound. In some embodiments, the nucleic acid compound targeting a sequence in Table 1 is an siRNA. In certain embodiments, the siRNA that targets one of the aforementioned human host cell factors or sequences is obtained from a commercially available source. For example, the siRNA can be from Qiagen (Druggable Set version 1 or 2), NM Set version 1, XM Set version 1, the kinome library from Invitrogen or the kinome library from IDT.

In certain embodiments, an siRNA duplex is created from a 21mer sequence in Table 1 as exemplified in the following example:

The sequence 5'-GAGCTTGAATTTGAAGGTGTA-3' (SEQ ID NO: 3) is modified to convert it into a ribonucleic acid (RNA) and to introduce overhangs (shown in lowercase letters) as follows:

```
5'---GCUUGAAUUUGAAGGUGUAtt-3'      (SEQ ID NO: 725)
3'-ctCGAACUUAAACUUCCACAU---5'      (SEQ ID NO: 726)
```

The first two are the antisense overhang, the sense overhang is always TT. siRNA duplexes based on the sequences in Table 1 that contain Us are created the same way, except that the sequence is already an RNA; i.e., the sequence in Table 1 containing Us correspond to host cell mRNA targets.

In some embodiments, the siRNA compound comprises the sequence /5Phos/rGrGrCrUrArCrGrGrArCrCrArAr-GrUrUrUrArUrCrCrGrGCG (SEQ ID NO: 177). This sequence is the sense sequence for a 25mer siRNA duplex for use in accordance with the embodiments described herein.

In some embodiments, the compound is a small molecule. In some embodiments, the small molecule is Betulinic acid (available from VWR International/Enzo Life Sciences Intl.); CCT018159 (4-(4-(2,3-Dihydro-1,4-benzodioxin-6-yl)-5-methyl-1H-pyrazol-3-yl)-6-ethylresorcinol; available from Calbiochem); Diphyllin (available from Sigma; see FIG. 13a); the FGF/VEGF receptor inhibitor 4-Hydroxy-3-benzimidazol-2-ylhydroquinolin-2-one; Hymenialdisine (available from Biomol International LP); KN-93 (available from Calbiochem); Podophyllotoxin (Podophyllinic Acid Lactone; available from MP Biomedicals); or Sirolimus (Rapamycin; available from LC Laboratories).

In some embodiments, the compound is not CCT018159. In some embodiments, the compound is not Diphyllin.

Also provided herein are compositions comprising a compound that targets one or more human host cell factors involved in influenza virus replication. Such compositions may be in a dose effective to modulate influenza virus replication. Such compositions may be in a dose effective to reduce or inhibit influenza virus replication. Such compositions may be pharmaceutical compositions, and may additionally comprise a pharmaceutically acceptable carrier known in the art or described herein. Such pharmaceutical compositions may be in a dose effective to treat influenza virus infection or to reduce or inhibit a symptom or disease associated with influenza virus infection. Compounds for use in these compositions and pharmaceutical compositions may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, such as an siRNA, optionally in an appropriate delivery vehicle; or (v) an aforementioned small molecule. Such compositions may also include another active agent, for example, another compound that targets a human host cell factor involved in influenza virus replication described herein. In certain embodiments, the compositions, including the pharmaceutical compositions, described herein contain the compound in an amount that is not significantly toxic to the cell, tissue, or subject for which it is intended. Methods of testing toxicity include any method known in the art, for example, as described in Sections 5 and 6 infra.

Provided herein are methods of reducing or inhibiting influenza virus replication, comprising contacting a cell infected with an influenza virus with a compound, or composition comprising the compound, that targets one or more human host cell factors involved in influenza virus replication, in an amount sufficient to reduce or inhibit replication of the influenza virus. In one embodiment, a method for reducing or inhibiting replication of an influenza virus comprises: (a) infecting a cell with an influenza virus; and (b) contacting the cell with such a compound or composition in an amount sufficient to reduce or inhibit replication of the influenza virus. Also provided herein are methods for reducing or inhibiting influenza virus replication, comprising: (a) contacting a cell with such a compound or composition in an amount sufficient to reduce or inhibit replication of an influenza virus; and (b) infecting the cell with the influenza virus. In some embodiments, a compound or composition comprising the compound is considered to reduce or inhibit influenza virus replication if it reduces the amount of influenza virus replication as measured compared to a control, such as, for example, influenza virus replication in the absence of the compound or composition, or influenza virus replication in the presence of a negative control. In some embodiments, the compound or composition is contacted to a cell at risk for influenza virus infection. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, such as an siRNA, optionally in an appropriate delivery vehicle; or (v) an aforementioned small molecule.

Provided herein are methods for treating an influenza virus infection, comprising administering to a subject in need thereof a pharmaceutical composition comprising a compound, e.g., nucleic acid compound (e.g., siRNA) or small molecule, that targets one or more human host cell factors involved in influenza virus replication in an amount sufficient to reduce the influenza virus infection. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, such as an siRNA, optionally in an appropriate delivery vehicle; or (v) an aforementioned small molecule.

Provided herein are methods for treating a symptom or disease associated with an influenza virus infection, comprising administering to a subject in need thereof a pharmaceutical composition comprising a compound, e.g., nucleic acid compound (e.g., siRNA) or small molecule, that targets one or more human host cell factors involved in influenza virus replication in an amount sufficient to reduce the symptom or disease associated with the influenza virus infection. In some embodiments, the subject is infected with an influenza virus. In some embodiments, the subject is at risk for infection with an influenza virus. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, such as an siRNA, optionally in an appropriate delivery vehicle; or (v) an aforementioned small molecule.

Also provided herein are methods for preventing a symptom or disease associated with an influenza virus infection, comprising administering to a subject in need thereof a composition comprising a compound, e.g., nucleic acid compound (e.g., siRNA) or small molecule, that targets one or more human host cell factors involved in influenza virus replication in an amount sufficient to prevent or reduce the symptom or disease associated with the influenza virus infection. In some embodiments, the subject is infected with an influenza virus. In some embodiments, the subject is at risk for infection with an influenza virus. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, such as an siRNA, optionally in an appropriate delivery vehicle; or (v) an aforementioned small molecule.

In certain embodiments of the aforementioned methods, the compounds, compositions, and pharmaceutical compositions are used in an amount that is not significantly toxic to the cell, tissue, or subject for which it is intended. Methods of testing toxicity include any method known in the art, for example, as described in Sections 5 and 6 infra. The aforementioned methods may optionally comprise use of the compound that targets a human host cell factor involved in influenza virus replication in combination with one or more additional active agents. Such additional active agents include, for example, one or more additional antiviral agents, e.g., an aforementioned compound that targets human host cell factors involved in influenza virus replication; an antibiotic; an immunomodulatory agent; or an agent used in the treatment or prophylaxis of one or more pulmonary diseases described herein (see, e.g., Section 5) or known in the art.

In certain of the above embodiments, the subject is a human. In certain of the above embodiments, the influenza virus is an influenza A virus. In some embodiments, the influenza virus is an influenza B virus. In some embodiments, the influenza virus is an influenza C virus. Any type, subtype, or strain of influenza virus described herein or known in the art may be targeted in accordance with the embodiments described herein. In some embodiments, the influenza virus is of human origin. In some embodiments, the influenza virus is of avian origin (e.g., H5N1). In some embodiments, the influenza virus is of swine origin (e.g., H1N1). In some embodiments, the compound or composition may have broad antiviral utility, e.g., it modulates replication of an influenza virus and one, or two, or three, or four, or five, or more additional viruses known in the art or yet to be discovered.

3.1 Terms

As used herein, the term "2'-O-methoxyethyl" (also 2'-MOE and 2'-O($CH_2$)$_2$—$OCH_3$) refers to an O-methoxyethyl modification of the 2' position of a furosyl ring. A 2'-O-methoxyethyl modified sugar is a modified sugar. As used herein, the term "2'-O-methoxyethyl nucleotide" means a nucleotide comprising a 2'-O-methoxyethyl modified sugar moiety.

As used herein, the term "5-methylcytosine" means a cytosine modified with a methyl group attached to the 5' position. A 5-methylcytosine is a modified nucleobase.

As used herein, the term "about" or "approximately" when used in conjunction with a number refers to any number within 1, 5 or 10% of the referenced number.

As used herein, the term "antisense compound" means an oligomeric compound that is capable of undergoing hybridization to a target nucleic acid through hydrogen bonding. As used herein, the term "antisense inhibition" means reduction of target nucleic acid levels in the presence of an antisense compound complementary to the target nucleic acid compared to target nucleic acid levels in the absence of the antisense compound. As used herein, the term "antisense oligonucleotide" means a single-stranded oligonucleotide having a nucleobase sequence that permits hybridization to a corresponding region or segment of a target nucleic acid. As used herein, the term "chimeric antisense compound" means an antisense compound that has at least 2 chemically distinct regions, each position having a plurality of subunits.

As used herein, the term "bicyclic sugar" means a furosyl ring modified by the bridging of two non-geminal ring atoms. A bicyclic sugar is a modified sugar. As used herein, the term "bicyclic nucleic acid" or "BNA" refers to a nucleoside or nucleotide wherein the furanose portion of the nucleoside includes a bridge connecting two carbon atoms on the furanose ring, thereby forming a bicyclic ring system.

As used herein, the term "cap structure" or "terminal cap moiety" means chemical modifications, which have been incorporated at either terminus of an antisense compound.

As used herein, the term "complementarity" means the capacity for pairing between nucleobases of a first nucleic acid and a second nucleic acid. As used herein, the term "mismatch" or "non-complementary nucleobase" means a nucleobase of first nucleic acid that is not capable of pairing with the corresponding nucleobase of a second or target nucleic acid.

As used herein, the term "compound," unless otherwise specified or apparent from the context, refers to any agent described herein that modulates, reduces, or inhibits influenza virus replication, including the compounds and structures provided herein or incorporated by reference herein, and solvates, hydrates, prodrugs, stereoisomers and pharmaceutically acceptable salts thereof. Compounds include, but are not limited to, nucleic acid molecules such as, e.g., double-stranded or single-stranded DNA, or double-stranded or single-stranded RNA, antisense RNA, an RNA interference (RNAi) molecule (e.g., a small interfering RNA (siRNA), micro-RNA (miRNA), or short hairpin RNA (shRNA)), intron sequences, triple helix nucleic acid molecules and aptamers; carbohydrates; proteinaceous molecules, such as, e.g., peptides (including dimers and multimers of such peptides), polypeptides, proteins, such as, e.g., post-translationally modified proteins, conjugates, antibodies, antibody fragments, etc. (including intrabodies); small molecules, including inorganic or organic compounds; and lipids. In one embodiment, a compound is one of the compounds identified in Section 5 below. In one embodiment, a compound is purified. In one embodiment, a compound is isolated.

As used herein, the term "effective amount" in the context of administering a treatment to a subject refers to the amount of a treatment which has a prophylactic and/or therapeutic effect(s). In certain embodiments, an "effective amount" in the context of administration of a treatment to a subject refers to the amount of a treatment which is sufficient to achieve one, two, three, four, or more of the following effects: (i) reduce or ameliorate the severity of a viral infection or a symptom or disease associated therewith; (ii) reduce the duration of a viral infection or a symptom or disease associated therewith; (iii) reduce or prevent the progression of a viral infection or a symptom or disease associated therewith; (iv) cause regression of a viral infection or a symptom or disease associated therewith; (v) prevent the development or onset of a viral infection or a symptom or disease associated therewith; (vi) reduce or prevent the recurrence of a viral infection or a symptom or disease associated therewith; (vii) reduce or prevent the spread of a virus from one cell to another cell, one tissue to another tissue, or one organ to another organ; (ix) reduce or prevent the spread of a virus from one subject to another subject; (x) reduce or prevent organ failure associated with a viral infection; (xi) reduce hospitalization of a subject; (xii) reduce hospitalization length; (xiii) increase the survival of a subject with a viral infection; (xiv) eliminate a virus infection; (xv) inhibit or reduce virus replication; (xvi) inhibit or reduce the entry of a virus into a host cell(s); (xviii) inhibit or reduce replication of the viral genome; (xix) inhibit or reduce synthesis of viral proteins; (xx) inhibit or reduce assembly of viral particles; (xxi) inhibit or reduce release of viral particles from a host cell(s); (xxii) reduce viral titer; and/or (xxiii) enhance or improve the prophylactic or therapeutic effect(s) of another therapy.

As used herein, the term "hybridization" means the annealing of complementary nucleic acid molecules. In certain embodiments, complementary nucleic acid molecules include, but are not limited to, an antisense compound or oligonucleotide and a nucleic acid target or the paired strands of an siRNA molecule. As used herein, the term "specifically hybridizable" means when there is a sufficient degree of complementarity between an antisense compound and a target sequence to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the term "in combination," in the context of the administration of two or more treatments or therapies to a subject, refers to the use of more than one compound or composition, e.g., more than one prophylactic agent and/or therapeutic agent. The two compounds may be formulated together in a single composition. The use of the term "in combination" does not restrict the order in which therapies are administered to a subject with a viral infection. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a viral infection.

As used herein, the term "infection" means the invasion by, multiplication and/or presence of a virus in a cell, tissue, or subject. In one embodiment, an infection is an "active" infection, i.e., one in which the virus is replicating in a cell, tissue, or subject. Such an infection may be characterized by the spread of the virus to other cells, tissues, organs, and/or subjects from the cells, tissues, organs, and/or subjects initially infected by the virus. An infection may also be a latent infection, i.e., one in which the virus is not replicating. In one embodiment, an infection refers to the pathological state resulting from the presence of the virus in a cell, tissue, or subject, or by the invasion of a cell, tissue, or subject by the virus.

In certain embodiments, a compound that inhibits or reduces viral replication reduces viral replication by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In a specific embodiment, the compound reduces virus replication by at least 2 log relative to virus replication in the absence of compound or the presence of a negative control. In certain embodiments, the compound reduces virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, the compound reduces the virus replication by approximately 2 logs or more, approximately 3 logs or more, approximately 4 logs or more, approximately 5 logs or more, or 2 to 10 logs or 2 to 5 logs relative to virus replication in the absence of compound or the presence of a negative control.

In one embodiment, a decrease in viral replication is measured using an assay described in Section 5 or Section 6, infra. In some embodiments, a decrease in viral replication is screened for using a library of compounds. In one embodiment, a decrease in viral replication is measured by: (a) contacting a compound or a member of a library of compounds with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection with the virus; and (b) measuring virus replication. The cells used in the assay should be susceptible to infection by the chosen virus and can be infected at different MOIs. The effect of a compound on virus replication can be assessed by measuring virus replication at different times post-infection. For example, virus replication may be measured 6 hours, 12 hours, 16 hours, 24 hours, 48 hours or 72 hours post-infection, using any method known to one of skill in the art can be used measure virus replication. In one embodiment, a decrease in viral replication is assessed by measuring viral titer (as determined, e.g., by plaque formation). In another embodiment, a decrease in viral replication is assessed by measuring the production of viral proteins (as determined, e.g., by Western blot analysis, ELISA or flow cytometry). In another embodiment, a decrease in viral replication is assessed by measuring the production of viral nucleic acids (as determined, e.g., by RT-PCR or Northern blot analysis) using techniques known to one of skill in the art. See Sections 5 and 6 below for more details of techniques for measuring viral replication. In some embodiments, viral replication is measured using a virus engineered to contain a reporter, such as the *Renilla* luciferase virus described in Section 6. In some embodiments, a compound is considered to decrease viral replication if it reduces the amount of viral replication as measured compared to a control, such as, for example, viral replication in the absence of the compound or viral replication in the presence of a negative control.

As used herein, the term "library" in the context of compounds refers to a plurality of compounds. A library can be a combinatorial library, e.g., a collection of compounds synthesized using combinatorial chemistry techniques, or a collection of unique chemicals with a low molecular weight (less than 1000 Daltons).

As used herein, the numeric term "log" refers to $\log_{10}$.

As used herein, the terms "manage," "managing," and "management," in the context of the administration of a treatment to a subject, refer to the beneficial effects that a subject derives from a treatment, which does not result in a cure of a viral infection. In certain embodiments, a subject is administered one or more treatments to "manage" a disease so as to prevent the progression or worsening of the viral infection.

As used herein, the term "modified internucleoside linkage" refers to a substitution or any change from a naturally occurring internucleoside linkage (i.e. a phosphodiester internucleoside bond). As used herein, the term "naturally occurring internucleoside linkage" means a 3' to 5' phosphodiester linkage.

As used herein, the term "modified nucleobase" means any nucleobase other than adenine, cytosine, guanine, thymine, or uracil. An "unmodified nucleobase" means the purine bases adenine (A) and guanine (G), and the pyrimidine bases thymine (T), cytosine (C) and uracil (U). As used herein, the term "modified nucleotide" means a nucleotide having, independently, a modified sugar moiety, modified internucleoside linkage, or modified nucleobase. A "modified nucleoside" means a nucleoside having, independently, a modified sugar moiety or modified nucleobase. As used herein, the term "modified oligonucleotide" means an oligonucleotide comprising a modified internucleoside linkage, a modified sugar, or a modified nucleobase. As used herein, the term "modified sugar" refers to a substitution or any change from a natural sugar.

As used herein, the term "motif" means the pattern of unmodified and modified nucleosides in an antisense compound.

As used herein, the phrase "multiplicity of infection" or "MOI" is the average number of virus per infected cell. The MOI is determined by dividing the number of virus added (ml added x PFU) by the number of cells added (ml added x cells/ml).

As used herein, the term "natural sugar" means a sugar found in DNA (2'-H) or RNA (2'-OH).

As used herein, the term "nucleic acid" refers to a molecule composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

As used herein, the term "nucleobase" means a heterocyclic moiety capable of pairing with a base of another nucleic acid. As used herein, the term "nucleobase sequence" means the order of contiguous nucleobases independent of any sugar, linkage, or nucleobase modification.

As used herein, the term "nucleoside" means a nucleobase linked to a sugar.

As used herein, the term "nucleotide" means a nucleoside having a phosphate group covalently linked to the sugar portion of the nucleoside.

As used herein, the term "oligomeric compound" means a polymer of linked monomeric subunits which is capable of hybridizing to at least a region of a nucleic acid molecule.

As used herein, the term "oligonucleoside" means an oligonucleotide in which the internucleoside linkages do not contain a phosphorus atom.

As used herein, the term "oligonucleotide" means a polymer of linked nucleosides each of which can be modified or unmodified, independent one from another.

As used herein, the term "pharmaceutically acceptable salt" refers to a salt of a compound prepared from a pharmaceutically acceptable acid or base including, but not limited to an inorganic acid, an inorganic base, an organic acid, or an organic base. Suitable pharmaceutically acceptable base addition salts of the compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric, and p-toluenesulfonic acid. Specific acids include hydrochloric, hydrobromic, phosphoric, sulfuric, and methanesulfonic acid. In one embodiment, the pharmaceutically acceptable salt is a hydrochloride or a mesylate salt. Others are well-known in the art. See for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a compound, or a pharmaceutically acceptable salt thereof, that further includes a stoichiometric or non-stoichiometric amount of water bound by non-covalent intermolecular forces.

As used herein and unless otherwise indicated, the term "solvate" means a compound, or a pharmaceutically acceptable salt thereof, that further includes a stoichiometric or non-stoichiometric amount of a solvent bound by non-covalent intermolecular forces.

As used herein, the term "phosphorothioate internucleoside linkage" means a linkage between nucleosides where the phosphodiester bond is modified by replacing one of the non-bridging oxygen atoms with a sulfur atom. A phosphorothioate linkage is a modified internucleoside linkage.

As used herein, the terms "prevent," "preventing" and "prevention" in the context of the administration of a treatment to a subject to prevent a viral infection or a symptom or disease associated with a viral infection refer to one or more of the following effects resulting from the administration of a treatment or a combination of treatments: (i) the inhibition of the development or onset of a viral infection and/or a symptom or disease associated therewith; (ii) the inhibition of the recurrence of a viral infection and/or a symptom or disease associated therewith; and.or (iii) delaying or forestalling the onset of a viral infection and/or a symptom or disease associated therewith.

As used herein and unless otherwise indicated, the term "prodrug" means a compound derivative that can hydrolyze, oxidize, or otherwise react under biological conditions (in vitro or in vivo) to provide the compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylic esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein, the term "prophylactic" refers to use of an agent in the prevention of a viral infection or a symptom or disease associated therewith. In some embodiments, the prophylactic agent does not result in the complete prevention of the viral infection or symptom or disease associated therewith. In a specific embodiment, a prophylactic agent is an agent which is known to be useful to or has been or is currently being used to prevent or impede the onset and/or development of a viral infection or a symptom or disease associated therewith.

As used herein, the term "prophylactically effective amount" refers to the amount of a treatment (e.g., with a prophylactic agent) which is sufficient to prevent a viral infection or a symptom or disease associated therewith in a subject. In certain embodiments, a "prophylactically effective amount" is the amount of a compound that reduces the incidence of a viral infection in a subject. In a specific embodiment, the incidence of a viral infection in a subject is reduced by at least 2.5%, at least 5%, at least 10%, at least 15%, at least 25%, at least 35%, at least 45%, at least 50%, at least 75%, at least 85%, by at least 90%, at least 95%, or at least 99% in a subject administered a compound relative to a subject or group of subjects (e.g., two, three, five, ten or more subjects) not administered the compound.

As used herein, the term "purified," in the context of a compound that is chemically synthesized, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds.

As used herein, the terms "purified" and "isolated" when used in the context of a compound (including nucleic acid molecules or proteinaceous agents) that is obtained from a natural source, e.g., cells, refers to a compound which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound that has been separated from the material (e.g., cellular components of the cells) from which it is isolated. Thus, a compound that is isolated includes preparations of a compound having less than about 30%, 20%, 10%, 5%, 2%, or 1% (by dry weight) of cellular materials and/or contaminating materials.

A "purified" or "isolated" nucleic acid sequence or nucleotide sequence, such as an siRNA, miRNA, shRNA, or a vector construct for producing such a molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

As used herein, the terms "replication," "viral replication" and "virus replication" in the context of a virus refer to one or more, or all, of the stages of a viral life cycle which result in infection with or propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the term "single-stranded oligonucleotide" means an oligonucleotide which is not hybridized to a complementary strand.

As used herein, the term "small interfering RNA" or "siRNA" refers to a double-stranded RNA molecule that reduces or inhibits the expression of a target human host cell factor. The term is understood to encompass RNA interference (RNAi). RNA interference (RNAi) refers to the process of sequence-specific post transcriptional gene silencing in mammals mediated by siRNAs (see, e.g., Fire et al, 1998, Nature 391, 806). Any nucleic acid compound or formulation that results in formation of an siRNA molecule may be used in accordance with the embodiments described herein. See, e.g., Section 5 below.

As used herein, the terms "small molecule" and "small molecular weight compound," and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, as well as solvates, hydrates, prodrugs, stereoisomers and pharmaceutically acceptable salts thereof. In one embodiment, the small molecule is an organic compound other than a peptide, peptidomimetic, amino acid, amino acid analog, polynucleotide, polynucleotide analog, nucleic acid, nucleotide or nucleotide analog.

As used herein and unless otherwise indicated, the term "stereoisomer" or "stereomerically pure compound" means one stereoisomer of a compound, in the context of an organic or inorganic molecule, that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound is characterized by an enantiomeric excess greater than about 60% of one stereoisomer of the compound over one or more other stereoisomers of the compound, greater than about 80% of one stereoisomer of the compound over one or more other stereoisomers of the compound, greater than about 90% of the compound over one ore more other stereoisomers of the compound, greater than about 94% of one stereoisomer of the compound over one or more other stereoisomers of the compound, or greater than about 97% of one stereoisomer of the compound over one or more other stereoisomers of the compound or greater than about 99% of one stereoisomer of the compound over one or more other stereoisomers of the compound. The compounds can have chiral centers and can occur as racemates, individual enantiomers or diastereomers, and mixtures thereof. All such isomeric forms are included within the embodiments disclosed herein, including mixtures thereof.

Various compounds contain one or more chiral centers, and can exist as racemic mixtures of enantiomers, mixtures of diastereomers or enantiomerically or optically pure compounds. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should also be noted that compounds, in the context of organic and inorganic molecules, can include E and Z isomers, or a mixture thereof, and cis and trans isomers or a mixture thereof. In certain embodiments, compounds are isolated as either the E or Z isomer. In other embodiments, compounds are a mixture of the E and Z isomers.

As used herein, the terms "subject" or "patient" are used interchangeably. As used herein, the term "subject" refers to an animal (e.g., bird, reptile, mammal), preferably a mammal including a non-primate (e.g., camel, donkey, zebra, cow, pig, horse, goat, sheep, cat, dog, rat, mouse) and a primate (e.g., a monkey, chimpanzee, human), and most preferably a human.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "synergistic," in the context of the effect of treatments (or one treatment in which two active agents are administered together), refers to a combination of treatments which is more effective than the additive effect of any two or more single treatments. In a specific embodiment, a synergistic effect of a combination of treatments permits the use of lower dosages of one or more treatments and/or less frequent administration of said treatments to a subject with a viral infection or a disease or symptom associated therewith. In certain embodiments, the ability to utilize lower dosages of treatments (e.g., the compounds described herein, or prophylactic or therapeutic agents) and/or to administer said treatments less frequently reduces the toxicity associated with the administration of said treatments to a subject without reducing the efficacy of said treatments in the prevention or treatment of a viral infection or a disease or symptom associated therewith. In some embodiments, a synergistic effect results in improved efficacy of treatments (e.g., prophylactic or therapeutic agents) in the prevention, management and/or treatment of a viral infection or a disease or symptom associated therewith. In some embodiments, a synergistic effect of a combination of treatments (e.g., the compounds described herein, or prophylactic or therapeutic agents) avoids or reduces adverse or unwanted side effects associated with the use of any single treatment.

As used herein, in the context of a nucleic acid compound (e.g., siRNA or antisense) that modulates the expression or activity of a human host cell factor involved in influenza virus replication, "targeted" or "targeted to" means having a nucleobase sequence that will allow its hybridization to a target nucleic acid (e.g., human host cell factor required for influenza virus replication) to induce a desired effect. In certain embodiments, a desired effect is a reduction in the amount of a target nucleic acid. In certain embodiments, a desired effect is reduction of the expression (protein or mRNA) and/or activity of the target human host cell factor. In certain embodiments, a desired effect is reduction of influenza virus replication. In the same context, "targeting" means the process of design and selection of a nucleic acid compound that will specifically hybridize to a target nucleic acid and induce a desired effect. In the same context, "target human host cell factor," "target gene," "target nucleic acid," "target RNA," "target RNA transcript" and "nucleic acid target" all refer to a nucleic acid capable of being targeted by such a nucleic acid compound. In the same context, "target region" means a portion of a target to which one or more nucleic acid compounds is targeted. In the same context, "target segment" refers to a smaller portion or sub-portion of a region within a target. For example, a target segment can be the sequence of nucleotides of a target nucleic acid to which a nucleic acid compound is targeted.

As used herein, the terms "therapies" and "therapy" can refer to any protocol(s), method(s), compound(s), composition(s), formulation(s), inhibitor(s), and/or agent(s) that can be used in the prevention, treatment, management, or amelioration of a viral infection or a symptom associated therewith. In certain embodiments, the terms "therapies" and "therapy" refer to biological therapy, supportive therapy, and/or other therapies useful in treatment, management, prevention, or amelioration of a viral infection or a symptom or disease associated therewith known to one of skill in the art.

As used herein, the term "therapeutically effective amount" refers to the amount of a treatment or therapy that is sufficient to treat, prevent, and/or manage a viral infection or a disease or symptom associated therewith. In certain embodiments, a "therapeutically effective amount" is the amount of a compound that reduces the severity, the duration and/or the symptoms associated with a viral infection or a disease or symptom associated therewith in a subject. In certain embodiments, a "therapeutically effective amount" is the amount of a compound that results in a reduction in viral titer by at least 1.5 logs, at least 2 logs, at least 3 logs, at least 4 logs, or at least 5 logs in a subject administered a compound relative to the viral titer in a subject or group of subjects (e.g., two, three, five, ten or more subjects) not administered a compound. In certain embodiments, a "therapeutically effective amount" is the amount of a compound that results in a reduction in viral titer by 1.5 to 10 logs, 1.5 to 5 logs, 2 to 10 logs, 2 to 5 logs, or 2 to 4 logs in a subject administered a compound relative to the viral titer in a subject or group of subjects (e.g., two, three, five, ten or more subjects) not administered a compound.

As used herein, the terms "therapeutic agent" and "therapeutic agents" refer to any agent(s) (e.g., a compound) that can be used in the prevention, treatment and/or management of a viral infection or a symptom or disease associated therewith. In a specific embodiment, a therapeutic agent is an agent that is known to be useful for, or has been or is currently being used for the prevention, treatment, and/or management of a viral infection or a symptom or disease associated therewith.

As used herein, the terms "treat," "treatment," and "treating" refer, in the context of administration of a therapy to a subject to treat a viral infection, to a beneficial or therapeutic effect of a therapy or a combination of therapies. In some embodiments, the terms "treat," "treatment," and "treating" refer to administering a compound or composition described herein to effect an alteration or improvement of a disease, condition, or symptom associated therewith. In specific embodiments, such terms refer to one, two, three, four, five or more of the following effects resulting from the administration of a therapy or treatment or a combination thereof: (i) the reduction or amelioration of the severity of a viral infection and/or a symptom or disease associated therewith; (ii) the reduction in the duration of a viral infection and/or a symptom or disease associated therewith; (iii) the regression of a viral infection and/or a symptom or disease associated therewith; (iv) the reduction of the titer of a virus; (v) the reduction in organ failure associated with a viral infection or a disease associated therewith; (vi) the reduction in hospitalization of a subject; (vii) the reduction in hospitalization length; (viii) the increase in the survival of a subject; (ix) the elimination of a virus infection or a symptom or disease associated therewith; (x) the reduction or inhibition of the progression of a viral infection and/or a symptom or disease associated therewith; (xi) the reduction or prevention of the spread of a virus from a cell, tissue, organ or subject to another cell, tissue, organ or subject; (xii) the inhibition or reduction in the entry of a virus into a host cell; (xiii) the inhibition or reduction in the replication of the viral genome; (xiv) the inhibition or reduction in the synthesis of viral proteins; (xv) the inhibition or reduction in the release of viral particles from a host cell; and/or (xvi) the enhancement or improvement the therapeutic effect of another therapy or treatment. In some embodiments, the terms "treat," "treatment," and "treating" refer to the administration of a compound to one or more cells, tissues, organs, subjects, or other virus substrate.

4. DESCRIPTION OF THE FIGURES

FIG. 1. A Genome-wide RNAi Screen for Influenza Virus Host Cellular Factors. (a) A schematic of the recombinant WSN-Ren virus showing the HA segment modified to express *Renilla* luciferase but maintaining the HA packaging sequences. (b) An arrayed genome-wide RNAi library (100,000 siRNAs targeting over 19,000 human genes) was transfected into A549 cells. Cells were subsequently infected with WSN-Ren and virus replication was monitored by measuring luciferase activities at the indicated times.

Figure 2:
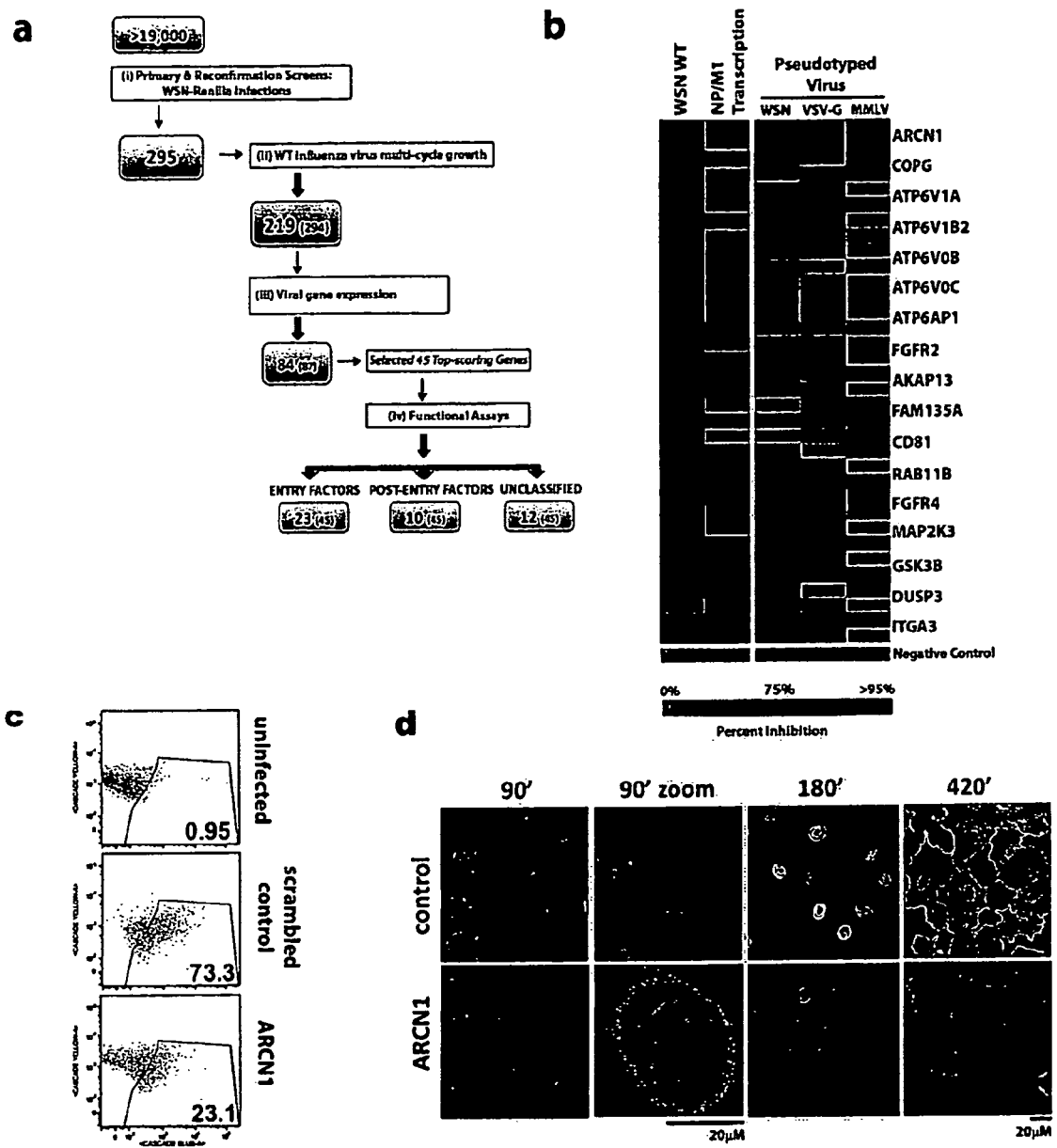

FIG. 2. Identification of Host Factors Involved in Influenza Virus Entry. (a) Illustration of the screen progression from primary genome-wide analysis to the identification of factors involved in entry and post-entry steps in the virus life cycle. The number of confirmed genes and number of genes tested at each stage (in parentheses) are indicated. (b) The relative effects of gene depletion (2 siRNAs/gene) on infection of luciferase-encoding HIV particles pseudotyped with WSN, VSV or MMLV envelopes (right panel). Effects of siRNA upon wild-type WSN virus replication and transcription of viral NP and M1 genes are also shown (left panel). (c) Infection of siRNA-transfected A549 cells with influenza virus virus-like particles (VLPs) carrying a beta-lactamase (Bla-M1) fusion protein. The percentages of cells containing detectable cytoplasmic beta-lactamase activity are indicated. (d) Cells depleted of ARCN1 and infected with wild-type WSN virus were fixed and stained for NP and nuclei at the indicated times and analyzed by confocal microscopy. The enlarged images at 90 min post-infection indicate the lack of incoming RNP complexes in the nucleus in cells depleted of ARCN1.

Figure 3:
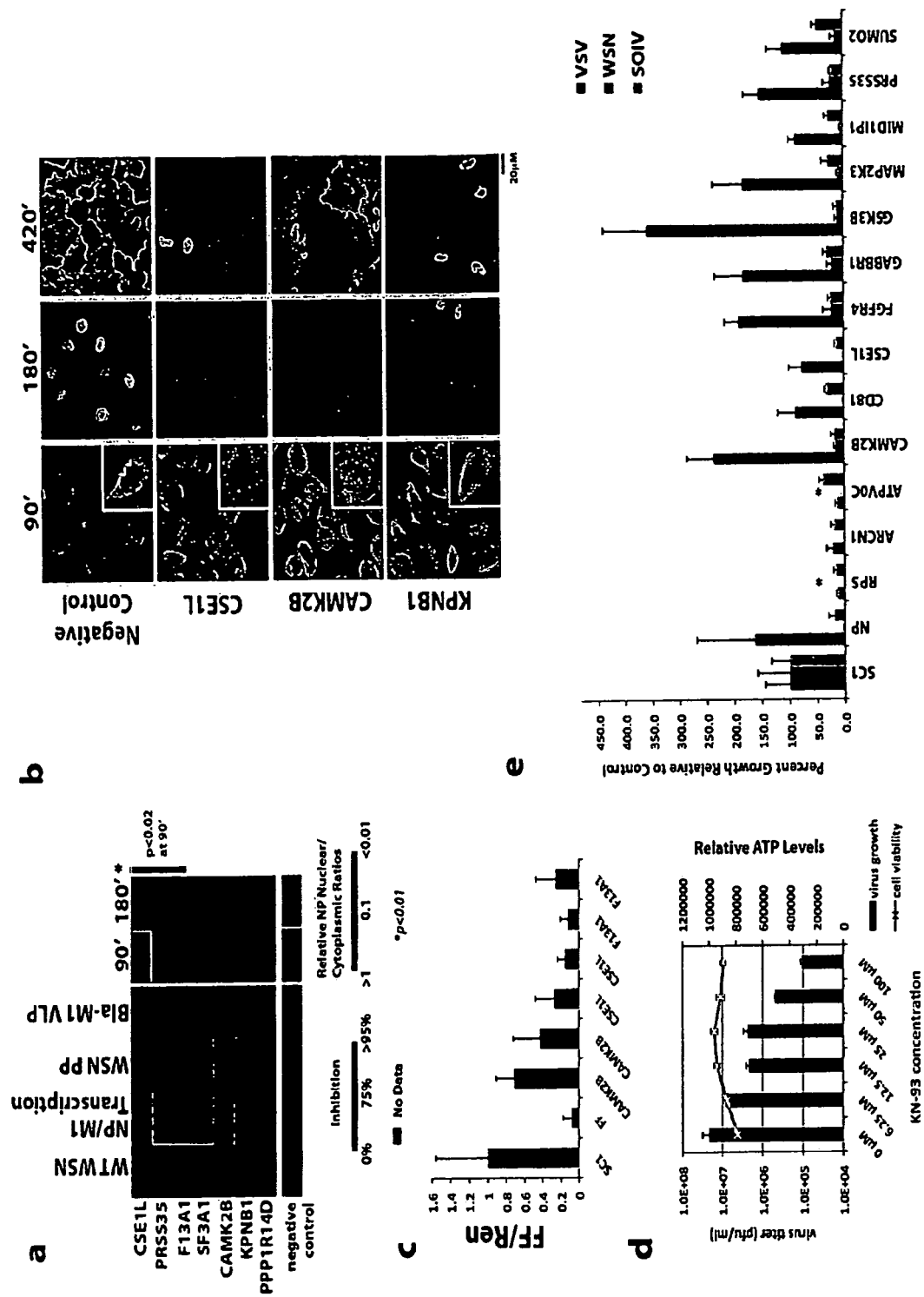

FIG. 3. Characterization of Factors in Post-Entry Replication Events and Conserved Requirement by Different Influenza Viruses. (a) The impact of host factor depletion on the nuclear localization of viral NP protein at 90 and 180 minutes after A/WSN/33 virus infection is shown (right panel). Significant effects ($p<0.01$ based on Welch T-test) are seen at 180 min with all genes and with CSE1L, PRSS35, F13A1 ($p<0.02$) at 90 min. Levels of virus replication (WT WSN), viral gene (NP/M1) transcription and entry of WSN pseudotyped particles or Bla-M1 VLPs in cells lacking these factors are shown in the left panel. Values relative to negative controls (bottom row) are depicted in a continuum. (b) Confocal imaging of influenza virus NP protein localization at the indicated times following A/WSN/33 virus infection in cells depleted of CSE1L, CAMK2B and KPNB1. Arrows in the 90' inset indicate nuclear RNPs. (c) The effects of host factor depletion on replication of an influenza virus mini-genome firefly reporter. The normalized fold reduction of firefly luciferase for each gene is shown relative to the scrambled siRNA control (SC1)+/−standard deviation. All reductions are significant ($p<0.05$) by Student's T-test. (FF=firefly luciferase siRNA). (d) KN-93, a selective inhibitor of CAMK2B, inhibits A/WSN/33 influenza viral replication in a dose-dependent manner in MDCK cells, without affecting cell viability (ATP levels). Mean titers+/−standard deviation of triplicate samples are shown. (e) A549 cells were transfected with siRNAs targeting the indicated genes and subsequently infected with influenza A/WSN/33 virus, swine-origin influenza A/Netherlands/602/2009 (H1N1) virus (SOIV) or VSV. Virus growth is shown as the average percent relative to the scrambled siRNA control (SC1)+/−standard deviation. *below level of detection ($1\times10^4$ pfu/ml). NP=siRNA for influenza A virus NP, RPS=siRNA for RPS27A.

Figure 4:
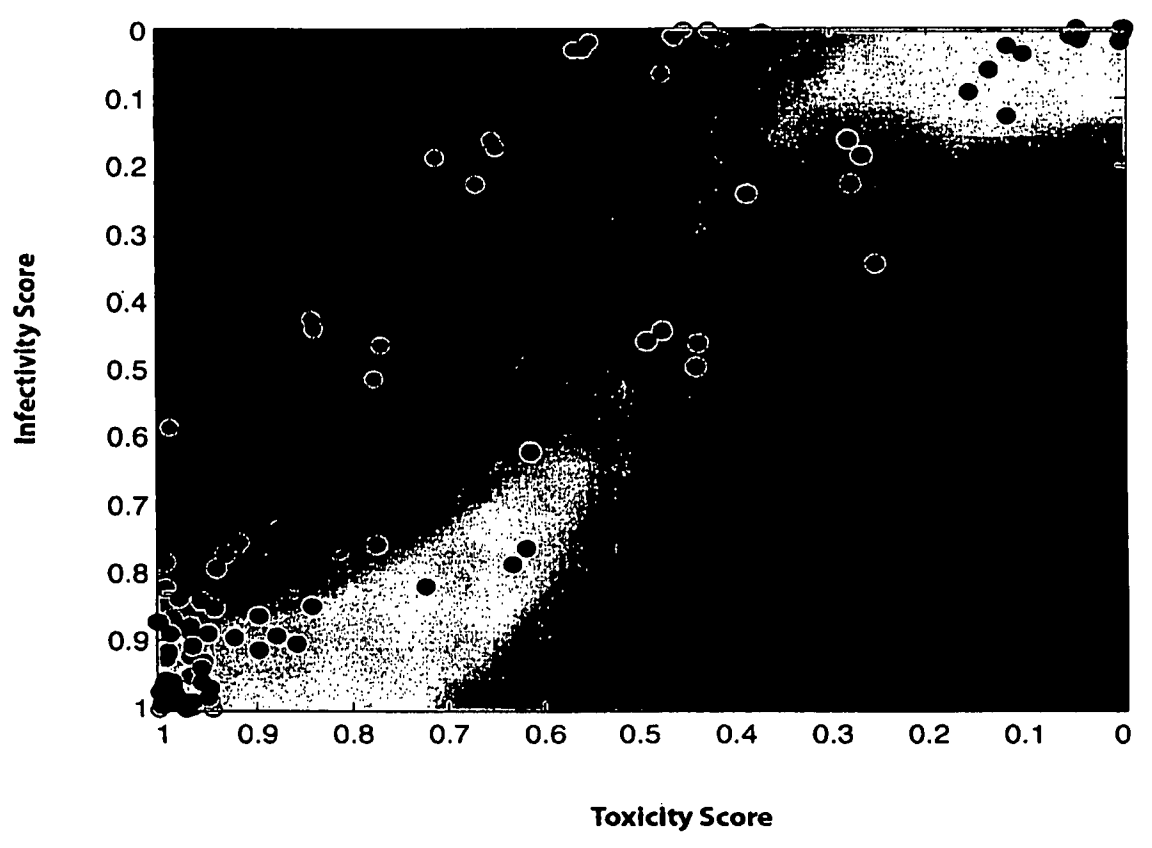

FIG. 4. Infectivity—toxicity relationship curve. To establish a threshold for discarding siRNAs that induce cellular toxicity, we investigated the impact of a dilution series (right to left on X-axis) of a toxic siRNA (siRPS27A-dark gray dots), an siRNA known to inhibit influenza virus Renilla luciferase reporter activity (siRNA targeting Renilla-light gray dots), and a negative control siRNA (black dots) on both influenza A virus replication and cellular toxicity assay. A score of zero represents low virus replication or reduced cell viability and a score of one represents maximum activity in corresponding assays. For example, the lowest dilution of positive control siRNA scores 1 in the infectivity score (bottom left), and the highest dilution scores 0 (top). The toxicity score for each of these are 1 and 0.4, respectively. Based on these relationships, a decision boundary was established (light gray curve; see Methods in Section 6 infra); if an siRNA fell below the boundary, it was considered to be toxic. Otherwise, it was considered a true hit ($p<0.05$). Three siRNAs were tested in ≥4 replicates. Toxic control (dark gray dots) fell below the decision boundary. Positive control (light gray dots) fell above the decision boundary. Negative non-toxic control (black dots) mostly fell below the decision boundary.

Figure 5:
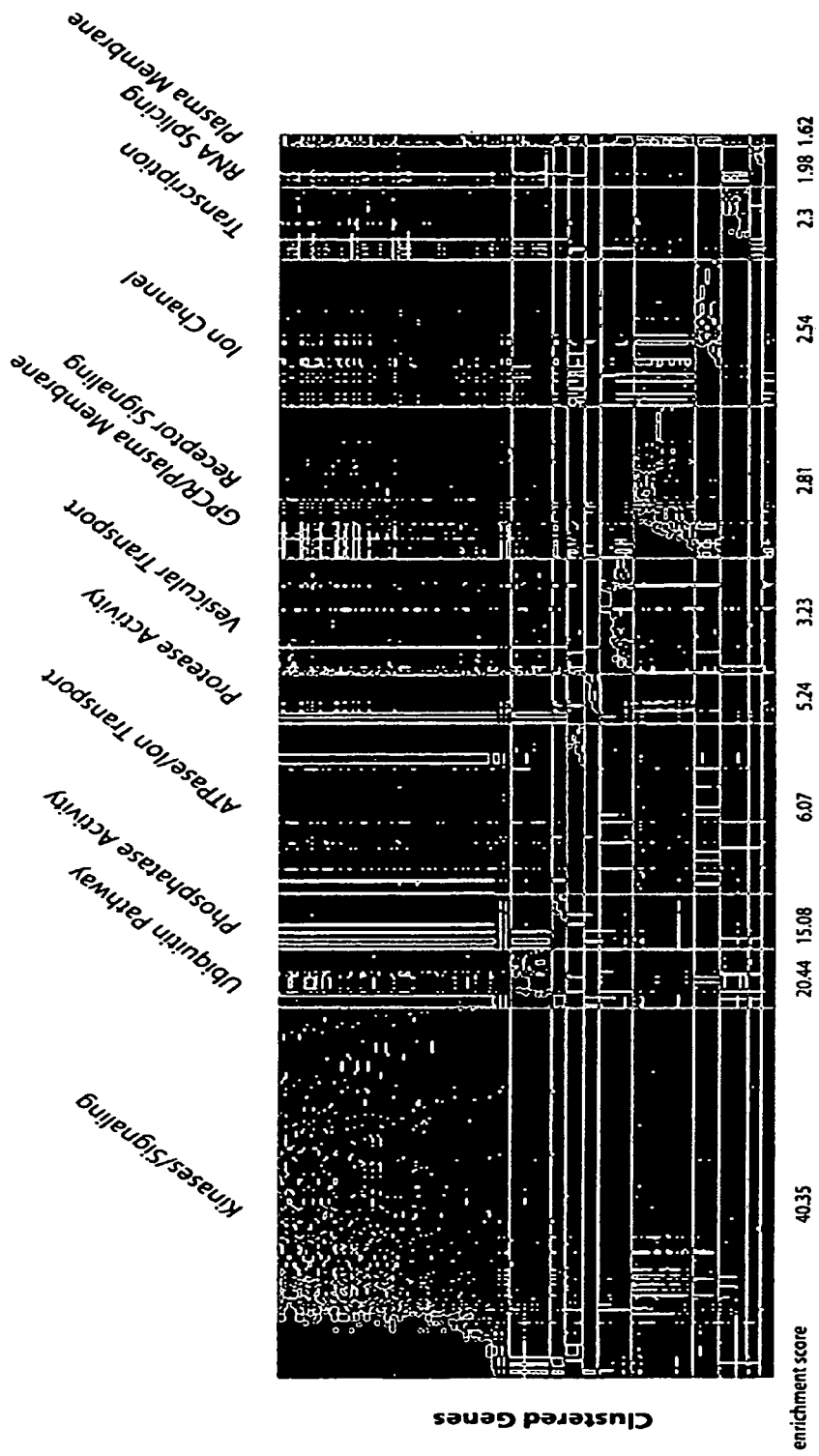

FIG. 5. Functional classification of influenza A virus-host cellular proteins. 177 of the 295 identified host proteins were classified into related functional groups revealing 11 highly overrepresented biological processes required for influenza virus replication. Host cellular genes are represented on the y-axis, and their inclusion in a primary functional category or secondary function category is indicated along the x-axis. Boundaries of gene clusters and biological processes are represented by gray lines. Enrichment scores for each functional class are also given. Functional classification and enrichment analysis was conducted using the Database for Annotation, Visualization and Integrated Discovery (DAVID) Bioinformatics Resource (Huang et al., 2009).

Figure 6:
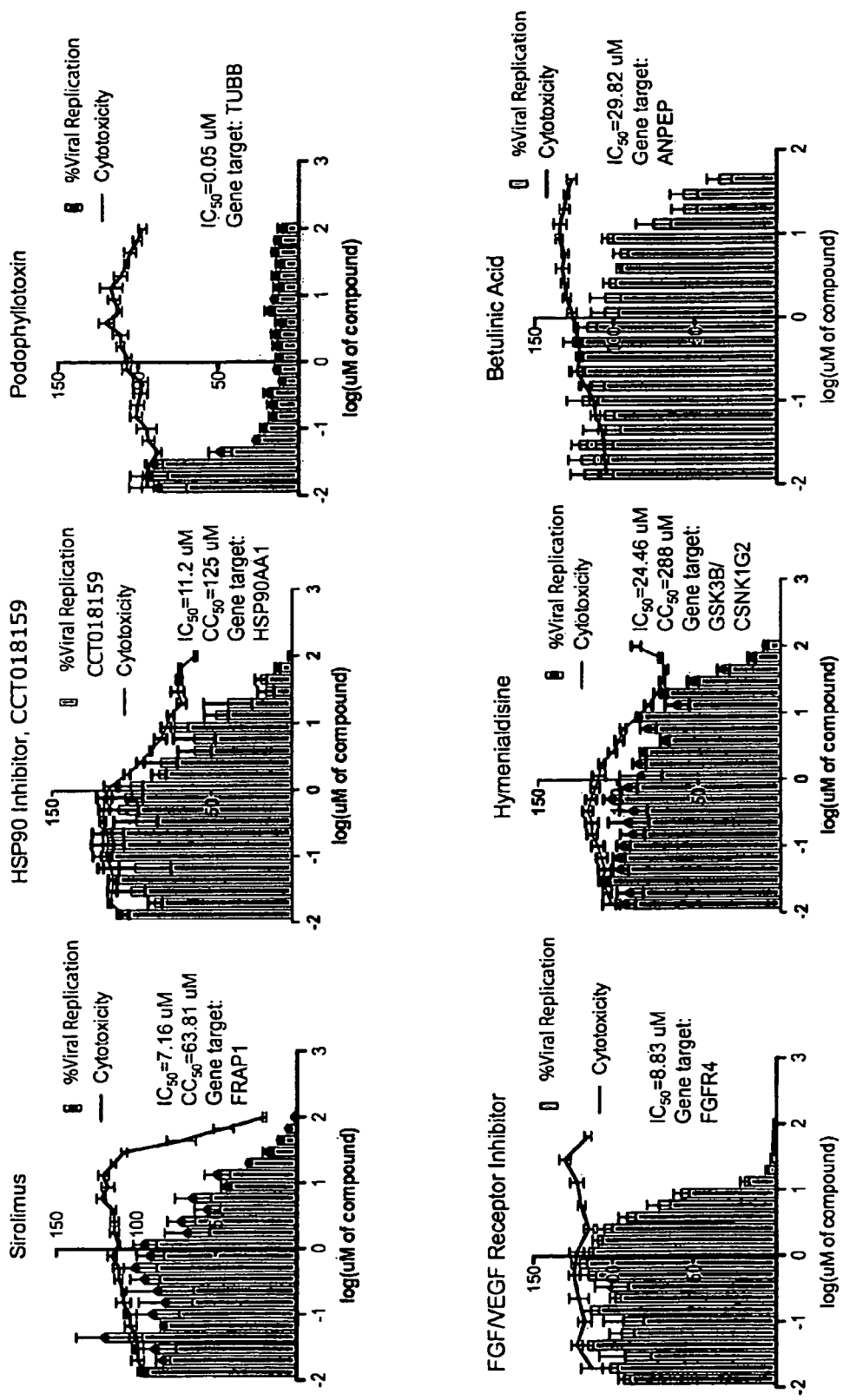

FIG. 6. Small molecule inhibitors targeting identified host factors reduce influenza virus growth. MDCK-HA cells were infected with WSN-Ren virus at an MOI of 0.03 in the presence of increasing concentrations of various inhibitors targeting specific host genes that were confirmed as host cellular factors for influenza virus entry. DMSO control was set to a 100%. Virus growth was assayed at 36 h post-infection and mean inhibition+/−standard deviation of triplicate samples are shown as grey bars. The concentrations for 50% inhibition ($IC_{50}$) and the respective target genes are indicated. Cell viability (toxicity) with increasing concentrations of each respective inhibitor was assessed in parallel experiments (black lines). Small molecules targeting host factors are as follows: Sirolimus (Rapamycin) and FRAP1 (mTOR; GeneID 2475) (Terada et al., 1992; Price et al., 1992; and Chung et al., 1992); HSP90 Inhibitor CCT018159 (4-(4-(2, 3-Dihydro-1,4-benzodioxin-6-yl)-5-methyl-1H-pyrazol-3-yl)-6-ethylresorcinol) and HSP90AA1 (GeneID 3320) (Hardcastle et al., 2005; Sharp et al., 2007; and Smith et al., 2006); Podophyllotoxin (Podophyllinic Acid Lactone) and TUBB (tubulin beta; Gene ID 203068 (Desbene at al., 2002); FGF/VEGF Receptor Inhibitor (4-Hydroxy-3-benzimidazol-2-ylhydroquinolin-2-one) and FGFR4 (GeneID 2264; possibly also FGFR2 (GeneID 2263), or VEGFB (GeneID 7423) (Renhowe et al., 2009); Hymenialdisine and GSK3b (GeneID 2932) (Supriyono at al., 1995; Meijer et al., 2000); and Betulinic Acid and ANPEP (aminopeptidase N; GeneID 290) (Melzig & Bormann, 1998).

Figure 7:
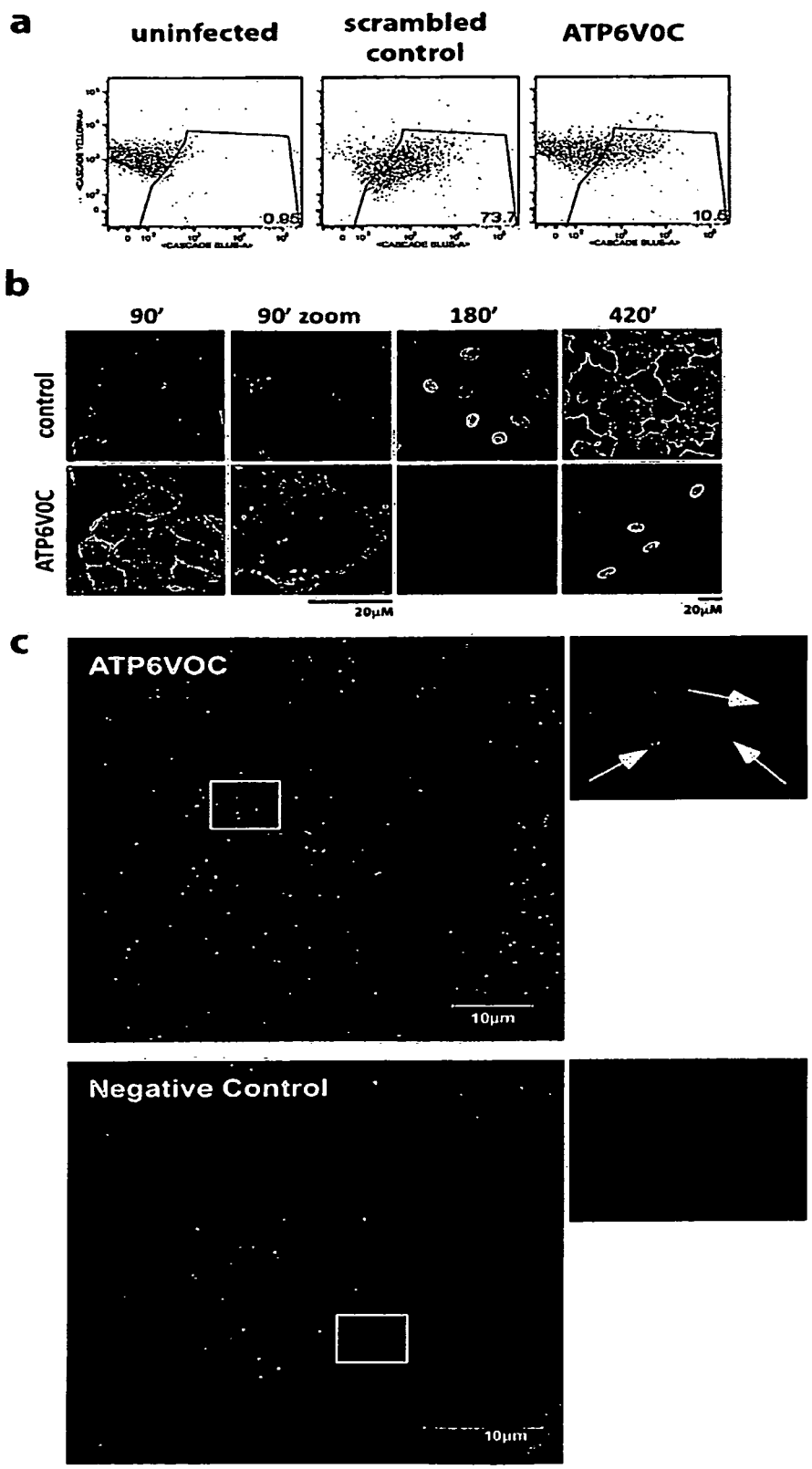

FIG. 7. The vATPase subunit, ATP6V0C, is a host gene involved in influenza virus entry. (a) Influenza virus VLPs carrying a Bla-M1 fusion protein were used to infect A549 cells pretransfected with the cognate siRNAs. The percentage of cells containing detectable cytoplasmic beta-lactamase activity is indicated. In cells transfected with a scrambled control siRNA, approximately 74% were infected by the VLPs as measured by cytoplasmic beta-lactamase activity (second panel). However, depletion of ATP6V0C resulted in reduced VLP entry (10.5%). (b) Viral replication kinetics in control and ATP6V0C-depleted cells was monitored by tracking the localization of influenza virus NP protein. Cells were stained for NP and nuclei and analyzed by confocal microscopy. At 90 minutes post infection an inhibition of incoming RNP accumulation in the nucleus was observed and a delay in the appearance of newly synthesized NP both in the nucleus (180 min) and cytoplasm (420 min) was seen. (c) Further confocal immunofluorescence analysis of HA and Early Endosome Antigen 1 (EEA1) proteins in ATP6V0C siRNA-transfected cells (top panel) or negative control siRNA-transfected cells (bottom panel), 20 minutes after infection with WSN virus. The compressed z-stack images shown at 100× magnification are representative of at least 20 cells. Scale bar represents 10 um. There is an increased number of HA-containing particles observed in the vATPase-deficient cells relative to the controls (n=199 versus n=90 in these examples). Approximately 19% ($38/199$) of the virions in the ATP6V0C siRNA-treated cells were judged to be co-localized with EEA1 (white arrows, insets).

Figure 8:
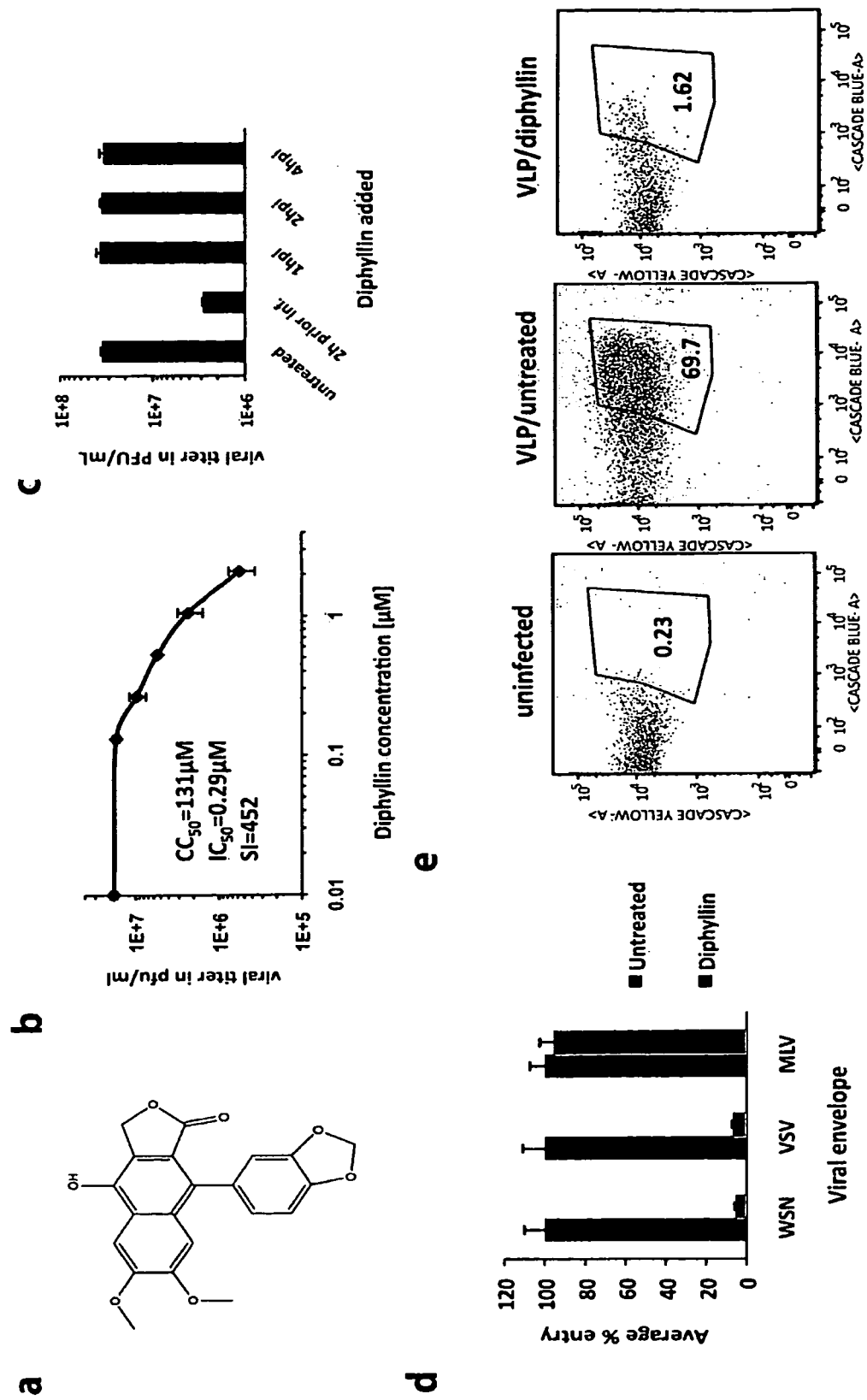

FIG. 8. Diphyllin, a small molecule targeting vATPases (Sorensen et al., 2007), inhibits influenza virus entry. (a) Chemical structure of diphyllin. (b) Dose-dependent inhibition of influenza A/WSN/33 virus (MOI=1) by diphyllin in A549 cells. The concentrations for 50% cytotoxicity ($CC_{50}$), 50% inhibition ($IC_{50}$) and the selective index (SI) are indicated. (c) Kinetic analysis of diphyllin-mediated inhibition of influenza virus in A549 cells. Compound was added to the cells at the indicated times pre- and post-infection (MOI=1). Viral titers were determined at 24 h. (d) Entry of the luciferase-expressing lentivirus particles pseudotyped with influenza virus (WSN), VSV or MMLV envelope in the absence or presence of diphyllin. (e) Entry of influenza virus VLPs carrying Bla-M1 in the presence of diphyllin. The percent entry is indicated.

Figure 9:
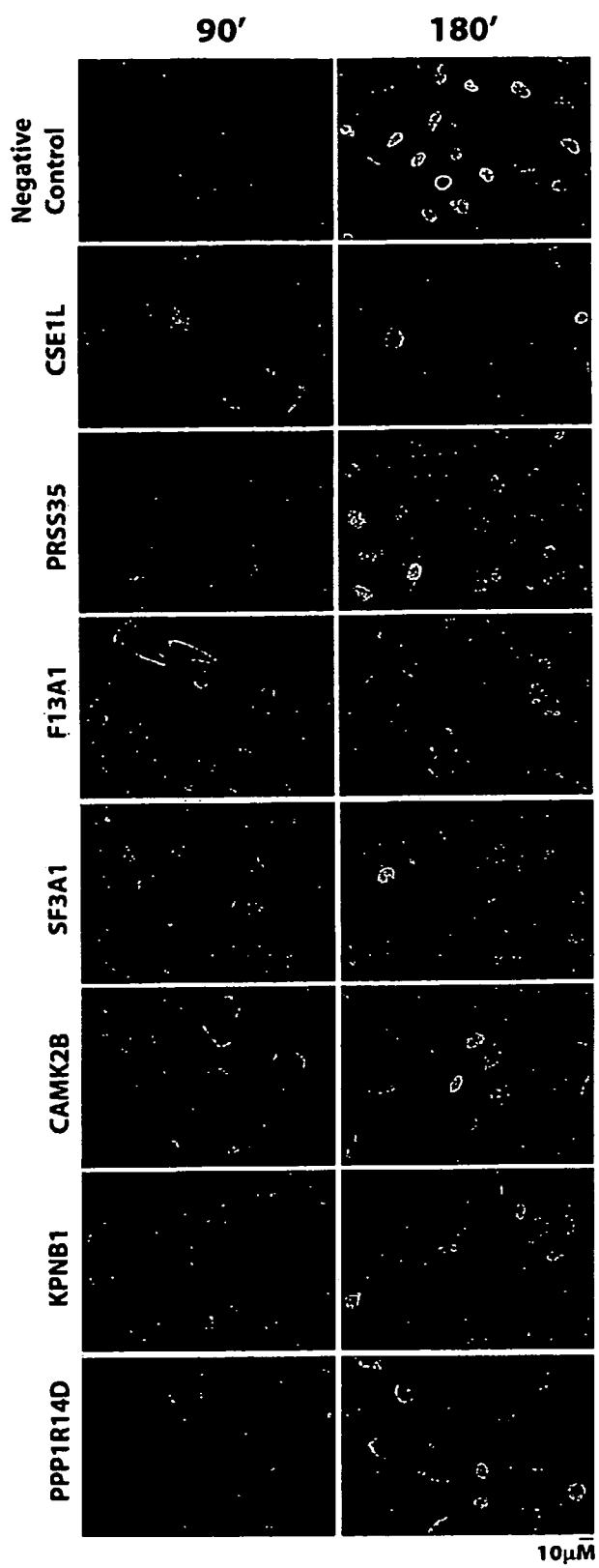

FIG. 9. High content imaging of viral infection in host-factor depleted cells. The high-content imaging-based analysis was performed using the Opera (Perkin-Elmer, Waltham, Mass.), a fully automated microscope system. 384-well plates containing A549 cells were transfected with siRNAs targeting the indicating genes. 48 h post infection cells were infected with A/WSN/33 virus and fixed at the indicated time points. After immunofluorescence labeling (see Section 6, infra, Methods), cells were imaged using a 40×0.9NA water immersion lens (Olympus), and representative images were selected. A total of 10-11 images for both the nuclear stain (Hoechst) and the Alexa488 labeled WSN-NP were taken in each well.

Figure 10:
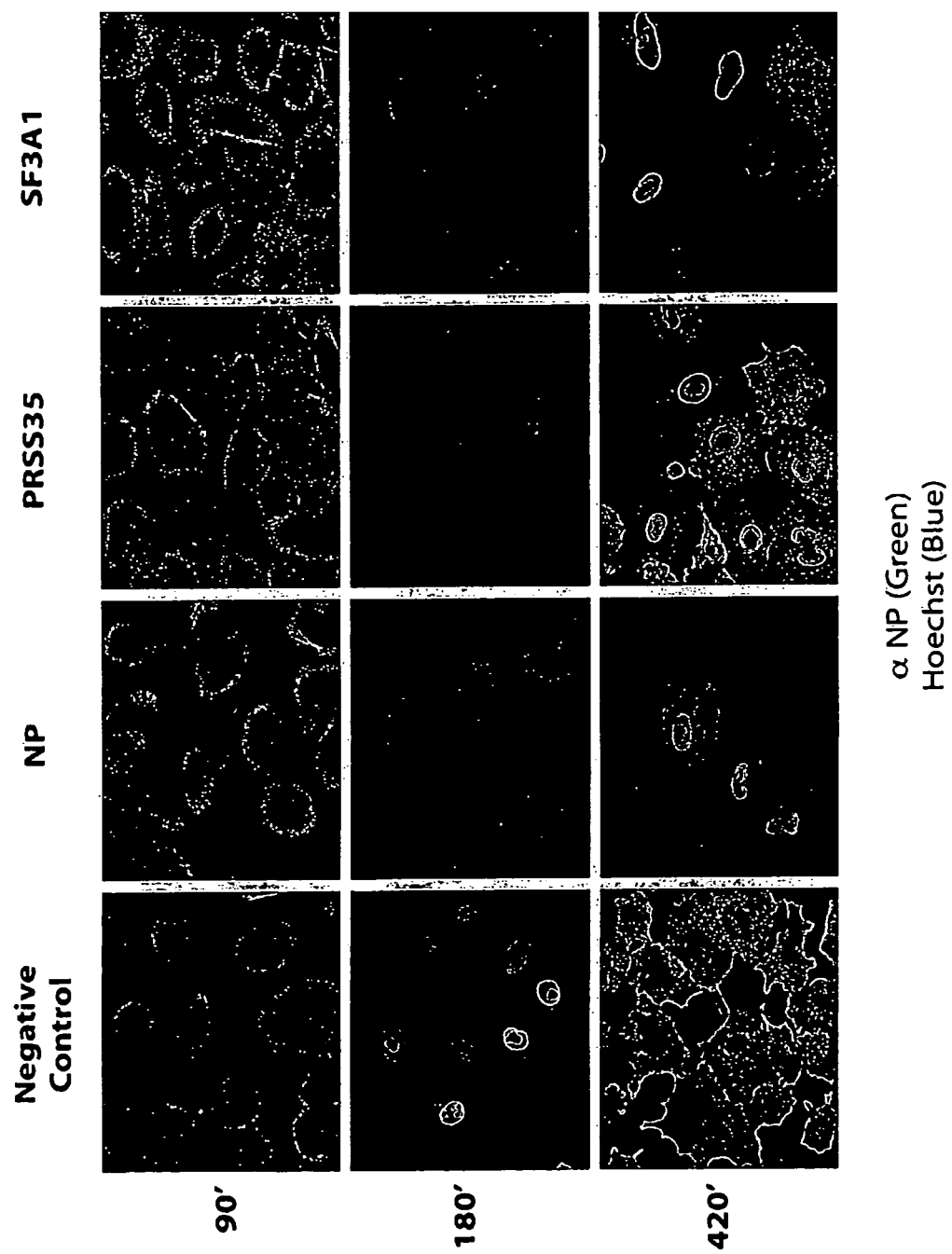

FIG. 10. Confocal imaging of influenza virus infected cells after host factor depletion. Additional confocal imaging at higher resolution was conducted to better visualize nuclear import of incoming vRNPs at 90' post infection. A549 cells pre-transfected for 48 h with the indicated siRNAs were infected with influenza A/WSN/33 virus (MOI=10) and stained for NP and nuclei at 90 min, 3 h and 7 h post infection.

Figure 11:
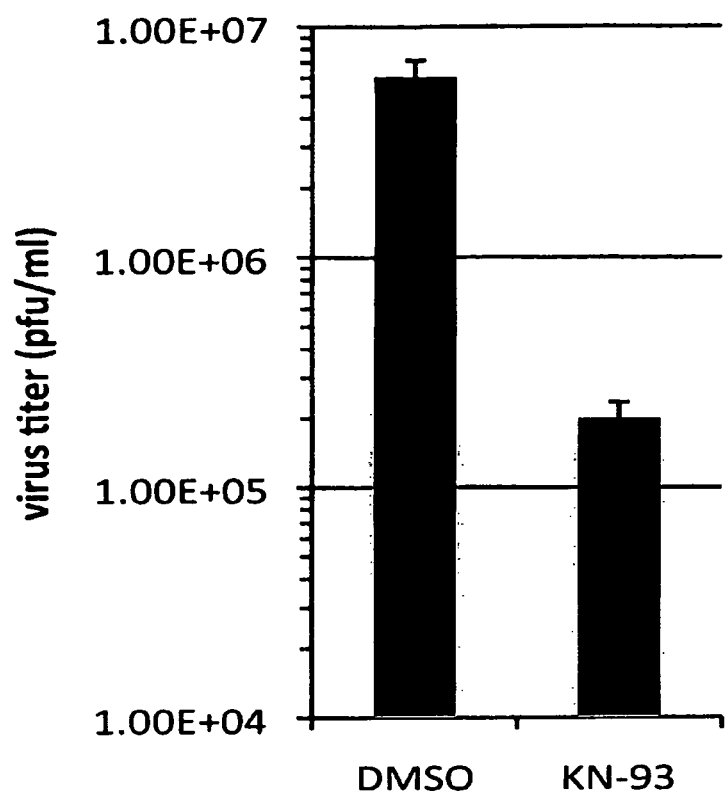

FIG. 11. CAMK2B inhibition in A549 cells impairs influenza virus growth. A549 cells were infected with influenza A/WSN/33 virus in the presence of DMSO or 20 µM KN-93. Viral growth was determined by plaque assay at 24 h post infection. The mean viral titer+/−standard deviation of triplicate samples is shown. These data are consistent with the inhibition of influenza virus replication by KN-93 in MDCK cells (FIGS. 3d and 3e).

Figure 12:
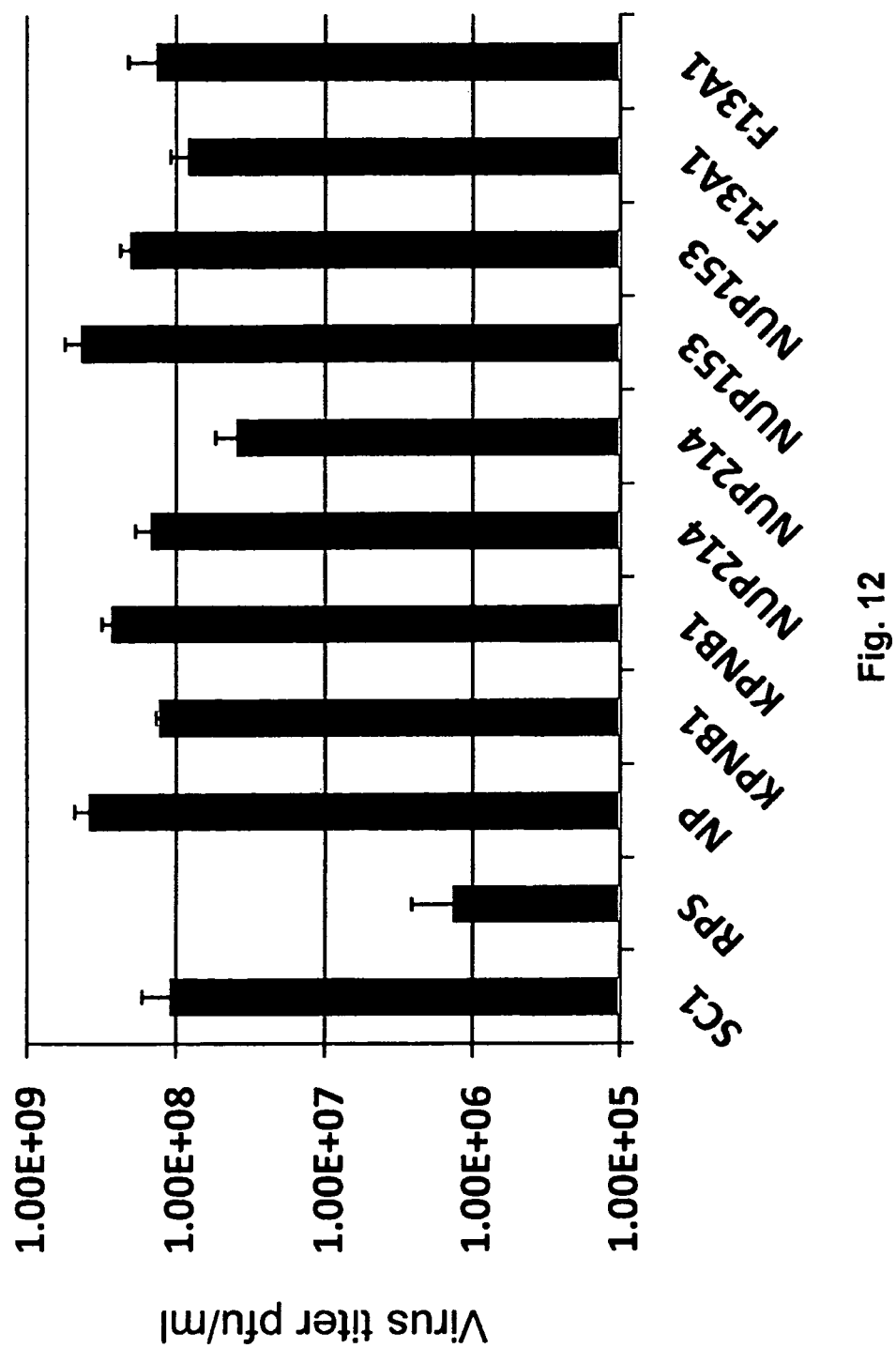

FIG. 12. Additional effects of influenza virus host factors on VSV replication. siRNA-transfected A549 cells were infected with VSV at a multiplicity of infection (MOI) of 0.01 at 48 h post siRNA transfection. At 36 h post infection supernatants were harvested and virus titers were determined by plaque assay on Vero cells. The mean viral titer+/−standard deviation of triplicate samples is shown.

5. DETAILED DESCRIPTION

The present application is based, in part, on the discovery that influenza virus replication can be modulated by pharmacologically targeting human host cell factors required for viral replication. Targeting host cell factors, rather than the viral factors required for influenza virus replication, may greatly reduce the emergence of viral resistance and expands the number of targets for antiviral intervention. Without being limited by theory, the embodiments provided herein are based in part on the discovery that compounds (including, e.g., nucleic acid compounds, such as siRNAs, and small molecules) that reduce or inhibit the expression or activity of specific classes of human host cell proteins reduce influenza virus replication and thus are useful as antiviral agents.

Provided herein are compounds, including but not limited to nucleic acid compounds (e.g., siRNAs) and small molecules, that target human host cell factors involved in influenza virus replication, compositions, including pharmaceutical compositions, comprising such compounds, and methods of using such compounds and compositions for modulating influenza virus replication. Provided herein are compounds, including but not limited to nucleic acid compounds (e.g., siRNAs) and small molecules, that target human host cell factors involved in influenza virus replication, compositions, including pharmaceutical compositions, comprising such compounds, and methods of using such compounds and compositions for reducing or inhibiting influenza virus replication, or for treating or preventing influenza virus infection, or a symptom associated therewith, in a subject in need thereof.

5.1 Compounds that Target Human Host Cells Factors Involved in Influenza Virus Replication Provided herein are compounds, including but not limited to nucleic acid compounds (e.g., siRNAs) and small molecules, that target human host cell factors involved in influenza virus replication. In some embodiments, the compound modulates influenza virus replication by altering the expression (e.g., mRNA or protein) and/or activity of the human host cell factor involved in influenza virus replication. In some embodiments, the compound reduces or inhibits influenza virus replication by reducing or inhibiting the expression (e.g., mRNA or protein) and/or activity of the human host cell factor involved in influenza virus replication. In some embodiments, the human host cell factor is required for influenza virus replication. In some embodiments, the human host cell factor interacts with a component of the influenza virus. In some embodiments, the interaction of the host cell factor with the component of the influenza virus is direct. In some embodiments, the host cell factor is not involved in the non-specific induction of an antiviral state, e.g., the cellular interferon system, recognition of double-stranded RNA, etc. In some embodiments, the human host cell factor does not interact with a component of the influenza virus. In some embodiments, the host cell factor is required for influenza virus replication in human cells but not in insect cells.

The compounds provided herein target human host cell factors involved in influenza virus replication and modulate influenza virus replication. In some embodiments, the compounds provided herein target human host cell factors involved in influenza virus replication and reduce or inhibit influenza virus replication. The targeted human host cell factor may be required for influenza virus replication. The targeted human host cell factor may be involved in or required for one or more of the following events of the influenza virus life cycle: entry; uncoating; nuclear import; viral RNA transcription; or viral RNA translation. In some embodiments, the human host cell factor is not involved in influenza virus entry. In some embodiments, the human host cell factor is not involved in the nuclear import stage. In some embodiments, the human host cell factor is not involved in influenza virus assembly, budding, or release from host cells. In some embodiments, the human host cell factor is required for replication of viruses whose entry into cells is low-pH-dependent. For example, the human host cell factor may be required for entry of such viruses into cells.

The effect of a compound on the different steps of the viral life cycle may be assayed using techniques known to one of skill in the art. RNA replication and transcription may be measured by measuring the replication and transcription of reporter gene product from an influenza virus mini-genome reporter construct, using, e.g., the assays disclosed herein. Such assays permit the identification of inhibitors of the viral polymerase or inhibitors of cellular proteins that are involved in viral RNA replication, translation or RNA trafficking. In some embodiments, the compound does not have an inhibitory effect on the overall host cell replication machinery, or has only a slight inhibitory effect compared to the effect on viral replication, as monitored by assays such as, e.g., the expression of a *Renilla* luciferase reporter from a control plasmid (e.g., Section 6 below).

In other embodiments, the inhibitors alter the kinetics of the viral cycle, e.g., the rate of viral replication or particle production is decreased. In some embodiments, the kinetic effect of a compound is measured by adding the compound to a cell at different times (e.g., before, concurrently with, or after) infection with a virus.

The targeted human host cell factor may be involved in or required for replication of more than one strain or sub-type of influenza. For example, the human host cell factor may be involved in or required for replication of an influenza A virus, an influenza B virus, and/or an influenza C virus. In some embodiments, the human host cell factor is involved in or required for replication of a human-origin, an avian-origin (e.g., H5N1), and/or a swine-origin (e.g., H1N1) influenza virus. In some embodiments, the human host cell factor is also required for replication of one or more other viruses, e.g., but not limited to, vesicular stomatitis virus (VSV). In some embodiments, the human host cell factor is not required for replication (including, e.g., entry) of viruses whose entry into cells is pH-independent, such as, e.g., murine leukemia virus (MMLV). In some embodiments, the human host cell factor is not required for replication (e.g., entry, genome replication, etc.) of one or more of human immunodeficiency virus (HIV), Dengue virus, hepatitis C virus (HCV), West Nile virus (WNV), or VSV. In some embodiments, the human host cell factor is uniquely required for influenza virus replication.

In some embodiments, a compound provided herein targets a component or regulator of, or factor that interacts with, one or more of the following categories of human host cell factors: cytoskeleton; ribonucleoprotein; spliceosome; ubiquitin/proteasome system; ribosome or other translation machinery; kinase; phosphatase; signaling (e.g., G-protein coupled receptors; signaling at the plasma membrane); mitochondrion or mitochondrial ribosome; plasminogen; stress response; v-ATPase; ion channel or other ion transport; nucleus; sumoylation; nuclear transport; nucleotide binding; cell cycle; vesicular transport (e.g., COPI vesicle); chromosome; or carboxylic acid metabolism. In some embodiments, a compound provided herein, and for use in the compositions and methods provided herein, targets a component or regulator of, or a factor that interacts with, one or more of the following categories of human host cell factors: IP3-PKC pathway; COPI vesicles; endosomal uptake, maturation, acidification, and fusion; actin organization and function; PI3K-AKT pathway; endosomal recycling pathway; MAPK pathway; proteases; calcium/calmodulin system; nuclear trafficking; trafficking; sumoylation; microtubule organization (including assembly) and function; autophagy; or ubiquitination. Exemplary, non-limiting, components or regulators of, or factors that interact with, these categories of human host cell factors that may be targeted in accordance with these embodiments are provided in Table 5 infra (see, e.g., the column labeled "Gene names"). In particular embodiments, the compound reduces or inhibits the expression and/or activity of a human host cell factor in one of the aforementioned categories.

In some embodiments, the compound modulates the expression and/or activity of one or more of the human host cell factors listed in Table 3. In specific embodiments, the compound reduces or inhibits the expression and/or activity of one or more of the human host cell factors listed in Table 3.

In some embodiments, the compound modulates the expression and/or activity of one or more of the human host cell factors listed in Table 7. In specific embodiments, the compound reduces or inhibits the expression and/or activity of one or more of the human host cell factors listed in Table 7.

In some embodiments, the compound modulates the expression and/or activity of one or more of the human host cell factors listed in Table 9. In specific embodiments, the compound reduces or inhibits the expression and/or activity of one or more of the human host cell factors listed in Table 9.

In some embodiments, the compound modulates the expression (e.g., mRNA or protein) and/or activity of one or more of the following human host cell factors: ACRC; AKAP13; AKT1; ANAPC2; ANPEP; ARCN1; BRWD3; CAD; CAMK2B; CANT1; CBLL1; CD81; CHAF1A; CLK1; CLOCK; COPA; COPB1; COPB2; COPG; CSE1L; CTSW; DTX2; DUSP3; EPHB2; EPS8L3; F13A1; FAM135A; FGFR2; FGFR4; FPR1, FRAP1 (mTOR); GABBR1; GRK6; GSK3B; HAND2; HIST3H3; HSP90AA1; IL1F9; ITGA3; JAK2; KCNJ11; KPNB1; MAP2K3; MAP3K11; MAP3K12; MC1R; MID1IP1; NEK6; NUP153; NUP214; OSBPL6; PHF2; PLK4; PPP1R12C; PPP1R14D; PRPH2; PRSS35; PSMD1; RAB11B; RBM5; RP11-45B20.2; RPS10; RPS20; SF3A1; SNRPA1; STK31; STK39; STX10; SUMO2; SUMO4; TBK1; TEAD3; TNPO3; TRPV2; TUBB; UBXD3; USE1; VEGFB (GeneID 7423); WDR18; WDR34; or one or more v-ATPase subunits, e.g., ATP6V0B, ATP6V0C, ATP6V1A, ATP6V1B2, or ATP6AP1 (gene ID numbers for representative human host cell factors are provided in Tables 3 and 9). In specific embodiments, the compound reduces or inhibits the expression and/or activity of one or more of the aforementioned human host cell factors.

In certain embodiments, the compound modulates the expression (e.g., mRNA or protein) and/or activity of one or more of the following human host cell factors: AKAP13; ARCN; BRWD3; CD81; COPG; CTSW; DUSP3; EPHB2; FAM135A; FGFR2; FGFR4; GABBR1; GSK3B; ITGA3; JAK2; MAP2K3; NEK6; RAB11B; or one or more of the v-ATPase subunits, ATP6V0B, ATP6V0C, ATP6V1A, ATP6V1B2, or ATP6AP1. In certain embodiments, the compound modulates the expression (e.g., mRNA or protein) and/or activity of one or more of the following human host cell factors: CAMK2B; CSE1L; F13A1; KPNB1; MAP3K12; PP1R14D; PRSS35; RPS10; SF3A1; or SUMO4. In certain embodiments, the compound modulates the expression (e.g., mRNA or protein) and/or activity of one or more of the following human host cell factors: ACRC; DTX2; EPS8L3; FPR1; MAP3K11; NUP214; PRPH2; RP11-45B20.2; STX10; SUMO2; TRPV2; or TUBB. In certain embodiments, the compound modulates the expression (e.g., mRNA or protein) and/or activity of one or more of the following human host cell factors: ANPEP; CAM2 KB; FGFR4; FRAP1 (mTOR); GSK3B/CSNK1G2; HSP90AA1; or TUBB. In specific embodiments, the compound reduces or inhibits the expression and/or activity of one or more of the aforementioned human host cell factors.

The compound may be any compound described herein, known in the art, or yet to be discovered that targets one or more of the aforementioned categories of human host cell factors, a specific factor(s) in such a category, and/or one of the aforementioned human host cell factors. In certain embodiments, the compound is not toxic to the human host cell.

In certain embodiments, the compound does not target AKT1, ARCN1, COPG, GRK6, HAND2, HIST3H3, an HSP90 (e.g., HSP90AA1), NUP153, RBM5, RPS10, RPS20, or a v-ATPase subunit. In certain embodiments, the compound does not reduce or inhibit the expression and/or activity of AKT1, ARCN1, COPG, GRK6, HAND2, HIST3H3, an HSP90 (e.g., HSP90AA1), NUP153, RBM5, RPS10, RPS20, or a v-ATPase subunit. In certain embodiments, the compound does not target AKAP13, CD81, CAMK2B, CSE1L, DUSP3, FGFR2, FGFR4, GSK3B, ITGA3, KPNB1, MAP2K3, or RAB11B. In certain embodiments, the compound does not reduce or inhibit the expression and/or activity of AKAP13, CD81, CAMK2B, CSE1L, DUSP3, FGFR2, FGFR4, GSK3B, ITGA3, KPNB1, MAP2K3, or RAB11B.

In some embodiments, the compound is an agent that reduces or inhibits the expression (e.g., mRNA or protein) and/or activity of a human host cell factor involved in influenza virus replication. In some embodiments, the compound is an agent that reduces or inhibits the expression (e.g., mRNA or protein) and/or activity of a human host cell factor required for influenza virus replication. In some embodiments, the compound reduces or inhibits the interaction of a human host cell factor with a component of the influenza virus. In some embodiments, the compound does not trigger a non-influenza-specific antiviral state. For example, in some embodiments, an siRNA compound does not induce a non-specific antiviral state, for example, it does not induce an interferon response. In some embodiments, the compound reduces or inhibits the interaction of a human host cell factor with a component of the influenza virus. In some embodiments, the compound reduces or inhibits a direct interaction of a human host cell factor with a component of the influenza virus. In some embodiments, the compound reduces or inhibits influenza virus replication in human cells but not in insect cells. In some embodiments, the compound reduces or inhibits one or more of the following events of the influenza viral life cycle: entry; uncoating; nuclear import; viral RNA transcription; or viral RNA translation. In some embodiments, the compound does not reduce influenza virus entry. In some embodiments, the compound does not reduce the nuclear import stage. In some embodiments, the compound does not reduce or inhibit influenza virus assembly, budding, or release from host cells. In some embodiments, the compound reduces or inhibits replication of viruses whose entry into cells is low-pH-dependent. For example, the compound may reduce or inhibit entry of such viruses into cells.

In some embodiments, the compound reduces or inhibits replication of more than one strain or sub-type of influenza. For example, the compound may reduce or inhibit replication of influenza virus A, an influenza B virus, and/or an influenza C virus. In some embodiments, the compound reduces or inhibits replication of a human-origin, an avian-origin (e.g., H5N1), and/or a swine-origin (e.g., H1N1) influenza virus. In some embodiments, the compound reduces or inhibits replication of another virus in addition to influenza virus such as, e.g., vesicular stomatitis virus (VSV). In some embodiments, the compound does not reduce or inhibit replication (including, e.g., entry) of viruses whose entry into cells is pH-independent, such as, e.g., MMLV. In some embodiments, the compound does not reduce or inhibit replication (e.g., entry, genome replication, etc.) of one or more of HIV, Dengue virus, HCV, WNV, or VSV. In some embodiments, the compound reduces or inhibits influenza virus replication and not the replication of other viruses.

The compounds provided herein include compounds of any structure described herein or incorporated by reference herein, and solvates, hydrates, prodrugs, stereoisomers and pharmaceutically acceptable salts thereof. Such compounds include, but are not limited to, nucleic acid molecules including, but not limited to, double-stranded or single-stranded DNA, or double-stranded or single-stranded RNA, antisense RNA, RNA interference (RNAi) molecules (e.g., small interfering RNA (siRNA), micro-RNA (miRNA), short hairpin RNA (shRNA), etc.), intron sequences, triple helix nucleic acid molecules and aptamers; carbohydrates; proteinaceous molecules, including, but not limited to, peptides (including dimers and multimers of such peptides), polypeptides, proteins, including post-translationally modified proteins, conjugates, antibodies or antibody fragments (including intrabodies), etc.; small molecules, including inorganic or organic compounds; and lipids. In one embodiment, a compound is purified. In one embodiment, a compound is isolated.

5.1.1 Nucleic Acid Compounds

In some embodiments, the compound is a nucleic acid compound. The nucleic acid compound may be any nucleic acid compound known in the art or described herein that is able to modulate the expression and/or activity of a human host cell factor described herein may. In some embodiments, the nucleic acid compound is an antisense compound. In some embodiments, the nucleic acid compound is an siRNA. In some embodiments, the nucleic acid compound has a sequence optimized for use as an siRNA, according to methods known in the art. In certain embodiments, the nucleic acid compound is a modified oligonucleotide. In some embodiments, the nucleic acid compound comprises an oligonucleotide of 12 to 30 linked nucleosides, for example, 12 to 15, 15 to 20, 20 to 25, or 25 to 30 linked nucleosides, which may be targeted to a nucleic acid encoding a human host cell factor involved in influenza virus replication. In some embodiments, the antisense or siRNA compound reduces or inhibits the expression and/or activity of an aforementioned human host cell factor, or a factor in one of the aforementioned categories.

In some embodiments, the compound targets a nucleotide sequence selected from Table 1 (see also Table 9). In certain embodiments, e.g., when targeting of a deoxyribonucleic acid (DNA) sequence is desired, the nucleobases represented by a "U" (uracil) in a sequence in Table 1 may be replaced with thymine nucleobases (represented by a "T"). In certain embodiments, e.g., when targeting a ribonucleic acid (RNA) sequence is desired, the nucleobases represented by a "T" (thymine) in a sequence in Table 1 may be replaced with uracil nucleobases (represented by a "U"). For example, the nucleotide sequence "AAGTAGGGATAAATTACTCTA" (SEQ ID NO: 90) in Table 1 may be replaced with the nucleotide sequence "AAGUAGGGAUAAAUUACUCUA" (SEQ ID NO: 724)

In certain embodiments, the nucleic acid compound targeting a sequence in Table 1 is an antisense compound. In some embodiments, the nucleic acid compound targeting a sequence in Table 1 is an siRNA. In certain embodiments, the siRNA that targets one of the aforementioned human host cell factors or sequences is obtained from a commercially available source. For example, the siRNA can be from Qiagen (Druggable Set version 1 or 2), NM Set version 1, XM Set version 1, the kinome library from Invitrogen or the kinome library from IDT.

In certain embodiments, an siRNA duplex is created from a 21mer sequence in Table 1 as exemplified in the following example:

The sequence 5'-GAGCTTGAATTTGAAGGTGTA-3' (SEQ ID NO: 3) is modified to convert it into a ribonucleic acid (RNA) and to introduce overhangs (shown in lowercase letters) as follows:

```
5'---GCUUGAAUUUGAAGGUGUAtt-3'    (SEQ ID NO: 725)
3'-ctCGAACUUAAACUUCCACAU---5'    (SEQ ID NO: 726)
```

The first two are the antisense overhang, the sense overhang is always TT. siRNA duplexes based on the sequences in Table 1 that contain Us are created the same way, except that the sequence is already and RNA; i.e., the sequence in Table 1 containing Us correspond to host cell mRNA targets.

In some embodiments, the siRNA compound comprises the sequence /5Phos/rGrGrCrUrArCrGrGrArCrCrArAr-GrUrUrArUrCrCrGrGCG (SEQ ID NO: 177). This sequence is the sense sequence for a 25mer siRNA duplex for use in accordance with the embodiments described herein.

See Sections 5.1.1 and 5.1.2 below for more details on generating, formulating, and using antisense compounds and siRNA.

5.1.1.1 Antisense Compounds

Antisense compounds for use in the embodiments described herein include, but are not limited to, oligomeric compounds, oligonucleotides, oligonucleosides, oligonucleotide analogs, oligonucleotide mimetics, and antisense oligonucleotides. Antisense compounds may target a nucleic acid, meaning that the antisense compound is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain embodiments an antisense oligonucleotide has a nucleobase sequence that, when written in the 5' to 3' direction, comprises the reverse complement of the target segment of a target nucleic acid to which it is targeted.

In certain embodiments an antisense compound targeted to a nucleic acid is 12 to 30 subunits in length. In other words, antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments, the linked subunits are linked nucleobases, nucleosides, or nucleotides. In certain embodiments, the antisense compound is an antisense oligonucleotide, and the linked subunits are nucleotides. Antisense compounds may also be shortened or lengthened, or have mismatches introduced, without eliminating their activity.

Antisense Compound Motifs

In certain embodiments, antisense compounds targeted to a nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, or increased inhibitory activity. A second region of a chimeric antisense compound may optionally serve as a substrate for the cellular endonuclease RNaseH, which cleaves the RNA strand of an RNA:DNA duplex.

Antisense compounds having a gapmer motif are considered chimeric antisense compounds. As used herein, the term "gapmer" means an antisense compound in which an internal position having a plurality of nucleotides that supports RNaseH cleavage is positioned between external regions having one or more nucleotides that are chemically distinct from the nucleosides of the internal region. A "gap segment" means the plurality of nucleotides that make up the internal region of a gapmer. In certain embodiments, the antisense compound as a "wingmer" motif, having a wing-gap or gap-wing configuration, i.e. an X-Y or Y-Z configuration as described above for the gapmer configuration. Thus, wingmer configurations for use herein include, but are not limited to, for example 5-10, 8-4, 4-12, 12-4, 3-14, 16-2, 18-1, 10-3, 2-10, 1-10 or 8-2. A "wing segment" means the external region of a gapmer. In certain embodiments, an antisense compound targeted to a nucleic acid has a gap-widened motif. As used herein, the term "gap-widened" means an antisense compound has a gap segment of 12 or more contiguous 2'-deoxyribonucleotides positioned between and immediately adjacent to 5' and 3' wing segments having from one to six nucleotides having modified sugar moieties.

In certain embodiments, the antisense compound comprises one or more chemically modified nucleosides. In certain embodiments, the chemical modification comprises a 2'-sugar modification. In certain embodiments, the chemical modification comprises a 2'-MOE sugar modification.

Target Nucleic Acids, Target Regions and Nucleotide Sequences

It is understood that the sequences set forth herein are independent of any modification to a sugar moiety, an internucleoside linkage, or a nucleobase. As such, antisense compounds defined by a sequence or target sequence may comprise, independently, one or more modifications to a sugar moiety, an internucleoside linkage, or a nucleobase.

In certain embodiments, a target region of a human host cell factor involved in influenza virus replication is a structurally defined region of the nucleic acid. For example, a target region may encompass a 3' UTR, a 5' UTR, an exon, an intron, a coding region, a translation initiation region, translation termination region, or other defined nucleic acid region. The structurally defined regions for a gene can be obtained by accession number from sequence databases such as NCBI and such information is incorporated herein by reference. In certain other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain other embodiments, the desired effect is reduction of levels of protein encoded by the target nucleic acid or a phenotypic change associated with the target nucleic acid. In certain embodiments, the reduction is 70% or greater, 75% or greater, 80% or greater, 85% or greater, 90% or greater, 95% or greater, or 100% at a concentration of 100 nM in T-24 cells.

A target region may contain one or more target segments. Multiple target segments within a target region may be overlapping. Alternatively, they may be non-overlapping. In certain embodiments, target segments within a target region are separated by no more than about 300 nucleotides. In other embodiments, target segments within a target region are separated by no more than about, 250, 200, 150, 100, 90, 80, 70, 60, 50, 40, 30, 20, or 10 nucleotides on the target nucleic acid. In certain embodiments, target segments within a target region are separated by no more than about 5 nucleotides on the target nucleic acid. In certain embodiments, target segments are contiguous.

Suitable target segments may be found within a 5' UTR, a coding region, a 3' UTR, an intron, or an exon. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in mRNA levels are indicative of inhibition of gene expression. Reductions in levels of a protein are also indicative of inhibition of target mRNA expression. Further, phenotypic changes are indicative of inhibition of gene expression. For example, phenotypic changes may include a reduction in influenza virus replication, infection, or a symptom or disease associated therewith, as described herein infra.

Hybridization

In certain embodiments, hybridization occurs between an antisense compound disclosed herein and a target nucleic acid. The most common mechanism of hybridization involves hydrogen bonding (e.g., Watson-Crick, Hoogsteen or reversed Hoogsteen hydrogen bonding) between complementary nucleobases of the nucleic acid molecules. Hybridization can occur under varying conditions. Stringent conditions are sequence-dependent and are determined by the nature and composition of the nucleic acid molecules to be hybridized. Methods of determining whether a sequence is specifically hybridizable to a target nucleic acid are well known in the art. In certain embodiments, the antisense compounds provided herein are specifically hybridizable with a target nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid). Non-complementary nucleobases between an antisense compound and a target nucleic acid may be tolerated provided that the antisense compound remains able to specifically hybridize to a target nucleic acid. Moreover, an antisense compound may hybridize over one or more segments of a target nucleic acid such that intervening or adjacent segments are not involved in the hybridization event (e.g., a loop structure, mismatch or hairpin structure). In certain embodiments, the antisense compounds provided herein are at least 70%, at least 75%, at least 80%, at least 85%, at least 90%, at least 95%, at least 96%, at least 97%, at least 98% or at least 99% complementary to a target nucleic acid. Percent complementarity of an antisense compound with a target nucleic acid can be determined using routine methods, e.g., using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein are fully complementary (i.e., 100% complementary) to a target nucleic acid. For example, antisense compound may be fully complementary to a target nucleic acid, or a target region, or a target segment or target sequence thereof. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In certain embodiments, non-complementary nucleobase is located in the wing segment of a gapmer antisense oligonucleotide. In certain embodiments, antisense compounds up to 20 nucleobases in length comprise no more than 4, no more than 3, no more than 2 or no more than 1 non-complementary nucleobase(s) relative to a target nucleic acid. In certain embodiments, antisense compounds up to 30 nucleobases in length comprise no more than 6, no more than 5, no more than 4, no more than 3, no more than 2 or no more than 1 non-complementary nucleobase(s) relative to a target nucleic acid.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

In certain embodiments, the antisense compounds provided herein include those comprising a portion which consists of at least 8, 9, 10, 11, 12, 13, 14, 15, 16, 17, 18, 19, 20, 21, 22, 23, 24, or 25 contiguous nucleobases of the nucleobase sequence set forth in Table 1 supra or elsewhere herein, or incorporated by reference herein. In certain embodiments, the antisense compounds are complementary to an equal-length portion of the nucleobase sequence. In certain embodiments, the antisense compounds are at least 75%, 80%, 85%, 90%, 95%, or 100% (fully) complementary to the nucleobase sequence.

Identity

The antisense compounds provided herein may also have a defined percent identity to a particular nucleotide sequence.

As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds are at least 70%, 75%, 80%, 85%, 90%, 95%, 96%, 97%, 98%, 99% or 100% identical to one or more of the antisense compounds or sequences thereof, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds for use herein can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C($R_1$)($R_2$) for the ring oxygen at the 4'-position. Modified sugars include, but are not limited to: substituted sugars, especially 2'-substituted sugars having a 2'-F, 2'-OCH$_2$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=22, including α-L-Methyleneoxy (4'-CH2-O-2') BNA, β-D-Methyleneoxy (4'-CH2-O-2') BNA and Ethyleneoxy (4'-(CH2)2-O-2') BNA. Bicyclic modified sugars also include (6'S)-6'methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. The substituent at the 2' position can also be selected from alyl, amino, azido, thio, O-allyl, O—C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl. Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a nucleic acid comprise one or more modified nucleobases. In certain embodiments, gap-widened antisense oligonucleotides targeted to a nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

5.1.1.2 siRNA

In some embodiments, the nucleic acid compound for use in the embodiments described herein is an siRNA compound. During recent years, RNAi has emerged as one of the most efficient methods for inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) interfering (also referred to as "inhibitor") RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24). See also, e.g. Fire A et al., Nature 391: p 806-811 (1998), Elbashir S. M. et al., Genes Dev. 15: p 188-200 (2001), and Sharp P. A. Genes Dev. 15: p 485-490 (2001).

In some embodiments, a compound provided herein is an siRNA compound. As used herein, siRNAs are double stranded nucleic acid molecules that when introduced into a cell, trigger RNA interference (RNAi). Nonlimiting examples of targets for siRNA molecules which may be used in accordance with the embodiments described herein are provided in Table 1 infra. In some embodiments, the siRNA is long enough to induce RNAi but small enough to avoid inducing an immune response. In certain embodiments, the siRNA compound may be generated, analyzed, and modified in accordance with the provisions of Section 5.1.1.

Provided herein are nucleic acids and nucleotide sequences that can be used for preparation of a double stranded nucleic acid molecule that reduces or inhibits expression of a human host cell factor described herein. The double stranded nucleic acid is designed based on the nucleotide sequence of the target nucleic acid. With knowledge of the target gene sequence, an appropriate siRNA can be designed and synthesized using techniques known in the art and described herein. See, e.g., Kazunori Taira, et al.: RNAi Jikken Protocol, Yodosha (2003); Elbashir S. M. et al.: Genes Dev. 15: p 188-200 (2001); Bernstein E., Denli A M., Hannon G J: The rest is silence. RNA. 2001 November; 7(11):1509-21; and Nishikura K.: A short primer on RNAi: RNA-directed RNA polymerase acts as a key catalyst. Cell. 2001 Nov. 16; 107(4): 415-8. For example, a region downstream of an initiation codon may be selected, in which the sequence $AA(N_{19-29})TT$ or $AA(N_{21-31})$ is searched for, and the GC content of this sequence is calculated. A GC content of 50% is ideal; however, a sequence having a GC content of anywhere from at least 30% to 70% may be selected. The sequence selected using these criteria is then checked to determine if it is specific for the target gene by a BLAST (e.g. EST database of NCBI) search. Then, to evaluate whether or not the interference effect is exhibited, a double stranded nucleic acid with the chosen sequence is introduced or expressed within the cell, and the amount of target mRNA is measured (e.g. Northern blot or RT-PCR methods) or the amount of target protein is measured (e.g. Western blot or fluorescent antibody method), or using an assay for the target's activity known to persons skilled in the art.

In some embodiments, the double stranded nucleic acid comprises an antisense strand and a sense strand thereof. The antisense strand comprises an antisense sequence of 18 to 29, preferably 19 to 25 nucleotides, which is completely complementary to a partial sequence of the oligonucleotide, and further, comprises 1 to 4 bases at the 3'-end that protrude when annealed with the sense strand (overhang). The sense strand ordinarily comprises a completely complementary sequence to the antisense strand and comprises 1 to 4 bases protruding at the 3' end (overhang). To the extent that the antisense strand and the sense strand form a double strand, one or more mutations or substitutions may be present in the sense strand. The nucleic acid of the sense strand and the antisense strand may be RNA, DNA, or a mixture thereof. In some embodiments, the antisense strand sequence is RNA. In some embodiments, both the sense strand and the antisense strand are RNA. The overhang portion may be formed with deoxyribonucleotides G, A, T, and C and/or ribonucleotides G, A, U, and C, but a deoxyribonucleotide T and a ribonucleotide U are preferable. The number of overhang nucleotides is preferably 2 or 3, with 2 being preferable in some embodiments. Suitable examples include UU (RNA) and TT (DNA).

Methods for preparing the double stranded nucleic acid compounds for use as siRNA are known in the art and include, e.g., chemical synthesis, methods of in vitro synthesis, and methods of effecting expression within a cell using an expression vector (see, e.g. Takashi Morita, et al: Tanpakushitu Kakusan Kouso (Proteins, Nucleic Acids and Enzymes) Vol. 47 No. 14 p 1939-1945 (2002); Asako Sugimoto, Kagaku to Seibutsu (Chemistry and Biology) Vol. 40 No. 11: p 713-718 (2002); Makoto Miyagishi, et al.: Jikken Igaku (Experimental Medicine) Vol. 20 No. 18 p 2667-2672 (2002); Kazunori Taira, et al.: RNAi Jikken Protocol, Yodosha (2003)).

In chemical synthesis, double stranded nucleic acid is prepared by annealing an artificially synthesized sense strand and antisense strand. The resultant double stranded nucleic acid can be introduced into a cell using any suitable reagent known in the art, such as FuGENE6 (Roche) or Lipofectamine 2000 (Invitrogen). In in vitro synthesis, a double stranded siRNA is expressed by association with, e.g., a T7 promoter and T7 RNA polymerase. An oligonucleotide comprising a sequence corresponding to 19-29 bases of the target gene is ligated downstream of the binding site of T7 RNA polymerase, and sense RNA and antisense strand RNA are synthesized by in vitro transcription, and they are annealed in vitro. The prepared siRNA can be introduced into a cell by, e.g., lipofection methods using FuGENE6 (Roche). Intracellular expression of siRNA can be effected using an siRNA expression vector. For example, a sense strand and an antisense strand may be simultaneously expressed from both ends by two kinds of promoters, from separate transcription units, or be expressing siRNA precursors which adopt a hairpin structure. As an expression vector, for example, pSilencer siRNA Expression Vector (Ambion Inc.) can be used.

For further information on how to design and prepare siRNA to known genes, see, for example, Chalk A M, Wahlestedt C, Sonnhammer E L. Improved and automated prediction of effective siRNA Biochem. Biophys. Res. Commun. 2004 Jun. 18; 319(1):264-74; Sioud M, Leirdal M., Potential design rules and enzymatic synthesis of siRNAs, Methods Mol. Biol. 2004; 252:457-69; Levenkova N, Gu Q, Rux J J.: Gene specific siRNA selector Bioinformatics. 2004 Feb. 12; 20(3):430-2. and Ui-Tei K, Naito Y, Takahashi F, Haraguchi T, Ohki-Hamazaki H, Juni A, Ueda R, Saigo K., Guidelines for the selection of highly effective siRNA sequences for mammalian and chick RNA interference Nucleic Acids Res. 2004 Feb. 9; 32(3):936-48. See also Liu Y, Braasch D A, Nulf C J, Corey D R. Efficient and isoform-selective inhibition of cellular gene expression by peptide nucleic acids Biochemistry, 2004 Feb. 24; 43(7):1921-7. See also PCT publications WO 2004/015107 (Atugen) and WO 02/44321 (Tuschl et al), and also Chiu Y L, Rana T M. siRNA function in RNAi: a chemical modification analysis, RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have also been developed and may be used in accordance with the embodiments described herein. The method generally involves transcription of short hairpin RNAs that are efficiently processed to form siRNAs within cells. Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553. These reports describe methods to generate siRNAs capable of specifically targeting host genes.

For methods on the delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 pp 132-138.

See also U.S. Pat. Nos. 5,486,603, 5,859,221, 5,898,031, 5,976,567, 6,107,094, 6,153,737, 6,476,205, 6,506,559, 6,815,432, 6,858,225, 7,056,704, 7,078,196, 7,432,250, and 7,626,015, and U.S. Patent Application Publication No. 20090306356, U.S. Patent Application Publication No. 20090306194, which are incorporated herein by reference in their entireties and the disclosures of which may be adapted to design, generate, administer and deliver siRNAs and compositions comprising them in accordance with the present embodiments.

5.1.2 Small Molecule Compounds

In some embodiments, the compound is a small molecule. In some embodiments, the small molecule is Betulinic acid (available from VWR International/Enzo Life Sciences Intl.); CCT018159 (4-(4-(2,3-Dihydro-1,4-benzodioxin-6-yl)-5-methyl-1H-pyrazol-3-yl)-6-ethylresorcinol; available from Calbiochem); Diphyllin (available from Sigma; see FIG. 13a); the FGF/VEGF receptor inhibitor 4-Hydroxy-3-benzimidazol-2-ylhydroquinolin-2-one; Hymenialdisine (available from Biomol International LP); KN-93 (available from Calbiochem); Podophyllotoxin (Podophyllinic Acid Lactone; available from MP Biomedicals); or Sirolimus (Rapamycin; available from LC Laboratories).

In some embodiments, the compound is not CCT018159. In some embodiments, the compound is not Diphyllin.

5.1.3 Additional Compounds

In addition to the compounds provided above, any compound or library of compounds from any source can be tested for modulation, reduction or inhibition of influenza virus replication, or for use as antiviral agents, by targeting one or more of the classes of human host cell proteins or specific human host cell proteins described herein. Such compounds include, but are not limited to, proteins, polypeptides, peptides, nucleic acids, including dominant negative mutants, ribozyme or triple helix molecules, antibodies (including antibodies for intracellular use, referred to herein as intrabodies), small organic molecules, or inorganic molecules.

In a specific embodiment, an antibody is used, for example, an intrabody. Antibodies used include immunoglobulin molecules and immunologically active portions of immunoglobulin molecules, i.e., molecules that contain an antigen binding site that specifically binds to one or more of the classes of human host cell proteins or specific human host cell proteins described herein. Antibodies include, but are not limited to, monoclonal antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. In certain embodiments, the antibodies used are commercially or publicly available. In other embodiments, the antibodies described in this section can produced by any method well known in the art, e.g., as described in U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties).

In other embodiments, small molecular weight compounds are used. In preferred embodiments, the compound is in a form so that it can be delivered into a human host cell, preferably, in vivo.

In some embodiments, the compounds are known inhibitors of the host cell proteins described herein. In some embodiments, the compounds are identified by screening for their ability to inhibit the classes of host cell proteins described herein, and are then tested for their ability to inhibit or reduce influenza virus replication.

5.2 Biological Assays

5.2.1 Testing of Nucleic Acid Compounds

5.2.1.1 In Vitro Testing of Nucleic Acid Compounds

The methods of treating cells with antisense compounds described herein may be modified appropriately for treatment with other nucleic acid compounds, such as siRNAs. With respect to siRNAs, see also Section 5.1.1.2 above and the references cited therein.

Cell Culture and Antisense Compounds Treatment

The effects of antisense compounds on the level, activity or expression of nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, Hep3B cells and primary hepatocytes.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide. Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 µg/µL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 500 nM.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of nucleic acids can be assessed by measuring protein levels. Protein levels can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, histone deacetylase activity), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In certain embodiments, administration of an antisense compound targeted to a nucleic acid encoding a human host cell factor results in reduction of expression (e.g., mRNA or protein levels) of the human host cell factor by at least 5, 10, 15, 20, 25, 30, 35, 40, 45, 50, 55, 60, 65, 70, 75, 80, 85, 90, 95, 96, 97, 98, 99, or 100%, or a range defined by any two of these values.

5.2.1.2 In Vivo Testing of Nucleic Acid Compounds

Antisense compounds are tested in animals to assess their ability to inhibit expression of the target and produce the desired effect, such as reduction in influenza virus replication, reduction in influenza virus infection, and/or prevention or reduction of symptoms or disease associated with influenza virus infection, measurable by the methods provided herein. The methods described herein for testing antisense compounds may be adapted for testing other nucleic acid compounds, such as siRNAs. With respect to siRNAs, see also Section 5.1.1.2 above and the references cited therein.

Testing may be performed in normal animals, or in experimental influenza disease models known in the art and described below. For administration to animals, antisense oligonucleotides are formulated in a pharmaceutically acceptable diluent, such as phosphate-buffered saline. Administration include any suitable route of administration, such as parenteral, intraperitoneal, intravenous, pulmonary, intranasally, topically, and subcutaneous. Following a period of treatment with antisense oligonucleotides, RNA is isolated from a relevant tissue (e.g., lung tissue or other epithelial tissue) and changes in target nucleic acid expression are measured.

5.2.2 Cellular Assays for Assessing the Effect of a Compound on Viral Replication The effect of a compound on virus replication can be assessed by any assay known in the art. Such assays may involve: (a) contacting a compound or a member of a library of compounds with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection with an influenza virus; and (b) measuring virus replication. The cells can be infected at different MOIs and the effect of a compound on virus replication can be assessed. For example, the MOIs may be 0.001, 0.005, 0.01, 0.05, 0.1, 0.5, 1, 2.5, or 5. The effect of different concentrations of a compound on virus replication can also be assessed. The cells or other substrate that contains cells (e.g., embryonated eggs) used in the assay should be susceptible to infection by the influenza virus. The cells may be primary cells or established cell lines. For example, the following cells may be used in the assay for influenza virus replication: chicken cells (e.g., primary chick embryo cells or chick kidney cells), Vero cells, MDCK cells, human respiratory epithelial cells (e.g., A549 cells), calf kidney cells, and mink lung cells. In one embodiment, the cells used to assess the effect of a compound on virus replication are selected from the following cells or cell lines: MEF, 293T, Huh 7.5, Detroit, and human tracheobronchial epithelial (HTBE; primary lung cells) cells. In one embodiment, the cell or cell line is biologically relevant to virus infection.

Influenza virus replication can be measured at different times post-infection. For example, virus replication may be measured 6 hours, 12 hours, 16 hours, 24 hours, 48 hours or 72 hours post-infection. Any method known to one of skill in the art can be used measure virus replication. For example, viral replication may be assessed by measuring viral titer (as determined, e.g., by plaque formation), the production of viral proteins (as determined, e.g., by western blot analysis, ELISA or flow cytometry), or the production of viral nucleic acids (as determined, e.g., by RT-PCR or Northern blot analysis) using techniques known to one of skill in the art. See Sections 5.3.1.1-5.3.1.6 below for more details of techniques for measuring viral replication.

In the assays described above, a compound is considered to inhibit (or reduce) influenza virus replication if the replication of the virus is decreased in the cell contacted with the compound relative to the replication of the virus in a cell contacted with a negative control (e.g., PBS or saline).

In certain embodiments, a compound is considered to reduce or inhibit viral replication if it reduces the virus replication by at least 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In certain embodiments, a compound is considered to reduce or inhibit viral replication if it reduces the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In some embodiments, a compound is considered to reduce or inhibit viral replication if it reduces the virus replication by approximately 2 logs or more, approximately 3 logs or more, approximately 4 logs or more, approximately 5 logs or more, or 2 to 10 logs or 2 to 5 logs relative to virus replication in the absence of compound or the presence of a negative control.

In certain embodiments, a compound is considered to reduce or inhibit viral replication if it reduces the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to replication of the viral genome in the absence of a compound or relative to a negative control in an assay described herein or others known to one of skill in the art. In certain embodiments, a compound is considered to reduce or inhibit viral replication if it reduces the replication of a viral genome by about 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to replication of the viral genome in the absence of a compound or relative to a negative control in an assay described herein or others known to one of skill in the art. In certain embodiments, a compound is considered to reduce or inhibit viral replication if it reduces the replication of a viral genome by at least 1 log, 1.5 logs, 2 logs, 2.5 logs, 3 logs, 3.5 logs, 4 logs, 4.5 logs, 5 logs or more relative to replication of the viral genome in the absence of a compound or relative to a negative control in an assay described herein or others known to one of skill in the art.

In certain embodiments, a compound is considered to reduce or inhibit viral replication if it reduces the synthesis of viral proteins by at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to the synthesis of viral proteins in the absence of a compound or relative to a negative control in an assay described herein or others known to one of skill in the art in an assay described herein or others known to one of skill in the art. In certain embodiments, a compound is considered to reduce or inhibit viral replication if it reduces the synthesis of viral proteins at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to the synthesis of viral proteins in the absence of a compound or relative to a negative control in an assay described herein or others known to one of skill in the art. In certain embodiments, a compound is considered to reduce or inhibit viral replication if it reduces the synthesis of viral proteins approximately 1 log, 1.5 logs, 2 logs, 2.5 logs, 3 logs, 3.5 logs, 4 logs, 4.5 logs, 5 logs relative to the synthesis of viral proteins in the absence of a compound or relative to a negative control in an assay described herein or others known to one of skill in the art.

In certain embodiments, a compound is considered to reduce or inhibit viral replication if it results in 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more reduction of viral yield per round of viral replication. In certain embodiments, a compound results in about a 2 fold or more reduction of viral yield per round of viral replication. In a specific embodiment, a compound results in about a 10 fold or more reduction of viral yield per round of viral replication.

In certain embodiments, a compound is considered to reduce or inhibit viral replication if it reduces viral replication by at least 2 wells of hemagglutinin (HA) in a hemagglutination assay (see Section 5.2.1.7 below), which equals approximately a 75% reduction in viral titer.

In certain embodiments, a compound is considered to reduce or inhibit viral replication if it reduces viral titer by 50% or more, by 55% or more, by 60% or more, by 65% or more, by 70% or more, by 75% or more, by 80% or more, by 85% or more, by 90% or more, or by 95% or more.

Standard assays for influenza virus replication have been described, See, e.g., Sidwell et al., Antiviral Research, 2000, 48:1-16.

In some embodiments, the effect of a compound on the replication of an influenza A virus is determined. In some embodiments, the effect of a compound on the replication of an influenza B virus is determined. In some embodiments, the effect of a compound on the replication of an influenza C virus is determined. In some embodiments, the effect of a compound on the replication of a currently circulating influenza virus is determined. In some embodiments, the effect of a compound on replication of H1N1 influenza virus is determined. In some embodiments, the effect of a compound on replication of H5N1 influenza virus is determined. In some embodiments, the effect of a compound on replication of an attenuated influenza virus is determined. In some embodiments, the effect of a compound on the replication of a naturally occurring strain, variant or mutant of an influenza virus, a mutagenized influenza virus, a reassortant influenza virus and/or a genetically engineered influenza virus can be assessed. In a specific embodiment, the effect of a compound on the replication of a vaccine strain of an influenza virus is determined.

5.2.2.1 Viral Titer Assay

In this non-limiting example, a monolayer of the target mammalian cell line is infected with different amounts (e.g., multiplicity of 3 plaque forming units (pfu) or 5 pfu) of influenza virus and subsequently cultured in the presence or absence of various dilutions of compounds (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

5.2.2.2 Flow Cytometry Assay

Flow cytometry can be utilized to detect expression of virus antigens in infected target cells cultured in the presence or absence of compounds (See, e.g., McSharry et al., Clinical Microbiology Rev., 1994, 7:576-604). Non-limiting examples of viral antigens that can be detected on cell surfaces by flow cytometry include, but are not limited to HA of influenza. In other embodiments, intracellular viral antigens or viral nucleic acid can be detected by flow cytometry with techniques known in the art.

5.2.2.3 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei).

The CPE assay can provide a measure of the effect of a compound on virus replication. In a non-limiting example of such an assay, compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). When assaying a compound for its potential activity, CPE is read microscopically after a known positive control drug (an antiviral) is evaluated in parallel with compounds in each test. A non-limiting example of a positive control is ribavirin for influenza. The data is expressed as 50% effective concentrations or approximated virus-inhibitory concentration, 50% endpoint (EC50) and cell-inhibitory concentration, 50% endpoint (IC50). General selectivity index ("SI") is calculated as the IC50 divided by the EC50. These values can be calculated using any method known in the art, e.g., the computer software program Mac-Synergy II by M. N. Prichard, K. R. Asaltine, and C. Shipman, Jr., University of Michigan, Ann Arbor, Mich.

In one embodiment, a compound has an SI of greater than 3, 4, 5, 6, 7, 8, 9, 10, 11, 12, 13, 14, 15, 20, 21, 22, 23, 24, 25, 30, 35, 39, 40, 45, 50, 60, 70, 80, 90, 100, 200, 300, 400, 500, 1,000, or 10,000. In some embodiments, a compound has an SI of greater than 10. In a specific embodiment, compounds with an SI of greater than 10 are further assessed in other in vitro and in vivo assays described herein or others known in the art to characterize safety and efficacy.

5.2.2.4 Neutral Red (NR) Dye Uptake Assay

The NR Dye Uptake assay can be used to validate the CPE inhibition assay (See Section 5.3.1.3). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An $EC_{50}$ is determined for samples with infected cells and contacted with compounds, and an $IC_{50}$ is determined for samples with uninfected cells contacted with compounds.

5.2.2.5 Virus Yield Assay

Lysed cells and supernatants from infected cultures such as those in the CPE inhibition assay (See Section 5.3.1.3) can be used to assay for virus yield (production of viral particles after the primary infection). In a non-limiting example, these supernatants are serially diluted and added onto monolayers of susceptible cells (e.g., Vero cells). Development of CPE in these cells is an indication of the presence of infectious viruses in the supernatant.

5.2.2.6 Plaque Assay

In a non-limiting example of a plaque assay, the virus is diluted into various concentrations and added to each well containing a monolayer of the target cells in triplicate. The plates are then incubated for a period of time to achieve effective infection of the control sample (e.g., 1 hour with shaking every fifteen minutes). After the incubation period, an equal amount of 1% agarose is added to an equal volume of each compound dilution prepared in 2× concentration. In certain embodiments, final compound concentrations between 0.03 µg/ml to 100 µg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

5.2.2.7 Hemagglutination Assays

In a non-limiting example of a hemagglutination assay, cells are contacted with a compound and are concurrently or subsequently infected with the virus (e.g., at an MOI of 1) and the virus is incubated under conditions to permit virus replication (e.g., 20-24 hours). The compounds are preferably present throughout the course of infection. Viral replication and release of viral particles is then determined by hemagglutination assays using 0.5% chicken red blood cells. In some embodiments, a compound is considered to reduce or inhibit viral replication if it reduces viral replication by at least 2 wells of HA, which equals approximately a 75% reduction in viral titer. In specific embodiments, a compound reduces viral titer in this assay by 50% or more, by 55% or more, by 60% or more, by 65% or more, by 70% or more, by 75% or more, by 80% or more, by 85% or more, by 90% or more, or by 95% or more.

5.2.3 Cytotoxicity Assays

In some embodiments, compounds differentially affect the viability of uninfected cells and cells infected with virus. The differential effect of a compound on the viability of virally infected and uninfected cells may be assessed using techniques known to one of skill in the art or described herein. In certain embodiments, compounds are more toxic to cells infected with a virus than uninfected cells. In specific embodiments, compounds preferentially affect the viability of cells infected with a virus. In preferred embodiments, the compounds are not so cytotoxic that they are unsafe for administration to an animal or human subject.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; or THP-1, monocytic cells. In certain embodiments, cytotoxicity is assessed in one or more of the following cell lines: MDCK, MEF, Huh 7.5, Detroit, or human tracheobronchial epithelial (HTBE) cells.

Compounds can be tested for in vivo toxicity in animal models. For example, animal models, described herein and/or others known in the art, used to test the activities of compounds can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the embodiments described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified in accordance with the embodiments described herein that exhibits large therapeutic indices is preferred. While a compound identified in accordance with the embodiments described herein that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the embodiments described herein for use in humans. The dosage of such agents lies preferably within a range of circulating concentrations that include the $ED_{50}$ with little or no toxicity. The dosage may vary within this range depending upon the dosage form employed and the route of administration utilized. For any agent used in the methods and compositions described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 5.5.4, infra.

5.2.4 Apoptosis Assay

Any technique known to one of skill in the art can be used to determine whether a compound has an apoptotic effect. For example, a fluorescence-based assay for caspase-3 activity can be used to detect whether a compound has a pro- or anti-apoptotic effect. In one example of such an assays, cells are seeded into 60 mm tissue culture treated dishes at $1.5 \times 10^6$ cells per dish and allowed to incubate for 24 hours. After incubation, the medium is aspirated and the cells are washed with PBS. Fresh DMEM post-infection medium was added, containing compounds at the same concentrations as has been used for the viral infections. As a positive control for the induction of apoptosis, cells are treated with any known inducer of apoptosis, for example, staurosporin at a concentration of 5 μM. Cells are incubated for 6 hours. Subsequently, they are harvested, washed twice with PBS, lysed and incubated with the colorimetric substrate for an additional hour, at which time fluorescence is measured. An increase in fluorescence relative to a negative control or cells not treated with the compound indicates that the compound is pro-apoptotic.

5.2.5 Animal Model Studies

Compounds and compositions are preferably assayed in vivo for the desired therapeutic or prophylactic activity prior to use in humans. For example, in vivo assays can be used to determine whether it is preferable to administer a compound and/or another therapeutic agent. For example, to assess the use of a compound to prevent a viral infection, the compound can be administered before the animal is infected with the virus. Alternatively, or in addition, a compound can be administered to the animal at the same time that the animal is infected with the virus. To assess the use of a compound to treat or manage a viral infection, in one embodiment, the compound is administered after a viral infection in the animal. In another embodiment, a compound is administered to the animal at the same time that the animal is infected with the virus to treat and/or manage the viral infection. In a specific embodiment, the compound is administered to the animal more than one time.

Compounds can be tested for antiviral activity against virus in animal models systems including, but are not limited to, rats, mice, chicken, cows, monkeys, pigs, goats, sheep, dogs, rabbits, guinea pigs, etc. In a specific embodiment, compounds are tested in a mouse model system. Such model systems are widely used and well-known to the skilled artisan. Compounds can also be tested for replication enhancing activity toward virus replication in animal models systems including, but are not limited to, rats, mice, chicken, cows, monkeys, pigs, goats, sheep, dogs, rabbits, guinea pigs, etc. In a specific embodiment, compounds are tested in a mouse model system. Such model systems are widely used and well-known to the skilled artisan. Non-limiting examples of animal models for influenza virus are provided in Section 5.2.5.1 below.

Animals are infected with virus and concurrently or subsequently treated with a compound or placebo. Alternatively, animals are treated with a compound or placebo and subsequently infection with virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of a compound on the virulence of a virus can also be determined using in vivo assays in which the titer of the virus in an infected subject administered a compound, the length of survival of an infected subject administered a compound, the immune response in an infected subject administered a compound, the number, duration and/or severity of the symptoms in an infected subject administered a compound, and/or the time period before onset of one or more symptoms in an infected subject administered a compound is assessed. Techniques known to one of skill in the art can be used to measure such effects.

5.2.5.1 Influenza Virus Animal Models

Animal models, such as ferret, mouse, guinea pig, and chicken, developed for use to test antiviral agents against influenza virus have been described, See, e.g., Sidwell et al., Antiviral Res., 2000, 48:1-16; Lowen A. C. et al. PNAS, 2006, 103: 9988-92; and McCauley et al., Antiviral Res., 1995, 27:179-186. For mouse models of influenza, non-limiting examples of parameters that can be used to assay antiviral activity of compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+(epithelial layer columnar and even in outline with only slightly increased proliferation; cilia still visible on many cells); 2+(prominent changes in the epithelial layer ranging from attenuation to marked proliferation; cells disorganized and layer outline irregular at the luminal border); 3+(epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+(focal squamous metaplasia of the epithelial layer); 2+(diffuse squamous metaplasia of much of the epithelial layer, cilia may be evident focally); 2.5+(diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+(few infected cells); 1+(few infected cells, as widely separated individual cells); 1.5+(few infected cells, as widely separated singles and in small clusters); 2+(moderate numbers of infected cells, usually affecting clusters of adjacent cells in portions of the epithelial layer lining bronchioles, or in small sublobular foci in alveoli); 3+(numerous infected cells, affecting most of the epithelial layer in bronchioles, or widespread in large sublobular foci in alveoli).

5.2.6 Assays in Humans

In one embodiment, a compound that is a candidate for use in human subjects is assessed human subjects suffering from an influenza virus infection. In accordance with this embodiment, a candidate compound or a control compound is administered to the human subject, and the effect of a test compound on viral replication is determined by, e.g., analyzing the level of the virus or viral nucleic acids in a biological sample (e.g., serum or plasma). A candidate compound that inhibits virus replication can be identified by comparing the level of virus replication in a subject or group of subjects treated with a control compound to that in a subject or group of subjects treated with the candidate compound. Alternatively, a decrease in viral replication can be detected by comparing the level of virus replication in a subject or group of subjects before and after the administration of a candidate compound. Techniques known to those of skill in the art can be used to obtain the biological sample and analyze the mRNA or protein expression.

In another embodiment, the effect of a candidate compound on the severity of one or more symptoms associated with an influenza virus infection is assessed in a subject having an influenza virus infection. In accordance with this embodiment, a candidate compound or a control compound is administered to a human subject suffering from an influenza virus infection and the effect of the candidate compound on one or more symptoms of the virus infection is determined. A candidate compound that reduces one or more symptoms can be identified by comparing the subjects treated with a control compound to the subjects treated with the candidate compound. Techniques known to physicians familiar with infectious diseases can be used to determine whether a candidate compound reduces one or more symptoms associated with the influenza virus infection.

5.3 Compositions

Provided herein are compositions comprising a compound that targets one or more human host cell factors involved in influenza virus replication. Such compositions may be in a dose effective to modulate influenza virus replication. Such compositions may be in a dose effective to reduce or inhibit influenza virus replication. Such compositions may be pharmaceutical compositions, and may additionally comprise a pharmaceutically acceptable carrier known in the art or described herein. Such pharmaceutical compositions may be in a dose effective to reduce or inhibit a symptom or disease associated with influenza virus infection. Compounds for use in these compositions and pharmaceutical compositions may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned nucleic acid compound, e.g., an siRNA; or (v) an aforementioned small molecule. Such compositions may also include another active agent, for example, another compound that targets a human host cell factor involved in influenza virus replication described herein. In certain embodiments, the compositions, including the pharmaceutical compositions, described herein contain the compound in an amount that is not significantly toxic to the cell, tissue, or subject for which it is intended. Methods of testing toxicity include any method known in the art, for example, as described in Sections 5.2.3 and 6 infra.

Any compound described herein may optionally be in the form of a composition comprising the compound and a carrier, excipient or diluent. In certain embodiments provided herein, compositions (including pharmaceutical compositions) comprise a compound and a pharmaceutically acceptable carrier, excipient, or diluent.

In other embodiments, provided herein are pharmaceutical compositions comprising an effective amount of a compound and a pharmaceutically acceptable carrier, excipient, or diluent. In a specific embodiment, the pharmaceutical compositions comprise one or more of the compounds that reduce or inhibit influenza virus infection or replication described herein. The pharmaceutical compositions are suitable for veterinary and/or human administration.

The pharmaceutical compositions provided herein can be in any form that allows for the composition to be administered to a subject, preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Specific lactose free dosage forms comprise a compound, microcrystalline cellulose, pre gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, NY, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsions, gels, lotions, or creams, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a compound preferably in purified form, together with a suitable amount of carrier so as to provide the form for proper administration to the patient. The formulation should suit the mode of administration. In a specific embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, topical, parenteral, e.g., intravenous, intradermal, subcutaneous, oral (e.g., inhalation), intranasal, transdermal (topical), transmucosal, intra-synovial and rectal administration. In a specific embodiment, the composition is formulated in accordance with routine procedures as a composition adapted for topical, intravenous, pulmonary, subcutaneous, intramuscular, oral, intranasal or topical administration to human beings. In a specific embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams or lotions; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the compositions described herein. The embodiments described herein thus encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their noncontrolled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Agents that increase the solubility of one or more of the compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more compounds so as to improve delivery. In this regard, stearates can serve as a lipid vehicle for the formulation, as an emulsifying agent or surfactant, and as a delivery enhancing or penetration enhancing agent. Different salts, hydrates or solvates of the compounds can be used to further adjust the properties of the resulting composition.

In certain specific embodiments, the compositions are in oral, injectable, or transdermal dosage forms. In one specific embodiment, the compositions are in oral dosage forms. In one specific embodiment, the compositions are in intranasal dosage forms. In another specific embodiment, the compositions are in the form of injectable dosage forms. In one specific embodiment, the compositions are in topical dosage forms. In another specific embodiment, the compositions are in the form of transdermal dosage forms.

In certain embodiments, it is beneficial to deliver a compound targeted to a human host cell factor involved in influenza virus replication to a lung or other epithelial tissue of an individual infected with, or at risk for infection with, an influenza virus.

5.3.1 Compositions Comprising Nucleic Acid Compounds

With regard to nucleic acid molecules, such as siRNAs, administration may be carried out by known methods, wherein a nucleic acid is introduced into a desired target cell in vitro or in vivo. Commonly used gene transfer techniques include calcium phosphate, DEAE-dextran, electroporation and microinjection and viral methods (Graham, F. L. and van der Eb, A. J. (1973) Virol. 52, 456; McCutchan, J. H. and Pagano, J. S. (1968), J. Natl. Cancer Inst. 41, 351; Chu, G. et al (1987), Nucl. Acids Res. 15, 1311; Fraley, R. et al. (1980), J. Biol. Chem. 255, 10431; Capecchi, M. R. (1980), Cell 22, 479). A recent addition to this arsenal of techniques for the introduction of DNA into cells is the use of cationic liposomes (Feigner, P. L. et al. (1987), Proc. Natl. Acad. Sci USA 84, 7413). Commercially available cationic lipid formulations are e.g. Tfx 50 (Promega) or Lipofectamin2000 (Life Technologies). For diagnostic or therapeutic applications, a composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes. A further preferred administration method is injection

5.4 Prophylactic and Therapeutic Uses

Provided herein are methods of reducing or inhibiting influenza virus replication, comprising contacting a cell infected with an influenza virus with a compound, or composition comprising the compound, that targets one or more human host cell factors involved in influenza virus replication, in an amount sufficient to reduce or inhibit replication of the influenza virus. In one embodiment, a method for reducing or inhibiting replication of an influenza virus comprises: (a) infecting a cell with an influenza virus; and (b) contacting the cell with such a compound or composition in an amount sufficient to reduce or inhibit replication of the influenza virus. Also provided herein are methods for reducing or inhibiting influenza virus replication, comprising: (a) contacting a cell with such a compound or composition in an amount sufficient to reduce or inhibit replication of an influenza virus; and (b) infecting the cell with the influenza virus. In some embodiments, a compound or composition comprising the compound is considered to reduce or inhibit influenza virus replication if it reduces the amount of influenza virus replication as measured compared to a control, such as, for example, influenza virus replication in the absence of the compound or composition, or influenza virus replication in the presence of a negative control. In some embodiments, the compound or composition is contacted to a cell at risk for influenza virus infection. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned siRNA; or (v) an aforementioned small molecule.

In certain embodiments, the cell is contacted with an influenza virus concurrently with the compound, or within, for example, 5 seconds, 15 seconds, 30 seconds, 1 minute, 5 minutes, 15 minutes, 30 minutes, 1 hour, 2 hours, 6 hours, 12 hours, 16 hours or 24 hours, of each other.

Provided herein are methods for treating an influenza virus infection, comprising administering to a subject in need thereof a pharmaceutical composition comprising a compound, e.g., nucleic acid compound (e.g., siRNA) or small molecule, that targets one or more human host cell factors involved in influenza virus replication in an amount sufficient to reduce the influenza virus infection. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned siRNA; or (v) an aforementioned small molecule.

Provided herein are methods for treating a symptom or disease associated with an influenza virus infection, comprising administering to a subject in need thereof a pharmaceutical composition comprising a compound, e.g., nucleic acid compound (e.g., siRNA) or small molecule, that targets one or more human host cell factors involved in influenza virus replication in an amount sufficient to reduce the symptom or disease associated with the influenza virus infection. In some embodiments, the subject is infected with an influenza virus. In some embodiments, the subject is at risk for infection with an influenza virus. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned siRNA; or (v) an aforementioned small molecule.

Also provided herein are methods for preventing a symptom or disease associated with an influenza virus infection, comprising administering to a subject in need thereof a composition comprising a compound, e.g., nucleic acid compound (e.g., siRNA) or small molecule, that targets one or more human host cell factors involved in influenza virus replication in an amount sufficient to prevent or reduce the symptom or disease associated with the influenza virus infection. In some embodiments, the subject is infected with an influenza virus. In some embodiments, the subject is at risk for infection with an influenza virus. In some embodiments, the subject is a human. Compounds for use in such methods may include, by non-limiting example, (i) a compound that targets an aforementioned category of human host cell factor; (ii) a compound that targets a human host cell factor in such a category; (iii) a compound that targets an aforementioned human host cell factor; (iv) an aforementioned siRNA; or (v) an aforementioned small molecule.

In certain embodiments of the aforementioned methods, the compounds, compositions, and pharmaceutical compositions used in an amount that is not significantly toxic to the cell, tissue, or subject for which it is intended. Methods of testing toxicity include any method known in the art, for example, as described supra and in Section 6 below. The aforementioned methods may optionally comprise use of the compound that targets a human host cell factor involved in influenza virus replication in combination with one or more additional active agents. Such additional active agents include, for example, one or more additional antiviral agents, e.g., an aforementioned compound that targets human host cell factors involved in influenza virus replication; an antibiotic; an immunomodulatory agent; and an agent used in the treatment or prophylaxis of one or more pulmonary diseases described herein or known in the art.

In certain of the above embodiments, the subject is a human. In certain of the above embodiments, the influenza virus is an influenza A virus. In some embodiments, the influenza virus is an influenza B virus. In some embodiments, the influenza virus is an influenza C virus. Any type, subtype, or strain of influenza virus described herein or known in the art may be targeted in accordance with the embodiments described herein. In some embodiments, the influenza virus is of human origin. In some embodiments, the influenza virus is of avian origin (e.g., H5N1). In some embodiments, the influenza virus is of swine origin (e.g., H1N1).

Provided herein are methods of preventing, treating and/or managing an influenza virus infection, said methods comprising administering to a subject in need thereof one or more compounds described herein. In a specific embodiment, provided herein is a method of preventing, treating and/or managing an influenza virus infection, said method comprising administering to a subject in need thereof a dose of a prophylactically or therapeutically effective amount of one or more compounds described herein or a composition (e.g., a pharmaceutical composition) comprising a compound described herein. A compound or a composition described herein may be used as any line of therapy (e.g., a first, second, third, fourth or fifth line therapy) for an influenza virus infection. In some embodiments, the subject to be treated is severely ill. In some embodiments, the subject to be treated is unresponsive, or poorly responsive, to one or more previous antiviral therapies.

Non-limiting examples of influenza virus infections to be treated in accordance with this aspect include one or more of an influenza A virus, influenza B virus, or influenza C virus. In one embodiment, the influenza A virus is an H5N1 isolate. In another embodiment, the influenza A virus is an H1N1 isolate.

In a specific embodiment, the influenza virus infects humans. In some embodiments, the influenza virus is a naturally occurring strain, variant or mutant of an influenza virus, a mutagenized influenza virus, a reassortant influenza virus and/or a genetically engineered influenza virus.

In specific embodiments, a compound described herein is the only active ingredient administered to prevent, treat and/or manage an influenza virus infection. In a certain embodiment, the compound is the only active ingredient in a composition that is administered to prevent, treat and/or manage an influenza virus infection or symptom or disease associated therewith. In other embodiments, more than one such compound, or the compound together with another therapy, is administered in order to achieve a synergistic effect.

In some embodiments, the compound specifically interferes with the replication of an influenza virus. In other embodiments, the compound interferes with the replication of influenza virus and one or more other viruses. In some embodiments, the compound reduces the viral replication of one type, subtype or strain of influenza virus more than another. For example, the compound may reduce the replication of an influenza A virus more than it reduces the replication of an influenza B virus, and vice versa.

The choice of compounds to be used depends on a number of factors, including but not limited to the type of viral infection, health and age of the patient, and toxicity or side effects.

The embodiments described herein encompass methods for preventing, treating, and/or managing an influenza virus infection for which no antiviral therapy is available. The embodiments described herein also encompass methods for preventing, treating, and/or managing an influenza virus infection as an alternative to other conventional therapies.

Also provided herein are methods of preventing, treating and/or managing an influenza virus infection, said methods comprising administering to a subject in need thereof one or more of the compounds described herein and one or more other therapies (e.g., prophylactic or therapeutic agents). In a specific embodiment, the other therapies are currently being used, have been used or are known to be useful in the prevention, treatment and/or management of a viral infection. Non-limiting examples of such therapies are provided below. In a specific embodiment, one or more compounds described herein are administered to a subject in combination with one or more therapies. In another embodiment, one or more compounds described herein are administered to a subject in combination with a supportive therapy, a pain relief therapy, or another therapy that does not have antiviral activity. In some embodiments, the therapy is a treatment of pulmonary disease.

The combination therapies can be administered sequentially or concurrently. In one embodiment, the combination therapies comprise an comprise a compound that targets a human host cell factor involved in influenza virus replication described and at least one other therapy which has the same mechanism of action. In another embodiment, the combination therapies described herein and at least one other therapy which has a different mechanism of action than the compound.

In a specific embodiment, the combination therapies improve the prophylactic and/or therapeutic effect of a compound described herein by functioning together with the compound to have an additive or synergistic effect. In another embodiment, the combination therapies reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

5.4.1 Patient Population

In some embodiments, a compound described herein, a composition comprising a compound described herein, or a combination therapy is administered to a subject suffering from an influenza virus infection. In other embodiments, a compound described herein, a composition comprising a compound described herein, or a combination therapy is administered to a subject predisposed to, at risk for, or susceptible to an influenza virus infection. In some embodiments, a compound described herein, a composition comprising a compound described herein, or a combination therapy is administered to a subject that lives in a region where there has been or might be an outbreak with an influenza virus infection. In some embodiments, the influenza virus infection is an active infection. In some embodiments, the influenza virus infection is chronic.

In certain embodiments, the compound, the composition comprising the compound or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, the compound, a composition comprising the compound or a combination therapy is administered to a human at risk for an influenza virus infection. In certain embodiments, a compound described herein, a composition comprising a compound described herein or a combination therapy is administered to a human with an influenza virus infection. In certain embodiments, the subject is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound described herein, a composition comprising a compound described herein or a combination therapy is administered to a human infant. In other embodiments, a compound described herein, a composition comprising a compound described herein or a combination therapy is administered to a human child. In other embodiments, a compound described herein, a composition comprising a compound described herein or a combination therapy is administered to a human adult. In yet other embodiments, a compound described herein, a composition comprising a compound described herein or a combination therapy is administered to an elderly human.

In certain embodiments, a compound described herein, a composition comprising a compound described herein or a combination therapy is administered to a pet, e.g., a dog or cat. In certain embodiments, a compound described herein, a composition comprising a compound described herein or a combination therapy is administered to a farm animal or livestock, e.g., pig, cow, horse, chicken, etc. In certain embodiments, a compound described herein, a compound comprising a compound described herein or a combination therapy is administered to a bird, e.g., duck or chicken.

In certain embodiments, a compound described herein, a composition comprising a compound described herein or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a compound, a composition comprising a compound described herein or a combination therapy is administered to a subject receiving or recovering from immunosuppressive therapy. In certain embodiments, a compound described herein, a composition comprising a compound described herein or a combination therapy is administered to a subject that has or is at risk of getting cancer, AIDS, another viral infection, or a bacterial infection. In certain embodiments, a compound described herein, a composition comprising a compound described herein or a combination therapy is administered to a subject that is, will or has undergone surgery, chemotherapy and/or radiation therapy. In certain embodiments, a compound described herein, a composition comprising a compound described herein or a combination therapy is administered to a subject that has, will have or had a tissue transplant. In certain embodiments, a compound described herein, a composition comprising a compound described herein or a combination therapy is administered to a subject that smokes, has asthma, emphysema, allergies, bronchitis, cystic fibrosis, pulmonary fibrosis, or another disease which makes the subject susceptible to an influenza virus infection. In some embodiments, the compound, a composition comprising the compound or a combination therapy is administered to a subject that lives or works at a nursing home, a group home (i.e., a home for 10 or more subjects), or a prison. In some embodiments, the compound, a composition comprising the compound or a combination therapy is administered to a subject that attends or works at a school (e.g., elementary school, middle school, junior high school, high school or university) or daycare. In some embodiments, a compound described herein, a composition comprising a compound described herein or a combination therapy is administered to a subject that works in the healthcare area, such as a doctor or a nurse, or in a hospital. In certain embodiments, a compound described herein, a composition comprising a compound described herein or a combination therapy is administered to a subject that is pregnant or plans on becoming pregnant.

In some embodiments, a patient is administered a compound described herein, a composition comprising a compound described herein or a combination therapy before any adverse effects or intolerance to therapies other than the compound develops. In some embodiments, a compound described herein, a composition comprising a compound described herein or a combination therapy is administered to refractory patients. In a certain embodiment, a refractory patient is a patient refractory to a standard antiviral therapy. In certain embodiments, a patient with a viral infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, a compound described herein, a composition comprising a compound described herein or a combination therapy is administered to a patient to prevent the onset or reoccurrence of an influenza virus infection in a patient at risk of developing such an infection. In some embodiments, a compound described herein, a composition comprising a compound described herein or a combination therapy is administered to a patient who is susceptible to adverse reactions to conventional therapies.

In some embodiments, a compound described herein, a composition comprising a compound described herein or a combination therapy to a patient who has proven refractory to therapies other than the compound, but are no longer on these therapies. In certain embodiments, the patients being managed or treated in accordance with the methods described herein are patients already being treated with antibiotics, antivirals, antifungals, or other biological therapy/immunotherapy. Among these patients are refractory patients, patients who are too young for conventional therapies, and patients with reoccurring viral infections despite management or treatment with existing therapies.

In some embodiments, the subject being administered a compound described herein, a composition comprising a compound described herein or a combination therapy has not received a therapy prior to the administration of the compound or composition or combination therapy. In other embodiments, a compound described herein, a composition comprising a compound described herein or a combination therapy is administered to a subject who has received a therapy prior to administration of the compound, composition or combination therapy. In some embodiments, the subject administered a compound described herein, a composition comprising a compound described herein or a combination therapy was refractory to a prior therapy or experienced adverse side effects to the prior therapy or the prior therapy was discontinued due to unacceptable levels of toxicity to the subject.

5.4.2 Mode of Administration

When administered to a patient, a compound described herein is preferably administered as a component of a composition that optionally comprises a pharmaceutically acceptable vehicle. The composition can be administered orally, or by any other convenient route, for example, topically, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound described herein locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In specific embodiments, the compound can be administered topically, ocularly, intranasally or by an inhaler or nebulizer.

In another embodiment, the compound is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, the compound is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising the compound is placed in close proximity to the tissue infected with a virus to be prevented, treated and/or managed. In accordance with this embodiment, the close proximity of the controlled-release system to the infection may result in only a fraction of the dose of the compound required if it is systemically administered.

In certain embodiments, it may be preferable to administer a compound described herein via the natural route of infection of the influenza virus against which the compound has antiviral activity. For example, it may be desirable to administer the compound into the lungs by any suitable route to treat or prevent an infection of the respiratory tract by an influenza virus. Pulmonary administration can also be employed, e.g., by use of an inhaler or nebulizer, and formulation with an aerosolizing agent for use as a spray.

5.4.3 Agents for Use in Combination with the Compounds

Therapeutic or prophylactic agents that can be used in combination with the compounds described herein for the prevention, treatment and/or management of influenza virus infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steroidal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of an influenza virus infection or symptom or disease associated therewith can be used in combination with the compounds described herein in the compositions and methods described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 199 9; Cecil Textbook of Medicine, 20th Ed., Bennett and Plum (eds.), W.B. Saunders, Philadelphia, 1996, and Physicians' Desk Reference (61$^{st}$ ed. 1007) for information regarding therapies (e.g., prophylactic or therapeutic agents) which have been or are currently being used for preventing, treating and/or managing influenza virus infections.

5.4.3.1 Antiviral Agents

Antiviral agents that can be used in combination with compounds described herein include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with the compounds that target human host cell factors involved in influenza virus replication described herein include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.4.3.2 Antibacterial Agents

Antibacterial agents, including antibiotics, that can be used in combination with the compounds described herein include, but are not limited to, aminoglycoside antibiotics, glycopeptides, amphenicol antibiotics, ansamycin antibiotics, cephalosporins, cephamycins oxazolidinones, penicillins, quinolones, streptogramins, tetracycline, and analogs thereof. In some embodiments, antibiotics are administered in combination with the compound to prevent and/or treat a bacterial infection.

In a specific embodiment, the compounds described herein are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with the compounds described herein include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.4.4 Dosages & Frequency of Administration

The amount of a compound described herein, or the amount of a composition comprising a compound described herein, that will be effective in the prevention, treatment and/or management of an influenza virus infection can be determined by standard clinical techniques. In vitro or in vivo assays may optionally be employed to help identify optimal dosage ranges. The precise dose to be employed will also depend, e.g., on the route of administration, the type of infection, and the seriousness of the infection, and should be decided according to the judgment of the practitioner and each patient's or subject's circumstances.

In some embodiments, the dosage of a compound described herein is determined by extrapolating from the "no observed adverse effective level" (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, a compound described herein or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die ($L13_{10}$). In general the starting dose of a Phase I clinical trial is based on preclinical testing. A standard measure of toxicity of a drug in preclinical testing is the percentage of animals that die because of treatment. It is well within the skill of the art to correlate the $LD_{10}$ in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific influenza virus or symptom thereof (and/or other disease) to target are also factors to consider. In one embodiment, the standard conservative starting dose is about 1/10 the murine $LD_{10}$, although it may be even lower if other species (i.e., dogs) were more sensitive to the compound. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine $LD_{10}$. In other embodiments, a starting dose amount of a compound in a human is lower than the dose extrapolated from animal model studies. In another embodiment, a starting dose amount of a compound in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of compounds or compositions described herein include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 mg, about 150 mg to about 300 mg, about 150 mg to about 400 mg, 250 mg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a compound, per kilogram body weight per day. In specific embodiments, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% of a compound described herein by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound described herein per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a compound or a composition described herein, wherein the prophylactically or therapeutically effective amount is not the same for each dose.

In certain embodiments, a subject is administered a compound or a composition described herein in an amount effective to inhibit viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered a compound or a composition described herein in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition described herein in an amount effective to inhibit or reduce the spread of virus from a cell, tissue, or organ to another cell, tissue or organ by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce the spread of virus from a cell, tissue or organ to another cell, tissue or organ by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition described herein in an amount effective to inhibit or reduce viral titer by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral titer by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a compound or a composition in an amount effective to inhibit or reduce viral titer by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a compound or a composition described herein in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a compound or a composition described herein in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a compound or a composition described herein in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a dose of a compound or a composition described herein is administered to a subject every day, every other day, every couple of days, every third day, once a week, twice a week, three times a week, or once every two weeks. In other embodiments, two, three or four doses of a compound or a composition described herein is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition described herein is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of an influenza virus infection can be determined using references available to a clinician such as, e.g., the Physicians' Desk Reference (61$^{st}$ ed. 2007). In a specific embodiment, dosages lower than those which have been or are currently being used to prevent, treat and/or manage the infection are utilized in combination with one or more compounds or compositions described herein.

For compounds described herein which have already been approved for uses other than prevention, treatment or management of influenza virus infections, safe ranges of doses can be readily determined using references available to clinicians, such as e.g., the Physician's Desk Reference (61$^{st}$ ed. 2007).

The above-described administration schedules are provided for illustrative purposes only and should not be considered limiting. A person of ordinary skill in the art will readily understand that all doses are within the scope of the embodiments described herein.

5.4.4.1 Dosages for Nucleic Acid Compounds

The formulation of siRNA compositions and their subsequent administration is within the skill of those in the art. In general, for therapeutics, a subject in need of such treatment is administered a nucleic acid compound in accordance with the embodiments described herein, commonly in a pharmaceutically acceptable carrier, in doses ranging from 0.01 ug to 100 g per kg of body weight depending on the age of the patient and the severity of the disease state being treated. Further, the treatment regimen may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the compound may either be increased in the event the patient does not respond significantly to current dosage levels, or the dose may be decreased if an alleviation of the symptoms of the disease state is observed, or if the disease state has been ablated.

The dosages and regimens provided in Section 5.4.4 above may be adapted for the administration of nucleic acid compounds, such as, e.g., siRNAs.

5.5 Use of Compounds in Cell Culture and as Disinfectants

Also provided herein are the use of compounds described herein as ingredients in cell culture-related products in which it is desirable to modulate influenza viral replication, for example, to have antiviral activity. In one embodiment, one or more of the compounds described herein are added to cell culture media. In certain embodiments, compounds that prove too toxic or are not used in subjects are added to cell culture-related products, such as media. Also provided is the use of the compounds described herein as ingredients in disinfectants and soaps.

5.6 Kits

Also provided herein are kits that can be used in the above methods. In one embodiment, the kit comprises a compound described herein contained in an appropriate package. In some embodiments, a kit further comprises a negative control and/or a positive control, in an appropriate package(s). In some embodiments, the kit further comprises an influenza virus. In certain embodiments, the kit further comprises a reporter construct, in an appropriate package. In specific embodiments, the kit contains instructions for use.

6. EXAMPLE

This example describes the identification of host cell proteins that reduce or inhibit the replication of influenza virus. In particular, this example describes a genome-wide RNAi screen for siRNAs that inhibit host factors required for influenza virus replication in human cells, establishes particular classes of host proteins required for influenza virus replication, and demonstrates that siRNA and small molecule inhibition of these classes of proteins reduces influenza virus replication. See Konig et al., Nature, 2010, 463(7282):813-817, which is incorporated by reference herein in its entirety

6.1 Methods

*Renilla* Luciferase Influenza Virus.

The coding region for the viral hemagglutinin (HA) protein was replaced with that of *Renilla* luciferase and the packaging signals for the HA segment were incorporated, as previously described (Marsh et al., 2007). The recombinant WSN-Ren virus was generated by reverse genetics in the presence of complementing HA and amplified in HA-expressing MDCK cells (Marsh et al., 2007).

Genome-Wide RNAi Screen.

Genome-wide libraries comprising 98,737 synthetic siRNAs targeting 19,628 unique human genes were arrayed in 384-well plates (7 ng/siRNA) such that each well contained either two (47,560 wells) or one (3,617 wells) unique and identifiable siRNA per gene. The library matrix was introduced into A549 cells through a high throughput transfection process (Chanda et al., 2003; Aza-Blanc et al., 2003) and after 48 h the cells were infected with WSN-Ren virus at a multiplicity of infection (MOI) of 0.5. EnduRen Live Cell substrate (Promega) was added after 5 hours and relative luminescence for each well was analyzed on a plate reader (Viewlux) at 12 h, 24 h and 36 h after infection. For the toxicity screen Cell-titer-glo (Promega) reagent was added 72 h after siRNA transfection. The screens were run minimally in duplicate and analyzed using a scaling methodology that sets the positive control siRNA at an arbitrary value of 0.1, and the negative control siRNAs at 1.

Additional Information on RNAi Screen.

A 384-well plate-based assay was optimized to identify siRNAs that influence infection of human A549 cells by WSN-Ren virus. A toxicity assay was optimized to identify siRNAs that influence cell viability. The optimal ratio of the effect of the positive control siRNA (siRenilla (Ambion, AM4630) for the viral screen and siRPS27a (5'-AAGCUG-GAAGAUGGACGUACU-3') (SEQ ID NO: 727) to that of two negative control siRNA (scramble177 5'-GGTAAT-TGCGCGTGCAACT-3' (SEQ ID NO: 728) and scramble5701 5'-GCCGCTTAGTAGTCTCGTA-3' (SEQ ID NO: 729)) were used to optimize the assay conditions.

Genome-wide libraries comprising 98,737 synthetic siRNAs targeting 19,628 unique human genes in total were arrayed in 384-well plates (7 ng/siRNA) such that each well contained either two (47,560 wells) or one (3617 wells) unique and identifiable siRNA per gene). On average, there were 3 wells/gene or 6 siRNAs/gene. Each plate also contained the positive and the negative control siRNAs as indicated above. The library matrix was introduced into A549 cells through a high throughput transfection process (Chanda et al., 2003; Aza-Blanc et al., 2003). 1 pmol siRNA was incubated at RT for 20 min with 50 nl RNAimax in 20 ul Optimem/well and then transfected into 1500 A549 cells in 10 ul DMEM supplemented with 10% FBS and antibiotics. For the viral screen, after 48 h, the cells were infected at a multiplicity of infection (MOI) of 0.5 in 10 ul serum-free DMEM containing 0.875 ug/ml final concentration Trypsin (Sigma). After 5 hours, EnduRen Life Cell substrate (Promega) was added at a final concentration of 10 uM in 10 ul serum-free DMEM. Relative luminescence for each well was analyzed on a 384-well plate reader (Viewlux) at 12 h, 24 h and 36 h after infection. The screen was run twice (in independent experiments) to generate duplicate results and statistically analyzed as described below. All steps were performed using a fully integrated high-throughput cellular genomics robotic system (GNF Systems; www.gnfsystems.com).

To enable consistent comparison between assays, a scaling methodology was developed that sets the positive control (siRNA against luciferase) at an arbitrary value of 0.1, and the negative control siRNAs at 1. Luciferase activities of siRNAs targeting host factors are assigned a score based on the distribution of these values.

siRNAs targeting host factors were assigned a score based on the distribution of these values.

siRNA Libraries.

The following commercially available siRNA libraries were used in this study: the whole-genome library from Qiagen (Druggable Set version 2 (approx. 7000 genes targeted by ~28000 siRNA constructs), NM Set version 1 (approx. 10000 genes targeted by ~42000 constructs) and XM Set version 1 (approx. 5300 genes targeted by ~21000 constructs), the kinome library from Invitrogen (1287 siRNAs targeting 636 genes) and the kinome library from IDT (2176 siRNAs targeting 542 genes). In addition, druggable genome library version 1 from Qiagen, which is no longer commercially available, was used (approx. 5000 genes targeted by ~10000 siRNAs). All target influenza virus host proteins can be found in Table 3.

Bioinformatic Analysis of Screening Data siRNA Screening Data Analyses.

Screening data were normalized as previously described (Konig et al., 2007). The activity score for each gene in an assay was taken from the most potent siRNA per gene. Each screen was then analyzed using a Redundant siRNA Analysis (RSA) algorithm (Konig et al., 2007) and a p-value was assigned to each gene in a screen. The RSA p-value represents the likelihood of the corresponding siRNA signal distribution to be generated by chance, i.e., the smaller the p-value, the higher the expected confirmation rate (Konig et al., 2007). The minimum score of a gene among the 12 h-, 24 h-, and 36 h-A549 assays was chosen as the A549 activity score for the gene. With a hit criterion of an activity score <0.4, 1936 genes were defined as primary hits for the A549 influenza virus screen.

Ontology-Based Pattern Identification Analysis of siRNA Profiles.

For all genes screened, a data matrix was constructed based on inhibition across several biological assays: three A549 assays were screened at 12 h, 24 h and 36 h. Ontology-based Pattern Identification (OPI) is an algorithm that has been previously successfully applied to either predict gene functions based on their expression patterns Zhou et al., 2005; Young et al., 2005), or prioritize genes based on their phenotypic patterns (Rines et al., 2008). Here the algorithm was applied to identify gene clusters that not only share similar inhibition patterns, but also show statistical enrichment in certain functional categories. OPI clustering analysis on the 1449 genes resulted in 163 statistically significant clusters with permutation-based p-values≤0.05 and cluster size≤500. Therefore, genes that fall into any statistically significant OPI cluster were assigned a supporting score of 0.5. Additionally, a false discovery rate (FDR) analysis was conducted for each cluster, and those that fell below 0.5 were assigned a supporting score of 1.0, to reflect this additional stringency.

Gene Ontology Enrichment Analysis.

P-values of functional enrichment analyses using accumulated hypergeometric distribution (Zhou et al, 2005) were calculated on the primary hit lists. All gene members of GO groups with p-values less than $10^{-10}$ were considered to provide support for each other. See Table 3.

Reconfirmation Screens siRNAs for reconfirmation of 624 genes were individually re-arrayed such that each well of a 384-well plate contained a single siRNA (7 ng). 43 scrambled negative controls (Konig et al., 2007) were added to each plate in quadruplicate in addition to 3 commercially available controls (negative control GL2-Luciferase (Dharmacon), All-Star Negative Control (Qiagen) and Negative Control siRNA (Qiagen)) and the respective positive controls. The influenza virus infection assay was rerun as previously described. Additionally a parallel assay was run to assess potential cellular toxicity induced by the siRNA through addition of CellTiterGlo (Promega) detection reagent 72 hours after transfection. Each siRNA was screened a minimum of three times for each readout, in at least two independent assay runs.

The results from the influenza virus infection assay were analyzed such that an siRNA was considered to be confirmed only if the median signal of all readings was below 0.65 (~35% reduction). A gene was considered a true positive if there were at least two independent siRNAs confirmed based on this criterion, and that it met the toxicity criterion as described below.

Toxicity Filtering Strategy.

For the toxic control siRNA-siRPS27a, titration data series were measured for both infectivity assays and toxicity assays in 5 replicates. To estimate experimental noise level, each data series was curve-fitted using the standard sigmoidal model as defined:

$$\text{score} = \text{bottom} + \frac{\text{top} - \text{bottom}}{1 + \left(\frac{IC_{50}}{\text{concentration}}\right)^{slope}} \quad (1)$$

where bottom is reflected by a score of approximately 0, while top is reflected by the approximate score of 1. $IC_{50}$ is the siRNA concentration corresponding to the score representing 50% inhibition (around score 0.5), slope is a negative value representing Hill slope, score is the measured normalized activity value. Both data points and curve parameters were then linearly transformed so that all curves sit at a bottom value of 0 and a top value of 1. From the residue of the curve fitting, the intrinsic data noise in the experiment can be estimated as $\epsilon_T$ and $\epsilon_I$ for the toxicity assay and the infectivity assay, respectively.

The five infectivity curves and five toxicity curves form 25 unbiased toxicity-infectivity (T-I) relationship pairs, i.e., $$\text{Toxicity}(c) = \frac{1}{1 + \left(\frac{TOX_{50}}{c}\right)^{TOX\ slope}} + \varepsilon_T \quad (2)$$

$$\text{Infectivity}(c) = \frac{1}{1 + \left(\frac{INF_{50}}{c}\right)^{INF\ slope}} + \varepsilon_I \quad (3)$$

With increasing concentration of siRNA (zero to infinity), c, a series of infectivity and toxicity scores were determined. The boundary represents the average infectivity score for any given toxicity score, if the siRNA is toxic.

The next step was to establish the infectivity confidence threshold for any given toxicity score, so that the boundary is below 95% of the possible infectivity scores produced by a random toxic siRNA. If an siRNA of interest produces an infectivity score below the established threshold (lower score means higher activity), the false positive p-value is below 0.05. This can be simulated by using the Gaussian noise term $\varepsilon_T$ and $\varepsilon_I$ in equation (2) and (3).

More specifically, for any given observed toxicity score T between 0 and 1, at the incremental size of 0.01, we generated 1000 true toxicity scores based on the Bayesian probability of their occurrence, simulated based on equation (2). Each simulated true toxicity score then led to a true concentration c, and resulted in 1000 infectivity scores I according to equation (3). The 95 percentiles of the 1,000,000 simulated infectivity scores for each given observed toxicity score are used to construct the decision boundary.

FIG. 4 shows the decision boundary as a curve. When an siRNA falls into the region above the boundary, its effect on infectivity is unlikely to be caused by toxicity (p<0.05). When a toxicity score is <0.34, the infectivity score of an siRNA is highly likely to be affected by its toxicity, indicated by the flat horizontal line segment in the upper right corner of the plot. As toxicity scores get larger (weak toxicity) and the corresponding infectivity score is sufficiently low (above the curve), the effect of the siRNA on infectivity is most likely to be true. That the T-I data points from our positive control siRenilla (lighter gray dots) had most data points above the decision boundary was also verified, showing that the siRNA is a true hit, while toxic controls (darker gray dots for siRPS27a) fall below the decision boundary. The non-toxic negative control scrambled siRNA fell mostly below the decision boundary. Although some controls slightly cross the boundary at the high infectivity score end (weak infectivity and toxicity), they all fall into a region where infectivity score>0.6, which means that these siRNAs would not be hit picked and therefore do not introduce decision errors.

Selection for Hit Criteria.

The criteria for selection at each stage of the screen progress are as follows (FIG. 2a): (i) Genome-wide analysis was followed by bioinformatics analysis (see Methods), followed by reconfirmation analysis. After reconfirmation analysis, genes with at least 2 siRNAs that resulted in a 35% (~2 SD) or greater decrease in influenza virus reporter activity, without concomitant induction of cytotoxicity, were selected. (ii) WT influenza virus multi-cycle growth analyzed by hemagglutinin assay: >4 fold reduction of wild-type influenza virus multi-cycle growth using at least 2 siRNAs targeting the same gene. (iii) Viral gene expression analyzed by quantitative RT-PCR of NP and M1 influenza protein: transfection of 1 or more siRNAs per gene resulting in a 35% or greater decrease in influenza virus NP and M1 RNA transcription. (iv) Functional assays employed to characterize several of the host factors (validated in the HA-assay) in entry and post-entry steps of virus replication include: pseudotyped particle entry assay (pH-dependent/-independent), Bla-M1 influenza VLP entry assay, NP localization at 90 and 180 min post-infection and influenza mini-genome replication assay (as described infra). Of the 45 factors tested in functional assays, 12 did not meet the criteria for classification.

Cells and Viruses.

A549 cells, 293T cells, Vero cells and MDCK cells were maintained in Dulbecco's minimal essential medium containing antibiotics and 10% fetal bovine serum at 37° C. and 5% $CO_2$. Generation of and maintenance of MDCK cells expressing the HA protein of influenza A/WSN/33 virus was described previously (Marsh et al., 2007).

Influenza A virus A/WSN/33 and swine origin influenza A/Netherlands/602/2009 virus (SOIV) were grown in MDCK cells. Virus stocks were titered by plaque assay on MDCK cells. Vesicular stomatitis virus (VSV) was grown and titered in Vero cells. The WSN-Ren virus was grown and titered in MDCK-HA cells.

siRNA Transfections of A549 Cells.

A549 cells (passage 2-15) were transfected with siRNAs at a concentration of 30 nM in a reverse transfection procedure using RNAiMAX (Invitrogen, Carlsbad, Calif.). Knockdown was allowed to proceed for 48 h before cells were infected or tested in functional assays.

Inhibition of Virus Growth.

siRNA-transfected A549 cells were infected with either influenza A/WSN/33 virus or VSV (MOI of 0.01) or swine origin influenza A/Netherlands/602/2009 virus (SOIV) (MOI of 1) at 48 h post siRNA transfection. At 36 h post infection supernatants were harvested and virus titers were determined by plaque assay on MDCK cells (for A/WSN/33 and A/Netherlands/602/2009) or on Vero cells for VSV.

Screen for Inhibition of WT Influenza Virus Growth.

A549 cells were transfected with siRNAs as described above. At 48 h post transfection cells were infected with influenza A/WSN/33 virus at a multiplicity of infection (MOI) of 0.01. At 36 h post infection supernatants were harvested and titered by hemagglutination assay (HA assay). In brief, two-fold serial dilutions of the supernatant were incubated with chicken red blood cells at a final concentration of 0.25% for 60 min on ice. For each gene at least two different siRNAs were tested individually and the gene was called a required host factor if there was a difference of at least four-fold in hemagglutination titer for two or more siRNAs. Values for WSN WT in FIGS. 2b and 3a represent the mean of 2 replicates.

Quantitative RT-PCR.

A549 cells were reverse transfected with siRNAs using Lipofectamine RNAiMAX reagent (Invitrogen) in 96 well plates. Briefly, 2 pmol siRNAs were diluted in 20 ul of Opti-MEM (Invitrogen) and mixed with 200 nl of Lipofectamine RNAiMAX with 20 ul Opti-MEM for 20 min. A549 cells ($2 \times 10^5$ cells/ml) in 60 ul DMEM containing 10% FBS were added to each well. 48 h after transfection, influenza A/PR/8/34 virus (MOI=0.5) and TPCK trypsin (50 ng; 0.9 ug/ml final) in 10 ul of DMEM were added to cells. 8 h after infection, RNA samples were isolated using RNeasy 96 Total RNA Isolation kit (Qiagen).

For cDNA synthesis, QuantiTect Reverse Transcription Kit (Qiagen) was used in accordance to the manufacturer's protocol.

Real-time PCR was performed using SYBR Green PCR Master Mix (Applied Biosystems) with the primer sequences described below. IFNb: sense primer sequence 5'-TGA-CATCCCTGAGGAGATTAAGC-3' (SEQ ID NO: 730) and antisense primer sequence 5'-CTGGAGCATCTCATA- GATGGTCAAT-3' (SEQ ID NO: 731). PR8 NP: sense primer sequence 5'-TGGCATTCCAATTTGAATGAT-3' (SEQ ID NO: 732) and antisense primer sequence 5'-ATCCATTCCG-GTGCGAACAAG-3' (SEQ ID NO: 733). PR8 M1: sense primer sequence 5'-CCGTCGCTTTAAATACGGACT-3' (SEQ ID NO: 734) and antisense primer sequence 5'-AG-CACTCTGCTGTTCCTTTCG-3' (SEQ ID NO: 735). GAPDH was selected as the endogenous control gene and was amplified using sense primer sequence 5'-GAAGATG-GTGATGGGATTTC-3' (SEQ ID NO: 736) and antisense primer sequence 5'-GAAGGTGAAGGTCGGAGTC-3' (SEQ ID NO: 737). Primers for analyzing knock-down efficiency of siRNA treatment are shown in Table 2.

cDNA samples were amplified under standard thermal cycler protocol (50° C. for 2 minutes, 95° C. for 10 minutes, and 40 cycles of 95° C. for 15 seconds and 60° C. for 1 minute). Relative expression level was calculated using the endogenous control GAPDH. Fold changes were calculated against the median of negative control siRNAs, scramble 177 (5'-GGTAATTGCGCGTGCAACT-3') (SEQ ID NO: 738), 1212 (5'-ATCCGCGCGATAGTACGTA-3') (SEQ ID NO: 739), 6105 (5'-GTAAGCTCGTGCGACGTAT-3') (SEQ ID NO: 740), siGL2 (Dharmacon), siGL3 (Dharmacon) and siGFP-22 (Qiagen). Each value for relative expression levels in Tables 7 and 8 and FIGS. 2b and 3a represent the average of at least two independent results. The relative expression levels in Table 11 are comprised of the average of four replicates.

Entry Assays.

Pseudoparticles bearing different viral envelopes were used to elucidate genes involved in influenza virus entry. Specifically, siRNA-transfected A549 cells were incubated with an appropriate dilution of different pseudoparticles for one hour. The inoculum was removed, medium was added back and cells were incubated for 36 h. Entry efficiency was measured as the amount of luciferase secreted into the supernatant (*Renilla* Luciferase Assay System, Promega, Madison, Wis.). A gene was considered a hit in the pseudoparticle assay if one siRNA reduced luciferase signal by at least 65% compared to a scrambled control siRNA and a second siRNA resulted in a reduction of at least 50%. Pseudoparticles were generated by transfecting 293T cells with plasmids encoding (i) a minimal HIV provirus encoding the Gaussia luciferase reporter gene, (ii) HIV gag-pol, and (iii) a viral envelope protein (WSN-HA/NA, VSV-G or MMLV env) using FuGENE6 (Roche Applied Science, Indianapolis). Each data point in FIG. 2b and FIG. 3a represents the mean of at least 3 replicates.

The beta-lactamase-M1 (Bla-M1) virus-like particle (VLP) assay was performed as follows: Bla-M1 VLPs contain WSN HA, NA, and a Bla-M1 fusion protein, which is packaged as a structural component into the VLP and released upon fusion with the target cell. siRNA-transfected A549 cells were incubated with the Bla-M1 VLPs and centrifuged at 1.5 k rpm, for 90 min at 4° C. The cells were then transferred to 37° C. and incubated an additional 3-4 h. To detect beta-lactamase activity by flow cytometry, cells were detached and loaded with CCF2-AM substrate (Invitrogen). Flow cytometry was performed at the Mount Sinai Flow Cytometry Shared Resource Facility on an LSRII flow cytometer (Becton Dickinson, Miami, Fla.). Samples were gated on live cells and analyzed for their cleavage of CCF2 using FlowJo 8.5.2 software.

Influenza Mini-Genome Assay.

For the minigenome assay, 293T cells were transfected with siRNAs as described for A549 cells. At 48 h post transfection, cells were transfected with plasmids encoding the three polymerase subunits and the nucleoprotein of influenza virus A/WSN/33, the reporter construct pPOLI-Luc-RT, encoding firefly luciferase in the negative-sense orientation flanked by the noncoding regions of segment 8 of strain A/WSN/33 (Stertz et al., 2007) as well as the control reporter plasmid pRL-SV40-Rluc (Promega, Madison, Wis.). The amounts of polymerase encoding plasmids were titrated to achieve 50% of the system's maximum activity. At 36 h post transfection reporter activity was determined using the Dual-Glo Luciferase Assays system (Promega, Madison, Wis.). Each data point in FIG. 3c represents the mean of at least 6 replicates.

Immunofluorescence.

At 48 h post transfection siRNA-treated A549 cells were pre-chilled for 15 min on ice, washed with cold PBS and then infected with influenza virus A/WSN/33 at an MOI of 10 for 45 min on ice to synchronize the infection. Unbound virus was removed by three washes with cold PBS. Pre-warmed medium was added and cells were incubated at 37° C. At different time points post infection cells were fixed with 3% paraformaldehyde for 15 min at room temperature (RT) and subsequently permeabilized with 0.5% Triton-X-100 for 5 min at RT. Immunofluorescence staining was performed using the mouse monoclonal antibody HT103 against influenza A virus nucleoprotein (O'Neill et al., 1998) as a primary antibody and a donkey anti-mouse Alexa 488 secondary antibody (Invitrogen, Carlsbad, Calif.). In addition, nuclei were stained with DAPI (Invitrogen, Carlsbad, Calif.). Confocal laser scanning microscopy was performed at the MSSM-Microscopy Shared Resource Facility.

Immunofluorescence of EEA1 and Influenza Virus Particles.

A549 cells on cover slips were reverse transfected with 30 nM ATP6V0C siRNA or 5757 negative control siRNA (5'-GGTGCTCAGTCGCAATAGT-3') (SEQ ID NO: 741). 48 h post transfection, WSN virus was added to the cells at an MOI of 1 for 20 mins. The cells were then fixed with 4% PFA in PBS. WSN-HA was stained with a mouse monoclonal antibody; 2G9D1 (Palese lab, MSSM) and Cy3 conjugated secondary antibody (Jackson ImmunoResearch). Early endosomes were stained with a rabbit polyclonal EEA1 antibody (Abcam) and Cy5 conjugated secondary antibody (Jackson ImmunoResearch). DNA was stained with DAPI. The cover slips were imaged at 100× magnification and z stacks were collected using an Olympus FV1000 confocal microscope. The total number of HA positive virions in a single cell were manually counted.

High Content Imaging.

The high-content imaging-based analysis was performed using the Opera (Perkin-Elmer, Waltham, Mass.), a fully automated confocal microscope system. 384-well plates containing cells transfected with various siRNAs were exposed to the virus (MOI=5) and fixed at three different time points (T=0', T=90' and T=180'). After immunofluorescence labeling (as previously described), cells were imaged using a 20×0.7NA Water immersion lens (Olympus, Japan). A total of 10-11 images for both the nuclear stain (Hoechst) and the Alexa488 labeled WSN-NP were taken in each well.

Cellular features were then extracted from the images using a custom Acapella script (Perkin-Elmer), and the median value for each of these features was calculated to provide a well-level feature set. The ratio of nuclear versus cytoplasmic WSN-NP intensity (Nuc/Cyto ratio) was determined. The mean value and the standard deviation was calculated for each siRNA and each time point. The non-targeting siRNAs for which Nuc/Cyto ratio was four standard deviations away from the mean were discarded as outliers. A Welch TTest was then performed between each siRNA and non-targeting siRNAs. The siRNAs with pValue<0.01 and at least a 15% difference in signal from controls were selected as relevant and imaged again with the Opera this time using a 40×0.9NA water immersion lens (Olympus). Representative images were selected from the 10 images collected in the different controls (FIG. 9). Data shown in FIG. 3a were generated by background subtraction of all values using the scrambled negative control measurements at 0' as a baseline (negative values were set to 0.001), and then scaled such that the negative control 180' value equaled 1.

Small Molecule Inhibitors.

HSP90 Inhibitor, CCT018159 (Calbiochem), Podophyllotoxin (MP Biomedicals), FGF/VEGF Receptor Tyrosine Kinase Inhibitor (Calbiochem, 341607), Sirolimus (LC Laboratories), Hymenialdisine (Biomol International LP), Betulinic Acid (VWR International (Enzo Life Sciences Intl)), were dissolved in their respective diluent DMSO or ethanol (for Podophyllotoxin) and titrated in DMSO starting from 100 uM. Inhibition of WSN-Ren virus growth in MDCK-HA cells was determined by *Renilla* luciferase activity at 36 h post infection (or 24 h post infection for Sirolimus). Cellular toxicity was determined by CellTiterGlo assay (Promega Corp., Madison, Wis.).

Diphyllin was identified in a high-throughput screen of small molecular weight compounds as having influenza virus inhibitory activity. The screen assay was described previously (Hoffmann et al., 2008) and diphyllin was identified from a library supplied by ChemDiv (San Diego, Calif.). The screen was performed at the National Screening Laboratory for the Regional Centers of Excellence in Biodefense (NSRB), Harvard Medical School, Boston.

Diphyllin and KN-93 were purchased from Sigma and Calbiochem, respectively and dissolved in DMSO. Cellular toxicity was determined by the CellTiterGlo assay (Promega Corp., Madison, Wis.) and inhibition of virus growth was determined by standard plaque assay.

Interferon Bioassay.

48 hours after transfection of siRNAs, A549 cells were either mock treated or infected with influenza A/PR/8/34 virus (MOI=3). Control samples were also infected with a recombinant PR/8/34 virus expressing a truncated NS1 protein (residues 1-113), as a positive control for IFN induction. After 1 hour of adsorption, DMEM containing 10% fetal calf serum was added, and the cells incubated for 18 hours at 37° C. in 5% $CO_2$. Levels of interferon secreted by the cells were determined as previously described (Donelan et al., 2003) with some variations. At 18 hours post infection, supernatants were harvested and virus present in the supernatant was UV inactivated by placing the 96-well plate in a UV chamber delivering 200 $J/cm^2$. 2-fold dilutions of the inactivated supernatants were added to Vero cells previously seeded in 96-well plates. Following a 24 h incubation the Vero cells were infected with a GFP-expressing Newcastle disease virus (NDV-GFP) (Park et al., 2003). Cells expressing GFP were visualized 24 h post infection by fluorescence microscopy. Each image was analyzed with the software ImageJ (NIH) and the Mean Fluorescence Value per unit area of each image was calculated.

Inhibition of Virus Growth.

siRNA-transfected A549 cells were infected with either influenza A/WSN/33 virus or VSV at a multiplicity of infection (MOI) of 0.01 or swine origin influenza A/Netherlands/602/2009 virus (SOIV) at an MOI of 1 at 48 h post siRNA transfection. At 36 h post infection supernatants were harvested and virus titers were determined by plaque assay on MDCK cells (for A/WSN/33 and A/Netherlands/602/2009) or on Vero cells for VSV. Each sample in FIG. 3e is represented by at least 3 replicates.

6.2 Results

A genome-wide RNAi screen with human lung epithelial (A549) cells was performed in order to characterize host cell factors involved in influenza virus replication in human cells. To facilitate the readout for the high-throughput screen, the coding region for the influenza A/WSN/33 virus hemagglutinin (HA) protein was replaced with that of *Renilla* luciferase (FIG. 1a) (Marsh et al., 2007). As no HA is produced, this recombinant virus cannot complete its replication cycle. Thus the RNAi screen focused on the cellular requirements for viral entry, uncoating, nuclear import, and viral RNA transcription/translation, but was not expected to identify factors involved in virus assembly, budding or release.

An arrayed siRNA library targeting over 19,000 human genes was employed to transfect human A549 cells (FIG. 1b). These cells were infected with the modified influenza virus (WSN-Ren), and luciferase readings were taken after 12, 24, and 36 h. Data from two independent screens were analyzed using a Redundant siRNA Activity (RSA) and ontology-based analyses (see *Methods* supra; Konig et al., 2007). Using these methodologies, 295 cellular genes for which at least 2 siRNAs reduced viral infection by 35% or greater (~2 standard deviations from mean of negative controls), without a concomitant induction of significant cellular toxicity (FIG. 4 and Table 3), were confirmed. The majority of the factors identified through this analysis represent host genes that have not previously been implicated in mediating influenza virus replication.

Analysis of over-represented biological annotations identified over 170 statistically enriched categories (Table 4), which fell into 11 broadly related functional groups (FIG. 5). Signaling molecules, including those involved in the PI3K/AKT pathway, molecules that function to regulate cytoskeletal dynamics, and proteins involved in ubiquitination, phosphatase, and protease activities were overrepresented amongst the 295 factors, underscoring the importance of these cellular functions during influenza virus infection (Tables 5 and 6). Consistent with these observations, small molecule inhibition of two identified AKT pathway regulators, mTOR (FRAP1) and HSP90AA1, as well as microtubule assembly (TUBB), were found to result in a dose-dependent inhibition of influenza virus replication (FIG. 6) (Sato et al., 2000; Sarbassov et al., 2005).

To verify that the genes identified through the use of the reporter virus reflect the requirements in the context of a wild-type (WT) virus infection, 219 of 295 identified genes were confirmed to inhibit multi-cycle replication of WT WSN virus with at least two siRNAs per gene. Furthermore, 76% of the remaining genes had one siRNA that inhibited WT influenza replication, indicating a high confirmation rate (FIG. 2a, Table 7). For a subset of these genes additional assays were undertaken to confirm that depletion of these genes resulted in reduced viral gene expression (FIG. 2a, Table 7), and also to ensure that inhibition of viral replication was not being triggered by a non-specific siRNA-mediated induction of an antiviral state (Table 8).

Next, to identify factors specifically involved in virus entry steps, 45 of the top-scoring genes in the WT WSN assay were selected to be tested in a pseudotyped particle (PP) entry assay, designed to identify host factors that impede low-pH-dependent entry mediated specifically by influenza virus HA (WSN) and vesicular stomatitis virus (VSV)-G protein, while not affecting pH-independent entry promoted by the murine leukemia virus (MMLV) envelope (Env) (Beer et al., 2005; McClure et al., 1990). WSN-PP infection was reduced in the presence of siRNAs targeting 23 of these genes, including CD81, FGFR4, GSK3B, MAP2K3 and the v-ATPase subunit ATP6V0C (FIGS. 2a, 2b, and 7a-c; Table 9). These genes were also required for efficient VSV-G-PP (but not MMLV-PP) infection, suggesting a role in low-pH-dependent virus entry. Importantly, small molecule inhibitors of FGFR4, GSK3B, and v-ATPase activities attenuated replication of WSN virus, further highlighting their importance in influenza virus infection (FIGS. 6 and 8a-e).

The COPI coat complex is made up of seven subunits. COPI association with endosomes is pH-dependent and coatomer complex is required for the formation of intermediate transport vesicles between the early and late endosomes (Whitney et al., 1995; Aniento et al., 1996). Consistent with this role, depletion of COPG and ARCN1 both blocked WSN-PP infection (FIG. 2b). The requirement for ARCN1 during the influenza virus entry step was further demonstrated using a more direct virus-like particle (VLP) assay (FIG. 2c) (Tscherne et al.), as well as immunolocalization studies (FIG. 2d).

To evaluate those factors involved in influenza virus replication but not influenza virus entry, the localization of the influenza virus nucleoprotein (NP) in siRNA-depleted cells after infection with influenza A/WSN/33 virus was monitored (FIGS. 3a and 9). In comparison to controls, cells depleted of CSE1L, PRSS35, F13A1, SF3A1, CAMK2B, KPNB1, and PPP1R14D showed a significant decrease (p<0.01) of nuclear to cytoplasmic ratios of NP protein at 180 min. With the exception of F13A1, depleting these factors did not inhibit entry by WSN pseudotyped virus or β-lactamase (Bla)-M1 VLPs (FIG. 3a), confirming their role in post-entry steps of influenza virus infection. Depletion of CSE1L, PRSS35, and F13A1 also led to a statistically significant (p<0.02) reduction of nuclear to cytoplasmic NP ratios at 90 minutes post-infection, suggesting that they are involved in early post-entry steps, such as viral uncoating or nuclear import of viral ribonucleoproteins (vRNPs; see also FIG. 10). Consistent with a role in nuclear trafficking, imaging at higher resolution confirmed that RNAi-mediated inhibition of CSE1L, but not CAMK2B or KPNB1, results in a decrease in nuclear vRNPs typically seen 90 min after infection with influenza virus (FIG. 3b) (Kutay et al., 1997). Furthermore, CSE1L specifically inhibited influenza virus gene expression in a mini-genome replicon assay, indicating that CSE1L activity is required for the nuclear import of vRNPs as well as newly synthesized viral proteins (FIG. 3c; Table 10).

Calcium/calmodulin-dependent protein kinase (CaM kinase) II beta (CAMK2B) is a ubiquitously expressed calcium sensor that regulates diverse cellular functions, including actin cytoskeletal regulation and CREB-dependent transcription (Colbran et al., 2004). The data presented here implicate this kinase in the regulation of influenza viral RNA transcription as siRNA-knockdown of the kinase had an effect on expression of an influenza mini-genome (FIG. 3c), but did not delay nuclear accumulation of vRNPs at 90 min post-infection (FIG. 3b). A specific inhibitor of CAMK2B, KN-93, was also shown to inhibit influenza virus growth (FIGS. 3d and 11) (Sumi et al., 1991).

Finally, the requirements for twelve identified host cellular factors in the replication of a swine-origin influenza virus (SOIV) isolate from the 2009 pandemic (A/Netherlands/602/2009 (H1N1)) in comparison with influenza A/WSN/33 virus and VSV was assessed. Viral growth in siRNA-treated A549 cells revealed that all these proteins are required for both SOIV and WSN replication but none of these factors, with the exception of the vATPase and COPI factors, inhibited VSV replication (FIGS. 3e and 12; Table 11).

6.3 Discussion

Influenza A virus is an RNA virus that encodes up to eleven proteins and this small coding capacity demands that the virus utilize the host cellular machinery for many aspects of its life cycle (Palese & Shaw, 2007). Here genome-wide RNAi screening using an siRNA library was employed to identify 295 human host cell factors required for early-stage influenza virus replication. Within this group, those involved in kinase-regulated signaling, ubiquitination and phosphatase activity are the most highly enriched. Moreover, 219 of the 295 factors were confirmed to be required for efficient wild-type influenza virus growth and further analysis of a subset of genes revealed 23 factors necessary for viral entry, including members of the vacuolar ATPase (vATPase) and COPI-protein families, fibroblast growth factor receptor (FGFR) proteins, and glycogen synthase kinase 3 (GSK3)-beta. Additionally, 10 proteins were confirmed to be involved in post-entry steps of influenza virus replication. These include nuclear import components, proteases, and the calcium/calmodulin-dependent protein kinase (CaM kinase) II beta (CAMK2B). Growth of swine-origin H1N1 influenza virus was also found to be dependent on the identified host factors. Small molecule inhibitors of several of the identified human host cell factors, including vATPase and CAMK2B, were also found to antagonize influenza virus replication.

This genome-wide analysis of influenza virus host factor requirements has revealed a number of cellular proteins and biological pathways previously unknown to be involved in the influenza virus life cycle. These include the identification of COPI complex, FGFR, GSK3B, CAMK2B, PRSS35, and others. This study focused on host factors that regulate the early steps of influenza virus replication and provided new insight into the host-pathogen interactions that orchestrate the viral replication cycle and novel targets for the development of host factor-directed antiviral therapies.

7. TABLES AND TABLE LEGENDS

TABLE 1

Nucleobases are represented by their one-letter code, i.e., adenine (A), guanine (G), cytosine (C), thymidine (T), and uracil (U)

| SEQUENCE | SEQ ID NO. |
|---|---|
| CCCACTTGTGTCAATATTAAA | 1 |
| AAGGCTGAGATGCGTCGTAAA | 2 |
| GAGCTTGAATTTGAAGGTGTA | 3 |
| ATGGAGGTTGATGGTAAGGTA | 4 |
| ACCATGTTACCCTGTAATTAA | 5 |
| CACGGTTAATGAAGTCTGCTA | 6 |
| CAGCCACAGAATATTATGTAA | 7 |
| TCCCAGCTATCTATAACCTTA | 8 |
| CATGGCAATTGTCATTAGCAA | 9 |
| TCCTAGTGTTTGTGAAATAAA | 10 |

TABLE 1-continued

Nucleobases are represented by their one-letter code, i.e., adenine (A), guanine (G), cytosine (C), thymidine (T), and uracil (U)

| SEQUENCE | SEQ ID NO. |
|---|---|
| CACAGTGACATTCAAGTTCAT | 11 |
| TAGCAAATGCTCCCTCCTTAA | 12 |
| CACGACCATCCTGAACCCACA | 13 |
| CAGGATCTCTGACATCCTGAA | 14 |
| CAGGATAATGTTATCAAAGTA | 15 |
| CTGACGGTATCAAATATATTA | 16 |
| CAAATGAACTTGTAAACCTAA | 17 |
| CAAGGAGAGATGGGACACTAA | 18 |
| GCUGGAGCUAUGGUCAGUU | 19 |
| CCGCCTGACCTTCGGACCCTA | 20 |
| CAGGAGGTTCTGGGCCTCTGA | 21 |
| GUGACACAGCUACCAAUUC | 22 |
| AACCAGTGACACAGCTACCAA | 23 |
| TCGGTTATATTTGCCAAGATA | 24 |
| CAAGAACTCTTTGACATCTAA | 25 |
| CTGGATGCCATCCAAGTTGTA | 26 |
| ACGGATATCCTGCATGTCCAA | 27 |
| CCCGGAGATGATCCCAACAAA | 28 |
| CACCATAGAATCTCACACCAA | 29 |
| CAGAGAGATACTCGCAGGCAA | 30 |
| CAGCAGCTGATCATGGATGAA | 31 |
| CAGGATAAGACGGAATGGAAA | 32 |
| CGCAAGGATTATGATCCCAAA | 33 |
| CCGAGCCACCTTCTACCTAAA | 34 |
| AGGCCCGTGTATTTAATGAAA | 35 |
| CAGAGGATCTTTCCAACCACA | 36 |
| CCAGTGAATTCTGGTGGCAAA | 37 |
| GAGCCTGAGATTGACCTGGAA | 38 |
| CAGGAGCTCTTCCAGGATCAA | 39 |
| CCGTAGTGAGATCACTTCATA | 40 |
| TACGGCTAACAGAGACCTGAA | 41 |
| CACCCTCTCCTTGTCACAGAA | 42 |
| CTCCATTGCATTCATGTACTA | 43 |
| AGCCATCATACGAGATCTTAA | 44 |
| ATGATTGGCAATGACAAACAA | 45 |
| AACCGGATTGCCATTTATGAA | 46 |
| TTGAATAAACTTACAGCCAAA | 47 |
| CCGCATCACCTCCGCGTACTA | 48 |

TABLE 1-continued

Nucleobases are represented by their one-letter code, i.e., adenine (A), guanine (G), cytosine (C), thymidine (T), and uracil (U)

| SEQUENCE | SEQ ID NO. |
|---|---|
| CACGGACGGACAGAAGCCCAA | 49 |
| CCGCCTGTTTGGGTTAACAAA | 50 |
| CAGGATTACACTGAAAGTAAT | 51 |
| CACGAAGAACTAAGAATATTA | 52 |
| CAGCAATTACATTAAATTCAA | 53 |
| CCGGAAGGAGTACTCCCAGAA | 54 |
| AGCCATTTACTTGCACCGGAA | 55 |
| TAGGTACTGTTAAGTAAGTAA | 56 |
| CCCGATGACAATAGTGATGAT | 57 |
| CAGCATTGTCCTGCAGCTGAA | 58 |
| AAAGGAGATCGAGGAGAGAAA | 59 |
| CAGGGAGCACTATGAAAGGAA | 60 |
| CCACGAAAUCGCCCAUCAU | 61 |
| CACATGGTACCTGGATTCAGA | 62 |
| CCGGCCTTGACCGGAGGAGAA | 63 |
| GGAGACCUUCAACCUCUAU | 64 |
| UACCUGUGGCAUCACCAAG | 65 |
| CGCGTTCATAACTGTCCTCAA | 66 |
| CACCTTCTATGTAGGCATCTA | 67 |
| AAGGAACATCAGGCATGCTAA | 68 |
| CCCATCTGACAAGGGAAATTA | 69 |
| CGGAGGAGCGTTGCCATTCAA | 70 |
| CTGGCGGACTTCCAGATCGAA | 71 |
| ACCACGGAAGTCGAGAATTAA | 72 |
| CACTCAAGAACTGTCAAGTAA | 73 |
| TCAGTTGGTAGAAATAATCAA | 74 |
| CACGGATTTAGTCCCACCCTA | 75 |
| GAGGAGCGATGTGATGAATAA | 76 |
| CCCGCGGATCTACGTGGGCAA | 77 |
| CCGTATTTACTTAACAAGATT | 78 |
| CACAGTTATTACTGCAGTGAA | 79 |
| AAGACAGTCTTTAAAGTGTAA | 80 |
| CCCUCUCAACCUCACUCUU | 81 |
| CTGGATTGACTTTGCTGTCAA | 82 |
| GCUUCAUCGAGCAGCAGUU | 83 |
| CAAGACAGAGATGGACCGCAA | 84 |
| GGUCCUUUUGGCCAGAUCU | 85 |

TABLE 1-continued

Nucleobases are represented by their one-letter code, i.e., adenine (A), guanine (G), cytosine (C), thymidine (T), and uracil (U)

| SEQUENCE | SEQ ID NO. |
|---|---|
| TGGGTAGAAGTCACTATATAA | 86 |
| TTGATGTGTTTCAACAGCCTA | 87 |
| TACTGCATTCTCAATTAGAAA | 88 |
| CTGTCTTTAAGTAGGGATAAA | 89 |
| AAGTAGGGATAAATTACTCTA | 90 |

TABLE 2

| Gene Name | Sense or Antisense Primer | SEQ ID NO. | Primer Sequence 5'-3' |
|---|---|---|---|
| ARCN | sense | 91 | GGGGTGCTAAAGTGGAGACTAC |
| ARCN | antisense | 92 | CACAGCCATTTCCACTCTCC |
| ATP6VOC | sense | 93 | CCCGAGTATGCTTCGTTTTCG |
| ATP6VOC | antisense | 94 | CATGACCACTGGGATGATGGA |
| CD81 | sense | 95 | TTCCACGAGACGCTTGACTG |
| CD81 | antisense | 96 | CTTCCCGGAGAAGAGGTCATC |
| CSE1L | sense | 97 | CAGAACACGCTGACAAGTATCT |
| CSE1L | antisense | 98 | AGCCCTGCGTCTAGTATCAATA |
| FGFR4v1 | sense | 99 | AGGCCTCTGAGGAAGTGGA |
| FGFR4v1 | antisense | 100 | CTGCCCAAGGGCTACTGTC |
| GABBR1 | sense | 101 | CCCGACTTCCATCTGGTG |
| GABBR1 | antisense | 102 | GTGGCGTTCGATTCACCT |
| GSK3B | sense | 103 | ATTTCCAGGGGATAGTGGTGT |
| GSK3B | antisense | 104 | GGTCGGAAGACCTTAGTCCAAG |
| MAP2K3 | sense | 105 | GGAGGCTGATGACTTGGTGAC |
| MAP2K3 | antisense | 106 | CTGCTCCTGTGAGTTCACGG |
| PRSS35 | sense | 107 | CCCTGGGTGGACCCTCATT |
| PRSS35 | antisense | 108 | CATTCGATGCCACACACTGTAT |
| MID1IP1 | sense | 109 | ACAGCCACTACGTGCTTCTC |
| MID1IP1 | antisense | 110 | CTTTGCGCGTGAGTTTCGAG |
| SUMO2 | sense | 111 | GAAAGCCTATTGTGAACGACAGT |
| SUMO2 | antisense | 112 | TCTGCTGTTGGAACACATCAA |
| CAMK2B | sense | 113 | CCTACGCGAAAATCTGTGACC |
| CAMK2B | antisense | 114 | TGGAAGTCCATCCCTTCAACC |

TABLE 3

Scores of 295 confirmed genes required for influenza virus replication.

| geneID | symbol | Description | GenbankID | target sequence | SEQ ID NO. | Avg Score 12 h | Avg Score 24 h | Avg Score 36 h |
|---|---|---|---|---|---|---|---|---|
| 70 | ACTC1 | actin, alpha, cardiac muscle 1 | NM_005159 | TCCTAG CACCAT GAAGAT TAA | 685 | 0.347406 | 0.654357 | 0.723359 |
| 70 | ACTC1 | actin, alpha, cardiac muscle 1 | NM_005159 | CTGATC GTATGC AGAAGG AAA | 115 | 0.773109 | 0.753557 | 0.63823 |
| 92 | ACVR2A | activin A receptor, type IIA | NM_001616 | TCCACG GTTGCT AAATTA TAA | 116 | 1.060619 | 0.789506 | 0.495063 |
| 92 | ACVR2A | activin A receptor, type IIA | NM_001616 | ACCAAT CAAACT GGTGTT GAA | 117 | 0.770721 | 0.631887 | 0.57984 |
| 147 | ADRA1B | adrenergic, alpha-1B-, receptor | NM_000679 | CCCUUC UAUGCC CUCUUCU | 118 | 0.94438 | 0.614155 | 0.305548 |
| 147 | ADRA1B | adrenergic, alpha-1B-, receptor | NM_000679 | GCUAAG ACGUUG GGCAUUG | 119 | 0.632903 | 0.844488 | 1.005673 |
| 157 | ADRBK2 | adrenergic, beta, receptor kinase 2 | NM_005160 | CAAGTG TATGGG ATTAAC TAA | 120 | 0.325952 | 0.417845 | 0.453045 |
| 157 | ADRBK2 | adrenergic, beta, receptor kinase 2 | NM_005160 | GGAGAC UGUCCU UUCAUUG | 121 | 0.905301 | 0.670602 | 0.536821 |

TABLE 3-continued

Scores of 295 confirmed genes required for influenza virus replication.

| | | | | | | | |
|---|---|---|---|---|---|---|---|
| 207 | AKT1 | v-akt murine thymoma viral oncogene homolog 1 | NM_001014432 | /5 Phos/rCr GrUrCrArCr CrArArCr GrArArCr GrArGrUr UrUrGrAr GrUAC | 122 | 0.529835 | 0.474022 | 0.350932 |
| 207 | AKT1 | v-akt murine thymoma viral oncogene homolog 1 | NM_005163 | UCACAC CACCUG ACCAAGA | 123 | 0.591034 | 0.853611 | 0.800257 |
| 290 | ANPEP | alanyl (membrane) aminopeptidase | NM_001150 | CACCAC CTTGGA CCAAAG TAA | 124 | 0.622428 | 0.458612 | 0.255443 |
| 290 | ANPEP | alanyl (membrane) aminopeptidase | NM_001150 | CCGAAA TGCCAC ACTGGT CAA | 125 | 0.576796 | 0.519796 | 0.476823 |
| 335 | APOA1 | apolipoprotein A-1 | NM_000039 | GAGACU AUGUGU CCCAGUU | 126 | 0.667998 | 0.304063 | 0.194785 |
| 335 | APOA1 | apolipoprotein A-1 | NM_000039 | CGCTCT CGAGGA GTACAC TAA | 127 | 0.372041 | 0.461591 | 0.333619 |
| 351 | APP | amyloid beta (A4) precursor protein (peptidase nexin-II, Alzheimer disease) | NM_000484 | CCAGGA GAGGAU GGAUGUU | 128 | 0.550365 | 0.454635 | 0.256527 |
| 351 | APP | amyloid beta (A4) precursor protein (protease nexin-II, Alzheimer disease) | NM_000484 | CTGGTC TTCAAT TACCAA GAA | 129 | 0.327726 | 0.577834 | 0.674344 |

TABLE 3-continued

Scores of 295 confirmed genes required for influenza virus replication.

| | | | | | | | | |
|---|---|---|---|---|---|---|---|---|
| 361 | AQP4 | aquaporin 4 | NM_001650 NM_004028 | CAGCCT GGGATC CACCAT CAA | 130 | 0.491265 | 0.444893 | 0.322574 |
| 361 | AQP4 | aquaporin 4 | NM_004028 | GACCAA UCUGGA GAGGUAU | 131 | 1.198531 | 0.790267 | 0.471709 |
| 369 | ARAF | v-raf murine sarcoma 3611 viral oncogene homolog | NM_001654 | CCACAG UGUCCA GGAUUUG | 132 | 0.584211 | 0.541323 | 0.408701 |
| 369 | ARAF | v-raf murine sarcoma 3611 viral oncogene homolog | NM_001654 | CGGUGA AGAUCG GUGACUU | 133 | 0.545849 | 0.640995 | 0.583783 |
| 372 | ARCN1 | archain 1 | NM_001655 | CCCACT TGTGTC AATATT AAA | 1 | 0.129613 | 0.265091 | 0.257022 |
| 372 | ARCN1 | archain 1 | NM_001655 | AAGGCT GAGATG CGTCGT AAA | 2 | 0.228491 | 0.339334 | 0.286881 |
| 523 | ATP6V1A | ATPase, H+ transporting, lysosomal 70 kDa, V1 subunit A | NM_001690 | GAGCTT GAATTT GAAGGT GTA | 3 | 9.77E-02 | 0.171685 | 0.185285 |
| 523 | ATP6V1A | ATPase, H+ transporting, lysosomal 70 kDa, V1 subunit A | NM_001690 | ATGGAG GTTGAT GGTAAG GTA | 4 | 0.172724 | 0.287558 | 0.253885 |

TABLE 3-continued

Scores of 295 confirmed genes required for influenza virus replication.

| | | | | | | | | |
|---|---|---|---|---|---|---|---|---|
| 526 | ATP6V1B2 | ATPase, H+ transporting, lysosomal 56/58 kDa, V1 subunit B2 | NM_001693 | ACCATG TTACCC TGTAAT TAA | 5 | 0.172019 | 0.262894 | 0.240605 |
| 526 | ATP6V1B2 | ATPase, H+ transporting, lysosomal 56/58 kDa, V1 subunit B2 | NM_001693 | CACGGT TAATGA AGTCTG CTA | 6 | 0.202485 | 0.341822 | 0.288774 |
| 527 | ATP6V0C | ATPase, H+ transporting, lysosomal 16 kDa, V0 subunit c | NM_001694 XM_001130742 | CAGCCA CAGAAT ATTATG TAA | 7 | 7.20E-02 | 0.151108 | 0.149564 |
| 527 | ATP6V0C | ATPase, H+ transporting, lysosomal 16 kDa, V0 subunit c | NM_001694 XM_001130742 | TCCCAG CTATCT ATAACC TTA | 8 | 0.075906 | 0.149046 | 0.134968 |
| 533 | ATP6V0B | ATPase, H+ transporting, lysosomal 21 kDa, V0 subunit b | NM_001039457 NM_004047 | CATGGC AATTGT CATTAG CAA | 9 | 8.02E-02 | 0.176384 | 0.203457 |
| 533 | ATP6V0B | ATPase, H+ transporting, lysosomal 21 kDa, V0 subunit b | NM_001039457 NM_004047 | TCCTAG TGTTTG TGAAAT AAA | 10 | 0.150147 | 0.301989 | 0.286479 |
| 537 | ATP6AP1 | ATPase, H+ transporting, lysosomal accessory protein 1 | NM_001183 | CAGGGA AGTCCT CACAGG CAA | 134 | 9.81E-02 | 0.184556 | 0.155526 |

TABLE 3-continued

Scores of 295 confirmed genes required for influenza virus replication.

| | | | | | | | |
|---|---|---|---|---|---|---|---|
| 537 | ATP6AP1 | ATPase, H+ transporting, lysosomal accessory protein 1 | NM_001183 | CACAGT GACATT CAAGTT CAT | 11 | 0.100942 | 0.168217 | 0.168016 |
| 602 | BCL3 | B-cell CLL/lymphoma 3 | NM_005178 | CGUGAA CGCGCA AAUGUAC | 135 | 0.572122 | 0.617782 | 0.512055 |
| 602 | BCL3 | B-cell CLL/lymphoma 3 | NM_005178 | UGGCUC CUCCCA AUUUCUU | 136 | 0.56567 | 0.605674 | 0.548143 |
| 658 | BMPR1B | "bone morphogenetic protein receptor, type 1B" | NM_001203 | /5Phos/rGr GrArCrCr CrArGrUr UrGrUrAr CrCrUrAr ArUrCrAr CrAGG | 137 | 0.298038 | 0.244694 | 0.18626 |
| 658 | BMPR1B | "bone morphogenetic protein receptor, type 1B" | NM_001203 | GGACUA UAGCUA AGCAGAU | 138 | 0.534118 | 0.410897 | 0.332256 |
| 790 | CAD | carbamoyl-phosphate synthetase 2, aspartate transcarbamylase, and dihydroorotase | NM_004341 | CAGCCA AGTGCT AGTAGA CAA | 139 | 1.175201 | 0.398712 | 0.200589 |
| 790 | CAD | carbamoyl-phosphate synthetase 2, aspartate transcarbamylase, and dihydroorotase | NM_004341 | CCCUGA GUCUGA GCAGUAU | 140 | 0.703365 | 0.386548 | 0.234267 |
| 816 | CAMK2B | calcium/calmodulin-dependent protein kinase II | NM_001220 NM_172078 NM_172079 NM_172080 | CACGAC CATCCT GAACCC ACA | 13 | 0.358294 | 0.334692 | 0.245548 |

TABLE 3-continued

Scores of 295 confirmed genes required for influenza virus replication.

| | | | | | | | | |
|---|---|---|---|---|---|---|---|---|
| | | beta | NM_172081<br>NM_172082<br>NM_172083<br>NM_172084<br>XM_001125861 | | | | | |
| 816 | CAMK2B | calcium/calmodulin-dependent protein kinase II beta | NM_001220<br>XM_001125861 | CAGGAT<br>CTCTGA<br>CATCCT<br>GAA | 14 | 0.445452 | 0.392538 | 0.286559 |
| 827 | CAPN6 | calpain 6 | NM_014289 | GGACCA<br>CUGACA<br>UUCCUAU | 141 | 1.01694 | 0.572227 | 0.373877 |
| 827 | CAPN6 | calpain 6 | NM_014289 | AAGGGT<br>GGTCCA<br>ACTGCC<br>AAA | 142 | 0.452513 | 0.540239 | 0.618952 |
| 975 | CD81 | CD81 molecule | NM_004356 | CACCTT<br>CTATGT<br>AGGCAT<br>CTA | 67 | 9.82E−02 | 0.259718 | 0.33035 |
| 975 | CD81 | CD81 molecule | NM_004356 | AAGGAA<br>CATCAG<br>GCATGC<br>TAA | 68 | 0.515166 | 0.434424 | 0.33558 |
| 1019 | CDK4 | cyclin-dependent kinase 4 | NM_000075 | GAGGCC<br>UAGAUU<br>UCCUUCA | 143 | 0.480387 | 0.509977 | 0.378204 |
| 1019 | CDK4 | cyclin-dependent kinase 4 | NM_000075 | CCGAAC<br>TGACCG<br>GGAGAT<br>CAA | 144 | 0.447714 | 0.671184 | 0.662527 |
| 1195 | CLK1 | CDC-like kinase 1 | NM_001024646 | /5Phos/rAr<br>GrUrArCr<br>UrUrCrAr<br>CrArUrCr<br>GrUrCrGr<br>UrUrCrAr<br>CrATG | 145 | 0.636302 | 0.615127 | 0.471126 |

TABLE 3-continued

Scores of 295 confirmed genes required for influenza virus replication.

| | | | | | | | | |
|---|---|---|---|---|---|---|---|---|
| 1195 | CLK1 | CDC-like kinase 1 | NM_001024646 | CACGATAGTAAGGAGCATTTA | 146 | 0.541698 | 0.684416 | 0.767254 |
| 1263 | PLK3 | polo-like kinase 3 (*Drosophila*) | NM_004073 | /5Phos/rGrGrCrGrGrArUrGrUrArUrGrGrUrCrArCrUrGrGrGrCrUGG | 147 | 0.562995 | 0.705248 | 0.695757 |
| 1263 | PLK3 | polo-like kinase 3 (*Drosophila*) | NM_004073 | CTGCATCAAGCAGGTTCACTA | 148 | 0.622336 | 0.763092 | 0.745796 |
| 1280 | COL2A1 | collagen, type II, alpha 1 | NM_001844 NM_033150 | CTGGTTTGGAGAAACCATCAA | 149 | 0.303328 | 0.374904 | 0.360047 |
| 1280 | COL2A1 | collagen, type II, alpha 1 | NM_001844 NM_033150 | AAGCCTGGTGATGATGGTGAA | 150 | 1.458969 | 0.583795 | 0.364302 |
| 1314 | COPA | coatomer protein complex, subunit alpha | NM_001098398 NM_004371 | CTGGATTTCAACAGCTCCAAA | 151 | 7.17E-02 | 0.151954 | 0.153127 |
| 1314 | COPA | coatomer protein complex, subunit alpha | NM_001098398 NM_004371 | CTGGCGCATGAATGAATCAAA | 152 | 0.103107 | 0.229328 | 0.257649 |
| 1385 | CREB1 | cAMP responsive element binding protein 1 | NM_004379 NM_134442 | AGGGCAGTTGTTGCTTCTTAA | 153 | 1.249505 | 0.725109 | 0.402442 |
| 1385 | CREB1 | cAMP responsive element binding protein 1 | NM_004379 NM_134442 | CAGCCGGGTACTACCATTCTA | 154 | 0.585505 | 0.687225 | 0.734996 |

TABLE 3-continued

Scores of 295 confirmed genes required for influenza virus replication.

| | | | | | | | | |
|---|---|---|---|---|---|---|---|---|
| 1394 | CRHR1 | corticotropin releasing hormone receptor 1 | NM_004382 XM_001128344 | CAGGTT GGTGAC AGCCGC CTA | 155 | 0.159133 | 0.223883 | 0.209908 |
| 1394 | CRHR1 | corticotropin releasing hormone receptor 1 | NM_004382 XM_001128344 | CCGCTA CAATAC CACAAA CAA | 156 | 0.727194 | 0.599286 | 0.451137 |
| 1434 | CSE1L | CSE1 chromosome segregation 1-like (yeast) | NM_001316 | CTGACG GTATCA AATATA TTA | 16 | 0.199703 | 0.39152 | 0.384412 |
| 1434 | CSE1L | CSE1 chromosome segregation 1-like (yeast) | NM_001316 | CAAATG AACTTG TAAACC TAA | 17 | 0.217456 | 0.439763 | 0.528634 |
| 1455 | CSNK1G2 | "casein kinase 1, gamma 2" | NM_001319 | /5Phos/rAr GrGrCrCr ArGrGrCr UrArUrCr ArCrArAr ArCrUrUr ArUAG | 157 | 0.616044 | 0.391756 | 0.267893 |
| 1455 | CSNK1G2 | casein kinase 1, gamma 2 | NM_001319 | TAGGAA AGAATC TCTATA CAA | 158 | 0.623013 | 0.6029 | 0.538519 |
| 1511 | CTSG | cathepsin G | NM_001911 | CACAGT GTTTGCC AGAGCC TTA | 159 | 9.29E-02 | 0.194499 | 0.200955 |
| 1511 | CTSG | cathepsin G | NM_001911 | UCCGCC ACCCUC AAUAUAA | 160 | 0.602165 | 0.71298 | 0.691934 |
| 1521 | CTSW | cathepsin W | NM_001335 | CGCGTT CATAAC TGTCCT CAA | 66 | 0.465528 | 0.548612 | 0.482702 |

TABLE 3-continued

Scores of 295 confirmed genes required for influenza virus replication.

| | | | | | | | |
|---|---|---|---|---|---|---|---|
| 1521 | CTSW | cathepsin W | NM_001335 | UACCUG UGGCAU CACCAAG | 65 | 0.632263 | 0.705134 | 0.731456 |
| 1613 | DAPK3 | death-associated protein kinase 3 | NM_001348 | CCGGCA GAAGGG CACGGG CAA | 161 | 0.557697 | 0.418559 | 0.327791 |
| 1613 | DAPK3 | death-associated protein kinase 3 | NM_001348 | CACCAA CATCTC AGCCGT GAA | 162 | 1.415664 | 0.945629 | 0.64896 |
| 1717 | DHCR7 | 7-dehydrocholesterol reductase | NM_001360 | CUGCAA AUUCAC AGGCAAU | 163 | 0.235651 | 0.271078 | 0.199161 |
| 1717 | DHCR7 | 7-dehydrocholesterol reductase | NM_001360 | CGGGAA GTGGTT TGACTT CAA | 164 | 0.356665 | 0.549026 | 0.674915 |
| 1733 | DIO1 | deiodinase, iodothyronine, type 1 | NM_213593 | TTGGGA GTTTAT GCAAGG TAA | 165 | 0.343347 | 0.456542 | 0.532248 |
| 1733 | DIO1 | deiodinase, iodothyronine, type 1 | NM_213593 | UAGCAG AUUUC UUGUCAU | 166 | 0.457812 | 0.560861 | 0.474465 |
| 1787 | TRDMT1 | tRNA aspartic acid methyltransferase 1 | NM_004412 | GGACGA AUAGCU UCUUACA | 167 | 0.713512 | 0.618552 | 0.556973 |
| 1787 | TRDMT1 | tRNA aspartic acid methyltransferase 1 | NM_004412 NM_176081 NM_176083 NM_176084 NM_176085 NM_176086 | CACATT CGGTTG AGCAAC ATT | 168 | 1.358406 | 0.721083 | 0.575658 |
| 1832 | DSP | desmoplakin | NM_001008844 NM_004415 | CAGAAG AATGAC TATGAC CAA | 169 | 0.652997 | 0.665617 | 0.526271 |

TABLE 3-continued

Scores of 295 confirmed genes required for influenza virus replication.

| | | | | | | | | |
|---|---|---|---|---|---|---|---|---|
| 1832 | DSP | desmoplakin | NM_001008844 NM_004415 | CCGACA TGAATC ACTAAG TAA | 170 | 0.571636 | 0.667903 | 0.597691 |
| 1845 | DUSP3 | dual specificity phosphatase 3 | NM_004090 | CCCGCG GATCTA CGTGGG CAA | 77 | 0.465773 | 0.550533 | 0.527897 |
| 1845 | DUSP3 | dual specificity phosphatase 3 | NM_004090 | CCGTAT TTACTT AACAAG ATT | 78 | 0.91563 | 0.847785 | 0.614104 |
| 2011 | MARK2 | MAP/microtubule affinity-regulating kinase 2 | NM_004954 | /5Phos/rUr CrCrGrCr UrUrCrAr CrGrUrGr GrArGrUr ArUrGrAr ArGAC | 171 | 6.22E-02 | 0.143927 | 0.146607 |
| 2011 | MARK2 | MAP/microtubule affinity-regulating kinase 2 | NM_004954 | /5Phos/rUr CrGrCrUr UrCrArCr GrUrGrGr ArGrUrAr UrGrArAr GrACC | 172 | 0.643683 | 0.697418 | 0.585071 |
| 2022 | ENG | endoglin | NM_000118 NM_001114753 | AAGGGA GAACTT GAAACA GAT | 173 | 0.126098 | 0.17892 | 0.189344 |
| 2022 | ENG | endoglin | NM_000118 NM_001114753 | CAGCAA TGAGGC GGTGGT CAA | 174 | 0.24663 | 0.343036 | 0.298319 |
| 2045 | EPHA7 | EPH receptor A7 | NM_004440 | TACGAG AAAGAT CAAAGG GAA | 175 | 0.397562 | 0.418848 | 0.349725 |
| 2045 | EPHA7 | EPH receptor A7 | NM_004440 | CAGGCT GCGAAG GAAGTA CTA | 176 | 0.662261 | 0.655207 | 0.552147 |

TABLE 3-continued

Scores of 295 confirmed genes required for influenza virus replication.

| | | | | | | | | |
|---|---|---|---|---|---|---|---|---|
| 2048 | EPHB2 | EPH receptor B2 | NM_004442 | /5Phos/rGr GrCrUrAr CrGrGrAr CrCrArAr GrUrUrUr ArUrCrCr GrGCG | 177 | 0.376567 | 0.332363 | 0.292629 |
| 2048 | EPHB2 | EPH receptor B2 | NM_004442 | GGAGAC CUUCAA CCUCUAU | 64 | 0.567862 | 0.498451 | 0.31717 |
| 2050 | EPHB4 | EPH receptor B4 | NM_004444 | CACGAG CTCCCT GGGAGG AAA | 178 | 0.542996 | 0.385256 | 0.312795 |
| 2050 | EPHB4 | EPH receptor B4 | NM_004444 | CTGGCG GGACAC CAGAAG AAA | 179 | 0.953659 | 0.542741 | 0.401283 |
| 2162 | F13A1 | coagulation factor XIII, A1 polypeptide | NM_000129 | CAAGGA GAGATG GGACAC TAA | 18 | 6.53E-02 | 0.238263 | 0.219108 |
| 2162 | F13A1 | coagulation factor XIII, A1 polypeptide | NM_000129 | GCUGGA GCUAUG GUCAGUU | 19 | 0.789945 | 0.566015 | 0.442407 |
| 2260 | FGFR1 | EMPTY | NM_023110 | CCUGCA UUGUGG AGAAUGA | 180 | 0.770886 | 0.254695 | 0.154736 |
| 2260 | FGFR1 | fibroblast growth factor receptor 1 (fms-related tyrosine kinase 2, Pfeiffer syndrome) | NM_023110 | CAGAGG AGAAAG AAACAG ATA | 181 | 0.70394 | 0.700727 | 0.514028 |
| 2263 | FGFR2 | fibroblast growth factor receptor 2 | NM_000141 NM_022969 NM_022970 NM_022971 | CCCATC TGACAA GGGAAA TTA | 69 | 0.172533 | 0.411176 | 0.409594 |

TABLE 3-continued

Scores of 295 confirmed genes required for influenza virus replication.

| | | | | | | | |
|---|---|---|---|---|---|---|---|
| 2263 | FGFR2 | fibroblast growth factor receptor 2 | NM_000141<br>NM_022969<br>NM_022970<br>NM_022971<br>NM_022972<br>NM_022973<br>NM_022974<br>NM_022975<br>NM_022976<br>NM_023028<br>NM_023029<br>NM_023030<br>NM_023031 | CGGAGG<br>AGCGTT<br>GCCATT<br>CAA | 70 | 1.110477 | 0.806708 | 0.535097 |
| 2264 | FGFR4 | fibroblast growth factor receptor 4 | NM_002011<br>NM_022963<br>NM_213647 | CCGCCT<br>GACCTT<br>CGGACC<br>CTA | 20 | 0.172161 | 0.308767 | 0.236158 |
| 2264 | FGFR4 | fibroblast growth factor receptor 4 | NM_002011<br>NM_022963<br>NM_213647 | CAGGAG<br>GTTCTG<br>GGCCTC<br>TGA | 21 | 0.350578 | 0.281419 | 0.20086 |
| 2322 | FLT3 | fms-related tyrosine kinase 3 | NM_004119 | CAGGTT<br>TAAAGC<br>CTACCC<br>ACA | 182 | 0.205922 | 0.327593 | 0.409226 |
| 2322 | FLT3 | fms-related tyrosine kinase 3 | NM_004119 | TACGTT<br>GATTTC<br>AGAGAA<br>TAT | 183 | 0.532347 | 0.673259 | 0.738482 |
| 2324 | FLT4 | fms-related tyrosine kinase 4 | NM_182925 | CACGCT<br>CTTGGT<br>CAACAG<br>GAA | 184 | 0.115189 | 0.289531 | 0.295762 |

Note: header row for 2263 FGFR2 includes NM_022972, NM_022973, NM_022974, NM_022975, NM_022976, NM_023028, NM_023029, NM_023030, NM_023031 (shown at top).

TABLE 3-continued

Scores of 295 confirmed genes required for influenza virus replication.

| | | | | | | | | |
|---|---|---|---|---|---|---|---|---|
| 2324 | FLT4 | fms-related tyrosine kinase 4 | NM_182925 | CGUGUC UGCCAU GUACAAG | 185 | 1.385206 | 0.886297 | 0.628062 |
| 2334 | AFF2 | AF4/FMR 2 family, member 2 | NM_002025 | CTGGGT AAGACT ACTCAG TAA | 186 | 1.268048 | 0.757327 | 0.437178 |
| 2334 | AFF2 | fragile X mental retardation 2 | NM_002025 | CACGTG ATAGTC ATAACC CTA | 187 | 0.632891 | 0.855378 | 0.959341 |
| 2342 | FNTB | farnesyltransferase, CAAX box, beta | NM_002028 | CACGTC CATAGA ACAGGC AAA | 188 | 7.94E-02 | 0.174705 | 0.20524 |
| 2342 | FNTB | farnesyltransferase, CAAX box, beta | NM_002028 | GGUGAU CCAGGC CACUACA | 189 | 0.300267 | 0.402552 | 0.259489 |
| 2346 | FOLH1 | folate hydrolase (prostate-specific membrane antigen) 1 | NM_004476 | AAGCAT AATATG AAAGCA TTT | 190 | 0.197298 | 0.39287 | 0.458664 |
| 2346 | FOLH1 | folate hydrolase (prostate-specific membrane antigen) 1 | NM_004476 | CACCAG GUUACC CAGCAAA | 191 | 0.667199 | 0.409842 | 0.244758 |
| 2357 | FPR1 | formyl peptide receptor 1 | NM_002029 | GUGACA CAGCUA CCAAUUC | 22 | 0.378523 | 0.468563 | 0.402488 |
| 2357 | FPR1 | formyl peptide receptor 1 | NM_002029 | AACCAG TGACAC AGCTAC CAA | 23 | 0.710528 | 0.606494 | 0.423796 |
| 2444 | FRK | fyn-related kinase | NM_002031 | GGUCCC AGCUCC AUUGAU | 192 | 1.086531 | 0.564586 | 0.303119 |

TABLE 3-continued

Scores of 295 confirmed genes required for influenza virus replication.

| | | | | | | | | |
|---|---|---|---|---|---|---|---|---|
| 2444 | FRK | fyn-related kinase | NM_002031 | CTGGGA GTACCT AGAACC CTA | 193 | 0.543945 | 0.550485 | 0.332667 |
| 2475 | FRAP1 | FK506 binding protein 12-rapamycin associated protein 1 | NM_004958 | /5Phos/rGr GrCrArAr CrArArGr CrGrArUr CrCrCrGr ArArCrGr ArGGA | 194 | 0.371406 | 0.58837 | 0.485254 |
| 2475 | FRAP1 | FK506 binding protein 12-rapamycin associated protein 1 | NM_004958 | GAGGCA UCUCGU UUGUACU | 195 | 0.81123 | 0.75011 | 0.537874 |
| 2539 | G6PD | glucose-6-phosphate dehydrogenase | NM_000402 NM_001042351 | CACCAA GATGAT GACCAA GAA | 196 | 0.345572 | 0.602254 | 0.730104 |
| 2539 | G6PD | glucose-6-phosphate dehydrogenase | NM_000402 NM_001042531 | ATCGGG TGACCT GGCCAA GAA | 197 | 0.43859 | 0.538907 | 0.434585 |
| 2550 | GABBR1 | gamma-aminobutyric acid (GABA) B receptor, 1 | NM_001470 NM_021903 NM_021904 NM_021905 | CACCCT CTCCAT GTCACA GAA | 42 | 0.242197 | 0.255169 | 0.177071 |
| 2550 | GABBR1 | gamma-aminobutyric acid (GABA) B receptor, 1 | NM_001470 NM_021903 NM_021904 NM_021905 | CTCCAT TGCATT CATGTA CTA | 43 | 0.591587 | 0.786134 | 0.839918 |
| 2580 | GAK | cyclin G associated kinase | NM_005255 XM_001127411 | AAGGCC TAACTA TGCCTC GAA | 198 | 0.340592 | 0.394833 | 0.282576 |
| 2580 | GAK | cyclin G associated kinase | NM_005255 | AGGGUG ACCUGG ACAUAUC | 199 | 0.462245 | 0.63912 | 0.716611 |

TABLE 3-continued

Scores of 295 confirmed genes required for influenza virus replication.

| | | | | | | | | |
|---|---|---|---|---|---|---|---|---|
| 2703 | GJA8 | gap junction protein, alpha 8, 50 kDa | NM_005267 | CAGCGG CAGCAA AGGCAC TAA | 200 | 0.458221 | 0.461855 | 0.419568 |
| 2703 | GJA8 | gap junction protein, alpha 8, 50 kDa | NM_005267 | UCAUCU UCAAGA CCCUCUU | 201 | 0.451748 | 0.537145 | 0.56189 |
| 2869 | GRK5 | G protein-coupled receptor kinase 5 | NM_005308 | CCGAAG GACCAT AGACAC AGA | 202 | 0.359907 | 0.332406 | 0.241538 |
| 2869 | GRK5 | G protein-coupled receptor kinase 5 | NM_005308 | GCGGCA GCAUCA GAACAAU | 203 | 0.845292 | 0.48597 | 0.296931 |
| 2870 | GRK6 | G protein-coupled receptor kinase 6 | NM_002082 | CCGGAG GTGGTG AAGAAT GAA | 204 | 0.894295 | 0.641728 | 0.479498 |
| 2870 | GRK6 | G protein-coupled receptor kinase 6 | NM_002082 | GGGUCC CUGCAA AGACCUU | 205 | 0.709849 | 0.663908 | 0.557602 |
| 2932 | GSK3B | glycogen synthase kinase 3 beta | NM_002093 | /5Phos/rGr GrGrCrAr CrCrArGr ArGrUrUr GrArUrCr UrUrUrGr GrAGG | 206 | 5.95E-02 | 0.106067 | 0.100391 |
| 2932 | GSK3B | glycogen synthase kinase 3 beta | NM_002093 | /5Phos/rAr GrCrArAr CrArCrUr GrGrUrCr ArCrGrUr UrUrGrGr ArAAG | 207 | 0.140815 | 0.133221 | 0.106799 |
| 2936 | GSR | EMPTY | NM_000637 | CGGAAG AUGAAG CCAUUCA | 208 | 0.920982 | 0.51246 | 0.310382 |

TABLE 3-continued

Scores of 295 confirmed genes required for influenza virus replication.

| | | | | | | | | |
|---|---|---|---|---|---|---|---|---|
| 2936 | GSR | glutathione reductase | NM_000637 | ACCGAU GACAAG GGUCAUA | 209 | 0.472315 | 0.557203 | 0.543758 |
| 3265 | HRAS | v-Ha-ras Harvey rat sarcoma viral oncogene homolog | NM_001130442 NM_005343 NM_176795 | CAGACT GTCTTG AACATC CCA | 210 | 0.538154 | 0.365001 | 0.24442 |
| 3265 | HRAS | v-Ha-ras Harvey rat sarcoma viral oncogene homolog | NM_001130442 NM_005343 NM_176795 | CCTGTG TGTGTT TGCCAT CCA | 211 | 0.719199 | 0.659826 | 0.57344 |
| 3320 | HSP90AA1 | heat shock protein 90 kDa alpha (cytosolic), class A member 1 | NM_001017963 NM_005348 | CAGAAT GAAGGA GAACCA GAA | 212 | 0.482469 | 0.256156 | 0.172544 |
| 3320 | HSP90AA1 | heat shock protein 90 kDa alpha (cytosolic), class A member 1 | NM_001017963 NM_005348 | CTGCTT AAAGTT GTAACA AAT | 213 | 1.427162 | 0.915139 | 0.631874 |
| 3356 | HTR2A | 5-hydroxytryptamine (serotonin) receptor 2A | NM_000621 | CUCGCC GAUGAU AACUUUG | 214 | 0.646324 | 0.539307 | 0.404079 |
| 3356 | HTR2A | 5-hydroxytryptamine (serotonin) receptor 2A | NM_000621 | TGGGAT TGAGTT GGTTAC CTA | 215 | 1.520438 | 0.852611 | 0.53368 |
| 3547 | IGSF1 | immunoglobulin superfamily, member 1 | NM_001555 NM_205833 | ATCGAT AGTGAT GGACCC TCA | 216 | 0.193911 | 0.227021 | 0.220041 |

TABLE 3-continued

Scores of 295 confirmed genes required for influenza virus replication.

| | | | | | | | | |
|---|---|---|---|---|---|---|---|---|
| 3547 | IGSF1 | immunoglobulin superfamily, member 1 | NM_001555 NM_205833 | TCGATA GTGATG GACCCT CAA | 217 | 0.268017 | 0.255527 | 0.236023 |
| 3568 | IL5RA | interleukin 5 receptor, alpha | NM_175728 | GCUGGG CUUCUG CUGAACU | 218 | 0.681915 | 0.483369 | 0.318573 |
| 3568 | IL5RA | interleukin 5 receptor, alpha | NM_000564 NM_175726 | CACCAG TCTTGT ATCTCT TAA | 219 | 0.814131 | 0.530594 | 0.362803 |
| 3581 | IL9R | interleukin 9 receptor | NM_002186 NM_176786 NR_024033 | CAGCTA TGAGCT GGCCTT CAA | 220 | 0.228236 | 0.3547 | 0.446801 |
| 3581 | IL9R | interleukin 9 receptor | NM_002186 | GGGUGA AGAGAA UCUUCUA | 221 | 0.591005 | 0.565778 | 0.445678 |
| 3674 | ITGA2B | integrin, alpha 2b (platelet glycoprotein IIb of IIb/IIIa complex, antigen CD41) | NM_000419 | CAGCCA GAATCC AAACAG CAA | 222 | 0.790304 | 0.299394 | 0.189931 |
| 3674 | ITGA2B | integrin, alpha 2b (platelet glycoprotein IIb of IIb/IIIa complex, antigen CD41) | NM_000419 | UGGCAG CCAGUU UGGAUUU | 223 | 1.060829 | 0.736319 | 0.444774 |

TABLE 3-continued

Scores of 295 confirmed genes required for influenza virus replication.

| | | | | | | | | |
|---|---|---|---|---|---|---|---|---|
| 3675 | ITGA3 | integrin, alpha 3 (antigen CD49C, alpha 3 subunit of VLA-3 receptor) | NM_002204 NM_005501 | CTCGCT TAGCAT GGTAAA TCA | 224 | 0.823417 | 0.474607 | 0.32931 |
| 3675 | ITGA3 | integrin, alpha 3 (antigen CD49C, alpha 3 subunit of VLA-3 receptor) | NM_002204 NM_005501 | CTGGAT TGACTT TGCTGT CAA | 82 | 0.540775 | 0.765083 | 0.633673 |
| 3717 | JAK2 | Janus kinase 2 (a protein tyrosine kinase) | NM_004972 | AGCCAT CATACG AGATCT TAA | 44 | 0.967243 | 0.466245 | 0.236812 |
| 3717 | JAK2 | Janus kinase 2 (a protein tyrosine kinase) | NM_004972 | CCAGAU UUCAGG CCUUCUU | 225 | 0.46513 | 0.759622 | 0.91968 |
| 3725 | JUN | jun oncogene | NM_002228 | CGCGCG CGAGTC GACAAG TAA | 226 | 0.520241 | 0.489764 | 0.287525 |
| 3725 | JUN | v-jun sarcoma virus 17 oncogene homolog (avian) | NM_002228 | TTCGTT AACATT GACCAA GAA | 227 | 0.426049 | 0.634569 | 0.712136 |
| 3760 | KCNJ3 | potassium inwardly-rectifying channel, subfamily J, member 3 | NM_002239 | ACCAGC CATAAC TAACAG CAA | 228 | 0.695807 | 0.317877 | 0.181925 |
| 3760 | KCNJ3 | potassium inwardly- | NM_002239 | ATGGAC TAGATG | 229 | 0.521729 | 0.471471 | 0.418717 |

TABLE 3-continued

Scores of 295 confirmed genes required for influenza virus replication.

| | | | | | | | | |
|---|---|---|---|---|---|---|---|---|
| | | rectifying channel, subfamily J, member 3 | | ATATTA CTA | | | | |
| 3767 | KCNJ11 | potassium inwardly-rectifying channel, subfamily J, member 11 | NM_000525 | GUUCAG CAUCUC UCCAGAU | 230 | 0.400141 | 0.25795 | 0.218759 |
| 3767 | KCNJ11 | potassium inwardly-rectifying channel, subfamily J, member 11 | NM_000525 | CAGCGC TTTGTG CCCATT GTA | 231 | 0.314883 | 0.570361 | 0.641923 |
| 3778 | KCNMA1 | EMPTY | NM_001014797 | UGGGAG ACGCUU CAUAACU | 232 | 0.27889 | 0.393026 | 0.362607 |
| 3778 | KCNMA1 | potassium large oonductance calcium-activated channel, subfamily M, alpha member 1 | NM_002247 | ACCGAG AGAGCC GTATAT TAA | 233 | 0.655375 | 0.641345 | 0.46731 |
| 3837 | KPNB1 | karyopherin (importin) beta 1 | NM_002265 | TCGGTT ATATTT GCCAAG ATA | 24 | 0.343415 | 0.486124 | 0.441224 |
| 3837 | KPNB1 | karyopherin (importin) beta 1 | NM_002265 | CAAGAA CTCTTT GACATC TAA | 25 | 0.356831 | 0.518794 | 0.494295 |

TABLE 3-continued

| Scores of 295 confirmed genes required for influenza virus replication. | | | | | | | | |
|---|---|---|---|---|---|---|---|---|
| 3984 | LIMK1 | LIM domain kinase 1 | NM_002314 | /5Phos/rArGrCrUrCrUrCrCrGrGrCrUrUrArUrArCrUrCrCrCrArGCG | 234 | 1.007584 | 0.595166 | 0.318947 |
| 3984 | LIMK1 | LIM domain kinase 1 | NM_002314 | AUCACCAAGGGACUGGUUA | 235 | 1.181749 | 0.858982 | 0.644375 |
| 4058 | LTK | leukocyte receptor tyrosine kinase | NM_002344 NM_206961 | ACAGATCTTTGGAGTGCCTAA | 236 | 0.835764 | 0.580696 | 0.391388 |
| 4058 | LTK | leukocyte receptor tyrosine kinase | NM_002344 NM_206961 | CAGGGATATTGCCGCCCGGAA | 237 | 1.063931 | 0.705212 | 0.501143 |
| 4193 | MDM2 | Mdm2, transformed 3T3 cell double minute 2, p53 binding protein (mouse) | NM_002392 | CAGGCAAATGTGCAATACCAA | 238 | 0.349235 | 0.398643 | 0.441268 |
| 4193 | MDM2 | Mdm2 p53 binding protein homolog (mouse) | NM_002392 | CCGGATCTTGATGCTGGTGTA | 239 | 0.738487 | 0.598079 | 0.370112 |
| 4296 | MAP3K11 | mitogen-activated protein kinase kinase kinase 11 | NM_002419 | CACATGGTACCTGGATTCAGA | 62 | 0.42297 | 0.483946 | 0.328504 |
| 4296 | MAP3K11 | mitogen-activated protein kinase kinase kinase 11 | NM_002419 | CCGGCCTTGACCGGAGGAGAA | 63 | 0.586356 | 0.505279 | 0.36445 |

TABLE 3-continued

Scores of 295 confirmed genes required for influenza virus replication.

| | | | | | | | |
|---|---|---|---|---|---|---|---|
| 4809 | NHP2L1 | NHP2 non-histone chromosome protein 2-like 1 (S. cerevisiae) | NM_001003796 NM_005008 | CAGCTA CTCTCT ATTGTT ATA | 240 | 0.108851 | 0.284659 | 0.3888 |
| 4809 | NHP2L1 | NHP2 non-histone chromosome protein 2-like 1 (S. cerevisiae) | NM_001003796 NM_005008 | CTGAGG TTGTGT ATCATA TTA | 241 | 0.12278 | 0.268459 | 0.309098 |
| 4886 | NPY1R | neuropeptide Y receptor Y1 | NM_000909 | GACUUG CUUGUU GCCAUCA | 242 | 0.268069 | 0.469101 | 0.620025 |
| 4886 | NPY1R | neuropeptide Y receptor Y1 | NM_000909 | CAAGAT ATATAT ACGCCT AAA | 243 | 0.801215 | 0.561755 | 0.415336 |
| 4914 | NTRK1 | "neurotrophic tyrosine kinase, receptor, type 1" | NM_001007792 | /5Phos/rAr CrCrArGr ArGrGrUr CrUrArCr GrCrCrAr UrCrArUr GrCGG | 244 | 0.400583 | 0.570384 | 0.610135 |
| 4914 | NTRK1 | neurotrophic tyrosine kinase, receptor, type 1 | NM_001007204 NM_001007792 NM_001012331 NM_002529 | CACGGA GGCAAT CGACTG CAT | 245 | 1.288761 | 0.692474 | 0.547716 |
| 4915 | NTRK2 | neurotrophic tyrosine kinase, receptor, type 2 | NM_001018064 | GAGCAU CAUGUA CAGGAAA | 246 | 0.185904 | 0.316496 | 0.222767 |
| 4915 | NTRK2 | neurotrophic tyrosine kinase, receptor, type 2 | NM_001007097 NM_001018064 NM_001018065 NM_001018066 NM_006180 | ACCACG AACAGA AGTAAT GAA | 247 | 1.318829 | 0.618446 | 0.348687 |

TABLE 3-continued

Scores of 295 confirmed genes required for influenza virus replication.

| | | | | | | | |
|---|---|---|---|---|---|---|---|
| 4920 | ROR2 | receptor tyrosine kinase-like orphan receptor 2 | NM_004560 | 248 | UUGCCU GUGCAC GCUUCAU | 0.148738 | 0.266509 | 0.247882 |
| 4920 | ROR2 | receptor tyrosine kinase-like orphan receptor 2 | NM_004560 | 249 | CCGGTT TGGGAA AGTCTA CAA | 0.74296 | 0.622392 | 0.402518 |
| 4923 | NTSR1 | neurotensin receptor 1 (high affinity) | NM_002531 | 250 | CTGGCT TAAGAA GGTCGC CTA | 0.102365 | 0.196537 | 0.210525 |
| 4923 | NTSR1 | neurotensin receptor 1 (high affinity) | NM_002531 | 251 | AAGGGC CTCTAA CAAGGA GAA | 0.345005 | 0.231992 | 0.163321 |
| 5062 | PAK2 | p21 (CDKN1A)-activated kinase 2 | NM_002577 | 252 | /5Phos/rAr GrCrGrCr CrGrCrUr GrUrGrGr UrUrCrAr UrUrCrUr UrAAG | 7.21E-02 | 0.147561 | 0.153507 |
| 5062 | PAK2 | p21 (CDKN1A)-activated kinase 2 | NM_002577 | 253 | /5Phos/rGr GrArGrCr UrArCrGr CrUrGrUr GrGrUrUr UrArUrUr CrUGG | 0.429581 | 0.481362 | 0.452969 |
| 5063 | PAK3 | p21 protein (Cdc42/Rac)-activated kinase 3 | NM_001128166 NM_001128167 NM_001128168 NM_001128172 NM_001128173 NM_002578 | 254 | CAAGAA GGAATT AATTAT TAA | 0.480869 | 0.537457 | 0.417104 |
| 5063 | PAK3 | p21 (CDKN1A)-activated kinase 3 | NM_002578 | 255 | CAGCAA CCCAAG AAGGAAU | 0.728695 | 0.595544 | 0.456057 |

TABLE 3-continued

Scores of 295 confirmed genes required for influenza virus replication.

| | | | | | | | |
|---|---|---|---|---|---|---|---|
| 5096 | PCCB | propionyl Coenzyme A carboxylase, beta polypeptide | NM_000532 | CAGGCC ACCTCT GTTAAC GAA | 256 | 0.45741 | 0.602919 | 0.593165 |
| 5096 | PCCB | propionyl Coenzyme A carboxylase, beta polypeptide | NM_000532 | CTCAGG ATGCTT GGATAT TAA | 257 | 0.723836 | 0.558057 | 0.503111 |
| 5165 | PDK3 | pyruvate dehydrogenase kinase, isozyme 3 | NM_005391 | CAGGUC UUGGAU AACUUUC | 258 | 0.348006 | 0.344589 | 0.219532 |
| 5165 | PDK3 | pyruvate dehydrogenase kinase, isozyme 3 | NM_001142386 NM_005391 | CTCGTT ACTTTG GGTAAA GAA | 259 | 0.847921 | 0.703907 | 0.603787 |
| 5253 | PHF2 | PHD finger protein 2 | NM_005392 NM_024517 | CTGGAT TTGTTTC TCAGGC AA | 260 | 7.57E-02 | 0.165235 | 0.185031 |
| 5253 | PHF2 | PHD finger protein 2 | NM_005392 NM_024517 | TCGCCT CTAGCT GGAAAC AAA | 261 | 0.63691 | 0.454126 | 0.280938 |
| 5310 | PKD1 | polycystic kidney disease 1 (autosomal dominant) | NM_001009944 | GACGUG UGGAUC GGCUUCU | 262 | 0.42731 | 0.543542 | 0.435714 |
| 5310 | PKD1 | polycystic kidney disease 1 (autosomal dominant) | NM_001009944 | CCCGTC CATTGT GGGTAG CAA | 263 | 0.486518 | 0.673849 | 0.633572 |
| 5422 | POLA1 | polymerase (DNA directed), alpha 1 | NM_016937 | CCAGAC CUGGUG AAUGUAA | 264 | 0.306117 | 0.438598 | 0.372639 |
| 5422 | POLA1 | polymerase (DNA | NM_016937 | CAGGAT CTTAAC | 265 | 0.564799 | 0.610176 | 0.486803 |

TABLE 3-continued

Scores of 295 confirmed genes required for influenza virus replication.

| | | | | | | | |
|---|---|---|---|---|---|---|---|
| 5566 | PRKACA | protein kinase, cAMP-dependent, catalytic, alpha | NM_002730 NM_207518 | 266 | ACAGAA GGTGGT GAAACT GAA | 0.885957 | 0.595288 | 0.425173 |
| 5566 | PRKACA | protein kinase, cAMP-dependent, catalytic, alpha | NM_002730 NM_207518 | 267 | CAGAAG GTGGTG AAACTG AAA | 0.907383 | 0.651552 | 0.475119 |
| 5580 | PRKCD | protein kinase C, delta | NM_212539 | 268 | CGCUGC CAUCCA CAAGAAA | 0.717175 | 0.403035 | 0.211423 |
| 5580 | PRKCD | protein kinase C, delta | NM_212539 | 269 | CCGGGA CACTAT ATTCCA GAA | 0.513114 | 0.564345 | 0.467735 |
| 5584 | PRKCI | protein kinase C, iota | NM_002740 | 270 | ACGCCG CTGGAG AAAGCT TTA | 1.100496 | 0.752762 | 0.492508 |
| 5584 | PRKCI | protein kinase C, iota | NM_002740 | 271 | GGAGAU ACAACC AGCACUU | 0.635398 | 0.83753 | 1.037426 |
| 5594 | MAPK1 | mitogen-activated protein kinase 1 | NM_002745 | 272 | /5Phos/rCr CrArCrCr ArArCrCr ArUrCrGr ArGrCrAr ArArUrGr ArAAG | 0.216511 | 0.173994 | 0.155731 |
| 5594 | MAPK1 | mitogen-activated protein kinase 1 | NM_002745 | 273 | /5 Phos/rCr ArCrCrAr ArCrCrAr UrCrGrAr GrCrArAr ArUrGrAr ArAGA | 0.600093 | 0.296237 | 0.173795 |

TABLE 3-continued

Scores of 295 confirmed genes required for influenza virus replication.

| 5605 | MAP2K2 | mitogen-activated protein kinase 2 | NM_002745 | CCGGCC TGCCAT GGCCAT CTT | 274 | 0.101058 | 0.29687 | 0.509927 |
|---|---|---|---|---|---|---|---|---|
| 5605 | MAP2K2 | mitogen-activated protein kinase 2 | NM_030662 | GUGGAU UUUGCC GGCUGGU | 275 | 0.574017 | 0.566833 | 0.566071 |
| 5605 | MAP2K3 | mitogen-activated protein kinase 3 | NM_002756 NM_145109 NM_145110 | CTGGAT GCCATC CAAGTT GTA | 26 | 0.141122 | 0.342405 | 0.378676 |
| 5606 | MAP2K3 | mitogen-activated protein kinase 3 | NM_002756 NM_145109 NM_145110 | CCGGGC CACCGT GAACTC ACA | 276 | 0.447182 | 0.583888 | 0.548603 |
| 5607 | MAP2K5 | mitogen-activated protein kinase 5 | NM_002757 NM_145160 NM_145161 NM_145162 | AAGACG TATGTT GGAACA AAT | 277 | 1.293805 | 0.794924 | 0.4229 |
| 5607 | MAP2K5 | mitogen-activated protein kinase 5 | NM_002757 NM_145160 NM_145161 NM_145162 | CAAGAC GTATGT TGGAAC AAA | 278 | 1.07881 | 0.810121 | 0.536994 |
| 5610 | EIF2AK2 | eukaryotic translation initiation factor 2-alpha kinase 2 | NM_002759 | /5Phos/rUr GrGrCrCr GrCrUrAr ArArCrUr UrGrCrAr UrArUrCr UrUUG | 279 | 0.475097 | 0.363097 | 0.244434 |
| 5610 | EIF2AK2 | eukaryotic translation initiation factor 2-alpha kinase 2 | NM_002759 | TACGTG TGAGTC CCAAAG CAA | 280 | 0.514118 | 0.517686 | 0.444547 |

TABLE 3-continued

Scores of 295 confirmed genes required for influenza virus replication.

| | | | | | | | |
|---|---|---|---|---|---|---|---|
| 5707 | PSMD1 | proteosome (prosome, macropain) 26S subunit, non-ATPase, 1 | NM_002807 | AAGCAG TGCATT TGTAGG AAA | 281 | 0.286945 | 0.693908 | 0.780448 |
| 5707 | PSMD1 | proteosome (prosome, macropain) 26S subunit, non-ATPase, 1 | NM_002807 | CTGCAT GTCTTT AATGCA GAA | 282 | 0.985269 | 0.774298 | 0.551981 |
| 5757 | PTMA | prothymosin, alpha | NM_001099285 NM_002823 | TTGTCC AACAAT AAACAG GAA | 283 | 0.222183 | 0.445287 | 0.450524 |
| 5757 | PTMA | prothymosin, alpha | NM_001099285 NM_002823 | TTGGTT TGTATG AGATGG TTA | 284 | 0.63134 | 0.83128 | 0.793193 |
| 5797 | PTPRM | EMPTY | NM_002845 | CCAGUU CACCAC CAAAAUA | 285 | 1.162729 | 0.716824 | 0.450535 |
| 5797 | PTPRM | protein tyrosine phosphatase, receptor type, M | NM_002845 | CUCGUU GCCACA GUUAUAA | 286 | 0.918752 | 0.78949 | 0.629143 |
| 5798 | PTPRN | protein tyrosine phosphatase, receptor type, N | NM_002846 | CAGGTC TGGCTT GGCACC CAA | 287 | 0.156852 | 0.467296 | 0.705878 |
| 5798 | PTPRN | protein tyrosine phosphatase, receptor type, N | NM_002846 | CTGGTG AAGTCT GAACTG GAA | 288 | 0.351441 | 0.495268 | 0.543469 |

TABLE 3-continued

Scores of 295 confirmed genes required for influenza virus replication.

| | | | | | | | |
|---|---|---|---|---|---|---|---|
| 5805 | PTS | 6-pyruvoyltetrahydropterin synthase | NM_000317 | TTCGAG TAGGTG AATCTT AAA | 289 | 1.797785 | 0.690829 | 0.367199 |
| 5805 | PTS | 6-pyruvoyltetrahydropterin synthase | NM_000317 | TAGGTG AATCTT AAAGAA ATA | 290 | 0.623979 | 0.679202 | 0.799458 |
| 5961 | PRPH2 | retinal degeneration, slow | | CAGCAC CACACC ATCCCT AAA | 291 | 0.207981 | 0.314487 | 0.284669 |
| 5961 | PRPH2 | retinal degeneration, slow | | CACGGA TTTAGT CCCACC CTA | 75 | 0.417302 | 0.549364 | 0.59512 |
| 6015 | RING1 | ring finger protein 1 | NM_002931 | GCUGGU GAAUGA GAAAUUC | 292 | 0.477836 | 0.536237 | 0.538214 |
| 6015 | RING1 | ring finger protein 1 | NM_002931 | CCGAAA GAAGCT GGTGTC CAA | 293 | 0.559832 | 0.666152 | 0.743391 |
| 6093 | ROCK1 | "Rho-associated, coiled-coil containing protein kinase 1" | NM_005406 | /5Phos/rCr GrGrUrUr ArGrArAr CrArArGr ArGrGrUr ArArArUr GrACG | 294 | 5.17E-02 | 0.118592 | 0.123273 |
| 6093 | ROCK1 | "Rho-associated, coiled-coil containing protein kinase 1" | NM_005406 | /5Phos/rGr GrUrUrAr GrArArCr ArArGrAr GrGrUrUr ArArUrGr ArAGG | 295 | 0.251923 | 0.267744 | 0.223982 |
| 6196 | RPS6KA2 | ribosomal protein S6 kinase, 90 kDa, polypeptide 2 | NM_001006932 NM_021135 | CTGGAA CACGCT GTACCG GAA | 686 | 0.364701 | 0.511616 | 0.518378 |

TABLE 3-continued

Scores of 295 confirmed genes required for influenza virus replication.

| | | | | | | | | |
|---|---|---|---|---|---|---|---|---|
| 6196 | RPS6KA2 | ribosomal protein S6 kinase, 90 kDa, polypeptide 2 | NM_001006932 | CAGCAA GAUCUG CACAAAG | 687 | 0.67855 | 0.629673 | 0.494396 |
| 6204 | RPS10 | RPS10, ribosomal protein S10 | NM_001014 | TTGAAT AAACTT ACAGCC AAA | 47 | 0.375022 | 0.605714 | 0.613794 |
| 6204 | RPS10 | ribosomal protein S10 | NM_001014 | AACCGG ATTGCC ATTTAT GAA | 46 | 0.751938 | 0.726815 | 0.59629 |
| 6224 | RPS20 | ribosomal protein S20 | NM_001023 | CCCTAA CAAGCC GCAACG TAA | 688 | 0.292758 | 0.402218 | 0.337312 |
| 6224 | RPS20 | ribosomal protein S20 | NM_001023 | TTCGCT CTCGCC GAGGAA CAA | 689 | 0.60169 | 0.45746 | 0.298139 |
| 6328 | SCN3A | sodium channel, voltage-gated, type III, alpha subunit | NM_001081676 NM_001081677 NM_006922 | CAGCGT AATTTC AGATGT TAT | 690 | 0.377089 | 0.378925 | 0.336799 |
| 6328 | SCN3A | sodium channel, voltage-gated, type III, alpha subunit | NM_001081676 NM_001081677 NM_006922 | CTCCCA TAATAA ATTATA TAA | 691 | 0.658364 | 0.6171 | 0.509542 |
| 6334 | SCN8A | sodium channel, voltage gated, type VIII, alpha subunit | NM_014191 | GGGAAG AGUUUG CCUUUCA | 692 | 0.658539 | 0.430628 | 0.283268 |

TABLE 3-continued

Scores of 295 confirmed genes required for influenza virus replication.

| | | | | | | | | |
|---|---|---|---|---|---|---|---|---|
| 6334 | SCN8A | sodium channel, voltage gated, type VIII, alpha subunit | NM_014191 | ACCATT GATATC AAACCA GAA | 693 | 0.686691 | 0.431679 | 0.296971 |
| 6340 | SCNN1G | sodium channel, nonvoltage-gated 1, gamma | NM_001039 | CAAGGC CGGCAA GTAAAC AAA | 694 | 1.244834 | 0.703456 | 0.381588 |
| 6340 | SCNN1G | sodium channel, nonvoltage-gated 1, gamma | NM_001039 | UGGGCU GCAAGU CAUUUUG | 695 | 0.547836 | 0.516556 | 0.534985 |
| 6357 | CCL13 | chemokine (C-C motif) ligand 13 | NM_005408 | CCGGAA AGCTCA CACCCT GAA | 696 | 0.544035 | 0.297011 | 0.175522 |
| 6357 | CCL13 | chemokine (C-C motif) ligand 13 | NM_005408 | ACTCTT AACCTT CAACAT GAA | 697 | 0.549927 | 0.721963 | 0.765856 |
| 6442 | SGCA | sarcoglycan, alpha (50 kDa dystrophin-associated glycoprotein) | NM_000023 | UGUGAC CCUGGU GGAUAAG | 698 | 0.19559 | 0317996 | 0.323205 |
| 6442 | SGCA | EMPTY | NM_000023 | UUGAGG UCACAG CCUACAA | 699 | 0.908422 | 0.646585 | 0.401652 |
| 6446 | SGK1 | serum/glucocorticoid regulated kinase | NM_005627 | /5 Phos/rAr GrCrGrUr UrArGrAr GrUrGrCr CrGrCrCr UrUrArGr ArCAG | 700 | 0.103063 | 0.206548 | 0.207365 |

TABLE 3-continued

Scores of 295 confirmed genes required for influenza virus replication.

| | | | | | | | |
|---|---|---|---|---|---|---|---|
| 6446 | SGK1 | serum/glucocorticoid regulated kinase 1 | NM_005627 | TACAGG CTTATTT GTAATG TA | 701 | 0.438563 | 0.447856 | 0.253796 |
| 6478 | SIAH2 | seven in absentia homolog 2 (Drosophila) | NM_005067 | ACCCGG AGTGCT TATCTT AAA | 702 | 1.233842 | 0.421482 | 0.189076 |
| 6478 | SIAH2 | seven in absentia homolog 2 (Drosophila) | NM_005067 | ACCAGA ACAUGA AGACAUA | 703 | 0.261154 | 0.392519 | 0.401569 |
| 6604 | SMARCD3 | SWI/SNF related, matrix associated, actin dependent regulator of chromatin, subfamily d, member 3 | NM_001003801 NM_001003802 NM_003078 | GTGGCA GTATGT GAAGAC CAA | 704 | 0.485754 | 0.43639 | 0.363875 |
| 6604 | SMARCD3 | SWI/SNF related, matrix associated, actin dependent regulator of chromatin, subfamily d, member 3 | NM_001003801 NM_001003802 NM_003078 | CTCAAG GTGATG ACAGAT GTA | 705 | 0.434246 | 0.51373 | 0.545736 |
| 6613 | SUMO2 | SMT3 suppressor of mif two 3 homolog 2 (S. cerevisiae) | NM_001005849 NM_066937 | CTGTCT TTAAGT AGGGAT AAA | 89 | 0.799709 | 0.384551 | 0.224997 |
| 6613 | SUMO2 | SMT3 suppressor of mif two 3 homolog 2 (S. cerevisiae) | NM_001005849 NM_066937 | AAGTAG GGATAA CTA | 90 | 0.679982 | 0.727311 | 0.61698 |

TABLE 3-continued

Scores of 295 confirmed genes required for influenza virus replication.

| | | | | | | | |
|---|---|---|---|---|---|---|---|
| 6624 | FSCN1 | fascin homolog 1, actin-bundling protein (Strongylocentrotus purpuratus) | NM_003088 | CTGAGC CTTATTT CTCTGG AA | 706 | 0.463411 | 0.602228 | 0.874638 |
| 6624 | FSCN1 | fascin homolog 1, actin-bundling protein (Strongylocentrotus purpuratus) | NM_003088 | AACTGG AAATAG CGAAAT AAA | 707 | 0.689875 | 0.696247 | 0.630604 |
| 6625 | SNRNP70 | small nuclear ribonucleo protein 70 kDa (U1) | NM_001009820 NM_003089 | AAGATT GAGCGG CGACAG CAA | 708 | 0.865553 | 0.351303 | 0.200878 |
| 6625 | SNRP70 | small nuclear ribonucleo protein 70 kDa polypeptide (RNP antigen) | NM_001009820 NM_003089 | CCGGAG AGAGTT TGAGGT GTA | 709 | 0.295152 | 0.425576 | 0.507144 |
| 6627 | SNRPA1 | small nuclear ribonucleo protein polypeptide A' | NM_003090 | AGCCTT GTTTGT GTTAGC AAA | 710 | 0.135945 | 0.249412 | 0.256044 |
| 6627 | SNRPA1 | small nuclear ribonucleo protein polypeptide A' | NM_003090 | TAGCCT TGTTTG TGTTAG CAA | 711 | 0.290838 | 0.441297 | 0.475206 |
| 6792 | CDKL5 | cyclin-dependent kinase-like 5 | NM_001037343 NM_003159 | AAGATA GACGCT TCATGT TAA | 712 | 0.446852 | 0.57682 | 0.596938 |

TABLE 3-continued

Scores of 295 confirmed genes required for influenza virus replication.

| | | | | | | | | |
|---|---|---|---|---|---|---|---|---|
| 6792 | CDKL5 | cyclin-dependent kinase-like 5 | NM_001037343 NM_003159 | AAGGCAATAATGCTAATTACA | 713 | 0.516039 | 0.856423 | 0.958541 |
| 6811 | STX5 | syntaxin 5 | NM_003164 XM_001128716 | CAGTGGAAATTGAAGAGCTAA | 714 | 0.609298 | 0.570421 | 0.435356 |
| 6811 | STX5 | syntaxin 5 | NM_003164 XM_001128716 | ATCAATAGCCTCAACAAACAA | 715 | 1.067683 | 0.800215 | 0.600268 |
| 7005 | TEAD3 | TEA domain family member 3 | NM_003214 | TAGCACCTCATTAGCCCACAA | 716 | 0.182135 | 0.285612 | 0.303818 |
| 7005 | TEAD3 | TEA domain family member 3 | NM_003214 | TGGGTATTTATGAGTTTCATA | 717 | 0.560458 | 0.714534 | 0.825321 |
| 7178 | TPT1 | tumor protein, translationally-controlled 1 | NM_003295 | CCGCGCTCGCTCCGAGTTTCA | 718 | 0.252724 | 0.29385 | 0.244265 |
| 7178 | TPT1 | tumor protein, translationally-controlled 1 | NM_003295 | CGCCGTCGTCGTCTCCCTTCA | 719 | 0.976549 | 0.794541 | 0.537606 |
| 7294 | TXK | TXK tyrosine kinase | NM_003328 | TAGGTGAATGGCGGTCACATA | 720 | 0.23241 | 0.266392 | 0.23849 |
| 7294 | TXK | TXK tyrosine kinase | NM_003328 | CCCGGTGACATTCTATTTCCA | 721 | 0.643421 | 0.765014 | 0.741716 |

TABLE 3-continued

Scores of 295 confirmed genes required for influenza virus replication.

| | | | | | | | | |
|---|---|---|---|---|---|---|---|---|
| 7341 | SUMO1 | SMT3 suppressor of mif two 3 homolog 1 (*S. cerevisiae*) | NM_001005781 NM_001005782 NM_003352 | CAGGTT GAAGTC AAGATG ACA | 296 | 1.108082 | 0.685798 | 0.416473 |
| 7341 | SUMO1 | SMT3 suppressor of mif two 3 homolog 1 (*S. cerevisiae*) | NM_001005781 NM_001005782 NM_003352 | CAGTTA CCTAAT CATGTT GAA | 297 | 1.126982 | 0.804388 | 0.592527 |
| 7423 | VEGFB | vascular endothelial growth factor B | NM_003377 XM_001128909 | AAGACC CAAACC TCTGCA TAA | 298 | 0.506389 | 0.612819 | 0.45103 |
| 7423 | VEGFB | vascular endothelial growth factor B | NM_003377 XM_001128909 | CAGTGT GAATGC AGACCT AAA | 299 | 0.49583 | 0.501911 | 0.465779 |
| 7786 | MAP3K12 | mitogen-activated protein kinase kinase kinase 12 | NM_006301 | CAGGGA GCACTA TGAAAG GAA | 60 | 0.357591 | 0.389537 | 0.404297 |
| 7786 | MAP3K12 | mitogen-activated protein kinase kinase kinase 12 | NM_006301 | CCACGA AAUCGC CCAUCAU | 61 | 0.366546 | 0.446482 | 0.377561 |
| 8021 | NUP214 | nucleoporin 214 kDa | NM_005085 | CCCGGA GATGAT CCCAAC AAA | 28 | 0.609111 | 0.444615 | 0.290697 |
| 8021 | NUP214 | nucleoporin 214 kDa | NM_005085 | CACCAT AGAATC TCACAC CAA | 29 | 0.847775 | 0.523336 | 0.390298 |
| 8290 | HIST3H3 | histone cluster 3, H3 | NM_003493 | TGAGAG GTTGCG CAACGT TCA | 300 | 0.526131 | 0.525846 | 0.47555 |

TABLE 3-continued

Scores of 295 confirmed genes required for influenza virus replication.

| | | | | | | | | |
|---|---|---|---|---|---|---|---|---|
| 8290 | HIST3H3 | | NM_003493 | histone 3, H3 | | 0.625392 | 0.592131 | 0.481698 |
| 8438 | RAD54L | RAD54-like (*S. cerevisiae*) | NM_003579 | CGCGCG CTTTGG GAACAG GAA | 301 | 0.166273 | 0.334684 | 0.366552 |
| 8438 | RAD54L | RAD54-like (*S. cerevisiae*) | NM_003579 | CCCAGA CUUUGG AUCUCUU | 302 | 0.643617 | 0.815526 | 0.870259 |
| 8476 | CDC42BPA | CDC42 binding protein kinase alpha (DMPK-like) | NM_003607 NM_014826 | TCGGAA AGATAT ACCCTG TAT | 303 | 7.27E-02 | 0.175345 | 0.22775 |
| 8476 | CDC42BPA | CDC42 binding protein kinase alpha (DMPK-like) | NM_003607 NM_014826 | CAGATA ATAGTC GGAAAC AAA | 304 | 0.645069 | 0.50481 | 0.342163 |
| 8558 | CDK10 | cyclin-dependent kinase 10 | NM_001098533 NM_003674 NM_052987 NM_052988 | TCCGAA CATCGT GGAGCT GAA | 305 | 0.463 | 0.383363 | 0.211016 |
| 8558 | CDK10 | cyclin-dependent kinase 10 | NM_001098533 NM_003674 NM_052987 NM_052988 | CCGGAA GCAGCC CTACAA CAA | 306 | 0.874208 | 0.429681 | 0.269138 |
| 8570 | KHSRP | KH-type splicing regulatory protein | NM_003685 | CAGGAT TCAGGC TGCAAA GTA | 307 | 0.805663 | 0.403406 | 0.26193 |
| 8570 | KHSRP | KH-type splicing regulatory protein | NM_003685 | CAGAGG AGGTGA ACAAAT TAA | 308 | 1.054217 | 0.845019 | 0.616769 |

TABLE 3-continued

Scores of 295 confirmed genes required for influenza virus replication.

| | | | | | | | | | |
|---|---|---|---|---|---|---|---|---|---|
| 8677 | STX10 | syntaxin 10 | NM_003765 | CAGAGA GATACT CGCAGG CAA | 30 | 0.214973 | 0.305058 | 0.269075 |
| 8677 | STX10 | syntaxin 10 | NM_003765 | CAGCAG CTGATC ATGGAT GAA | 31 | 0.722484 | 0.528514 | 0.424263 |
| 8831 | SYNGAP1 | synaptic Ras GTPase activating protein 1 homolog (rat) | NM_001130066 NM_006772 | CAGAGC AGTGGT ACCCTG TAA | 309 | 0.050958 | 0.172959 | 0.267611 |
| 8831 | SYNGAP1 | synaptic Ras GTPase activating protein 1 homolog (rat) | NM_001130066 NM_006772 | CCCGGC TGATGC AAAGCT TTA | 310 | 1.150128 | 0.756403 | 0.49555 |
| 8837 | CFLAR | CASP8 and FADD-like apoptosis regulator | NM_003879 | UGGGAG AUUCAU GCCCUUA | 311 | 0.418375 | 0.551165 | 0.548836 |
| 8837 | CFLAR | CASP8 and FADD-like apoptosis regulator | NM_003879 | UCCCAG AUUCUU GGCCAAU | 312 | 0.619186 | 0.907136 | 1.3807 |
| 9114 | ATP6V0D1 | ATPase, H+ transporting, lysosomal 38 kDa, V0 subunit d1 | NM_004691 | CACTTT CATGTT CCTCCC TAA | 313 | 7.52E-02 | 0.146686 | 0.158776 |
| 9114 | ATP6V0D1 | ATPase, H+ transporting, lysosomal | NM_004691 | CCGCGC CTTCAT CATCAC CAT | 314 | 8.39E-02 | 0.154211 | 0.174533 |

TABLE 3-continued

Scores of 295 confirmed genes required for influenza virus replication.

| | | | | | | | | |
|---|---|---|---|---|---|---|---|---|
| | | 38 kDa, V0 subunit d1 | | | | | | |
| 9135 | RABEP1 | rabaptin, RAB GTPase binding effector protein 1 | NM_001083585 NM_004703 | CTGGAA GACTTC ATAAAG CAA | 315 | 0.755622 | 0.50611 | 0.315664 |
| 9135 | RABEP1 | rabaptin, RAB GTPase binding effector protein 1 | NM_001083585 NM_004703 | CAGGAT AAAGCC GAACTG GTA | 316 | 0.565565 | 0.635827 | 0.623721 |
| 9149 | DYRK1B | dual-specificity tyrosine-(Y)-phosphorylation regulated kinase 1B | NM_004714 NM_006483 NM_006484 | CCGGAC CTACCG CTACAG CAA | 317 | 0.765068 | 0.246721 | 0.178211 |
| 9149 | DYRK1B | dual-specificity tyrosine-(Y)-phosphorylation regulated kinase 1B | NM_006483 | /5Phos/rAr CrCrArGr CrArUrGr ArCrArCr GrGrArGr ArUrGrAr ArGTA | 318 | 1.207635 | 0.735478 | 0.490083 |
| 9159 | PCSK7 | proprotein convertase subtilisin/kexin type 7 | NM_004716 | UGUGGC UUCCAA UCAAGUU | 319 | 0.33102 | 0.361034 | 0.349578 |
| 9159 | PCSK7 | proprotein convertase subtilisin/kexin type 7 | NM_004716 | TAGCTA TGACCT CAACTC TAA | 320 | 0.428791 | 0.418948 | 0.435923 |
| 9180 | OSMR | oncostatin M receptor | NM_003999 | TAGCAT AGATTG TCAAAT GTA | 321 | 0.81907 | 0.581167 | 0.374424 |

TABLE 3-continued

Scores of 295 confirmed genes required for influenza virus replication.

| | | | | | | | | |
|---|---|---|---|---|---|---|---|---|
| 9180 | OSMR | oncostatin M receptor | NM_003999 | TAGCTC TAATCT AATATA TAA | 322 | 0.450698 | 0.655214 | 0.567893 |
| 9201 | DCLK1 | doublecortin and CaM kinase-like 1 | NM_004734 | /5Phos/rGr GrCrUrCr CrUrCtUr ArCrGrUr CrArCrUr UrGrCrGr UrCGG | 323 | 0.478794 | 0.631689 | 0.674095 |
| 9201 | DCLK1 | doublecortin-like kinase 1 | NM_004734 | CUGGAG UACACC AAGAAUG | 324 | 0.810976 | 0.767491 | 0.537712 |
| 9230 | RAB11B | RAB11B, member RAS oncogene family | NM_004218 | CACGGA CGGACA GAAGCC CAA | 49 | 0.250073 | 0.75657 | 1.172027 |
| 9230 | RAB11B | RAB11B, member RAS oncogene family | NM_004218 | CGAGTT CAACCT GGAGAG CAA | 325 | 0.464859 | 0.384468 | 0.256445 |
| 9231 | DLG5 | discs, large homolog 5 (Drosophila) | NM_004747 | ACGGAA CTTGAT ACAGCA CAA | 326 | 0.619677 | 0.552558 | 0.469538 |
| 9231 | DLG5 | discs, large homolog 5 (Drosophila) | NM_004747 | TTCGAG TAACTT GCAGTT CAA | 327 | 0.842671 | 0.659563 | 0.536921 |
| 9256 | BZRAP1 | benzodiazapine receptor (peripheral) associated protein 1 | NM_004758 NM_024418 | CCGCCG TCTGGT GGTCCT CAA | 328 | 0.288357 | 0.376875 | 0.280788 |
| 9256 | BZRAP1 | benzodiazapine receptor (peripheral) associated protein 1 | NM_004758 NM_024418 | CACAGT GAGTAT GTAACT TGA | 329 | 0.580913 | 0.683818 | 0.759732 |

TABLE 3-continued

Scores of 295 confirmed genes required for influenza virus replication.

| | | | | | | | | |
|---|---|---|---|---|---|---|---|---|
| 9276 | COPB2 | coatomer protein complex, subunit beta 2 (beta prime) | | ACGATT CTTCAG AGTATG CAA | 330 | 6.67E-02 | 0.15003 | 0.165489 |
| 9276 | COPB2 | coatomer protein complex, subunit beta 2 (beta prime) | | CAGGTT TCAAGG GTAGTG AAA | 331 | 6.83E-02 | 0.151774 | 0.171681 |
| 9448 | MAP4K4 | mitogen-activated protein kinase kinase kinase kinase 4 | NM_004834 NM_145686 NM_145687 | AGGCAA GATCCT ACCCGG AAA | 332 | 0.1931 | 0.431206 | 0.607845 |
| 9448 | MAP4K4 | mitogen-activated protein kinase kinase kinase kinase 4 | NM_145686 | CGCAAU GACAAG GUGUUCU | 333 | 0.743605 | 0.640673 | 0.517063 |
| 9464 | HAND2 | heart and neural crest derivatives expressed 2 | NM_021973 | ATCCGG TTTATTT ATGTGC AA | 334 | 1.10595 | 0.724618 | 0.485519 |
| 9464 | HAND2 | heart and neural crest derivatives expressed 2 | NM_021973 | CCGGCG TGGGCG AATTCA GAA | 335 | 1.001765 | 0.750794 | 0.503635 |
| 9509 | ADAMTS2 | ADAM metallopeptidase with thrombospondin type 1 motif, 2 | NM_014244 | CCGCCG GAGGCT GGACCA CAA | 336 | 0.508142 | 0.509194 | 0.507483 |

TABLE 3-continued

Scores of 295 confirmed genes required for influenza virus replication.

| | | | | | | | |
|---|---|---|---|---|---|---|---|
| 9509 | ADAMTS2 | ADAM metallopeptidase with thrombospondin type 1 motif, 2 | NM_014244 | GACAGG CAAGTT CATCTT AAA | 337 | 2.018481 | 0.956037 | 0.54172 |
| 9575 | CLOCK | clock homolog (mouse) | NM_004898 | ATCCAG CAACTT GCACCT ATA | 338 | 0.125417 | 0.215884 | 0.196234 |
| 9575 | CLOCK | clock homolog (mouse) | NM_004898 | AAGGAG CCATCT ACCTAT GAA | 339 | 0.966905 | 0.814213 | 0.585925 |
| 9578 | CDC42BPB | CDC42 binding protein kinase beta (DMPK-like) | NM_006035 | /5Phos/rUr GrCrUrAr CrArCrGr CrCrGrAr GrArUrAr UrUrCrCr ArUTG | 340 | 0.937695 | 0.510266 | 0.270826 |
| 9578 | CDC42BPB | CDC42 binding protein kinase beta (DMPK-like) | NM_006035 | GCUCAG AUUGCG GAAAUCA | 341 | 0.495356 | 0.475883 | 0.366922 |
| 9625 | AATK | apoptosis-associated tyrosine kinase | NM_001080395 XM_001128317 | TCCGCT GAGATC AGAAGG CAA | 342 | 0.158789 | 0.276193 | 0.257094 |
| 9625 | AATK | apoptosis-associated tyrosine kinase | NM_001080395 XM_001128317 | CCGGTT CCGCTG AGATCA GAA | 343 | 1.24573 | 0.776562 | 0.501556 |

TABLE 3-continued

Scores of 295 confirmed genes required for influenza virus replication.

| | | | | | | | | |
|---|---|---|---|---|---|---|---|---|
| 9641 | IKBKE | "inhibitor of kappa light polypeptide gene enhancer in B-cells, kinase epsilon" | NM_014002 | /5Phos/rUr GrGrUrCr UrGrArCr UrGrArGr CrCrUrAr ArArGrUr UrGUG | 344 | 8.75E-02 | 0.112448 | 0.112461 |
| 9641 | IKBKE | "inhibitor of kappa light polypeptide gene enhancer in B-cells, kinase epsilon" | NM_014002 | /5Phos/rGr GrCrCrAr GrGrGrCr UrUrGrGr CrUrArCr ArArCrGr ArGGG | 345 | 0.457277 | 0.291264 | 0.183248 |
| 9943 | OXSR1 | oxidative-stress responsive 1 | NM_005109 | TAGGGA CTAACT ATAGCA CAA | 346 | 0.627872 | 0.57446 | 0.4758 |
| 9943 | OXSR1 | oxidative-stress responsive 1 | NM_005109 | CTGGAG TAGGGA CTAACT ATA | 347 | 0.540509 | 0.651843 | 0.761957 |
| 9972 | NUP153 | nucleoporin 153 kDa | NM_005124 | CACCAT TATGTG CGCTGA TAA | 348 | 0.767619 | 0.483003 | 0.357973 |
| 9972 | NUP153 | nucleoporin 153 kDa | NM_005124 | ATGGAA CGCGTT GAAATT GTA | 349 | 0.615664 | 0.780725 | 0.717573 |
| 10036 | CHAF1A | chromatin assembly factor 1, subunit A (p150) | NM_005483 | AAGGAA GAAGAG AAACGG TTA | 350 | 2.21111 | 0.464002 | 0.243969 |
| 10036 | CHAF1A | chromatin assembly factor 1, subunit A (p150) | NM_005483 | CTGCCC TTTAAT AAAGCA TTA | 351 | 0.618131 | 0.701682 | 0.709722 |

TABLE 3-continued

Scores of 295 confirmed genes required for influenza virus replication.

| | | | | | | | |
|---|---|---|---|---|---|---|---|
| 10055 | SAE1 | SUMO1 activating enzyme subunit 1 | NM_005500 | TCCGAC TACTTT CTCCTT CAA | 352 | 0.378247 | 0.29101 | 0.21647 |
| 10055 | SAE1 | SUMO1 activating enzyme subunit 1 | NM_005500 | CTGGAG CAGTGA GAAAGC AAA | 353 | 1.156138 | 0.641483 | 0.361527 |
| 10105 | PPIF | peptidylprolyl isomerase F | NM_005729 | CCGCGT GGTGCT GGAGCT GAA | 354 | 0.540586 | 0.410111 | 0.251383 |
| 10105 | PPIF | peptidylprolyl isomerase F (cyclophilin F) | NM_005729 | ATGGAT TTGTGT TCACCT TAA | 355 | 0.305517 | 0.459767 | 0.5028 |
| 10114 | HIPK3 | homeodomain interacting protein kinase 3 | NM_005734 | CAGCCT TACAGG GTTAAA GTA | 356 | 1.264034 | 0.730655 | 0.3141 |
| 10114 | HIPK3 | homeodomain interacting protein kinase 3 | NM_005734 | /5Phos/rUr GrCrArGr ArUrUrGr UrCrGrAr UrGrArAr UrUrGrUr CrCUG | 357 | 0.422791 | 0.520572 | 0.506432 |
| 10155 | TRIM28 | tripartite motif-containing 28 | NM_005762 | /5Phos/rUr GrGrUrGr ArArCrGr UrArCrUr GrUrCrUr ArUrUrGr CrAAC | 358 | 0.122321 | 0.122916 | 0.121966 |
| 10155 | TRIM28 | tripartite motif-containing 28 | NM_005762 | CTGGCC CTATTC TGTCAC GAA | 359 | 0.588564 | 0.789219 | 0.951407 |
| 10159 | ATP6AP2 | ATPase, H+ transporting, lysosomal | NM_005765 | AAGGAC TATCCT TGAGGC AAA | 360 | 0.102176 | 0.165671 | 0.178401 |

TABLE 3-continued

Scores of 295 confirmed genes required for influenza virus replication.

| | | | | | | | | |
|---|---|---|---|---|---|---|---|---|
| | | accessory protein 2 | | | | | | |
| 10159 | ATP6AP2 | ATPase, H+ transporting, lysosomal accessory protein 2 | NM_005765 | CAAGTG CTACAT GATATT TCA | 361 | 0.109724 | 0.178377 | 0.184493 |
| 10181 | RBM5 | RNA binding motif protein 5 | NM_005778 | CGCGTC TTTAGC TGTCAA TAA | 362 | 0.644015 | 0.460475 | 0.283885 |
| 10181 | RBM5 | RNA binding motif protein 5 | NM_005778 | AGGCAG CGCAUA UGGUUUG | 363 | 0.803528 | 0.812717 | 0.543793 |
| 10188 | TNK2 | tyrosine kinase, non-receptor, 2 | NM_001010938 NM_005781 | ACGCAA GTCGTG GATGAG TAA | 364 | 0.233498 | 0.481276 | 0.528621 |
| 10188 | TNK2 | tyrosine kinase, non-receptor, 2 | NM_001010938 NM_005781 | CAGGAT CTTGTG CCTGGA AAT | 365 | 0.629845 | 0.694594 | 0.602624 |
| 10280 | OPRS1 | opioid receptor, sigma 1 | NM_005866 NM_147157 NM_147158 NM_147159 NM_147160 | CCGGCT TGAGCT CACCAC CTA | 366 | 8.38E-02 | 0.17573 | 0.178957 |
| 10280 | OPRS1 | opioid receptor, sigma 1 | NM_005866 NM_147157 NM_147158 NM_147159 NM_147160 | CAGCGT CTTCCA TTCCAG AAA | 367 | 0.559791 | 0.331307 | 0.213019 |
| 10291 | SF3A1 | splicing factor 3a, subunit 1, 120 kDa | NM_001005409 NM_005877 | CAGGAT AAGACG GAATGG AAA | 32 | 0.282749 | 0.544105 | 0.546887 |
| 10291 | SF3A1 | splicing factor 3a, subunit 1, 120 kDa | NM_001005409 NM_005877 | CGCAAG GATTAT GATCCC AAA | 33 | 0.323336 | 0.642313 | 0.754521 |

TABLE 3-continued

Scores of 295 confirmed genes required for influenza virus replication.

| | | | | | | | |
|---|---|---|---|---|---|---|---|
| 10297 | APC2 | adenomatosis polyposis coli 2 | NM_005883 | GCAGCA CAAGAC GCAGAGA | 368 | 0.423287 | 0.24725 | 0.188822 |
| 10297 | APC2 | adenomatosis polyposis coli 2 | NM_005883 | CCGCGG TCTCTG GACAAT CAA | 369 | 0.622717 | 0.686279 | 0.713913 |
| 10381 | TUBB3 | tubulin, beta 3 | NM_006086 | TTGCTG TCAGAT ACCCTT AAA | 370 | 0.386364 | 0.519886 | 0.517537 |
| 10381 | TUBB3 | tubulin, beta 3 | NM_006086 | CACGGT GGTGGA GCCCTA CAA | 371 | 0.518898 | 0.523853 | 0.448388 |
| 10595 | ERN2 | endoplasmic reticulum to nucleus signaling 2 | NM_033266 | CAGGGA TTAATG AAACTG CCA | 372 | 0.247657 | 0.289822 | 0.211877 |
| 10595 | ERN2 | endoplasmic reticulum to nucleus signaling 2 | NM_033266 | CAGCCA CTCGAC GACCCT GAA | 373 | 0.542013 | 0.516073 | 0.393275 |
| 10616 | RBCK1 | chromosome 20 open reading frame 18 | NM_006462 | ATGGAC GAGAAG ACCAAG AAA | 374 | 0.551853 | 0.676003 | 0.653166 |
| 10616 | RBCK1 | RanBP-type and C3HC4-type zinc finger containing 1 | NM_006462 | AGGGAU GGUGCU UCUUUGA | 375 | 1.44113 | 0.831024 | 0.556541 |
| 10725 | NFAT5 | nuclear factor of activated T-cells 5, tonicity-responsive | NM_001113178 NM_066599 NM_138713 NM_138714 NM_173214 NM_173215 | CAGCTG GTGCTT TGAATG TAA | 376 | 0.174129 | 0.248752 | 0.241634 |

TABLE 3-continued

Scores of 295 confirmed genes required for influenza virus replication.

| | | | | | | | | |
|---|---|---|---|---|---|---|---|---|
| 10725 | NFAT5 | nuclear factor of activated T-cells 5, tonicity-responsive | NM_001113178 NM_006599 NM_138713 NM_138714 NM_173214 NM_173215 | CAGGAG TGCCAG AAATCT TAA | 722 | 0.847579 | 0.61692 | 0.487828 |
| 10733 | PLK4 | polo-like kinase 4 (*Drosophila*) | NM_014264 | UGCCAC AUGAAA AGCACUA | 377 | 0.409727 | 0.651994 | 0.757159 |
| 10733 | PLK4 | polo-like kinase 4 (*Drosophila*) | NM_014264 | /5Phos/rCr CrArGrUr UrArCrUr UrCrGrUr ArGrArAr ArUrCrCr ArGCC | 378 | 0.471899 | 0.541103 | 0.425052 |
| 10783 | NEK6 | NIMA (never in mitosis gene a)-related kinase 6 | NM_014397 | /5Phos/rGr CrArCrUr ArCrUrCr CrGrArGr ArArGrUr UrArCrGr ArGGC | 379 | 0.14093 | 0.199122 | 0.189364 |
| 10783 | NEK6 | NIMA (never in mitosis gene a)-related kinase 6 | NM_014397 | ACCACG GAAGTC GAGAAT TAA | 72 | 0.904584 | 0.741075 | 0.496828 |
| 10849 | CD3EAP | CD3c molecule, epsilon associated protein | NM_012099 | CAAGGG CAAATT GGCAGG CAA | 380 | 0.135737 | 0.213669 | 0.215571 |
| 10849 | CD3EAP | CD3c molecule, epsilon associated protein | NM_012099 | CAGATT AACACT GAGCCT CTA | 381 | 0.468259 | 0.300434 | 0.242723 |

TABLE 3-continued

Scores of 295 confirmed genes required for influenza virus replication.

| | | | | | | | | |
|---|---|---|---|---|---|---|---|---|
| 11113 | CIT | "citron (rho- interacting, serine/threonine kinase 21)" | NM_007174 | /5Phos/rGrGrCrGrCrCrArArCrGrArCrGrArGrArUrUrGrUrArCrAGG | 382 | 0.611229 | 0.506807 | 0.355392 |
| 11113 | CIT | citron (rho- interacting, serine/threonine kinase 21) | NM_007174 | GCAGAAGCUGAUGCUAAAC | 383 | 0.638261 | 0.655565 | 0.669154 |
| 11213 | IRAK3 | interleukin-1 receptor- associated kinase 3 | NM_007199 | /5Phos/rGrCrArArCrGrCrGrGrGrCrArArArGrUrUrArArGrArCrCGC | 384 | 0.484904 | 0.415173 | 0.336834 |
| 11213 | IRAK3 | interleukin-1 receptor- associated kinase 3 | NM_007199 | /5Phos/rGrCrCrArGrUrCrUrGrArGrGrUrUrArUrGrUrUrUrCrUrGGC | 385 | 0.727639 | 0.606541 | 0.512301 |
| 11214 | AKAP13 | A kinase (PRKA) anchor protein 13 | NM_006738 NM_007200 NM_144767 | CAGGATTACACTGAAAGTAAT | 51 | 0.830141 | 0.712512 | 0.540373 |
| 11214 | AKAP13 | A kinase (PRKA) anchor protein 13 | NM_006738 NM_007200 NM_144767 | CCGCCTGTTTGGGTTAACAAA | 50 | 1.229575 | 0.818424 | 0.550188 |
| 22820 | COPG | coatomer protein complex, subunit gamma | NM_016128 | CCGAGCCACCTTCTACCTAAA | 34 | 0.178853 | 0.252974 | 0.263188 |
| 22820 | COPG | coatomer protein complex, subunit gamma | NM_016128 | AGGCCCGTGTATTTAATGAAA | 35 | 0.286045 | 0.372547 | 0.404956 |

TABLE 3-continued

Scores of 295 confirmed genes required for influenza virus replication.

| | | | | | | | | |
|---|---|---|---|---|---|---|---|---|
| 23049 | SMG1 | Pl-3-kinase-related kinase SMG-1 | NM_015092 | ATCGATGTTGCCAGACTACTA | 386 | 0.153199 | 0.278908 | 0.309076 |
| 23049 | SMG1 | Pl-3-kinase-related kinase SMG-1 | NM_015092 | /5Phos/rUrGrGrUrCrUrUrGrArArCrArUrCrCrUrArUrUrGrGrCrAUG | 607 | 0.499316 | 0.467566 | 0.388136 |
| 23216 | TBC1D1 | TBC1 (tre-2/USP6, BUB2, cdc16) domain family, member 1 | NM_015173 | AGCCGAUGAUCAAACAAAA | 387 | 1.534564 | 0.719609 | 0.425221 |
| 23216 | TBC1D1 | TBC1 (tre-2/USP6, BUB2, cdc16) domain family, member 1 | NM_015173 | CAGUCAUGACCCAAGUUAC | 388 | 1.356796 | 0.840668 | 0.527817 |
| 23352 | UBR4 | ubiquitin protein ligase E3 component n-recognin 4 | NM_020765 | CTGCGTGAAGGTGAAAGTCAA | 389 | 0.162106 | 0.143455 | 0.139738 |
| 23352 | UBR4 | ubiquitin protein ligase E3 component n-recognin 4 | NM_020765 | CAGCAGGGTTATGCCCTTAAA | 390 | 0.375645 | 0.379222 | 0.31352 |
| 23386 | NUDCD3 | NudC domain containing 3 | NM_015332 | CCCTGCTTTAATAAACAGCAA | 391 | 0.862084 | 0.297446 | 0.179248 |

TABLE 3-continued

Scores of 295 confirmed genes required for influenza virus replication.

| | | | | | | | | |
|---|---|---|---|---|---|---|---|---|
| 23386 | NUDCD3 | NudC domain containing 3 | NM_015332 | CTCCTT GGTGTT GGTTTG CAA | 392 | 0.786834 | 0.721583 | 0.624745 |
| 23387 | KIAA0999 | KIAA0999 protein | NM_025164 | CAGGCA GGCGTG TAACAA GAA | 393 | 0.484382 | 0.361982 | 0.267667 |
| 23387 | KIAA0999 | KIAA0999 protein | NM_025164 | CTCCTA GTCTTT CATCCT GAA | 394 | 0.777993 | 0.447162 | 0.354917 |
| 23396 | PlP5K1C | phosphatidylinositol-4-phosphate 5-kinase, type I, gamma | NM_012398 | CCGCGT CGTGGT CATGAA CAA | 395 | 0.920965 | 0.786796 | 0.587757 |
| 23396 | PlP5K1C | phosphatidylinositol-4-phosphate 5-kinase, type I, gamma | NM_012398 | GACGGC GAGAGC GACACA TAA | 396 | 0.646516 | 0.638882 | 0.723557 |
| 23534 | TNPO3 | transportin 3 | NM_012470 | ACCGAA TGTCTT AGTGAA CTA | 397 | 0.499711 | 0.929678 | 1.308681 |
| 23534 | THPO3 | transportin 3 | NM_012470 | CTGGGA GATCAT GCAGGT TGA | 398 | 1.263664 | 0.936638 | 0.641943 |
| 23552 | CCRK | cell cycle related kinase | NM_001039803 NM_012119 NM_178432 | TGGCGA GATAGT TGCCCT CAA | 399 | 0.108309 | 0.191145 | 0.221822 |
| 23552 | CCRK | cell cycle related kinase | NM_001039803 NM_012119 NM_178432 | AAGGAG AAGTGC AGAGAG TAA | 400 | 0.246706 | 0.43947 | 0.593387 |
| 23604 | DAPK2 | death-associated | NM_014326 | /5Phos/rUr CrCrCrGr | 401 | 6.30E-02 | 0.128727 | 0.133498 |

TABLE 3-continued

Scores of 295 confirmed genes required for influenza virus replication.

| | | | | CrCrGrAr UrUrGrUr ArUrGrUr UrCrCrAr GrGUC | | | | |
|---|---|---|---|---|---|---|---|---|
| 23604 | DAPK2 | death-associated protein kinase 2 | NM_014326 | CGGAAT TTGTTG CTCCAG AAA | 402 | 0.27587 | 0.180591 | 0.159053 |
| 23765 | IL17RA | interleukin 17 receptor | NM_014339 | CAGCGG TCTGGT TATCGT CTA | 403 | 3.90E-02 | 0.117003 | 0.178157 |
| 23765 | IL17RA | interleukin 17 receptor A | NM_014339 | CCUCGA GGGUGC AGAGUUA | 404 | 0.880995 | 0.439163 | 0.255673 |
| 23770 | FKBP8 | FK506 binding protein 8, 38 kDa | NM_012181 | CTGCCA GGAACT GACCAC CTA | 405 | 0.159019 | 0.23809 | 0.246402 |
| 23770 | FKBP8 | FK506 binding protein 8, 38 kDa | NM_012181 | CTCCTA CGACCT CGCCAT CAA | 406 | 0.461388 | 0.561349 | 0.549438 |
| 25831 | HECTD1 | HECT domain containing 1 | NM_015382 | ACGGAA CGGAGA UCAGAAA | 407 | 0.557086 | 0.327846 | 0.233436 |
| 25831 | HECTD1 | HECT domain containing 1 | NM_015382 | CAGGAC TGGCAG AATGTT GAA | 408 | 0.949081 | 0.648627 | 0.406225 |
| 27092 | CACNG4 | calcium channel, voltage-dependent, gamma subunit 4 | NM_014405 | UCGGUA UCAUCG UCUACAU | 409 | 1.033245 | 0.548586 | 0.258206 |

TABLE 3-continued

Scores of 295 confirmed genes required for influenza virus replication.

| | | | | | | | | |
|---|---|---|---|---|---|---|---|---|
| 27092 | CACNG4 | calcium channel, voltage-dependent, gamma subunit 4 | NM_014405 | CTAGGTGGTTACAAATCATAA | 410 | 0.440471 | 0.575301 | 0.660781 |
| 27347 | STK39 | "serine threonine kinase 39 (STE20/SPS1 homolog, yeast)" | NM_013233 | /5Phos/rGrGrCrCrCrArCrCrCrArArUrGrCrUrArArUrGrArArGrAGG | 411 | 0.783287 | 0.495624 | 0.266388 |
| 27347 | STK39 | serine threonine kinase 39 (STE20/SPS1 homolog, yeast) | NM_013233 | GGGAUUUGAAAGCUGGUAA | 412 | 0.495515 | 0.515066 | 0.353855 |
| 28996 | HIPK2 | homeodomain interacting protein kinase 2 | NM_022740 | GGUGAACAUGACGACAGAU | 413 | 0.548999 | 0.472571 | 0.298812 |
| 28996 | HIPK2 | homeodomain interacting protein kinase 2 | NM_022740 | /5Phos/rGrCrGrArUrCrCrArArGrCrGrUrGrUrCrArArGrGrArGrAGC | 414 | 0.843731 | 0.7074 | 0.54996 |
| 29035 | C16orf72 | chromosome 16 open reading frame 72 | NM_014117 | CAGGCTCTCCTACACATGTAA | 415 | 0.216942 | 0.320613 | 0.362356 |
| 29035 | C16orf72 | chromosome 16 open reading frame 72 | NM_014117 | AAGCATTTGGCTGAATCTAAA | 416 | 0.410237 | 0.417257 | 0.412663 |
| 29110 | TBK1 | TANK-binding kinase 1 | NM_013254 | AAAGCGGCAGAGTTAGGTGAA | 417 | 1.348321 | 0.538185 | 0.265564 |

TABLE 3-continued

Scores of 295 confirmed genes required for influenza virus replication.

| | | | | | | | |
|---|---|---|---|---|---|---|---|
| 29110 | TBK1 | TANK-binding kinase 1 | NM_013254 | AGCCUU CUGGUG CAAUAUA | 418 | 0.311353 | 0.359205 | 0.272702 |
| 29127 | RACGAP1 | Rac GTPase activating protein 1 | NM_001126103 NM_001126104 NM_013277 | CACCAC AGACAC CAGATA TTA | 419 | 1.18459 | 0.576036 | 0.23423 |
| 29127 | RACGAP1 | Rac GTPase activating protein 1 | NM_013277 | CTGGTA GATAGA AGAGCT AAA | 420 | 0.980009 | 0.752819 | 0.547148 |
| 29882 | ANAPC2 | anaphase promoting complex subunit 2 | NM_013366 | AAGGTT CTTCTA CCGCAT CTA | 421 | 0.620776 | 0.579298 | 0.344874 |
| 29882 | ANAPC2 | anaphase promoting complex subunit 2 | NM_013366 | GAGAGT CTATAT GCAGAG TAA | 422 | 0.356716 | 0.597909 | 0.693865 |
| 29959 | NRBP1 | nuclear receptor binding protein 1 | NM_013392 | GAGGGA GUUCAU UCAAAAG | 423 | 0.75538 | 0.606244 | 0.412195 |
| 29959 | NRPB1 | nuclear receptor binding protein 1 | NM_013392 | AGGCGA GAAGAG GTGAAT CAA | 424 | 0.671267 | 0.700287 | 0.583559 |
| 30811 | HUNK | hormonally up-regulated Neu-associated kinase | NM_014586 | CACGGG CAAAGT GCCCTG TAA | 425 | 0.173145 | 0.324067 | 0.392618 |
| 30811 | HUNK | hormonally up-regulated Neu-associated kinase | NM_014586 | AACTAA GTACGT TGCAAA TAA | 426 | 0.653918 | 0.553241 | 0.377212 |

TABLE 3-continued

Scores of 295 confirmed genes required for influenza virus replication.

| 30815 | ST6GALNAC6 | ST6 (alpha-N-acetyl-neuraminyl-2,3-beta-galactosyl-1,3)-N-acetylgalactosaminide alpha-2,6-sialyltransferase 6 | NM_013443 | CTCAAT TTCCAG CACCAG AAA | 427 | 0.214406 | 0.234412 | 0.228304 |
| --- | --- | --- | --- | --- | --- | --- | --- | --- |
| 30815 | ST6GALNAC6 | ST6 (alpha-N-acetyl-neuraminyl-2,3-beta-galactosyl-1,3)-N-acetylgalactosaminide alpha-2,6-sialyltransferase 6 | NM_013443 | CCGGAG AGAAAT GAGTAG AAA | 428 | 0.594639 | 0.60538 | 0.524858 |
| 30849 | PIK3R4 | phosphoinositide-3-kinase, regulatory subunit 4 | NM_014602 | CAAGCA ATGCGT GGACTT TAA | 429 | 0.796839 | 0.623728 | 0.416338 |
| 30849 | PIK3R4 | phosphoinositide-3-kinase, regulatory subunit 4 | NM_014602 | AAGCAG AATTCT AGATCA GAA | 430 | 1.121535 | 0.708538 | 0.453707 |
| 50488 | MINK1 | misshapen-like kinase 1 (zebrafish) | NM_001024937 | CACGTA CGGGCG CATCAT TAA | 431 | 0.547035 | 0.612468 | 0.645602 |
| 50488 | MINK1 | misshapen-like kinase 1 (zebrafish) | NM_001024937 | /5Phos/rGr ArCrUrCr UrArCrGr CrCrGrGr GrArGrUr UrUrCrUr CrCGG | 432 | 0.977889 | 0.770388 | 0.593061 |

TABLE 3-continued

Scores of 295 confirmed genes required for influenza virus replication.

| | | | | | | | |
|---|---|---|---|---|---|---|---|
| 51061 | TXNDC11 | thioredoxin domain containing 11 | NM_015914 | CCUCAA GGAGCA GACCUUU | 433 | 0.586139 | 0.484452 | 0.327265 |
| 51061 | TXNDC11 | thioredoxin domain containing 11 | NM_015914 | UCCCUC AAUCAC AUCUUCA | 434 | 1.244746 | 0.746845 | 0.454411 |
| 51172 | NAGPA | N-acetylglucosamine-1-phosphodiester alpha-N-acetylglucosaminidase | NM_016256 | CACAGG AGACAG GTTCCT TTA | 435 | 0.890004 | 0.552641 | 0.368601 |
| 51172 | NAGPA | N-acetylglucosamine-1-phosphodiester alpha-N-acetylglucosaminidase | NM_016256 | TTGAAT AAATTG ATATAA TAA | 436 | 0.823518 | 0.706441 | 0.513843 |
| 51257 | 2-Mar | membrane-associated RING-CH protein II | NM_001005416 | CACGCT GGGTGC CGTGCA TAA | 437 | 0.17639 | 0.409973 | 0.605235 |
| 51257 | 2-Mar | membrane-associated ring finger (C3HC4) 2 | NM_001005416 | ACCAGA AAGUUC GCCUGAA | 438 | 1.54109 | 0.543491 | 0.319701 |
| 51390 | AIG1 | androgen-induced 1 | NM_016108 | CAGAGA GATGAT ATACCC GAA | 439 | 6.09E-02 | 0.172115 | 0.217546 |
| 51390 | AIG1 | androgen-induced 1 | NM_016108 | CAGATG TTTCTC ATTGCA TAA | 440 | 0.528202 | 0.786131 | 0.838113 |

TABLE 3-continued

Scores of 295 confirmed genes required for influenza virus replication.

| | | | | | | | |
|---|---|---|---|---|---|---|---|
| 51393 | TRPV2 | transient receptor potential cation channel, subfamily V, member 2 | NM_016113 | CAGAGG ATCTTT CCAACC ACA | 36 | 0.445984 | 0.446812 | 0.360887 |
| 51393 | TRPV2 | transient receptor potential cation channel, subfamily V, member 2 | NM_016113 | CCAGTG AATTCT GGTGGC AAA | 37 | 0.533687 | 0.527503 | 0.361642 |
| 51422 | PRKAG2 | protein kinase, AMP-activated, gamma 2 non-catalytic subunit | NM_016203 | AAGCGC GGTTAT GGACAC CAA | 441 | 0.653226 | 0.522137 | 0.410823 |
| 51422 | PRKAG2 | protein kinase, AMP-activated, gamma 2 non-catalytic subunit | NM_001040633 NM_016203 | AAGCAC GAGCCT GAACGG TTA | 442 | 1.1612 | 0.742033 | 0.446127 |
| 51526 | C20orf111 | chromosome 20 open reading frame 111 | NM_016470 | CACAAT GAAATC CGAAGC CAA | 443 | 0.692027 | 0.283994 | 0.170751 |
| 51526 | C20orf111 | chromosome 20 open reading frame 111 | NM_016470 | ACAGAT GATACC AAACCT AAA | 444 | 0.888514 | 0.652474 | 0.5125 |

TABLE 3-continued

Scores of 295 confirmed genes required for influenza virus replication.

| | | | | | | | | |
|---|---|---|---|---|---|---|---|---|
| 54507 | ADAMTSL4 | ADAMTS-like 4 | NM_019032 NM_025008 | CAGAAC CTCTAA GCCCGG AAA | 445 | 0.904116 | 0.559864 | 0.422927 |
| 54507 | ADAMTSL4 | ADAMTS-like 4 | NM_019032 NM_025008 | CAGCCT TTAACT CCCAGG AAT | 446 | 0.567265 | 0.644393 | 0.595544 |
| 54776 | PPP1R12C | protein phosphatase 1, regulatory (inhibitor) subunit 12C | NM_017607 | TTGGAG GAACTG GCCCGG AAA | 447 | 0.282736 | 0.461529 | 0.382121 |
| 54776 | PPP1R12C | protein phosphatase 1, regulatory (inhibitor) subunit 12C | NM_017607 | CAGGAG GACCTT CGGAAC CAA | 448 | 0.634139 | 0.625609 | 0.435292 |
| 54866 | PPP1R14D | protein phosphatase 1, regulatory (inhibitor) subunit 14D | NM_001130143 NM_017726 | GAGCCT GAGATT GACCTG GAA | 38 | 0.398403 | 0.617039 | 0.584702 |
| 54866 | PPP1R14D | protein phosphatase 1, regulatory (inhibitor) subunit 14D | NM_017726 | CAGGAG CTCTTC CAGGAT CAA | 39 | 0.492554 | 0.488339 | 0.428571 |
| 54980 | C2orf42 | chromosome 2 open reading frame 42 | NM_017880 | CTGCTC TTAGCT AAGATG CAA | 449 | 0.553707 | 0.244234 | 0.160061 |
| 54980 | C2orf42 | chromosome 2 open reading frame 42 | NM_017880 | CAGCGG TCTTAA AGAGAT TAT | 450 | 0.223761 | 0.311811 | 0.318977 |

TABLE 3-continued

Scores of 295 confirmed genes required for influenza virus replication.

| | | | | | | | | |
|---|---|---|---|---|---|---|---|---|
| 54991 | C1orf159 | chromosome 1 open reading frame 159 | NM_001114103 NM_017891 | CAGAAATTCATTGTGCAGAAA | 451 | 0.34693 | 0.395632 | 0.468466 |
| 54991 | C1orf159 | chromosome 1 open reading frame 159 | NM_001114103 NM_017891 | CAGGGCCTGCTACAGAAGAAA | 452 | 0.898839 | 0.551028 | 0.415977 |
| 55229 | PANK4 | pantothenate kinase 4 | NM_018216 | GCGAGTGGCTTCAGAGATTAA | 453 | 0.644987 | 0.579173 | 0.558438 |
| 55229 | PANK4 | pantothenate kinase 4 | NM_018216 | TCGACATAGGCGGGTCGTTAA | 454 | 0.78876 | 0.728918 | 0.595593 |
| 55577 | NAGK | N-acetylglucosamine kinase | NM_017567 | CCCGGTCTTGTTCCAGGGCAA | 455 | 0.61936 | 0.3689 | 0.32434 |
| 55577 | NAGK | N-acetylglucosamine kinase | NM_017567 | ACCTGAGTGAAAGCTACTTAA | 456 | 0.60317 | 0.662899 | 0.778051 |
| 55652 | SLC48A1 | solute carrier family 48 (heme transporter), member 1 | NM_017842 | CAGGACGAGTGTGGTCTCCCA | 457 | 9.36E-02 | 0.203141 | 0.211676 |
| 55652 | SLC48A1 | solute carrier family 48 (heme transporter), member 1 | NM_017842 | CTGGACCTATGCTGCAGGCAA | 458 | 0.134167 | 0.230319 | 0.258812 |
| 55850 | USE1 | unconventional SNARE in the ER 1 homolog (*S. cerevisiae*) | NM_018467 | ACCGGCCTCTGAGGTGATCAA | 459 | 0.943641 | 0.704182 | 0.388538 |

TABLE 3-continued

Scores of 295 confirmed genes required for influenza virus replication.

| | | | | | | | | |
|---|---|---|---|---|---|---|---|---|
| 55850 | USE1 | unconventional SNARE in the ER 1 homolog (S. cerevisiae) | NM_018467 | CTCAGA GAAAGC ACTGGC CAA | 460 | 0.88735 | 0.751997 | 0.510263 |
| 55851 | PSENEN | presenilin enhancer 2 homolog (C. elegans) | NM_172341 | CTCCCA GGACAG GCTCCT TAA | 461 | 0.103563 | 0.308653 | 0.372125 |
| 55851 | PSENEN | presenilin enhancer 2 | NM_172341 | CTCGCC CAAAGA AGACTA CAA | 462 | 0.373705 | 0.516368 | 0.56146 |
| 55872 | PBK | PDZ binding kinase | NM_018492 | /5Phos/rAr GrCrArUr ArCrUrAr UrGrCrAr GrCrGrUr UrGrGrGr ArAAG | 463 | 0.199475 | 0.112877 | 0.103714 |
| 55872 | PBK | PDZ binding kinase | NM_018492 | AACGCT GTAAAC TGTAAC ATT | 464 | 0.209704 | 0.426522 | 0.643573 |
| 56164 | STK31 | serine/threonine kinase 31 | NM_031414 | /5Phos/rCr CrGrUrCr UrUrGrUr ArGrCrAr UrUrGrUr UrCrCrAr ArAGA | 465 | 0.188272 | 0.173177 | 0.142995 |
| 56164 | STK31 | serine/threonine kinase 31 | NM_032944 | GCUCUA CUCAGA UGGAAAU | 466 | 0.810521 | 0.643003 | 0.39586 |
| 56300 | IL1F9 | interleukin 1 family, member 9 | NM_019618 | AGAGAG ACCAGC CCAUCAU | 467 | 0.667376 | 0.56949 | 0.44053 |
| 56300 | IL1F9 | interleukin 1 family, member 9 | NM_019618 | CAGGAG AGCTGG GTGGTA TAA | 468 | 0.542503 | 0.673445 | 0.68882 |

TABLE 3-continued

Scores of 295 confirmed genes required for influenza virus replication.

| | | | | | | | | |
|---|---|---|---|---|---|---|---|---|
| 56311 | ANKRD7 | ankyrin repeat domain 7 | NM_001077708 NM_019644 | CACCTT ATTCTT GGCACT ACA | 469 | 0.333656 | 0.470028 | 0.432781 |
| 56311 | ANKRD7 | ankyrin repeat domain 7 | NM_001077708 NM_019644 | AAGGAT GGGTAT ACTCCA CTA | 470 | 0.568311 | 0.691346 | 0.677036 |
| 56660 | KCNK12 | potassium channel, subfamily K, member 12 | NM_022055 | CTGCAT TTACTC GCTCTT CAA | 471 | 0.619404 | 0.471415 | 0.388128 |
| 56660 | KCNK12 | potassium channel, subfamily K, member 12 | NM_022055 | CTGGCG CTTTCTT AATCTT TA | 472 | 0.84876 | 0.68778 | 0.512211 |
| 56893 | UBQLN4 | ubiquilin 4 | NM_020131 | CACACT GGCCTT TGTAAA TAA | 473 | 0.516835 | 0.379367 | 0.263475 |
| 56893 | UBQLN4 | ubiquilin 4 | NM_020131 | AGAGAT GCTAAT GGAATT TAA | 474 | 0.529258 | 0.530628 | 0.403726 |
| 56997 | CABC1 | chaperone, ABC1 activity of bc1 complex homolog (S. pombe) | NM_020247 | CGCGGA CTTCAT GCCACT GAA | 475 | 0.489167 | 0.42863 | 0.373153 |
| 56997 | CABC1 | chaperone, ABC1 activity of bc1 complex homolog (S. pombe) | NM_020247 | CAGGGT CAGGAT AAACAT GAA | 476 | 0.429246 | 0.561566 | 0.598724 |

TABLE 3-continued

Scores of 295 confirmed genes required for influenza virus replication.

| | | | | | | | | |
|---|---|---|---|---|---|---|---|---|
| 57085 | AGTRAP | angiotensin II receptor-associated protein | NM_001040194 NM_001040195 NM_001040196 NM_001040197 NM_020350 | CAGGGA TTGCCT GAACCA AGA | 477 | 0.638173 | 0.607386 | 0.502316 |
| 57085 | AGTRAP | angiotensin II receptor-associated protein | NM_001040194 NM_001040195 NM_001040196 NM_001040197 NM_020350 | TTGGGT CTTCTC AGGACC GTA | 478 | 0.605429 | 0.664936 | 0.622262 |
| 57120 | GOPC | golgi associated PDZ and coiled-coil motif containing | NM_001017408 NM_020399 | CACCGT ATTTAT TTAGTC AAA | 479 | 0.806975 | 0.665273 | 0.548127 |
| 57120 | GOPC | golgi associated PDZ and coiled-coil motif containing | NM_001017408 NM_020399 | CAGCTG CAGCTT CATGCT AAA | 480 | 0.705161 | 0.590857 | 0.559338 |
| 57418 | WDR18 | WD repeat domain 18 | NM_024100 | CACAGT GGTGCT AGTCTG TTT | 481 | 1.516436 | 0.441194 | 0.27642 |
| 57418 | WDR18 | WD repeat domain 18 | NM_024100 | CTGCAT CGTGTG GGAACT TCA | 482 | 0.575068 | 0.597972 | 0.495122 |
| 57502 | NLGN4X | neuroligin 4, X-linked | NM_181332 | CCGUUA CCCAAU GAGAUCU | 483 | 0.844051 | 0.732299 | 0.591261 |
| 57502 | NLGN4X | neuroligin 4, X-linked | NM_181332 | UCCGAA AUACUA CUCAGUU | 723 | 1.612589 | 0.873639 | 0.610177 |
| 57534 | MIB1 | mindbomb homolog 1 (*Drosophila*) | NM_020774 | GCUCUA AGGCAU CACACUU | 484 | 0.684692 | 0.5657 | 0.473094 |

TABLE 3-continued

Scores of 295 confirmed genes required for influenza virus replication.

| | | | | | | | | |
|---|---|---|---|---|---|---|---|---|
| 57534 | MIB1 | mindbomb homolog 1 (Drosophila) | NM_020774 | ACCGAA TTACTA CACCGG GAA | 485 | 0.526567 | 0.687665 | 0.722057 |
| 57551 | TAOK1 | TAO kinase 1 | NM_020791 | GGACAA UAUGAU GGCAAAG | 486 | 0.277376 | 0.396557 | 0.336157 |
| 57551 | TAOK1 | TAO kinase 1 | NM_020791 | CAGTGC TAAAGT ACTACT GAA | 487 | 0.596057 | 0.630548 | 0.634735 |
| 57579 | FAM135A | family with sequence similarity 135, member A | NM_001105531 NM_020819 | CAGCAA TTACAT TAAATT CAA | 53 | 0.627823 | 0.832351 | 0.890621 |
| 57579 | FAM135A | family with sequence similarity 135, member A | NM_001105531 NM_020819 | CACGAA GAACTA AGAATA TTA | 52 | 0.643343 | 0.760063 | 0.688994 |
| 58526 | MID1IP1 | MID1 interacting protein 1 (gastrulation specific G12 homolog (zebrafish)) | NM_001098790 NM_001098791 NM_021242 | CAGCCA CTACGT GCTTCT CAA | 488 | 0.990597 | 0.727648 | 0.484586 |
| 58526 | MID1IP1 | MID1 interacting protein 1 (gastrulation specific G12 homolog (zebrafish)) | NM_001098790 NM_001098791 NM_021242 | CTCGCT CTTTAA CGCCAT GAA | 489 | 0.491054 | 0.579867 | 0.506256 |
| 64284 | RAB17 | RAB17, member RAS oncogene family | NM_022449 | AAGTGA GATCCT GGAAGT GAA | 490 | 0.864384 | 0.527264 | 0.318025 |

TABLE 3-continued

Scores of 295 confirmed genes required for influenza virus replication.

| | | | | | | | |
|---|---|---|---|---|---|---|---|
| 64284 | RAB17 | RAB17, member RAS oncogene family | NM_022449 | TCGCCT GAGATA TAAGTT GTA | 491 | 0.358138 | 0.516395 | 0.444483 |
| 64601 | VPS16 | vacuolar protein sorting 16 homolog (S. cerevisiae) | NM_022575 NM_080413 | CAGCAT GGACTG GGACCT GAA | 492 | 0.433574 | 0.341264 | 0.288715 |
| 64601 | VPS16 | vacuolar protein sorting 16 homolog (S. cerevisiae) | NM_022575 NM_080413 NM_080414 | CCGCAC GGAGCT GGCCAT CAA | 493 | 0.296463 | 0.45291 | 0.445158 |
| 65220 | NADK | NAD kinase | NM_023018 | CACGCA CCTCAT GGAGGA GAA | 494 | 0.478096 | 0.407404 | 0.336484 |
| 65220 | NADK | NAD kinase | NM_023018 | CCAGAC CATCAT GCACAT TCA | 495 | 0.447899 | 0.461939 | 0.505008 |
| 79574 | EPS8L3 | EPS8-like 3 | NM_024526 NM_133181 NM_139053 | AGCCAT TTACTT GCACCG GAA | 55 | 0.350105 | 0.561952 | 0.529498 |
| 79574 | EPS8L3 | EPS8-like 3 | NM_024526 NM_133181 NM_139053 | CCGGAA GGAGTA CTCCCA GAA | 54 | 0.386201 | 0.458315 | 0.527572 |
| 79641 | ROGD1 | rogdi homolog (Drosophila) | NM_024589 | CAGGGC TGTCTA AGAAAT AAA | 496 | 0.555572 | 0.568837 | 0.481464 |
| 79641 | ROGD1 | rogdi homolog (Drosophila) | NM_024589 | AAGCAA GAGAAC TTCATC CTA | 497 | 0.616731 | 0.691378 | 0.725866 |

TABLE 3-continued

Scores of 295 confirmed genes required for influenza virus replication.

| | | | | | | | |
|---|---|---|---|---|---|---|---|
| 79705 | LRRK1 | leucine-rich repeat kinase 1 | NM_024652 | CCCTGT TTGTTT GCACAT AAT | 498 | 0.615454 | 0.567642 | 0.462564 |
| 79705 | LRRK1 | leucine-rich repeat kinase 1 | NM_024652 | AGCGGA GGAAUG AAAAUUG | 499 | 0.850759 | 0.71624 | 0.496298 |
| 79872 | CBLL1 | Cas-Br-M (murine) ecotropic retroviral transforming sequence-like 1 | NM_024814 | CGCGAA CTCAAA GAACTA TAA | 500 | 0.27845 | 0.599651 | 0.642618 |
| 79872 | CBLL1 | Cas-Br-M (murine) ecotropic retroviral transforming sequence-like 1 | NM_024814 | GGGUGC AAGAGA ACAUAUU | 501 | 0.304778 | 0.563409 | 0.600037 |
| 80231 | CXorf21 | chromosome X open reading frame 21 | NM_025159 | GCACUC CUAGUC UCCAUAU | 502 | 0.393433 | 0.671994 | 0.667663 |
| 80231 | CXorf21 | chromosome X open reading frame 21 | NM_025159 | AAGGTT GTGGAG TTATAT AAA | 503 | 0.574544 | 0.621492 | 0.604511 |
| 80818 | ZNF436 | zinc finger protein 436 | NM_001077195 NM_030634 | AACGAG GTAAAT CCCAAG CAA | 504 | 0.177787 | 0.326918 | 0.389789 |
| 80818 | ZNF436 | zinc finger protein 436 | NM_001077195 NM_030634 | ACACAT GTTCTT GGTAAC TAA | 505 | 0.794224 | 0.765622 | 0.599686 |
| 84197 | SGK196 | protein kinase-like protein SgK196 | NM_032237 | CACGAT GATCTC ATGCCC TCA | 506 | 9.06E-02 | 0.166383 | 0.187301 |

TABLE 3-continued

Scores of 295 confirmed genes required for influenza virus replication.

| | | | | | | | | |
|---|---|---|---|---|---|---|---|---|
| 84197 | SGK196 | protein kinase-like protein SgK196 | NM_032237 | AACACT ATGCTT ACTGAA TAT | 507 | 0.80003 | 0.600668 | 0.424152 |
| 89891 | WDR34 | WD repeat domain 34 | NM_052844 | CATGGT CATCCG AGAGCT GAA | 508 | 0.531012 | 0.438428 | 0.26305 |
| 89891 | WDR34 | WD repeat domain 34 | NM_052844 | ACGGAG CACCAA GCTCAA GAA | 509 | 0.419737 | 0.444796 | 0.427026 |
| 90736 | FAM104B | family with sequence similarity 104, member B | NM_138362 | CTGGGC TTCCTG GGTCAA GTA | 510 | 0.121512 | 0.232044 | 0.271558 |
| 90736 | FAM104B | family with sequence similarity 104, member B | NM_138362 | CCCAAT TCCAAT TCCTTG TAA | 511 | 0.612913 | 0.787792 | 1.049092 |
| 92579 | G6PC3 | glucose 6 phosphatase, catalytic, 3 | NM_138387 | CACATG TTCAGT GCCCAG GAA | 512 | 0.141286 | 0.377787 | 0.36247 |
| 92579 | G6PC3 | glucose 6 phosphatase, catalytic, 3 | NM_138387 | GTGGCT CAACCT CATCTT CAA | 513 | 0.142379 | 0.261952 | 0.303557 |
| 93611 | FBXO44 | F-box protein 44 | NM_001014765 | UGUGAA UGGAGG CGAUGAG | 514 | 0.235476 | 0.396178 | 0.348825 |
| 93611 | FBXO44 | F-box protein 44 | NM_001014765 | CCCGAA AGGTCT TGACCT GAA | 515 | 0.579048 | 0.773523 | 0.72998 |

TABLE 3-continued

Scores of 295 confirmed genes required for influenza virus replication.

| | | | | | | | | |
|---|---|---|---|---|---|---|---|---|
| 93953 | ACRC | acidic repeat containing | NM_052957 | CCCGAT GACAAT AGTGAT GAT | 57 | 0.254396 | 0.245654 | 0.176945 |
| 93953 | ACRC | acidic repeat containing | NM_052957 | TAGGTA CTGTTA AGTAAG TAA | 56 | 0.635969 | 0.73525 | 0.586576 |
| 94234 | FOXQ1 | forkhead box Q1 | NM_033260 | CTCCAT CAAACG TGCCTT AAA | 516 | 0.299843 | 0.447654 | 0.503003 |
| 94234 | FOXQ1 | forkhead box Q1 | NM_033260 | CGCGCG GACTTT GCACTT TGA | 517 | 0.648835 | 1.168153 | 2.107078 |
| 96626 | LIMS3 | LIM and senescent cell antigen-like domains 3 | NM_033514 | CAGCCT TGACAG CGAAGA ATA | 518 | 0.879655 | 0.675756 | 0.549347 |
| 96626 | LIMS3 | LIM and senescent cell antigen-like domains 3 | NM_033514 | TCCAAG GCTGCT AACAAA TAA | 519 | 0.819435 | 0.624426 | 0.591773 |
| 113878 | DTX2 | deltex homolog 2 (Drosophila) | NM_020892 | GCUUCA UCGAGC AGCAGUU | 83 | 0.53263 | 0.23332 | 0.154954 |
| 113878 | DTX2 | deltex homolog 2 (Drosophila) | NM_001102594 NM_001102595 NM_001102596 NM_020892 | CAAGAC AGAGAT GGACCG CAA | 84 | 0.655186 | 0.468141 | 0.329376 |
| 114299 | PALM2 | paralemmin 2 | | AAGGCT GGACAA TCAAGC TTA | 520 | 0.394215 | 0.514481 | 0.527585 |

TABLE 3-continued

Scores of 295 confirmed genes required for influenza virus replication.

| | | | | | | | | |
|---|---|---|---|---|---|---|---|---|
| 114299 | PALM2 | paralemmin 2 | | AAGGTG CTAGGC TATGAT GAA | 521 | 0.595251 | 0.526448 | 0.412288 |
| 114788 | CSMD3 | CUB and Sushi multiple domains 3 | NM_198124 | CACCCA GCCCAA AGCUAAG | 522 | 0.569442 | 0.608563 | 0.634163 |
| 114788 | CSMD3 | CUB and Sushi multiple domains 3 | NM_052900 NM_198123 NM_198124 | CACGGT TTGCAC AATGGT ATA | 523 | 0.591463 | 0.694551 | 0.75186 |
| 114880 | OSBPL6 | oxysterol binding protein-like 6 | NM_032523 NM_145739 | CAGGTT GTCAGT GTAAAT ATT | 524 | 1.096729 | 0.719444 | 0.45093 |
| 114880 | OSBPL6 | oxysterol binding protein-like 6 | NM_032523 NM_145739 | CACATT CTGAAT GAATAA ATA | 525 | 1.158544 | 0.786005 | 0.534373 |
| 114971 | PTPMT1 | protein tyrosine phosphatase, mitochondrial 1 | NM_175732 XM_374879 | CACCTT GGACAA CCTCCA GAA | 526 | 0.82162 | 0.282374 | 0.171973 |
| 114971 | PTPMT1 | protein tyrosine phosphatase, mitochondrial 1 | NM_175732 XM_374879 | AACCTC CAGAAG GGAGTC CAA | 527 | 0.667621 | 0.627974 | 0.573823 |
| 115701 | ALPK2 | alpha-kinase 2 | NM_052947 | CGGCCT CATGCC TGTCTT CAA | 528 | 0.649019 | 0.402734 | 0.303672 |
| 115701 | ALPK2 | alpha-kinase 2 | NM_052947 | AGCGAA GACCTT GGCATT TAT | 529 | 0.94312 | 0.650214 | 0.487435 |
| 116447 | TOP1MT | topoisomerase (DNA) 1, mitochondrial | NM_052963 | CCAGAC GAAGAT CCAGGC AAA | 530 | 8.60E-02 | 0.17212 | 0.179116 |

TABLE 3-continued

Scores of 295 confirmed genes required for influenza virus replication.

| | | | | | | | | |
|---|---|---|---|---|---|---|---|---|
| 116447 | TOP1MT | topoisomerase (DNA) 1, mitochondrial | NM_052963 | GACGAA GAUCCA GGCAAAG | 531 | 0.318731 | 0.312125 | 0.209861 |
| 118442 | GPR62 | G protein-coupled receptor 62 | NM_080865 | TAGGCT CCATTC TGCCAT CTA | 532 | 0.107637 | 0.34081 | 0.533706 |
| 118442 | GPR62 | G protein-coupled receptor 62 | NM_080865 | CCCGCG GGCACU CUUGCAA | 533 | 1.001052 | 0.434702 | 0.278245 |
| 122525 | C14orf28 | chromosome 14 open reading frame 28 | NM_001017923 XM_071793 | AACAAA GAGGAA CATCAT TAT | 534 | 0.818519 | 0.61488 | 0.442405 |
| 122525 | C14orf28 | chromosome 14 open reading frame 28 | NM_001017923 XM_071793 | AAGTCC ATAAAG CTTCAT TAA | 535 | 1.018714 | 0.678254 | 0.582497 |
| 124583 | CANT1 | calcium activated nucleotidase 1 | NM_138793 | CCAGAT CATTGT GGCCCT CAA | 536 | 9.01E-02 | 0.15415 | 0.173949 |
| 124583 | CANT1 | calcium activated nucleotidase 1 | NM_138793 | AAGCAG TTTCCTT TCTTAT AA | 626 | 0.741698 | 0.598363 | 0.422152 |
| 126541 | OR10H4 | olfactory receptor, family 10, subfamily H, member 4 | NM_001004465 | CCCUCU CCGUCU CUGAGAU | 537 | 0.471744 | 0.394933 | 0.332012 |
| 126541 | OR10H4 | olfactory receptor, family 10, subfamily H, member 4 | NM_001004465 | TTGAGG ATTCCC TCTGCC GAA | 538 | 0.840398 | 0.559888 | 0.481215 |

TABLE 3-continued

Scores of 295 confirmed genes required for influenza virus replication.

| | | | | | | | |
|---|---|---|---|---|---|---|---|
| 127733 | UBXN10 | UBX domain protein 10 | NM_152376 | CTGGTA AATAAC CACAGT GTA | 539 | 0.588716 | 0.584026 | 0.44886 |
| 127733 | UBXD3 | UBX domain containing 3 | NM_152376 | CACCAG GACTTG AGCACA TAA | 540 | 0.502515 | 0.577923 | 0.563379 |
| 153571 | C5orf38 | chromosome 5 open reading frame 38 | NM_178569 | CCGCCA AAGAAT TTAGAA CGA | 541 | 0.485237 | 0.506168 | 0.421594 |
| 153571 | C5orf38 | chromosome 5 open reading frame 38 | NM_178569 | CCGCCT CTGGCA GGACCT GAA | 542 | 0.433421 | 0.523087 | 0.751442 |
| 166614 | DCLK2 | doublecortin and CaM kinase-like 2 | NM_152619 | /5Phos/rCr GrGrUrGr UrArCrCr GrCrGrGr GrArCrAr ArArUrCr CrUCG | 543 | 0.322198 | 0.197086 | 0.168504 |
| 166614 | DCLK2 | doublecortin-like kinase 2 | NM_001040261 | GGUCAU UGGUGA UGGCAAU | 544 | 0.553155 | 0.461216 | 0.288162 |
| 167681 | PRSS35 | protease, serine, 35 | NM_153362 | CCGTAG TGAGAT CACTTC ATA | 40 | 0.247475 | 0.473915 | 0.486554 |
| 167681 | PRSS35 | "protease, serine, 35" | NM_153362 | GGAGAA AGAGAC AGGUGUA | 545 | 0.255043 | 0.343875 | 0.302288 |
| 203068 | TUBB | tubulin, beta polypeptide | NM_178014 | TGGGTA GAAGTC ACTATA TAA | 86 | 0.342439 | 0.530177 | 0.554799 |
| 203068 | TUBB | tubulin, beta | NM_178014 | GGUCCU UUUGGC CAGAUCU | 85 | 0.513811 | 0.517138 | 0.367654 |

TABLE 3-continued

Scores of 295 confirmed genes required for influenza virus replication.

| | | | | | | | | |
|---|---|---|---|---|---|---|---|---|
| 204851 | HIPK1 | homeodomain interacting protein kinase 1 | | AGGGAA GCTGTA CACCAC TAA | 546 | 0.274163 | 0.319688 | 0.319285 |
| 204851 | HIPK1 | homeodomain interacting protein kinase 1 | | CAGGAG TTCTCA CGCAGG GAA | 547 | 0.482556 | 0.617195 | 0.699188 |
| 254065 | BRWD3 | bromodomain and WD repeat domain containing 3 | NM_153252 | CACAGT TATTAC TGCAGT GAA | 79 | 0.862698 | 0.728217 | 0.464032 |
| 254065 | BRWD3 | bromodomain and WD repeat domain containing 3 | NM_153252 | AAGACA GTCTTT AAAGTG TAA | 80 | 0.994112 | 0.741188 | 0.590877 |
| 256126 | SYCE2 | synaptonemal complex central element protein 2 | NM_001105578 XM_497609 | CAGGAA CAGCCT GAAGAC CAA | 548 | 0.539001 | 0.366574 | 0.260794 |
| 256126 | SYCE2 | synaptonemal complex central element protein 2 | NM_001105578 XM_497609 | GAGGAT CTATCA GATTTA TAA | 549 | 0.61555 | 0.569485 | 0.372681 |
| 283455 | KSR2 | kinase suppressor of ras 2 | NM_173598 | /5Phos/rGr CrArUrCr CrGrGrUr GrArCrCr UrCrGrAr ArUrCrCr ArAGC | 550 | 3.49E-02 | 9.87E-02 | 0.123383 |
| 283455 | KSR2 | kinase suppressor of ras 2 | NM_173598 | ATCCGG TGACCT CGAATC CAA | 551 | 1.098794 | 0.769922 | 0.488615 |

TABLE 3-continued

Scores of 295 confirmed genes required for influenza virus replication.

| 284230 | RPL36AP49 | ribosomal protein L36a pseudogene 49 | XM_001721447 XM_208185 XM_940333 | AAGCAT GGTTAA CGTCCC TAA | 552 | 0.427412 | 0.331614 | 0.261506 |
| --- | --- | --- | --- | --- | --- | --- | --- | --- |
| 284230 | RPL36AP49 | ribosomal protein L36a pseudogene 49 | XM_001721447 XM_208185 XM_940333 | AAGAGA ATGCTG GCTATT AAA | 553 | 0.29842 | 0.454847 | 0.492654 |
| 284366 | KLK9 | kallikrein-related peptidase 9 | NM_012315 | CACCTC CTTCTT GGAACA GCA | 554 | 0.289869 | 0.242241 | 0.172264 |
| 284366 | KLK9 | kallikrein-related peptidase 9 | NM_012315 | UGCCAC UACCUU GACUGGA | 555 | 0.599478 | 0.680461 | 0.700468 |
| 338599 | DUPD1 | dual specificity phosphatase and pro isomerase domain containing 1 | NM_001003892 | AGCGAC GACCAC AGUAAGA | 556 | 1.393718 | 0.578739 | 0.29759 |
| 338599 | DUPD1 | DUPD1, dual specificity phosphatase and pro isomerase domain containing 1 | NM_001003892 | CCACAG TAAGAT CCTGGT TCA | 557 | 0.567546 | 0.633947 | 0.468889 |
| 340024 | SLC6A19 | solute carrier family 6 (neutral amino acid transporter), member 19 | NM_001003841 | CACGAA CATCCT GACCCT CAT | 558 | 0.145676 | 0.167331 | 0.193004 |
| 340024 | SLC6A19 | solute carrier family 6 (neutral | NM_001003841 | CTCGGT GATTGT GTCCAT CAT | 559 | 0.383281 | 0.487078 | 0.565148 |

TABLE 3-continued

Scores of 295 confirmed genes required for influenza virus replication.

| | | | | | | | |
|---|---|---|---|---|---|---|---|
| 340260 | UNCX | amino acid transporter), member 19 | XM_294209 | CTGGAT TCTGGT ACCCTC CGA | 560 | 0.234348 | 0.317787 | 0.341701 |
| 340260 | UNCX | UNC homeobox | XM_935646 | CCGCCA TGTGCC CTTCTC CAT | 561 | 0.755314 | 0.574473 | 0.502236 |
| 377841 | ENTPD8 | ectonucleoside triphosphate diphospho hydrolase 8 | NM_001033113 NM_198585 | CACAGT TGAAGG GACAGG CAA | 562 | 5.80E-02 | 0.132054 | 0.135708 |
| 377841 | ENTPD8 | ectonucleoside triphosphate diphospho hydrolase 8 | NM_001033113 NM_198585 | CAGGGT GGTGCT GGCCAC AGA | 563 | 0.695552 | 0.486754 | 0.309951 |
| 387082 | SUMO4 | SMT3 suppressor of mif two 3 homolog 4 (S. cerevisiae) | NM_001002255 | TTGATG TGTTTC AACAGC CTA | 87 | 0.571193 | 0.450638 | 0.335206 |
| 387082 | SUMO4 | SMT3 suppressor of mif two 3 homolog 4 (S. cerevisiae) | NM_001002255 | TCCGAT TTGGTG GGCAAC CAA | 564 | 0.461921 | 0.728544 | 0.816882 |
| 387911 | RP11-45B20.2 | collagen triple helix repeat-containing | NM_001007537 | CAGCAT TGTCCT GCAGCT GAA | 58 | 0.442321 | 0.529807 | 0.471774 |
| 387911 | RP11-45B20.2 | collagen triple helix repeat-containing | NM_001007537 | AAAGGA GATCGA GGAGAG AAA | 59 | 0.481867 | 0.510741 | 0.458087 |
| 401007 | NF1L2 | neurofibromin 1-like 2 | XM_496596 | CTGGCT GCAAAT GGCCTC AAA | 565 | 0.299545 | 0.262081 | 0.278983 |

TABLE 3-continued

Scores of 295 confirmed genes required for influenza virus replication.

| | | | | | | | |
|---|---|---|---|---|---|---|---|
| 401007 | NF1L2 | neurofibromin 1-like 2 | XM_496596 | TTCAGT ATTCTT GGACTC TTA | 566 | 1.231267 | 0.83647 | 0.649473 |
| 401665 | OR51T1 | olfactory receptor, family 51, subfamily T, member 1 | NM_001004759 | CTCATA GTTCAG TGTCTT CAA | 567 | 0.736597 | 0.467362 | 0.321872 |
| 401665 | OR51T1 | olfactory receptor, family 51, subfamily T, member 1 | NM_001004759 | CAGCTT GAAGAC CAAGAC AAT | 568 | 1.564046 | 0.717321 | 0.372323 |
| 440396 | LOC440396 | LOC388275, similar to Heterogeneous nuclear ribonucleo protein A1 (Helix-destabilizing protein) (Single-strand binding protein) (hnRNP core protein A1) (HDP-1) (Topoisomerase-inhibitor suppressed) | | ATGGAT TTGGTA ATGATG GAA | 569 | 4.99E-02 | 0.147806 | 0.192162 |
| 440396 | LOC440396 | LOC284387, similar to Heterogeneous nuclear ribonucleo protein A1 (Helix-destabilizing protein) | | ACGGAC TGTGTG GTAATG AGA | 570 | 0.282308 | 0.373617 | 0.388951 |

TABLE 3-continued

Scores of 295 confirmed genes required for influenza virus replication.

| | | | | | | | |
|---|---|---|---|---|---|---|---|
| 440738 | MAP1LC3C | (Single-strand binding protein) (hnRNP core protein A1) (HDP-1) (Topoisomerase-inhibitor suppressed) microtubule-associated protein 1 light chain 3 gamma | NM_001004343 | CCCGGT GGTAGT GGAGCG CTA | 571 | 0.394702 | 0.325085 | 0.239898 |
| 440738 | MAP1LC3C | microtubule-associated protein 1 light chain 3 gamma | NM_001004343 | CGCAAC CATGGC AGAGAT CTA | 572 | 1.181658 | 0.570693 | 0.3015 |
| 441239 | LOC441239 | hypothetical gene supported by BC063653 | XM_001127100 XM_001714484 XM_001715572 XM_496884 XM_499305 XM_935515 XM_938593 | AACTGA CTTGCC CGAATT TAA | 573 | 0.394243 | 0.36773 | 0.353448 |
| 441239 | LOC441239 | hypothetical gene supported by BC063653 | XM_001127100 XM_001714484 XM_001715572 XM_496884 XM_499305 XM_935515 XM_938593 | AACCAG GGCGAC CTAGAA GAA | 574 | 1.354131 | 0.895284 | 0.611832 |
| 441670 | OR4M1 | olfactory receptor, family 4, subfamily M, member 1 | NM_001005500 | CGUCUC UGCUGU AUCCUGG | 575 | 0.785715 | 0.602125 | 0.381486 |
| 441670 | OR4M1 | olfactory receptor, family 4, | NM_001005500 | CCAGGA AAUAUC CUUAUCA | 576 | 0.38551 | 0.579294 | 0.663859 |

TABLE 3-continued

Scores of 295 confirmed genes required for influenza virus replication.

| geneID | Symbol | Description | Accession | Sequence | SEQ ID NO | Score 1 | Score 2 | Score 3 |
|---|---|---|---|---|---|---|---|---|
| 643641 | ZNF862 | zinc finger protein 862 | NM_001099220 XM_376720 | CCCGAT CTTCCTT CCACCT AA | 577 | 0.489018 | 0.420056 | 0.353445 |
| 643641 | LOC643641 | KIAA0543, KIAA0543 protein | NM_001099220 XM_376720 | AAGGTT ATACAG GACCAT TCA | 578 | 0.775603 | 0.656285 | 0.520766 |
| 653712 | LOC653712 | hypothetical LOC653712 | XM_001720301 XM_371663 XM_939842 | CTGCAC GGAGCT TCTGGT GAA | 579 | 0.809138 | 0.500396 | 0.342834 |
| 653712 | LOC653712 | hypothetical LOC653712 | XM_001720301 XM_371663 XM_939842 | CAGGAT CTTGTT GCCATG GTG | 580 | 0.540352 | 0.47637 | 0.464379 |
| 728683 | LOC728683 | similar to LOC442421 protein | XM_001128151 XM_001732880 XM_001732881 | CACCAG CCACTG TCATGT TAA | 581 | 0.10453 | 0.160286 | 0.168011 |
| 728683 | LOC728683 | similar to LOC442421 protein | XM_001128151 XM_001732880 XM_001732881 | CAGAAT CTGTCG GGAATA ATA | 582 | 0.758434 | 0.659482 | 0.604078 |
| 730974 | LOC730974 | hypothetical LOC730974 | XR_015335 XR_037751 | TTCCGC CAAGAG GAAGCA TAA | 583 | 0.325924 | 0.375453 | 0.353821 |
| 730974 | LOC730974 | hypothetical LOC730974 | XR_015335 XR_037126 XR_037751 | TCGGAC TGTCTG CAGCAT CAA | 584 | 0.943748 | 0.602692 | 0.446416 |

| geneID | AvgTox_Score | siRNA_SCORE | RSA_SCORE_LogP | SCORE_OPI_Support | SCORE_GOEnrich | SCORE_DrugInformation |
|---|---|---|---|---|---|---|
| 70 | 0.735303 | 0.21 | 0 | | 0 | 0 |
| 70 | 0.7761 | 0.21 | 0 | | 0 | 0 |
| 92 | 0.707438 | 0.79 | 0.3 | 0.5 | 1 | 0 |

TABLE 3-continued

Scores of 295 confirmed genes required for influenza virus replication.

| | | | | | | |
|---|---|---|---|---|---|---|
| 92 | 0.704019 | 0.79 | 0.3 | 0.5 | 1 | 0 |
| 147 | 0.727126 | 0.81 | 0.45 | | 0 | 1 |
| 147 | 1.046307 | 0.81 | 0.45 | | 0 | 1 |
| 157 | 0.810805 | 0.97 | 0.82 | 0.5 | 1 | 0 |
| 157 | 0.77952 | 0.97 | 0.82 | 0.5 | 1 | 0 |
| 207 | 0.732886 | 0.86 | 0.81 | | 1 | 1 |
| 207 | 0.865224 | 0.86 | 0.81 | | 1 | 1 |
| 290 | 0.653686 | 0.31 | 0.11 | | 0 | 1 |
| 290 | 0.780885 | 0.31 | 0.11 | | 0 | 1 |
| 335 | 0.515173 | 0.77 | 0.49 | 0.5 | 0 | 1 |
| 335 | 0.647621 | 0.77 | 0.49 | 0.5 | 0 | 1 |
| 351 | 0.632227 | 0.65 | 0.9 | | 0 | 1 |
| 351 | 0.705589 | 0.65 | 0.9 | | 0 | 1 |
| 361 | 0.575314 | 0.86 | 0.74 | | 0 | 0 |
| 361 | 0.710967 | 0.86 | 0.74 | | 0 | 0 |
| 369 | 0.592198 | 0.86 | 0.41 | | 1 | 0 |
| 369 | 0.727614 | 0.86 | 0.41 | | 1 | 0 |
| 372 | 0.569949 | 0.7 | 1 | | 1 | 0 |
| 372 | 0.564299 | 0.7 | 1 | | 1 | 0 |
| 523 | 0.514394 | 0.65 | 0.95 | | 0 | 1 |
| 523 | 0.854758 | 0.65 | 0.95 | | 0 | 1 |
| 526 | 0.536642 | 0.75 | 1 | | 0 | 0 |
| 526 | 0.596538 | 0.75 | 1 | | 0 | 0 |
| 527 | 0.653149 | 0.93 | 1 | 0.5 | 0 | 0 |
| 527 | 0.605312 | 0.93 | 1 | 0.5 | 0 | 0 |

TABLE 3-continued

Scores of 295 confirmed genes required for influenza virus replication.

| | | | | | | |
|---|---|---|---|---|---|---|
| 533 | 0.530704 | 0.8 | 1 | | 0 | 0 |
| 533 | 0.680679 | 0.8 | 1 | | 0 | 0 |
| 537 | 0.490448 | 0.92 | 1 | 0.5 | 1 | 0 |
| 537 | 0.611075 | 0.92 | 1 | 0.5 | 1 | 0 |
| 602 | 0.760749 | 0.91 | 0.64 | 1 | 0 | 0 |
| 602 | 0.673965 | 0.91 | 0.64 | 1 | 0 | 0 |
| 658 | 0.540783 | 0.91 | 0.98 | 1 | 1 | 0 |
| 658 | 0.625647 | 0.91 | 0.98 | 1 | 1 | 0 |
| 790 | 0.689253 | 0.91 | 0.66 | | 1 | 0 |
| 790 | 0.587985 | 0.91 | 0.66 | | 1 | 0 |
| 816 | 0.601074 | 0.89 | 0.8 | | 1 | 1 |
| 816 | 0.690823 | 0.89 | 0.8 | | 1 | 1 |
| 827 | 0.579959 | 0.83 | 0.52 | 0.5 | 0 | 0 |
| 827 | 0.830295 | 0.83 | 0.52 | 0.5 | 0 | 0 |
| 975 | 0.789971 | 0.78 | 0.54 | | 1 | 0 |
| 975 | 0.707072 | 0.78 | 0.54 | | 1 | 0 |
| 1019 | 0.695154 | 0.98 | 1 | | 1 | 1 |
| 1019 | 0.63883 | 0.98 | 1 | | 1 | 1 |
| 1195 | 0.735976 | 0.56 | 0.87 | | 0 | 0 |
| 1195 | 1.010533 | 0.56 | 0.87 | | 0 | 0 |
| 1263 | 0.887591 | 0.97 | 1 | 0.5 | 1 | 0 |
| 1263 | 0.806921 | 0.97 | 1 | 0.5 | 1 | 0 |
| 1280 | 0.784106 | 0.81 | 0.55 | | 0 | 0 |
| 1280 | 0.808607 | 0.81 | 0.55 | | 0 | 0 |
| 1314 | 0.473927 | 0.8 | 1 | 0.5 | 1 | 0 |
| 1314 | 0.441332 | 0.8 | 1 | 0.5 | 1 | 0 |

TABLE 3-continued

Scores of 295 confirmed genes required for influenza virus replication.

| | | | | |
|---|---|---|---|---|
| 1385 | 0.779215 | 0.86 | 0.52 | 1 | 0 |
| 1385 | 0.824071 | 0.86 | 0.52 | 1 | 0 |
| 1394 | 0.543627 | 0.77 | 0.41 | 0 | 1 |
| 1394 | 0.624222 | 0.77 | 0.41 | 0 | 1 |
| 1434 | 0.866126 | 0.7 | 0.82 | 0.5 | 0 | 0 |
| 1434 | 0.832922 | 0.7 | 0.82 | 0.5 | 0 | 0 |
| 1455 | 0.782913 | 0.87 | 0.6 | 0.5 | 1 | 1 |
| 1455 | 0.69354 | 0.87 | 0.6 | 0.5 | 1 | 1 |
| 1511 | 0.571486 | 0.87 | 0.55 | 0 | 1 |
| 1511 | 0.765517 | 0.87 | 0.55 | 0 | 1 |
| 1521 | 0.654385 | 0.62 | 0.66 | 0 | 0 |
| 1521 | 0.917989 | 0.62 | 0.66 | 0 | 0 |
| 1613 | 0.707419 | 0.89 | 0.47 | 0.5 | 1 | 0 |
| 1613 | 0.794945 | 0.89 | 0.47 | 0.5 | 1 | 0 |
| 1717 | 0.577509 | 0.82 | 0.81 | 0.5 | 0 | 1 |
| 1717 | 0.913854 | 0.82 | 0.81 | 0.5 | 0 | 1 |
| 1733 | 0.746473 | 0.87 | 0.48 | 0.5 | 0 | 0 |
| 1733 | 0.761296 | 0.87 | 0.48 | 0.5 | 0 | 0 |
| 1787 | 0.655509 | 0.81 | 0.45 | 0 | 1 |
| 1787 | 0.894078 | 0.81 | 0.45 | 0 | 1 |
| 1832 | 0.792765 | 0.71 | 0.38 | 0.5 | 0 | 0 |
| 1832 | 0.703002 | 0.71 | 0.38 | 0.5 | 0 | 0 |
| 1845 | 0.759097 | 0.82 | 0.6 | 0.5 | 1 | 1 |
| 1845 | 0.754704 | 0.82 | 0.6 | 0.5 | 1 | 1 |
| 2011 | 0.520347 | 0.94 | 1 | 0.5 | 1 | 0 |

TABLE 3-continued

Scores of 295 confirmed genes required for influenza virus replication.

| | | | | |
|---|---|---|---|---|
| 2011 | 0.705049 | 0.94 | 1 | 1 | 0 |
| 2022 | 0.525181 | 0.77 | 0.43 | 0 | 0 |
| 2022 | 0.597725 | 0.77 | 0.43 | 0 | 0 |
| 2045 | 0.857313 | 0.75 | 0.34 | 1 | 0 |
| 2045 | 0.739018 | 0.75 | 0.34 | 1 | 0 |
| 2048 | 0.826329 | 0.94 | 0.91 | 1 | 0 |
| 2048 | 0.57235 | 0.94 | 0.91 | 1 | 0 |
| 2050 | 0.688144 | 0.8 | 0.59 | 1 | 1 |
| 2050 | 0.601233 | 0.8 | 0.59 | 1 | 1 |
| 2162 | 0.508869 | 0.78 | 0.42 | 0 | 0 |
| 2162 | 0.681626 | 0.78 | 0.42 | 0 | 0 |
| 2260 | 0.64206 | 0.87 | 1 | 0.5 | 1 | 1 |
| 2260 | 0.756166 | 0.87 | 1 | 0.5 | 1 | 1 |
| 2263 | 0.524624 | 0.59 | 0.22 | 0 | 1 |
| 2263 | 0.703041 | 0.59 | 0.22 | 0 | 1 |
| 2264 | 0.507643 | 0.93 | 0.57 | 0.5 | 1 | 1 |
| 2264 | 0.61976 | 0.93 | 0.57 | 0.5 | 1 | 1 |
| 2322 | 0.652279 | 0.79 | 0.3 | 0.5 | 1 | 1 |
| 2322 | 0.672146 | 0.79 | 0.3 | 0.5 | 1 | 1 |
| 2324 | 0.618587 | 0.91 | 1 | 1 | 1 |
| 2324 | 0.768119 | 0.91 | 1 | 1 | 1 |
| 2334 | 0.679346 | 0.79 | 0.82 | 0 | 0 |
| 2334 | 0.902153 | 0.79 | 0.82 | 0 | 0 |
| 2342 | 0.468831 | 0.81 | 0.77 | 0.5 | 0 | 1 |
| 2342 | 0.74543 | 0.81 | 0.77 | 0.5 | 0 | 1 |
| 2346 | 0.750336 | 0.86 | 0.62 | 0 | 1 |

TABLE 3-continued

Scores of 295 confirmed genes required for influenza virus replication.

| | | | | |
|---|---|---|---|---|
| 2346 | 0.782733 | 0.86 | 0.62 | 0 | 1 |
| 2357 | 0.694342 | 0.68 | 1 | 1 | 0 |
| 2357 | 0.767736 | 0.68 | 1 | 1 | 0 |
| 2444 | 0.681864 | 0.97 | 0.75 | 0.5 | 1 | 0 |
| 2444 | 0.63313 | 0.97 | 0.75 | 0.5 | 1 | 0 |
| 2475 | 0.603786 | 0.98 | 0.98 | | 1 | 1 |
| 2475 | 0.683706 | 0.98 | 0.98 | | 1 | 1 |
| 2539 | 0.769819 | 0.68 | 0.52 | 0.5 | 1 | 1 |
| 2539 | 0.634969 | 0.68 | 0.52 | 0.5 | 1 | 1 |
| 2550 | 0.809697 | 0.85 | 0.56 | | 0 | 1 |
| 2550 | 0.791962 | 0.85 | 0.56 | | 0 | 1 |
| 2580 | 0.57373 | 0.83 | 1 | 0.5 | 1 | 0 |
| 2580 | 0.739812 | 0.83 | 1 | 0.5 | 1 | 0 |
| 2703 | 1.011241 | 0.88 | 1 | | 0 | 0 |
| 2703 | 0.691777 | 0.88 | 1 | | 0 | 0 |
| 2869 | 0.733474 | 0.77 | 1 | 0.5 | 1 | 1 |
| 2869 | 0.566124 | 0.77 | 1 | 0.5 | 1 | 1 |
| 2870 | 0.700002 | 0.89 | 0.45 | 0.5 | 1 | 0 |
| 2870 | 0.716112 | 0.89 | 0.45 | 0.5 | 1 | 0 |
| 2932 | 0.455989 | 0.97 | 1 | 0.5 | 1 | 0 |
| 2932 | 0.57909 | 0.97 | 1 | 0.5 | 1 | 0 |
| 2936 | 0.799983 | 0.9 | 0.63 | 0.5 | 1 | 1 |
| 2936 | 0.663906 | 0.9 | 0.63 | 0.5 | 1 | 1 |
| 3265 | 0.674664 | 0.8 | 0.45 | | 0 | 0 |
| 3265 | 0.715171 | 0.8 | 0.45 | | 0 | 0 |

TABLE 3-continued

| Scores of 295 confirmed genes required for influenza virus replication. | | | | | | |
|---|---|---|---|---|---|---|
| 3320 | 0.539544 | 0.83 | 0.55 | | 1 | 1 |
| 3320 | 0.833849 | 0.83 | 0.55 | | 1 | 1 |
| 3356 | 1.083386 | 0.89 | 0.59 | 0.5 | 0 | 1 |
| 3356 | 0.794039 | 0.89 | 0.59 | 0.5 | 0 | 1 |
| 3547 | 0.819288 | 0.79 | 0.56 | 0.5 | 0 | 0 |
| 3547 | 0.794808 | 0.79 | 0.56 | 0.5 | 0 | 0 |
| 3568 | 1.006051 | 0.84 | 0.86 | | 0 | 1 |
| 3568 | 0.671255 | 0.84 | 0.86 | | 0 | 1 |
| 3581 | 0.540886 | 0.78 | 0.9 | | 0 | 0 |
| 3581 | 0.830518 | 0.78 | 0.9 | | 0 | 0 |
| 3674 | 0.672121 | 0.82 | 0.6 | | 0 | 1 |
| 3674 | 0.757492 | 0.82 | 0.6 | | 0 | 1 |
| 3675 | 0.576261 | 0.46 | 0.16 | | 0 | 1 |
| 3675 | 0.761731 | 0.46 | 0.16 | | 0 | 1 |
| 3717 | 0.735741 | 0.88 | 0.53 | | 1 | 1 |
| 3717 | 0.674437 | 0.88 | 0.53 | | 1 | 1 |
| 3725 | 0.568722 | 0.68 | 0.44 | | 1 | 1 |
| 3725 | 0.770658 | 0.68 | 0.44 | | 1 | 1 |
| 3760 | 0.713122 | 0.82 | 0.59 | 0.5 | 0 | 1 |
| 3760 | 0.603543 | 0.82 | 0.59 | 0.5 | 0 | 1 |
| 3767 | 0.581609 | 0.84 | 0.65 | | 0 | 1 |
| 3767 | 0.659309 | 0.84 | 0.65 | | 0 | 1 |
| 3778 | 0.594434 | 0.82 | 0.61 | 0.5 | 1 | 1 |
| 3778 | 0.667675 | 0.82 | 0.61 | 0.5 | 1 | 1 |
| 3837 | 0.599864 | 0.68 | 0.99 | | 1 | 0 |
| 3837 | 0.6515 | 0.68 | 0.99 | | 1 | 0 |

TABLE 3-continued

Scores of 295 confirmed genes required for influenza virus replication.

| | | | | |
|---|---|---|---|---|
| 3984 | 0.670524 | 0.87 | 1 | 0.5 | 1 | 0 |
| 3984 | 0.877543 | 0.87 | 1 | 0.5 | 1 | 0 |
| 4058 | 0.588745 | 0.91 | 0.51 | | 1 | 0 |
| 4058 | 0.698869 | 0.91 | 0.51 | | 1 | 0 |
| 4193 | 0.651351 | 0.89 | 0.72 | 1 | 1 | 0 |
| 4193 | 0.643637 | 0.89 | 0.72 | 1 | 1 | 0 |
| 4296 | 0.550899 | 0.82 | 0.8 | 0.5 | 1 | 0 |
| 4296 | 0.630813 | 0.82 | 0.8 | 0.5 | 1 | 0 |
| 4809 | 0.571215 | 0.8 | 1 | | 0 | 0 |
| 4809 | 0.466502 | 0.8 | 1 | | 0 | 0 |
| 4886 | 0.604083 | 0.6 | 0.33 | | 0 | 1 |
| 4886 | 0.712266 | 0.6 | 0.33 | | 0 | 1 |
| 4914 | 0.771013 | 0.98 | 1 | 0.5 | 1 | 1 |
| 4914 | 0.827141 | 0.98 | 1 | 0.5 | 1 | 1 |
| 4915 | 0.49757 | 0.77 | 0.89 | | 1 | 0 |
| 4915 | 0.671895 | 0.77 | 0.89 | | 1 | 0 |
| 4920 | 0.636035 | 0.96 | 0.73 | 1 | 1 | 0 |
| 4920 | 0.602847 | 0.96 | 0.73 | 1 | 1 | 1 |
| 4923 | 0.607864 | 0.82 | 0.87 | | 0 | 0 |
| 4923 | 0.54677 | 0.82 | 0.87 | | 0 | 1 |
| 5062 | 0.655015 | 0.95 | 1 | 0.5 | 1 | 0 |
| 5062 | 0.898847 | 0.95 | 1 | 0.5 | 1 | 0 |
| 5063 | 0.720941 | 0.96 | 0.74 | | 1 | 0 |
| 5063 | 0.742867 | 0.96 | 0.74 | | 1 | 0 |
| 5096 | 0.71863 | 0.93 | 0.69 | | 0 | 0 |

TABLE 3-continued

Scores of 295 confirmed genes required for influenza virus replication.

| | | | | |
|---|---|---|---|---|
| 5096 | 0.753266 | 0.93 | 0.69 | 0 | 0 |
| 5165 | 0.694431 | 0.91 | 0.61 | 1 | 0 |
| 5165 | 0.921945 | 0.91 | 0.61 | 1 | 0 |
| 5253 | 0.481601 | 0.77 | 0.51 | 0 | 0 |
| 5253 | 0.554521 | 0.77 | 0.51 | 0 | 0 |
| 5310 | 0.637937 | 0.89 | 0.95 | 0 | 0 |
| 5310 | 0.989858 | 0.89 | 0.95 | 0 | 0 |
| 5422 | 0.766398 | 0.6 | 0.39 | 0 | 1 |
| 5422 | 0.629376 | 0.6 | 0.39 | 0 | 1 |
| 5566 | 0.672506 | 0.27 | 0 | 0 | 1 |
| 5566 | 0.636348 | 0.27 | 0 | 0 | 1 |
| 5580 | 0.669629 | 0.84 | 1 | 0.5 | 1 | 0 |
| 5580 | 0.804492 | 0.84 | 1 | 0.5 | 1 | 0 |
| 5584 | 0.680945 | 0.85 | 0.55 | 1 | 0 |
| 5584 | 1.08975 | 0.85 | 0.55 | 1 | 0 |
| 5594 | 0.622917 | 0.96 | 1 | 0.5 | 1 | 1 |
| 5594 | 0.502466 | 0.96 | 1 | 0.5 | 1 | 1 |
| 5605 | 0.705118 | 0.95 | 0.69 | 0.5 | 1 | 0 |
| 5605 | 0.714416 | 0.95 | 0.69 | 0.5 | 1 | 0 |
| 5606 | 0.653038 | 0.85 | 0.59 | 1 | 0 |
| 5606 | 0.670137 | 0.85 | 0.59 | 1 | 0 |
| 5607 | 0.93468 | 0.46 | 0.097 | 0 | 0 |
| 5607 | 1.078413 | 0.46 | 0.097 | 0 | 0 |
| 5610 | 0.525965 | 0.94 | 1 | 0.5 | 1 | 0 |
| 5610 | 0.643122 | 0.94 | 1 | 0.5 | 1 | 0 |
| 5707 | 0.569329 | 0.67 | 0.65 | 1 | 0 |

TABLE 3-continued

Scores of 295 confirmed genes required for influenza virus replication.

| | | | | |
|---|---|---|---|---|
| 5707 | 0.778502 | 0.67 | 0.65 | 1 | 0 |
| 5757 | 0.715009 | 0.64 | 0.41 | 0 | 0 |
| 5757 | 0.959038 | 0.64 | 0.41 | 0.5 | 0 | 0 |
| 5797 | 0.699244 | 0.86 | 0.81 | 0.5 | 1 | 0 |
| 5797 | 0.716302 | 0.86 | 0.81 | | 1 | 0 |
| 5798 | 0.802777 | 0.88 | 0.56 | | 1 | 0 |
| 5798 | 0.714115 | 0.88 | 0.56 | | 1 | 0 |
| 5805 | 0.788798 | 0.31 | 0.084 | | 0 | 0 |
| 5805 | 0.702588 | 0.31 | 0.084 | | 0 | 0 |
| 5961 | 0.54258 | 0.8 | 0.67 | | 0 | 0 |
| 5961 | 0.795384 | 0.8 | 0.67 | | 0 | 0 |
| 6015 | 0.657564 | 0.81 | 0.81 | | 0 | 0 |
| 6015 | 0.981143 | 0.81 | 0.81 | | 0 | 0 |
| 6093 | 0.459422 | 0.98 | 1 | 1 | 1 | 1 |
| 6093 | 0.636579 | 0.98 | 1 | 1 | 1 | 1 |
| 6196 | 0.659141 | 0.88 | 0.49 | | 1 | 0 |
| 6196 | 0.709386 | 0.88 | 0.49 | | 1 | 0 |
| 6204 | 0.618881 | 0.48 | 0.65 | 0.5 | 0 | 0 |
| 6204 | 0.749728 | 0.48 | 0.65 | 0.5 | 0 | 0 |
| 6224 | 0.553941 | 0.67 | 0.8 | 0.5 | 1 | 0 |
| 6224 | 0.63999 | 0.67 | 0.8 | | 1 | 0 |
| 6328 | 0.672997 | 0.8 | 0.44 | 0.5 | 0 | 0 |
| 6328 | 0.681957 | 0.8 | 0.44 | | 0 | 0 |
| 6334 | 0.532093 | 0.45 | 0.16 | | 0 | 0 |
| 6334 | 0.632198 | 0.45 | 0.16 | | 0 | 0 |

TABLE 3-continued

Scores of 295 confirmed genes required for influenza virus replication.

| | | | | |
|---|---|---|---|---|
| 6340 | 0.725168 | 0.91 | 0.65 | 0.5 | 0 | 0 |
| 6340 | 0.682036 | 0.91 | 0.65 | 0.5 | 0 | 0 |
| 6357 | 0.516765 | 0.87 | 0.72 | 1 | 0 | 0 |
| 6357 | 0.961768 | 0.87 | 0.72 | 1 | 0 | 0 |
| 6442 | 0.695221 | 0.86 | 0.54 | 0.5 | 0 | 0 |
| 6442 | 0.59258  | 0.86 | 0.54 | 0.5 | 0 | 0 |
| 6446 | 0.621463 | 0.83 | 0.79 |     | 1 | 0 |
| 6446 | 0.676564 | 0.83 | 0.79 |     | 1 | 0 |
| 6478 | 0.653397 | 0.67 | 0.34 |     | 0 | 0 |
| 6478 | 0.611277 | 0.67 | 0.34 |     | 0 | 0 |
| 6604 | 0.727677 | 0.85 | 0.85 |     | 0 | 0 |
| 6604 | 0.710092 | 0.85 | 0.85 |     | 0 | 0 |
| 6613 | 0.707157 | 0.62 | 0.45 | 0.5 | 0 | 0 |
| 6613 | 0.930313 | 0.62 | 0.45 | 0.5 | 0 | 0 |
| 6624 | 0.619903 | 0    | 0    |     | 0 | 0 |
| 6624 | 0.820361 | 0    | 0    |     | 0 | 0 |
| 6625 | 0.815749 | 0.69 | 0.44 |     | 0 | 0 |
| 6625 | 0.806522 | 0.69 | 0.44 |     | 0 | 0 |
| 6627 | 0.501572 | 0.63 | 0.41 | 0.5 | 0 | 0 |
| 6627 | 0.56687  | 0.63 | 0.41 | 0.5 | 0 | 0 |
| 6792 | 0.751137 | 0.86 | 1    |     | 1 | 0 |
| 6792 | 0.863349 | 0.86 | 1    |     | 1 | 0 |
| 6811 | 0.65269  | 0.87 | 0.65 | 0.5 | 0 | 0 |
| 6811 | 0.69508  | 0.87 | 0.65 | 0.5 | 0 | 0 |
| 7005 | 0.621546 | 0.76 | 0.5  | 0.5 | 0 | 0 |
| 7005 | 0.95027  | 0.76 | 0.5  | 0.5 | 0 | 0 |

TABLE 3-continued

Scores of 295 confirmed genes required for influenza virus replication.

| | | | | | | |
|---|---|---|---|---|---|---|
| 7178 | 0.605568 | 0.48 | 0.7 | | 0 | 0 |
| 7178 | 0.726609 | 0.48 | 0.7 | | 0 | 0 |
| 7294 | 0.520123 | 0.78 | 0.74 | 0.5 | 1 | 0 |
| 7294 | 0.769393 | 0.78 | 0.74 | 0.5 | 1 | 0 |
| 7341 | 0.726238 | 0 | 0 | | 0 | 0 |
| 7341 | 0.717658 | 0 | 0 | | 0 | 0 |
| 7423 | 0.640845 | 0.93 | 0.8 | 0.5 | 0 | 0 |
| 7423 | 0.719245 | 0.93 | 0.8 | 0.5 | 0 | 0 |
| 7786 | 0.624795 | 0.8 | 0.61 | 0.5 | 1 | 0 |
| 7786 | 0.670746 | 0.8 | 0.61 | 0.5 | 1 | 0 |
| 8021 | 0.592518 | 0.28 | 0 | | 0 | 0 |
| 8021 | 0.656624 | 0.28 | 0 | | 0 | 0 |
| 8290 | 0.718392 | 0.68 | 0.81 | | 0 | 0 |
| 8290 | 0.655095 | 0.68 | 0.81 | | 0 | 0 |
| 8438 | 0.886946 | 0.82 | 0.63 | | 0 | 0 |
| 8438 | 0.815758 | 0.82 | 0.63 | | 0 | 0 |
| 8476 | 0.633969 | 0.81 | 1 | | 1 | 0 |
| 8476 | 0.666884 | 0.81 | 1 | | 1 | 0 |
| 8558 | 0.750625 | 0.91 | 1 | | 1 | 0 |
| 8558 | 0.551374 | 0.91 | 1 | | 1 | 0 |
| 8570 | 0.628263 | 0.83 | 1 | | 0 | 0 |
| 8570 | 0.819785 | 0.83 | 1 | | 0 | 0 |
| 8677 | 0.540408 | 0.67 | 0.56 | | 0 | 0 |
| 8677 | 0.641043 | 0.67 | 0.56 | | 0 | 0 |
| 8831 | 0.529066 | 0.87 | 0.65 | 0.5 | 0 | 0 |

TABLE 3-continued

| Scores of 295 confirmed genes required for influenza virus replication. | | | | | | |
|---|---|---|---|---|---|---|
| 8831 | 0.705632 | 0.87 | 0.65 | 0.5 | 0 | 0 |
| 8837 | 0.628192 | 0.6 | 0.33 | 0.5 | 0 | 0 |
| 8837 | 0.718145 | 0.6 | 0.33 | 0.5 | 0 | 0 |
| 9114 | 0.45469 | 0.93 | 1 | 0.5 | 0 | 0 |
| 9114 | 0.586649 | 0.93 | 1 | 0.5 | 0 | 0 |
| 9135 | 0.634925 | 0.4 | 0.26 | | 0 | 0 |
| 9135 | 0.807152 | 0.4 | 0.26 | | 0 | 0 |
| 9149 | 0.793116 | 0.88 | 0.76 | 1 | 1 | 1 |
| 9149 | 0.754638 | 0.88 | 0.76 | 1 | 1 | 1 |
| 9159 | 0.576383 | 0.7 | 1 | 0.5 | 1 | 0 |
| 9159 | 0.634865 | 0.7 | 1 | 0.5 | 1 | 0 |
| 9180 | 0.721684 | 0.65 | 1 | | 0 | 1 |
| 9180 | 0.728862 | 0.65 | 1 | | 0 | 1 |
| 9201 | 0.717062 | 0.96 | 0.72 | | 1 | 0 |
| 9201 | 0.967089 | 0.96 | 0.72 | | 1 | 0 |
| 9230 | 0.742995 | 0.27 | 0 | | 0 | 0 |
| 9230 | 0.739319 | 0.27 | 0 | | 0 | 0 |
| 9231 | 1.098853 | 0.77 | 1 | 0.5 | 0 | 0 |
| 9231 | 0.767108 | 0.77 | 1 | 0.5 | 0 | 0 |
| 9256 | 0.65323 | 0.62 | 0.84 | | 0 | 0 |
| 9256 | 0.900219 | 0.62 | 0.84 | | 0 | 0 |
| 9276 | 0.416791 | 0.94 | 1 | | 1 | 0 |
| 9276 | 0.428096 | 0.94 | 1 | | 1 | 0 |
| 9448 | 0.664005 | 0.78 | 0.93 | | 1 | 0 |
| 9448 | 0.803517 | 0.78 | 0.93 | | 1 | 0 |
| 9464 | 0.807142 | 0.68 | 0.58 | | 0 | 0 |

TABLE 3-continued

Scores of 295 confirmed genes required for influenza virus replication.

| | | | | |
|---|---|---|---|---|
| 9464 | 0.784917 | 0.68 | 0.58 | 0 | 0 |
| 9509 | 0.644768 | 0.31 | 0.11 | 0 | 0 |
| 9509 | 0.88037 | 0.31 | 0.11 | 0 | 0 |
| 9575 | 0.523602 | 0.82 | 0.48 | 0 | 0 |
| 9575 | 0.699699 | 0.82 | 0.48 | 0 | 0 |
| 9578 | 0.844926 | 0.79 | 0.85 | 1 | 0 |
| 9578 | 0.611792 | 0.79 | 0.85 | 1 | 0 |
| 9625 | 0.504363 | 0.83 | 0.52 | 1 | 0 |
| 9625 | 0.783266 | 0.83 | 0.52 | 1 | 0 |
| 9641 | 0.432621 | 0.96 | 0.84 | 1 | 1 |
| 9641 | 0.487614 | 0.96 | 0.84 | 1 | 1 |
| 9943 | 1.074442 | 0.94 | 0.59 | 1 | 0 |
| 9943 | 0.83674 | 0.94 | 0.59 | 1 | 0 |
| 9972 | 0.579413 | 0.089 | 0 | 0 | 0 |
| 9972 | 0.903111 | 0.089 | 0 | 0 | 0 |
| 10036 | 0.524615 | 0.3 | 0 | 0 | 0 |
| 10036 | 0.778565 | 0.3 | 0 | 0 | 0 |
| 10055 | 0.530465 | 0.44 | 0.29 | 0 | 0 |
| 10055 | 0.682029 | 0.44 | 0.29 | 0 | 0 |
| 10105 | 0.731637 | 0.41 | 0.27 | 0.5 | 0 | 1 |
| 10105 | 0.569667 | 0.41 | 0.27 | 0.5 | 0 | 1 |
| 10114 | 0.615888 | 0.9 | 0.53 | 0.5 | 1 | 0 |
| 10114 | 0.597896 | 0.9 | 0.53 | 0.5 | 1 | 0 |
| 10155 | 0.4644 | 0.97 | 0.89 | 0.5 | 0 | 0 |
| 10155 | 0.951021 | 0.97 | 0.89 | 0.5 | 0 | 0 |

TABLE 3-continued

Scores of 295 confirmed genes required for influenza virus replication.

| | | | | |
|---|---|---|---|---|
| 10159 | 0.630936 | 0.91 | 1 | 0.5 | 0 | 0 |
| 10159 | 0.918019 | 0.91 | 1 | 0.5 | 0 | 0 |
| 10181 | 0.609415 | 0.85 | 0.68 | | 0 | 0 |
| 10181 | 0.944946 | 0.85 | 0.68 | | 0 | 0 |
| 10188 | 0.519002 | 0.97 | 0.8 | 0.5 | 1 | 0 |
| 10188 | 0.703757 | 0.97 | 0.8 | 0.5 | 1 | 0 |
| 10280 | 0.529035 | 0.88 | 1 | | 0 | 1 |
| 10280 | 0.694461 | 0.88 | 1 | | 0 | 1 |
| 10291 | 0.559818 | 0.79 | 1 | 0.5 | 0 | 0 |
| 10291 | 0.598957 | 0.79 | 1 | 0.5 | 0 | 0 |
| 10297 | 0.580359 | 0.73 | 0.42 | 0.5 | 0 | 0 |
| 10297 | 0.854253 | 0.73 | 0.42 | 0.5 | 0 | 0 |
| 10381 | 0.770944 | 0.72 | 0.92 | | 0 | 0 |
| 10381 | 0.637621 | 0.72 | 0.92 | | 0 | 0 |
| 10595 | 0.775854 | 0.9 | 0.78 | | 1 | 0 |
| 10595 | 0.755248 | 0.9 | 0.78 | | 1 | 0 |
| 10616 | 1.01773 | 0.84 | 0.65 | 0.5 | 0 | 0 |
| 10616 | 0.858523 | 0.84 | 0.65 | 0.5 | 0 | 0 |
| 10725 | 0.53129 | 0.63 | 0.92 | 0.5 | 0 | 0 |
| 10725 | 0.982819 | 0.63 | 0.92 | 0.5 | 0 | 0 |
| 10733 | 0.978733 | 0.73 | 1 | 0.5 | 1 | 0 |
| 10733 | 0.628258 | 0.73 | 1 | 0.5 | 1 | 0 |
| 10783 | 0.63095 | 0.97 | 0.81 | 0.5 | 1 | 0 |
| 10783 | 0.678218 | 0.97 | 0.81 | 0.5 | 1 | 0 |
| 10849 | 0.539895 | 0.69 | 0.74 | | 1 | 0 |
| 10849 | 0.552598 | 0.69 | 0.74 | | 1 | 0 |

TABLE 3-continued

Scores of 295 confirmed genes required for influenza virus replication.

| | | | |
|---|---|---|---|
| 11113 | 0.788585 | 0.94 | 0.58 | 0.5 | 1 | 0 |
| 11113 | 0.787589 | 0.94 | 0.58 | 0.5 | 1 | 0 |
| 11213 | 0.754786 | 0.91 | 0.97 | 0.5 | 1 | 0 |
| 11213 | 0.753182 | 0.91 | 0.97 | 0.5 | 1 | 0 |
| 11214 | 0.720095 | 0.74 | 0.53 | | 1 | 0 |
| 11214 | 0.965993 | 0.74 | 0.53 | | 1 | 0 |
| 22820 | 0.510154 | 0.64 | 0.81 | 0.5 | 0 | 0 |
| 22820 | 0.65477 | 0.64 | 0.81 | 0.5 | 0 | 0 |
| 23049 | 0.488445 | 0.93 | 0.68 | 0.5 | 1 | 0 |
| 23049 | 0.599912 | 0.93 | 0.68 | | 1 | 0 |
| 23216 | 0.809479 | 0.76 | 0.47 | | 0 | 0 |
| 23216 | 0.79844 | 0.76 | 0.47 | | 0 | 0 |
| 23352 | 0.540193 | 0.83 | 0.61 | 0.5 | 0 | 0 |
| 23352 | 0.953583 | 0.83 | 0.61 | 0.5 | 0 | 0 |
| 23386 | 0.580299 | 0.86 | 0.63 | 0.5 | 0 | 0 |
| 23386 | 0.9119 | 0.86 | 0.63 | 0.5 | 0 | 0 |
| 23387 | 0.563888 | 0.83 | 0.49 | | 1 | 0 |
| 23387 | 0.727789 | 0.83 | 0.49 | | 1 | 0 |
| 23396 | 0.856672 | 0.78 | 0.45 | | 1 | 0 |
| 23396 | 0.754701 | 0.78 | 0.45 | | 1 | 0 |
| 23534 | 0.803437 | 0.003 | 0 | | 0 | 0 |
| 23534 | 0.9486 | 0.003 | 0 | | 0 | 0 |
| 23552 | 0.553163 | 0.95 | 0.84 | 0.5 | 1 | 0 |
| 23552 | 0.706126 | 0.95 | 0.84 | 0.5 | 1 | 0 |
| 23604 | 0.606999 | 0.97 | 1 | | 1 | 0 |

TABLE 3-continued

Scores of 295 confirmed genes required for influenza virus replication.

| | | | | |
|---|---|---|---|---|
| 23604 | 0.472304 | 0.97 | 1 | 1 | 0 |
| 23765 | 0.424385 | 0.95 | 0.77 | 0.5 | 0 |
| 23765 | 0.589389 | 0.95 | 0.77 | 0.5 | 0 |
| 23770 | 0.473286 | 0.8 | 0.44 | | 0 |
| 23770 | 0.730983 | 0.8 | 0.44 | | 0 |
| 25831 | 0.515643 | 0.86 | 0.64 | | 0 |
| 25831 | 0.620564 | 0.86 | 0.64 | | 0 |
| 27092 | 0.733566 | 0.71 | 0.59 | | 0 |
| 27092 | 0.772176 | 0.71 | 0.59 | | 0 |
| 27347 | 0.547544 | 0.96 | 0.8 | 0.5 | 1 |
| 27347 | 0.63854 | 0.96 | 0.8 | 0.5 | 1 |
| 28996 | 0.608589 | 0.95 | 1 | | 0 |
| 28996 | 0.975852 | 0.95 | 1 | | 0 |
| 29035 | 0.638161 | 0.64 | 0.68 | | 1 |
| 29035 | 0.60655 | 0.64 | 0.68 | | 0 |
| 29110 | 0.65435 | 0.92 | 1 | 0.5 | 1 |
| 29110 | 0.540234 | 0.92 | 1 | 0.5 | 1 |
| 29127 | 0.765987 | 0.89 | 0.75 | | 0 |
| 29127 | 0.672359 | 0.89 | 0.75 | | 0 |
| 29882 | 0.571945 | 0.65 | 0.75 | | 1 |
| 29882 | 0.571554 | 0.65 | 0.75 | | 1 |
| 29959 | 0.735609 | 0.7 | 0.41 | | 1 |
| 29959 | 0.671623 | 0.7 | 0.41 | | 1 |
| 30811 | 0.807909 | 0.84 | 0.35 | 0.5 | 1 |
| 30811 | 0.667228 | 0.84 | 035 | 0.5 | 1 |
| 30815 | 0.558482 | 0.27 | 0 | | 0 | 0 |

TABLE 3-continued

Scores of 295 confirmed genes required for influenza virus replication.

| | | | |
|---|---|---|---|
| 30815 | 0.732777 | 0 | 0 |
| 30849 | 0.594893 | 0.54 | 1 | 1 |
| 30849 | 0.643575 | 0.54 | 1 | 1 |
| 50488 | 1.050075 | 0.64 | 1 | 0 |
| 50488 | 0.879156 | 0.64 | 1 | 0 |
| 51061 | 0.570467 | 0.54 | 0 | 0 |
| 51061 | 0.943811 | 0.54 | 0 | 0 |
| 51172 | 0.702328 | 0.18 | 0 | 0 |
| 51172 | 0.829529 | 0.18 | 0 | 0 |
| 51257 | 0.951947 | 0.38 | 0 | 0 |
| 51257 | 0.909845 | 0.38 | 0 | 0 |
| 51390 | 0.414764 | 0.6 | 0 | 0 |
| 51390 | 0.735298 | 0.6 | 0 | 0 |
| 51393 | 0.799912 | 0.7 | 0 | 0 |
| 51393 | 0.67239 | 0.7 | 0 | 0 |
| 51422 | 0.736125 | 0.49 | 0.5 | 1 | 1 |
| 51422 | 0.87999 | 0.49 | 0.5 | 1 | 1 |
| 51526 | 0.543605 | 0 | 0 | 0 |
| 51526 | 0.859317 | 0 | 0 | 0 |
| 54507 | 0.625535 | 0.6 | 0 | 0 |
| 54507 | 0.681468 | 0.6 | 0 | 0 |
| 54776 | 0.533713 | 1 | 0 | 0 |
| 54776 | 0.606923 | 1 | 0 | 0 |
| 54866 | 0.617601 | 0.71 | 0 | 0 |
| 54866 | 0.673746 | 0.71 | 0 | 0 |

TABLE 3-continued

Scores of 295 confirmed genes required for influenza virus replication.

| | | | | | | |
|---|---|---|---|---|---|---|
| 54980 | 0.536198 | 0.8 | 1 | | 0 | 0 |
| 54980 | 0.5812 | 0.8 | 1 | | 0 | 0 |
| 54991 | 0.639002 | 0.45 | 0.62 | | 0 | 0 |
| 54991 | 0.617151 | 0.45 | 0.62 | | 0 | 0 |
| 55229 | 0.77691 | 0.92 | 0.7 | | 1 | 0 |
| 55229 | 0.857237 | 0.92 | 0.7 | | 1 | 0 |
| 55577 | 1.042218 | 0.9 | 1 | 0.5 | 1 | 0 |
| 55577 | 0.94385 | 0.9 | 1 | 0.5 | 1 | 0 |
| 55652 | 0.544492 | 0.72 | 0.73 | | 0 | 0 |
| 55652 | 0.464607 | 0.72 | 0.73 | | 0 | 0 |
| 55850 | 0.671935 | 0.19 | 0 | | 0 | 0 |
| 55850 | 0.93047 | 0.19 | 0 | | 0 | 0 |
| 55851 | 0.54488 | 0.9 | 1 | | 1 | 1 |
| 55851 | 0.688179 | 0.9 | 1 | | 1 | 1 |
| 55872 | 0.635786 | 0.98 | 1 | 0.5 | 1 | 0 |
| 55872 | 0.662971 | 0.98 | 1 | 0.5 | 1 | 0 |
| 56164 | 0.673727 | 0.9 | 0.94 | 0.5 | 1 | 0 |
| 56164 | 0.646742 | 0.9 | 0.94 | 0.5 | 1 | 0 |
| 56300 | 0.814553 | 0.79 | 0.47 | | 1 | 0 |
| 56300 | 0.93926 | 0.79 | 0.47 | | 1 | 0 |
| 56311 | 0.928714 | 0.35 | 0.22 | | 0 | 0 |
| 56311 | 0.691761 | 0.35 | 0.22 | | 0 | 0 |
| 56660 | 0.62793 | 0.43 | 0.26 | | 0 | 0 |
| 56660 | 0.796393 | 0.43 | 0.26 | | 0 | 0 |
| 56893 | 0.631028 | 0.89 | 0.53 | | 1 | 0 |
| 56893 | 0.795072 | 0.89 | 0.53 | | 1 | 0 |

TABLE 3-continued

Scores of 295 confirmed genes required for influenza virus replication.

| | | | | | | |
|---|---|---|---|---|---|---|
| 56997 | 0.590049 | 0.79 | 1 | 0.5 | 1 | 0 |
| 56997 | 0.886047 | 0.79 | 1 | 0.5 | 1 | 0 |
| 57085 | 0.748443 | 0.79 | 0.63 | | 0 | 0 |
| 57085 | 0.893884 | 0.79 | 0.63 | | 0 | 0 |
| 57120 | 0.852028 | 0.084 | 0 | | 0 | 0 |
| 57120 | 0.74928 | 0.084 | 0 | | 0 | 0 |
| 57418 | 0.795512 | 0.17 | 0 | | 0 | 0 |
| 57418 | 0.6817 | 0.17 | 0 | | 0 | 0 |
| 57502 | 0.74481 | 0.21 | 0 | | 0 | 0 |
| 57502 | 0.907308 | 0.21 | 0 | | 0 | 0 |
| 57534 | 0.645918 | 0.37 | 0.27 | | 0 | 0 |
| 57534 | 0.96898 | 0.37 | 0.27 | | 0 | 0 |
| 57551 | 0.616897 | 0.96 | 0.72 | | 1 | 0 |
| 57551 | 1.150218 | 0.96 | 0.72 | | 1 | 0 |
| 57579 | 0.744458 | 0.49 | 0.3 | | 0 | 0 |
| 57579 | 0.925176 | 0.49 | 0.3 | | 0 | 0 |
| 58526 | 0.841227 | 0.094 | 0 | | 0 | 0 |
| 58526 | 0.673718 | 0.094 | 0 | | 0 | 0 |
| 64284 | 0.647428 | 0.43 | 0.23 | | 0 | 0 |
| 64284 | 0.613663 | 0.43 | 0.23 | | 0 | 0 |
| 64601 | 0.653329 | 0.6 | 0.77 | | 0 | 0 |
| 64601 | 0.62274 | 0.6 | 0.77 | | 0 | 0 |
| 65220 | 0.771576 | 0.89 | 1 | 0.5 | 1 | 0 |
| 65220 | 0.686813 | 0.89 | 1 | 0.5 | 1 | 0 |
| 79574 | 0.627411 | 0.76 | 0.86 | | 0 | 0 |

TABLE 3-continued

Scores of 295 confirmed genes required for influenza virus replication.

| | | | | |
|---|---|---|---|---|
| 79574 | 0.694177 | 0.76 | 0.86 | 0 | 0 |
| 79641 | 0.660543 | 0.5 | 0.75 | 0 | 0 |
| 79641 | 0.815792 | 0.5 | 0.75 | 0 | 0 |
| 79705 | 0.747353 | 0.95 | 0.71 | 0.5 | 1 | 0 |
| 79705 | 0.789938 | 0.95 | 0.71 | 0.5 | 1 | 0 |
| 79872 | 0.604098 | 0.89 | 0.59 | 0.5 | 0 | 0 |
| 79872 | 0.587805 | 0.89 | 0.59 | 0.5 | 0 | 0 |
| 80231 | 0.641364 | 0.76 | 0.72 | | 0 | 0 |
| 80231 | 0.760779 | 0.76 | 0.72 | | 0 | 0 |
| 80818 | 0.500757 | 0.65 | 0.42 | 0.5 | 0 | 0 |
| 80818 | 0.825228 | 0.65 | 0.42 | 0.5 | 0 | 0 |
| 84197 | 0.82977 | 0.88 | 1 | 0.5 | 1 | 0 |
| 84197 | 0.654127 | 0.88 | 1 | 0.5 | 1 | 0 |
| 89891 | 0.58477 | 0.8 | 0.66 | | 0 | 0 |
| 89891 | 0.638599 | 0.8 | 0.66 | | 0 | 0 |
| 90736 | 0.453645 | 0.64 | 0.82 | 1 | 0 | 0 |
| 90736 | 0.970707 | 0.64 | 0.82 | 1 | 0 | 0 |
| 92579 | 0.501989 | 0.77 | 0.87 | | 0 | 1 |
| 92579 | 0.665867 | 0.77 | 0.87 | | 0 | 1 |
| 93611 | 0.668641 | 0.63 | 0.66 | | 0 | 0 |
| 93611 | 1.125252 | 0.63 | 0.66 | | 0 | 0 |
| 93953 | 0.620661 | 0.58 | 0.37 | | 0 | 0 |
| 93953 | 0.75043 | 0.58 | 0.37 | | 0 | 0 |
| 94234 | 0.585521 | 0.17 | 0 | | 0 | 0 |
| 94234 | 0.879447 | 0.17 | 0 | | 0 | 0 |
| 96626 | 1.254983 | 0.019 | 0 | | 0 | 0 |

TABLE 3-continued

Scores of 295 confirmed genes required for influenza virus replication.

| | | | | |
|---|---|---|---|---|
| 96626 | 0.949434 | 0.019 | 0 | 0 |
| 113878 | 0.534481 | 0.83 | 0.57 | 0 |
| 113878 | 0.726053 | 0.83 | 0.57 | 0 |
| 114299 | 0.844378 | 0.066 | 0 | 0 |
| 114299 | 0.6313 | 0.066 | 0 | 0 |
| 114788 | 0.825459 | 0.12 | 0 | 0 |
| 114788 | 0.882159 | 0.12 | 0 | 0 |
| 114880 | 0.814979 | 0.38 | 0.24 | 0 |
| 114880 | 0.749792 | 0.38 | 0.24 | 0 |
| 114971 | 0.735513 | 0.82 | 0.81 | 1 | 0 |
| 114971 | 0.800088 | 0.82 | 0.81 | 1 | 0 |
| 115701 | 0.575299 | 0.96 | 1 | 0.5 | 1 | 0 |
| 115701 | 0.744051 | 0.96 | 1 | 0.5 | 1 | 0 |
| 116447 | 0.422886 | 0.85 | 0.75 | 0.5 | 1 |
| 116447 | 0.520039 | 0.85 | 0.75 | 0.5 | 0 | 1 |
| 118442 | 0.618044 | 0.68 | 0.34 | 0 | 0 |
| 118442 | 0.864459 | 0.68 | 0.34 | 0 | 0 |
| 122525 | 0.689707 | 0.88 | 0.68 | 0 | 0 |
| 122525 | 0.756717 | 0.88 | 0.68 | 0 | 0 |
| 124583 | 0.447266 | 0.78 | 0.52 | 0.5 | 0 |
| 124583 | 0.608924 | 0.78 | 0.52 | 0 | 0 |
| 126541 | 0.871359 | 0.91 | 0.65 | 0 | 0 |
| 126541 | 0.65345 | 0.91 | 0.65 | 0 | 0 |
| 127733 | 0.693112 | 0.35 | 0.22 | 0.5 | 0 |
| 127733 | 0.7995 | 0.35 | 0.22 | 0.5 | 0 |

TABLE 3-continued

Scores of 295 confirmed genes required for influenza virus replication.

| | | | | | |
|---|---|---|---|---|---|
| 153571 | 0.659744 | 0.4 | 0.6 | 0.5 | 0 | 0 |
| 153571 | 0.792561 | 0.4 | 0.6 | 0.5 | 0 | 0 |
| 166614 | 0.50323 | 0.98 | 1 | 0.5 | 1 | 0 |
| 166614 | 0.536599 | 0.98 | 1 | 0.5 | 1 | 0 |
| 167681 | 0.772587 | 0.7 | 0.74 | 0.5 | 0 | 0 |
| 167681 | 0.595733 | 0.7 | 0.74 | 0.5 | 0 | 0 |
| 203068 | 0.773416 | 0.62 | 0.3 | 0.5 | 0 | 1 |
| 203068 | 0.592089 | 0.62 | 0.3 | 0.5 | 0 | 1 |
| 204851 | 0.65027 | 0.93 | 1 | 0.5 | 1 | 0 |
| 204851 | 0.720627 | 0.93 | 1 | 0.5 | 1 | 0 |
| 254065 | 0.93162 | 0.2 | 0 | | 0 | 0 |
| 254065 | 0.745334 | 0.2 | 0 | | 0 | 0 |
| 256126 | 0.697274 | 0.79 | 0.65 | | 0 | 0 |
| 256126 | 0.633533 | 0.79 | 0.65 | | 0 | 0 |
| 283455 | 0.478162 | 0.97 | 1 | 0.5 | 1 | 0 |
| 283455 | 0.896556 | 0.97 | 1 | 0.5 | 1 | 0 |
| 284230 | 0.712518 | 0.65 | 0.63 | | 0 | 0 |
| 284230 | 0.621278 | 0.65 | 0.63 | | 0 | 0 |
| 284366 | 0.525325 | 0.75 | 0.73 | | 0 | 0 |
| 284366 | 0.870251 | 0.75 | 0.73 | | 0 | 0 |
| 338599 | 0.793643 | 0.89 | 0.58 | | 1 | 0 |
| 338599 | 0.696086 | 0.89 | 0.58 | | 1 | 0 |
| 340024 | 0.471788 | 0.92 | 0.78 | 0.5 | 0 | 0 |
| 340024 | 0.706444 | 0.92 | 0.78 | 0.5 | 0 | 0 |
| 340260 | 0.590378 | 0.77 | 0.69 | | 0 | 0 |
| 340260 | 0.665443 | 0.77 | 0.69 | | 0 | 0 |

TABLE 3-continued

Scores of 295 confirmed genes required for influenza virus replication.

| | | | | |
|---|---|---|---|---|
| 377841 | 0.481163 | 0.8 | 0.54 | 0.5 | 1 |
| 377841 | 0.714998 | 0.8 | 0.54 | 0.5 | 1 |
| 387082 | 0.637418 | 0.35 | 0.23 | 0 | 0 |
| 387082 | 0.68122 | 0.35 | 0.23 | 0 | 0 |
| 387911 | 0.70882 | 0 | 0 | | 0 |
| 387911 | 0.619996 | 0 | 0 | | 0 |
| 401007 | 0.725996 | 0.95 | 0.89 | 0 | 0 |
| 401007 | 0.986819 | 0.95 | 0.89 | 0 | 0 |
| 401665 | 0.559282 | 0.91 | 0.72 | 0.5 | 0 |
| 401665 | 0.583315 | 0.91 | 0.72 | 0.5 | 0 |
| 440396 | 0.600182 | 0.67 | 0.38 | 0 | 0 |
| 440396 | 0.807451 | 0.67 | 0.38 | 0 | 0 |
| 440738 | 0.679963 | 0.14 | 0 | 0 | 0 |
| 440738 | 0.807336 | 0.14 | 0 | 0 | 0 |
| 441239 | 0.77963 | 0.78 | 1 | 0 | 0 |
| 441239 | 0.725592 | 0.78 | 1 | 0 | 0 |
| 441670 | 0.691595 | 0 | 0 | 0 | 0 |
| 441670 | 0.727008 | 0 | 0 | 0 | 0 |
| 643641 | 0.709218 | 0.58 | 0.33 | 0 | 0 |
| 643641 | 0.688259 | 0.58 | 0.33 | 0 | 0 |
| 653712 | 1.00205 | 0.88 | 1 | 0.5 | 0 |
| 653712 | 0.773468 | 0.88 | 1 | 0.5 | 0 |

TABLE 3-continued

Scores of 295 confirmed genes required for influenza virus replication.

| | | | | | | |
|---|---|---|---|---|---|---|
| 728683 | 0.779763 | 0.9 | 1 | 0 | 0 | 0 |
| 728683 | 1.110111 | 0.9 | 1 | 0 | 0 | 0 |
| 730974 | 0.714602 | 0.85 | 0.61 | 0 | 0 | 0 |
| 730974 | 0.807114 | 0.85 | 0.61 | 0 | 0 | 0 |

Explanation of column headings in table:
Gene_ID: Entrez GeneID;
Symbol and Description:
Entrez Gene official Symbol and official full name;
GenebankID: Refseq mRNA;
target sequence: The best two siRNAs targeting each confirmed gene are shown;
Average: mean of scores in reconfirmation assays at three different time points after infection: Renilla luciferase activity at 12 h, 24 h and 36 h and Toxicity at 24 h;
siRNA_SCORE: evidence score calculated based on siRNA activity;
RSA_SCORE_LogP: evidence score calculated based on Redundant siRNA Analysis (RSA) (see Methods section);
SCORE_Network_Direct, SCORE_Network_Indirect, SCORE_MCODE: binary evidence scores if respective genes are contained in Network based on direct or indirect interactions or MCODE (Molecular Complex Detection analysis) respectively (1 or 0);
SCORE_OPI_Support: evidence score calculated based on grouping in one of the OPI (Ontology-based Pattern Identification) functional categories (see Methods section);
SCORE_GOEnrich: evidence score calculated based on gene ontology enrichment analysis;
SCORE_KnownViralPartners_Direct, SCORE_KnownViralPartners_Indirect: Evidence score calculated based on direct and indirect interactions with influenza virus proteins respectively;
SCORE_DrugInformation: binary evidence score on known drugs specific for respective gene;
Calculations for each evidence score are described in Materials and Methods.

TABLE 4

Overrepresented functional processes and protein domains of proteins required for influenza virus replication.

| GO | Description | GeneID | Hits | Log10(P) |
|---|---|---|---|---|
| GO:0004672 | (MF) protein kinase activity | 816\|5606\|6093\|8476\|9448\|23387\|23552\|23604\|29110\|1019\|2045\|2050\|3717\|4914\|5594\|6196\|6446\|8558\|9641\|10595\|30849\|204851\|283455\|92\|157\|207\|369\|658\|1195\|1263\|1455\|1613\|2011\|2048\|2260\|2263\|2264\|2322\|2324\|2444\|2475\|2580\|2869\|2870\|2932\|3984\|4058\|4296\|4915\|4920\|5062\|5063\|5165\|5566\|5580\|5584\|5605\|5607\|5610\|6792\|7294\|7786\|9149\|9201\|9578\|9625\|9943\|10114\|10188\|10733\|10783\|11113\|11213\|11214\|23049\|27347\|28996\|29959\|30811\|50488\|55872\|56164\|57551\|79705\|84197\|115701\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CLK1\|PLK3\|CSNK1G2\|DAPK3\|MARK2\|EPHB2\|FGFR1\|FGFR2\|FGFR4\|FLT3\|FLT4\|FRK\|FRAP1\|GAK\|GRK5\|GRK6\|GSK3B\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|CDKL5\|TXK\|MAP3K12\|DYRKIB\|DCLK1\|CDC42BPB\|AATK\|OXSR1\|HIPK3\|TNK2\|PLK4\|NEK6\|CIT\|IRAK3\|AKAP13\|SMG1\|STK39\|HIPK2\|NRBP1\|HUNK\|MINK1\|PBK\|STK31\|TAOK1\|LRRK1\|FLJ23356\|ALPK2\|DCLK2 | −58.128 |
| GO:0016773 | (MF) phospho-transferase activity, alcohol group as acceptor | 816\|5606\|6093\|8476\|9448\|23387\|23552\|23604\|29110\|1019\|2045\|2050\|3717\|4914\|5594\|6196\|6446\|8558\|9641\|10595\|30849\|204851\|283455\|92\|157\|207\|369\|658\|1195\|1263\|1455\|1613\|2011\|2048\|2260\|2263\|2264\|2322\|2324\|2444\|2475\|2580\|2869\|2870\|2932\|3984\|4058\|4296\|4915\|4920\|5062\|5063\|5165\|5566\|5580\|5584\|5605\|5607\|5610\|6792\|7294\|7786\|9149\|9201\|9578\|9625\|9943\|10114\|10188\|10733\|10783\|11113\|11213\|11214\|23049\|23396\|27347\|28996\|29959\|30811\|50488\|55229\|55577\|55872\|56164\|57551\|65220\|79705\|84197\|115701\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CLK1\|PLK3\|CSNK1G2\|DAPK3\|MARK2\|EPHB2\|FGFR1\|FGFR2\|FGFR4\|FLT3\|FLT4\|FRK\|FRAP1\|GAK\|GRK5\|GRK6\|GSK3B\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|CDKL5\|TXK\|MAP3K12\|DYRK1B\|DCLK1\|CDC42BPB\|AATK\|OXSR1\|HIPK3\|TNK2\|PLK4\|NEK6\|CIT\|IRAK3\|AKAP13\|SMG1\|PIP5K1C\|STK39\|HIPK2\|NRBP1\|HUNK\|MINK1\|PANK4\|NAGK\|PBK\|STK31\|TAOK1\|NADK\|LRRK1\|FLJ23356\|ALPK2\|DCLK2 | −55.91 |
| GO:0016301 | (MF) kinase activity | 816\|5606\|6093\|8476\|9448\|23387\|23552\|23604\|29110\|1019\|2045\|2050\|3717\|4914\|5594\|6196\|6446\|8558\|9641\|10595\|30849\|56997\|204851\|283455\|92\|157\|207\|369\|658\|1195\|1263\|1455\|1613\|2011\|2048\|2260\|2263\|2264\|2322\|2324\|2444\|2475\|2580\|2869\|2870\|2932\|3984\|4058\|4296\|4915\|4920\|5062\|5063\|5165\|5566\|5580\|5584\|5605\|5607\|5610\|6792\|7294\|7786\|9149\|9201\|9578\|9625\|9943\|10114\|10188\|10733\|10783\|11113\|11213\|11214\|23049\|23396\|27347\|28996\|29959\|30811\|50488\|55229\|55577\|55872\|56164\|57551\|65220\|79705\|84197\|115701\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|ERN2\|PIK3R4\|CABC1\|HIPK1\|KSR2\|ACVR2A\|ADRBK2\|AKT1\|ARAF\|BMPR1B\|CLK1\|PLK3\|CSNK1G2\|DAPK3\|MARK2\|EPHB2\|FGFR1\|FGFR2\|FGFR4\|FLT3\|FLT4\|FRK\|FRAP1\|GAK\|GRK5\|GRK6\|GSK3B\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|CDKL5\|TXK\|MAP3K12\|DYRK1B\|DCLK1\|CDC42BPB\|AATK\|OXSR1\|HIPK3\|TNK2\|PLK4\|NEK6\|CIT\|IRAK3\|AKAP13\|SMG1\|PIP5K1C\|STK39\|HIPK2\|NRBP1\|HUNK\|MINK1\|PANK4\|NAGK\|PBK\|STK31\|TAOK1\|NADK\|LRRK1\|FLJ23356\|ALPK2\|DCLK2 | −52.141 |
| GO:0006468 | (BP) protein amino acid phosphorylation | 816\|5606\|6093\|8476\|9448\|23387\|23552\|23604\|29110\|1019\|2045\|2050\|3717\|4914\|5594\|6196\|6446\|8558\|9641\|10595\|30849\|204851\|283455\|92\|157\|207\|369\|658\|975\|1195\|1263\|1385\|1455\|1613\|2011\|2048\|2260\|2263\|2264\|2322\|2324\|2357\|2444\|2580\|2869\|2870\|2932\|3725\|3984\|4058\|4296\|4915\|4920\|5062\|5063\|5165\|5566\|5580\|5584\|5605\|5607\|5610\|6792\|7294\|7786\|9149\|9201\|9578\|9625\|9943\|10114\|10188\|10733\|10783\|11113\|11213\|23049\|27347\|28996\|29959\|30811\|50488\|55872\|56164\|57551\|79705\|84197\|115701\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CD81\|CLK1\|PLK3\|CREB1\|CSNK1G2\|DAPK3\|MARK2\|EPHB2\|FGFR1\|FGFR2\|FGFR4\|FLT3\|FLT4\|FPR1\|FRK\|GAK\|GRK5\|GRK6\|GSK3B\|JUN\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|CDKL5\|TXK\|MAP3K12\|DYRK1B\|DCLK1\|CDC42BPB\|AATK\|OXSR1\|HIPK3\|TNK2\|PLK4\|NEK6\|CIT\|IRAK3\|SMG1\|STK39\|HIPK2\|NRBP1\|HUNK\|MINK1\|PBK\|STK31\|TAOK1\|LRRK1\|FLJ23356\|ALPK2\|DCLK2 | −50.831 |
| GO:0016310 | (BP) phosphorylation | 816\|5606\|6093\|8476\|9448\|23387\|23552\|23604\|29110\|537\|1019\|2045\|2050\|3717\|4914\|5594\|6196\|6446\|8558\|9641\|10595\|30849\|204851\|283455\|92\|157\|207\|369\|658\|975\|1195\|1263\|1385\|1455\|1613\|2011\|2048\|2260\|2263\|2264\|2322\|2324\|2357\|2444\|2475\|2580\|2869\|2870\|2932\|3725\|3984\|4058\|4296\|4915\|4920\|5062\|5063\|5165\|5566\|5580\|5584\|5605\|5607\|5610\|6792\|7294\|7786\|9149\|9201\|9578\|9625\|9943\|10114\|10188\|10733\|10783\|11113\|11213\|23049\|27347\|28996\|29959\| | CAMK2B\|MAP2K3\|ROCK1\|CDC42BPA\|MAP4K4\|KIAA0999\|CCRK\|DAPK2\|TBK1\|ATP6AP1\|CDK4\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CD81\|CLK1\|PLK3\|CREB1\|CSNK1G2\|DAPK3\|MARK2\|EPHB2\|FGFR1\|FGFR2\|FGFR4\|FLT3\|FLT4\|FPR1\|FRK\|FRAP1\|GAK\|GRK5\|GRK6\|GSK3B\|JUN\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|CDKL5\|TXK\|MAP3K12\| | −48.489 |

TABLE 4-continued

Overrepresented functional processes and protein domains of proteins required for influenza virus replication.

| GO | Description | GeneID | Hits | Log10(P) |
|---|---|---|---|---|
| | | 30811\|50488\|54866\|55872\|56164\|57551\|65220\|79705\|84197\|115701\|166614 | DYRK1B\|DCLK1\|CDC42BPB\|AATK\|OXSR1\|HIPK3\|TNK2\|PLK4\|NEK6\|CIT\|IRAK3\|SMG1\|STK39\|HIPK2\|NRBP1\|HUNK\|MINK1\|PPP1R14D\|PBK\|STK31\|TAOK1\|NADK\|LRRK1\|FLJ23356\|ALPK2\|DCLK2 | |
| GO:0016772 | (MF) transferase activity, transferring phosphorus-containing groups | 816\|5606\|6093\|8476\|9448\|23387\|23552\|23604\|29110\|1019\|2045\|2050\|3717\|4914\|5594\|6196\|6446\|8558\|9641\|10595\|30849\|56997\|204851\|283455\|92\|157\|207\|369\|658\|1195\|1263\|1455\|1613\|2011\|2048\|2260\|2263\|2264\|2322\|2324\|2444\|2475\|2580\|2869\|2870\|2932\|3984\|4058\|4296\|4915\|4920\|5062\|5063\|5165\|5422\|5566\|5580\|5584\|5605\|5607\|5610\|6792\|7294\|7786\|9149\|9201\|9578\|9625\|9943\|10114\|10188\|10733\|10783\|10849\|11113\|11213\|11214\|23049\|23396\|27347\|28996\|29959\|30811\|50488\|55229\|55577\|55872\|56164\|57551\|65220\|79705\|84197\|115701\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|ERN2\|PIK3R4\|CABC1\|HIPK1\|KSR2\|ACVR2A\|ADRBK2\|AKT1\|ARAF\|BMPR1B\|CLK1\|PLK3\|CSNK1G2\|DAPK3\|MARK2\|EPHB2\|FGFR1\|FGFR2\|FGFR4\|FLT3\|FLT4\|FRK\|FRAP1\|GAK\|GRK5\|GRK6\|GSK3B\|LIMK1\|LTK\|MAP3K11\|NTRK2\|ROR2\|PAK2\|PAK3\|PDK3\|POLA1\|PRKACA\|PRKCD\|PRKCI\|MAP2K2\|MAP2K5\|EIF2AK2\|CDKL5\|TXK\|MAP3K12\|DYRK1B\|DCLK1\|CDC42BPB\|AATK\|OXSR1\|HIPK3\|TNK2\|PLK4\|NEK6\|CD3EAP\|CIT\|IRAK3\|AKAP13\|SMG1\|PIP5K1C\|STK39\|HIPK2\|NRBP1\|HUNK\|MINK1\|PANK4\|NAGK\|PBK\|STK31\|TAOK1\|NADK\|LRRK1\|FLJ23356\|ALPK2\|DCLK2 | −48.363 |
| IPR017441 | (MF) Protein kinase ATP binding, conserved site | 816\|5606\|6093\|8476\|9448\|23387\|23552\|23604\|29110\|1019\|2045\|2050\|3717\|4914\|5594\|6196\|6446\|8558\|9641\|204851\|157\|207\|369\|658\|1195\|1263\|1455\|1613\|2011\|2048\|2260\|2264\|2322\|2324\|2444\|2869\|2870\|2932\|3984\|4058\|4296\|4915\|5062\|5063\|5566\|5584\|5605\|5607\|5610\|6792\|7294\|9149\|9201\|9578\|9625\|9943\|10114\|10188\|10733\|10783\|11113\|27347\|28996\|30811\|50488\|57551\|166614 | CAMK2B\|MAP2K3\|ROCK1\|CDC42BPA\|MAP4K4\|KIAA0999\|CCRK\|DAPK2\|TBK1\|CDK4\|EPHA7\|EPHB4\|JAK2\|NTRK1\|MAPK1\|RPS6KA2\|SGK1\|CDK10\|IKBKE\|HIPK1\|ADRBK2\|AKT1\|ARAF\|BMPR1B\|CLK1\|PLK3\|CSNK1G2\|DAPK3\|MARK2\|EPHB2\|FGFR1\|FGFR4\|FLT3\|FLT4\|FRK\|GRK5\|GRK6\|GSK3B\|LIMK1\|LTK\|MAP3K11\|NTRK2\|PAK2\|PAK3\|PRKACA\|PRKCI\|MAP2K2\|MAP2K5\|EIF2AK2\|CDKL5\|TXK\|DYRK1B\|DCLK1\|CDC42BPB\|AATK\|OXSR1\|HIPK3\|TNK2\|PLK4\|NEK6\|CIT\|STK39\|HIPK2\|HUNK\|MINK1\|TAOK1\|DCLK2 | −48.277 |
| GO:0004674 | (MF) protein serine/threonine kinase activity | 816\|5606\|6093\|8476\|9448\|23387\|23552\|23604\|29110\|1019\|5594\|6196\|6446\|8558\|9641\|10595\|30849\|204851\|283455\|92\|157\|207\|369\|658\|1195\|1263\|1455\|1613\|2011\|2475\|2580\|2869\|2870\|2932\|3984\|4296\|5062\|5063\|5566\|5580\|5584\|5605\|5607\|5610\|6792\|7786\|9149\|9201\|9578\|9625\|9943\|10114\|10733\|10783\|11113\|11213\|11214\|23049\|27347\|28996\|30811\|50488\|55872\|56164\|57551\|79705\|115701\|166614 | CAMK2B\|MAP2K3\|ROCK1\|CDC42BPA\|MAP4K4\|KIAA0999\|CCRK\|DAPK2\|TBK1\|CDK4\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CLK1\|PLK3\|CSNK1G2\|DAPK3\|MARK2\|FRAP1\|GAK\|GRK5\|GRK6\|GSK3B\|LIMK1\|MAP3K11\|PAK2\|PAK3\|PRKACA\|PRKCD\|PRKCI\|MAP2K2\|MAP2K5\|EIF2AK2\|CDKL5\|MAP3K12\|DYRK1B\|DCLK1\|CDC42BPB\|AATK\|OXSR1\|HIPK3\|PLK4\|NEK6\|CIT\|IRAK3\|AKAP13\|SMG1\|STK39\|HIPK2\|HUNK\|MINK1\|PBK\|STK31\|TAOK1\|LRRK1\|ALPK2\|DCLK2 | −47.124 |
| GO:0006793 | (BP) phosphorus metabolic process | 816\|5606\|6093\|8476\|9448\|23387\|23552\|23604\|29110\|537\|1019\|1845\|2045\|2050\|3717\|4914\|5594\|6196\|6446\|8558\|9641\|10595\|30849\|204851\|283455\|92\|157\|207\|369\|658\|975\|1195\|1263\|1385\|1455\|1613\|2011\|2048\|2260\|2263\|2264\|2322\|2324\|2357\|2444\|2475\|2580\|2869\|2870\|2932\|3725\|3984\|4058\|4296\|4915\|4920\|5062\|5063\|5165\|5566\|5580\|5584\|5605\|5607\|5610\|5797\|5798\|6792\|7294\|7786\|9149\|9201\|9578\|9625\|9943\|10114\|10188\|10733\|10783\|11113\|11213\|23049\|27347\|28996\|29959\|30811\|50488\|54866\|55872\|56164\|57551\|65220\|79705\|84197\|114971\|115701\|166614\|338599 | CAMK2B\|MAP2K3\|ROCK1\|CDC42BPA\|MAP4K4\|KIAA0999\|CCRK\|DAPK2\|TBK1\|ATP6AP1\|CDK4\|DUSP3\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CD81\|CLK1\|PLK3\|CREB1\|CSNK1G2\|DAPK3\|MARK2\|EPHB2\|FGFR1\|FGFR2\|FGFR4\|FLT3\|FLT4\|FPR1\|FRK\|FRAP1\|GAK\|GRK5\|GRK6\|GSK3B\|JUN\|LIMK1\|LTK\|MAP3K11\|NTRK2\|ROR2\|PAK2\|PAK3\|PDK3\|PRKACA\|PRKCD\|PRKCI\|MAP2K2\|MAP2K5\|EIF2AK2\|PTPRM\|PTPRN\|CDKL5\|TXK\|MAP3K12\|DYRK1B\|DCLK1\|CDC42BPB\|AATK\|OXSR1\|HIPK3\|TNK2\|PLK4\|NEK6\|CIT\|IRAK3\|SMG1\|STK39\|HIPK2\|NRBP1\|HUNK\|MINK1\|PPP1R14D\|PBK\|STK31\|TAOK1\|NADK\|LRRK1\|FLJ23356\|PTPMT1\|ALPK2\|DCLK2\|DUPD1 | −46.041 |
| GO:0006796 | (BP) phosphate metabolic process | 816\|5606\|6093\|8476\|9448\|23387\|23552\|23604\|29110\|537\|1019\|1845\|2045\|2050\|3717\|4914\|5594\|6196\|6446\|8558\|9641\|10595\|30849\|204851\|283455\|92\|157\|207\|369\|658\|975\|1195\|1263\|1385\|1455\|1613\|2011\|2048\|2260\|2263\|2264\|2322\|2324\|2357\|2444\|2475\|2580\|2869\|2870\|2932\|3725\|3984\|4058\|4296\|4915\|4920\|5062\|5063\|5165\|5566\|5580\|5584\|5605\|5607\|5610\|5797\|5798\|6792\|7294\|7786\|9149\|9201\|9578\|9625\|9943\|10114\|10188\| | CAMK2B\|MAP2K3\|ROCK1\|CDC42BPA\|MAP4K4\|KIAA0999\|CCRK\|DAPK2\|TBK1\|ATP6AP1\|CDK4\|DUSP3\|EPHA7\|EPHB4\|JAK2\|NTRK1\|MAPK1\|RPS6KA2\|SGK1\|CDK10\|IKBKE\|ERN2\|PIK3R4\|HIPK1\|KSR2\|ACVR2A\|ADRBK2\|AKT1\|ARAF\|BMPR1B\|CD81\|CLK1\|PLK3\|CREB1\|CSNK1G2\|DAPK3\|MARK2\|EPHB2\|FGFR1\|FGFR2\|FGFR4\|FLT3\|FLT4\|FPR1\|FRK\|FRAP1\|GAK\|GRK5\|GRK6\|GSK3B\|JUN\|LIMK1\|LTK\|MAP3K11\|NTRK2\|ROR2\| | −46.041 |

TABLE 4-continued

Overrepresented functional processes and protein domains of proteins required for influenza virus replication.

| GO | Description | GeneID | Hits | Log10(P) |
|---|---|---|---|---|
| | | 10733\|10783\|11113\|11213\|23049\|27347\|28996\|29959\|30811\|50488\|54866\|55872\|56164\|57551\|65220\|79705\|84197\|114971\|115701\|166614\|338599 | PAK2\|PAK3\|PDK3\|PRKACA\|PRKCD\|PRKCI\|MAP2K2\|MAP2K5\|EIF2AK2\|PTPRM\|PTPRN\|CDKL5\|TXK\|MAP3K12\|DYRK1B\|DCLK1\|CDC42BPB\|AATK\|OXSR1\|HIPK3\|TNK2\|PLK4\|NEK6\|CIT\|IRAK3\|SMG1\|STK39\|HIPK2\|NRBP1\|HUNK\|MINK1\|PPP1R14D\|PBK\|STK31\|TAOK1\|NADK\|LRRK1\|FLJ23356\|PTPMT1\|ALPK2\|DCLK2\|DUPD1 | |
| IPR008271 | (MF) Serine/threonine protein kinase, active site | 816\|5606\|6093\|8476\|9448\|23387\|23552\|23604\|1019\|5594\|6196\|6446\|8558\|10595\|30849\|204851\|283455\|92\|157\|207\|369\|658\|1195\|1263\|1455\|1613\|2011\|2580\|2870\|2932\|4296\|5062\|5063\|5566\|5584\|5605\|5607\|5610\|6792\|7786\|9149\|9201\|9578\|10114\|10783\|11113\|28996\|30811\|50488\|55872\|57551\|166614 | CAMK2B\|MAP2K3\|ROCK1\|CDC42BPA\|MAP4K4\|KIAA0999\|CCRK\|DAPK2\|CDK4\|MAPK1\|RPS6KA2\|SGK1\|CDK10\|ERN2\|PIK3R4\|HIPK1\|KSR2\|ACVR2A\|ADRBK2\|AKT1\|ARAF\|BMPR1B\|CLK1\|PLK3\|CSNK1G2\|DAPK3\|MARK2\|GAK\|GRK6\|GSK3B\|MAP3K11\|PAK2\|PAK3\|PRKACA\|PRKCI\|MAP2K2\|MAP2K5\|EIF2AK2\|CDKL5\|MAP3K12\|DYRK1B\|DCLK1\|CDC42BPB\|HIPK3\|NEK6\|CIT\|HIPK2\|HUNK\|MINK1\|PBK\|TAOK1\|DCLK2 | −36.695 |
| GO:0004713 | (MF) protein tyrosine kinase activity | 5606\|2045\|2050\|3717\|4914\|1195\|2048\|2260\|2263\|2264\|2322\|2324\|2444\|3984\|4058\|4296\|4915\|4920\|5605\|5607\|7294\|7786\|9149\|9625\|10188\|10733 | MAP2K3\|EPHA7\|EPHB4\|JAK2\|NTRK1\|CLK1\|EPHB2\|FGFR1\|FGFR2\|FGFR4\|FLT3\|FLT4\|FRK\|LIMK1\|LTK\|MAP3K11\|NTRK2\|ROR2\|MAP2K2\|MAP2K5\|TXK\|MAP3K12\|DYRK1B\|AATK\|TNK2\|PLK4 | −16.387 |
| IPR008266 | (MF) Tyrosine protein kinase, active site | 2045\|2050\|3717\|4914\|2048\|2260\|2264\|2322\|2324\|2444\|4058\|4915\|4920\|7294\|9625\|10188\|10733 | EPHA7\|EPHB4\|JAK2\|NTRK1\|EPHB2\|FGFR1\|FGFR4\|FLT3\|FLT4\|FRK\|LTK\|NTRK2\|ROR2\|TXK\|AATK\|TNK2\|PLK4 | −12.443 |
| GO:0019199 | (MF) transmembrane receptor protein kinase activity | 2045\|2050\|4914\|92\|658\|2048\|2260\|2263\|2264\|2322\|2324\|4058\|4915\|4920 | EPHA7\|EPHB4\|NTRK1\|ACVR2A\|BMPR1B\|EPHB2\|FGFR1\|FGFR2\|FGFR4\|FLT3\|FLT4\|LTK\|NTRK2\|ROR2 | −9.992 |
| GO:0004714 | (MF) transmembrane receptor protein tyrosine kinase activity | 2045\|2050\|4914\|2048\|2260\|2263\|2264\|2322\|2324\|4058\|4915\|4920 | EPHA7\|EPHB4\|NTRK1\|EPHB2\|FGFR1\|FGFR2\|FGFR4\|FLT3\|FLT4\|LTK\|NTRK2\|ROR2 | −8.817 |
| IPR017892 | (MF) Protein kinase, C-terminal | 6093\|8476\|6196\|6446\|207\|5566\|5584\|9578\|11113 | ROCK1\|CDC42BPA\|RPS6KA2\|SGK1\|AKT1\|PRKACA\|PRKCI\|CDC42BPB\|CIT | −7.624 |
| IPR000961 | (MF) AGC-kinase, C-terminal | 6093\|8476\|6196\|6446\|207\|5566\|5584\|9578\|11113 | ROCK1\|CDC42BPA\|RPS6KA2\|SGK1\|AKT1\|PRKACA\|PRKCI\|CDC42BPB\|CIT | −7.624 |
| GO:0019992 | (MF) diacylglycerol binding | 6093\|8476\|283455\|369\|5580\|5584\|9578\|11113\|11214\|29127 | ROCK1\|CDC42BPA\|KSR2\|ARAF\|PRKCD\|PRKCI\|CDC42BPB\|CIT\|AKAP13\|RACGAP1 | −7.265 |
| GO:0007243 | (BP) protein kinase cascade | 9448\|10159\|23604\|29110\|3717\|5594\|6196\|8837\|9641\|147\|207\|602\|975\|1613\|2011\|2260\|2357\|4296\|4920\|5566\|7786\|9943\|10783\|28996\|50488\|124583 | MAP4K4\|ATP6AP2\|DAPK2\|TBK1\|JAK2\|MAPK1\|RPS6KA2\|CFLAR\|IKBKE\|ADRA1B\|AKT1\|BCL3\|CD81\|DAPK3\|MARK2\|FGFR1\|FPR1\|MAP3K11\|ROR2\|PRKACA\|MAP3K12\|OXSR1\|NEK6\|HIPK2\|MINK1\|CANT1 | −6.911 |
| IPR002219 | (MF) Protein kinase C, phorbol ester/diacylglycerol binding | 6093\|8476\|283455\|369\|5584\|9578\|11113\|11214\|29127 | ROCK1\|CDC42BPA\|KSR2\|ARAF\|PRKCI\|CDC42BPB\|CIT\|AKAP13\|RACGAP1 | −6.252 |
| GO:0048194 | (BP) Golgi vesicle budding | 9276\|22820\|372\|1314\|5584 | COPB2\|COPG\|ARCN1\|COPA\|PRKCI | −5.897 |
| IPR001180 | (MF) Citron-like | 8476\|9448\|9578\|11113\|50488 | CDC42BPA\|MAP4K4\|CDC42BPB\|CIT\|MINK1 | −5.605 |
| GO:0046777 | (BP) protein amino acid auto-phosphorylation | 207\|3725\|4296\|5062\|5610\|6792\|7786\|23049 | AKT1\|JUN\|MAP3K11\|PAK2\|EIF2AK2\|CDKL5\|MAP3K12\|SMG1 | −5.303 |
| GO:0016540 | (BP) protein autoprocessing | 207\|3725\|4296\|5062\|5610\|6792\|7786\|23049 | AKT1\|JUN\|MAP3K11\|PAK2\|EIF2AK2\|CDKL5\|MAP3K12\|SMG1 | −5.168 |
| GO:0046961 | (MF) hydrogen ion transporting ATPase activity, rotational mechanism | 527\|533\|9114\|523\|526\|537 | ATP6V0C\|ATP6V0B\|ATP6V0D1\|ATP6V1A\|ATP6V1B2\|ATP6AP1 | −5.003 |

TABLE 4-continued

Overrepresented functional processes and protein domains of proteins required for influenza virus replication.

| GO | Description | GeneID | Hits | Log10(P) |
|---|---|---|---|---|
| GO:0016485 | (BP) protein processing | 207\|3725\|4296\|5062\|5610\|6792\|7786\|9159\|23049\|55851 | AKT1\|JUN\|MAP3K11\|PAK2\|EIF2AK2\|CDKL5\|MAP3K12\|PCSK7\|SMG1\|PSENEN | −4.974 |
| GO:0006900 | (BP) membrane budding | 9276\|22820\|372\|1314\|5584 | COPB2\|COPG\|ARCN1\|COPA\|PRKCI | −4.957 |
| GO:0030126 | (CC) COPI vesicle coat | 9276\|22820\|372\|1314 | COPB2\|COPG\|ARCN1\|COPA | −4.845 |
| GO:0030663 | (CC) COPI coated vesicle membrane | 9276\|22820\|372\|1314 | COPB2\|COPG\|ARCN1\|COPA | −4.845 |
| GO:0018105 | (BP) peptidyl-serine phosphorylation | 207\|2932\|7786\|10114\|23049 | AKT1\|GSK3B\|MAP3K12\|HIPK3\|SMG1 | −4.678 |
| GO:0005057 | (MF) receptor signaling protein activity | 3717\|5594\|9641\|92\|369\|658\|4296\|7786\|9201\|27347\|56300 | JAK2\|MAPK1\|IKBKE\|ACVR2A\|ARAF\|BMPR1B\|MAP3K11\|MAP3K12\|DCLK1\|STK39\|IL1F9 | −4.628 |
| GO:0004702 | (MF) receptor signaling protein serine/threonine kinase activity | 5594\|9641\|92\|658\|4296\|7786\|27347 | MAPK1\|IKBKE\|ACVR2A\|BMPR1B\|MAP3K11\|MAP3K12\|STK39 | −4.562 |
| GO:0048206 | (BP) vesicle targeting, cis-Golgi to rough ER | 9276\|22820\|372\|1314 | COPB2\|COPG\|ARCN1\|COPA | −4.53 |
| GO:0048204 | (BP) vesicle targeting, inter-Golgi cisterna | 9276\|22820\|372\|1314 | COPB2\|COPG\|ARCN1\|COPA | −4.53 |
| GO:0048200 | (BP) Golgi transport vesicle coating | 9276\|22820\|372\|1314 | COPB2\|COPG\|ARCN1\|COPA | −4.53 |
| GO:0048205 | (BP) COPI coating of Golgi vesicle | 9276\|22820\|372\|1314 | COPB2\|COPG\|ARCN1\|COPA | −4.53 |
| GO:0048220 | (BP) cis-Golgi to rough ER vesicle-mediated transport | 9276\|22820\|372\|1314 | COPB2\|COPG\|ARCN1\|COPA | −4.53 |
| GO:0048219 | (BP) inter-Golgi cisterna vesicle-mediated transport | 9276\|22820\|372\|1314 | COPB2\|COPG\|ARCN1\|COPA | −4.53 |
| GO:0030137 | (CC) COPI-coated vesicle | 9276\|22820\|372\|1314 | COPB2\|COPG\|ARCN1\|COPA | −4.484 |
| GO:0005829 | (CC) cytosol | 6093\|6224\|9276\|22820\|29110\|56893\|790\|1019\|2539\|5594\|30849\|51422\|207\|372\|1314\|2475\|2932\|2936\|3320\|3725\|3837\|4193\|5062\|5580\|5584\|5707\|6204\|7786\|8021\|29882\|65220 | ROCK1\|RPS20\|COPB2\|COPG\|TBK1\|UBQLN4\|CAD\|CDK4\|G6PD\|MAPK1\|PIK3R4\|PRKAG2\|AKT1\|ARCN1\|COPA\|FRAP1\|GSK3B\|GSR\|HSP90AA1\|JUN\|KPNB1\|MDM2\|PAK2\|PRKCD\|PRKCI\|PSMD1\|RPS10\|MAP3K12\|NUP214\|ANAPC2\|NADK | −4.432 |
| GO:0007167 | (BP) enzyme linked receptor protein signaling pathway | 2022\|2045\|2050\|3717\|4914\|92\|207\|658\|2048\|2260\|2263\|2264\|2322\|2324\|4058\|4915\|10849\|28996 | ENG\|EPHA7\|EPHB4\|JAK2\|NTRK1\|ACVR2A\|AKT1\|BMPR1B\|EPHB2\|FGFR1\|FGFR2\|FGFR4\|FLT3\|FLT4\|LTK\|NTRK2\|CD3EAP\|HIPK2 | −4.41 |
| GO:0018209 | (BP) peptidyl-serine modification | 207\|2932\|7786\|10114\|23049 | AKT1\|GSK3B\|MAP3K12\|HIPK3\|SMG1 | −4.324 |
| GO:0006903 | (BP) vesicle targeting | 9276\|22820\|372\|1314\|6811 | COPB2\|COPG\|ARCN1\|COPA\|STX5 | −4.324 |
| GO:0005007 | (MF) fibroblast growth factor receptor activity | 2260\|2263\|2264 | FGFR1\|FGFR2\|FGFR4 | −4.317 |
| GO:0044419 | (BP) interspecies interaction between organisms | 23352\|527\|29110\|5594\|8837\|10616\|290\|975\|1385\|3837\|4193\|5062\|5610\|23770\|28996 | UBR4\|ATP6V0C\|TBK1\|MAPK1\|CFLAR\|RBCK1\|ANPEP\|CD81\|CREB1\|KPNB1\|MDM2\|PAK2\|EIF2AK2\|FKBP8\|HIPK2 | −4.298 |
| GO:0016469 | (CC) proton-transporting two-sector ATPase complex | 527\|533\|9114\|523\|526\|537 | ATP6V0C\|ATP6V0B\|ATP6V0D1\|ATP6V1A\|ATP6V1B2\|ATP6AP1 | −4.268 |

TABLE 4-continued

Overrepresented functional processes and protein domains of proteins required for influenza virus replication.

| GO | Description | GeneID | Hits | Log10(P) |
|---|---|---|---|---|
| GO:0048199 | (BP) vesicle targeting, to, from or within Golgi | 9276\|22820\|372\|1314 | COPB2\|COPG\|ARCN1\|COPA | −4.172 |
| GO:0048193 | (BP) Golgi vesicle transport | 9276\|22820\|372\|1314\|5584\|8677\|29959\|55850\|57120 | COPB2\|COPG\|ARCN1\|COPA\|PRKCI\|STX10\|NRBP1\|USE1\|GOPC | −4.164 |
| GO:0046034 | (BP) ATP metabolic process | 527\|533\|523\|526\|537\|65220 | ATP6V0C\|ATP6V0B\|ATP6V1A\|ATP6V1B2\|ATP6AP1\|NADK | −4.156 |
| GO:0019829 | (MF) cation-transporting ATPase activity | 527\|533\|9114\|523\|526\|537 | ATP6V0C\|ATP6V0B\|ATP6V0D1\|ATP6V1A\|ATP6V1B2\|ATP6AP1 | −4.131 |
| GO:0051650 | (BP) establishment of vesicle localization | 9276\|22820\|372\|1314\|6811 | COPB2\|COPG\|ARCN1\|COPA\|STX5 | −4.025 |
| GO:0042802 | (MF) identical protein binding | 6093\|8476\|23604\|56893\|335\|3674\|207\|351\|3320\|4193\|4296\|5062\|5805\|7786\|9578\|9943\|11213\|29959\|57502 | ROCK1\|CDC42BPA\|DAPK2\|UBQLN4\|APOA1\|ITGA2B\|AKT1\|APP\|HSP90AA1\|MDM2\|MAP3K11\|PAK2\|PTS\|MAP3K12\|CDC42BPB\|OXSR1\|IRAK3\|NRBP1\|NLGN4X | −4.013 |
| GO:0051648 | (BP) vesicle localization | 9276\|22820\|372\|1314\|6811 | COPB2\|COPG\|ARCN1\|COPA\|STX5 | −3.935 |
| GO:0006754 | (BP) ATP biosynthetic process | 527\|533\|523\|526\|537 | ATP6V0C\|ATP6V0B\|ATP6V1A\|ATP6V1B2\|ATP6AP1 | −3.85 |
| IPR011009 | (MF) Protein kinase-like | 56997\|92\|2475\|4296\|5062\|5063\|23049 | CABC1\|ACVR2A\|FRAP1\|MAP3K11\|PAK2\|PAK3\|SMG1 | −3.844 |
| IPR000626 | (MF) Ubiquitin | 56893\|10616\|387082\|6613\|7341\|10291 | UBQLN4\|RBCK1\|SUMO4\|SUMO2\|SUMO1\|SF3A1 | −3.8 |
| GO:0004703 | (MF) G-protein coupled receptor kinase activity | 157\|2869\|2870 | ADRBK2\|GRK5\|GRK6 | −3.784 |
| IPR000239 | (MF) GPCR kinase | 157\|2869\|2870 | ADRBK2\|GRK5\|GRK6 | −3.784 |
| GO:0006901 | (BP) vesicle coating | 9276\|22820\|372\|1314 | COPB2\|COPG\|ARCN1\|COPA | −3.752 |
| IPR011989 | (MF) Armadillo-like helical | 1434\|22820\|30849\|2475\|3837\|5707\|10297\|23534\|25831 | CSE1L\|COPG\|PIK3R4\|FRAP1\|KPNB1\|PSMD1\|APC2\|TNPO3\|HECTD1 | −3.688 |
| IPR000095 | (MF) PAK-box/P21-Rho-binding | 8476\|5062\|5063\|9578 | CDC42BPA\|PAK2\|PAK3\|CDC42BPB | −3.675 |
| GO:0007169 | (BP) trans-membrane receptor protein tyrosine kinase signaling pathway | 2045\|2050\|4914\|207\|2048\|2260\|2263\|2264\|2322\|2324\|4058\|4915\|10849 | EPHA7\|EPHB4\|NTRK1\|AKT1\|EPHB2\|FGFR1\|FGFR2\|FGFR4\|FLT3\|FLT4\|LTK\|NTRK2\|CD3EAP | −3.6 |
| IPR006692 | (MF) Coatomer, WD associated region | 9276\|1314 | COPB2\|COPA | −3.536 |
| GO:0048186 | (MF) inhibin beta-A binding | 3547\|92 | IGSF1\|ACVR2A | −3.536 |
| GO:0046933 | (MF) hydrogen ion transporting ATP synthase activity, rotational mechanism | 527\|523\|526\|537 | ATP6V0C\|ATP6V1A\|ATP6V1B2\|ATP6AP1 | −3.487 |
| GO:0009205 | (BP) purine ribonucleoside triphosphate metabolic process | 527\|533\|523\|526\|537\|65220 | ATP6V0C\|ATP6V0B\|ATP6V1A\|ATP6V1B2\|ATP6AP1\|NADK | −3.443 |
| GO:0009144 | (BP) purine nucleoside triphosphate metabolic process | 527\|533\|523\|526\|537\|65220 | ATP6V0C\|ATP6V0B\|ATP6V1A\|ATP6V1B2\|ATP6AP1\|NADK | −3.443 |
| GO:0006890 | (BP) retrograde vesicle-mediated transport, Golgi to ER | 9276\|22820\|372\|1314 | COPB2\|COPG\|ARCN1\|COPA | −3.422 |
| GO:0009199 | (BP) ribonucleoside triphosphate metabolic process | 527\|533\|523\|526\|537\|65220 | ATP6V0C\|ATP6V0B\|ATP6V1A\|ATP6V1B2\|ATP6AP1\|NADK | −3.394 |

TABLE 4-continued

Overrepresented functional processes and protein domains of proteins required for influenza virus replication.

| GO | Description | GeneID | Hits | Log10(P) |
|---|---|---|---|---|
| GO:0051656 | (BP) establishment of organelle localization | 9276\|22820\|372\|1314\|6811 | COPB2\|COPG\|ARCN1\|COPA\|STX5 | −3.28 |
| GO:0004715 | (MF) non-membrane spanning protein tyrosine kinase activity | 3717\|1195\|2444\|7294\|10188 | JAK2\|CLK1\|FRK\|TXK\|TNK2 | −3.246 |
| GO:0006886 | (BP) intracellular protein transport | 1434\|9276\|22820\|3717\|207\|372\|602\|1314\|2932\|3837\|5584\|6811\|8021\|8677\|9972\|51172\|57120\|64601 | CSE1L\|COPB2\|COPG\|JAK2\|AKT1\|ARCN1\|BCL3\|COPA\|GSK3B\|KPNB1\|PRKCI\|STX5\|NUP214\|STX10\|NUP153\|NAGPA\|GOPC\|VPS16 | −3.234 |
| GO:0000287 | (MF) magnesium ion binding | 8476\|23387\|6196\|10595\|92\|658\|2011\|3778\|5063\|5607\|7786\|9578\|9943\|10188\|10783\|11213\|79705 | CDC42BPA\|KIAA0999\|RPS6KA2\|ERN2\|ACVR2A\|BMPR1B\|MARK2\|KCNMA1\|PAK3\|MAP2K5\|MAP3K12\|CDC42BPB\|OXSR1\|TNK2\|NEK6\|IRAK3\|LRRK1 | −3.203 |
| GO:0018193 | (BP) peptidyl-amino acid modification | 3717\|207\|975\|2932\|5165\|7786\|10114\|10188\|23049 | JAK2\|AKT1\|CD81\|GSK3B\|PDK3\|MAP3K12\|HIPK3\|TNK2\|SMG1 | −3.181 |
| IPR001876 | (MF) Zinc finger, RanBP2-type | 10181\|10616\|4193\|9972 | RBM5\|RBCK1\|MDM2\|NUP153 | −3.169 |
| IPR016024 | (MF) Armadillo-type fold | 1434\|22820\|30849\|2475\|3837\|5707\|10297\|23534\|25831 | CSE1L\|COPG\|PIK3R4\|FRAP1\|KPNB1\|PSMD1\|APC2\|TNPO3\|HECTD1 | −3.167 |
| GO:0046907 | (BP) intracellular transport | 1434\|9276\|22820\|3717\|10381\|70\|207\|372\|602\|1314\|2932\|3320\|3837\|5584\|6811\|8021\|8677\|9201\|9972\|23049\|29959\|51172\|55850\|57120\|64601\|203068 | CSE1L\|COPB2\|COPG\|JAK2\|TUBB3\|ACTC1\|AKT1\|ARCN1\|BCL3\|COPA\|GSK3B\|HSP90AA1\|KPNB1\|PRKCI\|STX5\|NUP214\|STX10\|DCLK1\|NUP153\|SMG1\|NRBP1\|NAGPA\|USE1\|GOPC\|VPS16\|TUBB | −3.155 |
| IPR002011 | (MF) Receptor tyrosine kinase, class II, conserved site | 4914\|4058\|4915 | NTRK1\|LTK\|NTRK2 | −3.133 |
| GO:0016050 | (BP) vesicle organization and biogenesis | 9276\|22820\|372\|1314\|5584 | COPB2\|COPG\|ARCN1\|COPA\|PRKCI | −3.106 |
| GO:0009141 | (BP) nucleoside triphosphate metabolic process | 527\|533\|523\|526\|537\|65220 | ATP6V0C\|ATP6V0B\|ATP6V1A\|ATP6V1B2\|ATP6AP1\|NADK | −3.079 |
| GO:0000060 | (BP) protein import into nucleus, translocation | 3717\|207\|602\|3837 | JAK2\|AKT1\|BCL3\|KPNB1 | −3.07 |
| IPR016248 | (MF) Fibroblast growth factor receptor | 2260\|2264 | FGFR1\|FGFR4 | −3.064 |
| GO:0009206 | (BP) purine ribonucleoside triphosphate biosynthetic process | 527\|533\|523\|526\|537 | ATP6V0C\|ATP6V0B\|ATP6V1A\|ATP6V1B2\|ATP6AP1 | −3.052 |
| GO:0009145 | (BP) purine nucleoside triphosphate biosynthetic process | 527\|533\|523\|526\|537 | ATP6V0C\|ATP6V0B\|ATP6V1A\|ATP6V1B2\|ATP6AP1 | −3.052 |
| GO:0009201 | (BP) ribo-nucleoside triphosphate biosynthetic process | 527\|533\|523\|526\|537 | ATP6V0C\|ATP6V0B\|ATP6V1A\|ATP6V1B2\|ATP6AP1 | −2.999 |
| GO:0005774 | (CC) vacuolar membrane | 527\|533\|9114\|537\|51257\|64601 | ATP6V0C\|ATP6V0B\|ATP6V0D1\|ATP6AP1\|MARCH2\|VPS16 | −2.977 |
| GO:0044453 | (CC) nuclear membrane part | 1434\|1717\|3837\|7341\|8021\|9972\|10280 | CSE1L\|DHCR7\|KPNB1\|SUMO1\|NUP214\|NUP153\|OPRS1 | −2.942 |
| GO:0018107 | (BP) peptidyl-threonine phosphorylation | 7786\|10114 | MAP3K12\|HIPK3 | −2.931 |
| GO:0009142 | (BP) nucleoside triphosphate biosynthetic process | 527\|533\|523\|526\|537 | ATP6V0C\|ATP6V0B\|ATP6V1A\|ATP6V1B2\|ATP6AP1 | −2.899 |

TABLE 4-continued

Overrepresented functional processes and protein domains of proteins required for influenza virus replication.

| GO | Description | GeneID | Hits | Log10(P) |
|---|---|---|---|---|
| GO:0051240 | (BP) positive regulation of multicellular organismal process | 10159\|92\|147\|207\|602\|658\|3356 | ATP6AP2\|ACVR2A\|ADRA1B\|AKT1\|BCL3\|BMPR1B\|HTR2A | −2.88 |
| GO:0000165 | (BP) MAPKKK cascade | 10159\|5594\|975\|2260\|2357\|4296\|4920\|7786\|28996\|50488 | ATP6AP2\|MAPK1\|CD81\|FGFR1\|FPR1\|MAP3K11\|ROR2\|MAP3K12\|HIP1C2\|MINK1 | −2.859 |
| GO:0044437 | (CC) vacuolar part | 527\|533\|9114\|537\|51257\|64601 | ATP6V0C\|ATP6V0B\|ATP6V0D1\|ATP6AP1\|MARCH2\|VPS16 | −2.851 |
| GO:0004693 | (MF) cyclin-dependent protein kinase activity | 23552\|1019\|8558\|6792 | CCRK\|CDK4\|CDK10\|CDKL5 | −2.849 |
| GO:0015992 | (BP) proton transport | 527\|533\|9114\|523\|526\|537 | ATP6V0C\|ATP6V0B\|ATP6V0D1\|ATP6V1A\|ATP6V1B2\|ATP6AP1 | −2.808 |
| IPR016257 | (MF) Tyrosine-protein kinase, ephrin receptor | 2045\|2050\|2048 | EPHA7\|EPHB4\|EPHB2 | −2.806 |
| IPR001090 | (MF) Ephrin receptor, ligand binding | 2045\|2050\|2048 | EPHA7\|EPHB4\|EPHB2 | −2.806 |
| IPR000194 | (MF) ATPase, F1/V1/A1 complex, alpha/beta subunit, nucleotide-binding | 523\|526\|9972 | ATP6V1A\|ATP6V1B2\|NUP153 | −2.806 |
| IPR001426 | (MF) Receptor tyrosine kinase, class V, conserved site | 2045\|2050\|2048 | EPHA7\|EPHB4\|EPHB2 | −2.806 |
| GO:0042625 | (MF) ATPase activity, coupled to transmembrane movement of ions | 527\|533\|9114\|523\|526\|537 | ATP6V0C\|ATP6V0B\|ATP6V0D1\|ATP6V1A\|ATP6V1B2\|ATP6AP1 | −2.781 |
| GO:0009150 | (BP) purine ribonucleotide metabolic process | 527\|533\|523\|526\|537\|65220 | ATP6V0C\|ATP6V0B\|ATP6V1A\|ATP6V1B2\|ATP6AP1\|NADK | −2.773 |
| IPR014930 | (MF) DMPK coiled coil | 8476\|9578 | CDC42BPA\|CDC42BPB | −2.768 |
| IPR000959 | (MF) POLO box duplicated region | 1263\|10733 | PLK3\|PLK4 | −2.768 |
| IPR010606 | (MF) Mib-herc2 | 25831\|57534 | HECTD1\|MIB1 | −2.768 |
| GO:0048184 | (MF) follistatin binding | 3547\|92 | IGSF1\|ACVR2A | −2.768 |
| GO:0016265 | (BP) death | 1434\|6093\|23604\|3717\|5594\|6446\|8837\|10595\|56997\|70\|207\|351\|602\|1613\|2932\|3356\|3778\|5062\|5610\|6478\|7178\|9135\|9231\|10114\|10783\|23770\|28996\|54507\|203068 | CSE1L\|ROCK1\|DAPK2\|JAK2\|MAPK1\|SGK1\|CFLAR\|ERN2\|CABC1\|ACTC1\|AKT1\|APP\|BCL3\|DAPK3\|GSK3B\|HTR2A\|KCNMA1\|PAK2\|EIF2AK2\|SIAH2\|TPT1\|RABEP1\|DLG5\|HIPK3\|NEK6\|FKBP8\|HIPK2\|ADAMTSL4\|TUBB | −2.76 |
| GO:0008219 | (BP) cell death | 1434\|6093\|23604\|3717\|5594\|6446\|8837\|10595\|56997\|70\|207\|351\|602\|1613\|2932\|3356\|3778\|5062\|5610\|6478\|7178\|9135\|9231\|10114\|10783\|23770\|28996\|54507\|203068 | CSE1L\|ROCK1\|DAPK2\|JAK2\|MAPK1\|SGK1\|CFLAR\|ERN2\|CABC1\|ACTC1\|AKT1\|APP\|BCL3\|DAPK3\|GSK3B\|HTR2A\|KCNMA1\|PAK2\|EIF2AK2\|SIAH2\|TPT1\|RABEP1\|DLG5\|HIPK3\|NEK6\|FKBP8\|HIPK2\|ADAMTSL4\|TUBB | −2.76 |
| GO:0051640 | (BP) organelle localization | 9276\|22820\|372\|1314\|6811 | COPB2\|COPG\|ARCN1\|COPA\|STX5 | −2.759 |
| GO:0001654 | (BP) eye development | 2703\|658\|5584\|6015\|23770 | GJA8\|BMPR1B\|PRKCI\|RING1\|FKBP8 | −2.759 |
| GO:0005798 | (CC) Golgi-associated vesicle | 9276\|22820\|372\|1314\|57120 | COPB2\|COPG\|ARCN1\|COPA\|GOPC | −2.744 |
| GO:0006818 | (BP) hydrogen transport | 527\|533\|9114\|523\|526\|537 | ATP6V0C\|ATP6V0B\|ATP6V0D1\|ATP6V1A\|ATP6V1B2\|ATP6AP1 | −2.738 |

TABLE 4-continued

Overrepresented functional processes and protein domains of proteins required for influenza virus replication.

| GO | Description | GeneID | Hits | Log10(P) |
|---|---|---|---|---|
| GO:0015672 | (BP) monovalent inorganic cation transport | 527\|533\|3760\|9114\|523\|526\|537\|6328\|6340\|6446\|3356\|3767\|3778\|6334\|56660 | ATP6V0C\|ATP6V0B\|KCNJ3\|ATP6V0D1\|ATP6V1A\|ATP6V1B2\|ATP6AP1\|SCN3A\|SCNN1G\|SGK1\|HTR2A\|KCNJ11\|KCNMA1\|SCN8A\|KCNK12 | −2.728 |
| IPR017442 | (MF) Serine/threonine protein kinase-related | 92\|4296\|5062\|5063 | ACVR2A\|MAP3K11\|PAK2\|PAK3 | −2.636 |
| GO:0030120 | (CC) vesicle coat | 9276\|22820\|372\|1314 | COPB2\|COPG\|ARCN1\|COPA | −2.59 |
| IPR000719 | (MF) Protein kinase, core | 92\|4296\|5062\|5063 | ACVR2A\|MAP3K11\|PAK2\|PAK3 | −2.587 |
| GO:0006915 | (BP) apoptosis | 1434\|6093\|23604\|3717\|5594\|6446\|8837\|10595\|70\|207\|351\|602\|1613\|2932\|3778\|5062\|5610\|6478\|7178\|9135\|9231\|10114\|10783\|23770\|28996\|54507\|203068 | CSE1L\|ROCK1\|DAPK2\|JAK2\|MAPK1\|SGK1\|CFLAR\|ERN2\|ACTC1\|AKT1\|APP\|BCL3\|DAPK3\|GSK3B\|KCNMA1\|PAK2\|EIF2AK2\|SIAH2\|TPT1\|RABEP1\|DLG5\|HIPK3\|NEK6\|FKBP8\|HIPK2\|ADAMTSL4\|TUBB | −2.584 |
| GO:0016023 | (CC) cytoplasmic membrane-bounded vesicle | 9276\|22820\|335\|526\|3674\|9230\|351\|372\|1314\|3320\|7423\|51393\|57085\|57120 | COPB2\|COPG\|APOA1\|ATP6V1B2\|ITGA2B\|RAB11B\|APP\|ARCN1\|COPA\|HSP90AA1\|VEGFB\|TRPV2\|AGTRAP\|GOPC | −2.584 |
| GO:0005654 | (CC) nucleoplasm | 1019\|1845\|5594\|6196\|51422\|207\|1385\|3725\|3837\|4193\|5422\|6015\|6604\|7005\|7341\|9575\|9972\|10036\|10849\|28996\|29882 | CDK4\|DUSP3\|MAPK1\|RPS6KA2\|PRKAG2\|AKT1\|CREB1\|JUN\|KPNB1\|MDM2\|POLA1\|RING1\|SMARCD3\|TEAD3\|SUMO1\|CLOCK\|NUP153\|CHAF1A\|CD3EAP\|HIPK2\|ANAPC2 | −2.569 |
| GO:0005003 | (MF) ephrin receptor activity | 2045\|2050\|2048 | EPHA7\|EPHB4\|EPHB2 | −2.551 |
| CORUM1261 | SRm160/300 complex | 6627\|6625 | SNRPA1\|SNRP70 | −2.551 |
| IPR000793 | (MF) ATPase, F1/V1/A1 complex, alpha/beta subunit, C-terminal | 523\|526 | ATP6V1A\|ATP6V1B2 | −2.551 |
| IPR004100 | (MF) ATPase, F1/V1/A1 complex, alpha/beta subunit, N-terminal | 523\|526 | ATP6V1A\|ATP6V1B2 | −2.551 |
| GO:0031988 | (CC) membrane-bounded vesicle | 9276\|22820\|335\|526\|3674\|9230\|351\|372\|1314\|3320\|7423\|51393\|57085\|57120 | COPB2\|COPG\|APOA1\|ATP6V1B2\|ITGA2B\|RAB11B\|APP\|ARCN1\|COPA\|HSP90AA1\|VEGFB\|TRPV2\|AGTRAP\|GOPC | −2.529 |
| GO:0031410 | (CC) cytoplasmic vesicle | 9276\|22820\|335\|526\|3674\|9230\|351\|372\|1314\|3320\|7423\|51393\|57085\|57120\|57534\|440738 | COPB2\|COPG\|APOA1\|ATP6V1B2\|ITGA2B\|RAB11B\|APP\|ARCN1\|COPA\|HSP90AA1\|VEGFB\|TRPV2\|AGTRAP\|GOPC\|MIB1\|MAP1LC3C | −2.529 |
| GO:0051649 | (BP) establishment of localization in cell | 1434\|9276\|22820\|335\|3717\|10381\|70\|207\|372\|602\|1314\|2932\|3320\|3356\|3837\|5584\|6811\|8021\|8677\|9201\|9972\|23049\|29959\|51172\|55850\|57120\|64601\|203068 | CSE1L\|COPB2\|COPG\|APOA1\|JAK2\|TUBB3\|ACTC1\|AKT1\|ARCN1\|BCL3\|COPA\|GSK3B\|HSP90AA1\|HTR2A\|KPNB1\|PRKCI\|STX5\|NUP214\|STX10\|DCLK1\|NUP153\|SMG1\|NRBP1\|NAGPA\|USE1\|GOPC\|VPS16\|TUBB | −2.525 |
| GO:0012501 | (BP) programmed cell death | 1434\|6093\|23604\|3717\|5594\|6446\|8837\|10595\|70\|207\|351\|602\|1613\|2932\|3778\|5062\|5610\|6478\|7178\|9135\|9231\|10114\|10783\|23770\|28996\|54507\|203068 | CSE1L\|ROCK1\|DAPK2\|JAK2\|MAPK1\|SGK1\|CFLAR\|ERN2\|ACTC1\|AKT1\|APP\|BCL3\|DAPK3\|GSK3B\|KCNMA1\|PAK2\|EIF2AK2\|SIAH2\|TPT1\|RABEP1\|DLG5\|HIPK3\|NEK6\|FKBP8\|HIPK2\|ADAMTSL4\|TUBB | −2.521 |
| GO:0051704 | (BP) multi-organism process | 23352\|527\|29110\|5594\|8837\|10616\|290\|602\|975\|1385\|1394\|3837\|4193\|5062\|5610\|7005\|23770\|28996\|57502 | UBR4\|ATP6V0C\|TBK1\|MAPK1\|CFLAR\|RBCK1\|ANPEP\|BCL3\|CD81\|CREB1\|CRHR1\|KPNB1\|MDM2\|PAK2\|EIF2AK2\|TEAD3\|FKBP8\|HIPK2\|NLGN4X | −2.492 |
| GO:0008283 | (BP) cell proliferation | 1434\|3568\|3581\|1019\|2050\|3717\|8558\|92\|147\|975\|1195\|1717\|2322\|2324\|2342\|2444\|3356\|4193\|4296\|5422\|5610\|6624\|7423\|9180\|9231\|29127 | CSE1L\|IL5RA\|IL9R\|CDK4\|EPHB4\|JAK2\|CDK10\|ACVR2A\|ADRA1B\|CD81\|CLK1\|DHCR7\|FLT3\|FLT4\|FNTB\|FRK\|HTR2A\|MDM2\|MAP3K11\|POLA1\|EIF2AK2\|FSCN1\|VEGFB\|OSMR\|DLG5\|RACGAP1 | −2.465 |
| GO:0033036 | (BP) macromolecule localization | 1434\|9276\|22820\|335\|3717\|9230\|207\|372\|602\|975\|1314\|2932\|3837\|5584\|6811\|7341\|8021\|8570\|8677\| | CSE1L\|COPB2\|COPG\|APOA1\|JAK2\|RAB11B\|AKT1\|ARCN1\|BCL3\|CD81\|COPA\|GSK3B\|KPNB1\|PRKCI\|STX5\| | −2.465 |

TABLE 4-continued

Overrepresented functional processes and protein domains of proteins required for influenza virus replication.

| GO | Description | GeneID | Hits | Log10(P) |
|---|---|---|---|---|
| | | 9135\|9972\|23049\|23534\|51172\|<br>55850\|57120\|64284\|64601 | SUMO1\|NUP214\|KHSRP\|STX10\|RABEP1\|<br>NUP153\|SMG1\|TNPO3\|NAGPA\|USE1\|<br>GOPC\|RAB17\|VPS16 | |
| GO:0030662 | (CC) coated vesicle membrane | 9276\|22820\|372\|1314 | COPB2\|COPG\|ARCN1\|COPA | −2.457 |
| GO:0031982 | (CC) vesicle | 9276\|22820\|335\|526\|3674\|9230\|<br>351\|372\|1314\|3320\|7423\|51393\|<br>57085\|57120\|57534\|440738 | COPB2\|COPG\|APOA1\|ATP6V1B2\|ITGA2B\|<br>RAB11B\|APP\|ARCN1\|COPA\|HSP90AA1\|<br>VEGFB\|TRPV2\|AGTRAP\|GOPC\|MIB1\|<br>MAP1LC3C | −2.453 |
| GO.0006163 | (BP) purine nucleotide metabolic process | 527\|533\|523\|526\|537\|65220 | ATP6V0C\|ATP6V0B\|ATP6V1A\|ATP6V1B2\|<br>ATP6AP1\|NADK | −2.451 |
| GO:0009259 | (BP) ribonucleotide metabolic process | 527\|533\|523\|526\|537\|65220 | ATP6V0C\|ATP6V0B\|ATP6V1A\|ATP6V1B2\|<br>ATP6AP1\|NADK | −2.451 |
| GO:0044433 | (CC) cytoplasmic vesicle part | 9276\|22820\|3674\|351\|372\|1314\|<br>7423\|57085 | COPB2\|COPG\|ITGA2B\|APP\|ARCN1\|<br>COPA\|VEGFB\|AGTRAP | −2.431 |
| GO:0030315 | (CC) T-tubule | 3760\|3767 | KCNJ3\|KCNJ11 | −2.406 |
| GO:0007188 | (BP) G-protein signaling, coupled to cAMP nucleotide second messenger | 147\|1394\|2357\|2869\|4886 | ADRA1B\|CRHR1\|FPR1\|GRK5\|NPY1R | −2.4 |
| GO:0043010 | (BP) camera-type eye development | 2703\|658\|6015\|23770 | GJA8\|BMPR1B\|RING1\|FKBP8 | −2.397 |
| GO:0048185 | (MF) activin binding | 3547\|92 | IGSF1\|ACVR2A | −2.38 |
| IPR003152 | (MF) PIK-related kinase, FATC | 2475\|23049 | FRAP1\|SMG1 | −2.38 |
| IPR003121 | (MF) SWIB/MDM2 | 4193\|6604 | MDM2\|SMARCD3 | −2.38 |
| IPR000158 | (MF) Cell division protein FtsZ, N-terminal | 10381\|203068 | TUBB3\|TUBB | −2.38 |
| GO:0008553 | (MF) hydrogen-exporting ATPase activity, phosphorylative mechanism | 9114\|526 | ATP6V0D1\|ATP6V1B2 | −2.38 |
| IPR015750 | (MF) Serine/threonine kinase Pak-related | 5062\|5063 | PAK2\|PAK3 | −2.38 |
| GO:0009152 | (BP) purine ribonucleotide biosynthetic process | 527\|533\|523\|526\|537 | ATP6V0C\|ATP6V0B\|ATP6V1A\|<br>ATP6V1B2\|ATP6AP1 | −2.33 |
| GO:0005643 | (CC) nuclear pore | 1434\|3837\|7341\|8021\|9972 | CSE1L\|KPNB1\|SUMO1\|NUP214\|NUP153 | −2.271 |
| GO:0051641 | (BP) cellular localization | 1434\|9276\|22820\|335\|3717\|<br>10381\|70\|207\|372\|602\|1314\|2932\|<br>3320\|3356\|3837\|5584\|6811\|8021\|<br>8677\|9201\|9972\|23049\|29959\|51172\|<br>55850\|57120\|64601\|203068 | CSE1L\|COPB2\|COPG\|APOA1\|JAK2\|<br>TUBB3\|ACTC1\|AKT1\|ARCN1\|BCL3\|<br>COPA\|GSK3B\|HSP90AA1\|HTR2A\|<br>KPNB1\|PRKCI\|STX5\|NUP214\|STX10\|<br>DCLK1\|NUP153\|SMG1\|NRBP1\|NAGPA\|<br>USE1\|GOPC\|VPS16\|TUBB | −2.264 |
| GO:0019933 | (BP) cAMP-mediated signaling | 147\|1394\|2357\|2869\|4886 | ADRA1B\|CRHR1\|FPR1\|GRK5\|NPY1R | −2.264 |
| GO:0015078 | (MF) hydrogen ion transmembrane transporter activity | 527\|533\|9114\|523\|526\|537 | ATP6V0C\|ATP6V0B\|ATP6V0D1\|<br>ATP6V1A\|ATP6V1B2\|ATP6AP1 | −2.261 |
| GO:0018210 | (BP) peptidyl-threonine modification | 7786\|10114 | MAP3K12\|HIPK3 | −2.249 |
| GO:0004691 | (MF) cAMP-dependent | 5566\|11214 | PRKACA\|AKAP13 | −2.238 |

TABLE 4-continued

Overrepresented functional processes and protein domains of proteins required for influenza virus replication.

| GO | Description | GeneID | Hits | Log10(P) |
|---|---|---|---|---|
| GO:0006913 | (BP) nucleo-cytoplasmic transport of protein kinase activity | 1434\|3717\|207\|602\|2932\|3837\|8021\|23049 | CSE1L\|JAK2\|AKT1\|BCL3\|GSK3B\|KPNB1\|NUP214\|SMG1 | −2.211 |
| GO:0008104 | (BP) protein localization | 1434\|9276\|22820\|335\|3717\|9230\|207\|372\|602\|975\|1314\|2932\|3837\|5584\|6811\|7341\|8021\|8677\|9135\|9972\|23534\|51172\|55850\|57120\|64284\|64601 | CSE1L\|COPB2\|COPG\|APOA1\|JAK2\|RAB11B\|AKT1\|ARCN1\|BCL3\|CD81\|COPA\|GSK3B\|KPNB1\|PRKCI\|STX5\|SUMO1\|NUP214\|STX10\|RABEP1\|NUP153\|TNPO3\|NAGPA\|USE1\|GOPC\|RAB17\|VPS16 | −2.204 |
| GO:0006164 | (BP) purine nucleotide biosynthetic process | 527\|533\|523\|526\|537 | ATP6V0C\|ATP6V0B\|ATP6V1A\|ATP6V1B2\|ATP6AP1 | −2.2 |
| GO:0000139 | (CC) Golgi membrane | 3265\|6093\|9276\|22820\|372\|1314\|6811\|8677\|9159\|10297\|30815\|57085\|57120 | HRAS\|ROCK1\|COPB2\|COPG\|ARCN1\|COPA\|STX5\|STX10\|PCSK7\|APC2\|ST6GALNAC6\|AGTRAP\|GOPC | −2.191 |
| GO:0007423 | (BP) sensory organ development | 2703\|658\|3778\|5584\|6015\|23770 | GJA8\|BMPR1B\|KCNMA1\|PRKCI\|RING1\|FKBP8 | −2.182 |
| GO:0005977 | (BP) glycogen metabolic process | 51422\|147\|207\|2932 | PRKAG2\|ADRA1B\|AKT1\|GSK3B | −2.175 |
| GO:0051169 | (BP) nuclear transport | 1434\|3717\|207\|602\|2932\|3837\|8021\|23049 | CSE1L\|JAK2\|AKT1\|BCL3\|GSK3B\|KPNB1\|NUP214\|SMG1 | −2.174 |
| GO:0006073 | (BP) glucan metabolic process | 51422\|147\|207\|2932 | PRKAG2\|ADRA1B\|AKT1\|GSK3B | −2.134 |
| IPR003533 | (MF) Doublecortin | 9201\|166614 | DCLK1\|DCLK2 | −2.118 |
| IPR001824 | (MF) Receptor tyrosine kinase, class III, conserved site | 2322\|2324 | FLT3\|FLT4 | −2.118 |
| GO:0043121 | (MF) neurotrophin binding | 4914\|4915 | NTRK1\|NTRK2 | −2.118 |
| IPR016130 | (MF) Protein-tyrosine phosphatase, active site | 1845\|5797\|5798\|114971\|338599 | DUSP3\|PTPRM\|PTPRN\|PTPMT1\|DUPD1 | −2.11 |
| IPR008979 | (MF) Galactose-binding like | 2045\|2050\|2048\|25831 | EPHA7\|EPHB4\|EPHB2\|HECTD1 | −2.11 |
| GO:0045197 | (BP) establishment and/or maintenance of epithelial cell apical/basal polarity | 2011\|5584 | MARK2\|PRKCI | −2.109 |
| GO:0003002 | (BP) regionalization | 92\|658\|4920\|6015\|23770\|57534 | ACVR2A\|BMPR1B\|ROR2\|RING1\|FKBP8\|MIB1 | −2.085 |
| GO:0009260 | (BP) ribonucleotide biosynthetic process | 527\|533\|523\|526\|537 | ATP6V0C\|ATP6V0B\|ATP6V1A\|ATP6V1B2\|ATP6AP1 | −2.08 |
| GO:0046930 | (CC) pore complex | 1434\|3837\|7341\|8021\|9972 | CSE1L\|KPNB1\|SUMO1\|NUP214\|NUP153 | −2.046 |
| GO:0015031 | (BP) protein transport | 1434\|9276\|22820\|335\|3717\|9230\|207\|372\|602\|1314\|2932\|3837\|5584\|6811\|8021\|8677\|9135\|9972\|23534\|51172\|55850\|57120\|64284\|64601 | CSE1L\|COPB2\|COPG\|APOA1\|JAK2\|RAB11B\|AKT1\|ARCN1\|BCL3\|COPA\|GSK3B\|KPNB1\|PRKCI\|STX5\|NUP214\|STX10\|RABEP1\|NUP153\|TNPO3\|NAGPA\|USE1\|GOPC\|RAB17\|VPS16 | −2.039 |
| IPR000387 | (MF) Protein-tyrosine phosphatase | 1845\|5797\|5798\|114971\|338599 | DUSP3\|PTPRM\|PTPRN\|PTPMT1\|DUPD1 | −2.037 |
| GO:0045184 | (BP) establishment of protein localization | 1434\|9276\|22820\|335\|3717\|9230\|207\|372\|602\|1314\|2932\|3837\|5584\|6811\|8021\|8677\|9135\|9972\|23534\|51172\|55850\|57120\|64284\|64601 | CSE1L\|COPB2\|COPG\|APOA1\|JAK2\|RAB11B\|AKT1\|ARCN1\|BCL3\|COPA\|GSK3B\|KPNB1\|PRKCI\|STX5\|NUP214\|STX10\|RABEP1\|NUP153\|TNPO3\|NAGPA\|USE1\|GOPC\|RAB17\|VPS16 | −2.032 |
| GO:0015077 | (MF) monovalent inorganic cation | 527\|533\|9114\|523\|526\|537 | ATP6V0C\|ATP6V0B\|ATP6V0D1\|ATP6V1A\|ATP6V1B2\|ATP6AP1 | −2.032 |

TABLE 4-continued

Overrepresented functional processes and protein domains of proteins required for influenza virus replication.

| GO | Description | GeneID | Hits | Log10(P) |
|---|---|---|---|---|
| | transmembrane transporter activity | | | |
| GO:0005635 | (CC) nuclear envelope | 1434\|1717\|3837\|5422\|7341\|8021\|9972\|10280 | CSE1L\|DHCR7\|KPNB1\|POLA1\|SUMO1\|NUP214\|NUP153\|OPRS1 | −2.026 |
| GO:0004690 | (MF) cyclic nucleotide-dependent protein kinase activity | 5566\|11214 | PRKACA\|AKAP13 | −2.014 |
| GO:0031965 | (CC) nuclear membrane | 1434\|1717\|3837\|7341\|8021\|9972\|10280 | CSE1L\|DHCR7\|KPNB1\|SUMO1\|NUP214\|NUP153\|OPRS1 | −2.008 |

Gene Ontology (GO) (http://www.geneontology.org) (Ashburner et al., 2000) or Interpro (IPR) domain classifications (http://www.ebi.ac.uk/interpro/) (Apweiler et al., 2001) found to be overrepresented within the 295 confirmed host cellular factors required for influenza virus replication are presented. Specifically, GO or IPR accessions (column 1) and descriptions of these categories (column 2), as well as GeneIDs (column 3) and gene names that fall within these classifications are listed (column 4). p values for each category were also calculated (column 5).

TABLE 5

| Functional Category | Gene Names | Cellular function | Replication block |
|---|---|---|---|
| IP3-PKC pathway | ROCK1, CDC42BPA, KSR2, ARAF, PRKCI, CDC42BPB, CIT, AKAP13, RACGAP1, EIF2AK2, CDK4, ACVR2A, MAPK1, PRKCD, MAP2K2, GRK5, ARAF, HIPK1, PAK3, MAP2K3, PTPMT1, LIMK1, PIP5K1C, PAK2, GRK6, SGK1 | Signaling | Entry (MAP2K3) |
| COPI vesicles | ARCN1, COPA, COPB2, COPG, USE1 | early endosome maturation, retrograde golgi to ER transport | Entry (ARCN1) |
| Endosomal uptake, maturation, acidification and fusion | ATP6V1A, ATP6V1B2, ATP6V0B, ATP6V0C, ATP6AP1, ATP6V0D1, ATP6AP2, RABEP1, PIP5K1C, VPS16, TRPV2, MARCH2, EPHB2 | vATPase complex: acidification of intracellular organelles, including endosomes | Entry (ATP6V1A, ATP6V1B2, ATP6V0B, ATP6V0C, ATP6AP1) |
| Actin organization and function | GAK, APC2, CIT, PAK2, CDC42BPB, PAK3, CDC42BPA, SGCA, FSCN1, OXSR1, CD81, FGFR2, FGFR4, ITGA3, AKAP13, ACTC1 FGFR1, LIMK1, ROCK1, PIK3R4 | Actin organization and function | Entry (CD81, FGFR2 FGFR4, ITGA3, AKAR13) |
| PI3K-AKT pathway | AKT1, BCL3, FRAP1, GSK3B, HRAS, HSP90AA1, IKBKE, ITGA3, JAK2, MAP2K2, MAPK1, MDM2, PIK3R4, PIK3R4 | Signaling | Entry (GSK3B) |
| Endosomal recycling pathway | RAB11B, RAB17 | Vesicle trafficking | Entry (RAB11B) |
| MAPK pathway | MAP2K3, DUSP3, MAP3K12, MAPK1/ERK, MAP2K2/MEK, ARAF, CAD, CREB1, EPHB2, FGFR4, HRAS, JUN, NTRK2, PAK2, PRKACA, PRKCD, MAP2K5, MAP4K4, HIPK3, ATP6AP2, STK39, MINK1, PBK, TAOK1, ZNF436, CANT1, KSR2 | Signaling | Entry (MAP2K3, DUSP3) |
| Proteases | CTSW, PCSK7, KLK9, ANPEP, PRSS35 | Post-translational processing | Post-entry (PRSS35) |
| Calcium/Calmodulin Proteins | CAMK2B, PRKACA, DAPK2, ADRA1B, CREB1, PRKAG2, DCLK2, GRK5, GRK6, KCNJ3, PKD1, PRKCD, STX5, CACGN4, AGTRAP | Calcium regulation and signaling | Post-entry (CAMK2B) |
| Nuclear trafficking | CSE1L, KPNB1, NUP214, NUP153, TNPO3 | Nuclear trafficking | Post-entry (KPNB1, CSE1L) |
| Trafficking | STX10, STX5, GOPC, CLL1, NRBP1 | Membrane and Receptor trafficking | ND |
| Sumoylation | SUMO2, SUMO1, SAE1, SUMO4 | Post-translational modification | ND |
| Microtubule organization and function | MID1IP1, TUBB, PRKCI, PLK4, MARK2, DCLK1, NUDCD3, RACGAP1, MAP1 LC3C | cytoskeletal organization | ND |
| Autophagy | PRKAG2, MAP1LC3C, FRAP1, HRAS | Stress response | ND |
| Ubiquitination | MDM2, UBQLN4, HECTD1, CBLL1, DTX2, EPS8L3, FBXO44 | Post-translational modification | ND |

ND = No Data

TABLE 6

Overrepresented functional pathways required for influenza virus replication.

| Ingenuity Canonical Pathways | −Log10(P-value) | Molecules |
|---|---|---|
| Nicotinate and Nicotinamide Metabolism | 1.00E+01 | EIF2AK2, CDK4, ACVR2A, MAPK1, PRKCD, MAP2K2, NADK (includes EG: 65220), GRK5, ARAF, HIPK1, PAK3, MAP2K3, LIMK1, PAK2, GRK6, SGK1 |
| Inositol Phosphate Metabolism | 9.84E+00 | EIF2AK2, CDK4, ACVR2A, MAPK1, PRKCD, MAP2K2, GRK5, ARAF, HIPK1, PAK3, MAP2K3, PTPMT1, LIMK1, PIP5K1C, PAK2, GRK6, SGK1 |
| Molecular Mechanisms of Cancer | 7.40E+00 | PRKACA, GSK3B, CDK4, PRKCD, MAPK1, CAMK2B, BCL3, JAK2, MAP2K2, MDM2, CFLAR, BMPR1B, AKT1, HIPK2, PRKAG2, SYNGAP1, HRAS, JUN, PAK3, MAP2K3, PSENEN, PAK2, PRKCI |
| B Cell Receptor Signaling | 7.37E+00 | GSK3B, MAPK1, CAMK2B, BCL3, FRAP1, MAP2K2, AKT1, IKBKE, HRAS, MAP3K12, NFAT5, JUN, CREB1, MAP3K11, MAP2K3 |
| IL-8 Signaling | 7.33E+00 | IRAK3, ROCK1, PRKCD, MAPK1, FLT4, FRAP1, MAP2K2, AKT1, ARAF, IKBKE, VEGFB (includes EG: 7423), HRAS, MAP4K4, LIMK1, PAK2, PRKCI |
| Ephrin Receptor Signaling | 7.18E+00 | ROCK1, MAPK1, JAK2, MAP2K2, AKT1, ITGA3, VEGFB (includes EG: 7423), HRAS, CREB1, PAK3, EPHB4, EPHB2, EPHA7, MAP4K4, LIMK1, PAK2 |
| GNRH Signaling | 6.90E+00 | PRKACA, MAPK1, PRKCD, CAMK2B, MAP2K2, PRKAG2, HRAS, JUN, PAK3, CREB1, MAP2K3, PAK2, PRKCI |
| Neurotrophin/TRK Signaling | 6.63E+00 | HRAS, JUN, CREB1, MAPK1, MAP2K3, MAP2K2, NTRK2, MAP2K5, NTRK1, AKT1 |
| Insulin Receptor Signaling | 6.42E+00 | PRKACA, GSK3B, MAPK1, JAK2, FRAP1, MAP2K2, AKT1, PRKAG2, HRAS, SCNN1G, PPP1R14D, PRKCI, SGK1 |
| PPAR(E±/RXR(E ± Activation | 6.34E+00 | APOA1, PRKACA, ACVR2A, MAPK1, BCL3, JAK2, HSP90AA1, MAP2K2, IKBKE, PRKAG2, HRAS, JUN, CLOCK, MAP2K3, MAP4K4 |
| LPS-stimulated MAPK Signaling | 6.20E+00 | IKBKE, HRAS, JUN, CREB1, PRKCD, MAPK1, BCL3, MAP2K3, MAP2K2, PRKCI |
| Melatonin Signaling | 6.20E+00 | PRKAG2, ARAF, PRKACA, PRKCD, MAPK1, CAMK2B, MAP2K3, MAP2K2, PRKCI, MAP2K5 |
| PI3K/AKT Signaling | 5.95E+00 | ITGA3, IKBKE, HRAS, GSK3B, MAPK1, BCL3, JAK2, HSP90AA1, FRAP1, MDM2, MAP2K2, AKT1 |
| Prostate Cancer Signaling | 5.72E+00 | HRAS, GSK3B, CREB1, MAPK1, BCL3, HSP90AA1, FRAP1, MDM2, MAP2K2, AKT1 |
| Axonal Guidance Signaling | 5.70E+00 | PRKACA, ROCK1, GSK3B, PRKCD, MAPK1, MAP2K2, AKT1, PRKAG2, ITGA3, VEGFB (includes EG: 7423), HRAS, NFAT5, PAK3, EPHB4, EPHB2, EPHA7, LIMK1, NTRK2, PAK2, PRKCI, NTRK1 |
| Erythropoietin Signaling | 5.56E+00 | HRAS, JUN, PRKCD, MAPK1, BCL3, JAK2, MAP2K2, PRKCI, AKT1 |
| Amyloid Processing | 5.54E+00 | PRKAG2, PRKACA, GSK3B, MAPK1, CAPN6, PSENEN, APP, AKT1 |
| Renin-Angiotensin Signaling | 5.51E+00 | PRKAG2, HRAS, PRKACA, JUN, PRKCD, MAPK1, PAK3, JAK2, MAP2K2, PRKCI, PAK2 |
| IL-17 Signaling | 5.30E+00 | HRAS, IL17RA, GSK3B, JUN, MAPK1, JAK2, MAP2K3, MAP2K2, AKT1 |
| Acute Myeloid Leukemia Signaling | 5.30E+00 | ARAF, HRAS, FLT3, MAPK1, MAP2K3, FRAP1, MAP2K2, MAP2K5, AKT1 |
| IL-6 Signaling | 5.29E+00 | IKBKE, HRAS, IL1F9, JUN, MAPK1, BCL3, JAK2, MAP2K3, MAP2K2, MAP4K4 |
| NF-ŒβB Activation by Viruses | 5.19E+00 | ITGA3, IKBKE, HRAS, EIF2AK2, PRKCD, MAPK1, BCL3, PRKCI, AKT1 |
| Germ Cell-Sertoli Cell Junction Signaling | 5.14E+00 | TUBB, ITGA3, HRAS, ACTC1, TUBB3, MAPK1, PAK3, MAP2K3, MAP2K2, LIMK1, PAK2, AKT1 |
| Integrin Signaling | 5.13E+00 | ACTC1, ROCK1, GSK3B, MAPK1, CAPN6, MAP2K2, TNK2, AKT1, ITGA3, HRAS, PAK3, MAP3K11, PAK2, ITGA2B (includes EG: 3674) |
| Glioma Signaling | 5.08E+00 | HRAS, CDK4, PRKCD, MAPK1, CAMK2B, FRAP1, MDM2, MAP2K2, PRKCI, AKT1 |
| Cholecystokinin/Gastrin-mediated Signaling | 4.96E+00 | HRAS, IL1F9, ROCK1, JUN, PRKCD, MAPK1, MAP2K3, MAP2K2, PRKCI, MAP2K5 |
| ERK/MAPK Signaling | 4.77E+00 | PRKACA, MAPK1, PRKCD, MAP2K2, PRKAG2, ITGA3, ARAF, HIST3H3 (includes EG: 8290), HRAS, PAK3, CREB1, PPP1R14D, PAK2, PRKCI |
| Synaptic Long Term Potentiation | 4.69E+00 | PRKAG2, HRAS, PRKACA, CREB1, PRKCD, MAPK1, CAMK2B, PPP1R14D, MAP2K2, PRKCI |
| CNTF Signaling | 4.64E+00 | HRAS, MAPK1, JAK2, RPS6KA2, FRAP1, MAP2K2, AKT1 |
| 14-3-3-mediated Signaling | 4.62E+00 | TUBB, HRAS, TUBB3, GSK3B, JUN, PRKCD, MAPK1, MAP2K2, PRKCI, AKT1 |
| Neuregulin Signaling | 4.53E+00 | ITGA3, HRAS, PRKCD, MAPK1, HSP90AA1, FRAP1, MAP2K2, PRKCI, AKT1 |
| FLT3 Signaling in Hematopoietic Progenitor Cells | 4.52E+00 | HRAS, CREB1, FLT3, MAPK1, RPS6KA2, FRAP1, MAP2K2, AKT1 |
| Cardiac Hypertrophy Signaling | 4.52E+00 | PRKACA, ROCK1, GSK3B, MAPK1, HAND2, FRAP1, MAP2K2, AKT1, PRKAG2, HRAS, JUN, CREB1, MAP2K3, ADRA1B |
| PPAR Signaling | 4.45E+00 | IKBKE, HRAS, IL1F9, JUN, MAPK1, BCL3, HSP90AA1, MAP2K2, MAP4K4 |
| IL-3 Signaling | 4.43E+00 | HRAS, JUN, PRKCD, MAPK1, JAK2, MAP2K2, PRKCI, AKT1 |
| NF-kB Signaling | 4.35E+00 | IRAK3, HRAS, EIF2AK2, PRKACA, IL1F9, GSK3B, BCL3, TBK1, MAP4K4, AKT1, BMPR1B |
| Thrombopoietin Signaling | 4.30E+00 | HRAS, JUN, PRKCD, MAPK1, JAK2, MAP2K2, PRKCI |
| Acute Phase Response Signaling | 4.28E+00 | IKBKE, HRAS, APOA1, IL1F9, JUN, MAPK1, BCL3, JAK2, MAP2K3, FRAP1, MAP2K2, AKT1 |
| BMP signaling pathway | 4.26E+00 | PRKAG2, HRAS, PRKACA, JUN, CREB1, MAPK1, MAP2K2, BMPR1B |
| NRF2-mediated Oxidative Stress Response | 4.13E+00 | HRAS, ACTC1, GSR, GSK3B, JUN, PRKCD, MAPK1, MAP2K3, MAP2K2, PRKCI, MAP2K5, AKT1 |
| G-Protein Coupled Receptor Signaling | 4.12E+00 | PRKACA, MAPK1, BCL3, CAMK2B, MAP2K2, AKT1, IKBKE, SYNGAP1, PRKAG2, HRAS, CREB1, HTR2A, ADRA1B |
| Aldosterone Signaling in Epithelial Cells | 4.05E+00 | PRKCD, MAPK1, SCNN1G, HSP90AA1, MAP2K2, PIP5K1C, PRKCI, SGK1 |
| IL-15 Production | 4.05E+00 | JAK2, MAP3K11, FRK, TXK, PRKCI |
| FGF Signaling | 4.01E+00 | HRAS, FGFR2, CREB1, MAPK1, MAP2K3, FGFR1, FGFR4, AKT1 |
| Melanoma Signaling | 4.00E+00 | HRAS, CDK4, MAPK1, MDM2, MAP2K2, AKT1 |
| JAK/Stat Signaling | 3.95E+00 | HRAS, MAPK1, SUMO1, JAK2, FRAP1, MAP2K2, AKT1 |

TABLE 6-continued

Overrepresented functional pathways required for influenza virus replication.

| Ingenuity Canonical Pathways | −Log10(P-value) | Molecules |
|---|---|---|
| CD27 Signaling in Lymphocytes | 3.94E+00 | IKBKE, JUN, BCL3, MAP2K3, MAP2K2, MAP2K5 |
| VEGF Signaling | 3.90E+00 | HRAS, VEGFB (includes EG: 7423), ACTC1, ROCK1, MAPK1, FLT4, MAP2K2, AKT1 |
| CD40 Signaling | 3.86E+00 | IKBKE, JUN, MAPK1, BCL3, MAP2K3, MAP2K2, MAP2K5 |
| Hypoxia Signaling in the Cardiovascular System | 3.86E+00 | JUN, CREB1, SUMO1, BCL3, HSP90AA1, MDM2, AKT1 |
| Hepatic Cholestasis | 3.85E+00 | IKBKE, PRKAG2, IRAK3, PRKACA, IL1F9, JUN, PRKCD, BCL3, PRKCI, FGFR4 |
| Apoptosis Signaling | 3.83E+00 | IKBKE, HRAS, ROCK1, MAPK1, BCL3, CAPN6, MAP2K2, MAP4K4 |
| Glucocorticoid Receptor Signaling | 3.82E+00 | PRKACA, MAPK1, BCL3, JAK2, CCL13, HSP90AA1, MAP2K2, AKT1, IKBKE, HRAS, NFAT5, JUN, CREB1, SUMO1 |
| CCR3 Signaling in Eosinophils | 3.77E+00 | HRAS, ROCK1, PRKCD, MAPK1, PAK3, MAP2K2, LIMK1, PRKCI, PAK2 |
| CDK5 Signaling | 3.72E+00 | ITGA3, PRKAG2, HRAS, PRKACA, MAPK1, PPP1R14D, MAP2K2, NTRK2 |
| IGF-1 Signaling | 3.72E+00 | PRKAG2, HRAS, PRKACA, JUN, MAPK1, MAP2K2, PRKCI, AKT1 |
| Corticotropin Releasing Hormone Signaling | 3.71E+00 | PRKAG2, PRKACA, JUN, CREB1, PRKCD, MAPK1, CRHR1, MAP2K2, PRKCI |
| Type II Diabetes Mellitus Signaling | 3.71E+00 | IKBKE, PRKAG2, KCNJ11, PRKCD, MAPK1, BCL3, FRAP1, PRKCI, AKT1 |
| PTEN Signaling | 3.65E+00 | ITGA3, IKBKE, HRAS, GSK3B, MAPK1, MAP2K2, AKT1, BMPR1B |
| Renal Cell Carcinoma Signaling | 3.61E+00 | HRAS, JUN, MAPK1, PAK3, MAP2K2, PAK2, AKT1 |
| 4-1BB Signaling in T Lymphocytes | 3.60E+00 | IKBKE, JUN, MAPK1, BCL3, MAP2K2 |
| Caveolar-mediated Endocytosis | 3.57E+00 | COPG, COPB2, ITGA3, ARCN1, ACTC1, COPA (includes EG: 1314), ITGA2B (includes EG: 3674) |
| Agrin Interactions at Neuromuscular Junction | 3.57E+00 | ITGA3, HRAS, ACTC1, JUN, MAPK1, PAK3, PAK2 |
| Prolactin Signaling | 3.54E+00 | HRAS, JUN, PRKCD, MAPK1, JAK2, MAP2K2, PRKCI |
| Nitric Oxide Signaling in the Cardiovascular System | 3.50E+00 | PRKAG2, VEGFB (includes EG: 7423), PRKACA, PRKCD, FLT4, HSP90AA1, AKT1 |
| Endometrial Cancer Signaling | 3.47E+00 | APC2, HRAS, GSK3B, MAPK1, MAP2K2, AKT1 |
| Chemokine Signaling | 3.46E+00 | HRAS, JUN, MAPK1, CAMK2B, CCL13, MAP2K2, LIMK1 |
| CXCR4 Signaling | 3.44E+00 | HRAS, ROCK1, JUN, PRKCD, MAPK1, PAK3, MAP2K2, PRKCI, PAK2, AKT1 |
| Neuropathic Pain Signaling In Dorsal Horn Neurons | 3.43E+00 | PRKAG2, PRKACA, CREB1, PRKCD, MAPK1, CAMK2B, PRKCI, NTRK2 |
| Oncostatin M Signaling | 3.29E+00 | OSMR, HRAS, MAPK1, JAK2, MAP2K2 |
| Natural Killer Cell Signaling | 3.25E+00 | HRAS, PRKCD, MAPK1, PAK3, MAP2K2, PRKCI, PAK2, AKT1 |
| Thyroid Cancer Signaling | 3.24E+00 | HRAS, MAPK1, MAP2K2, NTRK2, NTRK1 |
| fMLP Signaling in Neutrophils | 3.14E+00 | HRAS, NFAT5, PRKCD, MAPK1, BCL3, FPR1, MAP2K2, PRKCI |
| IL-10 Signaling | 3.13E+00 | IKBKE, IL1F9, JUN, BCL3, MAP2K3, MAP4K4 |
| CREB Signaling in Neurons | 3.09E+00 | PRKAG2, HRAS, PRKACA, CREB1, PRKCD, MAPK1, CAMK2B, MAP2K2, PRKCI, AKT1 |
| Melanocyte Development and Pigmentation Signaling | 3.09E+00 | PRKAG2, HRAS, PRKACA, CREB1, MAPK1, RPS6KA2, MAP2K2 |
| Role of PKR in Interferon Induction and Antiviral Response | 3.08E+00 | IKBKE, EIF2AK2, BCL3, MAP2K3, AKT1 |
| Role of NFAT in Regulation of the Immune Response | 3.07E+00 | IKBKE, HRAS, GSK3B, NFAT5, JUN, MAPK1, BCL3, MAP2K2, CSNK1G2, AKT1 |
| GM-CSF Signaling | 3.06E+00 | HRAS, MAPK1, CAMK2B, JAK2, MAP2K2, AKT1 |
| Angiopoietin Signaling | 3.02E+00 | IKBKE, HRAS, PAK3, BCL3, PAK2, AKT1 |
| p53 Signaling | 3.00E+00 | HIPK2, GSK3B, CABC1, CDK4, JUN, MDM2, AKT1 |
| Actin Cytoskeleton Signaling | 2.98E+00 | ITGA3, APC2, HRAS, ACTC1, ROCK1, MAPK1, PAK3, MAP2K2, LIMK1, PIP5K1C, PAK2 |
| HGF Signaling | 2.97E+00 | HRAS, JUN, PRKCD, MAPK1, MAP2K2, PRKCI, AKT1 |
| α-Adrenergic Signaling | 2.91E+00 | PRKAG2, HRAS, PRKACA, PRKCD, MAPK1, MAP2K2, PRKCI |
| HMGB1 Signaling | 2.88E+00 | HRAS, JUN, MAPK1, MAP2K3, MAP2K2, MAP2K5, AKT1 |
| Dendritic Cell Maturation | 2.87E+00 | IKBKE, COL2A1, FSCN1, IL1F9, CREB1, MAPK1, BCL3, JAK2, AKT1 |
| Sonic Hedgehog Signaling | 2.82E+00 | PRKAG2, PRKACA, GSK3B, DYRK1B |
| HIF1α Signaling | 2.80E+00 | HRAS, VEGFB (includes EG: 7423), JUN, MAPK1, HSP90AA1, MDM2, AKT1 |
| Chronic Myeloid Leukemia Signaling | 2.80E+00 | IKBKE, HRAS, CDK4, MAPK1, MDM2, MAP2K2, AKT1 |
| Toll-like Receptor Signaling | 2.77E+00 | IRAK3, EIF2AK2, JUN, MAP2K3, MAP4K4 |
| PDGF Signaling | 2.75E+00 | HRAS, EIF2AK2, JUN, MAPK1, JAK2, MAP2K2 |
| Fc Epsilon RI Signaling | 2.75E+00 | HRAS, PRKCD, MAPK1, MAP2K3, MAP2K2, PRKCI, AKT1 |
| T Cell Receptor Signaling | 2.70E+00 | IKBKE, HRAS, NFAT5, JUN, MAPK1, TXK, MAP2K2 |
| IL-2 Signaling | 2.58E+00 | HRAS, JUN, MAPK1, MAP2K2, AKT1 |

TABLE 6-continued

Overrepresented functional pathways required for influenza virus replication.

| Ingenuity Canonical Pathways | −Log10(P-value) | Molecules |
|---|---|---|
| Semaphorin Signaling in Neurons | 2.54E+00 | ROCK1, MAPK1, PAK3, LIMK1, PAK2 |
| Regulation of Actin-based Motility by Rho | 2.51E+00 | ACTC1, ROCK1, PAK3, LIMK1, PIP5K1C, PAK2 |
| TGF-β Signaling | 2.49E+00 | HRAS, JUN, ACVR2A, MAPK1, MAP2K2, BMPR1B |
| IL-12 Signaling and Production in Macrophages | 2.48E+00 | IKBKE, JUN, PRKCD, MAPK1, MAP2K2, PRKCI, AKT1 |
| Role of NANOG in Mammalian Embryonic Stem Cell Pluripotency | 2.48E+00 | HRAS, GSK3B, MAPK1, JAK2, MAP2K2, AKT1, BMPR1B |
| Huntington's Disease Signaling | 2.41E+00 | HRAS, JUN, CREB1, PRKCD, CAPN6, FRAP1, PRKCI, NTRK1, SGK1, AKT1 |
| Tight Junction Signaling | 2.38E+00 | PRKAG2, ACTC1, PRKACA, CDK4, JUN, MARK2, PRKCI, AKT1 |
| Death Receptor Signaling | 2.37E+00 | IKBKE, BCL3, TBK1, MAP4K4, CFLAR |
| Human Embryonic Stem Cell Pluripotency | 2.37E+00 | FGFR2, GSK3B, FGFR1, NTRK2, FGFR4, NTRK1, AKT1 |
| Androgen Signaling | 2.35E+00 | PRKAG2, PRKACA, JUN, PRKCD, MAPK1, HSP90AA1, PRKCI |
| Bladder Cancer Signaling | 2.33E+00 | HRAS, VEGFB (includes EG: 7423), CDK4, MAPK1, MDM2, MAP2K2 |
| IL-15 Signaling | 2.31E+00 | HRAS, MAPK1, JAK2, MAP2K2, AKT1 |
| SAPK/JNK Signaling | 2.26E+00 | HRAS, MINK1, MAP3K12, JUN, MAP3K11, MAP4K4 |
| B Cell Activating Factor Signaling | 2.24E+00 | IKBKE, NFAT5, JUN, BCL3 |
| IL-4 Signaling | 2.22E+00 | HRAS, NFAT5, JAK2, FRAP1, AKT1 |
| Thrombin Signaling | 2.21E+00 | HRAS, ROCK1, CREB1, PRKCD, MAPK1, CAMK2B, MAP2K2, PRKCI, AKT1 |
| Non-Small Cell Lung Cancer Signaling | 2.19E+00 | HRAS, CDK4, MAPK1, MAP2K2, AKT1 |
| Growth Hormone Signaling | 2.17E+00 | PRKCD, MAPK1, JAK2, RPS6KA2, PRKCI |
| Relaxin Signaling | 2.13E+00 | PRKAG2, PRKACA, JUN, CREB1, MAPK1, BCL3, AKT1 |

295 host factors required for influenza virus replication were classified using the Ingenuity pathway and GeneGo analysis software (http://www.genego.com; http://www.ingenuity.com). This table lists the overrepresented pathways (column 1), significance (p-value) for each pathway (column 2) and gene names that fall into the respective pathway for Ingenuity (column 3).

| GeneGO Canonical Pathways | pValue |
|---|---|
| Cytoskeleton remodeling_TGF, WNT and cytoskeletal remodeling | 2.50E−08 |
| Immune response_Oncostatin M signaling via MAPK in mouse cells | 6.67E−06 |
| Development_Mu-type opioid receptor signaling via Beta-arrestin | 2.98E−06 |
| Immune response_Oncostatin M signaling via MAPK in human cells | 5.00E−07 |
| Development_Delta-type opioid receptor mediated cardioprotection | 5.00E−07 |
| Development_Beta-adrenergic receptors signaling via beta-arrestin | 1.66E−05 |
| Development_FGFR signaling pathway | 2.74E−05 |
| Development_Regulation of CDK5 in CNS | 4.30E−06 |
| Transcription_CREB pathway | 5.87E−05 |
| Development_Growth hormone signaling via PI3K/AKT and MAPK cascades | 5.87E−05 |
| Development_A2A receptor signaling | 1.36E−05 |
| Development_Flt3 signaling | 7.82E−05 |
| Development_Thrombopoietin-regulated cell processes | 5.38E−05 |
| Signal transduction_PTEN pathway | 4.20E−05 |
| Cytoskeleton remodeling_Cytoskeleton remodeling | 9.74E−05 |
| Cytoskeleton remodeling_Integrin outside-in signaling | 9.98E−05 |
| Development_A2B receptor: action via G-protein alpha s | 5.70E−05 |
| Development_IGF-1 receptor signaling | 2.37E−04 |
| Development_Beta-adrenergic receptors transactivation of EGFR | 5.76E−04 |
| Development_A1 receptor signaling | 6.76E−04 |
| Translation _Regulation activity of EIF2 | 2.92E−04 |
| Development_Neurotrophin family signaling | 7.41E−04 |
| Development_VEGF-family signaling | 2.62E−04 |
| Cell adhesion_Chemokines and adhesion | 9.78E−04 |
| Neurophysiological process_NMDA-dependent postsynaptic long-term potentiation in CA1 hippocampal neurons | 6.30E−04 |
| Development_GDNF family signaling | 2.67E−04 |
| Development_Leptin signaling via PI3K-dependent pathway | 4.26E−04 |
| Regulation of lipid metabolism_Insulin signaling: generic cascades | 4.26E−04 |
| Development_EDG1 signaling via beta-arrestin | 1.60E−03 |
| Signal transduction_Erk Interactions: Inhibition of Erk | 3.90E−03 |
| Apoptosis and survival_Role of CDK5 in neuronal death and survival | 3.90E−03 |
| Development_CNTF receptor signaling | 3.90E−03 |
| Mucin expression in CF via TLRs, EGFR signaling pathways | 4.71E−03 |
| Translation _Regulation activity of EIF4F | 9.07E−03 |
| G-protein signaling_G-Protein alpha-s signaling cascades | 9.61E−03 |

-continued

| GeneGO Canonical Pathways | pValue |
|---|---|
| Cytoskeleton remodeling_CDC42 in cellular processes | 5.20E-04 |
| G-protein signaling_G-Protein alpha-12 signaling pathway | 3.10E-03 |
| Immune response_Fc epsilon R1 pathway | 4.44E-03 |
| Development_Delta- and kappa-type opioid receptors signaling via beta-arrestin | 5.88E-03 |
| G-protein signaling_Ras family GTPases in kinase cascades (scheme) | 2.28E-03 |
| Development_GDNF signaling | 2.28E-03 |
| Immune response_CCR5 signaling in macrophages and T lymphocytes | 4.81E-03 |
| Development_Prolactin receptor signaling | 4.81E-03 |
| Translation_Non-genomic (rapid) action of Androgen Receptor | 6.67E-03 |
| Apoptosis and survival_Apoptotic Activin A signaling | 9.83E-03 |
| Development_Angiotensin signaling via beta-Arrestin | 9.83E-03 |
| Apoptosis and survival_BAD phosphorylation | 2.40E-03 |
| Cell cycle_Regulation of G1/S transition (part 2) | 8.69E-03 |
| Development_EDG5 and EDG3 in cell proliferation and differentiation | 8.69E-03 |
| Translation_Insulin regulation of translation | 8.82E-03 |
| Neurophysiological process_HTR1A receptor signaling in neuronal cells | 8.82E-03 |
| Development_Membrane-bound ESR1: interaction with growth factors signaling | 8.82E-03 |
| Immune response_HTR2A-induced activation of cPLA2 | 6.00E-03 |
| Development_VEGF signaling and activation | 6.00E-03 |
| Development_EGFR signaling pathway | 9.93E-03 |
| Immune response_IL-4 signaling pathway | 4.00E-03 |
| Development_Ligand-independent activation of ESR1 and ESR2 | 4.00E-03 |
| Immune response_IL-15 signaling | 6.41E-03 |
| Development EPO-induced MAPK pathway | 2.89E-03 |
| Development_VEGF signaling via VEGFR2 - generic cascades | 2.89E-03 |
| Development_Activation of ERK by Alpha-1 adrenergic receptors | 2.89E-03 |
| Development_Endothelin-1/EDNRA transactivation of EGFR | 2.73E-03 |
| Immune response_IL-6 signaling pathway | 4.57E-03 |
| Development_PIP3 signaling in cardiac myocytes | 3.61E-03 |
| Developmeht_Beta-adrenergic receptors regulation of ERK | 3.61E-03 |
| Development_HGF signaling pathway | 3.61E-03 |
| Immune response_IL-4 - antiapoptotic action | 2.00E-04 |
| Cell adhesion_Integrin-mediated cell adhesion and migration | 5.60E-03 |
| Immune response_IL-3 activation and signaling pathway | 1.79E-02 |
| Immune response_ETV3 affect on CSF1-promoted macrophage differentiation | 1.79E-02 |
| Development_A3 receptor signaling | 1.88E-02 |
| DNA damage_Role of SUMO in p53 regulation | 2.65E-02 |
| Apoptosis and survival_HTR1A signaling | 3.32E-02 |
| Development_EDNRB signaling | 3.32E-02 |
| G-protein signaling_G-Protein beta/gamma signaling cascades | 3.80E-02 |
| G-protein signaling_Proinsulin C-peptide signaling | 6.62E-02 |
| Development_Endothelin-1/EDNRA signaling | 8.50E-02 |
| Oxidative stress_Role of ASK1 under oxidative stress | 8.59E-02 |
| Mucin expression in CF via IL-6, IL-17 signaling pathways | 8.59E-02 |
| Translation_Translation regulation by Alpha-1 adrenergic receptors | 5.50E-03 |
| Development_FGF-family signaling | 1.41E-02 |
| Regulation of lipid metabolism_Insulin regulation of glycogen metabolism | 2.76E-02 |
| Immune response_IL-9 signaling pathway | 4.54E-02 |
| Transcription_Role of AP-1 in regulation of cellular metabolism | 1.85E-02 |
| Signal transduction_cAMP signaling | 1.85E-02 |
| Immune response _Human NKG2D signaling | 1.85E-02 |
| Transcription_Receptor-mediated HIF regulation | 6.07E-02 |
| Cytoskeleton remodeling_Regulation of actin cytoskeleton by Rho GTPases | 3.70E-02 |
| Development_Alpha-2 adrenergic receptor activation of ERK | 4.05E-02 |
| Transport_Macropinocytosis regulation by growth factors | 8.06E-02 |
| Immune response _Murine NKG2D signaling | 1.29E-02 |
| Development_Dopamine D2 receptor transactivation of EGFR | 1.79E-02 |
| Development_ACM2 and ACM4 activation of ERK | 7.30E-02 |
| Signal transduction_AKT signaling | 7.30E-02 |
| Development_Angiotensin signaling via PYK2 | 7.30E-02 |
| Signal transduction_JNK pathway | 7.30E-02 |
| Transcriplion_Androgen Receptor nuclear signaling | 9.00E-03 |

TABLE 7

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| geneID | Symbol | Description | SEQ ID NO. | Target Sequence |
|---|---|---|---|---|
| 290 | ANPEP | alanyl (membrane) aminopeptidase | 124 | CACCACCTTGGACCAAAGTAA |
| 290 | ANPEP | alanyl (membrane) aminopeptidase | 125 | CCGAAATGCCACACTGGTCAA |
| 361 | AQP4 | aquaporin 4 | 131 | GACCAAUCUGGAGAGGUAU |
| 361 | AQP4 | aquaporin 4 | 130 | CAGCCTGGGATCCACCATCAA |
| 372 | ARCN1 | archain 1 | 2 | AAGGCTGAGATGCGTCGTAAA |
| 372 | ARCN1 | archain 1 | 1 | CCCACTTGTGTCAATATTAAA |
| 523 | ATP6V1A | ATPase, H+ transporting, lysosomal 70 kDa, V1 subunit A | 4 | ATGGAGGTTGATGGTAAGGTA |
| 523 | ATP6V1A | ATPase, H+ transporting, lysosomal 70 kDa, V1 subunit A | 3 | GAGCTTGAATTTGAAGGTGTA |
| 526 | ATP6V1B2 | ATPase, H+ transporting, lysosomal 56/58 kDa, V1 subunit B2 | 5 | ACCATGTTACCCTGTAATTAA |
| 526 | ATP6V1B2 | ATPase, H+ transporting, lysosomal 56/58 kDa, V1 subunit B2 | 6 | CACGGTTAATGAAGTCTGCTA |
| 526 | ATP6V1B2 | ATPase, H+ transporting lysosomal 56/58 kDa, V1 subunit B2 | 585 | CAGGCTGGTTTGGTAAAGAAA |
| 527 | ATP6V0C | ATPase, H+ transporting, lysosomal 16 kDa, V0 subunit c | 7 | CAGCCACAGAATATTATGTAA |
| 527 | ATP6V0C | ATPase, H+ transporting, lysosomal 16 kDa, V0 subunit c | 8 | TCCCAGCTATCTATAACCTTA |
| 533 | ATP6V0B | ATPase, H+ transporting, lysosomal 21 kDa, V0 subunit b | 9 | CATGGCAATTGTCATTAGCAA |
| 533 | ATP6V0B | ATPase, H+ transporting, lysosomal 21 kDa, V0 subunit b | 10 | TCCTAGTGTTTGTGAAATAAA |
| 537 | ATP6AP1 | ATPase, H+ transporting, lysosomal accessory protein 1 | 11 | CACAGTGACATTCAAGTTCAT |
| 537 | ATP6AP1 | ATPase, H+ transporting, lysosomal accessory protein 1 | 12 | TAGCAAATGCTCCCTCCTTAA |
| 537 | ATP6AP1 | ATPase, H+ transporting, lysosomal accessory protein 1 | 134 | CAGGGAAGTCCTCACAGGCAA |
| 816 | CAMK2B | calcium/calmodulin-dependent protein kinase II beta | 14 | CAGGATCTCTGACATCCTGAA |
| 816 | CAMK2B | calcium/calmodulin-dependent protein kinase II beta | 13 | CACGACCATCCTGAACCCACA |
| 816 | CAMK2B | calcium/calmodulin-dependent protein kinase II beta | 586 | CCCGGAAGCAGGAGATCATTA |
| 975 | CD81 | CD81 molecule | 67 | CACCTTCTATGTAGGCATCTA |
| 975 | CD81 | CD81 molecule | 68 | AAGGAACATCAGGCATGCTAA |
| 1314 | COPA | coatomer protein complex, subunit alpha | 151 | CTGGATTTCAACAGCTCCAAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h postinfection. Controls were set to the value of 1. An average value of column 10 and 11 is shown in column 12. A call for a confirmed gene (average value <0.65) is indicated in column 13.

| | | | | |
|---|---|---|---|---|
| 1314 | COPA | coatomer protein complex, subunit alpha | 152 | CTGGCGCATGAATGAATCAAA |
| 1394 | CRHR1 | corticotropin releasing hormone receptor 1 | 155 | CAGGTTGGTGACAGCCGCCTA |
| 1394 | CRHR1 | corticotropin releasing hormone receptor 1 | 156 | CCGCTACAATACCACAAACAA |
| 1434 | CSE1L | CSE1 chromosome segregation 1-like (yeast) | 16 | CTGACGGTATCAAATATATTA |
| 1434 | CSE1L | CSE1 chromosome segregation 1-like (yeast) | 17 | CAAATGAACTTGTAAACCTAA |
| 1434 | CSE1L | CSE1 chromosome segregation 1-like (yeast) | 15 | CAGGATAATGTTATCAAAGTA |
| 1434 | CSE1L | CSE1 chromosome segregation 1-like (yeast) | 587 | CACGGTTTGGATAATCTTAAA |
| 1521 | CTSW | cathepsin W | 65 | UACCUGUGGCAUCACCAAG |
| 1521 | CTSW | cathepsin W | 66 | CGCGTTCATAACTGTCCTCAA |
| 1521 | CTSW | cathepsin W | 588 | CACCGTGACCATCAACATGAA |
| 1832 | DSP | desmoplakin | 170 | CCGACATGAATCAGTAAGTAA |
| 1832 | DSP | desmoplakin | 169 | CAGAAGAATGACTATGACCAA |
| 1845 | DUSP3 | dual specificity phosphatase 3 | 77 | CCCGCGGATCTACGTGGGCAA |
| 1845 | DUSP3 | dual spedficity phosphatase 3 | 78 | CCGTATTTACTTAACAAGATT |
| 2022 | ENG | endoglin | 173 | AAGGGAGAACTTGAAACAGAT |
| 2022 | ENG | endoglin | 174 | CAGCAATGAGGCGGTGGTCAA |
| 2022 | ENG | endoglin | 589 | ACCAATAAATCAGACCATGAA |
| 2045 | EPHA7 | EPH receptor A7 | 590 | CCCAATGGAGTCATCACAGAA |
| 2045 | EPHA7 | EPH receptor A7 | 176 | CAGGCTGCGAAGGAAGTACTA |
| 2048 | EPHB2 | EPH receptor B2 | 177 | /5Phos/rGrGrCrUrArCrGrGrAr CrCrArArGrUrUrUrArUrCrCrGr GCG |
| 2048 | EPHB2 | EPH receptor B2 | 64 | GGAGACCUUCAACCUCUAU |
| 2050 | EPHB4 | EPH receptor B4 | 178 | CACGAGCTCCCTGGGAGGAAA |
| 2050 | EPHB4 | EPH receptor B4 | 179 | CTGGCGGGACACCAGAAGAAA |
| 2162 | F13A1 | coagulation factor XIII, A1 polypeptide | 18 | CAAGGAGAGATGGGACACTAA |
| 2162 | F13A1 | coagulation factor XIII, A1 polypeptide | 19 | GCUGGAGCUAUGGUCAGUU |
| 2263 | FGFR2 | fibroblast growth factor receptor 2 | 69 | CCCATCTGACAAGGGAAATTA |
| 2263 | FGFR2 | fibroblast growth factor receptor 2 | 70 | CGGAGGAGCGTTGCCATTCAA |
| 2264 | FGFR4 | fibroblast growth factor receptor 4 | 21 | CAGGAGGTTCTGGGCCTCTGA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 2264 | FGFR4 | fibroblast growth factor receptor 4 | 20 | CCGCCTGACCTTCGGACCCTA |
| 2357 | FPR1 | formyl peptide receptor 1 | 22 | GUGACACAGCUACCAAUUC |
| 2357 | FPR1 | formyl peptide receptor 1 | 23 | AACCAGTGACACAGCTACCAA /5Phos/rGrGrCrArArCrArArGrCr |
| 2475 | FRAP1 | FK506 binding protein 12-rapamycin associated protein 1 | 194 | GrArUrCrCrCrGrArArCrGrArGGA |
| 2475 | FRAP1 | FK506 binding protein 12-rapamycin associated protein 1 | 195 | GAGGCAUCUCGUUUGUACU |
| 2475 | FRAP1 | FK506 binding protein 12-rapamycin associated protein 1 | 591 | CAGGCCTATGGTCGAGATTTA |
| 2475 | FRAP1 | FK506 binding protein 12-rapamycin associated protein 1 | 592 | ACTCGCTGATCCAAATGACAA |
| 2539 | G6PD | glucose-6-phosphate dehydrogenase | 197 | ATCGGGTGACCTGGCCAAGAA |
| 2539 | G6PD | glucose-6-phosphate dehydrogenase | 593 | CTGCGTTATCCTCACCTTCAA |
| 2550 | GABBR1 | gamma-aminobutyric acid (GABA) B receptor, 1 | 42 | CACCCTCTCCTTGTCACAGAA |
| 2550 | GABBR1 | gamma-aminobutyric acid (GABA) B receptor, 1 | 43 | CTCCATTGCATTCATGTACTA |
| 2580 | GAK | cyclin G associated kinase | 198 | AAGGCCUAACUAUGCCUCGAA |
| 2580 | GAK | cyclin G associated kinase | 199 | AGGGUGACCUGGACAUAUC |
| 2932 | GSK3B | glycogen synthase kinase 3 beta | 73 | CACTCAAGAACTGTCAAGTAA |
| 2932 | GSK3B | glycogen synthase kinase 3 beta | 74 | TCAGTTGGTAGAAATAATCAA |
| 3320 | HSP90AA1 | heat shock protein 90 kDa alpha (cytosolic), class A member 1 | 212 | CAGAATGAAGGAGAACCAGAA |
| 3320 | HSP90AA1 | heat shock protein 90 kDa alpha (cytosolic), class A member 1 | 213 | CTGCTTAAAGTTGTAACAAAT |
| 3675 | ITGA3 | integrin, alpha 3 (antigen CD49C, alpha 3 subunit of VLA-3 receptor) | 81 | CCCUCUCAACCUCACUCUU |
| 3675 | ITGA3 | integrin, alpha 3 (antigen CD49C, alpha 3 subunit of VLA-3 receptor) | 82 | CTGGATTGACTTTGCTGTCAA |
| 3675 | ITGA3 | integrin, alpha 3 (antigen CD49C, alpha 3 subunit of VLA-3 receptor) | 594 | CCTCTCAACCTCACTCTTT |
| 3675 | ITGA3 | integrin, alpha 3 (antigen CD49C, alpha 3 subunit of VLA-3 receptor) | 595 | CACCATCAACATGGAGAACAA |
| 3717 | JAK2 | Janus kinase 2 (a protein tyrosine kinase) | 45 | ATGATTGGCAATGACAAACAA |
| 3717 | JAK2 | Janus kinase 2 (a protein tyrosine kinase) | 44 | AGCCATCATACGAGATCTTAA |
| 3837 | KPNB1 | karyopherin (importin) beta 1 | 25 | CAAGAACTCTTTGACATCTAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 3837 | KPNB1 | karyopherin (importin) beta 1 | 24 | TCGGTTATATTTGCCAAGATA |
|---|---|---|---|---|
| 4193 | MDM2 | Mdm2, transformed 3T3 cell double minute 2, p53 binding protein (mouse) | 238 | CAGGCAAATGTGCAATACCAA |
| 4193 | MDM2 | Mdm2, transformed 3T3 cell double minute 2, p53 binding protein (mouse) | 239 | CCGGATCTTGATGCTGGTGTA |
| 4296 | MAP3K11 | mitogen-activated protein kinase kinase kinase 11 | 62 | CACATGGTACCTGGATTCAGA |
| 4296 | MAP3K11 | mitogen-activated protein kinase kinase kinase 11 | 63 | CCGGCCTTGACCGGAGGAGAA |
| 4923 | NTSR1 | neurotensin receptor 1 (high affinity) | 250 | CTGGCTTAAGAAGGTCGCCTA |
| 4923 | NTSR1 | neurotensin receptor 1 (high affinity) | 251 | AAGGGCCTCTAACAAGGAGAA |
| 5063 | PAK3 | p21 protein (Cdc42/Rac)-activated kinase 3 | 254 | CAAGAAGGAATTAATTATTAA |
| 5063 | PAK3 | p21 protein (Cdc42/Rac)-activated kinase 3 | 255 | CAGCAACCCAAGAAGGAAU |
| 5566 | PRKACA | protein kinase, cAMP-dependent, catalytic, alpha | 267 | CAGAAGGTGGTGAAACTGAAA |
| 5566 | PRKACA | protein kinase, cAMP-dependent, catalytic, alpha | 266 | ACAGAAGGTGGTGAAACTGAA |
| 5584 | PRKCI | protein kinaseC, iota | 271 | GGAGAUACAACCAGCACUU |
| 5584 | PRKCI | protein kinase C, iota | 270 | ACGCCGCTGGAGAAAGCTTTA |
| 5606 | MAP2K3 | mitogen-activated protein kinase kinase 3 | 26 | CTGGATGCCATCCAAGTTGTA |
| 5606 | MAP2K3 | mitogen-activated protein kinase kinase 3 | 27 | ACGGATATCCTGCATGTCCAA |
| 5606 | MAP2K3 | mitogen-activated protein kinase kinase 3 | 276 | CCGGGCCACCGTGAACTCACA |
| 5757 | PTMA | prothymosin, alpha | 283 | TTGTCCAACAATAAACAGGAA |
| 5757 | PTMA | prothymosin, alpha | 284 | TTGGTTTGTATGAGATGGTTA |
| 5961 | PRPH2 | retinal degeneration, slow | 75 | CACGGATTTAGTCCCACCCTA |
| 5961 | PRPH2 | retinal degeneration, slow | 76 | GAGGAGCGATGTGATGAATAA |
| 5961 | PRPH2 | retinal degeneration, slow | 596 | CAAGAACGGCATGAAGTACTA |
| 6204 | RPS10 | ribosomal protein S10 | 47 | TTGAATAAACTTACAGCCAAA |
| 6204 | RPS10 | ribosomal protein S10 | 46 | AACCGGATTGCCATTTATGAA |
| 6204 | RPS10 | ribosomal protein S10 | 47 | TTGAATAAACTTACAGCCAAA |
| 6204 | RPS10 | ribosomal protein S10 | 597 | GACATTTCTACTGGTACCTTA |
| 6224 | RPS20 | ribosomal protein S20 | 689 | TTCGCTCTCGCCGAGGAACAA |
| 6224 | RPS20 | ribosomal protein S20 | 688 | CCCTAACAAGCCGCAACGTAA |
| 6224 | RPS20 | ribosomal protein S20 | 598 | CGCGGTCGTAAGGGCTGAGGA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h postinfection. Controls were set to the value of 1. An average value of column 10 and 11 is shown in column 12. A call for a confirmed gene (average value <0.65) is indicated in column 13.

| | | | | |
|---|---|---|---|---|
| 6357 | CCL13 | chemokine (C-C motif) ligand 13 | 696 | CCGGAAAGCTCACACCCTGAA |
| 6357 | CCL13 | chemokine (C-C motif) ligand 13 | 697 | ACTCTTAACCTTCAACATGAA |
| 6357 | CCL13 | chemokine (C-C motif) ligand 13 | 599 | AGGCAAAGAAACATTGTGAAA |
| 6357 | CCL13 | chemokine (C-C motif) ligand 13 | 600 | TGGGTCCAGAATTATATGAAA |
| 6446 | SGK1 | serum/glucocorticoid regulated kinase | 701 | TACAGGCTTATTTGTAATGTA |
| 6446 | SGK1 | serum/glucocorticoid regulated kinase | 601 | AGGCAGAAGAAGUGUUCUA |
| 6613 | SUMO2 | SMT3 suppressor of mif two 3 homolog 2 (S. cerevisiae) | 90 | AAGTAGGGATAAATTACTCTA |
| 6613 | SUMO2 | SMT3 suppressor of mif two 3 homolog 2 (S. cerevisiae) | 89 | CTGTCTTTAAGTAGGGATAAA |
| 6627 | SNRPA1 | small nuclear ribonucleoprotein polypeptide A' | 602 | CAGCATTGTTGAAATGCTTAA |
| 6627 | SNRPA1 | small nuclear ribonucleoprotein polypeptide A' | 603 | TCCACTCACTATGCTACCAAA |
| 6627 | SNRPA1 | small nuclear ribonudeoprotein polypeptide A' | 603 | TCCACTCACTATGCTACCAAA |
| 7786 | MAP3K12 | mitogen-activated protein kinase kinase kinase 12 | 60 | CAGGGAGCACTATGAAAGGAA |
| 7786 | MAP3K12 | mitogen-activated protein kinase kinase kinase 12 | 61 | CCACGAAAUCGCCCAUCAU |
| 8021 | NUP214 | nucleoporin 214 kDa | 28 | CCCGGAGATGATCCCAACAAA |
| 8021 | NUP214 | nucleoporin 214 kDa | 29 | CACCATAGAATCTCACACCAA |
| 8677 | STX10 | syntaxin 10 | 30 | CAGAGAGATACTCGCAGGCAA |
| 8677 | STX10 | syntaxin 10 | 31 | CAGCAGCTGATCATGGATGAA |
| 9114 | ATP6V0D1 | ATPase, H+ transporting, lysosomal 38 kDa, V0 subunit d1 | 313 | CACTTTCATGTTCCTCCCTAA |
| 9114 | ATP6V0D1 | ATPase, H+ transporting, lysosomal 38 kDa, V0 subunit d1 | 314 | CCGCGCCTTCATCATCACCAT |
| 9114 | ATP6V0D1 | ATPase, H+ transporting, lysosomal 38 kDa, V0 subunit d1 | 604 | AAGGCTCTCAATTGCACTCTT |
| 9114 | ATP6V0D1 | ATPase, H+ transporting, lysosomal 38 kDa, V0 subunit d1 | 605 | CAACTACATCCCTATCTTCTA |
| 9135 | RABEP1 | rabaptin, RAB GTPase binding effector protein 1 | 316 | CAGGATAAAGCCGAACTGGTA |
| 9135 | RABEP1 | rabaptin, RAB GTPase binding effector protein 1 | 315 | CTGGAAGACTTCATAAAGCAA |
| 9180 | OSMR | oncostatin M receptor | 321 | TAGCATAGATTGTCAAATGTA |
| 9180 | OSMR | oncostatin M receptor | 322 | TAGCTCTAATCTAATATATAA |
| 9230 | RAB11B | RAB11B, member RAS oncogene family | 49 | CACGGACGGACAGAAGCCCAA |
| 9230 | RAB11B | RAB11B, member RAS oncogene family | 48 | CCGCATCACCTCCGCGTACTA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 9230 RAB11B | RAB11B, member RAS oncogene family | 325 | CGAGTTCAACCTGGAGAGCAA |
| 9231 DLG5 | discs, large homolog 5 (Drosophila) | 326 | ACGGAACTTGATACAGCACAA |
| 9231 DLG5 | discs, large homolog 5 (Drosophila) | 327 | TTCGAGTAACTTGCAGTTCAA |
| 9256 BZRAP1 | benzodiazapine receptor (peripheral) associated protein 1 | 328 | CCGCCGTCTGGTGGTCCTCAA |
| 9256 BZRAP1 | benzodiazapine receptor (peripheral) associated protein 1 | 329 | CACAGTGAGTATGTAACTTGA |
| 9276 COPB2 | coatomer protein complex, subunit beta 2 (beta prime) | 330 | ACGATTCTTCAGAGTATGCAA |
| 9276 COPB2 | coatomer protein complex, subunit beta 2 (beta prime) | 331 | CAGGTTTCAAGGGTAGTGAAA |
| 9276 COPB2 | coatomer protein complex, subunit beta 2 (beta prime) | 681 | CAGTACGTATTTGGCATTCAA |
| 9276 COPB2 | coatomer protein complex, subunitA beta 2 (beta prime) | 606 | CCCAGTCAGGTTTCAAGGGTA |
| 9972 NUP153 | nucleoporin 153 kDa | 349 | ATGGAACGCGTTGAAATTGTA |
| 9972 NUP153 | nucleoporin 153 kDa | 348 | CACCATTATGTGCGCTGATAA |
| 10055 SAE1 | SUMO1 activating enzyme subunit 1 | 353 | CTGGAGCAGTGAGAAAGCAAA |
| 10055 SAE1 | SUMO1 activating enzyme subunit 1 | 352 | TCCGACTACTTTCTCCTTCAA |
| 10181 RBM5 | RNA binding motif protein 5 | 363 | AGGCAGCGCAUAUGGUUUG |
| 10181 RBM5 | RNA binding motif protein 5 | 362 | CGCGTCTTTAGCTGTCAATAA |
| 10291 SF3A1 | splicing factor 3a, subunit 1, 120 kDa | 32 | CAGGATAAGACGGAATGGAAA |
| 10291 SF3A1 | splicing factor 3a, subunit 1, 120 kDa | 33 | CGCAAGGATTATGATCCCAAA |
| 10381 TUBB3 | tubulin, beta 3 | 682 | GCGGATCAGCGTCTACTACAA |
| 10381 TUBB3 | tubulin, beta 3 | 371 | CACGGTGGTGGAGCCCTACAA |
| 10381 TUBB3 | tubulin, beta 3 | 370 | TTGCTGTCAGATACCCTTAAA |
| 10783 NEK6 | NIMA (never in mitosis gene a)-related kinase 6 | 71 | CTGGCGGACTTCCAGATCGAA |
| 10783 NEK6 | NIMA (never in mitosis gene a)-related kinase 6 | 72 | ACCACGGAAGTCGAGAATTAA |
| 11214 AKAP13 | A kinase (PRKA) anchor protein 13 | 51 | CAGGATTACACTGAAAGTAAT |
| 11214 AKAP13 | A kinase (PRKA) anchor protein 13 | 50 | CCGCCTGTTTGGGTTAACAAA |
| 22820 COPG | coatomer protein complex, subunit gamma | 34 | CCGAGCCACCTTCTACCTAAA |
| 22820 COPG | coatomer protein complex, subunit gamma | 35 | AGGCCCGTGTATTTAATGAAA |
| 22820 COPG | coatomer protein complex, subunit gamma | 608 | CAGGAAAGGGACATTGTAAAT |
| 23604 DAPK2 | death-associated protein kinase 2 | 609 | CTGGTTAAAGAGACCCGGAAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 23604 DAPK2 | death-associated protein kinase 2 | | 610 | UCACCUACAUCCUCUUAAG |
| 23604 DAPK2 | death-associated protein kinase 2 | | 401 | /5Phos/rUrCrCrCrGrCrCrGrArU rUrGrUrArUrGrUrArUrUrCrCrArGrG UC |
| 23604 DAPK2 | death-associated protein kinase 2 | | 402 | CGGAATTTGTTGCTCCAGAAA |
| 29127 RACGAP1 | Rac GTPase activating protein 1 | | 420 | CTGGTAGATAGAAGAGCTAAA |
| 29127 RACGAP1 | Rac GTPase activating protein 1 | | | |
| 29127 RACGAP1 | Rac GTPase activating protein 1 | | 419 | CACCACAGACACCAGATATTA |
| 29882 ANAPC2 | anaphase promoting complex subunit 2 | | 422 | GAGAGTCTATATGCAGAGTAA |
| 29882 ANAPC2 | anaphase promoting complex subunit 2 | | 421 | AAGGTTCTTCTACCGCATCTA |
| 29959 NRBP1 | nuclear receptor binding protein 1 | | 423 | GAGGGAGUUCAUUCAAAAG |
| 29959 NRBP1 | nuclear receptor binding protein 1 | | 424 | AGGCGAGAAGAGGTGAATCAA |
| 51393 TRPV2 | transient receptor potential cation channel, subfamily V, member 2 | | 37 | CCAGTGAATTCTGGTGGCAAA |
| 51393 TRPV2 | transient receptor potential cation channel, subfamily V, member 2 | | 36 | CAGAGGATCTTTCCAACCACA |
| 54866 PPP1R14D | protein phosphatase 1, regulatory (inhibitor) subunit 14D | | 39 | CAGGAGCTCTTCCAGGATCAA |
| 54866 PPP1R14D | protein phosphatase 1, regulatory (inhibitor) subunit 14D | | 38 | GAGCCTGAGATTGACCTGGAA |
| 57579 FAM135A | family with sequence similarity 135, member A | | 53 | CAGCAATTACATTAAATTCAA |
| 57579 FAM135A | family with sequence similarity 135, member A | | 52 | CACGAAGAACTAAGAATATTA |
| 79574 EPS8L3 | EPS8-like 3 | | 54 | CCGGAAGGAGTACTCCCAGAA |
| 79574 EPS8L3 | EPS8-like 3 | | 55 | AGCCATTTACTTGCACCGGAA |
| 80231 CXorf21 | chromosome X open reading frame 21 | | 503 | AAGGTTGTGGAGTTATATAAA |
| 80231 CXorf21 | chromosome X open reading frame 21 | | 611 | CTGGAAGTCATGTGTGAATCA |
| 93953 ACRC | acidic repeat containing | | 57 | CCCGATGACAATAGTGATGAT |
| 93953 ACRC | acidic repeat containing | | 56 | TAGGTACTGTTAAGTAAGTAA |
| 93953 ACRC | acidic repeat containing | | 56 | TAGGTACTGTTAAGTAAGTAA |
| 93953 ACRC | acidic repeat containing | | 612 | TCCGGAGTGTTGTCATGTGAA |
| 113878 DTX2 | deltex homolog 2 (*Drosophila*) | | 84 | CAAGACAGAGATGGACCGCAA |
| 113878 DTX2 | deltex homolog 2 (*Drosophila*) | | 83 | GCUUCAUCGAGCAGCAGUU |
| 113878 DTX2 | deltex homolog 2 (*Drosophila*) | | 613 | GGGAAAGAUGGAGGUAUUA |
| 113878 DTX2 | deltex homolog 2 (*Drosophila*) | | 614 | CGGGACCATCCTCATAGTTTA |
| 113878 DTX2 | deltex homolog 2 (*Drosophila*) | | 615 | ATGCTCTATAGCCAAAGCCAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 122525 | C14orf28 | chromosome 14 open reading frame 28 | 534 | AACAAAGAGGAACATCATTAT |
| 122525 | C14orf28 | chromosome 14 open reading frame 28 | 535 | AAGTCCATAAAGCTTCATTAA |
| 167681 | PRSS35 | protease, serine, 35 | 40 | CCGTAGTGAGATCACTTCATA |
| 167681 | PRSS35 | protease, serine, 35 | 545 | GGAGAAAGAGACAGGUGUA |
| 167681 | PRSS35 | protease, serine, 35 | 41 | TACGGCTAACAGAGACCTGAA |
| 203068 | TUBB | tubulin, beta | 86 | TGGGTAGAAGTCACTATATAA |
| 203068 | TUBB | tubulin, beta | 85 | GGUCCUUUUGGCCAGAUCU |
| 254065 | BRWD3 | bromodomain and WD repeat domain containing 3 | 80 | AAGACAGTCTTTAAAGTGTAA |
| 254065 | BRWD3 | bromodomain and WD repeat domain containing 3 | 79 | CACAGTTATTACTGCAGTGAA |
| 387082 | SUMO4 | SMT3 suppressor of mif two 3 homolog 4 (S. cerevisiae) | 88 | TACTGCATTCTCAATTAGAAA |
| 387082 | SUMO4 | SMT3 suppressor of mif two 3 homolog 4 (S. cerevisiae) | 87 | TTGATGTGTTTCAACAGCCTA |
| 387082 | SUMO4 | SMT3 suppressor of mif two 3 homolog 4 (S. cerevisiae) | 564 | TCCGATTTGGTGGGCAACCAA |
| 387911 | RP11-45820.2 | collagen triple helix repeat-containing | 59 | AAAGGAGATCGAGGAGAGAAA |
| 387911 | RP11-45820.2 | collagen triple helix repeat-containing | 58 | CAGCATTGTCCTGCAGCTGAA |
| 643641 | ZNF862 | KIAA0543, KIAA0543 protein | 578 | AAGGTTATACAGGACCATTCA |
| 643641 | ZNF862 | KIAA0543, KIAA0543 protein | 577 | CCCGATCTTCCTTCCACCTAA |
| 5610 | EIF2AK2 | eukaryotic translation initiation factor 2-alpha kinase 2 | 616 | CTCCACATGATAGGAGGTTTA |
| 5610 | EIF2AK2 | eukaryotic translation initiation factor 2-alpha kinase 2 | 617 | CGGAAAGACTTACGTTATTAA |
| 6093 | ROCK1 | "Rho-associated, coiled-coil containing protein kinase 1" | 618 | CAAGCTCGAATTACATCTTTA |
| 6093 | ROCK1 | "Rho-associated, coiled-coil containing protein kinase 1" | 295 | /5Phos/rGrGrUrUrArGrArArCrArArGrArGrGrUrArArArUrGrAr AGG |
| 6093 | ROCK1 | "Rho-associated, coiled-coil containing protein kinase 1" | 619 | AACGGTTAGAACAAGAGGTAA |
| 58526 | MID1IP1 | MID1 interacting protein 1 (gastrulation specific G12 homolog (zebrafish)) | 489 | CTCGCTCTTTAACGCCATGAA |
| 58526 | MID1IP1 | MID1 interacting protein 1 (gastrulation specific G12 homolog (zebrafish)) | 488 | CAGCCACTACGTGCTTCTCAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 157 | ADRBK2 | adrenergic, beta, receptor kinase 2 | 120 | CAAGTGTATGGGATTAACTAA |
|---|---|---|---|---|
| 157 | ADRBK2 | adrenergic, beta, receptor kinase 2 | 121 | GGAGACUGUCCUUUCAUUG |
| 207 | AKT1 | v-akt murine thymoma viral oncogene homolog 1 | 123 | UCACACCACCUGACCAAGA |
| 207 | AKT1 | v-akt murine thymoma viral oncogene homolog 1 | 122 | /5Phos/rCrGrUrGrArCrCrArUrGrArArCrGrArGrUrUrUrGrArGrUAC |
| 351 | APP | amyloid beta (A4) precursor protein (peptidase nexin-II, Alzheimer disease) | 128 | CCAGGAGAGGAUGGAUGUU |
| 351 | APP | amyloid beta (A4) precursor protein (peptidase nexin-II, Alzheimer disease) | 129 | CTGGTCTTCAATTACCAAGAA |
| 369 | ARAF | v-raf murine sarcoma 3611 viral oncogene homolog | 133 | CGGUGAAGAUCGGUGACUU |
| 369 | ARAF | v-raf murine sarcoma 3611 viral oncogene homolog | 132 | CCACAGUGUCCAGGAUUUG |
| 602 | BCL3 | B-cell CLL/lymphoma 3 | 135 | CGUGAACGCGCAAAUGUAC |
| 602 | BCL3 | B-cell CLL/lymphoma 3 | 136 | UGGCUCCUCCCAAUUUCUU |
| 827 | CAPN6 | calpain 6 | 42 | AAGGGTGGTCCAACTGCCAAA |
| 827 | CAPN6 | calpain 6 | 620 | CAAGGTCATTATGTCACTGCA |
| 827 | CAPN6 | calpain 6 | 141 | GGACCACUGACAUUCCUAU |
| 1195 | CLK1 | CDC-like kinase 1 | 146 | CACGATAGTAAGGAGCATTTA |
| 1195 | CLK1 | CDC-like kinase 1 | 145 | /5Phos/rArGrUrArCrUrUrCrArCrArUrCrGrUrCrGrUrUrCrArCATG |
| 1263 | PLK3 | polo-like kinase 3 (*Drosophila*) | 147 | /5Phos/rGrCrGrGrArUrGrUrArUrGrUrCrArCrUrGrGrGrCrUGG |
| 1263 | PLK3 | polo-like kinase 3 (*Drosophila*) | 148 | CTGCATCAAGCAGGTTCACTA |
| 1511 | CTSG | cathepsin G | 159 | CACAGTGTTGCCAGAGCCTTA |
| 1511 | CTSG | cathepsin G | 621 | CAGCCTTTCAGGAAAGATGCA |
| 1511 | CTSG | cathepsin G | 160 | UCCGCCACCCUCAAUAUAA |
| 1613 | DAPK3 | death-associated protein kinase 3 | 161 | CCGGCAGAAGGGCACGGGCAA |
| 1613 | DAPK3 | death-associated protein kinase 3 | 162 | CACCAACATCTCAGCCGTGAA |
| 1717 | DHCR7 | 7-dehydrocholesterol reductase | 164 | CGGGAAGTGGTTTGACTTCAA |
| 1717 | DHCR7 | 7-dehydrocholesterol reductase | 163 | CUGCAAAUUCACAGGCAAU |
| 1787 | TRDMT1 | tRNA aspartic acid methyltransferase 1 | 168 | CACATTCGGTTGAGCAACATT |
| 1787 | TRDMT1 | tRNA aspartic acid methyltransferase 1 | 167 | GGACGAAUAGCUUCUUACA |
| 2011 | MARK2 | MAP/microtubule affinity-regulating kinase 2 | 172 | /5Phos/rCrCrGrCrUrUrCrArCrGrUrGrArGrUrArUrGrArArGrACC |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 2011 | MARK2 | MAP/microtubule affinity-regulating kinase 2 | 171 | /5Phos/rUrCrCrGrCrUrUrCrArCrGrUrGrGrArGrUrArUrGrArArGAC |
| 2322 | FLT3 | frns-related tyrosine kinase 3 | 183 | TACGTTGATTTCAGAGAATAT |
| 2322 | FLT3 | frns-related tyrosine kinase 3 | 182 | CAGGTTTAAAGCCTACCCACA |
| 2342 | FNTB | farnesyltransferase, CAAX box, beta | 189 | GGUGAUCCAGGCCACUACA |
| 2342 | FNTB | farnesyltransferase, CAAX box, beta | 188 | CACGTCCATAGAACAGGCAAA |
| 2346 | FOLH1 | folate hydrolase (prostate-specific membrane antigen) 1 | 190 | AAGCATAATATGAAAGCATTT |
| 2346 | FOLH1 | folate hydrolase (prostate-specific membrane antigen) 1 | 191 | CACCAGGUUACCCAGCAAA |
| 2444 | FRK | fyn-related kinase | 193 | CTGGGAGTACCTAGAACCCTA |
| 2444 | FRK | fyn-related kinase | 192 | GGUCCCAGCUCCAUUUGAU |
| 2703 | GJA8 | gap junction protein, alpha 8, 50 kDa | 622 | CTCTGTGTCCCTATTCCTCAA |
| 2703 | GJA8 | gap junction protein, alpha 8, 50 kDa | 200 | CAGCGGCAGCAAAGGCACTAA |
| 2703 | GJA8 | gap junction protein, alpha 8, 50 kDa | 201 | UCAUCUUCAAGACCCUCUU |
| 2869 | GRK5 | G protein-coupled receptor kinase 5 | 202 | CCGAAGGACCATAGACAGAGA |
| 2869 | GRK5 | G protein-coupled receptor kinase 5 | 203 | GCGGCAGCAUCAGAACAAU |
| 2870 | GRK6 | G protein-coupled receptor kinase 6 | 204 | CCGGAGGTGGTGAAGAATGAA |
| 2870 | GRK6 | G protein-coupled receptor kinase 6 | 205 | GGGUCCCUGCAAAGACCUU |
| 2936 | GSR | glutathione reductase | 209 | ACCGAUGACAAGGGUCAUA |
| 2936 | GSR | glutathione reductase | 208 | CGGAAGAUGAAGCCAUUCA |
| 3265 | HRAS | v-Ha-ras Harvey rat sarcoma viral oncogene homolog | 623 | ACGGGUGAAGGACUCGGAU |
| 3265 | HRAS | v-Ha-ras Harvey rat sarcoma viral oncogene homolog | 624 | AGGAGCGATGACGGAATATAA |
| 3265 | HRAS | v-Ha-ras Harvey rat sarcoma viral oncogene homolog | 211 | CCTGTGTGTGTTTGCCATCAA |
| 3265 | HRAS | v-Ha-ras Harvey rat sarcoma viral oncogene homolog | 210 | CAGACTGTCTTGAACATCCCA |
| 3547 | IGSF1 | immunoglobulin superfamily, member 1 | 625 | AAGCAAGTTCCTGCTGCTGAA |
| 3547 | IGSF1 | immunoglobulin superfamily, member 1 | 217 | TCGATAGTGATGGACCCTCAA |
| 3547 | IGSF1 | immunoglobulin superfamily, member 1 | 216 | ATCGATAGTGATGGACCCTCA |
| 3547 | IGSF1 | immunoglobulin superfamily, member 1 | 627 | CTGGAGGAGCTCACTGGAGAA |
| 3568 | IL5RA | interleukin 5 receptor, alpha | 628 | CCACUAACUAUGAGAAAGC |
| 3568 | IL5RA | interleukin 5 receptor, alpha | 629 | CACCATTAAAGTTACTGGTTT |
| 3568 | IL5RA | interleukin 5 receptor, alpha | 218 | GCUGGGCUUCUGCUGAACU |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 3568 | IL5RA | interleukin 5 receptor, alpha | 219 | CACCAGTCTTGTATCTCTTAA |
|---|---|---|---|---|
| 3581 | IL9R | interleukin 9 receptor | 220 | CAGCTATGAGCTGGCCTTCAA |
| 3581 | IL9R | interleukin 9 receptor | 221 | GGGUGAAGAGAAUCUUCUA |
| 3581 | IL9R | interleukin 9 receptor | 630 | CAGUGUACACAAUGGGAAC |
| 3581 | IL9R | interleukin 9 receptor | 631 | CAGAGATAGTTGGGTGACAAA |
| 3674 | ITGA2B | integrin, alpha 2b (platelet glyco-protein IIb of IIb/IIIa complex, antigen CD41) | 223 | UGGCAGCCAGUUUGGAUUU |
| 3674 | ITGA2B | integrin, alpha 2b (platelet glyco-protein IIb of IIb/IIIa complex, antigen CD41) | 222 | CAGCCAGAATCCAAACAGCAA |
| 3674 | ITGA2B | integrin, alpha 2b (platelet glyco-protein IIb of IIb/IIIa complex, antigen CD41) | 632 | CCCAAACTTTACAAACCTTCA |
| 3725 | JUN | jun oncogene | 226 | CGCGCGCGAGTCGACAAGTAA |
| 3725 | JUN | jun oncogene | 227 | TTCGTTAACATTGACCAAGAA |
| 3760 | KCNJ3 | potassium inwardly-rectifying channel, subfamily J, member 3 | 633 | CTGTGTGAAGTTACACAATTA |
| 3760 | KCNJ3 | potassium inwardly-rectifying channel, subfamily J, member 3 | 634 | GGGAACCUUCCAGCCAAAU |
| 3760 | KCNJ3 | potassium inwardly-rectifying channel, subfamily J, member 3 | 229 | ATGGACTAGATGATATTACTA |
| 3760 | KCNJ3 | potassium inwardly-rectifying channel, subfamily J, member 3 | 228 | ACCAGCCATAACTAACAGCAA |
| 3767 | KCNJ11 | potassium inwardly-rectifying channel, subfamily J, member 11 | 231 | CAGCGCTTTGTGCCCATTGTA |
| 3767 | KCNJ11 | potassium inwardly-rectifying channel, subfamily J, member 11 | 230 | GUUCAGCAUCUCUCCAGAU |
| 3778 | KCNMA1 | potassium large conductance calcium-activated channel, subfamily M, alpha member 1 | 232 | UGGGAGACGCUUCAUAACU |
| 3778 | KCNMA1 | potassium large conductance calcium-activated channel, subfamily M, alpha member 1 | 233 | ACCGAGAGAGCCGTATATTAA |
| 3984 | LIMK1 | LIM domain kinase 1 | 234 | /5Phos/rArGrCrUrCrCrGrG rCrUrUrArUrArCrUrCrCrArG CG |
| 3984 | LIMK1 | LIM domain kinase 1 | 235 | AUCACCAAGGGACUGGUUA |
| 4809 | NHP2L1 | NHP2 non-histone chromosome protein 2-like 1 (*S. cerevisiae*) | 241 | CTGAGGTTGTGTATCATATTA |
| 4809 | NHP2L1 | NHP2 non-histone chromosome protein 2-like 1 (*S. cerevisiae*) | 240 | CAGCTACTCTCTATTGTTATA |
| 4886 | NPY1R | neuropeptide Y receptor Y1 | 242 | GACUUGCUUGUUGCCAUCA |
| 4886 | NPY1R | neuropeptide Y receptor Y1 | 242 | GACUUGCUUGUUGCCAUCA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 4886 | NPY1R | neuropeptide Y receptor Y1 | 243 | CAAGATATATATACGCCTAAA |
| 4920 | ROR2 | receptor tyrosine kinase-like orphan receptor 2 | 248 | UUGCCUGUGCACGCUUCAU |
| 4920 | ROR2 | receptor tyrosine kinase-like orphan receptor 2 | 249 | CCGGTTTGGGAAAGTCTACAA |
| 5096 | PCCB | propionyl Coenzyme A carboxylase, beta polypeptide | 635 | CATGCAAATATTCCATTGTAA |
| 5096 | PCCB | propionyl Coenzyme A carboxylase, beta polypeptide | 256 | CAGGCCACCTCTGTTAACGAA |
| 5096 | PCCB | propionyl Coenzyme A carboxylase, beta polypeptide | 257 | CTCAGGATGCTTGGATATTAA |
| 5165 | PDK3 | pyruvate dehydrogenase kinase, isozyme 3 | 258 | CAGGUCUUGGAUAACUUUC |
| 5165 | PDK3 | pyruvate dehydrogenase kinase, isozyme 3 | 259 | CTCGTTACTTTGGGTAAAGAA |
| 5253 | PHF2 | PHD finger protein 2 | 260 | CTGGATTTGTTTCTCAGGCAA |
| 5253 | PHF2 | PHD finger protein 2 | 261 | TCGCCTCTAGCTGGAAACAAA |
| 5310 | PKD1 | polycystic kidney disease 1 (autosomal dominant) | 263 | CCCGTCCATTGTGGGTAGCAA |
| 5310 | PKD1 | polycystic kidney disease 1 (autosomal dominant) | 262 | GACGUGUGGAUCGGCUUCU |
| 5605 | MAP2K2 | mitogen-activated protein kinase kinase 2 | 275 | GUGGAUUUUGCCGGCUGGU |
| 5605 | MAP2K2 | mitogen-activated protein kinase kinase 2 | 274 | CCGGCCTGCCATGGCCATCTT |
| 5607 | MAP2K5 | mitogen-activated protein kinase kinase 5 | 277 | AAGACGTATGTTGGAACAAAT |
| 5607 | MAP2K5 | mitogen-activated protein kinase kinase 5 | 278 | CAAGACGTATGTTGGAACAAA |
| 5797 | PTPRM | EMPTY | 286 | CUCGUUGCCACAGUUAUAA |
| 5797 | PTPRM | EMPTY | 285 | CCAGUUCACCACCAAAAUA |
| 5798 | PTPRN | protein tyrosine phosphatase, receptor type, N | 288 | CTGGTGAAGTCTGAACTGGAA |
| 5798 | PTPRN | protein tyrosine phosphatase, receptor type, N | 287 | CAGGTCTGGCTTGGCACCCAA |
| 5805 | PTS | 6-pyruvoyltetrahydropterin synthase | 290 | TAGGTGAATCTTAAAGAAATA |
| 5805 | PTS | 6-pyruvoyltetrahydropterin synthase | 289 | TTCGAGTAGGTGAATCTTAAA |
| 6015 | RING1 | ring finger protein 1 | 292 | GCUGGUGAAUGAGAAAUUC |
| 6015 | RING1 | ring finger protein 1 | 293 | CCGAAAGAAGCTGGTGTCCAA |
| 6196 | RPS6KA2 | ribosomal protein S6 kinase, 90 kDa, polypeptide 2 | 686 | CTGGAACACGCTGTACCGGAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 6196 | RPS6KA2 | ribosomal protein S6 kinase, 90 kDa, polypeptide 2 | 636 | CCGGAGGTCCTGAAGCGTCAA |
| 6196 | RPS6KA2 | ribosomal protein S6 kinase, 90 kDa, polypeptide 2 | 687 | CAGCAAGAUCUGCACAAAG |
| 6328 | SCN3A | sodium channel, voltage-gated, type III, alpha subunit | 690 | CAGCGTAATTTCAGATGTTAT |
| 6328 | SCN3A | sodium channel, voltage-gated, type III, alpha subunit | 691 | CTCCCATAATAAATTATATAA |
| 6328 | SCN3A | sodium channel, voltage-gated, type III, alpha subunit | 637 | AAAGCTGATAGTCTATGTCAA |
| 6442 | SGCA | sarcoglycan, alpha (50 kDa dystrophin-associated glycoprotein) | 698 | UGUGACCCUGGUGGAUAAG |
| 6442 | SGCA | sarcoglycan, alpha (50 kDa dystrophin-associated glycoprotein) | 699 | UUGAGGUCACAGCCUACAA |
| 6604 | SMARCD3 | SWI/SNF related, matrix associated, actin dependent regulator of chromatin, subfamily d, member 3 | 705 | CTCAAGGTGATGACAGATGTA |
| 6604 | SMARCD3 | SWI/SNF related, matrix associated, actin dependent regulator of chromatin, subfamily d, member 3 | 704 | GTGGCAGTATGTGAAGACCAA |
| 6624 | FSCN1 | fascin homolog 1, actin-bundling protein (*Strongylocentrotus purpuratus*) | 706 | CTGAGCCTTATTTCTCTGGAA |
| 6624 | FSCN1 | fascin homolog 1, actin-bundling protein (*Strongylocentrotus purpuratus*) | 707 | AACTGGAAATAGCGAAATAAA |
| 6625 | SNRP70 | small nuclear ribonucleoprotein 70 kDa (U1) | 709 | CCGGAGAGAGTTTGAGGTGTA |
| 6625 | SNRNP70 | small nuclear ribonucleoprotein 70 kDa (U1) | 708 | AAGATTGAGCGGCGACAGCAA |
| 6792 | CDKL5 | cyclin-dependent kinase-like 5 | 712 | AAGATAGACGCTTCATGTTAA |
| 6792 | CDKL5 | cyclin-dependent kinase-like 5 | 713 | AAGGCAATAATGCTAATTACA |
| 7005 | TEAD3 | TEA domain family member 3 | 716 | TAGCACCTCATTAGCCCACAA |
| 7005 | TEAD3 | TEA domain family member 3 | 717 | TGGGTATTTATGAGTTTCATA |
| 7294 | TXK | TXK tyrosine kinase | 720 | TAGGTGAATGGCGGTCACATA |
| 7294 | TXK | TXK tyrosine kinase | 721 | CCCGGTGACATTCTATTTCCA |
| 7423 | VEGFB | vascular endothelial growth factor B | 298 | AAGACCCAAACCTCTGCATAA |
| 7423 | VEGFB | vascular endothelial growth factor B | 299 | CAGTGTGAATGCAGACCTAAA |
| 8290 | HIST3H3 | histone cluster 3, H3 | | |
| 8290 | HIST3H3 | histone cluster 3, H3 | 300 | TGAGAGGTTGCGCAACGTTCA |
| 8290 | HIST3H3 | histone cluster 3, H3 | 638 | GCGCAAGTCAACGGGTGGCAA |
| 8438 | RAD54L | RAD54-like (*S. cerevisiae*) | 302 | CCCAGACUUUGGAUCUCUU |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 8438 | RAD54L | RAD54-like (*S. cerevisiae*) | 301 | CGCGCGCTTTGGGAACAGGAA |
|---|---|---|---|---|
| 8476 | CDC42BPA | CDC42 binding protein kinase alpha (DMPK-like) | 303 | TCGGAAAGATATACCCTGTAT |
| 8476 | CDC42BPA | CDC42 binding protein kinase alpha (DMPK-like) | 304 | CAGATAATAGTCGGAAACAAA |
| 8476 | CDC42BPA | CDC42 binding protein kinase alpha (DMPK-like) | 639 | UUCAGUGGCUCAGUCAGUA |
| 8476 | CDC42BPA | CDC42 binding protein kinase alpha (DMPK-like) | 640 | CAGACTTTCCGTAGCAGCTTA |
| 8558 | CDK10 | cyclin-dependent kinase 10 | 305 | TCCGAACATCGTGGAGCTGAA |
| 8558 | CDK10 | cyclin-dependent kinase 10 | 641 | UCUGCACAGGAACUUCAUU |
| 8558 | CDK10 | cyclic-dependent kinase 10 | 306 | CCGGAAGCAGCCCTACAACAA |
| 8831 | SYNGAP1 | synaptic Ras GTPase activating protein 1 homolog (rat) | 309 | CAGAGCAGTGGTACCCTGTAA |
| 8831 | SYNGAP1 | synaptic Ras GTPase activating protein 1 homolog (rat) | 310 | CCCGGCTGATGCAAAGCTTTA |
| 8837 | CFLAR | CASP8 and FADD-like apoptosis regulator | 311 | UGGGAGAUUCAUGCCCUUA |
| 8837 | CFLAR | CASP8 and FADD-like apoptosis regulator | 642 | CACCGACGAGTCTCAACTAAA |
| 8837 | CFLAR | CASP8 and FADD-like apoptosis regulator | 312 | UCCCAGAUUCUUGGCCAAU |
| 9159 | PCSK7 | proprotein convertase subtilisin/kexin type 7 | 320 | TAGCTATGACCTCAACTCTAA |
| 9159 | PCSK7 | proprotein convertase subtilisin/kexin type 7 | 319 | UGUGGCUUCCAAUCAAGUU |
| 9509 | ADAMTS2 | ADAM metallopeptidase with thrombospondin type 1 motif, 2 | 336 | CCGCCGGAGGCTGGACCACAA |
| 9509 | ADAMTS2 | ADAM metallopeptidase with thrombospondin type 1 motif, 2 | 337 | GACAGGCAAGTTCATCTTAAA |
| 9575 | CLOCK | clock homolog (mouse) | 338 | ATCCAGCAACTTGCACCTATA |
| 9575 | CLOCK | clock homolog (mouse) | 339 | AAGGAGCCATCTACCTATGAA |
| 9625 | AATK | apoptosis-associated tyrosine kinase | 342 | TCCGCTGAGATCAGAAGGCAA |
| 9625 | AATK | apoptosis-associated tyrosine kinase | 343 | CCGGTTCCGCTGAGATCAGAA |
| 9641 | IKBKE | "inhibitor of kappa light polypeptide gene enhancer in B-cells, kinase epsilon" | 345 | /5Phos/rGrGrCrCrArGrGrCr UrUrGrGrCrUrArCrArArCrGrAr GGG |
| 9641 | IKBKE | "inhibitor of kappa light polypeptide gene enhancer in B-cells, kinase epsilon" | 643 | CAAGCUGGAUAAGGUGAAU |
| 9641 | IKBKE | "inhibitor of kappa light polypeptide gene enhancer in B-cells, kinase epsilon" | 344 | /5Phos/rUrGrGrUrCrUrGrArCr UrGrArGrCrCrUrArArArGrUrUr GUG |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 9943 | OXSR1 | oxidative-stress responsive 1 | 346 | TAGGGACTAACTATAGCACAA |
| 9943 | OXSR1 | oxidative-stress responsive 1 | 347 | CTGGAGTAGGGACTAACTATA |
| 10105 | PPIF | peptidylprolyl isomerase F (cyclophilin F) | 354 | CCGCGTGGTGCTGGAGCTGAA |
| 10105 | PPIF | peptidylprolyl isomerase F (cyclophilin F) | 355 | ATGGATTTGTGTTCACCTTAA |
| 10114 | HIPK3 | homeodomain interacting protein kinase 3 | 357 | /5Phos/rUrGrCrArGrArUrGr UrCrGrArUrGrArArUrUrGrUrCr CUG |
| 10114 | HIPK3 | homeodomain interacting protein kinase 3 | 356 | CAGCCTTACAGGGTTAAAGTA |
| 10155 | TRIM28 | tripartite motif-containing 28 | 358 | /5Phos/rUrGrGrUrGrArArCrGr UrArCrUrGrUrCrUrArUrUrGrCr AAC |
| 10155 | TRIM28 | tripartite motif-containing 28 | 358 | /5Phos/rUrGrGrUrGrArArCrGr UrArCrUrGrUrCrUrArUrUrGrCr AAC |
| 10155 | TRIM28 | tripartite motif-containing 28 | 359 | CTGGCCCTATTCTGTCACGAA |
| 10159 | ATP6AP2 | ATPase, H+ transporting, lysosomal accessory protein 2 | 360 | AAGGACTATCCTTGAGGCAAA |
| 10159 | ATP6AP2 | ATPase, H+ transporting, lysosomal accessory protein 2 | 644 | AAGAGTGTATATGGTAGGGAA |
| 10159 | ATP6AP2 | ATPase, H+ transporting, lysosomal accessory protein 2 | 361 | CAAGTGCTACATGATATTTCA |
| 10159 | ATP6AP2 | ATPase, H+ transporting, lysosomal accessory protein 2 | 645 | ATGGGCTAATATGGATACTAA |
| 10188 | TNK2 | tyrosine kinase, non-receptor, 2 | 364 | ACGCAAGTCGTGGATGAGTAA |
| 10188 | TNK2 | tyrosine kinase, non-receptor, 2 | 365 | CAGGATCTTGTGCCTGGAAAT |
| 10297 | APC2 | adenomatosis polyposis coli 2 | 369 | CCGCGGTCTCTGGACAATCAA |
| 10297 | APC2 | adenomatosis polyposis coli 2 | 368 | GCAGCACAAGACGCAGAGA |
| 10595 | ERN2 | endoplasmic reticulum to nucleus signaling 2 | 646 | AAGGATGAAACTGGCTTCTAT |
| 10595 | ERN2 | endoplasmic reticulum to nucleus signaling 2 | 373 | CAGCCACTCGACGACCCTGAA |
| 10595 | ERN2 | endoplasmic reticulum to nucleus signaling 2 | 372 | CAGGGATTAATGAAACTGCCA |
| 10733 | PLK4 | polo-like kinase 4 (*Drosophila*) | 377 | UGCCACAUGAAAAGCACUA |
| 10733 | PLK4 | polo-like kinase 4 (*Drosophila*) | 647 | GGAGUAUGCAUCUCAAGAA |
| 10849 | CD3EAP | CD3e molecule, epsilon associated protein | 380 | CAAGGGCAAATTGGCAGGCAA |
| 10849 | CD3EAP | CD3e molecule, epsilon associated protein | 381 | CAGATTAACACTGAGCCTCTA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| 11113 | CIT | "citron (rho-interacting, serine/threonine kinase 21)" | 383 | GCAGAAGCUGAUGCUAAAC |
| 11113 | CIT | "citron (rho-interacting, serine/threonine kinase 21)" | 382 | /5Phos/rGrGrCrGrCrCrArArCrGrArCrGrArGrArUrUrGrUrArCrAGG |
| 23049 | SMG1 | PI-3-kinase-related kinase SMG-1 | 386 | ATCGATGTTGCCAGACTACTA |
| 23049 | SMG1 | PI-3-kinase-related kinase SMG-1 | 607 | /5Phos/rUrGrGrUrCrUrUrGrArArCrArArUrCrCrArUrUrGrGrCrAUG |
| 23216 | TBC1D1 | TBC1(tre-2/USP6, BUB2, cdc16) domain family, member 1 | 388 | CAGUCAUGACCCAAGUUAC |
| 23216 | TBC1D1 | TBC1 (tre-2/USP6, BUB2, cdc16) domain family, member 1 | 387 | AGCCGAUGAUCAAACAAAA |
| 23352 | UBR4 | ubiquitin protein ligase E3 component n-recognin 4 | 389 | CTGCGTGAAGGTGAAAGTCAA |
| 23352 | UBR4 | ubiquitin protein ligase E3 component n-recognin 4 | 648 | CACTAATGTGTTGGAAATCAA |
| 23352 | UBR4 | ubiquitin protein ligase E3 component n-recognin 4 | 649 | CCGCAGACUUUGUUAAGAU |
| 23352 | UBR4 | ubiquitin protein ligase E3 component n-recognin 4 | 390 | CAGCAGGGIATGCCCTTAAA |
| 23352 | UBR4 | ubiquitin protein ligase E3 component n-recognin 4 | 650 | CAGGCTGAGGATTCAGATGAA |
| 23387 | KIAA0999 | KIAA0999 protein | 651 | CCUGUUGCCUAUGCAAAAC |
| 23387 | SIK3 | KIAA0999 protein | 394 | CTCCTAGTCTTTCATCCTGAA |
| 23387 | SIK3 | KIAA0999 protein | 393 | CAGGCAGGCGTGTAACAAGAA |
| 23387 | KIAA0999 | KIAA0999 protein | 652 | GUCCCUCCACUUGACCAAU |
| 23396 | PIP5K1C | phosphatidylinositol-4-phosphate 5-kinase, type 1, gamma | 395 | CCGCGTCGTGGTCATGAACAA |
| 23396 | PIP5K1C | phosphatidylinositol-4-phosphate 5-kinase, type I, gamma | 396 | GACGGCGAGAGCGACACATAA |
| 23552 | CCRK | cell cycle related kinase | 399 | TGGCGAGATAGTTGCCCTCAA |
| 23552 | CCRK | cell cycle related kinase | 400 | AAGGAGAAGTGCAGAGAGTAA |
| 23552 | CCRK | cell cycle related kinase | 653 | UUGGAUCUGCUGGGUCAAU |
| 23552 | CCRK | cell cycle related kinase | 654 | AAGGACTTACGGTATCAGATA |
| 23765 | IL17RA | interleukin 17 receptor | 403 | CAGCGGTCTGGTTATCGTCTA |
| 23765 | IL17RA | interleukin 17 receptor | 404 | CCUCGAGGGUGCAGAGUUA |
| 23770 | FKBP8 | FK506 binding protein 8, 38 kDa | 405 | CTGCCAGGAACTGACCACCTA |
| 23770 | FKBP8 | FK506 binding protein 8, 38 kDa | 406 | CTCCTACGACCTCGCCATCAA |
| 27092 | CACNG4 | calcium channel, voltage-dependent, gamma subunit 4 | 410 | CTAGGTGGTTACAAATCATAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 27092 | CACNG4 | calcium channel, voltage-dependent, gamma subunit 4 | 409 | UCGGUAUCAUCGUCUACAU |
| 27092 | CACNG4 | calcium channel, voltage-dependent, gamma subunit 4 | 655 | CAGGAGAGCAACTTACCTTCA |
| 29035 | C16orf72 | chromosome 16 open reading frame 72 | 415 | CAGGCTCTCCTACACATGTAA |
| 29035 | C16orf72 | chromosome 16 open reading frame 72 | 416 | AAGCATTTGGCTGAATCTAAA |
| 29035 | C16orf72 | chromosome 16 open reading frame 72 | 656 | CACCTGGTTTCTATATAGTAA |
| 30811 | HUNK | hormonally up-regulated Neu-associated kinase | 425 | CACGGGCAAAGTGCCCTGTAA |
| 30811 | HUNK | hormonally up-regulated Neu-associated kinase | 426 | AACTAAGTACGTTGCAAATAA |
| 50488 | MINK1 | misshapen-like kinase 1 (zebrafish) | 431 | CACGTACGGGCGCATCATTAA |
| 50488 | MINK1 | misshapen-like kinase 1 (zebrafish) | 432 | /5Phos/rGrArCrUrCrUrArCrC rCrGrGrArGrUrUrUrCrUrC GG |
| 51061 | TXNDC11 | thioredoxin domain containing 11 | 434 | UCCCUCAAUCACAUCUUCA |
| 51061 | TXNDC11 | thioredoxin domain containing 11 | 433 | CCUCAAGGAGCAGACCUUU |
| 51390 | AIG1 | androgen-induced 1 | 439 | CAGAGAGATGATATACCCGAA |
| 51390 | AIG1 | androgen-induced 1 | 440 | CAGATGTTTCTCATTGCATAA |
| 54507 | ADAMTSL4 | ADAMTS-like 4 | 446 | CAGCCTTTAACTCCCAGGAAT |
| 54507 | ADAMTSL4 | ADAMTS-like 4 | 445 | CAGAACCTCTAAGCCCTGAAA |
| 54776 | PPP1R12C | protein phosphatase 1, regulatory (inhibitor) subunit 12C | 447 | TTGGAGGAACTGGCCCGGAAA |
| 54776 | PPP1R12C | protein phosphatase 1, regulatory (inhibitor) subunit 12C | 448 | CAGGAGGACCTTCGGAACCAA |
| 55229 | PANK4 | pantothenate kinase 4 | 453 | GCGAGTGGCTTCAGAGATTAA |
| 55229 | PANK4 | pantothenate kinase 4 | 454 | TCGACATAGGCGGGTCGTTAA |
| 55577 | NAGK | N-acetylglucosamine kinase | 455 | CCCGGTCTTGTTCCAGGGCAA |
| 55577 | NAGK | N-acetylglucosamine kinase | 456 | ACCTGAGTGAAAGCTACTTAA |
| 55652 | SLC48A1 | solute carrier family 48 (heme transporter), member 1 | 457 | CAGGACGAGTGTGGTCTCCCA |
| 55652 | SLC48A1 | solute carrier family 48 (heme transporter), member 1 | 458 | CTGGACCTATGCTGCAGGCAA |
| 55652 | SLC48A1 | solute carrier family 48 (heme transporter), member 1 | 657 | ACGCACGTGATGTACATGCAA |
| 55851 | PSENEN | presenilin enhancer 2 homolog (C. elegans) | 461 | CTCCCAGGACAGGCTCCTTAA |
| 55851 | PSENEN | presenilin enhancer 2 homolog (C. elegans) | 462 | CTCGCCCAAAGAAGACTACAA |
| 55872 | PBK | PDZ binding kinase | 464 | AACGCTGTAAACTGTAACATT |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 55872 PBK | PDZ binding kinase | | 463 | /5Phos/rArGrCrArUrArCrUrArUrGrCrArGrCrGrUrUrGrGrGrArAAG |
| 56300 IL1F9 | interleukin 1 family, member 9 | | 467 | AGAGAGACCAGCCCAUCAU |
| 56300 IL1F9 | interleukin 1 family, member 9 | | 468 | CAGGAGAGCTGGGTGGTATAA |
| 56311 ANKRD7 | ankyrin repeat domain 7 | | 469 | CACCTTATTCTTGGCACTACA |
| 56311 ANKRD7 | ankyrin repeat-domain 7 | | 470 | AAGGATGGGTATACTCCACTA |
| 56660 KCNK12 | potassium channel, subfamily K, member 12 | | 471 | CTGCATTTACTCGCTCTTCAA |
| 56660 KCNK12 | potassium channel, subfamily K, member 12 | | 472 | CTGGCGCTTTCTTAATCTTTA |
| 56893 UBQLN4 | ubiquilin 4 | | 658 | GGAGUUCAAAGAGGAAAUC |
| 56893 UBQLN4 | ubiquilin 4 | | 473 | CACACTGGCCTTTGTAAATAA |
| 56893 UBQLN4 | ubiquilin 4 | | 474 | AGAGATGCTAATGGAATTTAA |
| 56893 UBQLN4 | ubiquilin 4 | | 659 | GCCAUGAUGCAAGAGAUGA |
| 56997 CABC1 | chaperone, ABC1 activity of bc1 complex homolog (S. pombe) | | 476 | CAGGGTCAGGATAAACATGAA |
| 56997 CABC1 | chaperone, ABC1 activity of bc1 complex homolog (S. pombe) | | 660 | CAACAACTTGTTTCAATTTAA |
| 56997 CABC1 | chaperone, ABC1 activity of bc1 complex homolog (S. pombe) | | 475 | CGCGGACTTCATGCCACTGAA |
| 57120 GOPC | golgi associated PDZ and coiled-coil motif containing | | 480 | CAGCTGCAGCTTCATGCTAAA |
| 57120 GOPC | golgi associated PDZ and coiled-coil motif containing | | 479 | CACCGTATTTATTTAGTCAAA |
| 57502 NLGN4X | neuroligin 4, X-linked | | 483 | CCGUUACCCAAUGAGAUCU |
| 57502 NLGN4X | neuroligin 4, X-linked | | 723 | UCCGAAAUACUACUCAGUU |
| 57502 NLGN4X | neuroligin 4, X-linked | | 483 | UCCGAAAUACUACUCAGUU |
| 57502 NLGN4X | neuroggIn 4, X-linked | | 661 | CCCGGGTGTTTCCAACGTCAT |
| 57534 MIB1 | mindbomb homolog 1 (Drosophila) | | 484 | GCUCUAAGGCAUCACACUU |
| 57534 MIB1 | mindbomb homolog 1 (Drosophila) | | 485 | ACCGAATTACTACACCGGGAA |
| 79641 ROGDI | rogdi homolog (Drosophila) | | 496 | CAGGGCTGTCTAAGAAATAAA |
| 79641 ROGDI | rogdi homolog (Drosophila) | | 497 | AAGCAAGAGAACTTCATCCTA |
| 79705 LRRK1 | leucine-rich repeat kinase 1 | | 499 | AGCGGAGGAAUGAAAAUUG |
| 79705 LRRK1 | leucine-rich repeat kinase 1 | | 498 | CCCTGTTTGTTTGCACATAAT |
| 79872 CBLL1 | Cas-Br-M (murine) ecotropic retroviral transforming sequence-like 1 | | 501 | GGGUGCAAGAGAACAUAUU |
| 79872 CBLL1 | Cas-Br-M (murine) ecotropic retroviral transforming sequence-like 1 | | 500 | CGCGAACTCAAAGAACTATAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 80818 | ZNF436 | zinc finger protein 436 | 504 | AACGAGGTAAATCCCAAGCAA |
| 80818 | ZNF436 | zinc finger protein 436 | 505 | ACACATGTTCTTGGTAACTAA |
| 84197 | SGK196 | protein kinase-like protein SgK196 | 506 | CACGATGATCTCATGCCCTCA |
| 84197 | SGK196 | protein kinase-like protein SgK196 | 507 | AACACTATGCTTACTGAATAT |
| 89891 | WDR34 | WD repeat domain 34 | 508 | CATGGTCATCCGAGAGCTGAA |
| 89891 | WDR34 | WD repeat domain 34 | 509 | ACGGAGCACCAAGCTCAAGAA |
| 90736 | FAM104B | family with sequence similarity 104, member B | 510 | CTGGGCTTCCTGGGTCAAGTA |
| 90736 | FAM104B | family with sequence similarity 104, member B | 511 | CCCAATTCCAATTCCTTGTAA |
| 92579 | G6PC3 | glucose 6 phosphatase, catalytic, 3 | 513 | GTGGCTCAACCTCATCTTCAA |
| 92579 | G6PC3 | glucose 6 phosphatase, catalytic, 3 | 512 | CACATGTTCAGTGCCCAGGAA |
| 92579 | G6PC3 | glucose 6 phosphatase, catalytic, 3 | 662 | CTGGGAAATGGCCAGAAGATA |
| 92579 | G6PC3 | glucose 6 phosphatase, catalytic, 3 | 663 | CAGGTGCTGGCTGGCCTAATA |
| 93611 | FBXO44 | F-box protein 44 | 514 | UGUGAAUGGAGGCAUGAG |
| 93611 | FBXO44 | F-box protein 44 | 515 | CCCGAAAGGTCTTGACCTGAA |
| 94234 | FOXQ1 | forkhead box Q1 | 516 | CTCCATCAAACGTGCCTTAAA |
| 94234 | FOXQ1 | forkhead box Q1 | 517 | CGCGCGGACTTTGCACTTTGA |
| 96626 | LIMS3 | LIM and senescent cell antigen-like domains 3 | 518 | CAGCCTTGACAGCGAAGAATA |
| 96626 | LIMS3 | LIM and senescent cell antigen-like domains 3 | 519 | TCCAAGGCTGCTAACAAATAA |
| 114788 | CSMD3 | CUB and Sushi multiple domains 3 | 523 | CACGGTTTGCACAATGGTATA |
| 114788 | CSMD3 | CUB and Sushi multiple domains 3 | 522 | CACCCAGCCCAAAGCUAAG |
| 116447 | TOP1MT | topoisomerase (DNA) I, mitochondrial | 531 | GACGAAGAUCCAGGCAAAG |
| 116447 | TOP1MT | topoisomerase (DNA) I, mitochondrial | 530 | CCAGACGAAGATCCAGGCAAA |
| 118442 | GPR62 | G protein-coupled receptor 62 | 532 | TAGGCTCCATTCTGCCATCTA |
| 118442 | GPR62 | G protein-coupled receptor 62 | 533 | CCCGCGGGCACUCUUGCAA |
| 124583 | CANT1 | calcium activated nucleotidase 1 | 536 | CCAGATCATTGTGGCCCTCAA |
| 124583 | CANT1 | calcium activated nucleotidase 1 | 626 | AAGCAGTTTCCTTTCTTATAA |
| 126541 | OR10H4 | olfactory receptor, family 10, sub-family H, member 4 | 664 | GCCCUGAUAGGCUGUUUAU |
| 126541 | OR10H4 | olfactory receptor, family 10, sub-family H, member 4 | 537 | CCCUCUCCGUCUCUGAGAU |
| 126541 | OR10H4 | olfactory receptor, family 10, sub-family H, member 4 | 538 | TTGAGGATTCCCTCTGCCGAA |
| 153571 | C5orf38 | chromosome 5 open reading frame 38 | 541 | CCGCCAAAGAATTTAGAACGA |

TABLE 7-continued

Host proteins confirmed to be required for wild-type influenza virus growth and gene expression. siRNAs targeting 294 host cellular factors (column

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 92 | ACVR2A | activin A receptor, type IIA | 117 | ACCAATCAAACTGGTGTTGAA |
| 147 | ADRA1B | adrenergic, alpha-1B-, receptor | 119 | GCUAAGACGUUGGGCAUUG |
| 147 | ADRA1B | adrenergic, alpha-1B-, receptor | 118 | CCCUUCUAUGCCCUCUUCU |
| 335 | APOA1 | apolipoprotein A-I | 127 | CGCTCTCGAGGAGTACACTAA |
| 335 | APOA1 | apolipoprotein A-I | 126 | GAGACUAUGUGUCCCAGUU |
| 658 | BMPR1B | "bone morphogenetic protein receptor, type IB" | 138 | GGACUAUAGCUAAGCAGAU |
| 658 | BMPR1B | "bone morphogenetic protein receptor, type IB" | 137 | /5Phos/rGrGrArCrCrArGrUrUrGrUrArCrCrUrArAUrCrArCrAGG |
| 790 | CAD | carbamoyl-phosphate synthetase 2, aspartate transcarbamylase, and dihydroorotase | 140 | CCCUGAGUCUGAGCAGUAU |
| 790 | CAD | carbamoyl-phosphate synthetase 2, aspartate transcarbamylase, and dihydroorotase | 139 | CAGCCAAGTGCTAGTAGACAA |
| 1019 | CDK4 | cyclin-dependent kinase 4 | 143 | GAGGCCUAGAUUUCCUUCA |
| 1019 | CDK4 | cyclin-dependent kinase 4 | 669 | /5Phos/rArCrCrArGrGrArCrUrArArGrArCrArUrAUrCrUrGAC |
| 1280 | COL2A1 | collagen, type II, alpha 1 | 149 | CTGGTTTGGAGAAACCATCAA |
| 1280 | C012A1 | collagen, type II, alpha 1 | 150 | AAGCCTGGTGATGATGGTGAA |
| 1455 | CSNK1G2 | "casein kinase 1, gamma 2" | 158 | TAGGAAAGAATCTCTATACAA |
| 1455 | CSNK1G2 | "casein kinase 1, gamma 2" | 157 | /5Phos/rArGrGrCrArGrGrGrUrArUrCrArCrArArArCrUrUrArUAG |
| 1733 | DIO1 | deiodinase, iodothyronine, type I | 165 | TTGGGAGTTTATGCAAGGTAA |
| 1733 | DIO1 | deiodinase, iodothyronine, type I | 166 | UAGCAGAUUUUCUUGUCAU |
| 2324 | FLT4 | fms-related tyrosine kinase 4 | 184 | CACGCTCTTGGTCAACAGGAA |
| 2324 | FLT4 | fms-related tyrosine kinase 4 | 185 | CGUGUCUGCCAUGUACAAG |
| 2334 | AFF2 | fragile x mental retardation 2 | 187 | CACGTGATAGTCATAACCCTA |
| 2334 | AFF2 | fragile x mental retardation 2 | 186 | CTGGGTAAGACTACTCAGTAA |
| 3356 | HTR2A | 5-hydroxytryptamine (serotonin) receptor 2A | 214 | CUCGCCGAUGAUAACUUUG |
| 3356 | HTR2A | 5-hydroxytryptamine (serotonin) receptor 2A | 215 | TGGGATTGAGTTGGTTACCTA |
| 4058 | LTK | leukocyte receptor tyrosine kinase | 236 | ACAGATCTTTGGAGTGCCTAA |
| 4058 | LTK | leukocyte receptor tyrosine kinase | 237 | CAGGGATATTGCCGCCCGGAA |
| 5580 | PRKCD | protein kinase C, delta | 268 | CGCUGCCAUCCACAAGAAA |
| 5580 | PRKCD | protein kinase C, delta | 269 | CCGGGACACTATATTCCAGAA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 5594 | MAPK1 | mitogen-activated protein kinase 1 | 670 | CCCAUAUCUGGAGCAGUAU |
| 5594 | MAPK1 | mitogen-activated protein kinase 1 | 272 | /5Phos/rGrCrArCrCrArArCrCrA rUrCrGrArGrCrArArArUrGrArA AG |
| 5707 | PSMD1 | proteasome (prosome, macropain) 26S subunit, non-ATPase, 1 | 281 | AAGCAGTGCATTTGTAGGAAA |
| 5707 | PSMD1 | proteasome (prosome, macropain) 26S subunit, non-ATPase, 1 | 282 | CTGCATGTCTTTAATGCAGAA |
| 6334 | SCN8A | sodium channel, voltage gated, type VIII, alpha subunit | 692 | GGGAAGAGUUUGCCUUUCA |
| 6334 | SCN8A | sodium channel, voltage gated, type VIII, alpha subunit | 693 | ACCATTGATATCAAACCAGAA |
| 6340 | SCNN1G | sodium channel, nonvoltage-gated 1, gamma | 671 | ATCCCGGGACCTGAACTATTA |
| 6340 | SCNN1G | sodium channel, nonvoltage-gated 1, gamma | 694 | CAAGGCCGGCAAGTAAACAAA |
| 6340 | SCNN1G | sodium channel, nonvoltage-gated 1, gamma | 695 | UGGGCUGCAAGUCAUUUUG |
| 6478 | SIAH2 | seven in absentia homolog 2 (*Drosophila*) | 703 | ACCAGAACAUGAAGACAUA |
| 6478 | SIAH2 | seven in absentia homolog 2 (*Drosophila*) | 702 | ACCCGGAGUGCUUAUCUUAAA |
| 6811 | STX5 | syntaxin 5 | 714 | CAGTGGAAATTGAAGAGCTAA |
| 6811 | STX5 | syntaxin 5 | 715 | ATCAATAGCCTCAACAAACAA |
| 7178 | TPT1 | tumor protein, translationally-controlled 1 | 718 | CCGCGCTCGCTCCGAGTTTCA |
| 7178 | TPT1 | tumor protein, translationally-controlled 1 | 719 | CGCCGTCGTCGTCTCCCTTCA |
| 7341 | SUMO1 | SMT3 suppressor of mif two 3 homolog 1 (*S. cerevisiae*) | 297 | CAGTTACCTAATCATGTTGAA |
| 7341 | SUMO1 | SMT3 suppressor of mif two 3 homolog 1 (*S. cerevisiae*) | 296 | CAGGTTGAAGTCAAGATGACA |
| 8570 | KHSRP | KH-type splicing regulatory protein | 308 | CAGAGGAGGTGAACAAATTAA |
| 8570 | KHSRP | KH-type splicing regulatory protein | 307 | CAGGATTCAGGCTGCAAAGTA |
| 9201 | DCLK1 | doublecortin and CaM kinase-like 1 | 323 | /5Phos/rGrGrCrUrCrCrUrCrUrA rCrGrUrCrArCrUrUrGrCrGrUrC GG |
| 9201 | DCLK1 | doublecortin and CaM kinase-like 1 | 324 | CUGGAGUACACCAAGAAUG |
| 9448 | MAP4K4 | mitogen-activated protein kinase kinase kinase kinase 4 | 333 | CGCAAUGACAAGGUGUUCU |
| 9448 | MAP4K4 | mitogen-activated protein kinase kinase kinase kinase 4 | 672 | /5Phos/rGrGrArUrUrCrArGrGr ArUrCrArGrUrCrUrArUrGrArCr ATT |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 10036 | CHAF1A | chromatin assembly factor 1, subunit A (p150) | 351 | CTGCCCTTTAATAAAGCATTA |
| 10036 | CHAF1A | chromatin assembly factor 1, subunit A (p150) | 350 | AAGGAAGAAGAGAAACGGTTA |
| 10280 | OPRS1 | opioid receptor, sigma 1 | 366 | CCGGCTTGAGCTCACCACCTA |
| 10280 | OPRS1 | opioid receptor, sigma 1 | 367 | CAGCGTCTTCCATTCCAGAAA |
| 10725 | NFAT5 | nuclear factor of activated T-cells 5, tonicity-responsive | 376 | CAGCTGGTGCTTTGAATGTAA |
| 10725 | NFAT5 | nuclear factor of activated T-cells 5, tonicity-responsive | 722 | CAGGAGTGCCAGAAATCTTAA |
| 11213 | IRAK3 | interleukin-1 receptor-associated kinase 3 | 673 | AGCCAGAGAGCAAGAGAAA |
| 11213 | IRAK3 | interleukin-1 receptor-associated kinase 3 | 384 | /5Phos/rGrCrArArCrGrCrGrGrGrCrArArArGrUrUrArArGrArCrCGC |
| 23386 | NUDCD3 | NudC domain containing 3 | 392 | CTCCTTGGTGTTGGTTTGCAA |
| 23386 | NUDCD3 | NudC domain containing 3 | 391 | CCCTGCTTTAATAAACAGCAA |
| 25831 | HECTD1 | HECT domain containing 1 | 408 | CAGGACTGGCAGAATGTTGAA |
| 25831 | HECTD1 | HECT domain containing 1 | 407 | ACGGAACGGAGAUCAGAAA |
| 27347 | STK39 | "serine threonine kinase 39 (STE20/SPS1 homolog, yeast)" | 412 | GGGAUUUGAAAGCUGGUAA |
| 27347 | STK39 | "serine threonine kinase 39 (STE20/SPS1 homolog, yeast)" | 411 | /5Phos/rGrGrCrCrCrArCrCrArArUrGrCrUrArArUrGrArArGrAGG |
| 28996 | HIPK2 | homeodomain interacting protein kinase 2 | 413 | GGUGAACAUGACGACAGAU |
| 28996 | HIPK2 | homeodomain interacting protein kinase 2 | 414 | /5Phos/rGrCrGrArUrCrCrArArGrCrGrUrGrUrCrArArGrGrArGrAGC |
| 29110 | TBK1 | TANK-binding kinase 1 | 418 | AGCCUUCUGGUGCAAUAUC |
| 29110 | TBK1 | TANK-binding kinase 1 | 674 | CAGAACGTAGATTAGCTTATA |
| 29110 | TBK1 | TANK-binding kinase 1 | 417 | AAAGCGGCAGAGTTAGGTGAA |
| 30815 | ST6GALNAC6 | ST6 (alpha-N-acetyl-neuraminyl-2,3-beta-galactosyl-1,3)-N-acetylgalactosaminide alpha-2,6-sialyltransferase 6 | 428 | CCGGAGAGAAATGAGTAGCAA |
| 30815 | ST6GALNAC6 | ST6 (alpha-N-acetyl-neuraminyl-2,3-beta-galactosyl-1,3)-N-acetylgalactosaminide alpha-2,6-sialyltransferase 6 | 427 | CTCAATTTCCAGCACCAGAAA |
| 51172 | NAGPA | N-acetylglucosamine-1-phosphodiester alpha-N-acetylglucosaminidase | 436 | TTGAATAAATTGATATAATAA |
| 51172 | NAGPA | N-acetylglucosamine-1-phosphodiester alpha-N-acetylglucosaminidase | 435 | CACAGGAGACAGGTTCCTTTA |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 51257 | 3-Mar | membrane-associated ring finger (C3HC4) 2 | 437 | CACGCTGGGTGCCGTGCATAA |
| 51257 | 3-Mar | membrane-associated ring finger (C3HC4) 2 | 438 | ACCAGAAAGUUCGCCUGAA |
| 51422 | PRKAG2 | protein kinase, AMP-activated, gamma 2 non-catalytic subunit | 441 | AAGCGCGGTTATGGACACCAA |
| 51422 | PRKAG2 | protein kinase, AMP-activated, gamma 2 non-catalytic subunit | 442 | AAGCACGAGCCTGAACGGTTA |
| 51526 | C20orf111 | chromosome 20 open reading frame 111 | 443 | CACAATGAAATCCGAAGCCAA |
| 51526 | C20orf111 | chromosome 20 open reading frame 111 | 444 | ACAGATGATACCAAACCTAAA |
| 54980 | C2orf42 | chromosome 2 open reading frame 42 | 450 | CAGCGGTCTTAAAGAGATTAT |
| 54980 | C2orf42 | chromosome 2 open reading frame 42 | 449 | CTGCTCTTAGCTAAGATGCAA |
| 54991 | C1orf159 | chromosome 1 open reading frame 159 | 452 | CAGGGCCTGCTACAGAAGAAA |
| 54991 | C1orf159 | chromosome 1 open reading frame 159 | 451 | CAGAAATTCATTGTGCAGAAA |
| 55850 | USE1 | unconventional SNARE in the ER 1 homolog (S. cerevisiae) | 460 | CTCAGAGAAAGCACTGGCCAA |
| 55850 | USE1 | unconventional SNARE in the ER 1 homolog (S. cerevisiae) | 459 | ACCGGCCTCTGAGGTGATCAA |
| 56164 | STK31 | serine/threonine kinase 31 | 466 | GCUCUACUCAGAUGGAAAU |
| 56164 | STK31 | serine/threonine kinase 31 | 465 | /5Phos/rCrCrGrUrCrUrUrGrUr ArGrCrArUrGrGrUrUrCrCrArAr AGA |
| 57085 | AGTRAP | angiotensin II receptor-associated protein | 478 | TTGGGTCTTCTCAGGACCGTA |
| 57085 | AGTRAP | angiotensin II receptor-associated protein | 477 | CAGGGATTGCCTGAACCAAGA |
| 57418 | WDR18 | WD repeat domain 18 | 482 | CTGCATCGTGTGGGAACTTCA |
| 57418 | WDR18 | WD repeat domain 18 | 481 | CACAGTGGTGCTAGTCTGTTT |
| 64284 | RAB17 | RAB17, member RAS oncogene family | 491 | TCGCCTGAGATATAAGTTGTA |
| 64284 | RAB17 | RAB17, member RAS oncogene family | 490 | AAGTGAGATCCTGGAAGTGAA |
| 64601 | VPS16 | vacuolar protein sorting 16 homolog (S. cerevisiae) | 493 | CCGCACGGAGCTGGCCATCAA |
| 64601 | VPS16 | vacuolar protein sorting 16 homolog (S. cerevisiae) | 492 | CAGCATGGACTGGGACCTGAA |
| 65220 | NADK | NAD kinase | 495 | CCAGACCATCATGCACATTCA |
| 65220 | NADK | NAD kinase | 494 | CACGCACCTCATGGAGGAGAA |
| 114299 | PALM2 | paralemmin 2 | 520 | AAGGCTGGACAATCAAGCTTA |
| 114299 | PALM2 | paralemmin 2 | 675 | CAGAAAGGAGTCAAAGTCTAT |
| 115701 | ALPK2 | alpha-kinase 2 | 529 | AGCGAAGACCTTGGCATTTAT |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 115701 | ALPK2 | alpha-kinase 2 | 528 | CGGCCTCATGCCTGTCTTCAA |
| 127733 | UBXN10 | UBX domain containing 3 | 540 | CACCAGGACTTGAGCACATAA |
| 127733 | UBXN10 | UBX domain containing 3 | 539 | CTGGTAAATAACCACAGTGTA |
| 166614 | DCLK2 | doublecortin and CaM kinase-like 2 | 544 | GGUCAUUGGUGAUGGCAAU |
| 166614 | DCLK2 | doublecortin and CaM kinase-like 2 | 543 | /5Phos/rCrGrGrUrGrUrArCrCrGrCrGrGrGrArArArArUrCrCrUCG |
| 256126 | SYCE2 | synaptonemal complex central element protein 2 | 549 | GAGGATCTATCAGATTTATAA |
| 256126 | SYCE2 | synaptonemal complex central element protein 2 | 548 | CAGGAACAGCCTGAAGACCAA |
| 340260 | UNCX | UNC homeobox | 560 | CTGGATTCTGGTACCCTCCGA |
| 340260 | UNCX | UNC homeobox | 561 | CCGCCATGTGCCCTTCTCCAT |
| 440396 | LOC440396 | LOC284387, similar to Heterogeneous nuclear ribonucleoprotein A1 (Helix-destabilizing protein) (Single-strand binding protein) (hnRNP core protein A1) (HDP-1) (Topoisomerase-inhibitor suppressed) | 570 | ACGGACTGTGTGGTAATGAGA |
| 440396 | LOC440396 | LOC284387, similar to Heterogeneous nuclear ribonucleoprotein A1 (Helix-destabilizing protein) (Single-strand binding protein) (hnRNP core protein A1) (HDP-1) (Topoisomerase-inhibitor suppressed) | 676 | CACCGCCAAGTCTAAGTCAGA |
| 440738 | MAP1LC3C | microtubule-associated protein 1 light chain 3 gamma | 571 | CCCGGTGGTAGTGGAGCGCTA |
| 440738 | MAP1LC3C | microtubule-associated protein 1 light chain 3 gamma | 572 | CGCAACCATGGCAGAGATCTA |
| 441670 | OR4M1 | olfactory receptor, family 4, subfamily M, member 1 | 576 | CCAGGAAAUAUCCUUAUCA |
| 441670 | OR4M1 | olfactory receptor, family 4, subfamily M, member 1 | 575 | CGUCUCUGCUGUAUCCUGG |
| 1385 | CREB1 | cAMP responsive element binding protein 1 | 154 | CAGCCGGGTACTACCATTCTA |
| 1385 | CREB1 | cAMP responsive element binding protein 1 | 153 | AGGGCAGTTGTTGCTTCTTAA |
| 2260 | FGFR1 | fibroblast growth factor receptor 1 (fms-related tyrosine kinase 2, Pfeiffer syndrome) | 181 | CAGAGGAGAAAGAAACAGATA |
| 2260 | FGFR1 | fibroblast growth factor receptor 1 (fms-related tyrosine kinase 2, Pfeiffer syndrome) | 180 | CCUGCAUUGUGGAGAAUGA |
| 4914 | NTRK1 | "neurotrophic tyrosine kinase, receptor, type 1" | 245 | CACGGAGGCAATCGACTGCAT |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 4914 NTRK1 | "neurotrophic tyrosine kinase, receptor, type 1" | 244 | /5Phos/rArCrCrArGrArGrGrUrCrUrArCrGrCrCrArUrCrArUrGrCGG |
| 4915 NTRK2 | neurotrophic tyrosine kinase, receptor, type 2 | 246 | GAGCAUCAUGUACAGGAAA |
| 4915 NTRK2 | neurotrophic tyrosine kinase, receptor, type 2 | 247 | ACCACGAACAGAAGTAATGAA |
| 5062 PAK2 | p21 (CDKN1A)-activated kinase 2 | 252 | /5Phos/rArGrCrUrArCrGrCrUrGrUrGrGrUrUrArUrUrCrUrUrAAG |
| 5062 PAK2 | p21 (CDKN1A)-activated kinase 2 | 253 | /5Phos/rGrGrArGrCrUrArCrGrCrUrGrUrGrGrUrUrArUrUrCrUGG |
| 5422 POLA1 | polymerase (DNA directed), alpha | 264 | CCAGACCUGGUGAAUGUAA |
| 5422 POLA1 | polymerase (DNA directed), alpha | 265 | CAGGATCTTAACACTGAGACA |
| 9149 DYRK1B | dual-specificity tyrosine-(Y)-phosphorylation regulated kinase 1B | 677 | CTCGCTGAACCTGACCCGGAA |
| 9149 DYRK1B | dual-specificity tyrosine-(Y)-phosphorylation regulated kinase 1B | 317 | CCGGACCTACCGCTACAGCAA |
| 9464 HAND2 | heart and neural crest derivatives expressed 2 | 334 | ATCCGGTTTATTTATGTGCAA |
| 9464 HAND2 | heart and neural crest derivatives expressed 2 | 335 | CCGGCGTGGGCGAATTCAGAA |
| 9578 CDC42BPB | CDC42 binding protein kinase beta (DMPK-like) | 340 | /5Phos/rUrGrCrUrArCrArCrGrCrCrGrArGrArUrArUrUrCrCrArUTG |
| 9578 CDC42BPB | CDC42 binding protein kinase beta (DMPK-like) | 341 | GCUCAGAUUGCGGAAAUCA |
| 10616 RBCK1 | RanBP-type and C3HC4-type zinc finger containing 1 | 678 | CGGGTGCACCTTCATCAACAA |
| 10616 RBCK1 | RanBP-type and C3HC4-type zinc finger containing 1 | 375 | AGGGAUGGUGCUUCUUUGA |
| 23534 TNPO3 | transportin 3 | 397 | ACCGAATGTCTTAGTGAACTA |
| 23534 TNPO3 | transportin 3 | 398 | CTGGGAGATCATGCAGGTTGA |
| 30849 PIK3R4 | phosphoinositide-3-kinase, regulatory subunit 4 | 679 | AAGATGTACTTGACTAGTTTA |
| 30849 PIK3R4 | phosphoinositide-3-kinase, regulatory subunit 4 | 430 | AAGCAGAATTCTAGATCAGAA |
| 57551 TAOK1 | TAO kinase 1 | 486 | GGACAAUAUGAUGGCAAAG |
| 57551 TAOK1 | TAO kinase 1 | 487 | CAGTGCTAAAGTACTACTGAA |
| 114880 OSBPL6 | oxysterol binding protein-like 6 | 525 | CACATTCTGAATGAATAAATA |
| 114880 OSBPL6 | orysterol binding protein-like 6 | 524 | CAGGTTGTCAGTGTAAATATT |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 114971 PTPMT1 | protein tyrosine phosphatase, mitochondrial 1 | 526 | CACCTTGGACAACCTCCAGAA |
| 114971 PTPMT1 | protein tyrosine phosphatase, mitochondrial 1 | 527 | AACCTCCAGAAGGGAGTCCAA |
| 204851 HIPK1 | homeodomain interacting protein kinase 1 | 546 | AGGGAAGCTGTACACCACTAA |
| 204851 HIPK1 | homeodomain interacting protein kinase 1 | 547 | CAGGAGTTCTCACGCAGGGAA |
| 283455 KSR2 | kinase suppressor of ras 2 | 680 | TCCGTTGTGAGGGATGCCAAA |
| 283455 KSR2 | kinase suppressor of ras 2 | 551 | ATCCGGTGACCTCGAATCCAA |

| | WT virus growth (HA titer reduction) | | | | Viral gene expression (RT-PCR) | | | |
|---|---|---|---|---|---|---|---|---|
| geneID | wtWSN1 | wtWSN2 | mean reduction in HA titer | siRNAs confirming with WT Influenza Replication | confirmed for WT replication | NP ave | M1 ave | AVE_(NP, M1) | confirmed for RT-PCR |
| 290 | −4 | −4 | −4 | >=2 | Y | 0.276712682 | 0.29987259 | 0.288292636 | Y |
| 290 | −4 | −5 | −4.5 | >=2 | Y | 0.97878345 | 0.574486806 | 0.776635128 | Y |
| 361 | −6.5 | −5.5 | −6 | >=2 | Y | | | | Y |
| 361 | −2 | −2.5 | −2.25 | >=2 | Y | 0.116096271 | 0.106942002 | 0.111519137 | Y |
| 372 | −6 | −6 | −6 | >=2 | Y | 1.42E-02 | 1.02E-02 | 1.22E-02 | Y |
| 372 | −6 | −6 | −6 | >=2 | Y | 5.91E-03 | 6.47E-03 | 6.19E-03 | Y |
| 523 | −7 | −7 | −7 | >=2 | Y | 3.44E-02 | 5.11E-02 | 4.27E-02 | Y |
| 523 | −7 | −7 | −7 | >=2 | Y | 5.85E-02 | 3.13E-02 | 4.49E-02 | Y |
| 526 | −6 | −6 | −6 | >=2 | Y | 0.121477992 | 0.113347248 | 0.11741262 | Y |
| 526 | −6 | −6 | −6 | >=2 | Y | 2.52E-02 | 2.02E-02 | 2.27E-02 | Y |
| 526 | | | | >=2 | Y | 4.89E-02 | 3.61E-02 | 4.25E-02 | Y |
| 527 | −7 | −7 | −7 | >=2 | Y | 2.43E-02 | 1.75E-02 | 2.09E-02 | Y |
| 527 | −7 | −7 | −7 | >=2 | Y | 9.86E-03 | 2.43E-02 | 1.71E-02 | Y |
| 533 | −9 | −9 | −9 | >=2 | Y | 1.63E-02 | 1.13E-02 | 1.38E-02 | Y |
| 533 | −9 | −9 | −9 | >=2 | Y | 1.68E-02 | 0.015930397 | 1.63E-02 | Y |
| 537 | −6 | −6 | −6 | >=2 | Y | 1.07E-02 | 1.43E-02 | 1.25E-02 | Y |
| 537 | −6 | −6 | −6 | >=2 | Y | 8.45E-02 | 6.37E-02 | 7.41E-02 | Y |
| 537 | | | | >=2 | Y | 1.39E-02 | 5.86E-03 | 9.86E-03 | Y |
| 816 | −6 | −6 | −6 | >=2 | Y | 0.202739551 | 0.264986076 | 0.233862813 | Y |
| 816 | −5 | −5 | −5 | >=2 | Y | 9.58E-02 | 7.60E-02 | 8.59E-02 | Y |
| 816 | | | | >=2 | Y | 0.118015515 | 4.64E-02 | 8.22E-02 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | | |
|---|---|---|---|---|---|---|---|---|---|
| 975 | −8.5 | −9.5 | −9 | >=2 | Y | 0.033288732 | 1.78E-02 | 2.55E-02 | Y |
| 975 | −6.5 | −6.5 | −6.5 | >=2 | Y | 0.355094491 | 0.322617285 | 0.338855888 | Y |
| 1314 | −9.5 | −9.5 | −9.5 | >=2 | Y | 0.135288768 | 0.173932374 | 0.154610571 | Y |
| 1314 | −9.5 | −9.5 | −9.5 | >=2 | Y | 3.01E-02 | 2.56E-02 | 2.79E-02 | Y |
| 1394 | −7.5 | −8.5 | −8 | >=2 | Y | 8.30E-02 | 7.95E-02 | 8.13E-02 | Y |
| 1394 | −3.5 | −3.5 | −3.5 | >=2 | Y | 0.382687745 | 0.573688423 | 0.478188084 | Y |
| 1434 | −9 | −9 | −9 | >=2 | Y | 0.225386093 | 0.247194416 | 0.236290254 | Y |
| 1434 | −8 | −8 | −8 | >=2 | Y | 0.125066897 | 0.186081518 | 0.155574207 | Y |
| 1434 | −6.5 | −5.5 | −6 | >=2 | Y | 0.373784133 | 0.686648008 | 0.53021607 | Y |
| 1434 | | | | >=2 | Y | 0.818239448 | 0.740879592 | 0.77955952 | Y |
| 1521 | −2.5 | −2.5 | −2.5 | >=2 | Y | 0.231461644 | 0.175265844 | 0.203363744 | Y |
| 1521 | −2 | −3 | −2.5 | >=2 | Y | 0.11965879 | 0.123660199 | 0.121659495 | Y |
| 1521 | | | | >=2 | Y | 0.637934448 | 0.565303765 | 0.601619106 | Y |
| 1832 | −8.5 | −8.5 | −8.5 | >=2 | Y | | | | Y |
| 1832 | −2 | −2 | −2 | >=2 | Y | 0.220942878 | 0.229039136 | 0.224991007 | Y |
| 1845 | −6 | −6 | −6 | >=2 | Y | 0.148010379 | 0.118605762 | 0.133308071 | Y |
| 1845 | −2 | −2 | −2 | >=2 | Y | 0.166106049 | 0.213380168 | 0.189743108 | Y |
| 2022 | −9.5 | −9.5 | −9.5 | >=2 | Y | 0.245476213 | 0.240430849 | 0.242953531 | Y |
| 2022 | −3.5 | −3.5 | −3.5 | >=2 | Y | 0.344587177 | 0.251762053 | 0.298174615 | Y |
| 2022 | −2.5 | −2.5 | −2.5 | >=2 | Y | 1.134697849 | 1.097333909 | 1.116015879 | Y |
| 2045 | −8.5 | −9.5 | −9 | >=2 | Y | 0.223027951 | 0.230562172 | 0.226795061 | Y |
| 2045 | −2.5 | −2.5 | −2.5 | >=2 | Y | 0.450841207 | 0.480007028 | 0.465424118 | Y |
| 2048 | −2.5 | −2.5 | −2.5 | >=2 | Y | 0.323242146 | 0.421804646 | 0.372523396 | Y |
| 2048 | −2.5 | −2.5 | −2.5 | >=2 | Y | 1.158171743 | 0.953026309 | 1.055599026 | Y |
| 2050 | −5.5 | −6.5 | −6 | >=2 | Y | 0.189424625 | 0.121470154 | 0.155447389 | Y |
| 2050 | −3.5 | −3.5 | −3.5 | >=2 | Y | 0.942415004 | 7.528956844 | 4.235685924 | Y |
| 2162 | −6.5 | −6.5 | −6.5 | >=2 | Y | 3.18E-03 | 5.95E-03 | 4.57E-03 | Y |
| 2162 | −4.5 | −5.5 | −5 | >=2 | Y | 2.192961605 | 1.823711137 | 2.008336371 | Y |
| 2263 | −7.5 | −8.5 | −8 | >=2 | Y | 6.96E-02 | 6.82E-02 | 6.89E-02 | Y |
| 2263 | −6.5 | −6.5 | −6.5 | >=2 | Y | 0.310759578 | 0.28012525 | 0.295442414 | Y |
| 2264 | −5 | −6 | −5.5 | >=2 | Y | 7.21E-02 | 5.59E-02 | 6.40E-02 | Y |
| 2264 | −5 | −6 | −5.5 | >=2 | Y | 8.87E-02 | 8.89E-02 | 8.88E-02 | Y |
| 2357 | −7.5 | −7.5 | −7.5 | >=2 | Y | 1.130192474 | 1.215250396 | 1.172721435 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | | |
|---|---|---|---|---|---|---|---|---|---|
| 2357 | −5 | −5 | −5 | >=2 | Y | 0.756692772 | 0.559339357 | 0.658016065 | Y |
| 2475 | −7 | −7 | −7 | >=2 | Y | | | | |
| 2475 | −3 | −3 | −3 | >=2 | Y | 0.712210477 | 0.615008258 | 0.663609368 | Y |
| 2475 | | | | >=2 | Y | 0.711422314 | 0.574693285 | 0.463216786 | Y |
| 2475 | | | | >=2 | Y | 0.501709136 | 0.424724436 | 0.643057799 | Y |
| 2539 | −3 | −3 | −3 | >=2 | Y | 0.182636117 | 0.20704941 | 0.194842764 | Y |
| 2539 | −2.5 | −3.5 | −3 | >=2 | Y | | | | Y |
| 2550 | −6 | −6 | −6 | >=2 | Y | 0.238708534 | 0.20028687 | 0.219497702 | Y |
| 2550 | −6 | −6 | −6 | >=2 | Y | 9.17E−02 | 6.50E−02 | 7.83E−02 | Y |
| 2580 | −9 | −9 | −9 | >=2 | Y | 2.61E−02 | 2.35E−02 | 2.48E−02 | Y |
| 2580 | −3.5 | −2.5 | −3 | >=2 | Y | | | | Y |
| 2932 | −7.5 | −6.5 | −7 | >=2 | Y | 0.440007322 | 0.461256794 | 0.450632058 | Y |
| 2932 | −7.5 | −7.5 | −7.5 | >=2 | Y | 0.302074277 | 0.292786457 | 0.297430367 | Y |
| 3320 | −3.5 | −2.5 | −3 | >=2 | Y | 0.280282634 | 0.262304168 | 0.271293401 | Y |
| 3320 | −3.5 | −2.5 | −3 | >=2 | Y | 0.500345875 | 0.626750202 | 0.563548039 | Y |
| 3675 | −3.5 | −3.5 | −3.5 | >=2 | Y | 0.513097815 | 1.049249663 | 0.781173739 | Y |
| 3675 | −3 | −3 | −3 | >=2 | Y | 0.310963052 | 0.379833972 | 0.345398512 | Y |
| 3675 | | | | >=2 | Y | 0.443106766 | 0.342524552 | 0.392815659 | Y |
| 3675 | | | | >=2 | Y | 0.100605588 | 9.05E−02 | 9.56E−02 | Y |
| 3717 | −3 | −3 | −3 | >=2 | Y | 0.113663396 | 6.24E−02 | 8.80E−02 | Y |
| 3717 | −2 | −2 | −2 | >=2 | Y | 1.201552001 | 1.518853243 | 1.360202622 | Y |
| 3837 | −7 | −7 | −7 | >=2 | Y | 0.275694355 | 0.189335578 | 0.232514966 | Y |
| 3837 | −5 | −6 | −5.5 | >=2 | Y | 7.62E−02 | 6.83E−02 | 7.23E−02 | Y |
| 4193 | −6.5 | −6.5 | −6.5 | >=2 | Y | 0.425690698 | 0.106538088 | 0.266114393 | Y |
| 4193 | −3 | −3 | −3 | >=2 | Y | 2.641333263 | 1.147790017 | 1.89456164 | Y |
| 4296 | −4 | −5 | −4.5 | >=2 | Y | 0.14390299 | 0.129378518 | 0.136640754 | Y |
| 4296 | −3 | −3 | −3 | >=2 | Y | 0.196739061 | 8.82E−02 | 0.142453189 | Y |
| 4923 | −9 | −9 | −9 | >=2 | Y | 2.05E−02 | 8.87E−03 | 1.47E−02 | Y |
| 4923 | −2.5 | −2.5 | −2.5 | >=2 | Y | 3.48E−02 | 2.51E−02 | 3.00E−02 | Y |
| 5063 | −6 | −7 | −6.5 | >=2 | Y | 1.463575884 | 0.57794856 | 1.020762222 | Y |
| 5063 | −2.5 | −1.5 | −2 | >=2 | Y | | | | Y |
| 5566 | −3 | −3 | −3 | >=2 | Y | 0.449543156 | 0.335208496 | 0.392375826 | Y |
| 5566 | −2 | −3 | −2.5 | >=2 | Y | 1.013468695 | 1.164365531 | 1.088917113 | Y |
| 5584 | −4.5 | −4.5 | −4.5 | >=2 | Y | 0.46577858 | 0.510771815 | 0.488275198 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | | |
|---|---|---|---|---|---|---|---|---|---|
| 5584 | −3 | −3 | −3 | >=2 | Y | 1.553577104 | 2.98758892 | 2.270583012 | Y |
| 5606 | −8 | −8 | −8 | >=2 | Y | 7.18E−02 | 1.97E−02 | 4.57E−02 | Y |
| 5606 | −4 | −4 | −4 | >=2 | Y | 0.388898593 | 0.360233031 | 0.374565812 | Y |
| 5606 | | | | >=2 | Y | 3.29E−02 | 4.07E−02 | 3.68E−02 | Y |
| 5757 | −9 | −9 | −9 | >=2 | Y | 1.46E−02 | 1.19E−02 | 1.32E−02 | Y |
| 5757 | −3 | −3 | −3 | >=2 | Y | 0.221552223 | 9.10E−02 | 0.156281336 | Y |
| 5961 | −8.5 | −7.5 | −8 | >=2 | Y | 6.60E−02 | 6.79E−02 | 6.69E−02 | Y |
| 5961 | −3 | −3 | −3 | >=2 | Y | 1.555684907 | 1.402947925 | 1.479316416 | Y |
| 5961 | | | | >=2 | Y | 0.964064284 | 0.700986982 | 0.832525633 | Y |
| 6204 | −7.5 | −7.5 | −7.5 | >=2 | Y | 2.154080572 | 2.080193691 | 2.117137132 | Y |
| 6204 | −6 | −6 | −6 | >=2 | Y | 0.16677873 | 0.132387012 | 0.149582871 | Y |
| 6204 | | | | >=2 | Y | 0.489687133 | 0.201551999 | 0.345619566 | Y |
| 6204 | | | | >=2 | Y | 0.516445476 | 0.389104861 | 0.452775168 | Y |
| 6224 | −6.5 | −6.5 | −6.5 | >=2 | Y | 0.433346492 | 0.255444505 | 0.344395499 | Y |
| 6224 | −3.5 | −3.5 | −3.5 | >=2 | Y | 8.33E−02 | 7.84E−02 | 8.08E−02 | Y |
| 6224 | | | | >=2 | Y | 1.559176356 | 0.669989053 | 1.114582704 | Y |
| 6357 | −4 | −4 | −4 | >=2 | Y | 4.42E−02 | 2.20E−02 | 3.31E−02 | Y |
| 6357 | −2 | −2 | −2 | >=2 | Y | 0.168338881 | 0.181578463 | 0.174958672 | Y |
| 6357 | −3 | −3 | −3 | >=2 | Y | | | | Y |
| 6357 | −2 | −2 | −2 | >=2 | Y | | | | Y |
| 6446 | −4 | −5 | −4.5 | >=2 | Y | 0.223521487 | 0.264166238 | 0.243843863 | Y |
| 6446 | −2.5 | −2.5 | −2.5 | >=2 | Y | | | | Y |
| 6613 | −4 | −3 | −3.5 | >=2 | Y | 6.35E−02 | 9.21E−02 | 7.78E−02 | Y |
| 6613 | −3 | −4 | −3.5 | >=2 | Y | 9.01E−02 | 7.74E−02 | 8.37E−02 | Y |
| 6627 | −6 | −6 | −6 | >=2 | Y | 0.760619597 | 0.541460669 | 0.651040133 | Y |
| 6627 | −2 | −2 | −2 | >=2 | Y | 0.213779849 | 9.84E−02 | 0.156087654 | Y |
| 6627 | | | | >=2 | Y | 0.438291968 | 0.823924041 | 0.631108004 | Y |
| 7786 | −6 | −5 | −5.5 | >=2 | Y | 0.361562886 | 0.23725233 | 0.299407608 | Y |
| 7786 | −3 | −3 | −3 | >=2 | Y | | | | Y |
| 8021 | −9 | −9 | −9 | >=2 | Y | 5.83E−02 | 5.71E−02 | 5.77E−02 | Y |
| 8021 | −5 | −5 | −5 | >=2 | Y | 8.06E−02 | 0.125576159 | 0.103090402 | Y |
| 8677 | −9 | −9 | −9 | >=2 | Y | 2.16E−02 | 1.75E−02 | 0.019541345 | Y |
| 8677 | −5 | −7 | −6 | >=2 | Y | 0.32704471 | 0.283947323 | 0.305496021 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | | |
|---|---|---|---|---|---|---|---|---|---|
| 9114 | -9.5 | -9.5 | -9.5 | >=2 | Y | 3.84E-02 | 2.91E-02 | 3.38E-02 | Y |
| 9114 | -9.5 | -9.5 | -9.5 | >=2 | Y | 0.2451907 | 0.295460092 | 0.270325396 | Y |
| 9114 | | | | >=2 | Y | 0.125527457 | 0.127024337 | 0.126275897 | Y |
| 9114 | | | | >=2 | Y | 0.300934689 | 0.297950802 | 0.299442745 | Y |
| 9135 | -3 | -4 | -3.5 | >=-2 | Y | 0.357409642 | 0.338984125 | 0.348196883 | Y |
| 9135 | -3 | -3 | -3 | >=2 | Y | 0.407140397 | 0.511565327 | 0.459352862 | Y |
| 9180 | -2.5 | -3.5 | -3 | >=2 | Y | 1.375054711 | 1.111293449 | 1.24317408 | Y |
| 9180 | -2.5 | -1.5 | -2 | >=2 | Y | 0.194092258 | 0.220857847 | 0.207475053 | Y |
| 9230 | -7 | -8 | -7.5 | >=2 | Y | 0.316134796 | 0.323754957 | 0.319944876 | Y |
| 9230 | -5 | -4 | -4.5 | >=2 | Y | 0.518829968 | 0.210507289 | 0.364668628 | Y |
| 9230 | | | | >=2 | Y | 0.190252993 | 0.187018406 | 0.188635699 | Y |
| 9231 | -5.5 | -4.5 | -5 | >=2 | Y | 4.35E-02 | 4.79E-02 | 0.04568758 | Y |
| 9231 | -3.5 | -2.5 | -3 | >=2 | Y | 0.306875572 | 0.363093244 | 0.334984408 | Y |
| 9256 | -6 | -5 | -5.5 | >=2 | Y | 1.77E-02 | 2.49E-02 | 2.13E-02 | Y |
| 9256 | -3.5 | -2.5 | -3 | >=2 | Y | 0.220344648 | 0.297024739 | 0.258684693 | Y |
| 9276 | -9.5 | -9.5 | -9.5 | >=2 | Y | | | | Y |
| 9276 | -9.5 | -9.5 | -9.5 | >=2 | Y | | | | Y |
| 9276 | -9.5 | -9.5 | -9.5 | >=2 | Y | | | | Y |
| 9276 | -9.5 | -9.5 | -9.5 | >=2 | Y | 2.30E-02 | 2.17E-02 | 2.23E-02 | Y |
| 9972 | -7.5 | -7.5 | -7.5 | >=2 | Y | 0.3363035 | 0.315331675 | 0.325817587 | Y |
| 9972 | -7.5 | -7.5 | -7.5 | >=2 | Y | 2.236736858 | 3.11963013 | 2.678183494 | Y |
| 10055 | -3 | -2 | -2.5 | >=2 | Y | 0.439330276 | 0.643235083 | 0.541282679 | Y |
| 10055 | -3 | -3 | -3 | >=2 | Y | 4.78E-02 | 6.89E-02 | 5.84E-02 | Y |
| 10181 | -3 | -3 | -3 | >=2 | Y | 6.22E-02 | 9.34E-02 | 7.78E-02 | Y |
| 10181 | -2.5 | -2.5 | -2.5 | >=2 | Y | 0.790734052 | 0.74911088 | 0.769922466 | Y |
| 10291 | -6.5 | -6.5 | -6.5 | >=2 | Y | 0.136974065 | 9.12E-02 | 0.114109001 | Y |
| 10291 | -6.5 | -6.5 | -6.5 | >=2 | Y | 0.150457957 | 7.85E-02 | 0.114495102 | Y |
| 10381 | -9.5 | -9.5 | -9.5 | >=2 | Y | | | | Y |
| 10381 | -8.5 | -9.5 | -9 | >=2 | Y | | | | Y |
| 10381 | -6 | -6 | -6 | >=2 | Y | 4.36E-02 | 3.64E-02 | 0.039978728 | Y |
| 10783 | -5.5 | -4.5 | -5 | >=2 | Y | 0.547889106 | 0.535242792 | 0.541565949 | Y |
| 10783 | -5.5 | -5.5 | -5.5 | >=2 | Y | 1.572970546 | 1.555665365 | 1.564317956 | Y |
| 11214 | -2 | -3 | -2.5 | >=2 | Y | 5.31E-02 | 0.115648303 | 0.084391456 | Y |
| 11214 | -2 | -2 | -2 | >=2 | Y | 0.395669457 | 0.503400778 | 0.449535117 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | | |
|---|---|---|---|---|---|---|---|---|---|
| 22820 | −7 | −7 | −7 | >=2 | Y | 2.50E-02 | 1.96E-02 | 2.23E-02 | Y |
| 22820 | −2 | −3 | −2.5 | >=2 | Y | 0.329384041 | 0.285772176 | 0.307578109 | Y |
| 22820 | | | | >=2 | Y | 0.363517395 | 0.155612566 | 0.259564981 | Y |
| 23604 | −9 | −9 | −9 | >=2 | Y | 0.594485599 | 0.502650063 | 0.548567831 | Y |
| 23604 | −3.5 | −3.5 | −3.5 | >=2 | Y | | | | Y |
| 23604 | 0.5 | 0.5 | 0.5 | >=2 | Y | | | | Y |
| 23604 | | | | >=2 | Y | 0.403975913 | 0.279240635 | 0.341608274 | Y |
| 29127 | −5 | −5 | −5 | >=2 | Y | 0.905902229 | 0.631415528 | 0.768658879 | Y |
| 29127 | −3.5 | −2.5 | −3 | >=2 | Y | | | | Y |
| 29127 | 0 | 0 | 0 | >=2 | Y | 0.411101648 | 0.402318029 | 0.406709839 | Y |
| 29882 | −5 | −5 | −5 | >=2 | Y | 0.391276617 | 0.252454322 | 0.321865469 | Y |
| 29882 | −3 | −4 | −3.5 | >=2 | Y | 1.96E-02 | 1.00E-02 | 1.48E-02 | Y |
| 29959 | −5.5 | −4.5 | −5 | >=2 | Y | | | | Y |
| 29959 | −3.5 | −3.5 | −3.5 | >=2 | Y | 0.293423129 | 0.176108822 | 0.234765976 | Y |
| 51393 | −5 | −5 | −5 | >=2 | Y | 0.749756005 | 0.660982579 | 0.705369292 | Y |
| 51393 | −4 | −5 | −4.5 | >=2 | Y | 8.36E-02 | 0.109734118 | 9.67E-02 | Y |
| 54866 | −5 | −5 | −5 | >=2 | Y | 0.274867037 | 0.210698877 | 0.242782957 | Y |
| 54866 | −4 | −4 | −4 | >=2 | Y | 0.211288401 | 0.11031781 | 0.160803106 | Y |
| 57579 | −5 | −7 | −6 | >=2 | Y | 0.24570503 | 0.189513883 | 0.217609456 | Y |
| 57579 | −3 | −4 | −3.5 | >=2 | Y | 0.640587015 | 0.614963575 | 0.627775295 | Y |
| 79574 | −5.5 | −5.5 | −5.5 | >=2 | Y | 0.139594668 | 7.16E-02 | 0.105584956 | Y |
| 79574 | −4 | −4 | −4 | >=2 | Y | 2.64E-02 | 2.96E-02 | 2.80E-02 | Y |
| 80231 | −4 | −5 | −4.5 | >=2 | Y | 1.169027401 | 0.899644378 | 1.034335889 | Y |
| 80231 | −2 | −3 | −2.5 | >=2 | Y | 1.130320326 | 0.625270303 | 0.877795315 | Y |
| 93953 | −7 | −7 | −7 | >=2 | Y | 0.197332102 | 9.79E-02 | 0.147593538 | Y |
| 93953 | −6.5 | −5.5 | −6 | >=2 | Y | 0.674520348 | 0.701862137 | 0.688191243 | Y |
| 93953 | | | | >=2 | Y | 0.77333686 | 0.626216941 | 0.699776902 | Y |
| 93953 | | | | >=2 | Y | 0.825537741 | 0.875412955 | 0.850475348 | Y |
| 113878 | −2.5 | −2.5 | −2.5 | >=2 | Y | 3.12E-02 | 2.16E-02 | 2.64E-02 | Y |
| 113878 | −2 | −3 | −2.5 | >=2 | Y | 0.538612128 | 0.190512624 | 0.364562376 | Y |
| 113878 | −1.5 | −1.5 | −1.5 | >=2 | Y | 1.842557408 | 1.973498973 | 1.908028191 | Y |
| 113878 | | | | >=2 | Y | 0.267681487 | 0.338242301 | 0.302961894 | Y |
| 113878 | | | | >=2 | Y | 0.554341912 | 0.398169527 | 0.47625572 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | |
|---|---|---|---|---|---|---|---|---|
| 122525 | −4 | −4 | −4 | >=2 | Y | 0.491190122 | 0.429301414 | 0.460245768 | Y |
| 122525 | −3 | −3 | −3 | >=2 | Y | 0.562016671 | 0.378561163 | 0.470288917 | Y |
| 167681 | −6 | −7 | −6.5 | >=2 | Y | 0.06199709 | 0.02258516 | 4.23E-02 | Y |
| 167681 | −4 | −4 | −4 | >=2 | Y | | | | Y |
| 167681 | −2.5 | −2.5 | −2.5 | >=2 | Y | 0.283520162 | 0.19593595 | 0.239728056 | Y |
| 203068 | −3 | −3 | −3 | >=2 | Y | 1.099277504 | 0.990621594 | 1.044949549 | Y |
| 203068 | −2 | −3 | −2.5 | >=2 | Y | 0.381391092 | 0.267730642 | 0.324560867 | Y |
| 254065 | −4 | −3 | −3.5 | >=2 | Y | 1.142615952 | 1.237190897 | 1.189903425 | Y |
| 254065 | −3 | −3 | −3 | >=2 | Y | 4.40E-02 | 4.09E-02 | 4.24E-02 | Y |
| 387082 | −2 | −2 | −2 | >=2 | Y | 0.183816124 | 0.169065396 | 0.17644076 | Y |
| 387082 | −2 | −2 | −2 | >=2 | Y | 0.193737903 | 0.130439368 | 0.162088636 | Y |
| 387082 | | | | >=2 | Y | 0.608248428 | 0.537052488 | 0.572650458 | Y |
| 387911 | −8 | −9 | −8.5 | >=2 | Y | 0.274367112 | 7.78E-02 | 0.176098909 | Y |
| 387911 | −4 | −3 | −3.5 | >=2 | Y | 0.577150213 | 0.383806092 | 0.480478152 | Y |
| 643641 | −6.5 | −3.5 | −5 | >=2 | Y | 1.747783257 | 1.29430927 | 1.521046263 | Y |
| 643641 | −2 | −2 | −2 | >=2 | Y | 0.77428819 | 0.471919443 | 0.623103817 | Y |
| 5610 | −3.5 | −3.5 | −3.5 | >=2 | Y | 1.461658326 | 1.549028585 | 1.505343455 | N |
| 5610 | −2.5 | −1.5 | −2 | >=2 | Y | 0.870704551 | 0.963917105 | 0.917310828 | N |
| 6093 | −5.5 | −4.5 | −5 | >=2 | Y | 0.725195368 | 0.680611854 | 0.702904111 | N |
| 6093 | −2.5 | −2.5 | −2.5 | >=2 | Y | | | | N |
| 6093 | −2 | −2 | −2 | >=2 | Y | 0.678176541 | 0.664688776 | 0.671432659 | N |
| 58526 | −7 | −6 | −6.5 | >=2 | Y | 1.057494617 | 0.704782944 | 0.88113878 | N |
| 58526 | −4 | −3 | −3.5 | >=2 | Y | 1.189134883 | 1.383571521 | 1.286353202 | N |
| 157 | −7 | −7 | −7 | >=2 | Y | | | | |
| 157 | −4.5 | −6.5 | −5.5 | >=2 | Y | | | | |
| 207 | −7.5 | −7.5 | −7.5 | >=2 | Y | | | | |
| 207 | −7 | −6 | −6.5 | >=2 | Y | | | | |
| 351 | −7.5 | −7.5 | −7.5 | >=2 | Y | | | | |
| 351 | −5.5 | −6.5 | −6 | >=2 | Y | | | | |
| 369 | −4.5 | −4.5 | −4.5 | >=2 | Y | | | | |
| 369 | −2.5 | −1.5 | −2 | >=2 | Y | | | | |
| 602 | −7.5 | −7.5 | −7.5 | >=2 | Y | | | | |
| 602 | −2.5 | −2.5 | −2.5 | >=2 | Y | | | | |
| 827 | −4 | −4 | −4 | >=2 | Y | | | | |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA TABLE 7-continued Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 2936 | -5.5 | -4.5 | -5 | >=2 | Y |
| 3265 | -5.5 | -5.5 | -5.5 | >=2 | Y |
| 3265 | -3 | -4 | -3.5 | >=2 | Y |
| 3265 | -3 | -3 | -3 | >=2 | Y |
| 3265 | 1 | 1 | 1 | >=2 | Y |
| 3547 | -9 | -8 | -8.5 | >=2 | Y |
| 3547 | -8 | -10 | -9 | >=2 | Y |
| 3547 | -5 | -6 | -5.5 | >=2 | Y |
| 3547 | -4 | -3 | -3.5 | >=2 | Y |
| 3568 | -6.5 | -5.5 | -6 | >=2 | Y |
| 3568 | -4 | -5 | -4.5 | >=2 | Y |
| 3568 | 0.5 | 0.5 | 0.5 | >=2 | Y |
| 3568 | 1 | 1 | 1 | >=2 | Y |
| 3581 | -10 | -10 | -10 | >=2 | Y |
| 3581 | -7.5 | -7.5 | -7.5 | >=2 | Y |
| 3581 | -7.5 | -7.5 | -7.5 | >=2 | Y |
| 3581 | -3 | -3 | -3 | >=2 | Y |
| 3674 | -7.5 | -6.5 | -7 | >=2 | Y |
| 3674 | -3 | -3 | -3 | >=2 | Y |
| 3674 | -3 | -3 | -3 | >=2 | Y |
| 3725 | -10 | -10 | -10 | >=2 | Y |
| 3725 | -7 | -6 | -6.5 | >=2 | Y |
| 3760 | -8 | -9 | -8.5 | >=2 | Y |
| 3760 | -7.5 | -6.5 | -7 | >=2 | Y |
| 3760 | -7 | -8 | -7.5 | >=2 | Y |
| 3760 | 0 | 0 | 0 | >=2 | Y |
| 3767 | -7 | -7 | -7 | >=2 | Y |
| 3767 | -3 | -3 | -3 | >=2 | Y |
| 3778 | -7.5 | -7.5 | -7.5 | >=2 | Y |
| 3778 | -5 | -6 | -5.5 | >=2 | Y |
| 3984 | -5 | -3 | -4 | >=2 | Y |
| 3984 | -3.5 | -3.5 | -3.5 | >=2 | Y |
| 4809 | -10 | -10 | -10 | >=2 | Y |
| 4809 | -10 | -10 | -10 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 4886 | −7.5 | −7.5 | −7.5 | >=2 | Y |
| 4886 | −7.5 | −7.5 | −7.5 | >=2 | Y |
| 4886 | −2 | −2 | −2 | >=2 | Y |
| 4920 | −7.5 | −7.5 | −7.5 | >=2 | Y |
| 4920 | −6 | −4 | −5 | >=2 | Y |
| 5096 | −7 | −7 | −7 | >=2 | Y |
| 5096 | −7 | −6 | −6.5 | >=2 | Y |
| 5096 | −2 | −4 | −3 | >=2 | Y |
| 5165 | −7.5 | −7.5 | −7.5 | >=2 | Y |
| 5165 | −7 | −7 | −7 | >=2 | Y |
| 5253 | −10 | −10 | −10 | >=2 | Y |
| 5253 | −7 | −7 | −7 | >=2 | Y |
| 5310 | −7 | −7 | −7 | >=2 | Y |
| 5310 | −6.5 | −5.5 | −6 | >=2 | Y |
| 5605 | −7.5 | −7.5 | −7.5 | >=2 | Y |
| 5605 | −7 | −7 | −7 | >=2 | Y |
| 5607 | −6 | −7 | −6.5 | >=2 | Y |
| 5607 | −5 | −5 | −5 | >=2 | Y |
| 5797 | −7.5 | −7.5 | −7.5 | >=2 | Y |
| 5797 | −7.5 | −7.5 | −7.5 | >=2 | Y |
| 5798 | −10 | −10 | −10 | >=2 | Y |
| 5798 | −8 | −9 | −8.5 | >=2 | Y |
| 5805 | −7 | −7 | −7 | >=2 | Y |
| 5805 | −2 | −2 | −2 | >=2 | Y |
| 6015 | −7.5 | −7.5 | −7.5 | >=2 | Y |
| 6015 | −7 | −7 | −7 | >=2 | Y |
| 6196 | −10 | −10 | −10 | >=2 | Y |
| 6196 | −2 | −3 | −2.5 | >=2 | Y |
| 6196 | −1.5 | −4.5 | −3 | >=2 | Y |
| 6328 | −6 | −6 | −6 | >=2 | Y |
| 6328 | −4 | −4 | −4 | >=2 | Y |
| 6328 | −3 | −3 | −3 | >=2 | Y |
| 6442 | −7.5 | −7.5 | −7.5 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 6442 | -6.5 | -3.5 | -5 | >=2 | Y |
| 6604 | -8 | -8 | -8 | >=2 | Y |
| 6604 | -7 | -8 | -7.5 | >=2 | Y |
| 6624 | -10 | -10 | -10 | >=2 | Y |
| 6624 | -4 | -5 | -4.5 | >=2 | Y |
| 6625 | -7 | -7 | -7 | >=2 | Y |
| 6625 | -2 | -2 | -2 | >=2 | Y |
| 6792 | -5 | -4 | -4.5 | >=2 | Y |
| 6792 | -5 | -6 | -5.5 | >=2 | Y |
| 7005 | -10 | -10 | -10 | >=2 | Y |
| 7005 | -9 | -8 | -8.5 | >=2 | Y |
| 7294 | -9 | -10 | -9.5 | >=2 | Y |
| 7294 | -5 | -5 | -5 | >=2 | Y |
| 7423 | -10 | -10 | -10 | >=2 | Y |
| 7423 | -2 | -2 | -2 | >=2 | Y |
| 8290 | -7.5 | -7.5 | -7.5 | >=2 | Y |
| 8290 | -4 | -4 | -4 | >=2 | Y |
| 8290 | -1 | -2 | -1.5 | >=2 | Y |
| 8438 | -7.5 | -1.5 | -4.5 | >=2 | Y |
| 8438 | -7 | -7 | -7 | >=2 | Y |
| 8476 | -11 | -11 | -11 | >=2 | Y |
| 8476 | -4 | -5 | -4.5 | >=2 | Y |
| 8476 | -3.5 | -4.5 | -4 | >=2 | Y |
| 8476 | -2 | -3 | -2.5 | >=2 | Y |
| 8558 | -11 | -11 | -11 | >=2 | Y |
| 8558 | -7 | -7 | -7 | >=2 | Y |
| 8558 | 0 | -1 | -0.5 | >=2 | Y |
| 8831 | -9 | -9 | -9 | >=2 | Y |
| 8831 | -2 | -2 | -2 | >=2 | Y |
| 8837 | -4.5 | -3.5 | -4 | >=2 | Y |
| 8837 | -4 | -4 | -4 | >=2 | Y |
| 8837 | -2 | -5 | -3.5 | >=2 | Y |
| 9159 | -10 | -10 | -10 | >=2 | Y |
| 9159 | -7.5 | -7.5 | -7.5 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 9509 | −4 | −4 | −4 | >=2 | Y |
| 9509 | −2 | −2 | −2 | >=2 | Y |
| 9575 | −9 | −9 | −9 | >=2 | Y |
| 9575 | −6 | −7 | −6.5 | >=2 | Y |
| 9625 | −7 | −7 | −7 | >=2 | Y |
| 9625 | −3 | −3 | −3 | >=2 | Y |
| 9641 | −7 | −7 | −7 | >=2 | Y |
| 9641 | −1.5 | −3.5 | −2.5 | >=2 | Y |
| 9641 | 0 | 0 | 0 | >=2 | Y |
| 9943 | −6 | −7 | −6.5 | >=2 | Y |
| 9943 | −4 | −5 | −4.5 | >=2 | Y |
| 10105 | −10 | −10 | −10 | >=2 | Y |
| 10105 | −7 | −7 | −7 | >=2 | Y |
| 10114 | −7 | −7 | −7 | >=2 | Y |
| 10114 | −5 | −4 | −4.5 | >=2 | Y |
| 10155 | −7 | −6 | −6.5 | >=2 | Y |
| 10155 | −5 | −7 | −6 | >=2 | Y |
| 10155 | −1 | −2 | −1.5 | >=2 | Y |
| 10159 | −10 | −10 | −10 | >=2 | Y |
| 10159 | −9 | −9 | −9 | >=2 | Y |
| 10159 | −7 | −8 | −7.5 | >=2 | Y |
| 10159 | −4 | −4 | −4 | >=2 | Y |
| 10188 | −10 | −10 | −10 | >=2 | Y |
| 10188 | −5 | −5 | −5 | >=2 | Y |
| 10297 | −5 | −4 | −4.5 | >=2 | Y |
| 10297 | −3.5 | −2.5 | −3 | >=2 | Y |
| 10595 | −9 | −9 | −9 | >=2 | Y |
| 10595 | −7 | −7 | −7 | >=2 | Y |
| 10595 | −5 | −5 | −5 | >=2 | Y |
| 10733 | −8 | −8 | −8 | >=2 | Y |
| 10733 | −3 | −3 | −3 | >=2 | Y |
| 10849 | −9 | −10 | −9.5 | >=2 | Y |
| 10849 | −4 | −4 | −4 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 11113 | −7.5 | −7.5 | −7.5 | >=2 | Y |
| 11113 | −5 | −7 | −6 | >=2 | Y |
| 23049 | −8 | −7 | −7.5 | >=2 | Y |
| 23049 | −5 | −2 | −3.5 | >=2 | Y |
| 23216 | −4.5 | −5.5 | −5 | >=2 | Y |
| 23216 | −3.5 | −2.5 | −3 | >=2 | Y |
| 23352 | −10 | −10 | −10 | >=2 | Y |
| 23352 | −9 | −9 | −9 | >=2 | Y |
| 23352 | −7.5 | −7.5 | −7.5 | >=2 | Y |
| 23352 | −7 | −7 | −7 | >=2 | Y |
| 23352 | −6 | −6 | −6 | >=2 | Y |
| 23387 | −6.5 | −6.5 | −6.5 | >=2 | Y |
| 23387 | −5 | −6 | −5.5 | >=2 | Y |
| 23387 | −5 | −4 | −4.5 | >=2 | Y |
| 23387 | −3.5 | −3.5 | −3.5 | >=2 | Y |
| 23396 | −10 | −10 | −10 | >=2 | Y |
| 23396 | −7 | −7 | −7 | >=2 | Y |
| 23552 | −11 | −11 | −11 | >=2 | Y |
| 23552 | −8 | −9 | −8.5 | >=2 | Y |
| 23552 | −4.5 | −3.5 | −4 | >=2 | Y |
| 23552 | −3 | −3 | −3 | >=2 | Y |
| 23765 | −7 | −7 | −7 | >=2 | Y |
| 23765 | −2.5 | −2.5 | −2.5 | >=2 | Y |
| 23770 | −7 | −7 | −7 | >=2 | Y |
| 23770 | −5 | −4 | −4.5 | >=2 | Y |
| 27092 | −7 | −7 | −7 | >=2 | Y |
| 27092 | −4.5 | −3.5 | −4 | >=2 | Y |
| 27092 | −4 | −4 | −4 | >=2 | Y |
| 29035 | −10 | −10 | −10 | >=2 | Y |
| 29035 | −9 | −9 | −9 | >=2 | Y |
| 29035 | −9 | −9 | −9 | >=2 | Y |
| 30811 | −9 | −9 | −9 | >=2 | Y |
| 30811 | −6 | −6 | −6 | >=2 | Y |
| 50488 | −7 | −7 | −7 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | |
|---|---|---|---|---|
| 50488 | −5 | −5 | −5 | >=2 | Y |
| 51061 | −7.5 | −7.5 | −7.5 | >=2 | Y |
| 51061 | −7.5 | −7.5 | −7.5 | >=2 | Y |
| 51390 | −9 | −9 | −9 | >=2 | Y |
| 51390 | −8 | −9 | −8.5 | >=2 | Y |
| 54507 | −4 | −5 | −4.5 | >=2 | Y |
| 54507 | −3 | −4 | −3.5 | >=2 | Y |
| 54776 | −6 | −6 | −6 | >=2 | Y |
| 54776 | −3 | −2 | −2.5 | >=2 | Y |
| 55229 | −6 | −6 | −6 | >=2 | Y |
| 55229 | −4 | −4 | −4 | >=2 | Y |
| 55577 | −10 | −10 | −10 | >=2 | Y |
| 55577 | −2 | −2 | −2 | >=2 | Y |
| 55652 | −7 | −6 | −6.5 | >=2 | Y |
| 55652 | −6 | −7 | −6.5 | >=2 | Y |
| 55652 | −4 | −4 | −4 | >=2 | Y |
| 55851 | −10 | −10 | −10 | >=2 | Y |
| 55851 | −7 | −7 | −7 | >=2 | Y |
| 55872 | −7 | −7 | −7 | >=2 | Y |
| 55872 | −7 | −7 | −7 | >=2 | Y |
| 56300 | −5 | −6 | −5.5 | >=2 | Y |
| 56300 | −4 | −4 | −4 | >=2 | Y |
| 56311 | −5 | −5 | −5 | >=2 | Y |
| 56311 | −2 | −3 | −2.5 | >=2 | Y |
| 56660 | −5 | −5 | −5 | >=2 | Y |
| 56660 | −2 | −2 | −2 | >=2 | Y |
| 56893 | −7.5 | −7.5 | −7.5 | >=2 | Y |
| 56893 | −6 | −8 | −7 | >=2 | Y |
| 56893 | −4 | −4 | −4 | >=2 | Y |
| 56893 | −3 | −5 | −4 | >=2 | Y |
| 56997 | −6 | −7 | −6.5 | >=2 | Y |
| 56997 | −3 | −3 | −3 | >=2 | Y |
| 56997 | −2 | −2 | −2 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 57120 | −6 | −6 | −6 | >=2 | Y |
| 57120 | −4 | −3 | −3.5 | >=2 | Y |
| 57502 | −7.5 | −7.5 | −7.5 | >=2 | Y |
| 57502 | −1.5 | −5.5 | −3.5 | >=2 | Y |
| 57502 | −1.5 | −0.5 | −1 | >=2 | Y |
| 57502 | 0 | 0 | 0 | >=2 | Y |
| 57534 | −7.5 | −7.5 | −7.5 | >=2 | Y |
| 57534 | −5 | −4 | −4.5 | >=2 | Y |
| 79641 | −6 | −7 | −6.5 | >=2 | Y |
| 79641 | −4 | −4 | −4 | >=2 | Y |
| 79705 | −7.5 | −7.5 | −7.5 | >=2 | Y |
| 79705 | −7 | −7 | −7 | >=2 | Y |
| 79872 | −7 | −7 | −7 | >=2 | Y |
| 79872 | −7 | −7 | −7 | >=2 | Y |
| 80818 | −7 | −7 | −7 | >=2 | Y |
| 80818 | −3 | −3 | −3 | >=2 | Y |
| 84197 | −7 | −7 | −7 | >=2 | r |
| 84197 | −3 | −3 | −3 | >=2 | Y |
| 89891 | −10 | −10 | −10 | >=2 | Y |
| 89891 | −2 | −2 | −2 | >=2 | Y |
| 90736 | −10 | −10 | −10 | >=2 | Y |
| 90736 | −7 | −6 | −6.5 | >=2 | Y |
| 92579 | −11 | −11 | −11 | >=2 | Y |
| 92579 | −5 | −6 | −5.5 | >=2 | Y |
| 92579 | −2.5 | −2.5 | −2.5 | >=2 | Y |
| 92579 | −1 | −1 | −1 | >=2 | Y |
| 93611 | −7.5 | −7.5 | −7.5 | >=2 | Y |
| 93611 | −5 | −4 | −4.5 | >=2 | Y |
| 94234 | −10 | −10 | −10 | >=2 | Y |
| 94234 | −4 | −4 | −4 | >=2 | Y |
| 96626 | −7 | −7 | −7 | >=2 | Y |
| 96626 | −6 | −6 | −6 | >=2 | Y |
| 114788 | −6 | −6 | −6 | >=2 | Y |
| 114788 | −5.5 | −5.5 | −5.5 | >=2 | Y |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (exp

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | |
|---|---|---|---|---|---|---|---|
| 730974 | −3 | −4 | −3.5 | >=2 | Y | | |
| 70 | −9 | −9 | −9 | 1 | N | | |
| 70 | 0 | 0 | 0 | 1 | N | | |
| 92 | −3 | −3 | −3 | 1 | N | | |
| 92 | −1 | −1 | −1 | 1 | N | | |
| 147 | −5.5 | −6.5 | −6 | 1 | N | | |
| 147 | −1.5 | −1.5 | −1.5 | 1 | N | | |
| 335 | −6 | −6 | −6 | 1 | N | | |
| 335 | −0.5 | −0.5 | −0.5 | 1 | N | | |
| 658 | −2.5 | −2.5 | −2.5 | 1 | N | | |
| 658 | 1.5 | 1.5 | 1.5 | 1 | N | | |
| 790 | −2.5 | −2.5 | −2.5 | 1 | N | | |
| 790 | 0 | 1 | 0.5 | 1 | N | | |
| 1019 | −5.5 | −6.5 | −6 | 1 | N | | |
| 1019 | −0.5 | −0.5 | −0.5 | 1 | N | | |
| 1280 | −10 | −10 | −10 | 1 | N | | |
| 1280 | 0 | 0 | 0 | 1 | N | | |
| 1455 | −4 | −4 | −4 | 1 | N | 1.017841221 1.526072693 1.271956957 | |
| 1455 | 2 | 1 | 1.5 | 1 | N | | |
| 1733 | −5 | −4 | −4.5 | 1 | N | | |
| 1733 | 0 | 0 | 0 | 1 | N | | |
| 2324 | −7 | −7 | −7 | 1 | N | | |
| 2324 | 0.5 | 0.5 | 0.5 | 1 | N | | |
| 2334 | −2.5 | −2.5 | −2.5 | 1 | N | | |
| 2334 | 0 | −1 | −0.5 | 1 | N | | |
| 3356 | −2.5 | −3.5 | −3 | 1 | N | | |
| 3356 | −1 | −1 | −1 | 1 | N | | |
| 4058 | −3 | −3 | −3 | 1 | N | | |
| 4058 | −1 | −1 | −1 | 1 | N | | |
| 5580 | −1.5 | −2.5 | −2 | 1 | N | | |
| 5580 | 0 | −1 | −0.5 | 1 | N | | |
| 5594 | −2.5 | −1.5 | −2 | 1 | N | | |
| 5594 | −1.5 | −1.5 | −1.5 | 1 | N | | |
| 5707 | −5 | −5 | −5 | 1 | N | | |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 5707 | −1 | −1 | −1 | 1 | N |
| 6334 | −3 | −3 | −3 | 1 | N |
| 6334 | −0.5 | −1.5 | −1 | 1 | N |
| 6340 | −4 | −4 | −4 | 1 | N |
| 6340 | −1 | −1 | −1 | 1 | N |
| 6340 | 0 | −1 | −0.5 | 1 | N |
| 6478 | −3 | −3 | −3 | 1 | N |
| 6478 | 1 | 1 | 1 | 1 | N |
| 6811 | −5 | −5 | −5 | 1 | N |
| 6811 | −1 | −1 | −1 | 1 | N |
| 7178 | −6 | −7 | −6.5 | 1 | N |
| 7178 | 0 | 0 | 0 | 1 | N |
| 7341 | −2 | −2 | −2 | 1 | N |
| 7341 | −1 | −1 | −1 | 1 | N |
| 8570 | −3 | −4 | −3.5 | 1 | N |
| 8570 | −2 | −1 | −1.5 | 1 | N |
| 9201 | −4 | −3 | −3.5 | 1 | N |
| 9201 | −1.5 | −0.5 | −1 | 1 | N |
| 9448 | −4 | −4 | −4 | 1 | N |
| 9448 | 1.5 | 0.5 | 1 | 1 | N |
| 10036 | −7 | −7 | −7 | 1 | N |
| 10036 | 1 | 1 | 1 | 1 | N |
| 10280 | −4 | −6 | −5 | 1 | N |
| 10280 | 1 | 1 | 1 | 1 | N |
| 10725 | −10 | −10 | −10 | 1 | N |
| 10725 | 0 | 0 | 0 | 1 | N |
| 11213 | −4 | −4 | −4 | 1 | N |
| 11213 | −0.5 | −0.5 | −0.5 | 1 | N |
| 23386 | −4 | −4 | −4 | 1 | N |
| 23386 | −2 | −1 | −1.5 | 1 | N |
| 25831 | −6 | −6 | −6 | 1 | N |
| 25831 | −2 | −1 | −1.5 | 1 | N |
| 27347 | −2 | −2 | −2 | 1 | N |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | |
|---|---|---|---|---|---|
| 27347 | 0.5 | 0.5 | 0.5 | 1 | N |
| 28996 | −4 | −4 | −4 | 1 | N |
| 28996 | 0.5 | 0.5 | 0.5 | 1 | N |
| 29110 | −2 | −2 | −2 | 1 | N |
| 29110 | −1.5 | −1.5 | −1.5 | 1 | N |
| 29110 | 1 | 1 | 1 | 1 | N |
| 30815 | −4 | −4 | −4 | 1 | N |
| 30815 | −1 | −1 | −1 | 1 | N |
| 51172 | −2 | −2 | −2 | 1 | N |
| 51172 | −1 | −1 | −1 | 1 | N |
| 51257 | −8 | −8 | −8 | 1 | N |
| 51257 | 0 | 0 | 0 | 1 | N |
| 51422 | −3 | −3 | −3 | 1 | N |
| 51422 | −1 | 0 | −0.5 | 1 | N |
| 51526 | −5 | −5 | −5 | 1 | N |
| 51526 | −1 | 0 | −0.5 | 1 | N |
| 54980 | −8 | −7 | −7.5 | 1 | N |
| 54980 | −1.5 | −1 | −1.25 | 1 | N |
| 54991 | −3 | −3 | −3 | 1 | N |
| 54991 | −2 | −1 | −1.5 | 1 | N |
| 55850 | −3 | −3 | −3 | 1 | N |
| 55850 | −1 | −1 | −1 | 1 | N |
| 56164 | −2 | −3 | −2.5 | 1 | N |
| 56164 | 0.5 | 0.5 | 0.5 | 1 | N |
| 57085 | −4 | −4 | −4 | 1 | N |
| 57085 | −2 | −1 | −1.5 | 1 | N |
| 57418 | −4 | −5 | −4.5 | 1 | N |
| 57418 | 2 | 2 | 2 | 1 | N |
| 64284 | −6 | −7 | −6.5 | 1 | N |
| 64284 | 0 | 0 | 0 | 1 | N |
| 64601 | −4.5 | −3.5 | −4 | 1 | N |
| 64601 | −0.5 | −0.5 | −0.5 | 1 | N |
| 65220 | −8 | −7 | −7.5 | 1 | N |
| 65220 | −1 | −2 | −1.5 | 1 | N |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as log$_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | |
|---|---|---|---|---|---|---|---|---|
| 114299 | -2.5 | -2.5 | -2.5 | 1 | N | | | |
| 114299 | -1 | -1 | -1 | 1 | N | | | |
| 115701 | -2.5 | -1.5 | -2 | 1 | N | | | |
| 115701 | 0.5 | 0.5 | 0.5 | 1 | N | | | |
| 127733 | -8.5 | -7.5 | -8 | 1 | N | | | |
| 127733 | 0 | 1 | 0.5 | 1 | N | | | |
| 166614 | -5.5 | -4.5 | -5 | 1 | N | | | |
| 166614 | 0.5 | 0.5 | 0.5 | 1 | N | | | |
| 256126 | -2 | -2 | -2 | 1 | N | | | |
| 256126 | 0.5 | -0.5 | 0 | 1 | N | | | |
| 340260 | -3 | -3 | -3 | 1 | N | | | |
| 340260 | -0.5 | -0.5 | -0.5 | 1 | N | | | |
| 440396 | -8.5 | -8.5 | -8.5 | 1 | N | | | |
| 440396 | -1 | -1 | -1 | 1 | N | | | |
| 440738 | -2 | -4 | -3 | 1 | N | | | |
| 440738 | 1 | 1 | 1 | 1 | N | | | |
| 441670 | -5.5 | -4.5 | -5 | 1 | N | | | |
| 441670 | -1.5 | -1.5 | -1.5 | 1 | N | | | |
| 1385 | -1 | -2 | -1.5 | 0 | N | | | |
| 1385 | 3 | 3 | 3 | 0 | N | | | |
| 2260 | -1 | -2 | -1.5 | 0 | N | 0.215059719 | 0.188198725 | 0.201629222 |
| 2260 | 0 | 1 | 0.5 | 0 | N | 0.691544767 | 0.658772654 | 0.675158711 |
| 4914 | -1 | -1 | -1 | 0 | N | | | |
| 4914 | -0.5 | -1.5 | -1 | 0 | N | | | |
| 4915 | -1.5 | -1.5 | -1.5 | 0 | N | | | |
| 4915 | -1 | 0 | -0.5 | 0 | N | | | |
| 5062 | 0.5 | 0.5 | 0.5 | 0 | N | | | |
| 5062 | 0.5 | 0.5 | 0.5 | 0 | N | | | |
| 5422 | -1 | -1 | -1 | 0 | N | | | |
| 5422 | 1 | 1 | 1 | 0 | N | | | |
| 9149 | 2 | 1 | 1.5 | 0 | N | | | |
| 9149 | 2.5 | 1.5 | 2 | 0 | N | | | |
| 9464 | 0 | -1 | -0.5 | 0 | N | | | |

TABLE 7-continued

Host proteins confirmed to be required for wild-type influenza virus growth and gene expression. siRNAs targeting 294 host cellular factors (column 1-4) were tested for their ability to inhibit wild-type influenza virus growth in A549 cells (MOI = 0.01) as measured by hemagglutination assay at 36 h postinfection. Reduction in HA titer (expressed as $\log_2$) for duplicate samples is shown in columns 5 and 6 and the average in column 7. The number of siRNAs that meet the criteria for each gene are listed in column 8. A call for a confirmed gene (see Methods section) is indicated in column 9. The ability of the siRNAs to inhibit viral gene expression was examined using qRT-PCR on NP (column 10) and M1 (column 11) mRNA at 6 h post-infection. Controls were set to the value of 1. An average value of column 10 and 11 is shown in column 12. A call for a confirmed gene (average value <0.65) is indicated in column 13.

| | | | | | | | | |
|---|---|---|---|---|---|---|---|---|
| 9464 | 0 | −1 | −0.5 | 0 | N | | | |
| 9578 | −0.5 | −0.5 | −0.5 | 0 | N | | | |
| 9578 | 0 | 0 | 0 | 0 | N | | | |
| 10616 | −2 | −2 | −2 | 0 | N | | | |
| 10616 | 0 | 0 | 0 | 0 | N | | | |
| 23534 | −1 | −1 | −1 | 0 | N | 0.42175369 | 0.319519842 | 0.370636766 |
| 23534 | 0 | 0 | 0 | 0 | N | 1.11537820 | 1.096187878 | 1.10578304 |
| 30849 | −1 | −1 | −1 | 0 | N | | | |
| 30849 | −1 | −1 | −1 | 0 | N | | | |
| 57551 | −1 | −1 | −1 | 0 | N | | | |
| 57551 | 0 | 0 | 0 | 0 | N | | | |
| 114880 | −2 | −1 | −1.5 | 0 | N | | | |
| 114880 | −1 | −1 | −1 | 0 | N | | | |
| 114971 | −1 | −1 | −1 | 0 | N | | | |
| 114971 | 0 | −1 | −0.5 | 0 | N | | | |
| 204851 | −1 | −1 | −1 | 0 | N | | | |
| 204851 | −1 | −1 | −1 | 0 | N | | | |
| 283455 | −5.5 | −4.5 | −5 | 0 | N | | | |
| 283455 | 0.5 | 0.5 | 0.5 | 0 | N | | | |

TABLE 8

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| geneID | symbol | Description | GenbankID | target sequence | viral RT-PCR Viral RNA level (% of control) | IFN RT-PCR w/o PR8 virus | IFN RT-PCR with PR8 virus | IFN bioassay: % NDV Inhibition w/o PR8 virus | IFN bioassay: % NDV Inhibition with PR8 virus | IFN bioassay controls: % NDV Inhibition | | |
|---|---|---|---|---|---|---|---|---|---|---|---|---|
| | | | | | | | | | | siRNA | Mock PR8 | PR8 NS1mut |
| 361 | AQP4 | aquaporin 4 | NM_001650 NM_004028 | CAGCCTGGGATCCACCATCAA SEQ ID NO. 130 | 11.30 | 0.64 | 5.32 | | | No si | -2.49  4.06 | 72.67 |
| 372 | ARCN1 | archain 1 | NM_001655 | AAGGCTGAGATGCGTCGTAAA SEQ ID NO. 2 | 1.22 | 1.36 | 0.65 | | | SC1 | 9.18  14.65 | 73.72 |
| 372 | ARCN1 | archain 1 | NM_001655 | CCCACTTGTGTCAATATTAAA SEQ ID NO. 1 | 0.61 | 0.60 | 0.06 | | | NS1 | 0.73  67.67 | 81.73 |
| 523 | ATP6V1A | ATPase, H+ transporting, lysosomal 70kDa, V1 subunit A | NM_001690 | GAGCTTGAATTTGAAGGTGTA SEQ ID NO. 3 | 4.49 | 0.28 | 0.31 | | | | | |
| 523 | ATP6V1A | ATPase, H+ transporting, lysosomal 70kDa, V1 subunit A | NM_001690 | ATGGAGGTTGATGGTAAGGTA SEQ ID NO. 4 | 4.00 | 0.69 | 0.41 | | | IFN standard curve | | |
| 526 | ATP6V1B2 | ATPase, H+ transporting, lysosomal 56/58kDa, V1 subunit B2 | NM_001693 | CAGGCTCGTTTGGTAAAGAAA SEQ ID NO. 585 | 4.25 | 0.34 | 1.49 | | | units of IFN | % NDV inhibition | |
| 526 | ATP6V1B2 | ATPase, H+ transporting, lysosomal 56/58kDa, V1 subunit B2 | NM_001693 | CACGGTTAATGAAGTCTGCTA SEQ ID NO. 6 | 2.36 | 7.49 | 8.90 | 12.87 | 9.50 | 1000.00 | 80.61 | |
| 527 | ATP6V0C | ATPase, H+ transporting, lysosomal 16kDa, V0 subunit c | NM_001694 XM_001130742 | CAGCCACAGAATATTATGTAA SEQ ID NO. 7 | 2.21 | 0.31 | 0.59 | | | 500.00 | 79.00 | |
| 527 | ATP6V0C | ATPase, H+ transporting, lysosomal 16kDa, V0 subunit c | NM_001694 XM_001130742 | TCCCAGCTATCTATAACCTTA SEQ ID NO. 8 | 1.47 | 2.42 | 5.17 | | | 250.00 | 76.29 | |
| 533 | ATP6V0B | ATPase, H+ transporting, lysosomal 21kDa, V0 subunit b | NM_001039457 NM_004047 | CATGGCAATTGTCATTAGCAA SEQ ID NO. 9 | 1.38 | 0.45 | 0.22 | | | 125.00 | 73.64 | |
| 533 | ATP6V0B | ATPase, H+ transporting, lysosomal 21kDa, V0 subunit b | NM_001039457 NM_004047 | TCCTAGTGTTTGTGAAATAAA SEQ ID NO. 10 | 1.65 | 0.58 | 0.48 | | | 62.50 | 69.27 | |
| 537 | ATP6AP1 | ATPase, H+ transporting, lysosomal accessory protein 1 | NM_001183 | CAGGGAAGTCCTCACAGGCAA SEQ ID NO. 134 | 0.99 | 2.20 | 0.15 | | | 31.25 | 68.37 | |
| 537 | ATP6AP1 | ATPase, H+ transporting, lysosomal accessory protein 1 | NM_001183 | CACAGTGACATTCAAGTTCAT SEQ ID NO. 11 | 1.19 | 0.77 | 0.55 | | | | | |
| | | | NM_001220 NM_172078 NM_172079 NM_172080 NM_172081 NM_172082 | | 8.59 | | | | | | | |
| 816 | CAMK2B | calcium/calmodulin-dependent protein kinase II beta | NM_172083 XM_001125861 | CACGACCATCCTGAACCCACA SEQ ID NO. 13 | | 0.82 | 0.37 | | | 15.63 | 63.29 | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | | |
|---|---|---|---|---|---|---|---|---|
| | | | NM_001220 NM_172078 NM_172079 NM_172080 NM_172081 NM_172082 | | | | | |
| 816 | CAMK28 | calcium/calmodulin-dependent protein kinase II beta | NM_172083 XM_001125861 | CCCGGAAGCAGGAGATCATTA SEQ ID NO. 586 | 8.22 | 5.48 | 3.46 | 7.81 | 57.73 |
| 975 | CD81 | CD81 molecule | NM_004356 | CACCTTCTATGTAGGCATCTA SEQ ID NO. 67 | 2.55 | ND | 0.41 | 3.91 | 40.47 |
| 975 | CD81 | CD81 molecule | NM_004356 | AAGGAACATCAGGCATGCTAA SEQ ID NO. 68 | 33.89 | ND | 10.60 | 1.95 | 31.65 |
| 1314 | COPA | coatomer protein complex, subunit alpha | NM_001098398 NM_004371 | CTGGCGCATGAATGAATCAAA SEQ ID NO. 152 | 2.79 | ND | 0.38 | 0.98 | 32.05 |
| 1314 | COPA | coatomer protein complex, subunit alpha | NM_001098398 NM_004371 | CTGGATTTCAACAGCTCCAAA SEQ ID NO. 151 | 15.46 | ND | 1.34 | | |
| 1394 | CRHR1 | corticotropin releasing hormone receptor 1 | NM_004382 XM_001128344 | CAGGTTGGTGACAGCCGCCTA SEQ ID NO. 155 | 8.13 | ND | 2.89 | 0.49 | 29.23 |
| 1394 | CRHR1 | corticotropin releasing hormone receptor 1 | NM_004382 XM_001128344 | CCGCTACAATACCACAAACAA SEQ ID NO. 156 | 47.82 | ND | 4.18 | | |
| 1434 | CSE1L | CSE1 chromosome segregation 1-like (yeast) | NM_001316 | CTGACGGTATCAAATATATTA SEQ ID NO. 16 | 14.69 | 0.48 | 1.71 | | |
| 1434 | CSE1L | CSE1 chromosome segregation 1-like (yeast) | NM_001316 | CAAATGAACTTGTAAACCTAA SEQ ID NO. 17 | 2.38 | 0.85 | 1.49 | 4.63 | 14.28 |
| 1434 | CSE1L | CSE1 chromosome segregation 1-like (yeast) | NM_001316 | CACGTTTGATAATCTTAAA SEQ ID NO. 587 | 79.25 | 0.77 | 2.17 | | |
| 1434 | CSE1L | CSE1 chromosome segregation 1-like (yeast) | NM_001316 | CAGGATAATGTTATCAAAGTA SEQ ID NO. 15 | 62.06 | 0.31 | 19.65 | 27.19 | 4.70 |
| 1521 | CTSW | cathepsin W | NM_001335 | CGCGTTCATAACTGTCCTCAA SEQ ID NO. 66 | 6.54 | 3.08 | 1.13 | | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | | | |
|---|---|---|---|---|---|---|---|---|---|
| 1832 | DSP | desmoplakin | NM_001008844 NM_004415 | CAGAAGAATGACTATGACCAA SEQ ID NO. 169 | 22.50 | ND | 0.74 | | |
| 1845 | DUSP3 | dual specificity phosphatase 3 | NM_004090 | CCGTATTTACTTAACAAGATT SEQ ID NO. 78 | 18.19 | 24.18 | 56.23 | 15.92 | 19.11 |
| 1845 | DUSP3 | dual specificity phosphatase 3 | NM_004090 | CCCGCGGATCTACGTGGGCAA SEQ ID NO. 77 | 13.82 | 0.83 | 0.26 | 5.15 | 18.20 |
| 2022 | ENG | endoglin | NM_000118 NM_001114753 | AAGGAGAACTTGAAACAGAT SEQ ID NO. 173 | 24.30 | ND | 0.49 | | |
| 2022 | ENG | endoglin | NM_000118 NM_001114753 | CAGCAATGAGGCGGTGGTCAA SEQ ID NO. 174 | 29.82 | ND | 0.55 | | |
| 2022 | ENG | endoglin | NM_000118 NM_001114753 | ACCAATAAATCAGACCATGAA SEQ ID NO. 589 | 111.60 | ND | 0.37 | | |
| 2045 | EPHA7 | EPH receptor A7 | NM_004440 | CCCAATGGAGTCATCACAGAA SEQ ID NO. 590 | 22.68 | ND | 0.54 | | |
| 2045 | EPHA7 | EPH receptor A7 | NM_004440 | CAGGCTGCGAAGGAAGTACTA SEQ ID NO. 176 | 46.54 | ND | 2.81 | | |
| 2050 | EPHB4 | EPH receptor B4 | NM_004444 | CACGAGCTCCCCTGGGAGGAAA SEQ ID NO. 178 | 15.54 | ND | 0.25 | | |
| 2050 | EPHB4 | EPH receptor B4 | NM_004444 | CTGCGGGACACCAGAAGAAA SEQ ID NO. 179 | 100.02 | ND | 0.83 | | |
| 2162 | F13A1 | coagulation factor XIII, A1 polypeptide | NM_000129 NM_000141 NM_022969 NM_022970 NM_022971 NM_022972 NM_022973 | CAAGGAGAGATGGGACACTAA SEQ ID NO. 18 | 0.41 | 0.24 | 0.12 | | |
| 2263 | FGFR2 | fibroblast growth factor receptor 2 | NM_022974 NM_022975 NM_022976 NM_023028 NM_023029 NM_023030 NM_023031 NM_000141 NM_022969 NM_022970 NM_022971 NM_022972 NM_022973 | CCCATCTGACAAGGGAAATTA SEQ ID NO. 69 | 6.89 | | 1.04 | | |
| 2263 | FGFR2 | fibroblast growth factor receptor 2 | NM_022974 NM_022975 NM_022976 NM_023028 NM_023029 NM_023030 NM_023031 NM_002011 NM_022963 | CGGAGGAGCGTTGCCATTCAA SEQ ID NO. 70 | 29.54 | ND | 3.63 | | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| ID | Gene | Description | Accession | Sequence / SEQ ID NO | col6 | col7 | col8 | col9 | col10 |
|---|---|---|---|---|---|---|---|---|---|
| 2264 | FGFR4 | fibroblast growth factor receptor 4 | NM_213647 | CCGCCTGACCTTCGGACCCTA SEQ ID NO. 20 | 8.88 | 1.38 | 0.38 | | |
| 2264 | FGFR4 | fibroblast growth factor receptor 4 | NM_002011 NM_022963 NM_213647 | CAGAGGGTTCTGGGCCTCTGA SEQ ID NO. 21 | 6.67 | 0.84 | 0.67 | | |
| 2357 | FPR1 | formyl peptide receptor 1 | NM_002029 | AACCAGTGACACAGCTACCAA SEQ ID NO. 23 | 50.76 | 3.67 | 1.26 | | |
| 2539 | G6PD | glucose-6-phosphate dehydrogenase | NM_000402 NM_001042351 | ATCGGGTGACCTGGCCAAGAA SEQ ID NO. 197 | 19.48 | 0.44 | 1.90 | | |
| 2550 | GABBR1 | gamma-aminobutyric acid (GABA) B receptor, 1 | NM_001470 NM_021903 | CACCCTCTCCTTGTCACAGAA SEQ ID NO. 42 | 19.95 | ND | 1.00 | | |
| 2550 | GABBR1 | gamma-aminobutyric acid (GABA) B receptor, 1 | NM_001470 NM_021903 | CTCCATTGCATTCATGTACTA SEQ ID NO. 43 | 7.91 | ND | 1.58 | | |
| 2580 | GAK | cyclin G associated kinase | NM_005255 XM_001127411 | AAGGCTAACTATGCCTCGAA SEQ ID NO. 198 | 2.52 | 1.38 | 7.07 | | |
| 3320 | HSP90AA1 | heat shock protein 90kDa alpha (cytosolic) class a member 1 | NM_001017963 NM_005348 | CAGAATGAAGGAGAACCAGAA SEQ ID NO. 212 | 27.13 | ND | 1.38 | | |
| 3320 | HSP90AA1 | heat shock protein 90kDa alpha (cystolic), class a member 1 | NM_001017963 NM_005348 | CTGCTTAAAGTTGTAACAAAT SEQ ID NO. 213 | 56.35 | ND | 22.88 | | |
| 3675 | ITGA3 | integrin, alpha 3 (antigen CD49C, alpha 3 subunit OF VLA-3 receptor) | NM_002204 | CTTCGCTTAGCATGGTAAATCA SEQ ID NO. 224 | 64.71 | 7.28 | 4.52 | | |
| 3675 | ITGA3 | integrin, alpha 3 (antigen CD49C, alpha 3 subunit OF VLA-3 receptor) | NM_002204 | CTGGATTGACTTTGCTGTCAA SEQ ID NO. 82 | 56.99 | 0.80 | 136.48 | | |
| 3717 | JAK2 | Janus kinase 2 (a protein tyrosine kinase) | NM_004972 | ATGATTGGCAATGACAAACAA SEQ ID NO. 45 | 8.84 | ND | 1.97 | | |
| 3717 | JAK2 | Janus kinase 2 (a protein tyrosine kinase) | NM_004972 | AGCCATCATACGAGATCTTAA SEQ ID NO. 44 | 64.18 | ND | 0.84 | | |
| 3837 | KPN81 | karyopherin (importin) beta 1 | NM_002265 | CAAGAACTCTTTGACATCTAA SEQ ID NO. 25 | 23.25 | 2.79 | 2.87 | 8.38 | 15.51 |
| 3837 | KPN81 | karyopherin (importin) beta 1 | NM_002265 | TCGGTTATATTTGCCAAGATA SEQ ID NO. 24 | 7.36 | 4.00 | 2.34 | 12.10 | 12.11 |
| 4193 | MDM2 | Mdm2, transformed 3T3 cell double minute 2, p53 binding protein (MOUSE) | EMPTY | CAGGCAAATGTGCAATACCAA SEQ ID NO. 238 | 26.61 | 0.31 | 0.67 | | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | | |
|---|---|---|---|---|---|---|---|---|
| 4193 | MDM2 | Mdm2, transformed 3T3 cell double minute 2, p53 binding protein (mouse) | EMPTY | | CCGGATCTTGATGCTGGTGTA SEQ ID NO. 239 | 189.46 | 2.63 | 1.69 |
| 4296 | MAP3K11 | mitogen-activated protein kinase kinase kinase 11 | NM_002419 | | CCGGCCTTGACCGGAGGAGAA SEQ ID NO. 63 | 14.25 | 1.43 | 0.47 | 27.41 | 14.70 |
| 4296 | MAP3K11 | mitogen-activated protein kinase kinase kinase 11 | NM_002419 | | CACATGGTACCTGGATTCAGA SEQ ID NO. 62 | 13.91 | 0.68 | 7.13 | 14.89 | 21.34 |
| 4923 | NTSR1 | neurotensin receptor 1 (high affinity) | NM_002531 | | CTGGCTTAAGAAGGTCGCCTA SEQ ID NO. 250 | 1.47 | 3.38 | 0.22 |
| 4923 | NTSR1 | neurotensin receptor 1 (high affinity) | NM_002531 NM_001128166 NM_001128167 NM_001128168 NM_001128172 | | AAGGGCCTCTAACAAGGAGAA SEQ ID NO. 251 | 3.16 | 0.29 | 0.34 |
| 5063 | PAK3 | p21 protein (Cdc42/Rac)-activated kinase 3 | NM_001128173 NM_002578 | | CAAGAAGGAATTAATTATTAA SEQ ID NO. 254 | 110.93 | | |
| 5566 | PRKACA | protein kinase, cAMP-dependent, catalytic, alpha | NM_002730 NM_207518 | | CAGAAGGTGGTGAAACTGAAA SEQ ID NO. 267 | 40.38 | 4.67 | 1.02 |
| 5566 | PRKACA | protein kinase, cAMP-dependent, catalytic, alpha | NM_002730 NM_207518 | | ACAGAAGGTGGTGAAACTGAA SEQ ID NO. 266 | 107.38 | 0.40 | 0.61 |
| 5584 | PRKCI | protein kinase C, iota | NM_002740 | | ACGCCGCTGGAGAAAGCTTTA SEQ ID NO. 270 | 212.72 | 0.31 | 1.11 |
| 5606 | MAP2K3 | mitogen-activated protein kinase kinase 3 | NM_145110 XM_001130488 NM_002756 NM_145109 | | CTGGATGCCATCCAAGTTGTA SEQ ID NO. 26 | 4.57 | 0.48 | 3.29 |
| 5606 | MAP2K3 | mitogen-activated protein kinase kinase 3 | NM_145110 XM_001130488 | | CCGGGCCACCGTGAACTCACA SEQ ID NO. 276 | 3.68 | 3.51 | 10.72 |
| 5757 | PTMA | prothymosin, alpha | NM_001099285 NM_002823 | | TTGTCCAACATAAACAGGAA SEQ ID NO. 283 | 1.32 | 1.39 | 0.13 |
| 5757 | PTMA | prothymosin, alpha | NM_001099285 NM_002823 | | TTGGTTTGTATGAGATGGTTA SEQ ID NO. 284 | 17.80 | 0.37 | 0.50 |
| 5961 | PRPH2 | retinal degeneration, slow | EMPTY | | CACGGATTTAGTCCCACCCTA SEQ ID NO. 75 | 6.69 | 1.54 | 4.21 |
| | | | | | | | 6.75 | 0.37 | 14.69 | 14.74 |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | | |
|---|---|---|---|---|---|---|---|---|
| 5961 | PRPH2 | retinal degeneration, slow | EMPTY | | GAGGAGCGATGTGATGAATAA SEQ ID NO. 76 | 90.87 | 1.61 | 9.14 13.34 15.30 |
| 6093 | ROCK1 | "Rho-associated, coiled-coil containing protein kinase 1" | NM_005406 | | AACGGTTAGAACAAGAGGTAA SEQ ID NO. 619 | 51.60 | 1.37 | 3.55 |
| 6093 | ROCK1 | "Rho-associated, coiled-coil containing protein kinase 1" | NM_005406 | | CAAGCTCGAATTACATCTTTA SEQ ID NO. 618 | 50.20 | 1.00 | 1.75 |
| 6204 | RPS10 | ribosomal protein S10 | NM_001014 | | TTGAATAAACTTACAGCCAAA SEQ ID NO. 47 | 39.36 | 1.81 | 1.58 |
| 6204 | RPS10 | ribosomal protein S10 | NM_001014 | | AACCGATTGCCATTTATGAA SEQ ID NO. 46 | 15.53 | 0.59 | 1.13 |
| 6224 | RPS20 | ribosomal protein S20 | NM_001023 | | CCCTAACAAGCCGCAACGTAA SEQ ID NO. 688 | 8.16 | 0.77 | 4.55 |
| 6224 | RPS20 | ribosomal protein S20 | NM_001023 | | TTCGCTCTCGCCGAGGAACAA SEQ ID NO. 689 | 34.44 | ND | 3.51 |
| 6224 | RPS20 | ribosomal protein S20 | NM_001023 | | CGCGGTCGTAAGGGCTGAGGA SEQ ID NO. 598 | 111.46 | 2.39 | 1.88 |
| 6357 | CCL13 | chemokine (C-C motif) ligand 13 | NM_005408 | | CCGGAAAGCTCACACCCTGAA SEQ ID NO. 696 | 3.68 | 0.48 | 0.19 |
| 6357 | CCL13 | chemokine (C-C motif) ligand 13 | NM_005408 | | ACTCTTAACCTTCAACATGAA SEQ ID NO. 697 | 17.28 | 1.00 | 0.25 |
| 6446 | SGK1 | serum/glucocorticoid regulated kinase | NM_005627 | | TACAGGCTTATTTGTAATGTA SEQ ID NO. 701 | 23.71 | 0.35 | 1.51 |
| 6613 | SUMO2 | SMT3 suppressor of mif two 3 homolog 2 (S. cerevisiae) | NM_001005849 | NM_006937 | AAGTAGGGATAAATTACTCTA SEQ ID NO. 90 | 7.30 | 0.58 | 0.26 |
| 6613 | SUMO2 | SMT3 suppressor of mif two 3 homolog 2 (S. cerevisiae) | NM_001005849 | NM_006937 | CTGTCTTTAAGTAGGGATAAA SEQ ID NO. 89 | 8.59 | 0.62 | 0.24 |
| 6627 | SNRPA1 | small nuclear ribonucleoprotein polypeptide A' | NM_003090 | | TAGCCTTGTTTGTTGTTAGCAA SEQ ID NO. 711 | 15.61 | ND | 0.25 |
| 6627 | SNRPA1 | small nuclear ribonucleoprotein polypeptide A' | EMPTY | | CAGCATTGTTGAAATGCTTAA SEQ ID NO. 602 | 65.10 | 1.75 | 2.35 |
| 6627 | SNRPA1 | small nuclear ribonucleoprotein polypeptide A' | EMPTY | | TCCACTCACTATGCTACCAAA SEQ ID NO. 603 | 63.11 | 4.08 | 1.36 |
| 7786 | MAP3K12 | mitogen-activated protein kinase kinase kinase 12 | NM_006301 | | CAGGAGCACTATGAAAGGAA SEQ ID NO. 60 | 30.14 | 0.66 | 0.19 |
| 8021 | NUP214 | nucleoporin 214kDa | NM_005085 | | CACCATAGAATCTCACACCAA SEQ ID NO. 29 | 9.56 | 1.15 | 1.72 |
| 8021 | NUP214 | nucleoporin 214kDa | NM_005085 | | CCCGGAGATGATCCCAACAAA SEQ ID NO. 28 | 5.79 | 2.51 | 3.31 |
| 8677 | STX10 | syntaxin 10 | NM_003765 | | CAGCAGCTGATCATGGATGAA SEQ ID NO. 31 | 27.05 | 1.44 | 1.45 |
| 8677 | STX10 | syntaxin 10 ATPase, H+ transporting, lysosomal 38kDa, | NM_003765 | | CAGAGAGATACTCGCAGGCAA SEQ ID NO. 30 | 3.58 | 0.84 | 0.87 |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | |
|---|---|---|---|---|---|---|---|
| 9114 | ATP6V0D1 | ATPase, H+ transporting, lysosomal 38kDa, V0 subunit d1 | NM_004691 | CACTTTCATGTTCCTCCCTAA SEQ ID NO. 313 | 3.38 | ND | 0.99 |
| 9114 | ATP6V0D1 | ATPase, H+ transporting, lysosomal 38kDa, V0 subunit d1 | NM_004691 | CCGCGCCTTCATCATCACCAT SEQ ID NO. 314 | 27.03 | ND | 0.58 |
| 9114 | ATP6V0D1 | ATPase, H+ transporting, lysosomal 38kDa, V0 subunit d1 | NM_004691 | AAGGCTCTCAATTGCACTCTT SEQ ID NO. 604 | 12.63 | ND | 0.20 |
| 9114 | ATP6V0D1 | ATPase, H+ transporting, lysosomal 38kDa, V0 subunit d1 | NM_004691 | CAACTACATCCCTATCTTCTA SEQ ID NO. 605 | 29.94 | ND | 0.41 |
| 9135 | RABEP1 | rabaptin, RAB GTPase binding effector protein 1 | NM_001083585 NM_004703 | CAGGATAAAGCCGAACTGGTA SEQ ID NO. 316 | 34.82 | 2.09 | 0.77 |
| 9135 | RABEP1 | rabaptin, RAB GTPase binding effector protein 1 | NM_001083585 NM_004703 | CTGGAAGACTTCATAAAGCAA SEQ ID NO. 315 | 45.94 | 0.88 | 0.52 |
| 9180 | OSMR | oncostatin M receptor | NM_003999 | TAGCTCTAATCTAATATATAA SEQ ID NO. 322 | 20.30 | 0.34 | 0.45 |
| 9180 | OSMR | oncostatin M receptor | NM_003999 | TAGCATAGATTGTCAAATGTA SEQ ID NO. 321 | 126.96 | 1.20 | 1.52 |
| 9230 | RAB11B | RAB11B, member RAS oncogene family | EMPTY | CGAGTTCAACCTGGAGAGCAA SEQ ID NO. 325 | 18.86 | 8.43 | 17.34 |
| 9230 | RAB11B | RAB11B, member RAS oncogene family | EMPTY | CCGCATCACCTTCCGCGTACTA SEQ ID NO. 48 | 30.18 | 0.60 | 0.43 |
| 9231 | DLGS | discs, large homolog 5 (Drosophila) | NM_004747 | ACGGAACTTGATACAGCACAA SEQ ID NO. 326 | 4.57 | ND | 0.34 |
| 9231 | DLGS | discs, large homolog 5 (Drosophila) | NM_004747 | TTCGAGTAACTTGCAGTTCAA SEQ ID NO. 327 | 33.50 | ND | 1.35 |
| 9256 | BZRAP1 | benzodiazepine receptor (peripheral) associated protein 1 | EMPTY | CACAGTGAGTATGTAACTTGA SEQ ID NO. 329 | 24.59 | 0.55 | 0.80 |
| 9256 | BZRAP1 | benzodiazepine receptor (peripheral) associated protein 1 | EMPTY | CCGCCCGTCTGGTGGTCCTCAA SEQ ID NO. 328 | 2.01 | 2.93 | 4.11 |
| 9276 | COPB2 | coatomer protein complex, subunit beta 2 (beta prime) | NM_004766 NR_023350 | CCCAGTCAGGTTTCAAGGGTA SEQ ID NO. 606 | 2.23 | ND | 1.60 |
| 9972 | NUP153 | nucleoporin 153kDa | NM_005124 | ATGGAACGCGTTGAAATTGTA SEQ ID NO. 349 | 32.58 | ND | 0.50 |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| Gene ID | Symbol | Description | Accession | Sequence (SEQ ID NO) | 6 | 7 | 8 | 9 | 10 |
|---|---|---|---|---|---|---|---|---|---|
| 9972 | NUP153 | nucleoporin 153kDa | NM_005124 | CACCATTATGTGCGCTGATAA SEQ ID NO. 348 | 267.82 | ND | 0.76 | | |
| 10055 | SAE1 | SUMO1 activating enzyme subunit 1 | NM_005500 | TCCGACTACTTTCTCCTTCAA SEQ ID NO. 352 | 5.48 | 1.09 | 1.07 | | |
| 10055 | SAE1 | SUMO1 activating enzyme subunit 1 | NM_005500 | CTGAGCAGTGAGAAAGCAAA SEQ ID NO. 353 | 50.73 | 1.29 | 10.22 | | |
| 10181 | RBM5 | RNA binding motif protein 5 | NM_005778 | CAGGATATTACTATGATCCGA SEQ ID NO. 607 | 7.26 | 1.79 | 5.80 | | |
| 10181 | RBM5 | RNA binding motif protein 5 | NM_005778 | CGCGTCTTTAGCTGTCAATAA SEQ ID NO. 362 | 77.41 | 0.87 | 10.25 | | |
| 10291 | SF3A1 | splicing factor 3a, subunit 1, 120kDa | NM_001005409 NM_005877 | CAGGATAAGACGGAATGGAAA SEQ ID NO. 32 | 12.17 | 0.30 | 1.33 | | |
| 10291 | SF3A1 | splicing factor 3a, subunit 1, 120kDa | NM_001005409 NM_005877 | CGCAAGGATTATGATCCCAAA SEQ ID NO. 33 | 12.65 | 1.02 | 0.59 | | |
| 10381 | TUBB3 | tubulin, beta 3 | NM_006086 NM_006738 NM_007200 | TTGCTGTCAGATACCCTTAAA SEQ ID NO. 370 | 4.00 | ND | 1.16 | | |
| 11214 | AKAP13 | A kinase (PRKA) anchor protein 13 | NM_144767 NM_006738 NM_007200 | CAGGATTACACTGAAAGTAAT SEQ ID NO. 51 | 7.40 | 60.41 | 82.26 | 13.56 | 17.14 |
| 11214 | AKAP13 | A kinase (PRKA) anchor protein 13 | NM_144767 | CCGCCTGTTTGGGTTAACAAA SEQ ID NO. 50 | 36.95 | 3.27 | 4.80 | | |
| 22820 | COPG | coatomer protein complex, subunit gamma | NM_016128 | CCGAGCCACCTTCTACCTAAA SEQ ID NO. 34 | 2.23 | 1.72 | 0.39 | | |
| 22820 | COPG | coatomer protein complex, subunit gamma | NM_016128 | CAGGAAAGGGACATTGTAAAT SEQ ID NO. 608 | 25.96 | 1.45 | 1.19 | | |
| 23604 | DAPK2 | death-associated protein kinase 2 | NM_014326 | CGGAATTTGTTGCTCCAGAAA SEQ ID NO. 402 | 34.16 | ND | 1.56 | 9.92 | 17.26 |
| 23604 | DAPK2 | death-associated protein kinase 2 | NM_014326 | CTGGTTAAAGAGACCCGGAAA SEQ ID NO. 609 | 54.86 | ND | 2.18 | | |
| 29127 | RACGAP1 | Rac GTPase activating protein 1 | NM_001126104 NM_013277 NM_001126103 | CTGGTAGATAGAAGAGCTAAA SEQ ID NO. 420 | 76.87 | 0.23 | 1.39 | | |
| 29127 | RACGAP1 | Rac GTPase activating protein 1 | NM_001126104 NM_013277 | CACCACAGACACCAGATATTA SEQ ID NO. 419 | 40.76 | 1.13 | 5.18 | | |
| 29882 | ANAPC2 | anaphase promoting complex subunit 2 | NM_013366 | AAGGTTCTTCTACCGCATCTA SEQ ID NO. 421 | 1.48 | 1.47 | 0.59 | | |
| 29882 | ANAPC2 | anaphase promoting complex subunit 2 | NM_013366 | GAGAGTCTATATGCAGAGTAA SEQ ID NO. 422 | 32.19 | 0.47 | 0.45 | | |
| 29959 | NRBP1 | nuclear receptor binding protein 1 | NM_013392 | AGGCGAGAAGAGGTGAATCAA SEQ ID NO. 424 | 23.48 | ND | 2.71 | | |
| 51393 | TRPV2 | transient receptor potential cation channel, subfamily V, member 2 | NM_016113 | CAGAGGATCTTTCCAACCACA SEQ ID NO. 36 | 9.67 | 2.53 | 1.73 | | |
| 51393 | TRPV2 | transient receptor potential cation channel, subfamily V, member 2 | NM_016113 | CCAGTGAATTCTGTGTGGCAAA SEQ ID NO. 37 | 56.47 | 2.57 | 3.22 | | |
| 54866 | PPP1R14D | protein phosphatase 1, regulatory (inhibitor) subunit 14D | NM_017726 | CAGGAGCTCTTCCAGGATCAA SEQ ID NO. 39 | 24.28 | 2.53 | 0.89 | | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| 54866 | PPP1R14D | subunit 14D | NM_017726 | GAGCCTGAGATTGACCTGGAA SEQ ID NO. 38 | 16.08 | 1.39 | 1.41 | | |
| --- | --- | --- | --- | --- | --- | --- | --- | --- | --- |
| 57579 | FAM135A | family with sequence similarity 135, member A | NM_001105531 NM_020819 | CAGCAATTACATTAAATTCAA SEQ ID NO. 53 | 21.76 | 3.44 | 5.55 | | |
| 57579 | FAM135A | family with sequence similarity 135, member A | NM_001105531 NM_020819 | CACGAAGAACTAAGAATATTA SEQ ID NO. 52 | 64.25 | 2.11 | 0.44 | | |
| 58526 | MID1IP1 | MID1 interacting protein 1 (gastrulation specific G12 homolog (zebrafish)) | NM_001098791 NM_021242 NM_001098790 | CAGCCACTACGTGCTTCTCAA SEQ ID NO. 488 | 164.08 | 2.11 | 1.27 | | |
| 58526 | MID1IP1 | MID1 interacting protein 1 (gastrulation specific G12 homolog (zebrafish)) | NM_001098791 NM_021242 NM_001098790 | CTCGCTCTTTAACGCCATGAA SEQ ID NO. 489 | 71.87 | 2.26 | 1.71 | | |
| 79574 | EPS8L3 | EPS8-like 3 | NM_024526 NM_133181 | AGCCATTTACTTGCACCGGAA SEQ ID NO. 55 | 2.74 | 2.72 | 6.95 | | |
| 79574 | EPS8L3 | EPS8-like 3 | NM_024526 NM_133181 | CCGGAAGGAGTACTCCCAGAA SEQ ID NO. 54 | 11.69 | 0.24 | 5.38 | | |
| 80231 | CXorf21 | chromosome X open reading frame 21 | NM_139053 | CTGAAGTCATGTGTGAATCA SEQ ID NO. 611 | 87.78 | 0.47 | 0.23 | | |
| 80231 | CXorf21 | chromosome X open reading frame 21 | EMPTY | AAGTTGTGGAGTTATATAAA SEQ ID NO. 503 | 103.43 | 1.54 | 0.36 | | |
| 93953 | ACRC | acidic repeat containing | EMPTY | CCCATGACAATAGTGATGAT SEQ ID NO. 57 | 14.76 | 4.33 | 3.96 | | |
| 93953 | ACRC | acidic repeat containing | NM_052957 | TAGTACTGTTAAGTAAGTAA SEQ ID NO. 56 | 69.98 | 2.33 | 1.01 | | |
| 113878 | DTX2 | deltex homolog 2 (Drosophila) | NM_001102596 NM_020892 NM_001102594 NM_001102595 | CAAGACAGAGATGGACCGCAA SEQ ID NO. 84 | 2.80 | 1.27 | 3.03 | | |
| 113878 | DTX2 | deltex homolog 2 (Drosophila) | NM_001102596 NM_020892 NM_001102594 NM_001102595 | CGGGACCATCCTCATAGTTTA SEQ ID NO. 614 | 29.12 | 0.29 | 1.48 | | |
| 113878 | DTX2 | deltex homolog 2 (Drosophila) | NM_001102596 NM_020892 NM_001102594 NM_001102595 | CAGGGAAAGATGGAGGTATTA SEQ ID NO. 683 | 42.26 | 0.85 | 4.37 | | |
| 113878 | DTX2 | deltex homolog 2 (Drosophila) | NM_001102596 NM_020892 NM_001102594 NM_001102595 | CCAGTGCTACCTTCCAGACAA SEQ ID NO. 684 | 190.80 | 0.24 | 0.38 | | |

TABLE 8-continued

Examination of interferon induction in siRNA-transfected cells. A549 cells transfected with the indicated siRNAs were either mock infected (column 7) or infected with influenza A/PR/8/34 virus (MOI = 0.5) (column 8). At 6h post-infection RNA was collected and interferon (IFN)-β mRNA was quantified by qRT-PCR. Control samples were set to 1. For reference, siRNA-mediated reduction in viral gene expression (average of NP, M1 mRNA) is shown in column 6. A select number of siRNAs were also tested in an IFN bioassay to detect biologically-relevant amounts of IFN released from siRNA-transfected cells either mock infected (column 9) or infected with influenza A/PR/8/34 virus (MOI = 3) (column 10). Controls included (shaded): an siRNA targeting the viral NS1 protein as well as infection with a recombinant PR8 virus lacking NS1 expression. In both cases, this results in IFN induction. Furthermore a standard curve of recombinant IFN treatment is shown (shaded). ND = no data.

| | | | | | | | | | |
|---|---|---|---|---|---|---|---|---|---|
| 122525 | C14orf28 | chromosome 14 open reading frame 28 | NM_001017923 XM_071793 | AACAAAGAGGAACATCATTAT SEQ ID NO. 534 | 46.02 | 3.24 | 4.53 | | |
| 122525 | C14orf28 | chromosome 14 open reading frame 28 | NM_001017923 XM_071793 | AAGTCCATAAAGCTTCATTAA SEQ ID NO. 535 | 47.03 | 0.72 | 0.68 | | |
| 167681 | PRSS35 | protease, serine, 35 | NM_153362 | CCGTAGTGAGATCACTTCATA SEQ ID NO. 40 | 4.23 | 2.08 | 0.46 | | |
| 167681 | PRSS35 | protease, serine, 35 | NM_153362 | TACGGCTAACAGAGACCTGAA SEQ ID NO. 41 | 23.97 | 4.09 | 0.71 | | |
| 254065 | BRWD3 | bromodomain and WD repeat domain containing 3 | NM_153252 | CACAGTTATTACTGCAGTGAA SEQ ID NO. 79 | 4.30 | 2.33 | 17.53 | 35.45 | 11.75 |
| 254065 | BRWD3 | bromodomain and WD repeat domain containing 3 | NM_153252 | AAGACAGTCTTTAAAGTGTAA SEQ ID NO. 80 | 74.10 | 0.31 | 0.77 | 17.53 | 26.34 |
| 387082 | SUMO4 | SMT3 suppressor of mif two 3 homolog 4 (S. cerevisiae) | NM_001002255 | TTGATGTGTTTCAACAGCCTA SEQ ID NO. 87 | 14.90 | ND | 0.51 | | |
| 387082 | SUMO4 | SMT3 suppressor of mif two 3 homolog 4 (S. cerevisiae) | NM_001002255 | TACTGCATTCTCAATTAGAAA SEQ ID NO. 88 | 16.41 | ND | 1.11 | | |
| 387082 | SUMO4 | SMT3 suppressor of mif two 3 homolog 4 (S. cerevisiae) | NM_001002255 | TCCCATTTGGTGGGCAACCAA SEQ ID NO. 564 | 57.27 | ND | 0.91 | | |
| 387911 | RP11-45B20.2 | collagen triple helix repeat-containing | NM_001007537 | AAAGGAGATCGAGGAGAGAAA SEQ ID NO. 59 | 17.61 | 1.24 | 0.61 | | |
| 387911 | RP11-45B20.2 | collagen triple helix repeat-containing | NM_001007537 | CAGCATTGTCCTGCCAGCTGAA SEQ ID NO. 58 | 44.41 | 2.57 | 2.48 | | |
| 643641 | LOC643641 | KIAA0543, KIAA0543 protein | EMPTY | CCCGATCTTCCTTCCACCTAA SEQ ID NO. 577 | 62.31 | 3.47 | 0.58 | | |
| 643641 | LOC643641 | KIAA0543, KIAA0543 protein | EMPTY | AAGGTTATACAGGACCATTCA SEQ ID NO. 578 | 152.10 | 0.61 | 1.17 | | |

TABLE 9

Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

| Gene_ID | Symbol | Description | SEQ ID NO. | target sequence |
|---|---|---|---|---|
| 372 | ARCN1 | archain 1 | 1 | CCCACTTGTGTCAATATTAAA |
| 372 | ARCN1 | archain 1 | 2 | AAGGCTGAGATGCGTCGTAAA |
| 523 | ATP6V1A | ATPase, H+ transporting, lysosomal 70 kDa, V1 subunit A | 3 | GAGCTTGAATTTGAAGGTGTA |
| 523 | ATP6V1A | ATPase, H+ transporting, lysosomal 70 kDa, V1 subunit A | 4 | ATGGAGGTTGATGGTAAGGTA |
| 526 | ATP6V1B2 | ATPase, H+ transporting, lysosomal 56/58 kDa, V1 subunit B2 | 5 | ACCATGTTACCCTGTAATTAA |
| 526 | ATP6V1B2 | ATPase, H+ transporting, lysosomal 56/58 kDa, V1 subunit B2 | 6 | CACGGTTAATGAAGTCTGCTA |
| 527 | ATP6V0C | ATPase, H+ transporting, lysosomal 16 kDa, V0 subunit c | 7 | CAGCCACAGAATATTATGTAA |
| 527 | ATP6V0C | ATPase, H+ transporting, lysosomal 16 kDa, V0 subunit c | 8 | TCCCAGCTATCTATAACCTTA |
| 533 | ATP6V0B | ATPase, H+ transporting, lysosomal 21 kDa, V0 subunit b | 9 | CATGGCAATTGTCATTAGCAA |
| 533 | ATP6V0B | ATPase, H+ transporting, lysosomal 21 kDa, V0 subunit b | 10 | TCCTAGTGTTTGTGAAATAAA |
| 537 | ATP6AP1 | ATPase, H+ transporting, lysosomal accessory protein 1 | 11 | CACAGTGACATTCAAGTTCAT |
| 537 | ATP6AP1 | ATPase, H+ transporting, lysosomal accessory protein 1 | 12 | TAGCAAATGCTCCCTCCTTAA |
| 816 | CAMK2B | calcium/calmodulin-dependent protein kinase II beta | 13 | CACGACCATCCTGAACCCACA |
| 816 | CAMK2B | calcium/calmodulin-dependent protein kinase II beta | 14 | CAGGATCTCTGACATCCTGAA |
| 1434 | CSE1L | CSE1 chromosome segregation 1-like (yeast) | 15 | CAGGATAATGTTATCAAAGTA |
| 1434 | CSE1L | CSE1 chromosome segregation 1-like (yeast) | 16 | CTGACGGTATCAAATATATTA |
| 1434 | CSE1L | CSE1 chromosome segregation 1-like (yeast) | 17 | CAAATGAACTTGTAAACCTAA |
| 2162 | F13A1 | coagulation factor XIII, A1 polypeptide | 18 | CAAGGAGAGATGGGACACTAA |
| 2162 | F13A1 | coagulation factor XIII, A1 polypeptide | 19 | GCUGGAGCUAUGGUCAGUU |
| 2264 | FGFR4 | fibroblast growth factor receptor 4 | 20 | CCGCCTGACCTTCGGACCCTA |
| 2264 | FGFR4 | fibroblast growth factor receptor 4 | 21 | CAGGAGGTTCTGGGCCTCTGA |
| 2357 | FPR1 | formyl peptide receptor 1 | 22 | GUGACACAGCUACCAAUUC |

TABLE 9-continued

Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

| Gene_ID | Symbol | Description | SEQ ID NO. | target sequence |
|---|---|---|---|---|
| 2357 | FPR1 | formyl peptide receptor 1 | 23 | AACCAGTGACACAGCTACCAA |
| 3837 | KPNB1 | karyopherin (importin) beta 1 | 24 | TCGGTTATATTTGCCAAGATA |
| 3837 | KPNB1 | karyopherin (importin) beta 1 | 25 | CAAGAACTCTTTGACATCTAA |
| 5606 | MAP2K3 | mitogen-activated protein kinase kinase 3 | 26 | CTGGATGCCATCCAAGTTGTA |
| 5606 | MAP2K3 | mitogen-activated protein kinase kinase 3 | 27 | ACGGATATCCTGCATGTCCAA |
| 8021 | NUP214 | nucleoporin 214 kDa | 28 | CCCGGAGATGATCCCAACAAA |
| 8021 | NUP214 | nucleoporin 214 kDa | 29 | CACCATAGAATCTCACACCAA |
| 8677 | STX10 | syntaxin 10 | 30 | CAGAGAGATACTCGCAGGCAA |
| 8677 | STX10 | syntaxin 10 | 31 | CAGCAGCTGATCATGGATGAA |
| 10291 | SF3A1 | splicing factor 3a, subunit 1, 120 kDa | 32 | CAGGATAAGACGGAATGGAAA |
| 10291 | SF3A1 | splicing factor 3a, subunit 1, 120 kDa | 33 | CGCAAGGATTATGATCCCAAA |
| 22820 | COPG | coatomer protein complex, subunit gamma | 34 | CCGAGCCACCTTCTACCTAAA |
| 22820 | COPG | coatomer protein complex, subunit gamma | 35 | AGGCCCGTGTATTTAATGAAA |
| 51393 | TRPV2 | transient receptor potential cation channel, subfamily V, member 2 | 36 | CAGAGGATCTTTCCAACCACA |
| 51393 | TRPV2 | transient receptor potential cation channel, subfamily V, member 2 | 37 | CCAGTGAATTCTGGTGGCAAA |
| 54866 | PPP1R14D | protein phosphatase 1, regulatory (inhibitor) subunit 14D | 38 | GAGCCTGAGATTGACCTGGAA |
| 54866 | PPP1R14D | protein phosphatase 1, regulatory (inhibitor) subunit 14D | 39 | CAGGAGCTCTTCCAGGATCAA |
| 167681 | PRSS35 | protease, serine, 35 | 40 | CCGTAGTGAGATCACTTCATA |
| 167681 | PRSS35 | protease, serine, 35 | 41 | TACGGCTAACAGAGACCTGAA |
| 2550 | GABBR1 | gamma-aminobutyric acid (GABA) B receptor, 1 | 42 | CACCCTCTCCTTGTCACAGAA |
| 2550 | GABBR1 | gamma-aminobutyric acid (GABA) B receptor, 1 | 43 | CTCCATTGCATTCATGTACTA |
| 3717 | JAK2 | Janus kinase 2 (a protein tyrosine kinase) | 44 | AGCCATCATACGAGATCTTAA |
| 3717 | JAK2 | Janus kinase 2 (a protein tyrosine kinase) | 45 | ATGATTGGCAATGACAAACAA |
| 6204 | RPS10 | ribosomal protein S10 | 46 | AACCGGATTGCCATTTATGAA |

TABLE 9-continued

Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

| Gene_ID | Symbol | Description | SEQ ID NO. | target sequence |
|---|---|---|---|---|
| 6204 | RPS10 | RPS10, ribosomal protein S10 | 47 | TTGAATAAACTTACAGCCAAA |
| 9230 | RAB11B | RAB11B, member RAS oncogene family | 48 | CCGCATCACCTCCGCGTACTA |
| 9230 | RAB11B | RAB11B, member RAS oncogene family | 49 | CACGGACGGACAGAAGCCCAA |
| 11214 | AKAP13 | A kinase (PRKA) anchor protein 13 | 50 | CCGCCTGTTTGGGTTAACAAA |
| 11214 | AKAP13 | A kinase (PRKA) anchor protein 13 | 51 | CAGGATTACACTGAAAGTAAT |
| 57579 | FAM135A | family with sequence similarity 135, member A | 52 | CACGAAGAACTAAGAATATTA |
| 57579 | FAM135A | family with sequence similarity 135, member A | 53 | CAGCAATTACATTAAATTCAA |
| 79574 | EPS8L3 | EPS8-like 3 | 54 | CCGGAAGGAGTACTCCCAGAA |
| 79574 | EPS8L3 | EPS8-like 3 | 55 | AGCCATTTACTTGCACCGGAA |
| 93953 | ACRC | acidic repeat containing | 56 | TAGGTACTGTTAAGTAAGTAA |
| 93953 | ACRC | acidic repeat containing | 57 | CCCGATGACAATAGTGATGAT |
| 387911 | RP11-45820.2 | collagen triple helix repeat-containing | 58 | CAGCATTGTCCTGCAGCTGAA |
| 387911 | RP11-45820.2 | collagen triple helix repeat-containing | 59 | AAAGGAGATCGAGGAGAGAAA |
| 7786 | MAP3K12 | mitogen-activated protein kinase kinase kinase 12 | 60 | CAGGGAGCACTATGAAAGGAA |
| 7786 | MAP3K12 | mitogen-activated protein kinase kinase kinase 12 | 61 | CCACGAAAUCGCCCAUCAU |
| 4296 | MAP3K11 | mitogen-activated protein kinase kinase kinase 11 | 62 | CACATGGTACCTGGATTCAGA |
| 4296 | MAP3K11 | mitogen-activated protein kinase kinase kinase 11 | 63 | CCGGCCTTGACCGGAGGAGAA |
| 2048 | EPHB2 | EPH receptor B2 | 177 | /5Phos/rGrGrCrUrArCrGrGrArCrCrArArGrUrUrArUrCrGrGCG |
| 2048 | EPHB2 | EPH receptor B2 | 64 | GGAGACCUUCAACCUCUAU |
| 1521 | CTSW | cathepsin W | 65 | UACCUGUGGCAUCACCAAG |
| 1521 | CTSW | cathepsin W | 66 | CGCGTTCATAACTGTCCTCAA |
| 975 | CD81 | CD81 antigen | 67 | CACCTTCTATGTAGGCATCTA |
| 975 | CD81 | CD81 antigen | 68 | AAGGAACATCAGGCATGCTAA |
| 2263 | FGFR2 | fibroblast growth factor receptor 2 | 69 | CCCATCTGACAAGGGAAATTA |

TABLE 9-continued

Evaluation of host factors that regulate influenza virus entry. A subset of siRNAs targeting factors shown to be required for efficient growth of wild-type influenza virus (see TABLE 9-continued Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

Gene_ID Symbol   Description                   SEQ ID NO. target sequence

| | | Pseudotyped particle (Relative % entry) | | | VLP-BlaM1 (Relative % entry) | Entry | Post entry |
|---|---|---|---|---|---|---|---|
| Gene_ID | Symbol | WSN | VSV-G | MMLV | WSN | factors | factors |
| 372 | ARCN1 | 1.5 | 1.1 | 23.4 | 34.1 | Y | |
| 372 | ARCN1 | 1.2 | 0.9 | 14 | 25 | Y | |
| 523 | ATP6V1A | 17.5 | 50.8 | 90.2 | 53 | Y | |
| 523 | ATP6V1A | 11.2 | 13.5 | 35.9 | 48.2 | Y | |
| 526 | ATP6V1B2 | 9.9 | 10.6 | 84.2 | | Y | |
| 526 | ATP6V1B2 | 12.1 | 13.5 | 61.7 | | Y | |
| 527 | ATP6V0C | 4.1 | 8.7 | 122 | 15.5 | Y | |
| 527 | ATP6V0C | 2.5 | 13.1 | 187.6 | 41.1 | Y | |
| 533 | ATP6V0B | 8.2 | 34.4 | 82 | | Y | |
| 533 | ATP6V0B | 1.6 | 2 | 33.9 | | Y | |
| 537 | ATP6AP1 | 4 | 20.7 | 138.3 | | Y | |
| 537 | ATP6AP1 | 2.1 | 7.5 | 73.7 | | Y | |
| 816 | CAMK2B | 60 | 49.5 | | | | Y |
| 816 | CAMK2B | 105 | 99.6 | | | | Y |
| 1434 | CSE1L | 77.3 | 60 | | | | Y |
| 1434 | CSE1L | 44.6 | 31.9 | | | | Y |
| 1434 | CSE1L | 82.7 | 72 | | | | Y |
| 2162 | F13A1 | 5.9 | 6.3 | 30.2 | | | Y |
| 2162 | F13A1 | 3.7 | 12.8 | 44.8 | | | Y |
| 2264 | FGFR4 | 13.4 | 16.3 | 68 | | Y | |
| 2264 | FGFR4 | 32.8 | 21.8 | 56 | | Y | |
| 2357 | FPR1 | 19.5 | 54.4 | | | | |
| 2357 | FPR1 | 60.7 | 35.5 | | | | |
| 3837 | KPNB1 | 61 | 51.6 | | | | Y |
| 3837 | KPNB1 | 47.5 | 38.8 | | | | Y |
| 5606 | MAP2K3 | 10.6 | 10 | 97.9 | | Y | |
| 5606 | MAP2K3 | 11.3 | 33.7 | 48.9 | | Y | |
| 8021 | NUP214 | 6.5 | 14.8 | 56.1 | | | |
| 8021 | NUP214 | 97.7 | 104.7 | 193.4 | | | |

TABLE 9-continued

Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

| Gene_ID | Symbol | Description | | | | | | SEQ ID NO. target sequence | |
|---|---|---|---|---|---|---|---|---|---|
| 8677 | STX10 | 2.8 | 9.6 | 32.4 | | | | | |
| 8677 | STX10 | 17.6 | 20.4 | 31.3 | | | | | |
| 10291 | SF3A1 | 3.5 | 4 | 16 | 89.7 | | | Y | |
| 10291 | SF3A1 | 3.3 | 5.2 | 27.9 | 62.8 | | | Y | |
| 22820 | COPG | 4 | 3.1 | 38.5 | 51.1 | Y | | | |
| 22820 | COPG | 5.6 | 12.1 | 43.6 | 79.5 | Y | | | |
| 51393 | TRPV2 | 20.5 | 30.4 | | | | | | |
| 51393 | TRPV2 | 94.4 | 97.4 | | | | | | |
| 54866 | PPP1R14D | 59.6 | 64 | | | | | | Y |
| 54866 | PPP1R14D | 64.9 | 84.5 | | | | | | Y |
| 167681 | PRSS35 | 68.5 | 85.9 | | | | | | Y |
| 167681 | PRSS35 | 131 | 149 | | | | | | Y |
| 2550 | GABBR1 | 31.7 | 151.9 | 76.7 | 97 | Y | | | |
| 2550 | GABBR1 | 13 | 15.7 | 56.1 | 166.3 | Y | | | |
| 3717 | JAK2 | 44.4 | 41.1 | 161.2 | | Y | | | |
| 3717 | JAK2 | 18.1 | 20.6 | 50.4 | | Y | | | |
| 6204 | RPS10 | 136.8 | 120.7 | | | | | | Y |
| 6204 | RPS10 | 133 | 102.3 | | | | | | Y |
| 9230 | RAB11B | 20.9 | 27.3 | 115.6 | | Y | | | |
| 9230 | RAB11B | 8.2 | 10 | 50.8 | | Y | | | |
| 11214 | AKAP13 | 13 | 7.4 | 43.5 | | Y | | | |
| 11214 | AKAP13 | 26.4 | 17.2 | 89.2 | | Y | | | |
| 57579 | FAM135A | 5.3 | 10.9 | 57.4 | | Y | | | |
| 57579 | FAM135A | 14.9 | 19.1 | 54.8 | | Y | | | |
| 79574 | EPS8L3 | 33 | 43.3 | | 110.4 | | | | |
| 79574 | EPS8L3 | 32.8 | 33.8 | | 180.2 | | | | |
| 93953 | ACRC | 91.9 | 110.6 | | | | | | |
| 93953 | ACRC | 38.7 | 40.2 | | | | | | |
| 387911 | RP11-45820.2 | 32.4 | 21.1 | | 123.8 | | | | |
| 387911 | RP11-45820.2 | 44.8 | 32.1 | | 213.6 | | | | |
| 7786 | MAP3K12 | 261.9 | 282.2 | | | | | | Y |
| 7786 | MAP3K12 | 70.8 | 99.9 | | | | | | Y |

TABLE 9-continued

Evaluation of host factors that regulate influenza virus entry. A subset of siRNAs targeting factors shown to be required for efficient growth of wild-type influenza virus (see Table 7), were evaluated for their effects on infection with pseudotyped lentivirus particles. Particles bearing envelopes derived from either influenza virus HA (WSN) (column 5), Vesicular stomatitis virus (VSV)-G protein (column 6) or Murine leukemia virus (MMLV) Envelope (Env) (column 7) were examined. Additionally, the effects of host factor depletion on entry of an influenza virus-like particle (VLP) was also assessed using a b-lactamase (Bla)-M1 assay (see Methods section) (column 8). Identified entry factors are marked with a Y in column 9; post-entry factors are designated in column 10.

| Gene_ID | Symbol | Description | | | | | | SEQ ID NO. target sequence |
|---|---|---|---|---|---|---|---|---|
| 4296 | MAP3K11 | 64.2 | 121 | 90.4 | | | | |
| 4296 | MAP3K11 | 22.9 | 20.8 | 34.6 | | | | |
| 2048 | EPHB2 | 45.3 | 26 | 121.1 | 104.7 | Y | | |
| 2048 | EPHB2 | 28.1 | 22.1 | 83.0 | 103.2 | Y | | |
| 1521 | CTSW | 35.8 | 103.0 | 44.8 | 88.6 | Y | | |
| 1521 | CTSW | 24.8 | 33.7 | 55.4 | | Y | | |
| 975 | CD81 | 3 | 8.6 | 68.9 | | Y | | |
| 975 | CD81 | 18.9 | 3.6 | 68 | | Y | | |
| 2263 | FGFR2 | 93 | 25.2 | 332.7 | | Y | | |
| 2263 | FGFR2 | 32.7 | 46.5 | 252.3 | | Y | | |
| 10783 | NEK6 | 44.4 | 36.3 | 222.2 | | Y | | |
| 10783 | NEK6 | 33.4 | 36.6 | 297.5 | | Y | | |
| 2932 | GSK3B | 37.8 | 34.7 | 95.9 | | Y | | |
| 2932 | GSK3B | 13.7 | 33.4 | 30.4 | | Y | | |
| 5961 | PRPH2 | 8.3 | 12.5 | 339.8 | | | | |
| 5961 | PRPH2 | 233.3 | 140.7 | 363.8 | | | | |
| 1845 | DUSP3 | 13.6 | 2.6 | 37.7 | | Y | | |
| 1845 | DUSP3 | 22.6 | 9 | 79 | | Y | | |
| 254065 | BRWD3 | 30.5 | 48.6 | 67 | | Y | | |
| 254065 | BRWD3 | 14.2 | 3.6 | 68 | | Y | | |
| 3675 | ITGA3 | 10 | 19.6 | 48.9 | | Y | | |
| 3675 | ITGA3 | 47.5 | 36.4 | 152.5 | | Y | | |
| 113878 | DTX2 | 27.4 | 21.5 | 30.5 | | | | |
| 113878 | DTX2 | 21.7 | 46.5 | 41.6 | | | | |
| 203068 | TUBB | 29.5 | 29.5 | 282.4 | | | | |
| 203068 | TUBB | 77.6 | 98.8 | 248.6 | | | | |
| 387082 | SUMO4 | 58.5 | 72.8 | 273.7 | | | Y | |
| 387082 | SUMO4 | 63.7 | 113.2 | 351.1 | | | Y | |
| 6613 | SUMO2 | 109.8 | 100.4 | 279.2 | | | | |
| 6613 | SUMO2 | 32.8 | 59.2 | 347.1 | | | | |

TABLE 10

Effects of host factor depletion on expression of an influenza virus mini-genome reporter. 293T cells were transfected with siRNAs targeting the indicated genes and transfected again 48 h later with an influenza virus mini-genome reporter construct encoding firefly luciferase and expression plasmids for NP, PB1, PB2, PA. In addition a Renilla luciferase expression construct under the control of an SV40 promoter was co-transfected. The percent firefly (column 5) and Renilla luciferase (column 6) expression relative to the control (SC1) is shown.

| Gene ID | Gene Symbol | Description | SEQ ID NO. | target sequence | Ave expression relative to SC1 control | |
|---|---|---|---|---|---|---|
| | | | | | Influenza firefly luc reporter | Constitutive Renilla luc reporter |
| CONTROL | RPS27A | | | | 5.67 | 14.25 |
| CONTROL | SC1 | | | | 100.00 | 100.00 |
| CONTROL | FF | | | | 5.38 | 79.84 |
| 372 | ARCN1 | archain 1 | 1 | CCCACTTGTGTCAATATTAAA | 24.44 | 44.06 |
| 372 | ARCN1 | archain 1 | 2 | AAGGCTGAGATGCGTCGTAAA | 2.08 | 8.00 |
| 523 | ATP6V1A | ATPase, H+ transporting, lysosomal 70 kDa, V1 subunit A | 3 | GAGCTTGAATTTGAAGGTGTA | 54.82 | 66.45 |
| 523 | ATP6V1A | ATPase, H+ transporting, lysosomal 70 kDa, V1 subunit A | 4 | ATGGAGGTTGATGGTAAGGTA | 51.49 | 45.58 |
| 526 | ATP6V1B2 | ATPase, H+ transporting, lysosomal 56/58 kDa, V1 subunit B2 | 5 | CACGGTTAATGAAGTCTGCTA | 27.45 | 38.64 |
| 526 | ATP6V1B2 | ATPase, H+ transporting, lysosomal 56/58 kDa, V1 subunit B2 | 6 | ACCATGTTACCCTGTAATTAA | 50.97 | 79.99 |
| 527 | ATP6V0C | ATPase, H+ transporting, lysosomal 16 kDa, V0 subunit c | 7 | CAGCCACAGAATATTATGTAA | 55.07 | 43.16 |
| 527 | ATP6V0C | ATPase, H+ transporting, lysosomal 16 kDa, V0 subunit c | 8 | TCCCAGCTATCTATAACCTTA | 175.42 | 85.82 |
| 533 | ATP6V0B | ATPase, H+ transporting, lysosomal 21 kDa, V0 subunit b | 9 | TCCTAGTGTTTGTGAAATAAA | 65.64 | 65.35 |
| 533 | ATP6V0B | ATPase, H+ transporting, lysosomal 21 kDa, V0 subunit b | 10 | CATGGCAATTGTCATTAGCAA | 9.84 | 21.26 |
| 537 | ATP6AP1 | ATPase, H+ transporting, lysosomal accessory protein 1 | 11 | CACAGTGACATTCAAGTTCAT | 63.59 | 70.04 |
| 537 | ATP6AP1 | ATPase, H+ transporting, lysosomal accessory protein 1 | 12 | CAGGGAAGTCCTCACAGGCAA | 32.86 | 45.61 |
| 816 | CAMK2B | calcium/calmodulin-dependent protein kinase II beta | 13 | CAGGATCTCTGACATCCTGAA | 53.27 | 78.82 |
| 816 | CAMK2B | calcium/calmodulin-dependent protein kinase II beta | 14 | CACGACCATCCTGAACCCACA | 34.95 | 86.56 |
| 1434 | CSE1L | CSE1 chromosome segregation 1-like (yeast) | 15 | CAGGATAATGTTATCAAAGTA | 29.41 | 155.71 |
| 1434 | CSE1L | CSE1 chromosome segregation 1-like (yeast) | 16 | CTGACGGTATCAAATATATTA | 28.13 | 199.31 |
| 2162 | F13A1 | coagulation factor XIII, A1 polypeptide | 17 | CAAGGAGAGATGGGACACTAA | 3.83 | 32.16 |

TABLE 10-continued

Effects of host factor depletion on expression of an influenza virus mini-genome reporter. 293T cells were transfected with siRNAs targeting the indicated genes and transfected again 48 h later with an influenza virus mini-genome reporter construct encoding firefly luciferase and expression plasmids for NP, PB1, PB2, PA. In addition a Renilla luciferase expression construct under the control of an SV40 promoter was co-transfected. The percent firefly (column 5) and Renilla luciferase (column 6) expression relative to the control (SC1) is shown.

| Gene ID | Gene Symbol | Description | SEQ ID NO. | target sequence | Ave expression relative to SC1 control | |
|---|---|---|---|---|---|---|
| | | | | | Influenza firefly luc reporter | Constitutive Renilla luc reporter |
| 2162 | F13A1 | coagulation factor XIII, A1 polypeptide | 18 | GCUGGAGCUAUGGUCAGUU | 15.62 | 63.72 |
| 2264 | FGFR4 | fibroblast growth factor receptor 4 | 19 | CCGCCTGACCTTCGGACCCTA | 37.60 | 30.60 |
| 2264 | FGFR4 | fibroblast growth factor receptor 4 | 20 | CAGGAGGTTCTGGGCCTCTGA | 102.79 | 130.61 |
| 2357 | FPR1 | formyl peptide receptor 1 | 21 | AACCAGTGACACAGCTACCAA | 53.88 | 86.58 |
| 2357 | FPR1 | formyl peptide receptor 1 | 22 | GUGACACAGCUACCAAUUC | 168.96 | 81.53 |
| 2550 | GABBR1 | gamma-aminobutyric acid (GABA) B receptor, 1 | 23 | CTCCATTGCATTCATGTACTA | 83.18 | 88.23 |
| 2550 | GABBR1 | gamma-aminobutyric acid (GABA) B receptor, 1 | 24 | CACCCTCTCCTTGTCACAGAA | 39.24 | 149.09 |
| 2932 | GSK3B | glycogen synthase kinase 3 beta | 25 | CACTCAAGAACTGTCAAGTAA | 38.96 | 110.23 |
| 2932 | GSK3B | glycogen synthase kinase 3 beta | 26 | TCAGTTGGTAGAAATAATCAA | 127.38 | 125.29 |
| 3837 | KPNB1 | karyopherin (importin) beta 1 | 27 | TCGGTTATATTTGCCAAGATA | 13.98 | 14.07 |
| 3837 | KPNB1 | karyopherin (importin) beta 1 | 28 | CAAGAACTCTTTGACATCTAA | 7.79 | 9.82 |
| 5606 | MAP2K3 | mitogen-activated protein kinase kinase 3 | 29 | ACGGATATCCTGCATGTCCAA | 73.66 | 71.12 |
| 5606 | MAP2K3 | mitogen-activated protein kinase kinase 3 | 30 | CTGGATGCCATCCAAGTTGTA | 92.74 | 97.72 |
| 6204 | RPS10 | ribosomal protein S10 | 31 | AACCGGATTGCCATTTATGAA | 35.17 | 172.43 |
| 6204 | RPS10 | ribosomal protein S10 | 32 | TTGAATAAACTTACAGCCAAA | 140.03 | 227.25 |
| 8021 | NUP214 | nucleoporin 214 kDa | 33 | CCCGGAGATGATCCCAACAAA | 10.27 | 30.94 |
| 8021 | NUP214 | nucleoporin 214 kDa | 34 | CACCATAGAATCTCACACCAA | 8.52 | 26.66 |
| 8677 | STX10 | syntaxin 10 | 35 | CAGCAGCTGATCATGGATGAA | 40.85 | 83.43 |
| 8677 | STX10 | syntaxin 10 | 36 | CAGAGAGATACTCGCAGGCAA | 75.65 | 166.42 |
| 9230 | RAB11B | RAB11B, member RAS oncogene family | 37 | CCGCATCACCTCCGCGTACTA | 35.92 | 70.27 |
| 9230 | RAB11B | RAB11B, member RAS oncogene family | 38 | CACGGACGGACAGAAGCCCAA | 98.27 | 136.22 |
| 10291 | SF3A1 | splicing factor 3a, subunit 1, 120 kDa | 39 | CAGGATAAGACGGAATGGAAA | 2.32 | 2.97 |
| 10291 | SF3A1 | splicing factor 3a, subunit 1, 120 kDa | 40 | CGCAAGGATTATGATCCCAAA | 1.68 | 2.17 |
| 10783 | NEK6 | NIMA (never in mitosis gene a)-related kinase 6 | 41 | CTGGCGGACTTCCAGATCGAA | 288.96 | 298.85 |

TABLE 10-continued

Effects of host factor depletion on expression of an influenza virus mini-genome reporter. 293T cells were transfected with siRNAs targeting the indicated genes and transfected again 48 h later with an influenza virus mini-genome reporter construct encoding firefly luciferase and expression plasmids for NP, PB1, PB2, PA. In addition a Renilla luciferase expression construct under the control of an SV40 promoter was co-transfected. The percent firefly (column 5) and Renilla luciferase (column 6) expression relative to the control (SC1) is shown.

| Gene ID | Gene Symbol | Description | SEQ ID NO. | target sequence | Ave expression relative to SC1 control | |
|---|---|---|---|---|---|---|
| | | | | | Influenza firefly luc reporter | Constitutive Renilla luc reporter |
| 10783 | NEK6 | NIMA (never in mitosis gene a)-related kinase 6 | 42 | ACCACGGAAGTCGAGAATTAA | 254.31 | 131.97 |
| 51393 | TRPV2 | transient receptor potential cation channel, subfamily V, member 2 | 43 | CAGAGGATCTTTCCAACCACA | 95.81 | 83.01 |
| 51393 | TRPV2 | transient receptor potential cation channel, subfamily V, member 2 | 44 | CCAGTGAATTCTGGTGGCAAA | 107.80 | 138.50 |
| 54866 | PPP1R14D | protein phosphatase 1, regulatory (inhibitor) subunit 14D | 45 | CAGGAGCTCTTCCAGGATCAA | 31.33 | 47.81 |
| 54866 | PPP1R14D | protein phosphatase 1, regulatory (inhibitor) subunit 14D | 46 | GAGCCTGAGATTGACCTGGAA | 30.24 | 134.18 |
| 58526 | MID1IP1 | MID1 interacting protein 1 (gastrulation specific G12 homolog (zebrafish)) | 47 | CAGCCACTACGTGCTTCTCAA | 50.67 | 122.79 |
| 58526 | MID1IP1 | MID1 interacting protein 1 (gastrulation specific G12 homolog (zebrafish)) | 48 | CTCGCTCTTTAACGCCATGAA | 80.13 | 74.64 |
| 79574 | EPS8L3 | EPS8-like 3 | 49 | AGCCATTTACTTGCACCGGAA | 228.02 | 247.79 |
| 79574 | EPS8L3 | EPS8-like 3 | 50 | CCGGAAGGAGTACTCCCAGAA | 15.53 | 58.80 |
| 93953 | ACRC | acidic repeat containing | 51 | CCCGATGACAATAGTGATGAT | 28.38 | 42.33 |
| 93953 | ACRC | acidic repeat containing | 52 | TAGGTACTGTTAAGTAAGTAA | 298.50 | 116.52 |
| 167681 | PRSS35 | protease, serine, 35 | 53 | CCGTAGTGAGATCACTTCATA | 35.19 | 54.56 |
| 167681 | PRSS35 | protease, serine, 35 | 54 | GGAGAAAGAGACAGGUGUA | 34.02 | 46.48 |
| 387911 | RP11-45B20.2 | collagen triple helix repeat-containing | 55 | AAAGGAGATCGAGGAGAGAAA | 99.33 | 109.81 |
| 387911 | RP11-45B20.2 | collagen triple helix repeat-containing | 56 | CAGCATTGTCCTGCAGCTGAA | 90.66 | 108.48 |
| 57579 | FAM135A | family with sequence similarity 135, member A | 57 | CAGCAATTACATTAAATTCAA | 192.55 | 121.13 |
| 57579 | FAM135A | family with sequence similarity 135, member A | 58 | CACGAAGAACTAAGAATATTA | 62.22 | 93.42 |

TABLE 11

Expression levels of host factor after siRNA silencing. siRNA transfected A549 cells were analyzed 54 h post transfection by quantitative RT-PCR for the expression levels of 12 host genes found to inhibit WSN and SOIV (swine origin influenza A/Netherlands/602/2009 virus) replication (FIG. 3e; columns 1-3). The siRNA target is shown in column 4. The efficacy of the siRNAs to target their cognate mRNAs for degradation was examined using qRT-PCR (column 5). Negative controls were set to the value of 1. Standard deviation of quadruplicate experiments is depicted in column 6.

| Gene ID | Gene Symbol | Description | SEQ ID NO. | target sequence | Gene expression Relative (Negative Control = 1) | Standard deviation |
|---|---|---|---|---|---|---|
| 816 | CAMK2B | calcium/calmodulin-dependent protein kinase II beta | 13 | CACGACCATCCTGAACCCACA | 0.164 | 0.058 |
| 816 | CAMK2B | calcium/calmodulin-dependent protein kinase II beta | 14 | CAGGATCTCTGACATCCTGAA | 0.283 | 0.079 |
| 975 | CD81 | CD81 molecule | 67 | CACCTTCTATGTAGGCATCTA | 0.035 | 0.022 |
| 975 | CD81 | CD81 molecule | 68 | AAGGAACATCAGGCATGCTAA | 0.172 | 0.096 |
| 372 | ARCN1 | archain 1 | 1 | CCCACTTGTGTCAATATTAAA | 0.231 | 0.010 |
| 372 | ARCN1 | archain 1 | 2 | AAGGCTGAGATGCGTCGTAAA | 0.213 | 0.022 |
| 58526 | MID1IP1 | MID1 interacting protein 1 (gastrulation specific G12 homolog (zebrafish)) | 488 | CAGCCACTACGTGCTTCTCAA | 0.053 | 0.014 |
| 58526 | MID1IP1 | MID1 interacting protein 1 (gastrulation specific G12 homolog (zebrafish)) | 489 | CTCGCTCTTTAACGCCATGAA | 0.493 | 0.047 |
| 527 | ATP6V0C | ATPase, H+ transporting, lysosomal 16 kDa, V0 subunit c | 7 | CAGCCACAGAATATTATGTAA | 0.039 | 0.027 |
| 527 | ATP6V0C | ATPase, H+ transporting, lysosomal 16 kDa, V0 subunit c | 8 | TCCCAGCTATCTATAACCTTA | 0.024 | 0.014 |
| 5606 | MAP2K3 | mitogen-activated protein kinase kinase 3 | 26 | CTGGATGCCATCCAAGTTGTA | 0.139 | 0.029 |
| 5606 | MAP2K3 | mitogen-activated protein kinase kinase 3 | 27 | ACGGATATCCTGCATGTCCAA | 0.230 | 0.115 |
| 2264 | FGFR4 | fibroblast growth factor receptor 4 | 20 | CCGCCTGACCTTCGGACCCTA | 0.037 | 0.021 |
| 2264 | FGFR4 | fibroblast growth factor receptor 4 | 21 | CAGGAGGTTCTGGGCCTCTGA | 0.029 | 0.016 |
| 1434 | CSE1L | CSE1 chromosome segregation 1-like (yeast) | 15 | CAGGATAATGTTATCAAAGTA | 0.054 | 0.011 |
| 1434 | CSE1L | CSE1 chromosome segregation 1-like (yeast) | 16 | CTGACGGTATCAAATATATTA | 0.094 | 0.013 |
| 1434 | CSE1L | CSE1 chromosome segregation 1-like (yeast) | 17 | CAAATGAACTTGTAAACCTAA | 0.073 | 0.006 |
| 2932 | GSK3B | glycogen synthase kinase 3 beta | 73 | CACTCAAGAACTGTCAAGTAA | 0.121 | 0.069 |
| 2932 | GSK3B | glycogen synthase kinase 3 beta | 74 | TCAGTTGGTAGAAATAATCAA | 0.064 | 0.027 |
| 6613 | SUMO2 | SMT3 suppressor of mif two 3 homolog 2 (*S. cerevisiae*) | 89 | CTGTCTTTAAGTAGGGATAAA | 0.225 | 0.032 |
| 6613 | SUMO2 | SMT3 suppressor of mif two 3 homolog 2 (*S. cerevisiae*) | 90 | AAGTAGGGATAAATTACTCTA | 0.186 | 0.147 |
| 2550 | GABBR1 | gamma-aminobutyric acid (GABA) B receptor, 1 | 42 | CACCCTCTCCTTGTCACAGAA | 0.343 | 0.091 |

TABLE 11-continued

Expression levels of host factor after siRNA silencing. siRNA transfected A549 cells were analyzed 54 h post transfection by quantitative RT-PCR for the expression levels of 12 host genes found to inhibit WSN and SOIV (swine origin influenza A/Netherlands/602/2009 virus) replication (FIG. 3e; columns 1-3). The siRNA target is shown in column 4. The efficacy of the siRNAs to target their cognate mRNAs for degradation was examined using qRT-PCR (column 5). Negative controls were set to the value of 1. Standard deviation of quadruplicate experiments is depicted in column 6.

| Gene ID | Gene Symbol | Description | SEQ ID NO. | target sequence | Gene expression Relative (Negative Control = 1) | Standard deviation |
|---|---|---|---|---|---|---|
| 2550 | GABBR1 | gamma-aminobutyric acid (GABA) B receptor, 1 | 43 | CTCCATTGCATTCATGTACTA | 0.262 | 0.034 |
| 167681 | PRSS35 | protease, serine, 35 | 40 | CCGTAGTGAGATCACTTCATA | 0.072 | 0.008 |
| 167681 | PRSS35 | protease, serine, 35 | 41 | TACGGCTAACAGAGACCTGAA | 0.048 | 0.019 |

8. REFERENCES

The references listed in this section include those cited in Section 6 supra.

Ashburner, M. et al. Gene ontology: tool for the unification of biology. The Gene Ontology Consortium. *Nat Genet* 25, 25-29 (2000).

Apweiler, R. et al. The InterPro database, an integrated documentation resource for protein families, domains and functional sites. *Nucleic acids research* 29, 37-40 (2001).

Huang da, W., Sherman, B. T. & Lempicki, R. A. Systematic and integrative analysis of large gene lists using DAVID bioinformatics resources. *Nat Protoc* 4, 44-57 (2009).

Terada, N. et al. Rapamycin inhibits the phosphorylation of p70 S6 kinase in IL-2 and mitogen-activated human T cells. *Biochem Biophys Res Commun* 186, 1315-1321 (1992).

Price, D. J., Grove, J. R., Calvo, V., Avruch, J. & Bierer, B. E. Rapamycin-induced inhibition of the 70-kilodalton S6 protein kinase. *Science* 257, 973-977 (1992).

Chung, J., Kuo, C. J., Crabtree, G. R. & Blenis, J. Rapamycin-FKBP specifically blocks growth-dependent activation of and signaling by the 70 kd S6 protein kinases. *Cell* 69, 1227-1236 (1992).

Hardcastle, A. et al. Solid-phase immunoassays in mechanism-based drug discovery: their application in the development of inhibitors of the molecular chaperone heat-shock protein 90. *Assay Drug Dev Technol* 3, 273-285 (2005).

Sharp, S. Y. et al. In vitro biological characterization of a novel, synthetic diaryl pyrazole resorcinol class of heat shock protein 90 inhibitors. *Cancer Res* 67, 2206-2216 (2007).

Smith, N. F. et al. Preclinical pharmacokinetics and metabolism of a novel diaryl pyrazole resorcinol series of heat shock protein 90 inhibitors. *Mol Cancer Ther* 5, 1628-1637 (2006).

Desbene, S. & Giorgi-Renault, S. Drugs that inhibit tubulin polymerization: the particular case of podophyllotoxin and analogues. *Curr Med Chem Anticancer Agents* 2, 71-90 (2002).

Renhowe, P. A. et al. Design, structure-activity relationships and in vivo characterization of 4-amino-3-benzimidazol-2-ylhydroquinolin-2-ones: a novel class of receptor tyrosine kinase inhibitors. *J Med Chem* 52, 278-292 (2009).

Supriyono, A. et al. Bioactive alkaloids from the tropical marine sponge Axinella carteri. *Z Naturforsch C* 50, 669-674 (1995).

Meijer, L. et al. Inhibition of cyclin-dependent kinases, GSK-3beta and CK1 by hymenialdisine, a marine sponge constituent. *Chem Biol* 7, 51-63 (2000).

Melzig, M. F. & Bormann, H. Betulinic acid inhibits aminopeptidase N activity. *Planta Med* 64, 655-657 (1998).

Sorensen, M. G., Henriksen, K., Neutzsky-Wulff, A. V., Dziegiel, M. H. & Karsdal, M. A. Diphyllin, a novel and naturally potent V-ATPase inhibitor, abrogates acidification of the osteoclastic resorption lacunae and bone resorption. *J Bone Miner Res* 22, 1640-1648 (2007).

Marsh, G. A., Hatami, R. & Palese, P. Specific residues of the influenza A virus hemagglutinin viral RNA are important for efficient packaging into budding virions. *J Virol* 81, 9727-9736 (2007).

Chanda, S. K. et al. Genome-scale functional profiling of the mammalian AP-1 signaling pathway. *Proceedings of the National Academy of Sciences of the United States of America* 100, 12153-12158 (2003).

Aza-Blanc, P. et al. Identification of modulators of TRAIL-induced apoptosis via RNAi-based phenotypic screening. *Molecular cell* 12, 627-637 (2003).

Konig, R. et al. A probability-based approach for the analysis of large-scale RNAi screens. *Nat Methods* 4, 847-849 (2007).

Goto, H. & Kawaoka, Y. A novel mechanism for the acquisition of virulence by a human influenza A virus. *Proc Natl Acad Sci USA* 95, 10224-10228 (1998).

Zhou, Y. et al. In silico gene function prediction using ontology-based pattern identification. *Bioinformatics* (Oxford, England) 21, 1237-1245 (2005).

Young, J. A. et al. The *Plasmodium falciparum* sexual development transcriptome: a microarray analysis using ontology-based pattern identification. *Molecular and biochemical parasitology* 143, 67-79 (2005).

Rines, D. R. et al. Whole genome functional analysis identifies novel components required for mitotic spindle integrity in human cells. *Genome Biol* 9, R44 (2008).

Stertz, S. et al. The antiviral potential of interferon-induced cotton rat Mx proteins against orthomyxovirus (influenza), rhabdovirus, and bunyavirus. *J Interferon Cytokine Res* 27, 847-855 (2007).

O'Neill, R. E., Talon, J. & Palese, P. The influenza virus NEP (NS2 protein) mediates the nuclear export of viral ribonucleoproteins. *EMBO J* 17, 288-296 (1998).

Hoffmann, H. H., Palese, P. & Shaw, M. L. Modulation of influenza virus replication by alteration of sodium ion transport and protein kinase C activity. *Antiviral Res* 80, 124-134 (2008).

Donelan, N. R., Basler, C. F. & Garcia-Sastre, A. A recombinant influenza A virus expressing an RNA-binding-defective NS1 protein induces high levels of beta interferon and is attenuated in mice. *J Virol* 77, 13257-13266 (2003).

Park, M. S. et al. *Newcastle disease virus* (NDV)-based assay demonstrates interferonantagonist activity for the NDV V protein and the Nipah virus V, W, and C proteins. *J Virol* 77, 1501-1511 (2003).

Palese, P. & Shaw, M. L. Orthomyxoviridae: The Viruses and Their Replication, in Fields Virology, 5th Edition, Vol. 2. (eds. D. M. Knipe & P. M. Howley) 1647-1689 (Lippincott Williams & Wilkins, Philadelphia; 2007).

Wang, T. T. & Palese, P. Unraveling the mystery of swine influenza virus. Cell 137, 983-985 (2009).

Marsh, G. A., Hatami, R. & Palese, P. Specific residues of the influenza A virus hemagglutinin viral RNA are important for efficient packaging into budding virions. J Virol 81, 9727-9736 (2007).

Sato, S., Fujita, N. & Tsuruo, T. Modulation of Akt kinase activity by binding to Hsp90. Proc Natl Acad Sci USA 97, 10832-10837 (2000).

Sarbassov, D. D., Guertin, D. A., Ali, S. M. & Sabatini, D. M. Phosphorylation and regulation of Akt/PKB by the rictor-mTOR complex. Science 307, 1098-1101 (2005).

Beer, C., Andersen, D. S., Rojek, A. & Pedersen, L. Caveola-dependent endocytic entry of amphotropic murine leukemia virus. J Virol 79, 10776-10787 (2005).

McClure, M. O., Sommerfelt, M. A., Marsh, M. & Weiss, R. A. The pH independence of mammalian retrovirus infection. J Gen Virol 71 (Pt 4), 767-773 (1990).

Whitney, J. A., Gomez, M., Sheff, D., Kreis, T. E. & Mellman, I. Cytoplasmic coat proteins involved in endosome function. Cell 83, 703-713 (1995).

Aniento, F., Gu, F., Parton, R. G. & Gruenberg, J. An endosomal beta COP is involved in the pH-dependent formation of transport vesicles destined for late endosomes. J Cell Biol 133, 29-41 (1996).

Tscherne, D. M., Manicassamy, B. & Garcia-Sastre, A. An Enzymatic Virus-like Particle Assay For Sensitive Detection of Virus Entry. J of Virological Methods (in press).

Kutay, U., Bischoff, F. R., Kostka, S., Kraft, R. & Gorlich, D. Export of importin alpha from the nucleus is mediated by a specific nuclear transport factor. Cell 90, 1061-1071 (1997).

Colbran, R. J. Targeting of calcium/calmodulin-dependent protein kinase II. Biochem J 378, 1-16 (2004).

Sumi, M. et al. The newly synthesized selective Ca2+/calmodulin dependent protein kinase II inhibitor KN-93 reduces dopamine contents in PC12 h cells. Biochem Biophys Res Commun 181, 968-975 (1991).

9. EQUIVALENTS

Those skilled in the art will recognize or be able to ascertain, using no more than routine experimentation, many equivalents to the specific embodiments described herein. Such equivalents are intended to be encompassed by the embodiments described herein and exemplified in the paragraphs of Section 10.

All references cited herein are incorporated herein by reference in their entirety and for all purposes to the same extent as if each individual publication or patent or patent application was specifically and individually indicated to be incorporated by reference in its entirety for all purposes.

The invention is not to be limited in scope by the specific embodiments described herein. Indeed, various modifications of the invention in addition to the embodiments described herein will become apparent to those skilled in the art from the foregoing description and accompanying figures. Such modifications are intended to fall within the scope of the invention.

10. EXEMPLARY EMBODIMENTS

The following paragraphs provide non-limiting, exemplary embodiments.

1. A method of inhibiting replication of an influenza virus in a human subject, comprising administering to a human subject in need thereof an effective amount of a compound that reduces or inhibits the expression and/or activity of one or more of the following human host cell factors: AKAP13; ARCN; BRWD3; CD81; COPG; CTSW; DUSP3; EPHB2; FAM135A; FGFR2; FGFR4; GABBR1; GSK3B; ITGA3; JAK2; MAP2K3; NEK6; RAB11B; or one or more of the v-ATPase subunits, ATP6V0B, ATP6V0C, ATP6V1A, ATP6V1B2, or ATP6AP1.

2. A method of inhibiting replication of an influenza virus in a human subject, comprising administering to a human subject in need thereof an effective amount of a compound that reduces or inhibits the expression and/or activity of one or more of the following human host cell factors: CAMK2B; CSE1L; F13A1; KPNB1; MAP3K12; PP1R14D; PRSS35; RPS10; SF3A1; or SUMO4.

3. A method of inhibiting replication of an influenza virus in a human subject, comprising administering to a human subject in need thereof an effective amount of a compound that reduces or inhibits the expression and/or activity of one or more of the following human host cell factors: ACRC; DTX2; EPS8L3; FPR1; MAP3K11; NUP214; PRPH2; RP11-45B20.2; STX10; SUMO2; TRPV2; or TUBB.

4. A method of inhibiting replication of an influenza virus in a human subject, comprising administering to a human subject in need thereof an effective amount of a compound that reduces or inhibits the expression and/or activity of one or more of the following human host cell factors: ANPEP; CAM2 KB; FGFR4; FRAP1 (mTOR); GSK3B/CSNK1G2; HSP90AA1; or TUBB.

5. The method of any one of paragraphs 1 to 4 wherein the compound does not inhibit the expression or activity of v-ATPase subunit or an HSP90.

6. A method of inhibiting replication of an influenza virus in a human subject, comprising administering to a human subject in need thereof an effective amount of Betulinic acid, CCT018159, Diphyllin, KN-93, Podophyllotoxin, or Sirolimus.

7. The method of paragraph 6 wherein the compound is not CCT018159 or Diphyllin.

8. A method of inhibiting replication of an influenza virus in a human subject, comprising administering to a human subject in need thereof a nucleic acid compound that targets a sequence selected from the following:

| SEQUENCE | SEQ ID NO. |
|---|---|
| CCCACTTGTGTCAATATTAAA | 1 |
| AAGGCTGAGATGCGTCGTAAA | 2 |
| GAGCTTGAATTTGAAGGTGTA | 3 |
| ATGGAGGTTGATGGTAAGGTA | 4 |
| ACCATGTTACCCTGTAATTAA | 5 |
| CACGGTTAATGAAGTCTGCTA | 6 |
| CAGCCACAGAATATTATGTAA | 7 |
| TCCCAGCTATCTATAACCTTA | 8 |
| CATGGCAATTGTCATTAGCAA | 9 |
| TCCTAGTGTTTGTGAAATAAA | 10 |
| CACAGTGACATTCAAGTTCAT | 11 |
| TAGCAAATGCTCCCTCCTTAA | 12 |
| CACGACCATCCTGAACCCACA | 13 |
| CAGGATCTCTGACATCCTGAA | 14 |
| CAGGATAATGTTATCAAAGTA | 15 |
| CTGACGGTATCAAATATATTA | 16 |
| CAAATGAACTTGTAAACCTAA | 17 |
| CAAGGAGAGATGGGACACTAA | 18 |
| GCUGGAGCUAUGGUCAGUU | 19 |
| CCGCCTGACCTTCGGACCCTA | 20 |
| CAGGAGGTTCTGGGCCTCTGA | 21 |
| GUGACACAGCUACCAAUUC | 22 |
| AACCAGTGACACAGCTACCAA | 23 |
| TCGGTTATATTTGCCAAGATA | 24 |
| CAAGAACTCTTTGACATCTAA | 25 |
| CTGGATGCCATCCAAGTTGTA | 26 |
| ACGGATATCCTGCATGTCCAA | 27 |
| CCCGGAGATGATCCCAACAAA | 28 |
| CACCATAGAATCTCACACCAA | 29 |
| CAGAGAGATACTCGCAGGCAA | 30 |
| CAGCAGCTGATCATGGATGAA | 31 |
| CAGGATAAGACGGAATGGAAA | 32 |
| CGCAAGGATTATGATCCCAAA | 33 |
| CCGAGCCACCTTCTACCTAAA | 34 |
| AGGCCCGTGTATTTAATGAAA | 35 |
| CAGAGGATCTTTCCAACCACA | 36 |
| CCAGTGAATTCTGGTGGCAAA | 37 |
| GAGCCTGAGATTGACCTGGAA | 38 |
| CAGGAGCTCTTCCAGGATCAA | 39 |
| CCGTAGTGAGATCACTTCATA | 40 |

| SEQUENCE | SEQ ID NO. |
|---|---|
| TACGGCTAACAGAGACCTGAA | 41 |
| CACCCTCTCCTTGTCACAGAA | 42 |
| CTCCATTGCATTCATGTACTA | 43 |
| AGCCATCATACGAGATCTTAA | 44 |
| ATGATTGGCAATGACAAACAA | 45 |
| AACCGGATTGCCATTTATGAA | 46 |
| TTGAATAAACTTACAGCCAAA | 47 |
| CCGCATCACCTCCGCGTACTA | 48 |
| CACGGACGGACAGAAGCCCAA | 49 |
| CCGCCTGTTTGGGTTAACAAA | 50 |
| CAGGATTACACTGAAAGTAAT | 51 |
| CACGAAGAACTAAGAATATTA | 52 |
| CAGCAATTACATTAAATTCAA | 53 |
| CCGGAAGGAGTACTCCCAGAA | 54 |
| AGCCATTTACTTGCACCGGAA | 55 |
| TAGGTACTGTTAAGTAAGTAA | 56 |
| CCCGATGACAATAGTGATGAT | 57 |
| CAGCATTGTCCTGCAGCTGAA | 58 |
| AAAGGAGATCGAGGAGAGAAA | 59 |
| CAGGGAGCACTATGAAAGGAA | 60 |
| CCACGAAAUCGCCCAUCAU | 61 |
| CACATGGTACCTGGATTCAGA | 62 |
| CCGGCCTTGACCGGAGGAGAA | 63 |
| GGAGACCUUCAACCUCUAU | 64 |
| UACCUGUGGCAUCACCAAG | 65 |
| CGCGTTCATAACTGTCCTCAA | 66 |
| CACCTTCTATGTAGGCATCTA | 67 |
| AAGGAACATCAGGCATGCTAA | 68 |
| CCCATCTGACAAGGGAAATTA | 69 |
| CGGAGGAGCGTTGCCATTCAA | 70 |
| CTGGCGGACTTCCAGATCGAA | 71 |
| ACCACGAAGTCGAGAATTAA | 72 |
| CACTCAAGAACTGTCAAGTAA | 73 |
| TCAGTTGGTAGAAATAATCAA | 74 |
| CACGGATTTAGTCCCACCCTA | 75 |
| GAGGAGCGATGTGATGAATAA | 76 |
| CCCGCGGATCTACGTGGGCAA | 77 |
| CCGTATTTACTTAACAAGATT | 78 |

-continued

| SEQUENCE | SEQ ID NO. |
|---|---|
| CACAGTTATTACTGCAGTGAA | 79 |
| AAGACAGTCTTTAAAGTGTAA | 80 |
| CCCUCUCAACCUCACUCUU | 81 |
| CTGGATTGACTTTGCTGTCAA | 82 |
| GCUUCAUCGAGCAGCAGUU | 83 |
| CAAGACAGAGATGGACCGCAA | 84 |
| GGUCCUUUUGGCCAGAUCU | 85 |
| TGGGTAGAAGTCACTATATAA | 86 |
| TTGATGTGTTTCAACAGCCTA | 87 |
| TACTGCATTCTCAATTAGAAA | 88 |
| CTGTCTTTAAGTAGGGATAAA | 89 |
| AAGTAGGGATAAAT-TACTCTA; | 90 | or nucleic acid compound is an siRNA comprising the sequence /5Phos/rGrGrCrUrArCrGrGrArCrCrArAr-GrUrUrArUrCrCrGrGCG (SEQ ID NO: 177)
in an amount effective to reduce or inhibit influenza virus replication.

9. The method of paragraph 8 wherein the sequence has "U" substituted for "T".

10. The method of paragraph 8 wherein the sequence has "T" substituted for U".

11. The method of paragraph 8, 9 or 10, in which the nucleic acid compound is double-stranded.

12. A method of treating or managing an influenza virus infection, or a symptom or disease associated therewith, in a human subject, comprising administering to a human subject in need thereof an effective amount of a compound that reduces or inhibits the expression and/or activity of one or more of the following human host cell factors: AKAP13; ARCN; BRWD3; CD81; COPG; CTSW; DUSP3; EPHB2; FAM135A; FGFR2; FGFR4; GABBR1; GSK3B; ITGA3; JAK2; MAP2K3; NEK6; RAB11B; or one or more of the v-ATPase subunits, ATP6V0B, ATP6V0C, ATP6V1A, ATP6V1B2, or ATP6AP1.

13. A method of treating or managing an influenza virus infection, or a symptom or disease associated therewith, in a human subject, comprising administering to a human subject in need thereof an effective amount of a compound that reduces or inhibits the expression and/or activity of one or more of the following human host cell factors: CAMK2B; CSE1L; F13A1; KPNB1; MAP3K12; PP1R14D; PRSS35; RPS10; SF3A1; or SUMO4.

14. A method of treating or managing an influenza virus infection, or a symptom or disease associated therewith, in a human subject, comprising administering to a human subject in need thereof an effective amount of a compound that reduces or inhibits the expression and/or activity of one or more of the following human host cell factors: ACRC; DTX2; EPS8L3; FPR1; MAP3K11; NUP214; PRPH2; RP11-45B20.2; STX10; SUMO2; TRPV2; or TUBB.

15. A method of treating or managing an influenza virus infection, or a symptom or disease associated therewith, in a human subject, comprising administering to a human subject in need thereof an effective amount of a compound that reduces or inhibits the expression and/or activity of one or more of the following human host cell factors: ANPEP; CAM2 KB; FGFR4; FRAP1 (mTOR); GSK3B/CSNK1G2; HSP90AA1; or TUBB.

16. The method of any one of paragraphs 12 to 15 wherein the compound does not inhibit the expression and/or activity of v-ATPase subunit or an HSP90.

17. A method of treating or managing an influenza virus infection, or a symptom or disease associated therewith, in a human subject, comprising administering to a human subject in need thereof an effective amount of Betulinic acid, CCT018159, Diphyllin, KN-93, Podophyllotoxin, or Sirolimus.

18. The method of paragraph 17 wherein the compound is not CCT018159 or Diphyllin.

19. A method of treating or managing an influenza virus infection, or a symptom or disease associated therewith, in a human subject, comprising administering to a human subject in need thereof a nucleic acid compound that targets a sequence selected from the following:

| SEQUENCE | SEQ ID NO. |
|---|---|
| CCCACTTGTGTCAATATTAAA | 1 |
| AAGGCTGAGATGCGTCGTAAA | 2 |
| GAGCTTGAATTTGAAGGTGTA | 3 |
| ATGGAGGTTGATGGTAAGGTA | 4 |
| ACCATGTTACCCTGTAATTAA | 5 |
| CACGGTTAATGAAGTCTGCTA | 6 |
| CAGCCACAGAATATTATGTAA | 7 |
| TCCCAGCTATCTATAACCTTA | 8 |
| CATGGCAATTGTCATTAGCAA | 9 |
| TCCTAGTGTTTGTGAAATAAA | 10 |
| CACAGTGACATTCAAGTTCAT | 11 |
| TAGCAAATGCTCCCTCCTTAA | 12 |
| CACGACCATCCTGAACCCACA | 13 |
| CAGGATCTCTGACATCCTGAA | 14 |
| CAGGATAATGTTATCAAAGTA | 15 |
| CTGACGGTATCAAATATATTA | 16 |
| CAAATGAACTTGTAAACCTAA | 17 |
| CAAGGAGAGATGGGACACTAA | 18 |
| GCUGGAGCUAUGGUCAGUU | 19 |
| CCGCCTGACCTTCGGACCCTA | 20 |
| CAGGAGGTTCTGGGCCTCTGA | 21 |
| GUGACACAGCUACCAAUUC | 22 |
| AACCAGTGACACAGCTACCAA | 23 |
| TCGGTTATATTTGCCAAGATA | 24 |
| CAAGAACTCTTTGACATCTAA | 25 |
| CTGGATGCCATCCAAGTTGTA | 26 |
| ACGGATATCCTGCATGTCCAA | 27 |

-continued

| SEQUENCE | SEQ ID NO. |
|---|---|
| CCCGGAGATGATCCCAACAAA | 28 |
| CACCATAGAATCTCACACCAA | 29 |
| CAGAGAGATACTCGCAGGCAA | 30 |
| CAGCAGCTGATCATGGATGAA | 31 |
| CAGGATAAGACGGAATGGAAA | 32 |
| CGCAAGGATTATGATCCCAAA | 33 |
| CCGAGCCACCTTCTACCTAAA | 34 |
| AGGCCCGTGTATTTAATGAAA | 35 |
| CAGAGGATCTTTCCAACCACA | 36 |
| CCAGTGAATTCTGGTGGCAAA | 37 |
| GAGCCTGAGATTGACCTGGAA | 38 |
| CAGGAGCTCTTCCAGGATCAA | 39 |
| CCGTAGTGAGATCACTTCATA | 40 |
| TACGGCTAACAGAGACCTGAA | 41 |
| CACCCTCTCCTTGTCACAGAA | 42 |
| CTCCATTGCATTCATGTACTA | 43 |
| AGCCATCATACGAGATCTTAA | 44 |
| ATGATTGGCAATGACAAACAA | 45 |
| AACCGGATTGCCATTTATGAA | 46 |
| TTGAATAAACTTACAGCCAAA | 47 |
| CCGCATCACCTCCGCGTACTA | 48 |
| CACGGACGGACAGAAGCCCAA | 49 |
| CCGCCTGTTTGGGTTAACAAA | 50 |
| CAGGATTACACTGAAAGTAAT | 51 |
| CACGAAGAACTAAGAATATTA | 52 |
| CAGCAATTACATTAAATTCAA | 53 |
| CCGGAAGGAGTACTCCCAGAA | 54 |
| AGCCATTTACTTGCACCGGAA | 55 |
| TAGGTACTGTTAAGTAAGTAA | 56 |
| CCCGATGACAATAGTGATGAT | 57 |
| CAGCATTGTCCTGCAGCTGAA | 58 |
| AAAGGAGATCGAGGAGAGAAA | 59 |
| CAGGGAGCACTATGAAAGGAA | 60 |
| CCACGAAAUCGCCCAUCAU | 61 |
| CACATGGTACCTGGATTCAGA | 62 |
| CCGGCCTTGACCGGAGGAGAA | 63 |
| GGAGACCUUCAACCUCUAU | 64 |
| UACCUGUGGCAUCACCAAG | 65 |

| SEQUENCE | SEQ ID NO. |
|---|---|
| CGCGTTCATAACTGTCCTCAA | 66 |
| CACCTTCTATGTAGGCATCTA | 67 |
| AAGGAACATCAGGCATGCTAA | 68 |
| CCCATCTGACAAGGGAAATTA | 69 |
| CGGAGGAGCGTTGCCATTCAA | 70 |
| CTGGCGGACTTCCAGATCGAA | 71 |
| ACCACGGAAGTCGAGAATTAA | 72 |
| CACTCAAGAACTGTCAAGTAA | 73 |
| TCAGTTGGTAGAAATAATCAA | 74 |
| CACGGATTTAGTCCCACCCTA | 75 |
| GAGGAGCGATGTGATGAATAA | 76 |
| CCCGCGGATCTACGTGGGCAA | 77 |
| CCGTATTTACTTAACAAGATT | 78 |
| CACAGTTATTACTGCAGTGAA | 79 |
| AAGACAGTCTTTAAAGTGTAA | 80 |
| CCCUCUCAACCUCACUCUU | 81 |
| CTGGATTGACTTTGCTGTCAA | 82 |
| GCUUCAUCGAGCAGCAGUU | 83 |
| CAAGACAGAGATGGACCGCAA | 84 |
| GGUCCUUUUGGCCAGAUCU | 85 |
| TGGGTAGAAGTCACTATATAA | 86 |
| TTGATGTGTTTCAACAGCCTA | 87 |
| TACTGCATTCTCAATTAGAAA | 88 |
| CTGTCTTTAAGTAGGGATAAA | 89 |
| AAGTAGGGATAAAT-TACTCTA; | 90 | or wherein nucleic acid compound is an siRNA comprising the sequence /5Phos/rGrGrCrUrArCrGrGrArCrCrArAr-GrUrUrUrArUrCrCrGrGCG (SEQ ID NO: 177) in an amount effective to treat or manage the influenza virus infection.

20. The method of paragraph 19 wherein the sequence has "U" substituted for "T".

21. The method of paragraph 19 wherein the sequence has "T" substituted for U".

22. The method of paragraph 19, 20, or 21, in which the nucleic acid compound is double-stranded.

23. A method of preventing a symptom or disease associated with an influenza virus infection in a human subject, comprising administering to a human subject in need thereof an effective amount of a compound that reduces or inhibits the expression and/or activity of one or more of the following human host cell factors: AKAP13; ARCN; BRWD3; CD81; COPG; CTSW; DUSP3; EPHB2; FAM135A; FGFR2; FGFR4; GABBR1; GSK3B; ITGA3; JAK2; MAP2K3; NEK6; RAB11B; or one or more of the v-ATPase subunits, ATP6V0B, ATP6V0C, ATP6V1A, ATP6V1B2, or ATP6AP1.

24. A method of preventing a symptom or disease associated with an influenza virus infection in a human subject, comprising administering to a human subject in need thereof an effective amount of a compound that reduces or inhibits the expression and/or activity of one or more of the following human host cell factors: CAMK2B; CSE1L; F13A1; KPNB1; MAP3K12; PP1R14D; PRSS35; RPS10; SF3A1; or SUMO4.

25. A method of preventing a symptom or disease associated with an influenza virus infection in a human subject, comprising administering to a human subject in need thereof an effective amount of a compound that reduces or inhibits the expression and/or activity of one or more of the following human host cell factors: ACRC; DTX2; EPS8L3; FPR1; MAP3K11; NUP214; PRPH2; RP11-45B20.2; STX10; SUMO2; TRPV2; or TUBB.

26. A method of preventing a symptom or disease associated with an influenza virus infection in a human subject, comprising administering to a human subject in need thereof an effective amount of a compound that reduces or inhibits the expression and/or activity of one or more of the following human host cell factors: ANPEP; CAM2 KB; FGFR4; FRAP1 (mTOR); GSK3B/CSNK1G2; HSP90AA1; or TUBB.

27. The method of any one of paragraphs 23 to 26 wherein the compound does not inhibit the expression or activity of v-ATPase subunit or an HSP90.

28. A method of preventing a symptom or disease associated with an influenza virus infection in a human subject, comprising administering to a human subject in need thereof an effective amount of Betulinic acid, CCT018159, Diphyllin, KN-93, Podophyllotoxin, or Sirolimus.

29. The method of paragraph 28, wherein the compound is not CCT018159 or Diphyllin.

30. A method of preventing a symptom or disease associated with an influenza virus infection in a human subject, comprising administering to a human subject in need thereof a nucleic acid compound that targets a sequence selected from the following:

| SEQUENCE | SEQ ID NO. |
|---|---|
| CCCACTTGTGTCAATATTAAA | 1 |
| AAGGCTGAGATGCGTCGTAAA | 2 |
| GAGCTTGAATTTGAAGGTGTA | 3 |
| ATGGAGGTTGATGGTAAGGTA | 4 |
| ACCATGTTACCCTGTAATTAA | 5 |
| CACGGTTAATGAAGTCTGCTA | 6 |
| CAGCCACAGAATATTATGTAA | 7 |
| TCCCAGCTATCTATAACCTTA | 8 |
| CATGGCAATTGTCATTAGCAA | 9 |
| TCCTAGTGTTTGTGAAATAAA | 10 |
| CACAGTGACATTCAAGTTCAT | 11 |
| TAGCAAATGCTCCCTCCTTAA | 12 |
| CACGACCATCCTGAACCCACA | 13 |
| CAGGATCTCTGACATCCTGAA | 14 |
| CAGGATAATGTTATCAAAGTA | 15 |

-continued

| SEQUENCE | SEQ ID NO. |
|---|---|
| CTGACGGTATCAAATATATTA | 16 |
| CAAATGAACTTGTAAACCTAA | 17 |
| CAAGGAGAGATGGGACACTAA | 18 |
| GCUGGAGCUAUGGUCAGUU | 19 |
| CCGCCTGACCTTCGGACCCTA | 20 |
| CAGGAGGTTCTGGGCCTCTGA | 21 |
| GUGACACAGCUACCAAUUC | 22 |
| AACCAGTGACACAGCTACCAA | 23 |
| TCGGTTATATTTGCCAAGATA | 24 |
| CAAGAACTCTTTGACATCTAA | 25 |
| CTGGATGCCATCCAAGTTGTA | 26 |
| ACGGATATCCTGCATGTCCAA | 27 |
| CCCGGAGATGATCCCAACAAA | 28 |
| CACCATAGAATCTCACACCAA | 29 |
| CAGAGAGATACTCGCAGGCAA | 30 |
| CAGCAGCTGATCATGGATGAA | 31 |
| CAGGATAAGACGGAATGGAAA | 32 |
| CGCAAGGATTATGATCCCAAA | 33 |
| CCGAGCCACCTTCTACCTAAA | 34 |
| AGGCCCGTGTATTTAATGAAA | 35 |
| CAGAGGATCTTTCCAACCACA | 36 |
| CCAGTGAATTCTGGTGGCAAA | 37 |
| GAGCCTGAGATTGACCTGGAA | 38 |
| CAGGAGCTCTTCCAGGATCAA | 39 |
| CCGTAGTGAGATCACTTCATA | 40 |
| TACGGCTAACAGAGACCTGAA | 41 |
| CACCCTCTCCTTGTCACAGAA | 42 |
| CTCCATTGCATTCATGTACTA | 43 |
| AGCCATCATACGAGATCTTAA | 44 |
| ATGATTGGCAATGACAAACAA | 45 |
| AACCGGATTGCCATTTATGAA | 46 |
| TTGAATAAACTTACAGCCAAA | 47 |
| CCGCATCACCTCCGCGTACTA | 48 |
| CACGGACGGACAGAAGCCCAA | 49 |
| CCGCCTGTTTGGGTTAACAAA | 50 |
| CAGGATTACACTGAAAGTAAT | 51 |
| CACGAAGAACTAAGAATATTA | 52 |
| CAGCAATTACATTAAATTCAA | 53 |

| SEQUENCE | SEQ ID NO. |
|---|---|
| CCGGAAGGAGTACTCCCAGAA | 54 |
| AGCCATTTACTTGCACCGGAA | 55 |
| TAGGTACTGTTAAGTAAGTAA | 56 |
| CCCGATGACAATAGTGATGAT | 57 |
| CAGCATTGTCCTGCAGCTGAA | 58 |
| AAAGGAGATCGAGGAGAGAAA | 59 |
| CAGGGAGCACTATGAAAGGAA | 60 |
| CCACGAAAUCGCCCAUCAU | 61 |
| CACATGGTACCTGGATTCAGA | 62 |
| CCGGCCTTGACCGGAGGAGAA | 63 |
| GGAGACCUUCAACCUCUAU | 64 |
| UACCUGUGGCAUCACCAAG | 65 |
| CGCGTTCATAACTGTCCTCAA | 66 |
| CACCTTCTATGTAGGCATCTA | 67 |
| AAGGAACATCAGGCATGCTAA | 68 |
| CCCATCTGACAAGGGAAATTA | 69 |
| CGGAGGAGCGTTGCCATTCAA | 70 |
| CTGGCGGACTTCCAGATCGAA | 71 |
| ACCACGGAAGTCGAGAATTAA | 72 |
| CACTCAAGAACTGTCAAGTAA | 73 |
| TCAGTTGGTAGAAATAATCAA | 74 |
| CACGGATTTAGTCCCACCCTA | 75 |
| GAGGAGCGATGTGATGAATAA | 76 |
| CCCGCGGATCTACGTGGGCAA | 77 |
| CCGTATTTACTTAACAAGATT | 78 |
| CACAGTTATTACTGCAGTGAA | 79 |
| AAGACAGTCTTTAAAGTGTAA | 80 |
| CCCUCUCAACCUCACUCUU | 81 |
| CTGGATTGACTTTGCTGTCAA | 82 |
| GCUUCAUCGAGCAGCAGUU | 83 |
| CAAGACAGAGATGGACCGCAA | 84 |
| GGUCCUUUUGGCCAGAUCU | 85 |
| TGGGTAGAAGTCACTATATAA | 86 |
| TTGATGTGTTTCAACAGCCTA | 87 |
| TACTGCATTCTCAATTAGAAA | 88 |
| CTGTCTTTAAGTAGGGATAAA | 89 |
| AAGTAGGGATAAAT-TACTCTA; | 90 | or nucleic acid compound is an siRNA comprising the sequence /5Phos/rGrGrCrUrArCrGrGrArCrCrArAr-GrUrUrUrArUrCrCrGrGCG (SEQ ID NO: 177) in an amount effective to prevent the symptom or disease.

31. The method of paragraph 30 wherein the sequence has "U" substituted for "T".

32. The method of paragraph 30 wherein the sequence has "T" substituted for U".

33. The method of paragraph 30, 31, or 32, in which the nucleic acid compound is double-stranded.

34. The method of paragraph 8, 19 or 30, wherein the nucleic acid compound that targets the sequence is an siRNA.

35. The method of any one of the preceding paragraphs wherein the influenza virus is an influenza A virus.

36. The method of paragraph 35, in which the influenza A virus is an H1N1 virus.

What is claimed is:

1. A method of inhibiting replication of an influenza virus in a human subject, or treating or managing an influenza virus infection, or a symptom or disease associated therewith, in a human subject, comprising administering to a human subject in need thereof an effective amount of compound KN-93.

2. The method of claim 1, in which the method is inhibiting replication of an influenza virus in a human subject.

3. The method of claim 1, in which the method is treating or managing an influenza virus infection, or a symptom or disease associated therewith, in a human subject.

4. The method of claim 1, wherein the influenza virus is an influenza A virus.

5. The method of claim 4, wherein the influenza A virus is an H1N1 virus.

* * * * *

SEQUENCE LISTING

<160> NUMBER OF SEQ ID NOS: 832

<210> SEQ ID NO 1
<211> LENGTH: 21
<212> TYPE: DNA
<213> ORGANISM: Artificial Sequence
<220> FEATURE:
<223> OTHER INFORMATION: target sequence

<400> SEQUENCE: 1
cccacttgtg tcaatattaa a                                           21

<210> SEQ ID NO 2
<211> LENGTH: 21
<212> TYPE: DNA
<213> ORGANISM: Artificial Sequence
<220> FEATURE:
<223> OTHER INFORMATION: target sequence

<400> SEQUENCE: 2
aaggctgaga tgcgtcgtaa a                                           21

<210> SEQ ID NO 3
<211> LENGTH: 21
<212> TYPE: DNA
<213> ORGANISM: Artificial Sequence
<220> FEATURE:
<223> OTHER INFORMATION: target sequence

<400> SEQUENCE: 3
gagcttgaat tgaaggtgt a                                              21

<210> SEQ ID NO 4
<211> LENGTH: 21
<212> TYPE: DNA
<213> ORGANISM: Artificial Sequence
<220> FEATURE:
<223> OTHER INFORMATION: target sequence

<400> SEQUENCE: 4
atggaggttg atggtaaggt a                                             21

<210> SEQ ID NO 5
<211> LENGTH: 21
<212> TYPE: DNA
<213> ORGANISM: Artificial Sequence
<220> FEATURE:
<223> OTHER INFORMATION: target sequence

<400> SEQUENCE: 5
accatgttac cctgtaatta a                                             21

<210> SEQ ID NO 6
<211> LENGTH: 21
<212> TYPE: DNA
<213> ORGANISM: Artificial Sequence
<220> FEATURE:
<223> OTHER INFORMATION: target sequence

<400> SEQUENCE: 6
cacggttaat gaagtctgct a                                             21

<210> SEQ ID NO 7
<211> LENGTH: 21
<212> TYPE: DNA
<213> ORGANISM: Artificial Sequence
<220> FEATURE:
<223> OTHER INFORMATION: target sequence

<400> SEQUENCE: 7
cagccacaga atattatgta a                                             21

<210> SEQ ID NO 8
<211> LENGTH: 21
<212> TYPE: DNA
<213> ORGANISM: Artificial Sequence
<220> FEATURE:
<223> OTHER INFORMATION: target sequence

<400> SEQUENCE: 8
tcccagctat ctataacctt a                                             21

<210> SEQ ID NO 9
<211> LENGTH: 21
<212> TYPE: DNA
<213> ORGANISM: Artificial Sequence
<220> FEATURE:

```
<223> OTHER INFORMATION: target sequence

<400> SEQUENCE: 9
catggcaatt gtcattagca a                                              21

<210> SEQ ID NO 10
<211> LENGTH: 21
<212> TYPE: DNA
<213> ORGANISM: Artificial Sequence
<220> FEATURE:
<223> OTHER INFORMATION: target sequence

<400> SEQUENCE: 10
tcctagtgtt tgtgaaataa a                                              21

<210> SEQ ID NO 11
<211> LENGTH: 21
<212> TYPE: DNA
<213> ORGANISM: Artificial Sequence
<220> FEATURE:
<223> OTHER INFORMATION: target sequence

<400> SEQUENCE: 11
cacagtgaca ttcaagttca t                                              21

<210> SEQ ID NO 12
<211> LENGTH: 21
<212> TYPE: DNA
<213> ORGANISM: Artificial Sequence
<220> FEATURE:
<223> OTHER INFORMATION: target sequence

<400> SEQUENCE: 12
tagcaaatgc tccctcctta a                                              21

<210> SEQ ID NO 13
<211> LENGTH: 21
<212> TYPE: DNA
<213> ORGANISM: Artificial Sequence
<220> FEATURE:
<223> OTHER INFORMATION: target sequence

<400> SEQUENCE: 13
cacgaccatc ctgaacccac a                                              21

<210> SEQ ID NO 14
<211> LENGTH: 21
<212> TYPE: DNA
<213> ORGANISM: Artificial Sequence
<220> FEATURE:
<223> OTHER INFORMATION: target sequence

<400> SEQUENCE: 14
caggatctct gacatcctga a                                              21

<210> SEQ ID NO 15
<211> LENGTH: 21
<212> TYPE: DNA
<213> ORGANISM: Artificial Sequence
<220> FEATURE:
<223> OTHER INFORMATION: target sequence

<400> SEQUENCE: 15
caggataatg ttatcaaagt a                                              21
```

```
<210> SEQ ID NO 16
<211> LENGTH: 21
<212> TYPE: DNA
<213> ORGANISM: Artificial Sequence
<220> FEATURE:
<223> OTHER INFORMATION: target sequence

<400> SEQUENCE: 16
ctgacggtat caaatatatt a                                              21

<210> SEQ ID NO 17
<211> LENGTH: 21
<212> TYPE: DNA
<213> ORGANISM: Artificial Sequence
<220> FEATURE:
<223> OTHER INFORMATION: target sequence

<400> SEQUENCE: 17
caaatgaact tgtaaaccta a                                              21

<210> SEQ ID NO 18
<211> LENGTH: 21
<212> TYPE: DNA
<213> ORGANISM: Artificial Sequence
<220> FEATURE:
<223> OTHER INFORMATION: target sequence

<400> SEQUENCE: 18
caaggagaga tgggacacta a                                              21

<210> SEQ ID NO 19
<211> LENGTH: 19
<212> TYPE: RNA
<213> ORGANISM: Artificial Sequence
<220> FEATURE:
<223> OTHER INFORMATION: target sequence

<400> SEQUENCE: 19
gcuggagcua uggucaguu                                                 19

<210> SEQ ID NO 20
<211> LENGTH: 21
<212> TYPE: DNA
<213> ORGANISM: Artificial Sequence
<220> FEATURE:
<223> OTHER INFORMATION: target sequence

<400> SEQUENCE: 20
ccgcctgacc ttcggaccct a                                              21

<210> SEQ ID NO 21
<211> LENGTH: 21
<212> TYPE: DNA
<213> ORGANISM: Artificial Sequence
<220> FEATURE:
<223> OTHER INFORMATION: target sequence

<400> SEQUENCE: 21
caggaggttc tgggcctctg a                                              21

<210> SEQ ID NO 22
<211> LENGTH: 19
<212> TYPE: RNA
<213> ORGANISM: Artificial Sequence
<220> FEATURE:
<223> OTHER INFORMATION: target sequence
```

```
<400> SEQUENCE: 22
gugacacagc uaccaauuc                                               19

<210> SEQ ID NO 23
<211> LENGTH: 21
<212> TYPE: DNA
<213> ORGANISM: Artificial Sequence
<220> FEATURE:
<223> OTHER INFORMATION: target sequence

<400> SEQUENCE: 23
aaccagtgac acagctacca a                                            21

<210> SEQ ID NO 24
<211> LENGTH: 21
<212> TYPE: DNA
<213> ORGANISM: Artificial Sequence
<220> FEATURE:
<223> OTHER INFORMATION: target sequence

<400> SEQUENCE: 24
tcggttatat ttgccaagat a                                            21

<210> SEQ ID NO 25
<211> LENGTH: 21
<212> TYPE: DNA
<213> ORGANISM: Artificial Sequence
<220> FEATURE:
<223> OTHER INFORMATION: target sequence

<400> SEQUENCE: 25
caagaactct ttgacatcta a                                            21

<210> SEQ ID NO 26
<211> LENGTH: 21
<212> TYPE: DNA
<213> ORGANISM: Artificial Sequence
<220> FEATURE:
<223> OTHER INFORMATION: target sequence

<400> SEQUENCE: 26
ctggatgcca tccaagttgt a                                            21

<210> SEQ ID NO 27
<211> LENGTH: 21
<212> TYPE: DNA
<213> ORGANISM: Artificial Sequence
<220> FEATURE:
<223> OTHER INFORMATION: target sequence

<400> SEQUENCE: 27
acggatatcc tgcatgtcca a                                            21

<210> SEQ ID NO 28
<211> LENGTH: 21
<212> TYPE: DNA
<213> ORGANISM: Artificial Sequence
<220> FEATURE:
<223> OTHER INFORMATION: target sequence

<400> SEQUENCE: 28
cccggagatg atcccaacaa a                                            21

<210> SEQ ID NO 29
<211> LENGTH: 21
```

```
<212> TYPE: DNA
<213> ORGANISM: Artificial Sequence
<220> FEATURE:
<223> OTHER INFORMATION: target sequence

<400> SEQUENCE: 29
caccatagaa tctcacacca a                                        21

<210> SEQ ID NO 30
<211> LENGTH: 21
<212> TYPE: DNA
<213> ORGANISM: Artificial Sequence
<220> FEATURE:
<223> OTHER INFORMATION: target sequence

<400> SEQUENCE: 30
cagagagata ctcgcaggca a                                        21

<210> SEQ ID NO 31
<211> LENGTH: 21
<212> TYPE: DNA
<213> ORGANISM: Artificial Sequence
<220> FEATURE:
<223> OTHER INFORMATION: target sequence

<400> SEQUENCE: 31
cagcagctga tcatggatga a                                        21

<210> SEQ ID NO 32
<211> LENGTH: 21
<212> TYPE: DNA
<213> ORGANISM: Artificial Sequence
<220> FEATURE:
<223> OTHER INFORMATION: target sequence

<400> SEQUENCE: 32
caggataaga cggaatggaa a                                        21

<210> SEQ ID NO 33
<211> LENGTH: 21
<212> TYPE: DNA
<213> ORGANISM: Artificial Sequence
<220> FEATURE:
<223> OTHER INFORMATION: target sequence

<400> SEQUENCE: 33
cgcaaggatt atgatcccaa a                                        21

<210> SEQ ID NO 34
<211> LENGTH: 21
<212> TYPE: DNA
<213> ORGANISM: Artificial Sequence
<220> FEATURE:
<223> OTHER INFORMATION: target sequence

<400> SEQUENCE: 34
ccgagccacc ttctacctaa a                                        21

<210> SEQ ID NO 35
<211> LENGTH: 21
<212> TYPE: DNA
<213> ORGANISM: Artificial Sequence
<220> FEATURE:
<223> OTHER INFORMATION: target sequence

<400> SEQUENCE: 35
```
aggcccgtgt atttaatgaa a					21

<210> SEQ ID NO 36
<211> LENGTH: 21
<212> TYPE: DNA
<213> ORGANISM: Artificial Sequence
<220> FEATURE:
<223> OTHER INFORMATION: target sequence

<400> SEQUENCE: 36
cagaggatct ttccaaccac a					21

<210> SEQ ID NO 37
<211> LENGTH: 21
<212> TYPE: DNA
<213> ORGANISM: Artificial Sequence
<220> FEATURE:
<223> OTHER INFORMATION: target sequence

<400> SEQUENCE: 37
ccagtgaatt ctggtggcaa a					21

<210> SEQ ID NO 38
<211> LENGTH: 21
<212> TYPE: DNA
<213> ORGANISM: Artificial Sequence
<220> FEATURE:
<223> OTHER INFORMATION: target sequence

<400> SEQUENCE: 38
gagcctgaga ttgacctgga a					21

<210> SEQ ID NO 39
<211> LENGTH: 21
<212> TYPE: DNA
<213> ORGANISM: Artificial Sequence
<220> FEATURE:
<223> OTHER INFORMATION: target sequence

<400> SEQUENCE: 39
caggagctct tccaggatca a					21

<210> SEQ ID NO 40
<211> LENGTH: 21
<212> TYPE: DNA
<213> ORGANISM: Artificial Sequence
<220> FEATURE:
<223> OTHER INFORMATION: target sequence

<400> SEQUENCE: 40
ccgtagtgag atcacttcat a					21

<210> SEQ ID NO 41
<211> LENGTH: 21
<212> TYPE: DNA
<213> ORGANISM: Artificial Sequence
<220> FEATURE:
<223> OTHER INFORMATION: target sequence

<400> SEQUENCE: 41
tacggctaac agagacctga a					21

<210> SEQ ID NO 42
<211> LENGTH: 21
<212> TYPE: DNA
<213> ORGANISM: Artificial Sequence

```
<220> FEATURE:
<223> OTHER INFORMATION: target sequence

<400> SEQUENCE: 42
caccctctcc ttgtcacaga a                                              21

<210> SEQ ID NO 43
<211> LENGTH: 21
<212> TYPE: DNA
<213> ORGANISM: Artificial Sequence
<220> FEATURE:
<223> OTHER INFORMATION: target sequence

<400> SEQUENCE: 43
ctccattgca ttcatgtact a                                              21

<210> SEQ ID NO 44
<211> LENGTH: 21
<212> TYPE: DNA
<213> ORGANISM: Artificial Sequence
<220> FEATURE:
<223> OTHER INFORMATION: target sequence

<400> SEQUENCE: 44
agccatcata cgagatctta a                                              21

<210> SEQ ID NO 45
<211> LENGTH: 21
<212> TYPE: DNA
<213> ORGANISM: Artificial Sequence
<220> FEATURE:
<223> OTHER INFORMATION: target sequence

<400> SEQUENCE: 45
atgattggca atgacaaaca a                                              21

<210> SEQ ID NO 46
<211> LENGTH: 21
<212> TYPE: DNA
<213> ORGANISM: Artificial Sequence
<220> FEATURE:
<223> OTHER INFORMATION: target sequence

<400> SEQUENCE: 46
aaccggattg ccatttatga a                                              21

<210> SEQ ID NO 47
<211> LENGTH: 21
<212> TYPE: DNA
<213> ORGANISM: Artificial Sequence
<220> FEATURE:
<223> OTHER INFORMATION: target sequence

<400> SEQUENCE: 47
ttgaataaac ttacagccaa a                                              21

<210> SEQ ID NO 48
<211> LENGTH: 21
<212> TYPE: DNA
<213> ORGANISM: Artificial Sequence
<220> FEATURE:
<223> OTHER INFORMATION: target sequence

<400> SEQUENCE: 48
ccgcatcacc tccgcgtact a                                              21
```

```
<210> SEQ ID NO 49
<211> LENGTH: 21
<212> TYPE: DNA
<213> ORGANISM: Artificial Sequence
<220> FEATURE:
<223> OTHER INFORMATION: target sequence

<400> SEQUENCE: 49
cacggacgga cagaagccca a                                            21

<210> SEQ ID NO 50
<211> LENGTH: 21
<212> TYPE: DNA
<213> ORGANISM: Artificial Sequence
<220> FEATURE:
<223> OTHER INFORMATION: target sequence

<400> SEQUENCE: 50
ccgcctgttt gggttaacaa a                                            21

<210> SEQ ID NO 51
<211> LENGTH: 21
<212> TYPE: DNA
<213> ORGANISM: Artificial Sequence
<220> FEATURE:
<223> OTHER INFORMATION: target sequence

<400> SEQUENCE: 51
caggattaca ctgaaagtaa t                                            21

<210> SEQ ID NO 52
<211> LENGTH: 21
<212> TYPE: DNA
<213> ORGANISM: Artificial Sequence
<220> FEATURE:
<223> OTHER INFORMATION: target sequence

<400> SEQUENCE: 52
cacgaagaac taagaatatt a                                            21

<210> SEQ ID NO 53
<211> LENGTH: 21
<212> TYPE: DNA
<213> ORGANISM: Artificial Sequence
<220> FEATURE:
<223> OTHER INFORMATION: target sequence

<400> SEQUENCE: 53
cagcaattac attaaattca a                                            21

<210> SEQ ID NO 54
<211> LENGTH: 21
<212> TYPE: DNA
<213> ORGANISM: Artificial Sequence
<220> FEATURE:
<223> OTHER INFORMATION: target sequence

<400> SEQUENCE: 54
ccggaaggag tactcccaga a                                            21

<210> SEQ ID NO 55
<211> LENGTH: 21
<212> TYPE: DNA
<213> ORGANISM: Artificial Sequence
<220> FEATURE:
<223> OTHER INFORMATION: target sequence
```

-continued

<400> SEQUENCE: 55
agccatttac ttgcaccgga a                                              21

<210> SEQ ID NO 56
<211> LENGTH: 21
<212> TYPE: DNA
<213> ORGANISM: Artificial Sequence
<220> FEATURE:
<223> OTHER INFORMATION: target sequence

<400> SEQUENCE: 56
taggtactgt taagtaagta a                                              21

<210> SEQ ID NO 57
<211> LENGTH: 21
<212> TYPE: DNA
<213> ORGANISM: Artificial Sequence
<220> FEATURE:
<223> OTHER INFORMATION: target sequence

<400> SEQUENCE: 57
cccgatgaca atagtgatga t                                              21

<210> SEQ ID NO 58
<211> LENGTH: 21
<212> TYPE: DNA
<213> ORGANISM: Artificial Sequence
<220> FEATURE:
<223> OTHER INFORMATION: target sequence

<400> SEQUENCE: 58
cagcattgtc ctgcagctga a                                              21

<210> SEQ ID NO 59
<211> LENGTH: 21
<212> TYPE: DNA
<213> ORGANISM: Artificial Sequence
<220> FEATURE:
<223> OTHER INFORMATION: target sequence

<400> SEQUENCE: 59
aaaggagatc gaggagagaa a                                              21

<210> SEQ ID NO 60
<211> LENGTH: 21
<212> TYPE: DNA
<213> ORGANISM: Artificial Sequence
<220> FEATURE:
<223> OTHER INFORMATION: target sequence

<400> SEQUENCE: 60
cagggagcac tatgaaagga a                                              21

<210> SEQ ID NO 61
<211> LENGTH: 19
<212> TYPE: RNA
<213> ORGANISM: Artificial Sequence
<220> FEATURE:
<223> OTHER INFORMATION: target sequence

<400> SEQUENCE: 61
ccacgaaauc gcccaucau                                                 19

<210> SEQ ID NO 62

```
<210> SEQ ID NO 62
<211> LENGTH: 21
<212> TYPE: DNA
<213> ORGANISM: Artificial Sequence
<220> FEATURE:
<223> OTHER INFORMATION: target sequence

<400> SEQUENCE: 62
cacatggtac ctggattcag a                                              21

<210> SEQ ID NO 63
<211> LENGTH: 21
<212> TYPE: DNA
<213> ORGANISM: Artificial Sequence
<220> FEATURE:
<223> OTHER INFORMATION: target sequence

<400> SEQUENCE: 63
ccggccttga ccggaggaga a                                              21

<210> SEQ ID NO 64
<211> LENGTH: 19
<212> TYPE: RNA
<213> ORGANISM: Artificial Sequence
<220> FEATURE:
<223> OTHER INFORMATION: target sequence

<400> SEQUENCE: 64
ggagaccuuc aaccucuau                                                 19

<210> SEQ ID NO 65
<211> LENGTH: 19
<212> TYPE: RNA
<213> ORGANISM: Artificial Sequence
<220> FEATURE:
<223> OTHER INFORMATION: target sequence

<400> SEQUENCE: 65
uaccuguggc aucaccaag                                                 19

<210> SEQ ID NO 66
<211> LENGTH: 21
<212> TYPE: DNA
<213> ORGANISM: Artificial Sequence
<220> FEATURE:
<223> OTHER INFORMATION: target sequence

<400> SEQUENCE: 66
cgcgttcata actgtcctca a                                              21

<210> SEQ ID NO 67
<211> LENGTH: 21
<212> TYPE: DNA
<213> ORGANISM: Artificial Sequence
<220> FEATURE:
<223> OTHER INFORMATION: target sequence

<400> SEQUENCE: 67
caccttctat gtaggcatct a                                              21

<210> SEQ ID NO 68
<211> LENGTH: 21
<212> TYPE: DNA
<213> ORGANISM: Artificial Sequence
<220> FEATURE:
<223> OTHER INFORMATION: target sequence

<400> SEQUENCE: 68
```
aaggaacatc aggcatgcta a                                              21

<210> SEQ ID NO 69
<211> LENGTH: 21
<212> TYPE: DNA
<213> ORGANISM: Artificial Sequence
<220> FEATURE:
<223> OTHER INFORMATION: target sequence

<400> SEQUENCE: 69
cccatctgac aagggaaatt a                                              21

<210> SEQ ID NO 70
<211> LENGTH: 21
<212> TYPE: DNA
<213> ORGANISM: Artificial Sequence
<220> FEATURE:
<223> OTHER INFORMATION: target sequence

<400> SEQUENCE: 70
cggaggagcg ttgccattca a                                              21

<210> SEQ ID NO 71
<211> LENGTH: 21
<212> TYPE: DNA
<213> ORGANISM: Artificial Sequence
<220> FEATURE:
<223> OTHER INFORMATION: target sequence

<400> SEQUENCE: 71
ctggcggact tccagatcga a                                              21

<210> SEQ ID NO 72
<211> LENGTH: 21
<212> TYPE: DNA
<213> ORGANISM: Artificial Sequence
<220> FEATURE:
<223> OTHER INFORMATION: target sequence

<400> SEQUENCE: 72
accacggaag tcgagaatta a                                              21

<210> SEQ ID NO 73
<211> LENGTH: 21
<212> TYPE: DNA
<213> ORGANISM: Artificial Sequence
<220> FEATURE:
<223> OTHER INFORMATION: target sequence

<400> SEQUENCE: 73
cactcaagaa ctgtcaagta a                                              21

<210> SEQ ID NO 74
<211> LENGTH: 21
<212> TYPE: DNA
<213> ORGANISM: Artificial Sequence
<220> FEATURE:
<223> OTHER INFORMATION: target sequence

<400> SEQUENCE: 74
tcagttggta gaaataatca a                                              21

<210> SEQ ID NO 75
<211> LENGTH: 21
<212> TYPE: DNA

```
<213> ORGANISM: Artificial Sequence
<220> FEATURE:
<223> OTHER INFORMATION: target sequence

<400> SEQUENCE: 75
cacggattta gtcccaccct a                                              21

<210> SEQ ID NO 76
<211> LENGTH: 21
<212> TYPE: DNA
<213> ORGANISM: Artificial Sequence
<220> FEATURE:
<223> OTHER INFORMATION: target sequence

<400> SEQUENCE: 76
gaggagcgat gtgatgaata a                                              21

<210> SEQ ID NO 77
<211> LENGTH: 21
<212> TYPE: DNA
<213> ORGANISM: Artificial Sequence
<220> FEATURE:
<223> OTHER INFORMATION: target sequence

<400> SEQUENCE: 77
cccgcggatc tacgtgggca a                                              21

<210> SEQ ID NO 78
<211> LENGTH: 21
<212> TYPE: DNA
<213> ORGANISM: Artificial Sequence
<220> FEATURE:
<223> OTHER INFORMATION: target sequence

<400> SEQUENCE: 78
ccgtatttac ttaacaagat t                                              21

<210> SEQ ID NO 79
<211> LENGTH: 21
<212> TYPE: DNA
<213> ORGANISM: Artificial Sequence
<220> FEATURE:
<223> OTHER INFORMATION: target sequence

<400> SEQUENCE: 79
cacagttatt actgcagtga a                                              21

<210> SEQ ID NO 80
<211> LENGTH: 21
<212> TYPE: DNA
<213> ORGANISM: Artificial Sequence
<220> FEATURE:
<223> OTHER INFORMATION: target sequence

<400> SEQUENCE: 80
aagacagtct ttaaagtgta a                                              21

<210> SEQ ID NO 81
<211> LENGTH: 19
<212> TYPE: RNA
<213> ORGANISM: Artificial Sequence
<220> FEATURE:
<223> OTHER INFORMATION: target sequence

<400> SEQUENCE: 81
cccucucaac cucacucuu                                                 19
```

```
<210> SEQ ID NO 82
<211> LENGTH: 21
<212> TYPE: DNA
<213> ORGANISM: Artificial Sequence
<220> FEATURE:
<223> OTHER INFORMATION: target sequence

<400> SEQUENCE: 82
ctggattgac tttgctgtca a                                            21

<210> SEQ ID NO 83
<211> LENGTH: 19
<212> TYPE: RNA
<213> ORGANISM: Artificial Sequence
<220> FEATURE:
<223> OTHER INFORMATION: target sequence

<400> SEQUENCE: 83
gcuucaucga gcagcaguu                                               19

<210> SEQ ID NO 84
<211> LENGTH: 21
<212> TYPE: DNA
<213> ORGANISM: Artificial Sequence
<220> FEATURE:
<223> OTHER INFORMATION: target sequence

<400> SEQUENCE: 84
caagacagag atggaccgca a                                            21

<210> SEQ ID NO 85
<211> LENGTH: 19
<212> TYPE: RNA
<213> ORGANISM: Artificial Sequence
<220> FEATURE:
<223> OTHER INFORMATION: target sequence

<400> SEQUENCE: 85
gguccuuuug gccagaucu                                               19

<210> SEQ ID NO 86
<211> LENGTH: 21
<212> TYPE: DNA
<213> ORGANISM: Artificial Sequence
<220> FEATURE:
<223> OTHER INFORMATION: target sequence

<400> SEQUENCE: 86
tgggtagaag tcactatata a                                            21

<210> SEQ ID NO 87
<211> LENGTH: 21
<212> TYPE: DNA
<213> ORGANISM: Artificial Sequence
<220> FEATURE:
<223> OTHER INFORMATION: target sequence

<400> SEQUENCE: 87
ttgatgtgtt tcaacagcct a                                            21

<210> SEQ ID NO 88
<211> LENGTH: 21
<212> TYPE: DNA
<213> ORGANISM: Artificial Sequence
<220> FEATURE:
```

<223> OTHER INFORMATION: target sequence

<400> SEQUENCE: 88
tactgcattc tcaattagaa a                                          21

<210> SEQ ID NO 89
<211> LENGTH: 21
<212> TYPE: DNA
<213> ORGANISM: Artificial Sequence
<220> FEATURE:
<223> OTHER INFORMATION: target sequence

<400> SEQUENCE: 89
ctgtctttaa gtagggataa a                                          21

<210> SEQ ID NO 90
<211> LENGTH: 21
<212> TYPE: DNA
<213> ORGANISM: Artificial Sequence
<220> FEATURE:
<223> OTHER INFORMATION: target sequence

<400> SEQUENCE: 90
aagtagggat aaattactct a                                          21

<210> SEQ ID NO 91
<211> LENGTH: 22
<212> TYPE: DNA
<213> ORGANISM: Artificial Sequence
<220> FEATURE:
<223> OTHER INFORMATION: sense primer - ARCN

<400> SEQUENCE: 91
ggggtgctaa agtggagact ac                                         22

<210> SEQ ID NO 92
<211> LENGTH: 20
<212> TYPE: DNA
<213> ORGANISM: Artificial Sequence
<220> FEATURE:
<223> OTHER INFORMATION: antisense primer - ARCN

<400> SEQUENCE: 92
cacagccatt tccactctcc                                            20

<210> SEQ ID NO 93
<211> LENGTH: 22
<212> TYPE: DNA
<213> ORGANISM: Artificial Sequence
<220> FEATURE:
<223> OTHER INFORMATION: sense primer - ATP6VOC

<400> SEQUENCE: 93
cccgagtatg cttcgttttt cg                                         22

<210> SEQ ID NO 94
<211> LENGTH: 21
<212> TYPE: DNA
<213> ORGANISM: Artificial Sequence
<220> FEATURE:
<223> OTHER INFORMATION: antisense primer - ATP6VOC

<400> SEQUENCE: 94
catgaccact gggatgatgg a                                          21

```
<210> SEQ ID NO 95
<211> LENGTH: 20
<212> TYPE: DNA
<213> ORGANISM: Artificial Sequence
<220> FEATURE:
<223> OTHER INFORMATION: sense primer - CD81

<400> SEQUENCE: 95
ttccacgaga cgcttgactg                                               20

<210> SEQ ID NO 96
<211> LENGTH: 21
<212> TYPE: DNA
<213> ORGANISM: Artificial Sequence
<220> FEATURE:
<223> OTHER INFORMATION: antisense primer - CD81

<400> SEQUENCE: 96
cttcccggag aagaggtcat c                                             21

<210> SEQ ID NO 97
<211> LENGTH: 22
<212> TYPE: DNA
<213> ORGANISM: Artificial Sequence
<220> FEATURE:
<223> OTHER INFORMATION: sense primer - CSE1L

<400> SEQUENCE: 97
cagaacacgc tgacaagtat ct                                            22

<210> SEQ ID NO 98
<211> LENGTH: 22
<212> TYPE: DNA
<213> ORGANISM: Artificial Sequence
<220> FEATURE:
<223> OTHER INFORMATION: antisense primer - CSE1L

<400> SEQUENCE: 98
agccctgcgt ctagtatcaa ta                                            22

<210> SEQ ID NO 99
<211> LENGTH: 19
<212> TYPE: DNA
<213> ORGANISM: Artificial Sequence
<220> FEATURE:
<223> OTHER INFORMATION: sense primer - FGFR4v1

<400> SEQUENCE: 99
aggcctctga ggaagtgga                                                19

<210> SEQ ID NO 100
<211> LENGTH: 19
<212> TYPE: DNA
<213> ORGANISM: Artificial Sequence
<220> FEATURE:
<223> OTHER INFORMATION: antisense primer - FGFR4v1

<400> SEQUENCE: 100
ctgcccaagg gctactgtc                                                19

<210> SEQ ID NO 101
<211> LENGTH: 18
<212> TYPE: DNA
<213> ORGANISM: Artificial Sequence
<220> FEATURE:
<223> OTHER INFORMATION: sense primer - GABBR1
```

```
<400> SEQUENCE: 101
cccgacttcc atctggtg                                                    18

<210> SEQ ID NO 102
<211> LENGTH: 18
<212> TYPE: DNA
<213> ORGANISM: Artificial Sequence
<220> FEATURE:
<223> OTHER INFORMATION: antisense primer - GABBR1

<400> SEQUENCE: 102
gtggcgttcg attcacct                                                    18

<210> SEQ ID NO 103
<211> LENGTH: 21
<212> TYPE: DNA
<213> ORGANISM: Artificial Sequence
<220> FEATURE:
<223> OTHER INFORMATION: sense primer - GSK3B

<400> SEQUENCE: 103
atttccaggg gatagtggtg t                                                21

<210> SEQ ID NO 104
<211> LENGTH: 22
<212> TYPE: DNA
<213> ORGANISM: Artificial Sequence
<220> FEATURE:
<223> OTHER INFORMATION: antisense primer - GSK3B

<400> SEQUENCE: 104
ggtcggaaga ccttagtcca ag                                               22

<210> SEQ ID NO 105
<211> LENGTH: 21
<212> TYPE: DNA
<213> ORGANISM: Artificial Sequence
<220> FEATURE:
<223> OTHER INFORMATION: sense primer - MAP2K3

<400> SEQUENCE: 105
ggaggctgat gacttggtga c                                                21

<210> SEQ ID NO 106
<211> LENGTH: 20
<212> TYPE: DNA
<213> ORGANISM: Artificial Sequence
<220> FEATURE:
<223> OTHER INFORMATION: antisense primer - MAP2K3

<400> SEQUENCE: 106
ctgctcctgt gagttcacgg                                                  20

<210> SEQ ID NO 107
<211> LENGTH: 19
<212> TYPE: DNA
<213> ORGANISM: Artificial Sequence
<220> FEATURE:
<223> OTHER INFORMATION: sense primer - PRSS35

<400> SEQUENCE: 107
ccctgggtgg accctcatt                                                   19

<210> SEQ ID NO 108
<211> LENGTH: 22
```

```
<212> TYPE: DNA
<213> ORGANISM: Artificial Sequence
<220> FEATURE:
<223> OTHER INFORMATION: antisense primer - PRSS35

<400> SEQUENCE: 108
cattcgatgc cacacactgt at                                              22

<210> SEQ ID NO 109
<211> LENGTH: 20
<212> TYPE: DNA
<213> ORGANISM: Artificial Sequence
<220> FEATURE:
<223> OTHER INFORMATION: sense primer - MID1IP1

<400> SEQUENCE: 109
acagccacta cgtgcttctc                                                 20

<210> SEQ ID NO 110
<211> LENGTH: 20
<212> TYPE: DNA
<213> ORGANISM: Artificial Sequence
<220> FEATURE:
<223> OTHER INFORMATION: antisense primer - MID1IP1

<400> SEQUENCE: 110
ctttgcgcgt gagtttcgag                                                 20

<210> SEQ ID NO 111
<211> LENGTH: 23
<212> TYPE: DNA
<213> ORGANISM: Artificial Sequence
<220> FEATURE:
<223> OTHER INFORMATION: sense primer - SUMO2

<400> SEQUENCE: 111
gaaagcctat tgtgaacgac agt                                             23

<210> SEQ ID NO 112
<211> LENGTH: 21
<212> TYPE: DNA
<213> ORGANISM: Artificial Sequence
<220> FEATURE:
<223> OTHER INFORMATION: antisense primer - SUMO2

<400> SEQUENCE: 112
tctgctgttg gaacacatca a                                               21

<210> SEQ ID NO 113
<211> LENGTH: 21
<212> TYPE: DNA
<213> ORGANISM: Artificial Sequence
<220> FEATURE:
<223> OTHER INFORMATION: sense primer - CAMK2B

<400> SEQUENCE: 113
cctacgcgaa aatctgtgac c                                               21

<210> SEQ ID NO 114
<211> LENGTH: 21
<212> TYPE: DNA
<213> ORGANISM: Artificial Sequence
<220> FEATURE:
<223> OTHER INFORMATION: antisense primer - CAMK2B

<400> SEQUENCE: 114
```
tggaagtcca tcccttcaac c                                                     21

<210> SEQ ID NO 115
<211> LENGTH: 21
<212> TYPE: DNA
<213> ORGANISM: Artificial Sequence
<220> FEATURE:
<223> OTHER INFORMATION: target sequence

<400> SEQUENCE: 115
ctgatcgtat gcagaaggaa a                                                     21

<210> SEQ ID NO 116
<211> LENGTH: 21
<212> TYPE: DNA
<213> ORGANISM: Artificial Sequence
<220> FEATURE:
<223> OTHER INFORMATION: target sequence

<400> SEQUENCE: 116
tccacggttg ctaaattata a                                                     21

<210> SEQ ID NO 117
<211> LENGTH: 21
<212> TYPE: DNA
<213> ORGANISM: Artificial Sequence
<220> FEATURE:
<223> OTHER INFORMATION: target sequence

<400> SEQUENCE: 117
accaatcaaa ctggtgttga a                                                     21

<210> SEQ ID NO 118
<211> LENGTH: 19
<212> TYPE: RNA
<213> ORGANISM: Artificial Sequence
<220> FEATURE:
<223> OTHER INFORMATION: target sequence

<400> SEQUENCE: 118
cccuucuaug cccucuucu                                                        19

<210> SEQ ID NO 119
<211> LENGTH: 19
<212> TYPE: RNA
<213> ORGANISM: Artificial Sequence
<220> FEATURE:
<223> OTHER INFORMATION: target sequence

<400> SEQUENCE: 119
gcuaagacgu ugggcauug                                                        19

<210> SEQ ID NO 120
<211> LENGTH: 21
<212> TYPE: DNA
<213> ORGANISM: Artificial Sequence
<220> FEATURE:
<223> OTHER INFORMATION: target sequence

<400> SEQUENCE: 120
caagtgtatg ggattaacta a                                                     21

<210> SEQ ID NO 121
<211> LENGTH: 19
<212> TYPE: RNA
<213> ORGANISM: Artificial Sequence

```
<220> FEATURE:
<223> OTHER INFORMATION: target sequence

<400> SEQUENCE: 121
ggagacuguc cuuucauug                                                    19

<210> SEQ ID NO 122
<211> LENGTH: 25
<212> TYPE: RNA
<213> ORGANISM: Artificial Sequence
<220> FEATURE:
<223> OTHER INFORMATION: target sequence

<400> SEQUENCE: 122
cgugaccaug aacgaguuug aguac                                             25

<210> SEQ ID NO 123
<211> LENGTH: 19
<212> TYPE: RNA
<213> ORGANISM: Artificial Sequence
<220> FEATURE:
<223> OTHER INFORMATION: target sequence

<400> SEQUENCE: 123
ucacaccacc ugaccaaga                                                    19

<210> SEQ ID NO 124
<211> LENGTH: 21
<212> TYPE: DNA
<213> ORGANISM: Artificial Sequence
<220> FEATURE:
<223> OTHER INFORMATION: target sequence

<400> SEQUENCE: 124
caccaccttg gaccaaagta a                                                 21

<210> SEQ ID NO 125
<211> LENGTH: 21
<212> TYPE: DNA
<213> ORGANISM: Artificial Sequence
<220> FEATURE:
<223> OTHER INFORMATION: target sequence

<400> SEQUENCE: 125
ccgaaatgcc acactggtca a                                                 21

<210> SEQ ID NO 126
<211> LENGTH: 19
<212> TYPE: RNA
<213> ORGANISM: Artificial Sequence
<220> FEATURE:
<223> OTHER INFORMATION: target sequence

<400> SEQUENCE: 126
gagacuaugu gucccaguu                                                    19

<210> SEQ ID NO 127
<211> LENGTH: 21
<212> TYPE: DNA
<213> ORGANISM: Artificial Sequence
<220> FEATURE:
<223> OTHER INFORMATION: target sequence

<400> SEQUENCE: 127
cgctctcgag gagtacacta a                                                 21
```

```
<210> SEQ ID NO 128
<211> LENGTH: 19
<212> TYPE: RNA
<213> ORGANISM: Artificial Sequence
<220> FEATURE:
<223> OTHER INFORMATION: target sequence

<400> SEQUENCE: 128
ccaggagagg auggauguu                                                    19

<210> SEQ ID NO 129
<211> LENGTH: 21
<212> TYPE: DNA
<213> ORGANISM: Artificial Sequence
<220> FEATURE:
<223> OTHER INFORMATION: target sequence

<400> SEQUENCE: 129
ctggtcttca attaccaaga a                                                 21

<210> SEQ ID NO 130
<211> LENGTH: 21
<212> TYPE: DNA
<213> ORGANISM: Artificial Sequence
<220> FEATURE:
<223> OTHER INFORMATION: target sequence

<400> SEQUENCE: 130
cagcctggga tccaccatca a                                                 21

<210> SEQ ID NO 131
<211> LENGTH: 19
<212> TYPE: RNA
<213> ORGANISM: Artificial Sequence
<220> FEATURE:
<223> OTHER INFORMATION: target sequence

<400> SEQUENCE: 131
gaccaaucug gagagguau                                                    19

<210> SEQ ID NO 132
<211> LENGTH: 19
<212> TYPE: RNA
<213> ORGANISM: Artificial Sequence
<220> FEATURE:
<223> OTHER INFORMATION: target sequence

<400> SEQUENCE: 132
ccacaguguc caggauuug                                                    19

<210> SEQ ID NO 133
<211> LENGTH: 19
<212> TYPE: RNA
<213> ORGANISM: Artificial Sequence
<220> FEATURE:
<223> OTHER INFORMATION: target sequence

<400> SEQUENCE: 133
cggugaagau cggugacuu                                                    19

<210> SEQ ID NO 134
<211> LENGTH: 21
<212> TYPE: DNA
<213> ORGANISM: Artificial Sequence
<220> FEATURE:
<223> OTHER INFORMATION: target sequence
```

```
<400> SEQUENCE: 134
cagggaagtc ctcacaggca a                                              21

<210> SEQ ID NO 135
<211> LENGTH: 19
<212> TYPE: RNA
<213> ORGANISM: Artificial Sequence
<220> FEATURE:
<223> OTHER INFORMATION: target sequence

<400> SEQUENCE: 135
cgugaacgcg caaauguac                                                 19

<210> SEQ ID NO 136
<211> LENGTH: 19
<212> TYPE: RNA
<213> ORGANISM: Artificial Sequence
<220> FEATURE:
<223> OTHER INFORMATION: target sequence

<400> SEQUENCE: 136
uggcuccucc caauuucuu                                                 19

<210> SEQ ID NO 137
<211> LENGTH: 25
<212> TYPE: RNA
<213> ORGANISM: Artificial Sequence
<220> FEATURE:
<223> OTHER INFORMATION: target sequence

<400> SEQUENCE: 137
ggacccaguu guaccuaauc acagg                                          25

<210> SEQ ID NO 138
<211> LENGTH: 19
<212> TYPE: RNA
<213> ORGANISM: Artificial Sequence
<220> FEATURE:
<223> OTHER INFORMATION: target sequence

<400> SEQUENCE: 138
ggacuauagc uaagcagau                                                 19

<210> SEQ ID NO 139
<211> LENGTH: 21
<212> TYPE: DNA
<213> ORGANISM: Artificial Sequence
<220> FEATURE:
<223> OTHER INFORMATION: target sequence

<400> SEQUENCE: 139
cagccaagtg ctagtagaca a                                              21

<210> SEQ ID NO 140
<211> LENGTH: 19
<212> TYPE: RNA
<213> ORGANISM: Artificial Sequence
<220> FEATURE:
<223> OTHER INFORMATION: target sequence

<400> SEQUENCE: 140
cccugagucu gagcaguau                                                 19

<210> SEQ ID NO 141
```

```
<211> LENGTH: 19
<212> TYPE: RNA
<213> ORGANISM: Artificial Sequence
<220> FEATURE:
<223> OTHER INFORMATION: target sequence

<400> SEQUENCE: 141
ggaccacuga cauuccuau                                                  19

<210> SEQ ID NO 142
<211> LENGTH: 21
<212> TYPE: DNA
<213> ORGANISM: Artificial Sequence
<220> FEATURE:
<223> OTHER INFORMATION: target sequence

<400> SEQUENCE: 142
aagggtggtc caactgccaa a                                               21

<210> SEQ ID NO 143
<211> LENGTH: 19
<212> TYPE: RNA
<213> ORGANISM: Artificial Sequence
<220> FEATURE:
<223> OTHER INFORMATION: target sequence

<400> SEQUENCE: 143
gaggccuaga uuuccuuca                                                  19

<210> SEQ ID NO 144
<211> LENGTH: 21
<212> TYPE: DNA
<213> ORGANISM: Artificial Sequence
<220> FEATURE:
<223> OTHER INFORMATION: target sequence

<400> SEQUENCE: 144
ccgaactgac cgggagatca a                                               21

<210> SEQ ID NO 145
<211> LENGTH: 25
<212> TYPE: DNA
<213> ORGANISM: Artificial Sequence
<220> FEATURE:
<223> OTHER INFORMATION: target sequence

<400> SEQUENCE: 145
aguacuucac aucgucguuc acatg                                           25

<210> SEQ ID NO 146
<211> LENGTH: 21
<212> TYPE: DNA
<213> ORGANISM: Artificial Sequence
<220> FEATURE:
<223> OTHER INFORMATION: target sequence

<400> SEQUENCE: 146
cacgatagta aggagcattt a                                               21

<210> SEQ ID NO 147
<211> LENGTH: 25
<212> TYPE: RNA
<213> ORGANISM: Artificial Sequence
<220> FEATURE:
<223> OTHER INFORMATION: target sequence

<400> SEQUENCE: 147
```
ggcggaugua uggucacugg gcugg                                          25

<210> SEQ ID NO 148
<211> LENGTH: 21
<212> TYPE: DNA
<213> ORGANISM: Artificial Sequence
<220> FEATURE:
<223> OTHER INFORMATION: target sequence

<400> SEQUENCE: 148
ctgcatcaag caggttcact a                                              21

<210> SEQ ID NO 149
<211> LENGTH: 21
<212> TYPE: DNA
<213> ORGANISM: Artificial Sequence
<220> FEATURE:
<223> OTHER INFORMATION: target sequence

<400> SEQUENCE: 149
ctggtttgga gaaaccatca a                                              21

<210> SEQ ID NO 150
<211> LENGTH: 21
<212> TYPE: DNA
<213> ORGANISM: Artificial Sequence
<220> FEATURE:
<223> OTHER INFORMATION: target sequence

<400> SEQUENCE: 150
aagcctggtg atgatggtga a                                              21

<210> SEQ ID NO 151
<211> LENGTH: 21
<212> TYPE: DNA
<213> ORGANISM: Artificial Sequence
<220> FEATURE:
<223> OTHER INFORMATION: target sequence

<400> SEQUENCE: 151
ctggatttca acagctccaa a                                              21

<210> SEQ ID NO 152
<211> LENGTH: 21
<212> TYPE: DNA
<213> ORGANISM: Artificial Sequence
<220> FEATURE:
<223> OTHER INFORMATION: target sequence

<400> SEQUENCE: 152
ctggcgcatg aatgaatcaa a                                              21

<210> SEQ ID NO 153
<211> LENGTH: 21
<212> TYPE: DNA
<213> ORGANISM: Artificial Sequence
<220> FEATURE:
<223> OTHER INFORMATION: target sequence

<400> SEQUENCE: 153
agggcagttg ttgcttctta a                                              21

<210> SEQ ID NO 154
<211> LENGTH: 21
<212> TYPE: DNA

```
<213> ORGANISM: Artificial Sequence
<220> FEATURE:
<223> OTHER INFORMATION: target sequence

<400> SEQUENCE: 154
cagccgggta ctaccattct a                                              21

<210> SEQ ID NO 155
<211> LENGTH: 21
<212> TYPE: DNA
<213> ORGANISM: Artificial Sequence
<220> FEATURE:
<223> OTHER INFORMATION: target sequence

<400> SEQUENCE: 155
caggttggtg acagccgcct a                                              21

<210> SEQ ID NO 156
<211> LENGTH: 21
<212> TYPE: DNA
<213> ORGANISM: Artificial Sequence
<220> FEATURE:
<223> OTHER INFORMATION: target sequence

<400> SEQUENCE: 156
ccgctacaat accacaaaca a                                              21

<210> SEQ ID NO 157
<211> LENGTH: 25
<212> TYPE: RNA
<213> ORGANISM: Artificial Sequence
<220> FEATURE:
<223> OTHER INFORMATION: target sequence

<400> SEQUENCE: 157
aggccagggu aucacaaacu uauag                                          25

<210> SEQ ID NO 158
<211> LENGTH: 21
<212> TYPE: DNA
<213> ORGANISM: Artificial Sequence
<220> FEATURE:
<223> OTHER INFORMATION: target sequence

<400> SEQUENCE: 158
taggaaagaa tctctataca a                                              21

<210> SEQ ID NO 159
<211> LENGTH: 21
<212> TYPE: DNA
<213> ORGANISM: Artificial Sequence
<220> FEATURE:
<223> OTHER INFORMATION: target sequence

<400> SEQUENCE: 159
cacagtgttg ccagagcctt a                                              21

<210> SEQ ID NO 160
<211> LENGTH: 19
<212> TYPE: RNA
<213> ORGANISM: Artificial Sequence
<220> FEATURE:
<223> OTHER INFORMATION: target sequence

<400> SEQUENCE: 160
uccgccaccc ucaauauaa                                                 19
```

<210> SEQ ID NO 161
<211> LENGTH: 21
<212> TYPE: DNA
<213> ORGANISM: Artificial Sequence
<220> FEATURE:
<223> OTHER INFORMATION: target sequence

<400> SEQUENCE: 161
ccggcagaag ggcacgggca a                                              21

<210> SEQ ID NO 162
<211> LENGTH: 21
<212> TYPE: DNA
<213> ORGANISM: Artificial Sequence
<220> FEATURE:
<223> OTHER INFORMATION: target sequence

<400> SEQUENCE: 162
caccaacatc tcagccgtga a                                              21

<210> SEQ ID NO 163
<211> LENGTH: 19
<212> TYPE: RNA
<213> ORGANISM: Artificial Sequence
<220> FEATURE:
<223> OTHER INFORMATION: target sequence

<400> SEQUENCE: 163
cugcaaauuc acaggcaau                                                 19

<210> SEQ ID NO 164
<211> LENGTH: 21
<212> TYPE: DNA
<213> ORGANISM: Artificial Sequence
<220> FEATURE:
<223> OTHER INFORMATION: target sequence

<400> SEQUENCE: 164
cgggaagtgg tttgacttca a                                              21

<210> SEQ ID NO 165
<211> LENGTH: 21
<212> TYPE: DNA
<213> ORGANISM: Artificial Sequence
<220> FEATURE:
<223> OTHER INFORMATION: target sequence

<400> SEQUENCE: 165
ttgggagttt atgcaaggta a                                              21

<210> SEQ ID NO 166
<211> LENGTH: 19
<212> TYPE: RNA
<213> ORGANISM: Artificial Sequence
<220> FEATURE:
<223> OTHER INFORMATION: target sequence

<400> SEQUENCE: 166
uagcagauuu ucuugucau                                                 19

<210> SEQ ID NO 167
<211> LENGTH: 19
<212> TYPE: RNA
<213> ORGANISM: Artificial Sequence
<220> FEATURE:

<223> OTHER INFORMATION: target sequence

<400> SEQUENCE: 167
ggacgaauag cuucuuaca                                                    19

<210> SEQ ID NO 168
<211> LENGTH: 21
<212> TYPE: DNA
<213> ORGANISM: Artificial Sequence
<220> FEATURE:
<223> OTHER INFORMATION: target sequence

<400> SEQUENCE: 168
cacattcggt tgagcaacat t                                                 21

<210> SEQ ID NO 169
<211> LENGTH: 21
<212> TYPE: DNA
<213> ORGANISM: Artificial Sequence
<220> FEATURE:
<223> OTHER INFORMATION: target sequence

<400> SEQUENCE: 169
cagaagaatg actatgacca a                                                 21

<210> SEQ ID NO 170
<211> LENGTH: 21
<212> TYPE: DNA
<213> ORGANISM: Artificial Sequence
<220> FEATURE:
<223> OTHER INFORMATION: target sequence

<400> SEQUENCE: 170
ccgacatgaa tcagtaagta a                                                 21

<210> SEQ ID NO 171
<211> LENGTH: 25
<212> TYPE: RNA
<213> ORGANISM: Artificial Sequence
<220> FEATURE:
<223> OTHER INFORMATION: target sequence

<400> SEQUENCE: 171
uccgcuucac guggaguaug aagac                                             25

<210> SEQ ID NO 172
<211> LENGTH: 25
<212> TYPE: RNA
<213> ORGANISM: Artificial Sequence
<220> FEATURE:
<223> OTHER INFORMATION: target sequence

<400> SEQUENCE: 172
ccgcuucacg uggaguauga agacc                                             25

<210> SEQ ID NO 173
<211> LENGTH: 21
<212> TYPE: DNA
<213> ORGANISM: Artificial Sequence
<220> FEATURE:
<223> OTHER INFORMATION: target sequence

<400> SEQUENCE: 173
aagggagaac ttgaaacaga t                                                 21

```
<210> SEQ ID NO 174
<211> LENGTH: 21
<212> TYPE: DNA
<213> ORGANISM: Artificial Sequence
<220> FEATURE:
<223> OTHER INFORMATION: target sequence

<400> SEQUENCE: 174
cagcaatgag gcggtggtca a                                      21

<210> SEQ ID NO 175
<211> LENGTH: 21
<212> TYPE: DNA
<213> ORGANISM: Artificial Sequence
<220> FEATURE:
<223> OTHER INFORMATION: target sequence

<400> SEQUENCE: 175
tacgagaaag atcaaaggga a                                      21

<210> SEQ ID NO 176
<211> LENGTH: 21
<212> TYPE: DNA
<213> ORGANISM: Artificial Sequence
<220> FEATURE:
<223> OTHER INFORMATION: target sequence

<400> SEQUENCE: 176
caggctgcga aggaagtact a                                      21

<210> SEQ ID NO 177
<211> LENGTH: 25
<212> TYPE: RNA
<213> ORGANISM: Artificial Sequence
<220> FEATURE:
<223> OTHER INFORMATION: target sequence

<400> SEQUENCE: 177
ggcuacggac caaguuuauc cggcg                                  25

<210> SEQ ID NO 178
<211> LENGTH: 21
<212> TYPE: DNA
<213> ORGANISM: Artificial Sequence
<220> FEATURE:
<223> OTHER INFORMATION: target sequence

<400> SEQUENCE: 178
cacgagctcc ctgggaggaa a                                      21

<210> SEQ ID NO 179
<211> LENGTH: 21
<212> TYPE: DNA
<213> ORGANISM: Artificial Sequence
<220> FEATURE:
<223> OTHER INFORMATION: target sequence

<400> SEQUENCE: 179
ctggcgggac accagaagaa a                                      21

<210> SEQ ID NO 180
<211> LENGTH: 19
<212> TYPE: RNA
<213> ORGANISM: Artificial Sequence
<220> FEATURE:
<223> OTHER INFORMATION: target sequence
```

```
<400> SEQUENCE: 180
ccugcauugu ggagaauga                                               19

<210> SEQ ID NO 181
<211> LENGTH: 21
<212> TYPE: DNA
<213> ORGANISM: Artificial Sequence
<220> FEATURE:
<223> OTHER INFORMATION: target sequence

<400> SEQUENCE: 181
cagaggagaa agaaacagat a                                            21

<210> SEQ ID NO 182
<211> LENGTH: 21
<212> TYPE: DNA
<213> ORGANISM: Artificial Sequence
<220> FEATURE:
<223> OTHER INFORMATION: target sequence

<400> SEQUENCE: 182
caggtttaaa gcctacccac a                                            21

<210> SEQ ID NO 183
<211> LENGTH: 21
<212> TYPE: DNA
<213> ORGANISM: Artificial Sequence
<220> FEATURE:
<223> OTHER INFORMATION: target sequence

<400> SEQUENCE: 183
tacgttgatt tcagagaata t                                            21

<210> SEQ ID NO 184
<211> LENGTH: 21
<212> TYPE: DNA
<213> ORGANISM: Artificial Sequence
<220> FEATURE:
<223> OTHER INFORMATION: target sequence

<400> SEQUENCE: 184
cacgctcttg gtcaacagga a                                            21

<210> SEQ ID NO 185
<211> LENGTH: 19
<212> TYPE: RNA
<213> ORGANISM: Artificial Sequence
<220> FEATURE:
<223> OTHER INFORMATION: target sequence

<400> SEQUENCE: 185
cgugucugcc auguacaag                                               19

<210> SEQ ID NO 186
<211> LENGTH: 21
<212> TYPE: DNA
<213> ORGANISM: Artificial Sequence
<220> FEATURE:
<223> OTHER INFORMATION: target sequence

<400> SEQUENCE: 186
ctgggtaaga ctactcagta a                                            21

<210> SEQ ID NO 187
<211> LENGTH: 21
```

```
<212> TYPE: DNA
<213> ORGANISM: Artificial Sequence
<220> FEATURE:
<223> OTHER INFORMATION: target sequence

<400> SEQUENCE: 187
cacgtgatag tcataaccct a                                          21

<210> SEQ ID NO 188
<211> LENGTH: 21
<212> TYPE: DNA
<213> ORGANISM: Artificial Sequence
<220> FEATURE:
<223> OTHER INFORMATION: target sequence

<400> SEQUENCE: 188
cacgtccata gaacaggcaa a                                          21

<210> SEQ ID NO 189
<211> LENGTH: 19
<212> TYPE: RNA
<213> ORGANISM: Artificial Sequence
<220> FEATURE:
<223> OTHER INFORMATION: target sequence

<400> SEQUENCE: 189
ggugauccag gccacuaca                                             19

<210> SEQ ID NO 190
<211> LENGTH: 21
<212> TYPE: DNA
<213> ORGANISM: Artificial Sequence
<220> FEATURE:
<223> OTHER INFORMATION: target sequence

<400> SEQUENCE: 190
aagcataata tgaaagcatt t                                          21

<210> SEQ ID NO 191
<211> LENGTH: 19
<212> TYPE: RNA
<213> ORGANISM: Artificial Sequence
<220> FEATURE:
<223> OTHER INFORMATION: target sequence

<400> SEQUENCE: 191
caccagguua cccagcaaa                                             19

<210> SEQ ID NO 192
<211> LENGTH: 19
<212> TYPE: RNA
<213> ORGANISM: Artificial Sequence
<220> FEATURE:
<223> OTHER INFORMATION: target sequence

<400> SEQUENCE: 192
ggucccagcu ccauuugau                                             19

<210> SEQ ID NO 193
<211> LENGTH: 21
<212> TYPE: DNA
<213> ORGANISM: Artificial Sequence
<220> FEATURE:
<223> OTHER INFORMATION: target sequence

<400> SEQUENCE: 193
```

```
ctgggagtac ctagaaccct a                                              21

<210> SEQ ID NO 194
<211> LENGTH: 25
<212> TYPE: RNA
<213> ORGANISM: Artificial Sequence
<220> FEATURE:
<223> OTHER INFORMATION: target sequence

<400> SEQUENCE: 194
ggcaacaagc gaucccgaac gagga                                          25

<210> SEQ ID NO 195
<211> LENGTH: 19
<212> TYPE: RNA
<213> ORGANISM: Artificial Sequence
<220> FEATURE:
<223> OTHER INFORMATION: target sequence

<400> SEQUENCE: 195
gaggcaucuc guuuguacu                                                 19

<210> SEQ ID NO 196
<211> LENGTH: 21
<212> TYPE: DNA
<213> ORGANISM: Artificial Sequence
<220> FEATURE:
<223> OTHER INFORMATION: target sequence

<400> SEQUENCE: 196
caccaagatg atgaccaaga a                                              21

<210> SEQ ID NO 197
<211> LENGTH: 21
<212> TYPE: DNA
<213> ORGANISM: Artificial Sequence
<220> FEATURE:
<223> OTHER INFORMATION: target sequence

<400> SEQUENCE: 197
atcgggtgac ctggccaaga a                                              21

<210> SEQ ID NO 198
<211> LENGTH: 21
<212> TYPE: DNA
<213> ORGANISM: Artificial Sequence
<220> FEATURE:
<223> OTHER INFORMATION: target sequence

<400> SEQUENCE: 198
aaggcctaac tatgcctcga a                                              21

<210> SEQ ID NO 199
<211> LENGTH: 19
<212> TYPE: RNA
<213> ORGANISM: Artificial Sequence
<220> FEATURE:
<223> OTHER INFORMATION: target sequence

<400> SEQUENCE: 199
agggugaccu ggacauauc                                                 19

<210> SEQ ID NO 200
<211> LENGTH: 21
<212> TYPE: DNA
<213> ORGANISM: Artificial Sequence
```

```
<220> FEATURE:
<223> OTHER INFORMATION: target sequence

<400> SEQUENCE: 200
cagcggcagc aaaggcacta a                                              21

<210> SEQ ID NO 201
<211> LENGTH: 19
<212> TYPE: RNA
<213> ORGANISM: Artificial Sequence
<220> FEATURE:
<223> OTHER INFORMATION: target sequence

<400> SEQUENCE: 201
ucaucuucaa gacccucuu                                                 19

<210> SEQ ID NO 202
<211> LENGTH: 21
<212> TYPE: DNA
<213> ORGANISM: Artificial Sequence
<220> FEATURE:
<223> OTHER INFORMATION: target sequence

<400> SEQUENCE: 202
ccgaaggacc atagacagag a                                              21

<210> SEQ ID NO 203
<211> LENGTH: 19
<212> TYPE: RNA
<213> ORGANISM: Artificial Sequence
<220> FEATURE:
<223> OTHER INFORMATION: target sequence

<400> SEQUENCE: 203
gcggcagcau cagaacaau                                                 19

<210> SEQ ID NO 204
<211> LENGTH: 21
<212> TYPE: DNA
<213> ORGANISM: Artificial Sequence
<220> FEATURE:
<223> OTHER INFORMATION: target sequence

<400> SEQUENCE: 204
ccggaggtgg tgaagaatga a                                              21

<210> SEQ ID NO 205
<211> LENGTH: 19
<212> TYPE: RNA
<213> ORGANISM: Artificial Sequence
<220> FEATURE:
<223> OTHER INFORMATION: target sequence

<400> SEQUENCE: 205
gggucccugc aaagaccuu                                                 19

<210> SEQ ID NO 206
<211> LENGTH: 25
<212> TYPE: RNA
<213> ORGANISM: Artificial Sequence
<220> FEATURE:
<223> OTHER INFORMATION: target sequence

<400> SEQUENCE: 206
gggcaccaga guugaucuuu ggagg                                          25
```

```
<210> SEQ ID NO 207
<211> LENGTH: 25
<212> TYPE: RNA
<213> ORGANISM: Artificial Sequence
<220> FEATURE:
<223> OTHER INFORMATION: target sequence

<400> SEQUENCE: 207
agcaacacug gucacguuug gaaag                                          25

<210> SEQ ID NO 208
<211> LENGTH: 19
<212> TYPE: RNA
<213> ORGANISM: Artificial Sequence
<220> FEATURE:
<223> OTHER INFORMATION: target sequence

<400> SEQUENCE: 208
cggaagauga agccauuca                                                 19

<210> SEQ ID NO 209
<211> LENGTH: 19
<212> TYPE: RNA
<213> ORGANISM: Artificial Sequence
<220> FEATURE:
<223> OTHER INFORMATION: target sequence

<400> SEQUENCE: 209
accgaugaca agggucaua                                                 19

<210> SEQ ID NO 210
<211> LENGTH: 21
<212> TYPE: DNA
<213> ORGANISM: Artificial Sequence
<220> FEATURE:
<223> OTHER INFORMATION: target sequence

<400> SEQUENCE: 210
cagactgtct tgaacatccc a                                              21

<210> SEQ ID NO 211
<211> LENGTH: 21
<212> TYPE: DNA
<213> ORGANISM: Artificial Sequence
<220> FEATURE:
<223> OTHER INFORMATION: target sequence

<400> SEQUENCE: 211
cctgtgtgtg tttgccatca a                                              21

<210> SEQ ID NO 212
<211> LENGTH: 21
<212> TYPE: DNA
<213> ORGANISM: Artificial Sequence
<220> FEATURE:
<223> OTHER INFORMATION: target sequence

<400> SEQUENCE: 212
cagaatgaag gagaaccaga a                                              21

<210> SEQ ID NO 213
<211> LENGTH: 21
<212> TYPE: DNA
<213> ORGANISM: Artificial Sequence
<220> FEATURE:
<223> OTHER INFORMATION: target sequence
```

```
<400> SEQUENCE: 213
ctgcttaaag ttgtaacaaa t                                              21

<210> SEQ ID NO 214
<211> LENGTH: 19
<212> TYPE: RNA
<213> ORGANISM: Artificial Sequence
<220> FEATURE:
<223> OTHER INFORMATION: target sequence

<400> SEQUENCE: 214
cucgccgaug auaacuuug                                                 19

<210> SEQ ID NO 215
<211> LENGTH: 21
<212> TYPE: DNA
<213> ORGANISM: Artificial Sequence
<220> FEATURE:
<223> OTHER INFORMATION: target sequence

<400> SEQUENCE: 215
tgggattgag ttggttacct a                                              21

<210> SEQ ID NO 216
<211> LENGTH: 21
<212> TYPE: DNA
<213> ORGANISM: Artificial Sequence
<220> FEATURE:
<223> OTHER INFORMATION: target sequence

<400> SEQUENCE: 216
atcgatagtg atggaccctc a                                              21

<210> SEQ ID NO 217
<211> LENGTH: 21
<212> TYPE: DNA
<213> ORGANISM: Artificial Sequence
<220> FEATURE:
<223> OTHER INFORMATION: target sequence

<400> SEQUENCE: 217
tcgatagtga tggaccctca a                                              21

<210> SEQ ID NO 218
<211> LENGTH: 19
<212> TYPE: RNA
<213> ORGANISM: Artificial Sequence
<220> FEATURE:
<223> OTHER INFORMATION: target sequence

<400> SEQUENCE: 218
gcugggcuuc ugcugaacu                                                 19

<210> SEQ ID NO 219
<211> LENGTH: 21
<212> TYPE: DNA
<213> ORGANISM: Artificial Sequence
<220> FEATURE:
<223> OTHER INFORMATION: target sequence

<400> SEQUENCE: 219
caccagtctt gtatctctta a                                              21

<210> SEQ ID NO 220
```

```
<211> LENGTH: 21
<212> TYPE: DNA
<213> ORGANISM: Artificial Sequence
<220> FEATURE:
<223> OTHER INFORMATION: target sequence

<400> SEQUENCE: 220
cagctatgag ctggccttca a                                              21

<210> SEQ ID NO 221
<211> LENGTH: 19
<212> TYPE: RNA
<213> ORGANISM: Artificial Sequence
<220> FEATURE:
<223> OTHER INFORMATION: target sequence

<400> SEQUENCE: 221
gggugaagag aaucuucua                                                 19

<210> SEQ ID NO 222
<211> LENGTH: 21
<212> TYPE: DNA
<213> ORGANISM: Artificial Sequence
<220> FEATURE:
<223> OTHER INFORMATION: target sequence

<400> SEQUENCE: 222
cagccagaat ccaaacagca a                                              21

<210> SEQ ID NO 223
<211> LENGTH: 19
<212> TYPE: RNA
<213> ORGANISM: Artificial Sequence
<220> FEATURE:
<223> OTHER INFORMATION: target sequence

<400> SEQUENCE: 223
uggcagccag uuuggauuu                                                 19

<210> SEQ ID NO 224
<211> LENGTH: 21
<212> TYPE: DNA
<213> ORGANISM: Artificial Sequence
<220> FEATURE:
<223> OTHER INFORMATION: target sequence

<400> SEQUENCE: 224
ctcgcttagc atggtaaatc a                                              21

<210> SEQ ID NO 225
<211> LENGTH: 19
<212> TYPE: RNA
<213> ORGANISM: Artificial Sequence
<220> FEATURE:
<223> OTHER INFORMATION: target sequence

<400> SEQUENCE: 225
ccagauuuca ggccuucuu                                                 19

<210> SEQ ID NO 226
<211> LENGTH: 21
<212> TYPE: DNA
<213> ORGANISM: Artificial Sequence
<220> FEATURE:
<223> OTHER INFORMATION: target sequence

<400> SEQUENCE: 226
```

```
cgcgcgcgag tcgacaagta a                                              21

<210> SEQ ID NO 227
<211> LENGTH: 21
<212> TYPE: DNA
<213> ORGANISM: Artificial Sequence
<220> FEATURE:
<223> OTHER INFORMATION: target sequence

<400> SEQUENCE: 227
ttcgttaaca ttgaccaaga a                                              21

<210> SEQ ID NO 228
<211> LENGTH: 21
<212> TYPE: DNA
<213> ORGANISM: Artificial Sequence
<220> FEATURE:
<223> OTHER INFORMATION: target sequence

<400> SEQUENCE: 228
accagccata actaacagca a                                              21

<210> SEQ ID NO 229
<211> LENGTH: 21
<212> TYPE: DNA
<213> ORGANISM: Artificial Sequence
<220> FEATURE:
<223> OTHER INFORMATION: target sequence

<400> SEQUENCE: 229
atggactaga tgatattact a                                              21

<210> SEQ ID NO 230
<211> LENGTH: 19
<212> TYPE: RNA
<213> ORGANISM: Artificial Sequence
<220> FEATURE:
<223> OTHER INFORMATION: target sequence

<400> SEQUENCE: 230
guucagcauc ucuccagau                                                 19

<210> SEQ ID NO 231
<211> LENGTH: 21
<212> TYPE: DNA
<213> ORGANISM: Artificial Sequence
<220> FEATURE:
<223> OTHER INFORMATION: target sequence

<400> SEQUENCE: 231
cagcgctttg tgcccattgt a                                              21

<210> SEQ ID NO 232
<211> LENGTH: 19
<212> TYPE: RNA
<213> ORGANISM: Artificial Sequence
<220> FEATURE:
<223> OTHER INFORMATION: target sequence

<400> SEQUENCE: 232
ugggagacgc uucauaacu                                                 19

<210> SEQ ID NO 233
<211> LENGTH: 21
<212> TYPE: DNA
```

```
<213> ORGANISM: Artificial Sequence
<220> FEATURE:
<223> OTHER INFORMATION: target sequence

<400> SEQUENCE: 233
accgagagag ccgtatatta a                                              21

<210> SEQ ID NO 234
<211> LENGTH: 25
<212> TYPE: RNA
<213> ORGANISM: Artificial Sequence
<220> FEATURE:
<223> OTHER INFORMATION: target sequence

<400> SEQUENCE: 234
agcucuccgg cuuauacucc cagcg                                          25

<210> SEQ ID NO 235
<211> LENGTH: 19
<212> TYPE: RNA
<213> ORGANISM: Artificial Sequence
<220> FEATURE:
<223> OTHER INFORMATION: target sequence

<400> SEQUENCE: 235
aucaccaagg gacuggduua                                                19

<210> SEQ ID NO 236
<211> LENGTH: 21
<212> TYPE: DNA
<213> ORGANISM: Artificial Sequence
<220> FEATURE:
<223> OTHER INFORMATION: target sequence

<400> SEQUENCE: 236
acagatcttt ggagtgccta a                                              21

<210> SEQ ID NO 237
<211> LENGTH: 21
<212> TYPE: DNA
<213> ORGANISM: Artificial Sequence
<220> FEATURE:
<223> OTHER INFORMATION: target sequence

<400> SEQUENCE: 237
cagggatatt gccgcccgga a                                              21

<210> SEQ ID NO 238
<211> LENGTH: 21
<212> TYPE: DNA
<213> ORGANISM: Artificial Sequence
<220> FEATURE:
<223> OTHER INFORMATION: target sequence

<400> SEQUENCE: 238
caggcaaatg tgcaatacca a                                              21

<210> SEQ ID NO 239
<211> LENGTH: 21
<212> TYPE: DNA
<213> ORGANISM: Artificial Sequence
<220> FEATURE:
<223> OTHER INFORMATION: target sequence

<400> SEQUENCE: 239
ccggatcttg atgctggtgt a                                              21
```

```
<210> SEQ ID NO 240
<211> LENGTH: 21
<212> TYPE: DNA
<213> ORGANISM: Artificial Sequence
<220> FEATURE:
<223> OTHER INFORMATION: target sequence

<400> SEQUENCE: 240
cagctactct ctattgttat a                                              21

<210> SEQ ID NO 241
<211> LENGTH: 21
<212> TYPE: DNA
<213> ORGANISM: Artificial Sequence
<220> FEATURE:
<223> OTHER INFORMATION: target sequence

<400> SEQUENCE: 241
ctgaggttgt gtatcatatt a                                              21

<210> SEQ ID NO 242
<211> LENGTH: 19
<212> TYPE: RNA
<213> ORGANISM: Artificial Sequence
<220> FEATURE:
<223> OTHER INFORMATION: target sequence

<400> SEQUENCE: 242
gacuugcuug uugccauca                                                 19

<210> SEQ ID NO 243
<211> LENGTH: 21
<212> TYPE: DNA
<213> ORGANISM: Artificial Sequence
<220> FEATURE:
<223> OTHER INFORMATION: target sequence

<400> SEQUENCE: 243
caagatatat atacgcctaa a                                              21

<210> SEQ ID NO 244
<211> LENGTH: 25
<212> TYPE: RNA
<213> ORGANISM: Artificial Sequence
<220> FEATURE:
<223> OTHER INFORMATION: target sequence

<400> SEQUENCE: 244
accagagguc uacgccauca ugcgg                                          25

<210> SEQ ID NO 245
<211> LENGTH: 21
<212> TYPE: DNA
<213> ORGANISM: Artificial Sequence
<220> FEATURE:
<223> OTHER INFORMATION: target sequence

<400> SEQUENCE: 245
cacggaggca atcgactgca t                                              21

<210> SEQ ID NO 246
<211> LENGTH: 19
<212> TYPE: RNA
<213> ORGANISM: Artificial Sequence
<220> FEATURE:
```

<223> OTHER INFORMATION: target sequence

<400> SEQUENCE: 246
gagcaucaug uacaggaaa					19

<210> SEQ ID NO 247
<211> LENGTH: 21
<212> TYPE: DNA
<213> ORGANISM: Artificial Sequence
<220> FEATURE:
<223> OTHER INFORMATION: target sequence

<400> SEQUENCE: 247
accacgaaca gaagtaatga a					21

<210> SEQ ID NO 248
<211> LENGTH: 19
<212> TYPE: RNA
<213> ORGANISM: Artificial Sequence
<220> FEATURE:
<223> OTHER INFORMATION: target sequence

<400> SEQUENCE: 248
uugccugugc acgcuucau					19

<210> SEQ ID NO 249
<211> LENGTH: 21
<212> TYPE: DNA
<213> ORGANISM: Artificial Sequence
<220> FEATURE:
<223> OTHER INFORMATION: target sequence

<400> SEQUENCE: 249
ccggtttggg aaagtctaca a					21

<210> SEQ ID NO 250
<211> LENGTH: 21
<212> TYPE: DNA
<213> ORGANISM: Artificial Sequence
<220> FEATURE:
<223> OTHER INFORMATION: target sequence

<400> SEQUENCE: 250
ctggcttaag aaggtcgcct a					21

<210> SEQ ID NO 251
<211> LENGTH: 21
<212> TYPE: DNA
<213> ORGANISM: Artificial Sequence
<220> FEATURE:
<223> OTHER INFORMATION: target sequence

<400> SEQUENCE: 251
aagggcctct aacaaggaga a					21

<210> SEQ ID NO 252
<211> LENGTH: 25
<212> TYPE: RNA
<213> ORGANISM: Artificial Sequence
<220> FEATURE:
<223> OTHER INFORMATION: target sequence

<400> SEQUENCE: 252
agcuacgcug ugguuuauuc uuaag					25

```
<210> SEQ ID NO 253
<211> LENGTH: 25
<212> TYPE: RNA
<213> ORGANISM: Artificial Sequence
<220> FEATURE:
<223> OTHER INFORMATION: target sequence

<400> SEQUENCE: 253
ggagcuacgc ugugguuuau ucugg                                              25

<210> SEQ ID NO 254
<211> LENGTH: 21
<212> TYPE: DNA
<213> ORGANISM: Artificial Sequence
<220> FEATURE:
<223> OTHER INFORMATION: target sequence

<400> SEQUENCE: 254
caagaaggaa ttaattatta a                                                  21

<210> SEQ ID NO 255
<211> LENGTH: 19
<212> TYPE: RNA
<213> ORGANISM: Artificial Sequence
<220> FEATURE:
<223> OTHER INFORMATION: target sequence

<400> SEQUENCE: 255
cagcaaccca agaaggaau                                                     19

<210> SEQ ID NO 256
<211> LENGTH: 21
<212> TYPE: DNA
<213> ORGANISM: Artificial Sequence
<220> FEATURE:
<223> OTHER INFORMATION: target sequence

<400> SEQUENCE: 256
caggccacct ctgttaacga a                                                  21

<210> SEQ ID NO 257
<211> LENGTH: 21
<212> TYPE: DNA
<213> ORGANISM: Artificial Sequence
<220> FEATURE:
<223> OTHER INFORMATION: target sequence

<400> SEQUENCE: 257
ctcaggatgc ttggatatta a                                                  21

<210> SEQ ID NO 258
<211> LENGTH: 19
<212> TYPE: RNA
<213> ORGANISM: Artificial Sequence
<220> FEATURE:
<223> OTHER INFORMATION: target sequence

<400> SEQUENCE: 258
caggucuugg auaacuuuc                                                     19

<210> SEQ ID NO 259
<211> LENGTH: 21
<212> TYPE: DNA
<213> ORGANISM: Artificial Sequence
<220> FEATURE:
<223> OTHER INFORMATION: target sequence
```

```
<400> SEQUENCE: 259
ctcgttactt tgggtaaaga a                                              21

<210> SEQ ID NO 260
<211> LENGTH: 21
<212> TYPE: DNA
<213> ORGANISM: Artificial Sequence
<220> FEATURE:
<223> OTHER INFORMATION: target sequence

<400> SEQUENCE: 260
ctggatttgt ttctcaggca a                                              21

<210> SEQ ID NO 261
<211> LENGTH: 21
<212> TYPE: DNA
<213> ORGANISM: Artificial Sequence
<220> FEATURE:
<223> OTHER INFORMATION: target sequence

<400> SEQUENCE: 261
tcgcctctag ctggaaacaa a                                              21

<210> SEQ ID NO 262
<211> LENGTH: 19
<212> TYPE: RNA
<213> ORGANISM: Artificial Sequence
<220> FEATURE:
<223> OTHER INFORMATION: target sequence

<400> SEQUENCE: 262
gacgugugga ucggcuucu                                                 19

<210> SEQ ID NO 263
<211> LENGTH: 21
<212> TYPE: DNA
<213> ORGANISM: Artificial Sequence
<220> FEATURE:
<223> OTHER INFORMATION: target sequence

<400> SEQUENCE: 263
cccgtccatt gtgggtagca a                                              21

<210> SEQ ID NO 264
<211> LENGTH: 19
<212> TYPE: RNA
<213> ORGANISM: Artificial Sequence
<220> FEATURE:
<223> OTHER INFORMATION: target sequence

<400> SEQUENCE: 264
ccagaccugg ugaauguaa                                                 19

<210> SEQ ID NO 265
<211> LENGTH: 21
<212> TYPE: DNA
<213> ORGANISM: Artificial Sequence
<220> FEATURE:
<223> OTHER INFORMATION: target sequence

<400> SEQUENCE: 265
caggatctta acactgagac a                                              21

<210> SEQ ID NO 266
<211> LENGTH: 21
```

```
<212> TYPE: DNA
<213> ORGANISM: Artificial Sequence
<220> FEATURE:
<223> OTHER INFORMATION: target sequence

<400> SEQUENCE: 266
acagaaggtg gtgaaactga a                                              21

<210> SEQ ID NO 267
<211> LENGTH: 21
<212> TYPE: DNA
<213> ORGANISM: Artificial Sequence
<220> FEATURE:
<223> OTHER INFORMATION: target sequence

<400> SEQUENCE: 267
cagaaggtgg tgaaactgaa a                                              21

<210> SEQ ID NO 268
<211> LENGTH: 19
<212> TYPE: RNA
<213> ORGANISM: Artificial Sequence
<220> FEATURE:
<223> OTHER INFORMATION: target sequence

<400> SEQUENCE: 268
cgcugccauc cacaagaaa                                                 19

<210> SEQ ID NO 269
<211> LENGTH: 21
<212> TYPE: DNA
<213> ORGANISM: Artificial Sequence
<220> FEATURE:
<223> OTHER INFORMATION: target sequence

<400> SEQUENCE: 269
ccgggacact atattccaga a                                              21

<210> SEQ ID NO 270
<211> LENGTH: 21
<212> TYPE: DNA
<213> ORGANISM: Artificial Sequence
<220> FEATURE:
<223> OTHER INFORMATION: target sequence

<400> SEQUENCE: 270
acgccgctgg agaaagcttt a                                              21

<210> SEQ ID NO 271
<211> LENGTH: 19
<212> TYPE: RNA
<213> ORGANISM: Artificial Sequence
<220> FEATURE:
<223> OTHER INFORMATION: target sequence

<400> SEQUENCE: 271
ggagauacaa ccagcacuu                                                 19

<210> SEQ ID NO 272
<211> LENGTH: 25
<212> TYPE: RNA
<213> ORGANISM: Artificial Sequence
<220> FEATURE:
<223> OTHER INFORMATION: target sequence

<400> SEQUENCE: 272
```

```
gcaccaacca ucgagcaaau gaaag                                           25

<210> SEQ ID NO 273
<211> LENGTH: 25
<212> TYPE: RNA
<213> ORGANISM: Artificial Sequence
<220> FEATURE:
<223> OTHER INFORMATION: target sequence

<400> SEQUENCE: 273
caccaaccau cgagcaaaug aaaga                                           25

<210> SEQ ID NO 274
<211> LENGTH: 21
<212> TYPE: DNA
<213> ORGANISM: Artificial Sequence
<220> FEATURE:
<223> OTHER INFORMATION: target sequence

<400> SEQUENCE: 274
ccggcctgcc atggccatct t                                               21

<210> SEQ ID NO 275
<211> LENGTH: 19
<212> TYPE: RNA
<213> ORGANISM: Artificial Sequence
<220> FEATURE:
<223> OTHER INFORMATION: target sequence

<400> SEQUENCE: 275
guggauuuug ccggcuggu                                                  19

<210> SEQ ID NO 276
<211> LENGTH: 21
<212> TYPE: DNA
<213> ORGANISM: Artificial Sequence
<220> FEATURE:
<223> OTHER INFORMATION: target sequence

<400> SEQUENCE: 276
ccgggccacc gtgaactcac a                                               21

<210> SEQ ID NO 277
<211> LENGTH: 21
<212> TYPE: DNA
<213> ORGANISM: Artificial Sequence
<220> FEATURE:
<223> OTHER INFORMATION: target sequence

<400> SEQUENCE: 277
aagacgtatg ttggaacaaa t                                               21

<210> SEQ ID NO 278
<211> LENGTH: 21
<212> TYPE: DNA
<213> ORGANISM: Artificial Sequence
<220> FEATURE:
<223> OTHER INFORMATION: target sequence

<400> SEQUENCE: 278
caagacgtat gttggaacaa a                                               21

<210> SEQ ID NO 279
<211> LENGTH: 25
<212> TYPE: RNA
<213> ORGANISM: Artificial Sequence
```

```
<220> FEATURE:
<223> OTHER INFORMATION: target sequence

<400> SEQUENCE: 279
uggccgcuaa acuugcauau cuuug                                          25

<210> SEQ ID NO 280
<211> LENGTH: 21
<212> TYPE: DNA
<213> ORGANISM: Artificial Sequence
<220> FEATURE:
<223> OTHER INFORMATION: target sequence

<400> SEQUENCE: 280
tacgtgtgag tcccaaagca a                                              21

<210> SEQ ID NO 281
<211> LENGTH: 21
<212> TYPE: DNA
<213> ORGANISM: Artificial Sequence
<220> FEATURE:
<223> OTHER INFORMATION: target sequence

<400> SEQUENCE: 281
aagcagtgca tttgtaggaa a                                              21

<210> SEQ ID NO 282
<211> LENGTH: 21
<212> TYPE: DNA
<213> ORGANISM: Artificial Sequence
<220> FEATURE:
<223> OTHER INFORMATION: target sequence

<400> SEQUENCE: 282
ctgcatgtct ttaatgcaga a                                              21

<210> SEQ ID NO 283
<211> LENGTH: 21
<212> TYPE: DNA
<213> ORGANISM: Artificial Sequence
<220> FEATURE:
<223> OTHER INFORMATION: target sequence

<400> SEQUENCE: 283
ttgtccaaca ataaacagga a                                              21

<210> SEQ ID NO 284
<211> LENGTH: 21
<212> TYPE: DNA
<213> ORGANISM: Artificial Sequence
<220> FEATURE:
<223> OTHER INFORMATION: target sequence

<400> SEQUENCE: 284
ttggtttgta tgagatggtt a                                              21

<210> SEQ ID NO 285
<211> LENGTH: 19
<212> TYPE: RNA
<213> ORGANISM: Artificial Sequence
<220> FEATURE:
<223> OTHER INFORMATION: target sequence

<400> SEQUENCE: 285
ccaguucacc accaaaaua                                                 19
```

```
<210> SEQ ID NO 286
<211> LENGTH: 19
<212> TYPE: RNA
<213> ORGANISM: Artificial Sequence
<220> FEATURE:
<223> OTHER INFORMATION: target sequence

<400> SEQUENCE: 286
cucguugcca caguuauaa                                                    19

<210> SEQ ID NO 287
<211> LENGTH: 21
<212> TYPE: DNA
<213> ORGANISM: Artificial Sequence
<220> FEATURE:
<223> OTHER INFORMATION: target sequence

<400> SEQUENCE: 287
caggtctggc ttggcaccca a                                                 21

<210> SEQ ID NO 288
<211> LENGTH: 21
<212> TYPE: DNA
<213> ORGANISM: Artificial Sequence
<220> FEATURE:
<223> OTHER INFORMATION: target sequence

<400> SEQUENCE: 288
ctggtgaagt ctgaactgga a                                                 21

<210> SEQ ID NO 289
<211> LENGTH: 21
<212> TYPE: DNA
<213> ORGANISM: Artificial Sequence
<220> FEATURE:
<223> OTHER INFORMATION: target sequence

<400> SEQUENCE: 289
ttcgagtagg tgaatcttaa a                                                 21

<210> SEQ ID NO 290
<211> LENGTH: 21
<212> TYPE: DNA
<213> ORGANISM: Artificial Sequence
<220> FEATURE:
<223> OTHER INFORMATION: target sequence

<400> SEQUENCE: 290
taggtgaatc ttaaagaaat a                                                 21

<210> SEQ ID NO 291
<211> LENGTH: 21
<212> TYPE: DNA
<213> ORGANISM: Artificial Sequence
<220> FEATURE:
<223> OTHER INFORMATION: target sequence

<400> SEQUENCE: 291
cagcaccaca ccatccctaa a                                                 21

<210> SEQ ID NO 292
<211> LENGTH: 19
<212> TYPE: RNA
<213> ORGANISM: Artificial Sequence
<220> FEATURE:
<223> OTHER INFORMATION: target sequence
```

```
<400> SEQUENCE: 292
gcuggugaau gagaaauuc                                                 19

<210> SEQ ID NO 293
<211> LENGTH: 21
<212> TYPE: DNA
<213> ORGANISM: Artificial Sequence
<220> FEATURE:
<223> OTHER INFORMATION: target sequence

<400> SEQUENCE: 293
ccgaaagaag ctggtgtcca a                                              21

<210> SEQ ID NO 294
<211> LENGTH: 25
<212> TYPE: RNA
<213> ORGANISM: Artificial Sequence
<220> FEATURE:
<223> OTHER INFORMATION: target sequence

<400> SEQUENCE: 294
cgguuagaac aagagguaaa ugacg                                          25

<210> SEQ ID NO 295
<211> LENGTH: 25
<212> TYPE: RNA
<213> ORGANISM: Artificial Sequence
<220> FEATURE:
<223> OTHER INFORMATION: target sequence

<400> SEQUENCE: 295
gguuagaaca agagguaaau gaagg                                          25

<210> SEQ ID NO 296
<211> LENGTH: 21
<212> TYPE: DNA
<213> ORGANISM: Artificial Sequence
<220> FEATURE:
<223> OTHER INFORMATION: target sequence

<400> SEQUENCE: 296
caggttgaag tcaagatgac a                                              21

<210> SEQ ID NO 297
<211> LENGTH: 21
<212> TYPE: DNA
<213> ORGANISM: Artificial Sequence
<220> FEATURE:
<223> OTHER INFORMATION: target sequence

<400> SEQUENCE: 297
cagttaccta atcatgttga a                                              21

<210> SEQ ID NO 298
<211> LENGTH: 21
<212> TYPE: DNA
<213> ORGANISM: Artificial Sequence
<220> FEATURE:
<223> OTHER INFORMATION: target sequence

<400> SEQUENCE: 298
aagacccaaa cctctgcata a                                              21

<210> SEQ ID NO 299
```

```
<210> SEQ ID NO 299
<211> LENGTH: 21
<212> TYPE: DNA
<213> ORGANISM: Artificial Sequence
<220> FEATURE:
<223> OTHER INFORMATION: target sequence

<400> SEQUENCE: 299
cagtgtgaat gcagacctaa a                                          21

<210> SEQ ID NO 300
<211> LENGTH: 21
<212> TYPE: DNA
<213> ORGANISM: Artificial Sequence
<220> FEATURE:
<223> OTHER INFORMATION: target sequence

<400> SEQUENCE: 300
tgagaggttg cgcaacgttc a                                          21

<210> SEQ ID NO 301
<211> LENGTH: 21
<212> TYPE: DNA
<213> ORGANISM: Artificial Sequence
<220> FEATURE:
<223> OTHER INFORMATION: target sequence

<400> SEQUENCE: 301
cgcgcgcttt gggaacagga a                                          21

<210> SEQ ID NO 302
<211> LENGTH: 19
<212> TYPE: RNA
<213> ORGANISM: Artificial Sequence
<220> FEATURE:
<223> OTHER INFORMATION: target sequence

<400> SEQUENCE: 302
cccagacuuu ggaucucuu                                             19

<210> SEQ ID NO 303
<211> LENGTH: 21
<212> TYPE: DNA
<213> ORGANISM: Artificial Sequence
<220> FEATURE:
<223> OTHER INFORMATION: target sequence

<400> SEQUENCE: 303
tcggaaagat ataccctgta t                                          21

<210> SEQ ID NO 304
<211> LENGTH: 21
<212> TYPE: DNA
<213> ORGANISM: Artificial Sequence
<220> FEATURE:
<223> OTHER INFORMATION: target sequence

<400> SEQUENCE: 304
cagataatag tcggaaacaa a                                          21

<210> SEQ ID NO 305
<211> LENGTH: 21
<212> TYPE: DNA
<213> ORGANISM: Artificial Sequence
<220> FEATURE:
<223> OTHER INFORMATION: target sequence

<400> SEQUENCE: 305
```

```
tccgaacatc gtggagctga a                                              21

<210> SEQ ID NO 306
<211> LENGTH: 21
<212> TYPE: DNA
<213> ORGANISM: Artificial Sequence
<220> FEATURE:
<223> OTHER INFORMATION: target sequence

<400> SEQUENCE: 306
ccggaagcag ccctacaaca a                                              21

<210> SEQ ID NO 307
<211> LENGTH: 21
<212> TYPE: DNA
<213> ORGANISM: Artificial Sequence
<220> FEATURE:
<223> OTHER INFORMATION: target sequence

<400> SEQUENCE: 307
caggattcag gctgcaaagt a                                              21

<210> SEQ ID NO 308
<211> LENGTH: 21
<212> TYPE: DNA
<213> ORGANISM: Artificial Sequence
<220> FEATURE:
<223> OTHER INFORMATION: target sequence

<400> SEQUENCE: 308
cagaggaggt gaacaaatta a                                              21

<210> SEQ ID NO 309
<211> LENGTH: 21
<212> TYPE: DNA
<213> ORGANISM: Artificial Sequence
<220> FEATURE:
<223> OTHER INFORMATION: target sequence

<400> SEQUENCE: 309
cagagcagtg gtaccctgta a                                              21

<210> SEQ ID NO 310
<211> LENGTH: 21
<212> TYPE: DNA
<213> ORGANISM: Artificial Sequence
<220> FEATURE:
<223> OTHER INFORMATION: target sequence

<400> SEQUENCE: 310
cccggctgat gcaaagcttt a                                              21

<210> SEQ ID NO 311
<211> LENGTH: 19
<212> TYPE: RNA
<213> ORGANISM: Artificial Sequence
<220> FEATURE:
<223> OTHER INFORMATION: target sequence

<400> SEQUENCE: 311
ugggagauuc augcccuua                                                 19

<210> SEQ ID NO 312
<211> LENGTH: 19
<212> TYPE: RNA
```

```
<213> ORGANISM: Artificial Sequence
<220> FEATURE:
<223> OTHER INFORMATION: target sequence

<400> SEQUENCE: 312
ucccagauuc uuggccaau                                                 19

<210> SEQ ID NO 313
<211> LENGTH: 21
<212> TYPE: DNA
<213> ORGANISM: Artificial Sequence
<220> FEATURE:
<223> OTHER INFORMATION: target sequence

<400> SEQUENCE: 313
cactttcatg ttcctcccta a                                              21

<210> SEQ ID NO 314
<211> LENGTH: 21
<212> TYPE: DNA
<213> ORGANISM: Artificial Sequence
<220> FEATURE:
<223> OTHER INFORMATION: target sequence

<400> SEQUENCE: 314
ccgcgccttc atcatcacca t                                              21

<210> SEQ ID NO 315
<211> LENGTH: 21
<212> TYPE: DNA
<213> ORGANISM: Artificial Sequence
<220> FEATURE:
<223> OTHER INFORMATION: target sequence

<400> SEQUENCE: 315
ctggaagact tcataaagca a                                              21

<210> SEQ ID NO 316
<211> LENGTH: 21
<212> TYPE: DNA
<213> ORGANISM: Artificial Sequence
<220> FEATURE:
<223> OTHER INFORMATION: target sequence

<400> SEQUENCE: 316
caggataaag ccgaactggt a                                              21

<210> SEQ ID NO 317
<211> LENGTH: 21
<212> TYPE: DNA
<213> ORGANISM: Artificial Sequence
<220> FEATURE:
<223> OTHER INFORMATION: target sequence

<400> SEQUENCE: 317
ccggacctac cgctacagca a                                              21

<210> SEQ ID NO 318
<211> LENGTH: 25
<212> TYPE: DNA
<213> ORGANISM: Artificial Sequence
<220> FEATURE:
<223> OTHER INFORMATION: target sequence

<400> SEQUENCE: 318
accagcauga cacggagaug aagta                                          25
```

```
<210> SEQ ID NO 319
<211> LENGTH: 19
<212> TYPE: RNA
<213> ORGANISM: Artificial Sequence
<220> FEATURE:
<223> OTHER INFORMATION: target sequence

<400> SEQUENCE: 319
uguggcuucc aaucaaguu                                            19

<210> SEQ ID NO 320
<211> LENGTH: 21
<212> TYPE: DNA
<213> ORGANISM: Artificial Sequence
<220> FEATURE:
<223> OTHER INFORMATION: target sequence

<400> SEQUENCE: 320
tagctatgac ctcaactcta a                                         21

<210> SEQ ID NO 321
<211> LENGTH: 21
<212> TYPE: DNA
<213> ORGANISM: Artificial Sequence
<220> FEATURE:
<223> OTHER INFORMATION: target sequence

<400> SEQUENCE: 321
tagcatagat tgtcaaatgt a                                         21

<210> SEQ ID NO 322
<211> LENGTH: 21
<212> TYPE: DNA
<213> ORGANISM: Artificial Sequence
<220> FEATURE:
<223> OTHER INFORMATION: target sequence

<400> SEQUENCE: 322
tagctctaat ctaatatata a                                         21

<210> SEQ ID NO 323
<211> LENGTH: 25
<212> TYPE: RNA
<213> ORGANISM: Artificial Sequence
<220> FEATURE:
<223> OTHER INFORMATION: target sequence

<400> SEQUENCE: 323
ggcuccucua cgucacuugc gucgg                                     25

<210> SEQ ID NO 324
<211> LENGTH: 19
<212> TYPE: RNA
<213> ORGANISM: Artificial Sequence
<220> FEATURE:
<223> OTHER INFORMATION: target sequence

<400> SEQUENCE: 324
cuggaguaca ccaagaaug                                            19

<210> SEQ ID NO 325
<211> LENGTH: 21
<212> TYPE: DNA
<213> ORGANISM: Artificial Sequence
<220> FEATURE:
```

-continued

```
<223> OTHER INFORMATION: target sequence

<400> SEQUENCE: 325
cgagttcaac ctggagagca a                                              21

<210> SEQ ID NO 326
<211> LENGTH: 21
<212> TYPE: DNA
<213> ORGANISM: Artificial Sequence
<220> FEATURE:
<223> OTHER INFORMATION: target sequence

<400> SEQUENCE: 326
acggaacttg atacagcaca a                                              21

<210> SEQ ID NO 327
<211> LENGTH: 21
<212> TYPE: DNA
<213> ORGANISM: Artificial Sequence
<220> FEATURE:
<223> OTHER INFORMATION: target sequence

<400> SEQUENCE: 327
ttcgagtaac ttgcagttca a                                              21

<210> SEQ ID NO 328
<211> LENGTH: 21
<212> TYPE: DNA
<213> ORGANISM: Artificial Sequence
<220> FEATURE:
<223> OTHER INFORMATION: target sequence

<400> SEQUENCE: 328
ccgccgtctg gtggtcctca a                                              21

<210> SEQ ID NO 329
<211> LENGTH: 21
<212> TYPE: DNA
<213> ORGANISM: Artificial Sequence
<220> FEATURE:
<223> OTHER INFORMATION: target sequence

<400> SEQUENCE: 329
cacagtgagt atgtaacttg a                                              21

<210> SEQ ID NO 330
<211> LENGTH: 21
<212> TYPE: DNA
<213> ORGANISM: Artificial Sequence
<220> FEATURE:
<223> OTHER INFORMATION: target sequence

<400> SEQUENCE: 330
acgattcttc agagtatgca a                                              21

<210> SEQ ID NO 331
<211> LENGTH: 21
<212> TYPE: DNA
<213> ORGANISM: Artificial Sequence
<220> FEATURE:
<223> OTHER INFORMATION: target sequence

<400> SEQUENCE: 331
caggtttcaa gggtagtgaa a                                              21
```

```
<210> SEQ ID NO 332
<211> LENGTH: 21
<212> TYPE: DNA
<213> ORGANISM: Artificial Sequence
<220> FEATURE:
<223> OTHER INFORMATION: target sequence

<400> SEQUENCE: 332
aggcaagatc ctacccggaa a                                              21

<210> SEQ ID NO 333
<211> LENGTH: 19
<212> TYPE: RNA
<213> ORGANISM: Artificial Sequence
<220> FEATURE:
<223> OTHER INFORMATION: target sequence

<400> SEQUENCE: 333
cgcaaugaca agguguucu                                                 19

<210> SEQ ID NO 334
<211> LENGTH: 21
<212> TYPE: DNA
<213> ORGANISM: Artificial Sequence
<220> FEATURE:
<223> OTHER INFORMATION: target sequence

<400> SEQUENCE: 334
atccggttta tttatgtgca a                                              21

<210> SEQ ID NO 335
<211> LENGTH: 21
<212> TYPE: DNA
<213> ORGANISM: Artificial Sequence
<220> FEATURE:
<223> OTHER INFORMATION: target sequence

<400> SEQUENCE: 335
ccggcgtggg cgaattcaga a                                              21

<210> SEQ ID NO 336
<211> LENGTH: 21
<212> TYPE: DNA
<213> ORGANISM: Artificial Sequence
<220> FEATURE:
<223> OTHER INFORMATION: target sequence

<400> SEQUENCE: 336
ccgccggagg ctggaccaca a                                              21

<210> SEQ ID NO 337
<211> LENGTH: 21
<212> TYPE: DNA
<213> ORGANISM: Artificial Sequence
<220> FEATURE:
<223> OTHER INFORMATION: target sequence

<400> SEQUENCE: 337
gacaggcaag ttcatcttaa a                                              21

<210> SEQ ID NO 338
<211> LENGTH: 21
<212> TYPE: DNA
<213> ORGANISM: Artificial Sequence
<220> FEATURE:
<223> OTHER INFORMATION: target sequence
```

```
<400> SEQUENCE: 338
atccagcaac ttgcacctat a                                              21

<210> SEQ ID NO 339
<211> LENGTH: 21
<212> TYPE: DNA
<213> ORGANISM: Artificial Sequence
<220> FEATURE:
<223> OTHER INFORMATION: target sequence

<400> SEQUENCE: 339
aaggagccat ctacctatga a                                              21

<210> SEQ ID NO 340
<211> LENGTH: 25
<212> TYPE: DNA
<213> ORGANISM: Artificial Sequence
<220> FEATURE:
<223> OTHER INFORMATION: target sequence

<400> SEQUENCE: 340
ugcuacacgc cgagauauuc cautg                                          25

<210> SEQ ID NO 341
<211> LENGTH: 19
<212> TYPE: RNA
<213> ORGANISM: Artificial Sequence
<220> FEATURE:
<223> OTHER INFORMATION: target sequence

<400> SEQUENCE: 341
gcucagauug cggaaauca                                                 19

<210> SEQ ID NO 342
<211> LENGTH: 21
<212> TYPE: DNA
<213> ORGANISM: Artificial Sequence
<220> FEATURE:
<223> OTHER INFORMATION: target sequence

<400> SEQUENCE: 342
tccgctgaga tcagaaggca a                                              21

<210> SEQ ID NO 343
<211> LENGTH: 21
<212> TYPE: DNA
<213> ORGANISM: Artificial Sequence
<220> FEATURE:
<223> OTHER INFORMATION: target sequence

<400> SEQUENCE: 343
ccggttccgc tgagatcaga a                                              21

<210> SEQ ID NO 344
<211> LENGTH: 25
<212> TYPE: RNA
<213> ORGANISM: Artificial Sequence
<220> FEATURE:
<223> OTHER INFORMATION: target sequence

<400> SEQUENCE: 344
uggucugacu gagccuaaag uugug                                          25

<210> SEQ ID NO 345
<211> LENGTH: 25
```

```
<212> TYPE: RNA
<213> ORGANISM: Artificial Sequence
<220> FEATURE:
<223> OTHER INFORMATION: target sequence

<400> SEQUENCE: 345
ggccagggcu uggcuacaac gaggg                                      25

<210> SEQ ID NO 346
<211> LENGTH: 21
<212> TYPE: DNA
<213> ORGANISM: Artificial Sequence
<220> FEATURE:
<223> OTHER INFORMATION: target sequence

<400> SEQUENCE: 346
tagggactaa ctatagcaca a                                          21

<210> SEQ ID NO 347
<211> LENGTH: 21
<212> TYPE: DNA
<213> ORGANISM: Artificial Sequence
<220> FEATURE:
<223> OTHER INFORMATION: target sequence

<400> SEQUENCE: 347
ctggagtagg gactaactat a                                          21

<210> SEQ ID NO 348
<211> LENGTH: 21
<212> TYPE: DNA
<213> ORGANISM: Artificial Sequence
<220> FEATURE:
<223> OTHER INFORMATION: target sequence

<400> SEQUENCE: 348
caccattatg tgcgctgata a                                          21

<210> SEQ ID NO 349
<211> LENGTH: 21
<212> TYPE: DNA
<213> ORGANISM: Artificial Sequence
<220> FEATURE:
<223> OTHER INFORMATION: target sequence

<400> SEQUENCE: 349
atggaacgcg ttgaaattgt a                                          21

<210> SEQ ID NO 350
<211> LENGTH: 21
<212> TYPE: DNA
<213> ORGANISM: Artificial Sequence
<220> FEATURE:
<223> OTHER INFORMATION: target sequence

<400> SEQUENCE: 350
aaggaagaag agaaacggtt a                                          21

<210> SEQ ID NO 351
<211> LENGTH: 21
<212> TYPE: DNA
<213> ORGANISM: Artificial Sequence
<220> FEATURE:
<223> OTHER INFORMATION: target sequence

<400> SEQUENCE: 351
``` ctgccctttα ataaagcatt a          21

<210> SEQ ID NO 352
<211> LENGTH: 21
<212> TYPE: DNA
<213> ORGANISM: Artificial Sequence
<220> FEATURE:
<223> OTHER INFORMATION: target sequence

<400> SEQUENCE: 352
tccgactact ttctccttca a          21

<210> SEQ ID NO 353
<211> LENGTH: 21
<212> TYPE: DNA
<213> ORGANISM: Artificial Sequence
<220> FEATURE:
<223> OTHER INFORMATION: target sequence

<400> SEQUENCE: 353
ctggagcagt gagaaagcaa a          21

<210> SEQ ID NO 354
<211> LENGTH: 21
<212> TYPE: DNA
<213> ORGANISM: Artificial Sequence
<220> FEATURE:
<223> OTHER INFORMATION: target sequence

<400> SEQUENCE: 354
ccgcgtggtg ctggagctga a          21

<210> SEQ ID NO 355
<211> LENGTH: 21
<212> TYPE: DNA
<213> ORGANISM: Artificial Sequence
<220> FEATURE:
<223> OTHER INFORMATION: target sequence

<400> SEQUENCE: 355
atggatttgt gttcacctta a          21

<210> SEQ ID NO 356
<211> LENGTH: 21
<212> TYPE: DNA
<213> ORGANISM: Artificial Sequence
<220> FEATURE:
<223> OTHER INFORMATION: target sequence

<400> SEQUENCE: 356
cagccttaca gggttaaagt a          21

<210> SEQ ID NO 357
<211> LENGTH: 25
<212> TYPE: RNA
<213> ORGANISM: Artificial Sequence
<220> FEATURE:
<223> OTHER INFORMATION: target sequence

<400> SEQUENCE: 357
ugcagauugu cgaugaauug uccug          25

<210> SEQ ID NO 358
<211> LENGTH: 25
<212> TYPE: RNA
<213> ORGANISM: Artificial Sequence

```
<220> FEATURE:
<223> OTHER INFORMATION: target sequence

<400> SEQUENCE: 358
uggugaacgu acugucuauu gcaac                                            25

<210> SEQ ID NO 359
<211> LENGTH: 21
<212> TYPE: DNA
<213> ORGANISM: Artificial Sequence
<220> FEATURE:
<223> OTHER INFORMATION: target sequence

<400> SEQUENCE: 359
ctggccctat tctgtcacga a                                                21

<210> SEQ ID NO 360
<211> LENGTH: 21
<212> TYPE: DNA
<213> ORGANISM: Artificial Sequence
<220> FEATURE:
<223> OTHER INFORMATION: target sequence

<400> SEQUENCE: 360
aaggactatc cttgaggcaa a                                                21

<210> SEQ ID NO 361
<211> LENGTH: 21
<212> TYPE: DNA
<213> ORGANISM: Artificial Sequence
<220> FEATURE:
<223> OTHER INFORMATION: target sequence

<400> SEQUENCE: 361
caagtgctac atgatatttc a                                                21

<210> SEQ ID NO 362
<211> LENGTH: 21
<212> TYPE: DNA
<213> ORGANISM: Artificial Sequence
<220> FEATURE:
<223> OTHER INFORMATION: target sequence

<400> SEQUENCE: 362 cgcgtctttta gctgtcaata a                                               21

<210> SEQ ID NO 363
<211> LENGTH: 19
<212> TYPE: RNA
<213> ORGANISM: Artificial Sequence
<220> FEATURE:
<223> OTHER INFORMATION: target sequence

<400> SEQUENCE: 363
aggcagcgca uagguuug                                                    19

<210> SEQ ID NO 364
<211> LENGTH: 21
<212> TYPE: DNA
<213> ORGANISM: Artificial Sequence
<220> FEATURE:
<223> OTHER INFORMATION: target sequence

<400> SEQUENCE: 364
acgcaagtcg tggatgagta a                                                21
```

```
<210> SEQ ID NO 365
<211> LENGTH: 21
<212> TYPE: DNA
<213> ORGANISM: Artificial Sequence
<220> FEATURE:
<223> OTHER INFORMATION: target sequence

<400> SEQUENCE: 365
caggatcttg tgcctggaaa t                                              21

<210> SEQ ID NO 366
<211> LENGTH: 21
<212> TYPE: DNA
<213> ORGANISM: Artificial Sequence
<220> FEATURE:
<223> OTHER INFORMATION: target sequence

<400> SEQUENCE: 366
ccggcttgag ctcaccacct a                                              21

<210> SEQ ID NO 367
<211> LENGTH: 21
<212> TYPE: DNA
<213> ORGANISM: Artificial Sequence
<220> FEATURE:
<223> OTHER INFORMATION: target sequence

<400> SEQUENCE: 367
cagcgtcttc cattccagaa a                                              21

<210> SEQ ID NO 368
<211> LENGTH: 19
<212> TYPE: DNA
<213> ORGANISM: Artificial Sequence
<220> FEATURE:
<223> OTHER INFORMATION: target sequence

<400> SEQUENCE: 368
gcagcacaag acgcagaga                                                 19

<210> SEQ ID NO 369
<211> LENGTH: 21
<212> TYPE: DNA
<213> ORGANISM: Artificial Sequence
<220> FEATURE:
<223> OTHER INFORMATION: target sequence

<400> SEQUENCE: 369
ccgcggtctc tggacaatca a                                              21

<210> SEQ ID NO 370
<211> LENGTH: 21
<212> TYPE: DNA
<213> ORGANISM: Artificial Sequence
<220> FEATURE:
<223> OTHER INFORMATION: target sequence

<400> SEQUENCE: 370
ttgctgtcag ataccctta a                                               21

<210> SEQ ID NO 371
<211> LENGTH: 21
<212> TYPE: DNA
<213> ORGANISM: Artificial Sequence
<220> FEATURE:
<223> OTHER INFORMATION: target sequence
```

-continued

```
<400> SEQUENCE: 371
cacggtggtg gagccctaca a                                              21

<210> SEQ ID NO 372
<211> LENGTH: 21
<212> TYPE: DNA
<213> ORGANISM: Artificial Sequence
<220> FEATURE:
<223> OTHER INFORMATION: target sequence

<400> SEQUENCE: 372
cagggattaa tgaaactgcc a                                              21

<210> SEQ ID NO 373
<211> LENGTH: 21
<212> TYPE: DNA
<213> ORGANISM: Artificial Sequence
<220> FEATURE:
<223> OTHER INFORMATION: target sequence

<400> SEQUENCE: 373
cagccactcg acgaccctga a                                              21

<210> SEQ ID NO 374
<211> LENGTH: 21
<212> TYPE: DNA
<213> ORGANISM: Artificial Sequence
<220> FEATURE:
<223> OTHER INFORMATION: target sequence

<400> SEQUENCE: 374
atggacgaga agaccaagaa a                                              21

<210> SEQ ID NO 375
<211> LENGTH: 19
<212> TYPE: RNA
<213> ORGANISM: Artificial Sequence
<220> FEATURE:
<223> OTHER INFORMATION: target sequence

<400> SEQUENCE: 375
agggauggug cuucuuuga                                                 19

<210> SEQ ID NO 376
<211> LENGTH: 21
<212> TYPE: DNA
<213> ORGANISM: Artificial Sequence
<220> FEATURE:
<223> OTHER INFORMATION: target sequence

<400> SEQUENCE: 376
cagctggtgc tttgaatgta a                                              21

<210> SEQ ID NO 377
<211> LENGTH: 19
<212> TYPE: RNA
<213> ORGANISM: Artificial Sequence
<220> FEATURE:
<223> OTHER INFORMATION: target sequence

<400> SEQUENCE: 377
ugccacauga aaagcacua                                                 19

<210> SEQ ID NO 378
```

```
<211> LENGTH: 25
<212> TYPE: RNA
<213> ORGANISM: Artificial Sequence
<220> FEATURE:
<223> OTHER INFORMATION: target sequence

<400> SEQUENCE: 378
ccaguuacuu cguagaaauc cagcc                                      25

<210> SEQ ID NO 379
<211> LENGTH: 25
<212> TYPE: RNA
<213> ORGANISM: Artificial Sequence
<220> FEATURE:
<223> OTHER INFORMATION: target sequence

<400> SEQUENCE: 379
gcacuacucc gagaaguuac gaggc                                      25

<210> SEQ ID NO 380
<211> LENGTH: 21
<212> TYPE: DNA
<213> ORGANISM: Artificial Sequence
<220> FEATURE:
<223> OTHER INFORMATION: target sequence

<400> SEQUENCE: 380
caagggcaaa ttggcaggca a                                          21

<210> SEQ ID NO 381
<211> LENGTH: 21
<212> TYPE: DNA
<213> ORGANISM: Artificial Sequence
<220> FEATURE:
<223> OTHER INFORMATION: target sequence

<400> SEQUENCE: 381
cagattaaca ctgagcctct a                                          21

<210> SEQ ID NO 382
<211> LENGTH: 25
<212> TYPE: RNA
<213> ORGANISM: Artificial Sequence
<220> FEATURE:
<223> OTHER INFORMATION: target sequence

<400> SEQUENCE: 382
ggcgccaacg acgagauugu acagg                                      25

<210> SEQ ID NO 383
<211> LENGTH: 19
<212> TYPE: RNA
<213> ORGANISM: Artificial Sequence
<220> FEATURE:
<223> OTHER INFORMATION: target sequence

<400> SEQUENCE: 383
gcagaagcug augcuaaac                                             19

<210> SEQ ID NO 384
<211> LENGTH: 25
<212> TYPE: RNA
<213> ORGANISM: Artificial Sequence
<220> FEATURE:
<223> OTHER INFORMATION: target sequence

<400> SEQUENCE: 384
```

```
gcaacgcggg caaaguuaag accgc                                         25

<210> SEQ ID NO 385
<211> LENGTH: 25
<212> TYPE: RNA
<213> ORGANISM: Artificial Sequence
<220> FEATURE:
<223> OTHER INFORMATION: target sequence

<400> SEQUENCE: 385
gccagucuga gguuauguuu cuggc                                         25

<210> SEQ ID NO 386
<211> LENGTH: 21
<212> TYPE: DNA
<213> ORGANISM: Artificial Sequence
<220> FEATURE:
<223> OTHER INFORMATION: target sequence

<400> SEQUENCE: 386
atcgatgttg ccagactact a                                             21

<210> SEQ ID NO 387
<211> LENGTH: 19
<212> TYPE: RNA
<213> ORGANISM: Artificial Sequence
<220> FEATURE:
<223> OTHER INFORMATION: target sequence

<400> SEQUENCE: 387
agccgaugau caaacaaaa                                                19

<210> SEQ ID NO 388
<211> LENGTH: 19
<212> TYPE: RNA
<213> ORGANISM: Artificial Sequence
<220> FEATURE:
<223> OTHER INFORMATION: target sequence

<400> SEQUENCE: 388
cagucaugac ccaaguuac                                                19

<210> SEQ ID NO 389
<211> LENGTH: 21
<212> TYPE: DNA
<213> ORGANISM: Artificial Sequence
<220> FEATURE:
<223> OTHER INFORMATION: target sequence

<400> SEQUENCE: 389
ctgcgtgaag gtgaaagtca a                                             21

<210> SEQ ID NO 390
<211> LENGTH: 21
<212> TYPE: DNA
<213> ORGANISM: Artificial Sequence
<220> FEATURE:
<223> OTHER INFORMATION: target sequence

<400> SEQUENCE: 390
cagcagggtt atgcccttaa a                                             21

<210> SEQ ID NO 391
<211> LENGTH: 21
<212> TYPE: DNA
```

```
<213> ORGANISM: Artificial Sequence
<220> FEATURE:
<223> OTHER INFORMATION: target sequence

<400> SEQUENCE: 391
ccctgcttta ataaacagca a                                              21

<210> SEQ ID NO 392
<211> LENGTH: 21
<212> TYPE: DNA
<213> ORGANISM: Artificial Sequence
<220> FEATURE:
<223> OTHER INFORMATION: target sequence

<400> SEQUENCE: 392
ctccttggtg ttggtttgca a                                              21

<210> SEQ ID NO 393
<211> LENGTH: 21
<212> TYPE: DNA
<213> ORGANISM: Artificial Sequence
<220> FEATURE:
<223> OTHER INFORMATION: target sequence

<400> SEQUENCE: 393
caggcaggcg tgtaacaaga a                                              21

<210> SEQ ID NO 394
<211> LENGTH: 21
<212> TYPE: DNA
<213> ORGANISM: Artificial Sequence
<220> FEATURE:
<223> OTHER INFORMATION: target sequence

<400> SEQUENCE: 394
ctcctagtct ttcatcctga a                                              21

<210> SEQ ID NO 395
<211> LENGTH: 21
<212> TYPE: DNA
<213> ORGANISM: Artificial Sequence
<220> FEATURE:
<223> OTHER INFORMATION: target sequence

<400> SEQUENCE: 395
ccgcgtcgtg gtcatgaaca a                                              21

<210> SEQ ID NO 396
<211> LENGTH: 21
<212> TYPE: DNA
<213> ORGANISM: Artificial Sequence
<220> FEATURE:
<223> OTHER INFORMATION: target sequence

<400> SEQUENCE: 396
gacggcgaga gcgacacata a                                              21

<210> SEQ ID NO 397
<211> LENGTH: 21
<212> TYPE: DNA
<213> ORGANISM: Artificial Sequence
<220> FEATURE:
<223> OTHER INFORMATION: target sequence

<400> SEQUENCE: 397
accgaatgtc ttagtgaact a                                              21
```

<210> SEQ ID NO 398
<211> LENGTH: 21
<212> TYPE: DNA
<213> ORGANISM: Artificial Sequence
<220> FEATURE:
<223> OTHER INFORMATION: target sequence

<400> SEQUENCE: 398
ctgggagatc atgcaggttg a                                             21

<210> SEQ ID NO 399
<211> LENGTH: 21
<212> TYPE: DNA
<213> ORGANISM: Artificial Sequence
<220> FEATURE:
<223> OTHER INFORMATION: target sequence

<400> SEQUENCE: 399
tggcgagata gttgccctca a                                             21

<210> SEQ ID NO 400
<211> LENGTH: 21
<212> TYPE: DNA
<213> ORGANISM: Artificial Sequence
<220> FEATURE:
<223> OTHER INFORMATION: target sequence

<400> SEQUENCE: 400
aaggagaagt gcagagagta a                                             21

<210> SEQ ID NO 401
<211> LENGTH: 25
<212> TYPE: RNA
<213> ORGANISM: Artificial Sequence
<220> FEATURE:
<223> OTHER INFORMATION: target sequence

<400> SEQUENCE: 401
ucccgccgau uguauguucc agguc                                         25

<210> SEQ ID NO 402
<211> LENGTH: 21
<212> TYPE: DNA
<213> ORGANISM: Artificial Sequence
<220> FEATURE:
<223> OTHER INFORMATION: target sequence

<400> SEQUENCE: 402
cggaatttgt tgctccagaa a                                             21

<210> SEQ ID NO 403
<211> LENGTH: 21
<212> TYPE: DNA
<213> ORGANISM: Artificial Sequence
<220> FEATURE:
<223> OTHER INFORMATION: target sequence

<400> SEQUENCE: 403
cagcggtctg gttatcgtct a                                             21

<210> SEQ ID NO 404
<211> LENGTH: 19
<212> TYPE: RNA
<213> ORGANISM: Artificial Sequence
<220> FEATURE:

<223> OTHER INFORMATION: target sequence

<400> SEQUENCE: 404
ccucgagggu gcagaguua                                                        19

<210> SEQ ID NO 405
<211> LENGTH: 21
<212> TYPE: DNA
<213> ORGANISM: Artificial Sequence
<220> FEATURE:
<223> OTHER INFORMATION: target sequence

<400> SEQUENCE: 405
ctgccaggaa ctgaccacct a                                                     21

<210> SEQ ID NO 406
<211> LENGTH: 21
<212> TYPE: DNA
<213> ORGANISM: Artificial Sequence
<220> FEATURE:
<223> OTHER INFORMATION: target sequence

<400> SEQUENCE: 406
ctcctacgac ctcgccatca a                                                     21

<210> SEQ ID NO 407
<211> LENGTH: 19
<212> TYPE: RNA
<213> ORGANISM: Artificial Sequence
<220> FEATURE:
<223> OTHER INFORMATION: target sequence

<400> SEQUENCE: 407
acggaacgga gaucagaaa                                                        19

<210> SEQ ID NO 408
<211> LENGTH: 21
<212> TYPE: DNA
<213> ORGANISM: Artificial Sequence
<220> FEATURE:
<223> OTHER INFORMATION: target sequence

<400> SEQUENCE: 408
caggactggc agaatgttga a                                                     21

<210> SEQ ID NO 409
<211> LENGTH: 19
<212> TYPE: RNA
<213> ORGANISM: Artificial Sequence
<220> FEATURE:
<223> OTHER INFORMATION: target sequence

<400> SEQUENCE: 409
ucgguaucau cgucuacau                                                        19

<210> SEQ ID NO 410
<211> LENGTH: 21
<212> TYPE: DNA
<213> ORGANISM: Artificial Sequence
<220> FEATURE:
<223> OTHER INFORMATION: target sequence

<400> SEQUENCE: 410
ctaggtggtt acaaatcata a                                                     21

```
<210> SEQ ID NO 411
<211> LENGTH: 25
<212> TYPE: RNA
<213> ORGANISM: Artificial Sequence
<220> FEATURE:
<223> OTHER INFORMATION: target sequence

<400> SEQUENCE: 411
ggcccaccca augcuaauga agagg                                              25

<210> SEQ ID NO 412
<211> LENGTH: 19
<212> TYPE: RNA
<213> ORGANISM: Artificial Sequence
<220> FEATURE:
<223> OTHER INFORMATION: target sequence

<400> SEQUENCE: 412
gggauuugaa agcugguaa                                                     19

<210> SEQ ID NO 413
<211> LENGTH: 19
<212> TYPE: RNA
<213> ORGANISM: Artificial Sequence
<220> FEATURE:
<223> OTHER INFORMATION: target sequence

<400> SEQUENCE: 413
ggugaacaug acgacagau                                                     19

<210> SEQ ID NO 414
<211> LENGTH: 25
<212> TYPE: RNA
<213> ORGANISM: Artificial Sequence
<220> FEATURE:
<223> OTHER INFORMATION: target sequence

<400> SEQUENCE: 414
gcgauccaag cgugucaagg agagc                                              25

<210> SEQ ID NO 415
<211> LENGTH: 21
<212> TYPE: DNA
<213> ORGANISM: Artificial Sequence
<220> FEATURE:
<223> OTHER INFORMATION: target sequence

<400> SEQUENCE: 415
caggctctcc tacacatgta a                                                  21

<210> SEQ ID NO 416
<211> LENGTH: 21
<212> TYPE: DNA
<213> ORGANISM: Artificial Sequence
<220> FEATURE:
<223> OTHER INFORMATION: target sequence

<400> SEQUENCE: 416
aagcatttgg ctgaatctaa a                                                  21

<210> SEQ ID NO 417
<211> LENGTH: 21
<212> TYPE: DNA
<213> ORGANISM: Artificial Sequence
<220> FEATURE:
<223> OTHER INFORMATION: target sequence
```

<400> SEQUENCE: 417
aaagcggcag agttaggtga a                                              21

<210> SEQ ID NO 418
<211> LENGTH: 19
<212> TYPE: RNA
<213> ORGANISM: Artificial Sequence
<220> FEATURE:
<223> OTHER INFORMATION: target sequence

<400> SEQUENCE: 418
agccuucugg ugcaauauc                                                 19

<210> SEQ ID NO 419
<211> LENGTH: 21
<212> TYPE: DNA
<213> ORGANISM: Artificial Sequence
<220> FEATURE:
<223> OTHER INFORMATION: target sequence

<400> SEQUENCE: 419
caccacagac accagatatt a                                              21

<210> SEQ ID NO 420
<211> LENGTH: 21
<212> TYPE: DNA
<213> ORGANISM: Artificial Sequence
<220> FEATURE:
<223> OTHER INFORMATION: target sequence

<400> SEQUENCE: 420
ctggtagata gaagagctaa a                                              21

<210> SEQ ID NO 421
<211> LENGTH: 21
<212> TYPE: DNA
<213> ORGANISM: Artificial Sequence
<220> FEATURE:
<223> OTHER INFORMATION: target sequence

<400> SEQUENCE: 421
aaggttcttc taccgcatct a                                              21

<210> SEQ ID NO 422
<211> LENGTH: 21
<212> TYPE: DNA
<213> ORGANISM: Artificial Sequence
<220> FEATURE:
<223> OTHER INFORMATION: target sequence

<400> SEQUENCE: 422
gagagtctat atgcagagta a                                              21

<210> SEQ ID NO 423
<211> LENGTH: 19
<212> TYPE: RNA
<213> ORGANISM: Artificial Sequence
<220> FEATURE:
<223> OTHER INFORMATION: target sequence

<400> SEQUENCE: 423
gagggaguuc auucaaaag                                                 19

<210> SEQ ID NO 424
<211> LENGTH: 21

```
<212> TYPE: DNA
<213> ORGANISM: Artificial Sequence
<220> FEATURE:
<223> OTHER INFORMATION: target sequence

<400> SEQUENCE: 424
aggcgagaag aggtgaatca a                                              21

<210> SEQ ID NO 425
<211> LENGTH: 21
<212> TYPE: DNA
<213> ORGANISM: Artificial Sequence
<220> FEATURE:
<223> OTHER INFORMATION: target sequence

<400> SEQUENCE: 425
cacgggcaaa gtgccctgta a                                              21

<210> SEQ ID NO 426
<211> LENGTH: 21
<212> TYPE: DNA
<213> ORGANISM: Artificial Sequence
<220> FEATURE:
<223> OTHER INFORMATION: target sequence

<400> SEQUENCE: 426
aactaagtac gttgcaaata a                                              21

<210> SEQ ID NO 427
<211> LENGTH: 21
<212> TYPE: DNA
<213> ORGANISM: Artificial Sequence
<220> FEATURE:
<223> OTHER INFORMATION: target sequence

<400> SEQUENCE: 427
ctcaatttcc agcaccagaa a                                              21

<210> SEQ ID NO 428
<211> LENGTH: 21
<212> TYPE: DNA
<213> ORGANISM: Artificial Sequence
<220> FEATURE:
<223> OTHER INFORMATION: target sequence

<400> SEQUENCE: 428
ccggagagaa atgagtagca a                                              21

<210> SEQ ID NO 429
<211> LENGTH: 21
<212> TYPE: DNA
<213> ORGANISM: Artificial Sequence
<220> FEATURE:
<223> OTHER INFORMATION: target sequence

<400> SEQUENCE: 429
caagcaatgc gtggacttta a                                              21

<210> SEQ ID NO 430
<211> LENGTH: 21
<212> TYPE: DNA
<213> ORGANISM: Artificial Sequence
<220> FEATURE:
<223> OTHER INFORMATION: target sequence

<400> SEQUENCE: 430
```
aagcagaatt ctagatcaga a                                              21

<210> SEQ ID NO 431
<211> LENGTH: 21
<212> TYPE: DNA
<213> ORGANISM: Artificial Sequence
<220> FEATURE:
<223> OTHER INFORMATION: target sequence

<400> SEQUENCE: 431
cacgtacggg cgcatcatta a                                              21

<210> SEQ ID NO 432
<211> LENGTH: 25
<212> TYPE: RNA
<213> ORGANISM: Artificial Sequence
<220> FEATURE:
<223> OTHER INFORMATION: target sequence

<400> SEQUENCE: 432
gacucuacgc cgggaguuuc uccgg                                          25

<210> SEQ ID NO 433
<211> LENGTH: 19
<212> TYPE: RNA
<213> ORGANISM: Artificial Sequence
<220> FEATURE:
<223> OTHER INFORMATION: target sequence

<400> SEQUENCE: 433
ccucaaggag cagaccuuu                                                 19

<210> SEQ ID NO 434
<211> LENGTH: 19
<212> TYPE: RNA
<213> ORGANISM: Artificial Sequence
<220> FEATURE:
<223> OTHER INFORMATION: target sequence

<400> SEQUENCE: 434
ucccucaauc acaucuuca                                                 19

<210> SEQ ID NO 435
<211> LENGTH: 21
<212> TYPE: DNA
<213> ORGANISM: Artificial Sequence
<220> FEATURE:
<223> OTHER INFORMATION: target sequence

<400> SEQUENCE: 435
cacaggagac aggttccttt a                                              21

<210> SEQ ID NO 436
<211> LENGTH: 21
<212> TYPE: DNA
<213> ORGANISM: Artificial Sequence
<220> FEATURE:
<223> OTHER INFORMATION: target sequence

<400> SEQUENCE: 436
ttgaataaat tgatataata a                                              21

<210> SEQ ID NO 437
<211> LENGTH: 21
<212> TYPE: DNA
<213> ORGANISM: Artificial Sequence

```
<220> FEATURE:
<223> OTHER INFORMATION: target sequence

<400> SEQUENCE: 437
cacgctgggt gccgtgcata a                                              21

<210> SEQ ID NO 438
<211> LENGTH: 19
<212> TYPE: RNA
<213> ORGANISM: Artificial Sequence
<220> FEATURE:
<223> OTHER INFORMATION: target sequence

<400> SEQUENCE: 438
accagaaagu ucgccugaa                                                 19

<210> SEQ ID NO 439
<211> LENGTH: 21
<212> TYPE: DNA
<213> ORGANISM: Artificial Sequence
<220> FEATURE:
<223> OTHER INFORMATION: target sequence

<400> SEQUENCE: 439
cagagagatg atatacccga a                                              21

<210> SEQ ID NO 440
<211> LENGTH: 21
<212> TYPE: DNA
<213> ORGANISM: Artificial Sequence
<220> FEATURE:
<223> OTHER INFORMATION: target sequence

<400> SEQUENCE: 440
cagatgtttc tcattgcata a                                              21

<210> SEQ ID NO 441
<211> LENGTH: 21
<212> TYPE: DNA
<213> ORGANISM: Artificial Sequence
<220> FEATURE:
<223> OTHER INFORMATION: target sequence

<400> SEQUENCE: 441
aagcgcggtt atggacacca a                                              21

<210> SEQ ID NO 442
<211> LENGTH: 21
<212> TYPE: DNA
<213> ORGANISM: Artificial Sequence
<220> FEATURE:
<223> OTHER INFORMATION: target sequence

<400> SEQUENCE: 442
aagcacgagc ctgaacggtt a                                              21

<210> SEQ ID NO 443
<211> LENGTH: 21
<212> TYPE: DNA
<213> ORGANISM: Artificial Sequence
<220> FEATURE:
<223> OTHER INFORMATION: target sequence

<400> SEQUENCE: 443
cacaatgaaa tccgaagcca a                                              21
```

```
<210> SEQ ID NO 444
<211> LENGTH: 21
<212> TYPE: DNA
<213> ORGANISM: Artificial Sequence
<220> FEATURE:
<223> OTHER INFORMATION: target sequence

<400> SEQUENCE: 444
acagatgata ccaaacctaa a                                             21

<210> SEQ ID NO 445
<211> LENGTH: 21
<212> TYPE: DNA
<213> ORGANISM: Artificial Sequence
<220> FEATURE:
<223> OTHER INFORMATION: target sequence

<400> SEQUENCE: 445
cagaacctct aagccctgaa a                                             21

<210> SEQ ID NO 446
<211> LENGTH: 21
<212> TYPE: DNA
<213> ORGANISM: Artificial Sequence
<220> FEATURE:
<223> OTHER INFORMATION: target sequence

<400> SEQUENCE: 446
cagcctttaa ctcccaggaa t                                             21

<210> SEQ ID NO 447
<211> LENGTH: 21
<212> TYPE: DNA
<213> ORGANISM: Artificial Sequence
<220> FEATURE:
<223> OTHER INFORMATION: target sequence

<400> SEQUENCE: 447
ttggaggaac tggcccggaa a                                             21

<210> SEQ ID NO 448
<211> LENGTH: 21
<212> TYPE: DNA
<213> ORGANISM: Artificial Sequence
<220> FEATURE:
<223> OTHER INFORMATION: target sequence

<400> SEQUENCE: 448
caggaggacc ttcggaacca a                                             21

<210> SEQ ID NO 449
<211> LENGTH: 21
<212> TYPE: DNA
<213> ORGANISM: Artificial Sequence
<220> FEATURE:
<223> OTHER INFORMATION: target sequence

<400> SEQUENCE: 449
ctgctcttag ctaagatgca a                                             21

<210> SEQ ID NO 450
<211> LENGTH: 21
<212> TYPE: DNA
<213> ORGANISM: Artificial Sequence
<220> FEATURE:
<223> OTHER INFORMATION: target sequence
```

-continued

```
<400> SEQUENCE: 450
cagcggtctt aaagagatta t                                              21

<210> SEQ ID NO 451
<211> LENGTH: 21
<212> TYPE: DNA
<213> ORGANISM: Artificial Sequence
<220> FEATURE:
<223> OTHER INFORMATION: target sequence

<400> SEQUENCE: 451
cagaaattca ttgtgcagaa a                                              21

<210> SEQ ID NO 452
<211> LENGTH: 21
<212> TYPE: DNA
<213> ORGANISM: Artificial Sequence
<220> FEATURE:
<223> OTHER INFORMATION: target sequence

<400> SEQUENCE: 452
cagggcctgc tacagaagaa a                                              21

<210> SEQ ID NO 453
<211> LENGTH: 21
<212> TYPE: DNA
<213> ORGANISM: Artificial Sequence
<220> FEATURE:
<223> OTHER INFORMATION: target sequence

<400> SEQUENCE: 453
gcgagtggct tcagagatta a                                              21

<210> SEQ ID NO 454
<211> LENGTH: 21
<212> TYPE: DNA
<213> ORGANISM: Artificial Sequence
<220> FEATURE:
<223> OTHER INFORMATION: target sequence

<400> SEQUENCE: 454
tcgacatagg cgggtcgtta a                                              21

<210> SEQ ID NO 455
<211> LENGTH: 21
<212> TYPE: DNA
<213> ORGANISM: Artificial Sequence
<220> FEATURE:
<223> OTHER INFORMATION: target sequence

<400> SEQUENCE: 455
cccggtcttg ttccagggca a                                              21

<210> SEQ ID NO 456
<211> LENGTH: 21
<212> TYPE: DNA
<213> ORGANISM: Artificial Sequence
<220> FEATURE:
<223> OTHER INFORMATION: target sequence

<400> SEQUENCE: 456
acctgagtga aagctactta a                                              21

<210> SEQ ID NO 457
```

```
<211> LENGTH: 21
<212> TYPE: DNA
<213> ORGANISM: Artificial Sequence
<220> FEATURE:
<223> OTHER INFORMATION: target sequence

<400> SEQUENCE: 457
caggacgagt gtggtctccc a                                              21

<210> SEQ ID NO 458
<211> LENGTH: 21
<212> TYPE: DNA
<213> ORGANISM: Artificial Sequence
<220> FEATURE:
<223> OTHER INFORMATION: target sequence

<400> SEQUENCE: 458
ctggacctat gctgcaggca a                                              21

<210> SEQ ID NO 459
<211> LENGTH: 21
<212> TYPE: DNA
<213> ORGANISM: Artificial Sequence
<220> FEATURE:
<223> OTHER INFORMATION: target sequence

<400> SEQUENCE: 459
accggcctct gaggtgatca a                                              21

<210> SEQ ID NO 460
<211> LENGTH: 21
<212> TYPE: DNA
<213> ORGANISM: Artificial Sequence
<220> FEATURE:
<223> OTHER INFORMATION: target sequence

<400> SEQUENCE: 460
ctcagagaaa gcactggcca a                                              21

<210> SEQ ID NO 461
<211> LENGTH: 21
<212> TYPE: DNA
<213> ORGANISM: Artificial Sequence
<220> FEATURE:
<223> OTHER INFORMATION: target sequence

<400> SEQUENCE: 461
ctcccaggac aggctcctta a                                              21

<210> SEQ ID NO 462
<211> LENGTH: 21
<212> TYPE: DNA
<213> ORGANISM: Artificial Sequence
<220> FEATURE:
<223> OTHER INFORMATION: target sequence

<400> SEQUENCE: 462
ctcgcccaaa gaagactaca a                                              21

<210> SEQ ID NO 463
<211> LENGTH: 25
<212> TYPE: RNA
<213> ORGANISM: Artificial Sequence
<220> FEATURE:
<223> OTHER INFORMATION: target sequence

<400> SEQUENCE: 463
```
agcauacuau gcagcguugg gaaag                                          25

<210> SEQ ID NO 464
<211> LENGTH: 21
<212> TYPE: DNA
<213> ORGANISM: Artificial Sequence
<220> FEATURE:
<223> OTHER INFORMATION: target sequence

<400> SEQUENCE: 464
aacgctgtaa actgtaacat t                                              21

<210> SEQ ID NO 465
<211> LENGTH: 25
<212> TYPE: RNA
<213> ORGANISM: Artificial Sequence
<220> FEATURE:
<223> OTHER INFORMATION: target sequence

<400> SEQUENCE: 465
ccgucuugua gcaugguucc aaaga                                          25

<210> SEQ ID NO 466
<211> LENGTH: 19
<212> TYPE: RNA
<213> ORGANISM: Artificial Sequence
<220> FEATURE:
<223> OTHER INFORMATION: target sequence

<400> SEQUENCE: 466
gcucuacuca gauggaaau                                                 19

<210> SEQ ID NO 467
<211> LENGTH: 19
<212> TYPE: RNA
<213> ORGANISM: Artificial Sequence
<220> FEATURE:
<223> OTHER INFORMATION: target sequence

<400> SEQUENCE: 467
agagagacca gcccaucau                                                 19

<210> SEQ ID NO 468
<211> LENGTH: 21
<212> TYPE: DNA
<213> ORGANISM: Artificial Sequence
<220> FEATURE:
<223> OTHER INFORMATION: target sequence

<400> SEQUENCE: 468
caggagagct gggtggtata a                                              21

<210> SEQ ID NO 469
<211> LENGTH: 21
<212> TYPE: DNA
<213> ORGANISM: Artificial Sequence
<220> FEATURE:
<223> OTHER INFORMATION: target sequence

<400> SEQUENCE: 469
caccttattc ttggcactac a                                              21

<210> SEQ ID NO 470
<211> LENGTH: 21
<212> TYPE: DNA

```
<213> ORGANISM: Artificial Sequence
<220> FEATURE:
<223> OTHER INFORMATION: target sequence

<400> SEQUENCE: 470
aaggatgggt atactccact a                                              21

<210> SEQ ID NO 471
<211> LENGTH: 21
<212> TYPE: DNA
<213> ORGANISM: Artificial Sequence
<220> FEATURE:
<223> OTHER INFORMATION: target sequence

<400> SEQUENCE: 471
ctgcatttac tcgctcttca a                                              21

<210> SEQ ID NO 472
<211> LENGTH: 21
<212> TYPE: DNA
<213> ORGANISM: Artificial Sequence
<220> FEATURE:
<223> OTHER INFORMATION: target sequence

<400> SEQUENCE: 472
ctggcgcttt cttaatcttt a                                              21

<210> SEQ ID NO 473
<211> LENGTH: 21
<212> TYPE: DNA
<213> ORGANISM: Artificial Sequence
<220> FEATURE:
<223> OTHER INFORMATION: target sequence

<400> SEQUENCE: 473
cacactggcc tttgtaaata a                                              21

<210> SEQ ID NO 474
<211> LENGTH: 21
<212> TYPE: DNA
<213> ORGANISM: Artificial Sequence
<220> FEATURE:
<223> OTHER INFORMATION: target sequence

<400> SEQUENCE: 474
agagatgcta atggaattta a                                              21

<210> SEQ ID NO 475
<211> LENGTH: 21
<212> TYPE: DNA
<213> ORGANISM: Artificial Sequence
<220> FEATURE:
<223> OTHER INFORMATION: target sequence

<400> SEQUENCE: 475
cgcggacttc atgccactga a                                              21

<210> SEQ ID NO 476
<211> LENGTH: 21
<212> TYPE: DNA
<213> ORGANISM: Artificial Sequence
<220> FEATURE:
<223> OTHER INFORMATION: target sequence

<400> SEQUENCE: 476
cagggtcagg ataaacatga a                                              21
```

<210> SEQ ID NO 477
<211> LENGTH: 21
<212> TYPE: DNA
<213> ORGANISM: Artificial Sequence
<220> FEATURE:
<223> OTHER INFORMATION: target sequence

<400> SEQUENCE: 477
cagggattgc ctgaaccaag a                                              21

<210> SEQ ID NO 478
<211> LENGTH: 21
<212> TYPE: DNA
<213> ORGANISM: Artificial Sequence
<220> FEATURE:
<223> OTHER INFORMATION: target sequence

<400> SEQUENCE: 478
ttgggtcttc tcaggaccgt a                                              21

<210> SEQ ID NO 479
<211> LENGTH: 21
<212> TYPE: DNA
<213> ORGANISM: Artificial Sequence
<220> FEATURE:
<223> OTHER INFORMATION: target sequence

<400> SEQUENCE: 479
caccgtattt atttagtcaa a                                              21

<210> SEQ ID NO 480
<211> LENGTH: 21
<212> TYPE: DNA
<213> ORGANISM: Artificial Sequence
<220> FEATURE:
<223> OTHER INFORMATION: target sequence

<400> SEQUENCE: 480
cagctgcagc ttcatgctaa a                                              21

<210> SEQ ID NO 481
<211> LENGTH: 21
<212> TYPE: DNA
<213> ORGANISM: Artificial Sequence
<220> FEATURE:
<223> OTHER INFORMATION: target sequence

<400> SEQUENCE: 481
cacagtggtg ctagtctgtt t                                              21

<210> SEQ ID NO 482
<211> LENGTH: 21
<212> TYPE: DNA
<213> ORGANISM: Artificial Sequence
<220> FEATURE:
<223> OTHER INFORMATION: target sequence

<400> SEQUENCE: 482
ctgcatcgtg tgggaacttc a                                              21

<210> SEQ ID NO 483
<211> LENGTH: 19
<212> TYPE: RNA
<213> ORGANISM: Artificial Sequence
<220> FEATURE:

<223> OTHER INFORMATION: target sequence

<400> SEQUENCE: 483
ccguuaccca augagaucu                                            19

<210> SEQ ID NO 484
<211> LENGTH: 19
<212> TYPE: RNA
<213> ORGANISM: Artificial Sequence
<220> FEATURE:
<223> OTHER INFORMATION: target sequence

<400> SEQUENCE: 484
gcucuaaggc aucacacuu                                            19

<210> SEQ ID NO 485
<211> LENGTH: 21
<212> TYPE: DNA
<213> ORGANISM: Artificial Sequence
<220> FEATURE:
<223> OTHER INFORMATION: target sequence

<400> SEQUENCE: 485
accgaattac tacaccggga a                                         21

<210> SEQ ID NO 486
<211> LENGTH: 19
<212> TYPE: RNA
<213> ORGANISM: Artificial Sequence
<220> FEATURE:
<223> OTHER INFORMATION: target sequence

<400> SEQUENCE: 486
ggacaauaug auggcaaag                                            19

<210> SEQ ID NO 487
<211> LENGTH: 21
<212> TYPE: DNA
<213> ORGANISM: Artificial Sequence
<220> FEATURE:
<223> OTHER INFORMATION: target sequence

<400> SEQUENCE: 487
cagtgctaaa gtactactga a                                         21

<210> SEQ ID NO 488
<211> LENGTH: 21
<212> TYPE: DNA
<213> ORGANISM: Artificial Sequence
<220> FEATURE:
<223> OTHER INFORMATION: target sequence

<400> SEQUENCE: 488
cagccactac gtgcttctca a                                         21

<210> SEQ ID NO 489
<211> LENGTH: 21
<212> TYPE: DNA
<213> ORGANISM: Artificial Sequence
<220> FEATURE:
<223> OTHER INFORMATION: target sequence

<400> SEQUENCE: 489
ctcgctcttt aacgccatga a                                         21

```
<210> SEQ ID NO 490
<211> LENGTH: 21
<212> TYPE: DNA
<213> ORGANISM: Artificial Sequence
<220> FEATURE:
<223> OTHER INFORMATION: target sequence

<400> SEQUENCE: 490
aagtgagatc ctggaagtga a                                              21

<210> SEQ ID NO 491
<211> LENGTH: 21
<212> TYPE: DNA
<213> ORGANISM: Artificial Sequence
<220> FEATURE:
<223> OTHER INFORMATION: target sequence

<400> SEQUENCE: 491
tcgcctgaga tataagttgt a                                              21

<210> SEQ ID NO 492
<211> LENGTH: 21
<212> TYPE: DNA
<213> ORGANISM: Artificial Sequence
<220> FEATURE:
<223> OTHER INFORMATION: target sequence

<400> SEQUENCE: 492
cagcatggac tgggacctga a                                              21

<210> SEQ ID NO 493
<211> LENGTH: 21
<212> TYPE: DNA
<213> ORGANISM: Artificial Sequence
<220> FEATURE:
<223> OTHER INFORMATION: target sequence

<400> SEQUENCE: 493
ccgcacggag ctggccatca a                                              21

<210> SEQ ID NO 494
<211> LENGTH: 21
<212> TYPE: DNA
<213> ORGANISM: Artificial Sequence
<220> FEATURE:
<223> OTHER INFORMATION: target sequence

<400> SEQUENCE: 494
cacgcacctc atggaggaga a                                              21

<210> SEQ ID NO 495
<211> LENGTH: 21
<212> TYPE: DNA
<213> ORGANISM: Artificial Sequence
<220> FEATURE:
<223> OTHER INFORMATION: target sequence

<400> SEQUENCE: 495
ccagaccatc atgcacattc a                                              21

<210> SEQ ID NO 496
<211> LENGTH: 21
<212> TYPE: DNA
<213> ORGANISM: Artificial Sequence
<220> FEATURE:
<223> OTHER INFORMATION: target sequence
```

```
<400> SEQUENCE: 496
cagggctgtc taagaaataa a                                              21

<210> SEQ ID NO 497
<211> LENGTH: 21
<212> TYPE: DNA
<213> ORGANISM: Artificial Sequence
<220> FEATURE:
<223> OTHER INFORMATION: target sequence

<400> SEQUENCE: 497
aagcaagaga acttcatcct a                                              21

<210> SEQ ID NO 498
<211> LENGTH: 21
<212> TYPE: DNA
<213> ORGANISM: Artificial Sequence
<220> FEATURE:
<223> OTHER INFORMATION: target sequence

<400> SEQUENCE: 498
ccctgtttgt ttgcacataa t                                              21

<210> SEQ ID NO 499
<211> LENGTH: 19
<212> TYPE: RNA
<213> ORGANISM: Artificial Sequence
<220> FEATURE:
<223> OTHER INFORMATION: target sequence

<400> SEQUENCE: 499
agcggaggaa ugaaaauug                                                 19

<210> SEQ ID NO 500
<211> LENGTH: 21
<212> TYPE: DNA
<213> ORGANISM: Artificial Sequence
<220> FEATURE:
<223> OTHER INFORMATION: target sequence

<400> SEQUENCE: 500
cgcgaactca aagaactata a                                              21

<210> SEQ ID NO 501
<211> LENGTH: 19
<212> TYPE: RNA
<213> ORGANISM: Artificial Sequence
<220> FEATURE:
<223> OTHER INFORMATION: target sequence

<400> SEQUENCE: 501
gggugcaaga gaacauauu                                                 19

<210> SEQ ID NO 502
<211> LENGTH: 19
<212> TYPE: RNA
<213> ORGANISM: Artificial Sequence
<220> FEATURE:
<223> OTHER INFORMATION: target sequence

<400> SEQUENCE: 502
gcacuccuag ucuccauau                                                 19

<210> SEQ ID NO 503
<211> LENGTH: 21
```

```
<212> TYPE: DNA
<213> ORGANISM: Artificial Sequence
<220> FEATURE:
<223> OTHER INFORMATION: target sequence

<400> SEQUENCE: 503
aaggttgtgg agttatataa a                                              21

<210> SEQ ID NO 504
<211> LENGTH: 21
<212> TYPE: DNA
<213> ORGANISM: Artificial Sequence
<220> FEATURE:
<223> OTHER INFORMATION: target sequence

<400> SEQUENCE: 504
aacgaggtaa atcccaagca a                                              21

<210> SEQ ID NO 505
<211> LENGTH: 21
<212> TYPE: DNA
<213> ORGANISM: Artificial Sequence
<220> FEATURE:
<223> OTHER INFORMATION: target sequence

<400> SEQUENCE: 505
acacatgttc ttggtaacta a                                              21

<210> SEQ ID NO 506
<211> LENGTH: 21
<212> TYPE: DNA
<213> ORGANISM: Artificial Sequence
<220> FEATURE:
<223> OTHER INFORMATION: target sequence

<400> SEQUENCE: 506
cacgatgatc tcatgccctc a                                              21

<210> SEQ ID NO 507
<211> LENGTH: 21
<212> TYPE: DNA
<213> ORGANISM: Artificial Sequence
<220> FEATURE:
<223> OTHER INFORMATION: target sequence

<400> SEQUENCE: 507
aacactatgc ttactgaata t                                              21

<210> SEQ ID NO 508
<211> LENGTH: 21
<212> TYPE: DNA
<213> ORGANISM: Artificial Sequence
<220> FEATURE:
<223> OTHER INFORMATION: target sequence

<400> SEQUENCE: 508
catggtcatc cgagagctga a                                              21

<210> SEQ ID NO 509
<211> LENGTH: 21
<212> TYPE: DNA
<213> ORGANISM: Artificial Sequence
<220> FEATURE:
<223> OTHER INFORMATION: target sequence

<400> SEQUENCE: 509
```

```
acggagcacc aagctcaaga a                                              21

<210> SEQ ID NO 510
<211> LENGTH: 21
<212> TYPE: DNA
<213> ORGANISM: Artificial Sequence
<220> FEATURE:
<223> OTHER INFORMATION: target sequence

<400> SEQUENCE: 510
ctgggcttcc tgggtcaagt a                                              21

<210> SEQ ID NO 511
<211> LENGTH: 21
<212> TYPE: DNA
<213> ORGANISM: Artificial Sequence
<220> FEATURE:
<223> OTHER INFORMATION: target sequence

<400> SEQUENCE: 511
cccaattcca attccttgta a                                              21

<210> SEQ ID NO 512
<211> LENGTH: 21
<212> TYPE: DNA
<213> ORGANISM: Artificial Sequence
<220> FEATURE:
<223> OTHER INFORMATION: target sequence

<400> SEQUENCE: 512
cacatgttca gtgcccagga a                                              21

<210> SEQ ID NO 513
<211> LENGTH: 21
<212> TYPE: DNA
<213> ORGANISM: Artificial Sequence
<220> FEATURE:
<223> OTHER INFORMATION: target sequence

<400> SEQUENCE: 513
gtggctcaac ctcatcttca a                                              21

<210> SEQ ID NO 514
<211> LENGTH: 19
<212> TYPE: RNA
<213> ORGANISM: Artificial Sequence
<220> FEATURE:
<223> OTHER INFORMATION: target sequence

<400> SEQUENCE: 514
ugugaaugga ggcgaugag                                                 19

<210> SEQ ID NO 515
<211> LENGTH: 21
<212> TYPE: DNA
<213> ORGANISM: Artificial Sequence
<220> FEATURE:
<223> OTHER INFORMATION: target sequence

<400> SEQUENCE: 515
cccgaaaggt cttgacctga a                                              21

<210> SEQ ID NO 516
<211> LENGTH: 21
<212> TYPE: DNA
<213> ORGANISM: Artificial Sequence
```

<220> FEATURE:
<223> OTHER INFORMATION: target sequence

<400> SEQUENCE: 516
ctccatcaaa cgtgccttaa a                                              21

<210> SEQ ID NO 517
<211> LENGTH: 21
<212> TYPE: DNA
<213> ORGANISM: Artificial Sequence
<220> FEATURE:
<223> OTHER INFORMATION: target sequence

<400> SEQUENCE: 517
cgcgcggact ttgcactttg a                                              21

<210> SEQ ID NO 518
<211> LENGTH: 21
<212> TYPE: DNA
<213> ORGANISM: Artificial Sequence
<220> FEATURE:
<223> OTHER INFORMATION: target sequence

<400> SEQUENCE: 518
cagccttgac agcgaagaat a                                              21

<210> SEQ ID NO 519
<211> LENGTH: 21
<212> TYPE: DNA
<213> ORGANISM: Artificial Sequence
<220> FEATURE:
<223> OTHER INFORMATION: target sequence

<400> SEQUENCE: 519
tccaaggctg ctaacaaata a                                              21

<210> SEQ ID NO 520
<211> LENGTH: 21
<212> TYPE: DNA
<213> ORGANISM: Artificial Sequence
<220> FEATURE:
<223> OTHER INFORMATION: target sequence

<400> SEQUENCE: 520
aaggctggac aatcaagctt a                                              21

<210> SEQ ID NO 521
<211> LENGTH: 21
<212> TYPE: DNA
<213> ORGANISM: Artificial Sequence
<220> FEATURE:
<223> OTHER INFORMATION: target sequence

<400> SEQUENCE: 521
aaggtgctag gctatgatga a                                              21

<210> SEQ ID NO 522
<211> LENGTH: 19
<212> TYPE: RNA
<213> ORGANISM: Artificial Sequence
<220> FEATURE:
<223> OTHER INFORMATION: target sequence

<400> SEQUENCE: 522
cacccagccc aaagcuaag                                                 19

<210> SEQ ID NO 523
<211> LENGTH: 21
<212> TYPE: DNA
<213> ORGANISM: Artificial Sequence
<220> FEATURE:
<223> OTHER INFORMATION: target sequence

<400> SEQUENCE: 523
cacggtttgc acaatggtat a                                              21

<210> SEQ ID NO 524
<211> LENGTH: 21
<212> TYPE: DNA
<213> ORGANISM: Artificial Sequence
<220> FEATURE:
<223> OTHER INFORMATION: target sequence

<400> SEQUENCE: 524
caggttgtca gtgtaaatat t                                              21

<210> SEQ ID NO 525
<211> LENGTH: 21
<212> TYPE: DNA
<213> ORGANISM: Artificial Sequence
<220> FEATURE:
<223> OTHER INFORMATION: target sequence

<400> SEQUENCE: 525
cacattctga atgaataaat a                                              21

<210> SEQ ID NO 526
<211> LENGTH: 21
<212> TYPE: DNA
<213> ORGANISM: Artificial Sequence
<220> FEATURE:
<223> OTHER INFORMATION: target sequence

<400> SEQUENCE: 526
caccttggac aacctccaga a                                              21

<210> SEQ ID NO 527
<211> LENGTH: 21
<212> TYPE: DNA
<213> ORGANISM: Artificial Sequence
<220> FEATURE:
<223> OTHER INFORMATION: target sequence

<400> SEQUENCE: 527
aacctccaga agggagtcca a                                              21

<210> SEQ ID NO 528
<211> LENGTH: 21
<212> TYPE: DNA
<213> ORGANISM: Artificial Sequence
<220> FEATURE:
<223> OTHER INFORMATION: target sequence

<400> SEQUENCE: 528
cggcctcatg cctgtcttca a                                              21

<210> SEQ ID NO 529
<211> LENGTH: 21
<212> TYPE: DNA
<213> ORGANISM: Artificial Sequence
<220> FEATURE:
<223> OTHER INFORMATION: target sequence

```
<400> SEQUENCE: 529
agcgaagacc ttggcattta t                                              21

<210> SEQ ID NO 530
<211> LENGTH: 21
<212> TYPE: DNA
<213> ORGANISM: Artificial Sequence
<220> FEATURE:
<223> OTHER INFORMATION: target sequence

<400> SEQUENCE: 530
ccagacgaag atccaggcaa a                                              21

<210> SEQ ID NO 531
<211> LENGTH: 19
<212> TYPE: RNA
<213> ORGANISM: Artificial Sequence
<220> FEATURE:
<223> OTHER INFORMATION: target sequence

<400> SEQUENCE: 531
gacgaagauc caggcaaag                                                 19

<210> SEQ ID NO 532
<211> LENGTH: 21
<212> TYPE: DNA
<213> ORGANISM: Artificial Sequence
<220> FEATURE:
<223> OTHER INFORMATION: target sequence

<400> SEQUENCE: 532
taggctccat tctgccatct a                                              21

<210> SEQ ID NO 533
<211> LENGTH: 19
<212> TYPE: RNA
<213> ORGANISM: Artificial Sequence
<220> FEATURE:
<223> OTHER INFORMATION: target sequence

<400> SEQUENCE: 533
cccgcgggca cucuugcaa                                                 19

<210> SEQ ID NO 534
<211> LENGTH: 21
<212> TYPE: DNA
<213> ORGANISM: Artificial Sequence
<220> FEATURE:
<223> OTHER INFORMATION: target sequence

<400> SEQUENCE: 534
aacaaagagg aacatcatta t                                              21

<210> SEQ ID NO 535
<211> LENGTH: 21
<212> TYPE: DNA
<213> ORGANISM: Artificial Sequence
<220> FEATURE:
<223> OTHER INFORMATION: target sequence

<400> SEQUENCE: 535
aagtccataa agcttcatta a                                              21

<210> SEQ ID NO 536
```

```
<211> LENGTH: 21
<212> TYPE: DNA
<213> ORGANISM: Artificial Sequence
<220> FEATURE:
<223> OTHER INFORMATION: target sequence

<400> SEQUENCE: 536
ccagatcatt gtggccctca a                                                    21

<210> SEQ ID NO 537
<211> LENGTH: 19
<212> TYPE: RNA
<213> ORGANISM: Artificial Sequence
<220> FEATURE:
<223> OTHER INFORMATION: target sequence

<400> SEQUENCE: 537
cccucuccgu cucugagau                                                       19

<210> SEQ ID NO 538
<211> LENGTH: 21
<212> TYPE: DNA
<213> ORGANISM: Artificial Sequence
<220> FEATURE:
<223> OTHER INFORMATION: target sequence

<400> SEQUENCE: 538
ttgaggattc cctctgccga a                                                    21

<210> SEQ ID NO 539
<211> LENGTH: 21
<212> TYPE: DNA
<213> ORGANISM: Artificial Sequence
<220> FEATURE:
<223> OTHER INFORMATION: target sequence

<400> SEQUENCE: 539
ctggtaaata accacagtgt a                                                    21

<210> SEQ ID NO 540
<211> LENGTH: 21
<212> TYPE: DNA
<213> ORGANISM: Artificial Sequence
<220> FEATURE:
<223> OTHER INFORMATION: target sequence

<400> SEQUENCE: 540
caccaggact tgagcacata a                                                    21

<210> SEQ ID NO 541
<211> LENGTH: 21
<212> TYPE: DNA
<213> ORGANISM: Artificial Sequence
<220> FEATURE:
<223> OTHER INFORMATION: target sequence

<400> SEQUENCE: 541
ccgccaaaga atttagaacg a                                                    21

<210> SEQ ID NO 542
<211> LENGTH: 21
<212> TYPE: DNA
<213> ORGANISM: Artificial Sequence
<220> FEATURE:
<223> OTHER INFORMATION: target sequence

<400> SEQUENCE: 542
```
ccgcctctgg caggacctga a                                              21

<210> SEQ ID NO 543
<211> LENGTH: 25
<212> TYPE: RNA
<213> ORGANISM: Artificial Sequence
<220> FEATURE:
<223> OTHER INFORMATION: target sequence

<400> SEQUENCE: 543
cgguguaccg cgggacaaau ccucg                                          25

<210> SEQ ID NO 544
<211> LENGTH: 19
<212> TYPE: RNA
<213> ORGANISM: Artificial Sequence
<220> FEATURE:
<223> OTHER INFORMATION: target sequence

<400> SEQUENCE: 544
ggucauuggu gauggcaau                                                 19

<210> SEQ ID NO 545
<211> LENGTH: 19
<212> TYPE: RNA
<213> ORGANISM: Artificial Sequence
<220> FEATURE:
<223> OTHER INFORMATION: target sequence

<400> SEQUENCE: 545
ggagaaagag acaggugua                                                 19

<210> SEQ ID NO 546
<211> LENGTH: 21
<212> TYPE: DNA
<213> ORGANISM: Artificial Sequence
<220> FEATURE:
<223> OTHER INFORMATION: target sequence

<400> SEQUENCE: 546
agggaagctg tacaccacta a                                              21

<210> SEQ ID NO 547
<211> LENGTH: 21
<212> TYPE: DNA
<213> ORGANISM: Artificial Sequence
<220> FEATURE:
<223> OTHER INFORMATION: target sequence

<400> SEQUENCE: 547
caggagttct cacgcaggga a                                              21

<210> SEQ ID NO 548
<211> LENGTH: 21
<212> TYPE: DNA
<213> ORGANISM: Artificial Sequence
<220> FEATURE:
<223> OTHER INFORMATION: target sequence

<400> SEQUENCE: 548
caggaacagc ctgaagacca a                                              21

<210> SEQ ID NO 549
<211> LENGTH: 21
<212> TYPE: DNA

```
<213> ORGANISM: Artificial Sequence
<220> FEATURE:
<223> OTHER INFORMATION: target sequence

<400> SEQUENCE: 549
gaggatctat cagatttata a                                              21

<210> SEQ ID NO 550
<211> LENGTH: 25
<212> TYPE: RNA
<213> ORGANISM: Artificial Sequence
<220> FEATURE:
<223> OTHER INFORMATION: target sequence

<400> SEQUENCE: 550
gcauccggug accucgaauc caagc                                          25

<210> SEQ ID NO 551
<211> LENGTH: 21
<212> TYPE: DNA
<213> ORGANISM: Artificial Sequence
<220> FEATURE:
<223> OTHER INFORMATION: target sequence

<400> SEQUENCE: 551
atccggtgac ctcgaatcca a                                              21

<210> SEQ ID NO 552
<211> LENGTH: 21
<212> TYPE: DNA
<213> ORGANISM: Artificial Sequence
<220> FEATURE:
<223> OTHER INFORMATION: target sequence

<400> SEQUENCE: 552
aagcatggtt aacgtcccta a                                              21

<210> SEQ ID NO 553
<211> LENGTH: 21
<212> TYPE: DNA
<213> ORGANISM: Artificial Sequence
<220> FEATURE:
<223> OTHER INFORMATION: target sequence

<400> SEQUENCE: 553
aagagaatgc tggctattaa a                                              21

<210> SEQ ID NO 554
<211> LENGTH: 21
<212> TYPE: DNA
<213> ORGANISM: Artificial Sequence
<220> FEATURE:
<223> OTHER INFORMATION: target sequence

<400> SEQUENCE: 554
cacctccttc ttggaacagc a                                              21

<210> SEQ ID NO 555
<211> LENGTH: 19
<212> TYPE: RNA
<213> ORGANISM: Artificial Sequence
<220> FEATURE:
<223> OTHER INFORMATION: target sequence

<400> SEQUENCE: 555
ugccacuacc uugacugga                                                 19
```

<210> SEQ ID NO 556
<211> LENGTH: 19
<212> TYPE: RNA
<213> ORGANISM: Artificial Sequence
<220> FEATURE:
<223> OTHER INFORMATION: target sequence

<400> SEQUENCE: 556
agcgacgacc acaguaaga                                              19

<210> SEQ ID NO 557
<211> LENGTH: 21
<212> TYPE: DNA
<213> ORGANISM: Artificial Sequence
<220> FEATURE:
<223> OTHER INFORMATION: target sequence

<400> SEQUENCE: 557
ccacagtaag atcctggttc a                                           21

<210> SEQ ID NO 558
<211> LENGTH: 21
<212> TYPE: DNA
<213> ORGANISM: Artificial Sequence
<220> FEATURE:
<223> OTHER INFORMATION: target sequence

<400> SEQUENCE: 558
cacgaacatc ctgaccctca t                                           21

<210> SEQ ID NO 559
<211> LENGTH: 21
<212> TYPE: DNA
<213> ORGANISM: Artificial Sequence
<220> FEATURE:
<223> OTHER INFORMATION: target sequence

<400> SEQUENCE: 559
ctcggtgatt gtgtccatca t                                           21

<210> SEQ ID NO 560
<211> LENGTH: 21
<212> TYPE: DNA
<213> ORGANISM: Artificial Sequence
<220> FEATURE:
<223> OTHER INFORMATION: target sequence

<400> SEQUENCE: 560
ctggattctg gtaccctccg a                                           21

<210> SEQ ID NO 561
<211> LENGTH: 21
<212> TYPE: DNA
<213> ORGANISM: Artificial Sequence
<220> FEATURE:
<223> OTHER INFORMATION: target sequence

<400> SEQUENCE: 561
ccgccatgtg cccttctcca t                                           21

<210> SEQ ID NO 562
<211> LENGTH: 21
<212> TYPE: DNA
<213> ORGANISM: Artificial Sequence
<220> FEATURE:

<223> OTHER INFORMATION: target sequence

<400> SEQUENCE: 562
cacagttgaa gggacaggca a					21

<210> SEQ ID NO 563
<211> LENGTH: 21
<212> TYPE: DNA
<213> ORGANISM: Artificial Sequence
<220> FEATURE:
<223> OTHER INFORMATION: target sequence

<400> SEQUENCE: 563
cagggtggtg ctggccacag a					21

<210> SEQ ID NO 564
<211> LENGTH: 21
<212> TYPE: DNA
<213> ORGANISM: Artificial Sequence
<220> FEATURE:
<223> OTHER INFORMATION: target sequence

<400> SEQUENCE: 564
tccgatttgg tgggcaacca a					21

<210> SEQ ID NO 565
<211> LENGTH: 21
<212> TYPE: DNA
<213> ORGANISM: Artificial Sequence
<220> FEATURE:
<223> OTHER INFORMATION: target sequence

<400> SEQUENCE: 565
ctggctgcaa atggcctcaa a					21

<210> SEQ ID NO 566
<211> LENGTH: 21
<212> TYPE: DNA
<213> ORGANISM: Artificial Sequence
<220> FEATURE:
<223> OTHER INFORMATION: target sequence

<400> SEQUENCE: 566
ttcagtattc ttggactctt a					21

<210> SEQ ID NO 567
<211> LENGTH: 21
<212> TYPE: DNA
<213> ORGANISM: Artificial Sequence
<220> FEATURE:
<223> OTHER INFORMATION: target sequence

<400> SEQUENCE: 567
ctcatagttc agtgtcttca a					21

<210> SEQ ID NO 568
<211> LENGTH: 21
<212> TYPE: DNA
<213> ORGANISM: Artificial Sequence
<220> FEATURE:
<223> OTHER INFORMATION: target sequence

<400> SEQUENCE: 568
cagcttgaag accaagacaa t					21

```
<210> SEQ ID NO 569
<211> LENGTH: 21
<212> TYPE: DNA
<213> ORGANISM: Artificial Sequence
<220> FEATURE:
<223> OTHER INFORMATION: target sequence

<400> SEQUENCE: 569
atggatttgg taatgatgga a                                           21

<210> SEQ ID NO 570
<211> LENGTH: 21
<212> TYPE: DNA
<213> ORGANISM: Artificial Sequence
<220> FEATURE:
<223> OTHER INFORMATION: target sequence

<400> SEQUENCE: 570
acggactgtg tggtaatgag a                                           21

<210> SEQ ID NO 571
<211> LENGTH: 21
<212> TYPE: DNA
<213> ORGANISM: Artificial Sequence
<220> FEATURE:
<223> OTHER INFORMATION: target sequence

<400> SEQUENCE: 571
cccggtggta gtggagcgct a                                           21

<210> SEQ ID NO 572
<211> LENGTH: 21
<212> TYPE: DNA
<213> ORGANISM: Artificial Sequence
<220> FEATURE:
<223> OTHER INFORMATION: target sequence

<400> SEQUENCE: 572
cgcaaccatg gcagagatct a                                           21

<210> SEQ ID NO 573
<211> LENGTH: 21
<212> TYPE: DNA
<213> ORGANISM: Artificial Sequence
<220> FEATURE:
<223> OTHER INFORMATION: target sequence

<400> SEQUENCE: 573
aactgacttg cccgaattta a                                           21

<210> SEQ ID NO 574
<211> LENGTH: 21
<212> TYPE: DNA
<213> ORGANISM: Artificial Sequence
<220> FEATURE:
<223> OTHER INFORMATION: target sequence

<400> SEQUENCE: 574
aaccagggcg acctagaaga a                                           21

<210> SEQ ID NO 575
<211> LENGTH: 19
<212> TYPE: RNA
<213> ORGANISM: Artificial Sequence
<220> FEATURE:
<223> OTHER INFORMATION: target sequence
```

<400> SEQUENCE: 575
cgucucugcu guauccugg                                                        19

<210> SEQ ID NO 576
<211> LENGTH: 19
<212> TYPE: RNA
<213> ORGANISM: Artificial Sequence
<220> FEATURE:
<223> OTHER INFORMATION: target sequence

<400> SEQUENCE: 576
ccaggaaaua uccuuauca                                                        19

<210> SEQ ID NO 577
<211> LENGTH: 21
<212> TYPE: DNA
<213> ORGANISM: Artificial Sequence
<220> FEATURE:
<223> OTHER INFORMATION: target sequence

<400> SEQUENCE: 577
cccgatcttc cttccaccta a                                                     21

<210> SEQ ID NO 578
<211> LENGTH: 21
<212> TYPE: DNA
<213> ORGANISM: Artificial Sequence
<220> FEATURE:
<223> OTHER INFORMATION: target sequence

<400> SEQUENCE: 578
aaggttatac aggaccattc a                                                     21

<210> SEQ ID NO 579
<211> LENGTH: 21
<212> TYPE: DNA
<213> ORGANISM: Artificial Sequence
<220> FEATURE:
<223> OTHER INFORMATION: target sequence

<400> SEQUENCE: 579
ctgcacggag cttctggtga a                                                     21

<210> SEQ ID NO 580
<211> LENGTH: 21
<212> TYPE: DNA
<213> ORGANISM: Artificial Sequence
<220> FEATURE:
<223> OTHER INFORMATION: target sequence

<400> SEQUENCE: 580
caggatcttg ttgccatggt g                                                     21

<210> SEQ ID NO 581
<211> LENGTH: 21
<212> TYPE: DNA
<213> ORGANISM: Artificial Sequence
<220> FEATURE:
<223> OTHER INFORMATION: target sequence

<400> SEQUENCE: 581
caccagccac tgtcatgtta a                                                     21

<210> SEQ ID NO 582
<211> LENGTH: 21

```
<212> TYPE: DNA
<213> ORGANISM: Artificial Sequence
<220> FEATURE:
<223> OTHER INFORMATION: target sequence

<400> SEQUENCE: 582
cagaatctgt cgggaataat a                                              21

<210> SEQ ID NO 583
<211> LENGTH: 21
<212> TYPE: DNA
<213> ORGANISM: Artificial Sequence
<220> FEATURE:
<223> OTHER INFORMATION: target sequence

<400> SEQUENCE: 583
ttccgccaag aggaagcata a                                              21

<210> SEQ ID NO 584
<211> LENGTH: 21
<212> TYPE: DNA
<213> ORGANISM: Artificial Sequence
<220> FEATURE:
<223> OTHER INFORMATION: target sequence

<400> SEQUENCE: 584
tcggactgtc tgcagcatca a                                              21

<210> SEQ ID NO 585
<211> LENGTH: 21
<212> TYPE: DNA
<213> ORGANISM: Artificial Sequence
<220> FEATURE:
<223> OTHER INFORMATION: target sequence

<400> SEQUENCE: 585
caggctggtt tggtaaagaa a                                              21

<210> SEQ ID NO 586
<211> LENGTH: 21
<212> TYPE: DNA
<213> ORGANISM: Artificial Sequence
<220> FEATURE:
<223> OTHER INFORMATION: target sequence

<400> SEQUENCE: 586
cccggaagca ggagatcatt a                                              21

<210> SEQ ID NO 587
<211> LENGTH: 21
<212> TYPE: DNA
<213> ORGANISM: Artificial Sequence
<220> FEATURE:
<223> OTHER INFORMATION: target sequence

<400> SEQUENCE: 587
cacggtttgg ataatcttaa a                                              21

<210> SEQ ID NO 588
<211> LENGTH: 21
<212> TYPE: DNA
<213> ORGANISM: Artificial Sequence
<220> FEATURE:
<223> OTHER INFORMATION: target sequence

<400> SEQUENCE: 588
```

```
caccgtgacc atcaacatga a                                              21

<210> SEQ ID NO 589
<211> LENGTH: 21
<212> TYPE: DNA
<213> ORGANISM: Artificial Sequence
<220> FEATURE:
<223> OTHER INFORMATION: target sequence

<400> SEQUENCE: 589
accaataaat cagaccatga a                                              21

<210> SEQ ID NO 590
<211> LENGTH: 21
<212> TYPE: DNA
<213> ORGANISM: Artificial Sequence
<220> FEATURE:
<223> OTHER INFORMATION: target sequence

<400> SEQUENCE: 590
cccaatggag tcatcacaga a                                              21

<210> SEQ ID NO 591
<211> LENGTH: 21
<212> TYPE: DNA
<213> ORGANISM: Artificial Sequence
<220> FEATURE:
<223> OTHER INFORMATION: target sequence

<400> SEQUENCE: 591
caggcctatg gtcgagattt a                                              21

<210> SEQ ID NO 592
<211> LENGTH: 21
<212> TYPE: DNA
<213> ORGANISM: Artificial Sequence
<220> FEATURE:
<223> OTHER INFORMATION: target sequence

<400> SEQUENCE: 592
actcgctgat ccaaatgaca a                                              21

<210> SEQ ID NO 593
<211> LENGTH: 21
<212> TYPE: DNA
<213> ORGANISM: Artificial Sequence
<220> FEATURE:
<223> OTHER INFORMATION: target sequence

<400> SEQUENCE: 593
ctgcgttatc ctcaccttca a                                              21

<210> SEQ ID NO 594
<211> LENGTH: 19
<212> TYPE: DNA
<213> ORGANISM: Artificial Sequence
<220> FEATURE:
<223> OTHER INFORMATION: target sequence

<400> SEQUENCE: 594
cctctcaacc tcactcttt                                                 19

<210> SEQ ID NO 595
<211> LENGTH: 21
<212> TYPE: DNA
<213> ORGANISM: Artificial Sequence
```

```
<220> FEATURE:
<223> OTHER INFORMATION: target sequence

<400> SEQUENCE: 595
caccatcaac atggagaaca a                                              21

<210> SEQ ID NO 596
<211> LENGTH: 21
<212> TYPE: DNA
<213> ORGANISM: Artificial Sequence
<220> FEATURE:
<223> OTHER INFORMATION: target sequence

<400> SEQUENCE: 596
caagaacggc atgaagtact a                                              21

<210> SEQ ID NO 597
<211> LENGTH: 21
<212> TYPE: DNA
<213> ORGANISM: Artificial Sequence
<220> FEATURE:
<223> OTHER INFORMATION: target sequence

<400> SEQUENCE: 597
gacatttcta ctggtacctt a                                              21

<210> SEQ ID NO 598
<211> LENGTH: 21
<212> TYPE: DNA
<213> ORGANISM: Artificial Sequence
<220> FEATURE:
<223> OTHER INFORMATION: target sequence

<400> SEQUENCE: 598
cgcggtcgta agggctgagg a                                              21

<210> SEQ ID NO 599
<211> LENGTH: 21
<212> TYPE: DNA
<213> ORGANISM: Artificial Sequence
<220> FEATURE:
<223> OTHER INFORMATION: target sequence

<400> SEQUENCE: 599
aggcaaagaa acattgtgaa a                                              21

<210> SEQ ID NO 600
<211> LENGTH: 21
<212> TYPE: DNA
<213> ORGANISM: Artificial Sequence
<220> FEATURE:
<223> OTHER INFORMATION: target sequence

<400> SEQUENCE: 600
tgggtccaga attatatgaa a                                              21

<210> SEQ ID NO 601
<211> LENGTH: 19
<212> TYPE: RNA
<213> ORGANISM: Artificial Sequence
<220> FEATURE:
<223> OTHER INFORMATION: target sequence

<400> SEQUENCE: 601
aggcagaaga aguguucua                                                 19
```

<210> SEQ ID NO 602
<211> LENGTH: 21
<212> TYPE: DNA
<213> ORGANISM: Artificial Sequence
<220> FEATURE:
<223> OTHER INFORMATION: target sequence

<400> SEQUENCE: 602
cagcattgtt gaaatgctta a                                              21

<210> SEQ ID NO 603
<211> LENGTH: 21
<212> TYPE: DNA
<213> ORGANISM: Artificial Sequence
<220> FEATURE:
<223> OTHER INFORMATION: target sequence

<400> SEQUENCE: 603
tccactcact atgctaccaa a                                              21

<210> SEQ ID NO 604
<211> LENGTH: 21
<212> TYPE: DNA
<213> ORGANISM: Artificial Sequence
<220> FEATURE:
<223> OTHER INFORMATION: target sequence

<400> SEQUENCE: 604
aaggctctca attgcactct t                                              21

<210> SEQ ID NO 605
<211> LENGTH: 21
<212> TYPE: DNA
<213> ORGANISM: Artificial Sequence
<220> FEATURE:
<223> OTHER INFORMATION: target sequence

<400> SEQUENCE: 605
caactacatc cctatcttct a                                              21

<210> SEQ ID NO 606
<211> LENGTH: 21
<212> TYPE: DNA
<213> ORGANISM: Artificial Sequence
<220> FEATURE:
<223> OTHER INFORMATION: target sequence

<400> SEQUENCE: 606
cccagtcagg tttcaagggt a                                              21

<210> SEQ ID NO 607
<211> LENGTH: 25
<212> TYPE: RNA
<213> ORGANISM: Artificial Sequence
<220> FEATURE:
<223> OTHER INFORMATION: target sequence

<400> SEQUENCE: 607
uggucuugaa cauccuauug gcaug                                          25

<210> SEQ ID NO 608
<211> LENGTH: 21
<212> TYPE: DNA
<213> ORGANISM: Artificial Sequence
<220> FEATURE:
<223> OTHER INFORMATION: target sequence

```
<400> SEQUENCE: 608
caggaaaggg acattgtaaa t                                              21

<210> SEQ ID NO 609
<211> LENGTH: 21
<212> TYPE: DNA
<213> ORGANISM: Artificial Sequence
<220> FEATURE:
<223> OTHER INFORMATION: target sequence

<400> SEQUENCE: 609
ctggttaaag agacccggaa a                                              21

<210> SEQ ID NO 610
<211> LENGTH: 19
<212> TYPE: RNA
<213> ORGANISM: Artificial Sequence
<220> FEATURE:
<223> OTHER INFORMATION: target sequence

<400> SEQUENCE: 610
ucaccuacau ccucuuaag                                                 19

<210> SEQ ID NO 611
<211> LENGTH: 21
<212> TYPE: DNA
<213> ORGANISM: Artificial Sequence
<220> FEATURE:
<223> OTHER INFORMATION: target sequence

<400> SEQUENCE: 611
ctggaagtca tgtgtgaatc a                                              21

<210> SEQ ID NO 612
<211> LENGTH: 21
<212> TYPE: DNA
<213> ORGANISM: Artificial Sequence
<220> FEATURE:
<223> OTHER INFORMATION: target sequence

<400> SEQUENCE: 612
tccggagtgt tgtcatgtga a                                              21

<210> SEQ ID NO 613
<211> LENGTH: 19
<212> TYPE: RNA
<213> ORGANISM: Artificial Sequence
<220> FEATURE:
<223> OTHER INFORMATION: target sequence

<400> SEQUENCE: 613
gggaaagaug gagguauua                                                 19

<210> SEQ ID NO 614
<211> LENGTH: 21
<212> TYPE: DNA
<213> ORGANISM: Artificial Sequence
<220> FEATURE:
<223> OTHER INFORMATION: target sequence

<400> SEQUENCE: 614
cgggaccatc ctcatagttt a                                              21

<210> SEQ ID NO 615
```

```
<211> LENGTH: 21
<212> TYPE: DNA
<213> ORGANISM: Artificial Sequence
<220> FEATURE:
<223> OTHER INFORMATION: target sequence

<400> SEQUENCE: 615
atgctctata gccaaagcca a                                              21

<210> SEQ ID NO 616
<211> LENGTH: 21
<212> TYPE: DNA
<213> ORGANISM: Artificial Sequence
<220> FEATURE:
<223> OTHER INFORMATION: target sequence

<400> SEQUENCE: 616
ctccacatga taggaggttt a                                              21

<210> SEQ ID NO 617
<211> LENGTH: 21
<212> TYPE: DNA
<213> ORGANISM: Artificial Sequence
<220> FEATURE:
<223> OTHER INFORMATION: target sequence

<400> SEQUENCE: 617
cggaaagact tacgttatta a                                              21

<210> SEQ ID NO 618
<211> LENGTH: 21
<212> TYPE: DNA
<213> ORGANISM: Artificial Sequence
<220> FEATURE:
<223> OTHER INFORMATION: target sequence

<400> SEQUENCE: 618
caagctcgaa ttacatcttt a                                              21

<210> SEQ ID NO 619
<211> LENGTH: 21
<212> TYPE: DNA
<213> ORGANISM: Artificial Sequence
<220> FEATURE:
<223> OTHER INFORMATION: target sequence

<400> SEQUENCE: 619
aacggttaga acaagaggta a                                              21

<210> SEQ ID NO 620
<211> LENGTH: 21
<212> TYPE: DNA
<213> ORGANISM: Artificial Sequence
<220> FEATURE:
<223> OTHER INFORMATION: target sequence

<400> SEQUENCE: 620
caaggtcatt atgtcactgc a                                              21

<210> SEQ ID NO 621
<211> LENGTH: 21
<212> TYPE: DNA
<213> ORGANISM: Artificial Sequence
<220> FEATURE:
<223> OTHER INFORMATION: target sequence

<400> SEQUENCE: 621
```

-continued

```
cagcctttca ggaaagatgc a                                              21

<210> SEQ ID NO 622
<211> LENGTH: 21
<212> TYPE: DNA
<213> ORGANISM: Artificial Sequence
<220> FEATURE:
<223> OTHER INFORMATION: target sequence

<400> SEQUENCE: 622
ctctgtgtcc ctattcctca a                                              21

<210> SEQ ID NO 623
<211> LENGTH: 19
<212> TYPE: RNA
<213> ORGANISM: Artificial Sequence
<220> FEATURE:
<223> OTHER INFORMATION: target sequence

<400> SEQUENCE: 623
acgggugaag gacucggau                                                 19

<210> SEQ ID NO 624
<211> LENGTH: 21
<212> TYPE: DNA
<213> ORGANISM: Artificial Sequence
<220> FEATURE:
<223> OTHER INFORMATION: target sequence

<400> SEQUENCE: 624
aggagcgatg acggaatata a                                              21

<210> SEQ ID NO 625
<211> LENGTH: 21
<212> TYPE: DNA
<213> ORGANISM: Artificial Sequence
<220> FEATURE:
<223> OTHER INFORMATION: target sequence

<400> SEQUENCE: 625
aagcaagttc ctgctgctga a                                              21

<210> SEQ ID NO 626
<211> LENGTH: 21
<212> TYPE: DNA
<213> ORGANISM: Artificial Sequence
<220> FEATURE:
<223> OTHER INFORMATION: target sequence

<400> SEQUENCE: 626
aagcagtttc ctttcttata a                                              21

<210> SEQ ID NO 627
<211> LENGTH: 21
<212> TYPE: DNA
<213> ORGANISM: Artificial Sequence
<220> FEATURE:
<223> OTHER INFORMATION: target sequence

<400> SEQUENCE: 627
ctggaggagc tcactggaga a                                              21

<210> SEQ ID NO 628
<211> LENGTH: 19
<212> TYPE: RNA
```

<213> ORGANISM: Artificial Sequence
<220> FEATURE:
<223> OTHER INFORMATION: target sequence

<400> SEQUENCE: 628
ccacuaacua ugagaaagc                                                19

<210> SEQ ID NO 629
<211> LENGTH: 21
<212> TYPE: DNA
<213> ORGANISM: Artificial Sequence
<220> FEATURE:
<223> OTHER INFORMATION: target sequence

<400> SEQUENCE: 629
caccattaaa gttactggtt t                                             21

<210> SEQ ID NO 630
<211> LENGTH: 19
<212> TYPE: RNA
<213> ORGANISM: Artificial Sequence
<220> FEATURE:
<223> OTHER INFORMATION: target sequence

<400> SEQUENCE: 630
caguguacac aaugggaac                                                19

<210> SEQ ID NO 631
<211> LENGTH: 21
<212> TYPE: DNA
<213> ORGANISM: Artificial Sequence
<220> FEATURE:
<223> OTHER INFORMATION: target sequence

<400> SEQUENCE: 631
cagagatagt tgggtgacaa a                                             21

<210> SEQ ID NO 632
<211> LENGTH: 21
<212> TYPE: DNA
<213> ORGANISM: Artificial Sequence
<220> FEATURE:
<223> OTHER INFORMATION: target sequence

<400> SEQUENCE: 632
cccaaacttt acaaaccttc a                                             21

<210> SEQ ID NO 633
<211> LENGTH: 21
<212> TYPE: DNA
<213> ORGANISM: Artificial Sequence
<220> FEATURE:
<223> OTHER INFORMATION: target sequence

<400> SEQUENCE: 633
ctgtgtgaag ttacacaatt a                                             21

<210> SEQ ID NO 634
<211> LENGTH: 19
<212> TYPE: RNA
<213> ORGANISM: Artificial Sequence
<220> FEATURE:
<223> OTHER INFORMATION: target sequence

<400> SEQUENCE: 634
gggaaccuuc cagccaaau                                                19

<210> SEQ ID NO 635
<211> LENGTH: 21
<212> TYPE: DNA
<213> ORGANISM: Artificial Sequence
<220> FEATURE:
<223> OTHER INFORMATION: target sequence

<400> SEQUENCE: 635
catgcaaata ttccattgta a                                                   21

<210> SEQ ID NO 636
<211> LENGTH: 21
<212> TYPE: DNA
<213> ORGANISM: Artificial Sequence
<220> FEATURE:
<223> OTHER INFORMATION: target sequence

<400> SEQUENCE: 636
ccggaggtcc tgaagcgtca a                                                   21

<210> SEQ ID NO 637
<211> LENGTH: 21
<212> TYPE: DNA
<213> ORGANISM: Artificial Sequence
<220> FEATURE:
<223> OTHER INFORMATION: target sequence

<400> SEQUENCE: 637
aaagctgata gtctatgtca a                                                   21

<210> SEQ ID NO 638
<211> LENGTH: 21
<212> TYPE: DNA
<213> ORGANISM: Artificial Sequence
<220> FEATURE:
<223> OTHER INFORMATION: target sequence

<400> SEQUENCE: 638
gcgcaagtca acgggtggca a                                                   21

<210> SEQ ID NO 639
<211> LENGTH: 19
<212> TYPE: RNA
<213> ORGANISM: Artificial Sequence
<220> FEATURE:
<223> OTHER INFORMATION: target sequence

<400> SEQUENCE: 639
uucaguggcu cagucagua                                                      19

<210> SEQ ID NO 640
<211> LENGTH: 21
<212> TYPE: DNA
<213> ORGANISM: Artificial Sequence
<220> FEATURE:
<223> OTHER INFORMATION: target sequence

<400> SEQUENCE: 640
cagactttcc gtagcagctt a                                                   21

<210> SEQ ID NO 641
<211> LENGTH: 19
<212> TYPE: RNA
<213> ORGANISM: Artificial Sequence
<220> FEATURE:

<223> OTHER INFORMATION: target sequence

<400> SEQUENCE: 641
ucugcacagg aacuucauu                                            19

<210> SEQ ID NO 642
<211> LENGTH: 21
<212> TYPE: DNA
<213> ORGANISM: Artificial Sequence
<220> FEATURE:
<223> OTHER INFORMATION: target sequence

<400> SEQUENCE: 642
caccgacgag tctcaactaa a                                          21

<210> SEQ ID NO 643
<211> LENGTH: 19
<212> TYPE: RNA
<213> ORGANISM: Artificial Sequence
<220> FEATURE:
<223> OTHER INFORMATION: target sequence

<400> SEQUENCE: 643
caagcuggau aaggugaau                                             19

<210> SEQ ID NO 644
<211> LENGTH: 21
<212> TYPE: DNA
<213> ORGANISM: Artificial Sequence
<220> FEATURE:
<223> OTHER INFORMATION: target sequence

<400> SEQUENCE: 644
aagagtgtat atggtaggga a                                          21

<210> SEQ ID NO 645
<211> LENGTH: 21
<212> TYPE: DNA
<213> ORGANISM: Artificial Sequence
<220> FEATURE:
<223> OTHER INFORMATION: target sequence

<400> SEQUENCE: 645
atgggctaat atggatacta a                                          21

<210> SEQ ID NO 646
<211> LENGTH: 21
<212> TYPE: DNA
<213> ORGANISM: Artificial Sequence
<220> FEATURE:
<223> OTHER INFORMATION: target sequence

<400> SEQUENCE: 646
aaggatgaaa ctggcttcta t                                          21

<210> SEQ ID NO 647
<211> LENGTH: 19
<212> TYPE: RNA
<213> ORGANISM: Artificial Sequence
<220> FEATURE:
<223> OTHER INFORMATION: target sequence

<400> SEQUENCE: 647
ggaguaugca ucucaagaa                                             19

```
<210> SEQ ID NO 648
<211> LENGTH: 21
<212> TYPE: DNA
<213> ORGANISM: Artificial Sequence
<220> FEATURE:
<223> OTHER INFORMATION: target sequence

<400> SEQUENCE: 648
cactaatgtg ttggaaatca a                                              21

<210> SEQ ID NO 649
<211> LENGTH: 19
<212> TYPE: RNA
<213> ORGANISM: Artificial Sequence
<220> FEATURE:
<223> OTHER INFORMATION: target sequence

<400> SEQUENCE: 649
ccgcagacuu uguuaagau                                                 19

<210> SEQ ID NO 650
<211> LENGTH: 21
<212> TYPE: DNA
<213> ORGANISM: Artificial Sequence
<220> FEATURE:
<223> OTHER INFORMATION: target sequence

<400> SEQUENCE: 650
caggctgagg attcagatga a                                              21

<210> SEQ ID NO 651
<211> LENGTH: 19
<212> TYPE: RNA
<213> ORGANISM: Artificial Sequence
<220> FEATURE:
<223> OTHER INFORMATION: target sequence

<400> SEQUENCE: 651
ccuguugccu augcaaaac                                                 19

<210> SEQ ID NO 652
<211> LENGTH: 19
<212> TYPE: RNA
<213> ORGANISM: Artificial Sequence
<220> FEATURE:
<223> OTHER INFORMATION: target sequence

<400> SEQUENCE: 652
gucccuccac uugaccaau                                                 19

<210> SEQ ID NO 653
<211> LENGTH: 19
<212> TYPE: RNA
<213> ORGANISM: Artificial Sequence
<220> FEATURE:
<223> OTHER INFORMATION: target sequence

<400> SEQUENCE: 653
uuggaucugc ugggucaau                                                 19

<210> SEQ ID NO 654
<211> LENGTH: 21
<212> TYPE: DNA
<213> ORGANISM: Artificial Sequence
<220> FEATURE:
<223> OTHER INFORMATION: target sequence
```

-continued

<400> SEQUENCE: 654
aaggacttac ggtatcagat a                                              21

<210> SEQ ID NO 655
<211> LENGTH: 21
<212> TYPE: DNA
<213> ORGANISM: Artificial Sequence
<220> FEATURE:
<223> OTHER INFORMATION: target sequence

<400> SEQUENCE: 655
caggagagca acttaccttc a                                              21

<210> SEQ ID NO 656
<211> LENGTH: 21
<212> TYPE: DNA
<213> ORGANISM: Artificial Sequence
<220> FEATURE:
<223> OTHER INFORMATION: target sequence

<400> SEQUENCE: 656
cacctggttt ctatatagta a                                              21

<210> SEQ ID NO 657
<211> LENGTH: 21
<212> TYPE: DNA
<213> ORGANISM: Artificial Sequence
<220> FEATURE:
<223> OTHER INFORMATION: target sequence

<400> SEQUENCE: 657
acgcacgtga tgtacatgca a                                              21

<210> SEQ ID NO 658
<211> LENGTH: 19
<212> TYPE: RNA
<213> ORGANISM: Artificial Sequence
<220> FEATURE:
<223> OTHER INFORMATION: target sequence

<400> SEQUENCE: 658
ggaguucaaa gaggaaauc                                                 19

<210> SEQ ID NO 659
<211> LENGTH: 19
<212> TYPE: RNA
<213> ORGANISM: Artificial Sequence
<220> FEATURE:
<223> OTHER INFORMATION: target sequence

<400> SEQUENCE: 659
gccaugaugc aagagauga                                                 19

<210> SEQ ID NO 660
<211> LENGTH: 21
<212> TYPE: DNA
<213> ORGANISM: Artificial Sequence
<220> FEATURE:
<223> OTHER INFORMATION: target sequence

<400> SEQUENCE: 660
caacaacttg tttcaattta a                                              21

<210> SEQ ID NO 661
<211> LENGTH: 21

```
<212> TYPE: DNA
<213> ORGANISM: Artificial Sequence
<220> FEATURE:
<223> OTHER INFORMATION: target sequence

<400> SEQUENCE: 661
cccgggtgtt ccaacgtca t                                              21

<210> SEQ ID NO 662
<211> LENGTH: 21
<212> TYPE: DNA
<213> ORGANISM: Artificial Sequence
<220> FEATURE:
<223> OTHER INFORMATION: target sequence

<400> SEQUENCE: 662
ctgggaaatg gccagaagat a                                             21

<210> SEQ ID NO 663
<211> LENGTH: 21
<212> TYPE: DNA
<213> ORGANISM: Artificial Sequence
<220> FEATURE:
<223> OTHER INFORMATION: target sequence

<400> SEQUENCE: 663
caggtgctgg ctggcctaat a                                             21

<210> SEQ ID NO 664
<211> LENGTH: 19
<212> TYPE: RNA
<213> ORGANISM: Artificial Sequence
<220> FEATURE:
<223> OTHER INFORMATION: target sequence

<400> SEQUENCE: 664
gcccugauag gcuguuuau                                                19

<210> SEQ ID NO 665
<211> LENGTH: 21
<212> TYPE: DNA
<213> ORGANISM: Artificial Sequence
<220> FEATURE:
<223> OTHER INFORMATION: target sequence

<400> SEQUENCE: 665
cccaccagac tttctgtaag a                                             21

<210> SEQ ID NO 666
<211> LENGTH: 21
<212> TYPE: DNA
<213> ORGANISM: Artificial Sequence
<220> FEATURE:
<223> OTHER INFORMATION: target sequence

<400> SEQUENCE: 666
cagcgtctac actcacagct a                                             21

<210> SEQ ID NO 667
<211> LENGTH: 21
<212> TYPE: DNA
<213> ORGANISM: Artificial Sequence
<220> FEATURE:
<223> OTHER INFORMATION: target sequence

<400> SEQUENCE: 667
```

```
ccggactgtg ccttccgcaa a                                                    21

<210> SEQ ID NO 668
<211> LENGTH: 21
<212> TYPE: DNA
<213> ORGANISM: Artificial Sequence
<220> FEATURE:
<223> OTHER INFORMATION: target sequence

<400> SEQUENCE: 668
ctgggcctgg gcactggata a                                                    21

<210> SEQ ID NO 669
<211> LENGTH: 25
<212> TYPE: RNA
<213> ORGANISM: Artificial Sequence
<220> FEATURE:
<223> OTHER INFORMATION: target sequence

<400> SEQUENCE: 669
accaggaccu aaggacauau cugac                                                25

<210> SEQ ID NO 670
<211> LENGTH: 19
<212> TYPE: RNA
<213> ORGANISM: Artificial Sequence
<220> FEATURE:
<223> OTHER INFORMATION: target sequence

<400> SEQUENCE: 670
cccauaucug gagcaguau                                                       19

<210> SEQ ID NO 671
<211> LENGTH: 21
<212> TYPE: DNA
<213> ORGANISM: Artificial Sequence
<220> FEATURE:
<223> OTHER INFORMATION: target sequence

<400> SEQUENCE: 671
atcccgggac ctgaactatt a                                                    21

<210> SEQ ID NO 672
<211> LENGTH: 25
<212> TYPE: DNA
<213> ORGANISM: Artificial Sequence
<220> FEATURE:
<223> OTHER INFORMATION: target sequence

<400> SEQUENCE: 672
ggauucagga ucagucuaug acatt                                                25

<210> SEQ ID NO 673
<211> LENGTH: 19
<212> TYPE: DNA
<213> ORGANISM: Artificial Sequence
<220> FEATURE:
<223> OTHER INFORMATION: target sequence

<400> SEQUENCE: 673
agccagagag caagagaaa                                                       19

<210> SEQ ID NO 674
<211> LENGTH: 21
<212> TYPE: DNA
<213> ORGANISM: Artificial Sequence
```

<220> FEATURE:
<223> OTHER INFORMATION: target sequence

<400> SEQUENCE: 674
cagaacgtag attagcttat a                                              21

<210> SEQ ID NO 675
<211> LENGTH: 21
<212> TYPE: DNA
<213> ORGANISM: Artificial Sequence
<220> FEATURE:
<223> OTHER INFORMATION: target sequence

<400> SEQUENCE: 675
cagaaaggag tcaaagtcta t                                              21

<210> SEQ ID NO 676
<211> LENGTH: 21
<212> TYPE: DNA
<213> ORGANISM: Artificial Sequence
<220> FEATURE:
<223> OTHER INFORMATION: target sequence

<400> SEQUENCE: 676
caccgccaag tctaagtcag a                                              21

<210> SEQ ID NO 677
<211> LENGTH: 21
<212> TYPE: DNA
<213> ORGANISM: Artificial Sequence
<220> FEATURE:
<223> OTHER INFORMATION: target sequence

<400> SEQUENCE: 677
ctcgctgaac ctgacccgga a                                              21

<210> SEQ ID NO 678
<211> LENGTH: 21
<212> TYPE: DNA
<213> ORGANISM: Artificial Sequence
<220> FEATURE:
<223> OTHER INFORMATION: target sequence

<400> SEQUENCE: 678
cgggtgcacc ttcatcaaca a                                              21

<210> SEQ ID NO 679
<211> LENGTH: 21
<212> TYPE: DNA
<213> ORGANISM: Artificial Sequence
<220> FEATURE:
<223> OTHER INFORMATION: target sequence

<400> SEQUENCE: 679
aagatgtact tgactagttt a                                              21

<210> SEQ ID NO 680
<211> LENGTH: 21
<212> TYPE: DNA
<213> ORGANISM: Artificial Sequence
<220> FEATURE:
<223> OTHER INFORMATION: target sequence

<400> SEQUENCE: 680
tccgttgtga gggatgccaa a                                              21

```
<210> SEQ ID NO 681
<211> LENGTH: 21
<212> TYPE: DNA
<213> ORGANISM: Artificial Sequence
<220> FEATURE:
<223> OTHER INFORMATION: target sequence

<400> SEQUENCE: 681
cagtacgtat ttggcattca a                                          21

<210> SEQ ID NO 682
<211> LENGTH: 21
<212> TYPE: DNA
<213> ORGANISM: Artificial Sequence
<220> FEATURE:
<223> OTHER INFORMATION: target sequence

<400> SEQUENCE: 682
gcggatcagc gtctactaca a                                          21

<210> SEQ ID NO 683
<211> LENGTH: 21
<212> TYPE: DNA
<213> ORGANISM: Artificial Sequence
<220> FEATURE:
<223> OTHER INFORMATION: target sequence

<400> SEQUENCE: 683
cagggaaaga tggaggtatt a                                          21

<210> SEQ ID NO 684
<211> LENGTH: 21
<212> TYPE: DNA
<213> ORGANISM: Artificial Sequence
<220> FEATURE:
<223> OTHER INFORMATION: target sequence

<400> SEQUENCE: 684
ccagtgctac cttccagaca a                                          21

<210> SEQ ID NO 685
<211> LENGTH: 21
<212> TYPE: DNA
<213> ORGANISM: Artificial Sequence
<220> FEATURE:
<223> OTHER INFORMATION: target sequence

<400> SEQUENCE: 685
tcctagcacc atgaagatta a                                          21

<210> SEQ ID NO 686
<211> LENGTH: 21
<212> TYPE: DNA
<213> ORGANISM: Artificial Sequence
<220> FEATURE:
<223> OTHER INFORMATION: target sequence

<400> SEQUENCE: 686
ctggaacacg ctgtaccgga a                                          21

<210> SEQ ID NO 687
<211> LENGTH: 19
<212> TYPE: RNA
<213> ORGANISM: Artificial Sequence
<220> FEATURE:
<223> OTHER INFORMATION: target sequence
```

<400> SEQUENCE: 687
cagcaagauc ugcacaaag                                                    19

<210> SEQ ID NO 688
<211> LENGTH: 21
<212> TYPE: DNA
<213> ORGANISM: Artificial Sequence
<220> FEATURE:
<223> OTHER INFORMATION: target sequence

<400> SEQUENCE: 688
ccctaacaag ccgcaacgta a                                                 21

<210> SEQ ID NO 689
<211> LENGTH: 21
<212> TYPE: DNA
<213> ORGANISM: Artificial Sequence
<220> FEATURE:
<223> OTHER INFORMATION: target sequence

<400> SEQUENCE: 689
ttcgctctcg ccgaggaaca a                                                 21

<210> SEQ ID NO 690
<211> LENGTH: 21
<212> TYPE: DNA
<213> ORGANISM: Artificial Sequence
<220> FEATURE:
<223> OTHER INFORMATION: target sequence

<400> SEQUENCE: 690
cagcgtaatt tcagatgtta t                                                 21

<210> SEQ ID NO 691
<211> LENGTH: 21
<212> TYPE: DNA
<213> ORGANISM: Artificial Sequence
<220> FEATURE:
<223> OTHER INFORMATION: target sequence

<400> SEQUENCE: 691
ctcccataat aaattatata a                                                 21

<210> SEQ ID NO 692
<211> LENGTH: 19
<212> TYPE: RNA
<213> ORGANISM: Artificial Sequence
<220> FEATURE:
<223> OTHER INFORMATION: target sequence

<400> SEQUENCE: 692
gggaagaguu ugccuuuca                                                    19

<210> SEQ ID NO 693
<211> LENGTH: 21
<212> TYPE: DNA
<213> ORGANISM: Artificial Sequence
<220> FEATURE:
<223> OTHER INFORMATION: target sequence

<400> SEQUENCE: 693
accattgata tcaaaccaga a                                                 21

<210> SEQ ID NO 694

```
<211> LENGTH: 21
<212> TYPE: DNA
<213> ORGANISM: Artificial Sequence
<220> FEATURE:
<223> OTHER INFORMATION: target sequence

<400> SEQUENCE: 694
caaggccggc aagtaaacaa a                                              21

<210> SEQ ID NO 695
<211> LENGTH: 19
<212> TYPE: RNA
<213> ORGANISM: Artificial Sequence
<220> FEATURE:
<223> OTHER INFORMATION: target sequence

<400> SEQUENCE: 695
ugggcugcaa gucauuuug                                                 19

<210> SEQ ID NO 696
<211> LENGTH: 21
<212> TYPE: DNA
<213> ORGANISM: Artificial Sequence
<220> FEATURE:
<223> OTHER INFORMATION: target sequence

<400> SEQUENCE: 696
ccggaaagct cacaccctga a                                              21

<210> SEQ ID NO 697
<211> LENGTH: 21
<212> TYPE: DNA
<213> ORGANISM: Artificial Sequence
<220> FEATURE:
<223> OTHER INFORMATION: target sequence

<400> SEQUENCE: 697
actcttaacc ttcaacatga a                                              21

<210> SEQ ID NO 698
<211> LENGTH: 19
<212> TYPE: RNA
<213> ORGANISM: Artificial Sequence
<220> FEATURE:
<223> OTHER INFORMATION: target sequence

<400> SEQUENCE: 698
ugugacccug guggauaag                                                 19

<210> SEQ ID NO 699
<211> LENGTH: 19
<212> TYPE: RNA
<213> ORGANISM: Artificial Sequence
<220> FEATURE:
<223> OTHER INFORMATION: target sequence

<400> SEQUENCE: 699
uugaggucac agccuacaa                                                 19

<210> SEQ ID NO 700
<211> LENGTH: 25
<212> TYPE: RNA
<213> ORGANISM: Artificial Sequence
<220> FEATURE:
<223> OTHER INFORMATION: target sequence

<400> SEQUENCE: 700
```
agcguuagag ugccgccuua gacag                                            25

<210> SEQ ID NO 701
<211> LENGTH: 21
<212> TYPE: DNA
<213> ORGANISM: Artificial Sequence
<220> FEATURE:
<223> OTHER INFORMATION: target sequence

<400> SEQUENCE: 701
tacaggctta tttgtaatgt a                                                21

<210> SEQ ID NO 702
<211> LENGTH: 21
<212> TYPE: DNA
<213> ORGANISM: Artificial Sequence
<220> FEATURE:
<223> OTHER INFORMATION: target sequence

<400> SEQUENCE: 702
acccggagtg cttatcttaa a                                                21

<210> SEQ ID NO 703
<211> LENGTH: 19
<212> TYPE: RNA
<213> ORGANISM: Artificial Sequence
<220> FEATURE:
<223> OTHER INFORMATION: target sequence

<400> SEQUENCE: 703
accagaacau gaagacaua                                                   19

<210> SEQ ID NO 704
<211> LENGTH: 21
<212> TYPE: DNA
<213> ORGANISM: Artificial Sequence
<220> FEATURE:
<223> OTHER INFORMATION: target sequence

<400> SEQUENCE: 704
gtggcagtat gtgaagacca a                                                21

<210> SEQ ID NO 705
<211> LENGTH: 21
<212> TYPE: DNA
<213> ORGANISM: Artificial Sequence
<220> FEATURE:
<223> OTHER INFORMATION: target sequence

<400> SEQUENCE: 705
ctcaaggtga tgacagatgt a                                                21

<210> SEQ ID NO 706
<211> LENGTH: 21
<212> TYPE: DNA
<213> ORGANISM: Artificial Sequence
<220> FEATURE:
<223> OTHER INFORMATION: target sequence

<400> SEQUENCE: 706
ctgagcctta tttctctgga a                                                21

<210> SEQ ID NO 707
<211> LENGTH: 21
<212> TYPE: DNA

```
<213> ORGANISM: Artificial Sequence
<220> FEATURE:
<223> OTHER INFORMATION: target sequence

<400> SEQUENCE: 707
aactggaaat agcgaaataa a                                               21

<210> SEQ ID NO 708
<211> LENGTH: 21
<212> TYPE: DNA
<213> ORGANISM: Artificial Sequence
<220> FEATURE:
<223> OTHER INFORMATION: target sequence

<400> SEQUENCE: 708
aagattgagc ggcgacagca a                                               21

<210> SEQ ID NO 709
<211> LENGTH: 21
<212> TYPE: DNA
<213> ORGANISM: Artificial Sequence
<220> FEATURE:
<223> OTHER INFORMATION: target sequence

<400> SEQUENCE: 709
ccggagagag tttgaggtgt a                                               21

<210> SEQ ID NO 710
<211> LENGTH: 21
<212> TYPE: DNA
<213> ORGANISM: Artificial Sequence
<220> FEATURE:
<223> OTHER INFORMATION: target sequence

<400> SEQUENCE: 710
agccttgttt gtgttagcaa a                                               21

<210> SEQ ID NO 711
<211> LENGTH: 21
<212> TYPE: DNA
<213> ORGANISM: Artificial Sequence
<220> FEATURE:
<223> OTHER INFORMATION: target sequence

<400> SEQUENCE: 711
tagccttgtt tgtgttagca a                                               21

<210> SEQ ID NO 712
<211> LENGTH: 21
<212> TYPE: DNA
<213> ORGANISM: Artificial Sequence
<220> FEATURE:
<223> OTHER INFORMATION: target sequence

<400> SEQUENCE: 712
aagatagacg cttcatgtta a                                               21

<210> SEQ ID NO 713
<211> LENGTH: 21
<212> TYPE: DNA
<213> ORGANISM: Artificial Sequence
<220> FEATURE:
<223> OTHER INFORMATION: target sequence

<400> SEQUENCE: 713
aaggcaataa tgctaattac a                                               21
```

<210> SEQ ID NO 714
<211> LENGTH: 21
<212> TYPE: DNA
<213> ORGANISM: Artificial Sequence
<220> FEATURE:
<223> OTHER INFORMATION: target sequence

<400> SEQUENCE: 714
cagtggaaat tgaagagcta a                                            21

<210> SEQ ID NO 715
<211> LENGTH: 21
<212> TYPE: DNA
<213> ORGANISM: Artificial Sequence
<220> FEATURE:
<223> OTHER INFORMATION: target sequence

<400> SEQUENCE: 715
atcaatagcc tcaacaaaca a                                            21

<210> SEQ ID NO 716
<211> LENGTH: 21
<212> TYPE: DNA
<213> ORGANISM: Artificial Sequence
<220> FEATURE:
<223> OTHER INFORMATION: target sequence

<400> SEQUENCE: 716
tagcacctca ttagcccaca a                                            21

<210> SEQ ID NO 717
<211> LENGTH: 21
<212> TYPE: DNA
<213> ORGANISM: Artificial Sequence
<220> FEATURE:
<223> OTHER INFORMATION: target sequence

<400> SEQUENCE: 717
tgggtattta tgagtttcat a                                            21

<210> SEQ ID NO 718
<211> LENGTH: 21
<212> TYPE: DNA
<213> ORGANISM: Artificial Sequence
<220> FEATURE:
<223> OTHER INFORMATION: target sequence

<400> SEQUENCE: 718
ccgcgctcgc tccgagtttc a                                            21

<210> SEQ ID NO 719
<211> LENGTH: 21
<212> TYPE: DNA
<213> ORGANISM: Artificial Sequence
<220> FEATURE:
<223> OTHER INFORMATION: target sequence

<400> SEQUENCE: 719
cgccgtcgtc gtctcccttc a                                            21

<210> SEQ ID NO 720
<211> LENGTH: 21
<212> TYPE: DNA
<213> ORGANISM: Artificial Sequence
<220> FEATURE:

```
<223> OTHER INFORMATION: target sequence

<400> SEQUENCE: 720
taggtgaatg gcggtcacat a                                              21

<210> SEQ ID NO 721
<211> LENGTH: 21
<212> TYPE: DNA
<213> ORGANISM: Artificial Sequence
<220> FEATURE:
<223> OTHER INFORMATION: target sequence

<400> SEQUENCE: 721
cccggtgaca ttctatttcc a                                              21

<210> SEQ ID NO 722
<211> LENGTH: 21
<212> TYPE: DNA
<213> ORGANISM: Artificial Sequence
<220> FEATURE:
<223> OTHER INFORMATION: target sequence

<400> SEQUENCE: 722
caggagtgcc agaaatctta a                                              21

<210> SEQ ID NO 723
<211> LENGTH: 19
<212> TYPE: RNA
<213> ORGANISM: Artificial Sequence
<220> FEATURE:
<223> OTHER INFORMATION: target sequence

<400> SEQUENCE: 723
uccgaaauac uacucaguu                                                 19

<210> SEQ ID NO 724
<211> LENGTH: 21
<212> TYPE: RNA
<213> ORGANISM: Artificial Sequence
<220> FEATURE:
<223> OTHER INFORMATION: target sequence

<400> SEQUENCE: 724
aaguagggau aaauuacucu a                                              21

<210> SEQ ID NO 725
<211> LENGTH: 21
<212> TYPE: DNA
<213> ORGANISM: Artificial Sequence
<220> FEATURE:
<223> OTHER INFORMATION: sense strand of siRNA duplex created to
      introduce overhangs

<400> SEQUENCE: 725
gcuugaauuu gaagguguat t                                              21

<210> SEQ ID NO 726
<211> LENGTH: 21
<212> TYPE: DNA
<213> ORGANISM: Artificial Sequence
<220> FEATURE:
<223> OTHER INFORMATION: antisense strand of siRNA duplex created to
      introduce overhangs

<400> SEQUENCE: 726
uacaccuuca aauucaagct c                                              21
```

<210> SEQ ID NO 727
<211> LENGTH: 21
<212> TYPE: RNA
<213> ORGANISM: Artificial Sequence
<220> FEATURE:
<223> OTHER INFORMATION: siRPS27a sequence

<400> SEQUENCE: 727
aagcuggaag auggacguac u                                              21

<210> SEQ ID NO 728
<211> LENGTH: 19
<212> TYPE: DNA
<213> ORGANISM: Artificial Sequence
<220> FEATURE:
<223> OTHER INFORMATION: negative control siRNA (scramble 177)

<400> SEQUENCE: 728
ggtaattgcg cgtgcaact                                                 19

<210> SEQ ID NO 729
<211> LENGTH: 19
<212> TYPE: DNA
<213> ORGANISM: Artificial Sequence
<220> FEATURE:
<223> OTHER INFORMATION: negative control siRNA (scramble 5701)

<400> SEQUENCE: 729
gccgcttagt agtctcgta                                                 19

<210> SEQ ID NO 730
<211> LENGTH: 23
<212> TYPE: DNA
<213> ORGANISM: Artificial Sequence
<220> FEATURE:
<223> OTHER INFORMATION: IFNb sense primer

<400> SEQUENCE: 730
tgacatccct gaggagatta agc                                            23

<210> SEQ ID NO 731
<211> LENGTH: 25
<212> TYPE: DNA
<213> ORGANISM: Artificial Sequence
<220> FEATURE:
<223> OTHER INFORMATION: IFNb antisense primer

<400> SEQUENCE: 731
ctggagcatc tcatagatgg tcaat                                          25

<210> SEQ ID NO 732
<211> LENGTH: 21
<212> TYPE: DNA
<213> ORGANISM: Artificial Sequence
<220> FEATURE:
<223> OTHER INFORMATION: PR8 NP sense primer

<400> SEQUENCE: 732
tggcattcca atttgaatga t                                              21

<210> SEQ ID NO 733
<211> LENGTH: 21
<212> TYPE: DNA
<213> ORGANISM: Artificial Sequence
<220> FEATURE:

<223> OTHER INFORMATION: PR8 NP antisense primer

<400> SEQUENCE: 733
atccattccg gtgcgaacaa g    21

<210> SEQ ID NO 734
<211> LENGTH: 21
<212> TYPE: DNA
<213> ORGANISM: Artificial Sequence
<220> FEATURE:
<223> OTHER INFORMATION: PR8 M1 sense primer

<400> SEQUENCE: 734
ccgtcgcttt aaatacggac t    21

<210> SEQ ID NO 735
<211> LENGTH: 21
<212> TYPE: DNA
<213> ORGANISM: Artificial Sequence
<220> FEATURE:
<223> OTHER INFORMATION: PR8 M1 antisense primer

<400> SEQUENCE: 735
agcactctgc tgttcctttc g    21

<210> SEQ ID NO 736
<211> LENGTH: 20
<212> TYPE: DNA
<213> ORGANISM: Artificial Sequence
<220> FEATURE:
<223> OTHER INFORMATION: sense primer to amplify GAPDH

<400> SEQUENCE: 736
gaagatggtg atgggatttc    20

<210> SEQ ID NO 737
<211> LENGTH: 19
<212> TYPE: DNA
<213> ORGANISM: Artificial Sequence
<220> FEATURE:
<223> OTHER INFORMATION: antisense primer to amplify GAPDH

<400> SEQUENCE: 737
gaaggtgaag gtcggagtc    19

<210> SEQ ID NO 738
<211> LENGTH: 19
<212> TYPE: DNA
<213> ORGANISM: Artificial Sequence
<220> FEATURE:
<223> OTHER INFORMATION: negative control siRNA (scramble 177)

<400> SEQUENCE: 738
ggtaattgcg cgtgcaact    19

<210> SEQ ID NO 739
<211> LENGTH: 19
<212> TYPE: DNA
<213> ORGANISM: Artificial Sequence
<220> FEATURE:
<223> OTHER INFORMATION: negative control siRNA (1212)

<400> SEQUENCE: 739
atccgcgcga tagtacgta    19

```
<210> SEQ ID NO 740
<211> LENGTH: 19
<212> TYPE: DNA
<213> ORGANISM: Artificial Sequence
<220> FEATURE:
<223> OTHER INFORMATION: negative control siRNA (6105)

<400> SEQUENCE: 740
gtaagctcgt gcgacgtat                                               19

<210> SEQ ID NO 741
<211> LENGTH: 19
<212> TYPE: DNA
<213> ORGANISM: Artificial Sequence
<220> FEATURE:
<223> OTHER INFORMATION: 5757 negative control siRNA

<400> SEQUENCE: 741
ggtgctcagt cgcaatagt                                               19

<210> SEQ ID NO 742
<211> LENGTH: 19
<212> TYPE: DNA
<213> ORGANISM: Artificial Sequence
<220> FEATURE:
<223> OTHER INFORMATION: target sequence

<400> SEQUENCE: 742
gctggagcta tggtcagtt                                               19

<210> SEQ ID NO 743
<211> LENGTH: 19
<212> TYPE: DNA
<213> ORGANISM: Artificial Sequence
<220> FEATURE:
<223> OTHER INFORMATION: target sequence

<400> SEQUENCE: 743
gtgacacagc taccaattc                                               19

<210> SEQ ID NO 744
<211> LENGTH: 19
<212> TYPE: DNA
<213> ORGANISM: Artificial Sequence
<220> FEATURE:
<223> OTHER INFORMATION: target sequence

<400> SEQUENCE: 744
ccacgaaatc gcccatcat                                               19

<210> SEQ ID NO 745
<211> LENGTH: 19
<212> TYPE: DNA
<213> ORGANISM: Artificial Sequence
<220> FEATURE:
<223> OTHER INFORMATION: target sequence

<400> SEQUENCE: 745
ggagaccttc aacctctat                                               19

<210> SEQ ID NO 746
<211> LENGTH: 19
<212> TYPE: DNA
<213> ORGANISM: Artificial Sequence
<220> FEATURE:
<223> OTHER INFORMATION: target sequence
```

```
<400> SEQUENCE: 746
tacctgtggc atcaccaag                                                    19

<210> SEQ ID NO 747
<211> LENGTH: 19
<212> TYPE: DNA
<213> ORGANISM: Artificial Sequence
<220> FEATURE:
<223> OTHER INFORMATION: target sequence

<400> SEQUENCE: 747
ccctctcaac ctcactctt                                                    19

<210> SEQ ID NO 748
<211> LENGTH: 19
<212> TYPE: DNA
<213> ORGANISM: Artificial Sequence
<220> FEATURE:
<223> OTHER INFORMATION: target sequence

<400> SEQUENCE: 748
gcttcatcga gcagcagtt                                                    19

<210> SEQ ID NO 749
<211> LENGTH: 19
<212> TYPE: DNA
<213> ORGANISM: Artificial Sequence
<220> FEATURE:
<223> OTHER INFORMATION: target sequence

<400> SEQUENCE: 749
ggtccttttg gccagatct                                                    19

<210> SEQ ID NO 750
<211> LENGTH: 25
<212> TYPE: DNA
<213> ORGANISM: Artificial Sequence
<220> FEATURE:
<223> OTHER INFORMATION: target sequence

<400> SEQUENCE: 750
ggctacggac caagtttatc cggcg                                             25

<210> SEQ ID NO 751
<211> LENGTH: 21
<212> TYPE: RNA
<213> ORGANISM: Artificial Sequence
<220> FEATURE:
<223> OTHER INFORMATION: target sequence

<400> SEQUENCE: 751
cccacuugug ucaauauuaa a                                                 21

<210> SEQ ID NO 752
<211> LENGTH: 21
<212> TYPE: RNA
<213> ORGANISM: Artificial Sequence
<220> FEATURE:
<223> OTHER INFORMATION: target sequence

<400> SEQUENCE: 752
aaggcugaga ugcgucguaa a                                                 21

<210> SEQ ID NO 753
<211> LENGTH: 21
```

```
<212> TYPE: RNA
<213> ORGANISM: Artificial Sequence
<220> FEATURE:
<223> OTHER INFORMATION: target sequence

<400> SEQUENCE: 753
gagcuugaau uugaaggugu a                                              21

<210> SEQ ID NO 754
<211> LENGTH: 21
<212> TYPE: RNA
<213> ORGANISM: Artificial Sequence
<220> FEATURE:
<223> OTHER INFORMATION: target sequence

<400> SEQUENCE: 754
auggagguug augguaaggu a                                              21

<210> SEQ ID NO 755
<211> LENGTH: 21
<212> TYPE: RNA
<213> ORGANISM: Artificial Sequence
<220> FEATURE:
<223> OTHER INFORMATION: target sequence

<400> SEQUENCE: 755
accauguuac ccuguaauua a                                              21

<210> SEQ ID NO 756
<211> LENGTH: 21
<212> TYPE: RNA
<213> ORGANISM: Artificial Sequence
<220> FEATURE:
<223> OTHER INFORMATION: target sequence

<400> SEQUENCE: 756
cacgguuaau gaagucugcu a                                              21

<210> SEQ ID NO 757
<211> LENGTH: 21
<212> TYPE: RNA
<213> ORGANISM: Artificial Sequence
<220> FEATURE:
<223> OTHER INFORMATION: target sequence

<400> SEQUENCE: 757
cagccacaga auauuaugua a                                              21

<210> SEQ ID NO 758
<211> LENGTH: 21
<212> TYPE: RNA
<213> ORGANISM: Artificial Sequence
<220> FEATURE:
<223> OTHER INFORMATION: target sequence

<400> SEQUENCE: 758
ucccagcuau cuauaaccuu a                                              21

<210> SEQ ID NO 759
<211> LENGTH: 21
<212> TYPE: RNA
<213> ORGANISM: Artificial Sequence
<220> FEATURE:
<223> OTHER INFORMATION: target sequence

<400> SEQUENCE: 759
```
cauggcaauu gucauuagca a         21

<210> SEQ ID NO 760
<211> LENGTH: 21
<212> TYPE: RNA
<213> ORGANISM: Artificial Sequence
<220> FEATURE:
<223> OTHER INFORMATION: target sequence

<400> SEQUENCE: 760
uccuaguguu ugugaaauaa a         21

<210> SEQ ID NO 761
<211> LENGTH: 21
<212> TYPE: RNA
<213> ORGANISM: Artificial Sequence
<220> FEATURE:
<223> OTHER INFORMATION: target sequence

<400> SEQUENCE: 761
cacagugaca uucaaguuca u         21

<210> SEQ ID NO 762
<211> LENGTH: 21
<212> TYPE: RNA
<213> ORGANISM: Artificial Sequence
<220> FEATURE:
<223> OTHER INFORMATION: target sequence

<400> SEQUENCE: 762
uagcaaaugc ucccuccuua a         21

<210> SEQ ID NO 763
<211> LENGTH: 21
<212> TYPE: RNA
<213> ORGANISM: Artificial Sequence
<220> FEATURE:
<223> OTHER INFORMATION: target sequence

<400> SEQUENCE: 763
cacgaccauc cugaacccac a         21

<210> SEQ ID NO 764
<211> LENGTH: 21
<212> TYPE: RNA
<213> ORGANISM: Artificial Sequence
<220> FEATURE:
<223> OTHER INFORMATION: target sequence

<400> SEQUENCE: 764
caggaucucu gacauccuga a         21

<210> SEQ ID NO 765
<211> LENGTH: 21
<212> TYPE: RNA
<213> ORGANISM: Artificial Sequence
<220> FEATURE:
<223> OTHER INFORMATION: target sequence

<400> SEQUENCE: 765
caggauaaug uuaucaaagu a         21

<210> SEQ ID NO 766
<211> LENGTH: 21
<212> TYPE: RNA
<213> ORGANISM: Artificial Sequence

```
<220> FEATURE:
<223> OTHER INFORMATION: target sequence

<400> SEQUENCE: 766
cugacgguau caaauauauu a                                              21

<210> SEQ ID NO 767
<211> LENGTH: 21
<212> TYPE: RNA
<213> ORGANISM: Artificial Sequence
<220> FEATURE:
<223> OTHER INFORMATION: target sequence

<400> SEQUENCE: 767
caaaugaacu uguaaaccua a                                              21

<210> SEQ ID NO 768
<211> LENGTH: 21
<212> TYPE: RNA
<213> ORGANISM: Artificial Sequence
<220> FEATURE:
<223> OTHER INFORMATION: target sequence

<400> SEQUENCE: 768
caaggagaga ugggacacua a                                              21

<210> SEQ ID NO 769
<211> LENGTH: 21
<212> TYPE: RNA
<213> ORGANISM: Artificial Sequence
<220> FEATURE:
<223> OTHER INFORMATION: target sequence

<400> SEQUENCE: 769
ccgccugacc uucggacccu a                                              21

<210> SEQ ID NO 770
<211> LENGTH: 21
<212> TYPE: RNA
<213> ORGANISM: Artificial Sequence
<220> FEATURE:
<223> OTHER INFORMATION: target sequence

<400> SEQUENCE: 770
caggagguuc ugggccucug a                                              21

<210> SEQ ID NO 771
<211> LENGTH: 21
<212> TYPE: RNA
<213> ORGANISM: Artificial Sequence
<220> FEATURE:
<223> OTHER INFORMATION: target sequence

<400> SEQUENCE: 771
aaccagugac acagcuacca a                                              21

<210> SEQ ID NO 772
<211> LENGTH: 21
<212> TYPE: RNA
<213> ORGANISM: Artificial Sequence
<220> FEATURE:
<223> OTHER INFORMATION: target sequence

<400> SEQUENCE: 772
ucgguuauau uugccaagau a                                              21
```

```
<210> SEQ ID NO 773
<211> LENGTH: 21
<212> TYPE: RNA
<213> ORGANISM: Artificial Sequence
<220> FEATURE:
<223> OTHER INFORMATION: target sequence

<400> SEQUENCE: 773
caagaacucu uugacaucua a                                      21

<210> SEQ ID NO 774
<211> LENGTH: 21
<212> TYPE: RNA
<213> ORGANISM: Artificial Sequence
<220> FEATURE:
<223> OTHER INFORMATION: target sequence

<400> SEQUENCE: 774
cuggaugcca uccaaguugu a                                      21

<210> SEQ ID NO 775
<211> LENGTH: 21
<212> TYPE: RNA
<213> ORGANISM: Artificial Sequence
<220> FEATURE:
<223> OTHER INFORMATION: target sequence

<400> SEQUENCE: 775
acggauaucc ugcaugucca a                                      21

<210> SEQ ID NO 776
<211> LENGTH: 21
<212> TYPE: RNA
<213> ORGANISM: Artificial Sequence
<220> FEATURE:
<223> OTHER INFORMATION: target sequence

<400> SEQUENCE: 776
cccggagaug aucccaacaa a                                      21

<210> SEQ ID NO 777
<211> LENGTH: 21
<212> TYPE: RNA
<213> ORGANISM: Artificial Sequence
<220> FEATURE:
<223> OTHER INFORMATION: target sequence

<400> SEQUENCE: 777
caccauagaa ucucacacca a                                      21

<210> SEQ ID NO 778
<211> LENGTH: 21
<212> TYPE: RNA
<213> ORGANISM: Artificial Sequence
<220> FEATURE:
<223> OTHER INFORMATION: target sequence

<400> SEQUENCE: 778
cagagagaua cucgcaggca a                                      21

<210> SEQ ID NO 779
<211> LENGTH: 21
<212> TYPE: RNA
<213> ORGANISM: Artificial Sequence
<220> FEATURE:
<223> OTHER INFORMATION: target sequence
```

```
<400> SEQUENCE: 779
cagcagcuga ucauggauga a                                              21

<210> SEQ ID NO 780
<211> LENGTH: 21
<212> TYPE: RNA
<213> ORGANISM: Artificial Sequence
<220> FEATURE:
<223> OTHER INFORMATION: target sequence

<400> SEQUENCE: 780
caggauaaga cggaauggaa a                                              21

<210> SEQ ID NO 781
<211> LENGTH: 21
<212> TYPE: RNA
<213> ORGANISM: Artificial Sequence
<220> FEATURE:
<223> OTHER INFORMATION: target sequence

<400> SEQUENCE: 781
cgcaaggauu augaucccaa a                                              21

<210> SEQ ID NO 782
<211> LENGTH: 21
<212> TYPE: RNA
<213> ORGANISM: Artificial Sequence
<220> FEATURE:
<223> OTHER INFORMATION: target sequence

<400> SEQUENCE: 782
ccgagccacc uucuaccuaa a                                              21

<210> SEQ ID NO 783
<211> LENGTH: 21
<212> TYPE: RNA
<213> ORGANISM: Artificial Sequence
<220> FEATURE:
<223> OTHER INFORMATION: target sequence

<400> SEQUENCE: 783
aggcccgugu auuuaaugaa a                                              21

<210> SEQ ID NO 784
<211> LENGTH: 21
<212> TYPE: RNA
<213> ORGANISM: Artificial Sequence
<220> FEATURE:
<223> OTHER INFORMATION: target sequence

<400> SEQUENCE: 784
cagaggaucu uuccaaccac a                                              21

<210> SEQ ID NO 785
<211> LENGTH: 21
<212> TYPE: RNA
<213> ORGANISM: Artificial Sequence
<220> FEATURE:
<223> OTHER INFORMATION: target sequence

<400> SEQUENCE: 785
ccagugaauu cugguggcaa a                                              21

<210> SEQ ID NO 786
```

```
<211> LENGTH: 21
<212> TYPE: RNA
<213> ORGANISM: Artificial Sequence
<220> FEATURE:
<223> OTHER INFORMATION: target sequence

<400> SEQUENCE: 786
gagccugaga uugaccugga a                                              21

<210> SEQ ID NO 787
<211> LENGTH: 21
<212> TYPE: RNA
<213> ORGANISM: Artificial Sequence
<220> FEATURE:
<223> OTHER INFORMATION: target sequence

<400> SEQUENCE: 787
caggagcucu uccaggauca a                                              21

<210> SEQ ID NO 788
<211> LENGTH: 21
<212> TYPE: RNA
<213> ORGANISM: Artificial Sequence
<220> FEATURE:
<223> OTHER INFORMATION: target sequence

<400> SEQUENCE: 788
ccguagugag aucacuucau a                                              21

<210> SEQ ID NO 789
<211> LENGTH: 21
<212> TYPE: RNA
<213> ORGANISM: Artificial Sequence
<220> FEATURE:
<223> OTHER INFORMATION: target sequence

<400> SEQUENCE: 789
uacggcuaac agagaccuga a                                              21

<210> SEQ ID NO 790
<211> LENGTH: 21
<212> TYPE: RNA
<213> ORGANISM: Artificial Sequence
<220> FEATURE:
<223> OTHER INFORMATION: target sequence

<400> SEQUENCE: 790
cacccucucc uugucacaga a                                              21

<210> SEQ ID NO 791
<211> LENGTH: 21
<212> TYPE: RNA
<213> ORGANISM: Artificial Sequence
<220> FEATURE:
<223> OTHER INFORMATION: target sequence

<400> SEQUENCE: 791
cuccauugca uucauguacu a                                              21

<210> SEQ ID NO 792
<211> LENGTH: 21
<212> TYPE: RNA
<213> ORGANISM: Artificial Sequence
<220> FEATURE:
<223> OTHER INFORMATION: target sequence

<400> SEQUENCE: 792
```
agccaucaua cgagaucuua a                                21

<210> SEQ ID NO 793
<211> LENGTH: 21
<212> TYPE: RNA
<213> ORGANISM: Artificial Sequence
<220> FEATURE:
<223> OTHER INFORMATION: target sequence

<400> SEQUENCE: 793
augauuggca augacaaaca a                                21

<210> SEQ ID NO 794
<211> LENGTH: 21
<212> TYPE: RNA
<213> ORGANISM: Artificial Sequence
<220> FEATURE:
<223> OTHER INFORMATION: target sequence

<400> SEQUENCE: 794
aaccggauug ccauuuauga a                                21

<210> SEQ ID NO 795
<211> LENGTH: 21
<212> TYPE: RNA
<213> ORGANISM: Artificial Sequence
<220> FEATURE:
<223> OTHER INFORMATION: target sequence

<400> SEQUENCE: 795
uugaauaaac uuacagccaa a                                21

<210> SEQ ID NO 796
<211> LENGTH: 21
<212> TYPE: RNA
<213> ORGANISM: Artificial Sequence
<220> FEATURE:
<223> OTHER INFORMATION: target sequence

<400> SEQUENCE: 796
ccgcaucacc uccgcguacu a                                21

<210> SEQ ID NO 797
<211> LENGTH: 21
<212> TYPE: RNA
<213> ORGANISM: Artificial Sequence
<220> FEATURE:
<223> OTHER INFORMATION: target sequence

<400> SEQUENCE: 797
cacggacgga cagaagccca a                                21

<210> SEQ ID NO 798
<211> LENGTH: 21
<212> TYPE: RNA
<213> ORGANISM: Artificial Sequence
<220> FEATURE:
<223> OTHER INFORMATION: target sequence

<400> SEQUENCE: 798
ccgccuguuu ggguuaacaa a                                21

<210> SEQ ID NO 799
<211> LENGTH: 21
<212> TYPE: RNA

```
<213> ORGANISM: Artificial Sequence
<220> FEATURE:
<223> OTHER INFORMATION: target sequence

<400> SEQUENCE: 799
caggauuaca cugaaaguaa u                                              21

<210> SEQ ID NO 800
<211> LENGTH: 21
<212> TYPE: RNA
<213> ORGANISM: Artificial Sequence
<220> FEATURE:
<223> OTHER INFORMATION: target sequence

<400> SEQUENCE: 800
cacgaagaac uaagaauauu a                                              21

<210> SEQ ID NO 801
<211> LENGTH: 21
<212> TYPE: RNA
<213> ORGANISM: Artificial Sequence
<220> FEATURE:
<223> OTHER INFORMATION: target sequence

<400> SEQUENCE: 801
cagcaauuac auuaaauuca a                                              21

<210> SEQ ID NO 802
<211> LENGTH: 21
<212> TYPE: RNA
<213> ORGANISM: Artificial Sequence
<220> FEATURE:
<223> OTHER INFORMATION: target sequence

<400> SEQUENCE: 802
ccggaaggag uacucccaga a                                              21

<210> SEQ ID NO 803
<211> LENGTH: 21
<212> TYPE: RNA
<213> ORGANISM: Artificial Sequence
<220> FEATURE:
<223> OTHER INFORMATION: target sequence

<400> SEQUENCE: 803
agccauuuac uugcaccgga a                                              21

<210> SEQ ID NO 804
<211> LENGTH: 21
<212> TYPE: RNA
<213> ORGANISM: Artificial Sequence
<220> FEATURE:
<223> OTHER INFORMATION: target sequence

<400> SEQUENCE: 804
uagguacugu uaaguaagua a                                              21

<210> SEQ ID NO 805
<211> LENGTH: 21
<212> TYPE: RNA
<213> ORGANISM: Artificial Sequence
<220> FEATURE:
<223> OTHER INFORMATION: target sequence

<400> SEQUENCE: 805
cccgaugaca auagugauga u                                              21
```

<210> SEQ ID NO 806
<211> LENGTH: 21
<212> TYPE: RNA
<213> ORGANISM: Artificial Sequence
<220> FEATURE:
<223> OTHER INFORMATION: target sequence

<400> SEQUENCE: 806
cagcauuguc cugcagcuga a                                              21

<210> SEQ ID NO 807
<211> LENGTH: 21
<212> TYPE: RNA
<213> ORGANISM: Artificial Sequence
<220> FEATURE:
<223> OTHER INFORMATION: target sequence

<400> SEQUENCE: 807
aaaggagauc gaggagagaa a                                              21

<210> SEQ ID NO 808
<211> LENGTH: 21
<212> TYPE: RNA
<213> ORGANISM: Artificial Sequence
<220> FEATURE:
<223> OTHER INFORMATION: target sequence

<400> SEQUENCE: 808
cagggagcac uaugaaagga a                                              21

<210> SEQ ID NO 809
<211> LENGTH: 21
<212> TYPE: RNA
<213> ORGANISM: Artificial Sequence
<220> FEATURE:
<223> OTHER INFORMATION: target sequence

<400> SEQUENCE: 809
cacaugguac cuggauucag a                                              21

<210> SEQ ID NO 810
<211> LENGTH: 21
<212> TYPE: RNA
<213> ORGANISM: Artificial Sequence
<220> FEATURE:
<223> OTHER INFORMATION: target sequence

<400> SEQUENCE: 810
ccggccuuga ccggaggaga a                                              21

<210> SEQ ID NO 811
<211> LENGTH: 21
<212> TYPE: RNA
<213> ORGANISM: Artificial Sequence
<220> FEATURE:
<223> OTHER INFORMATION: target sequence

<400> SEQUENCE: 811
cgcguucaua acuguccuca a                                              21

<210> SEQ ID NO 812
<211> LENGTH: 21
<212> TYPE: RNA
<213> ORGANISM: Artificial Sequence
<220> FEATURE:

```
<223> OTHER INFORMATION: target sequence

<400> SEQUENCE: 812
caccuucuau guaggcaucu a                                              21

<210> SEQ ID NO 813
<211> LENGTH: 21
<212> TYPE: RNA
<213> ORGANISM: Artificial Sequence
<220> FEATURE:
<223> OTHER INFORMATION: target sequence

<400> SEQUENCE: 813
aaggaacauc aggcaugcua a                                              21

<210> SEQ ID NO 814
<211> LENGTH: 21
<212> TYPE: RNA
<213> ORGANISM: Artificial Sequence
<220> FEATURE:
<223> OTHER INFORMATION: target sequence

<400> SEQUENCE: 814
cccaucugac aagggaaauu a                                              21

<210> SEQ ID NO 815
<211> LENGTH: 21
<212> TYPE: RNA
<213> ORGANISM: Artificial Sequence
<220> FEATURE:
<223> OTHER INFORMATION: target sequence

<400> SEQUENCE: 815
cggaggagcg uugccauuca a                                              21

<210> SEQ ID NO 816
<211> LENGTH: 21
<212> TYPE: RNA
<213> ORGANISM: Artificial Sequence
<220> FEATURE:
<223> OTHER INFORMATION: target sequence

<400> SEQUENCE: 816
cuggcggacu uccagaucga a                                              21

<210> SEQ ID NO 817
<211> LENGTH: 21
<212> TYPE: RNA
<213> ORGANISM: Artificial Sequence
<220> FEATURE:
<223> OTHER INFORMATION: target sequence

<400> SEQUENCE: 817
accacggaag ucgagaauua a                                              21

<210> SEQ ID NO 818
<211> LENGTH: 21
<212> TYPE: RNA
<213> ORGANISM: Artificial Sequence
<220> FEATURE:
<223> OTHER INFORMATION: target sequence

<400> SEQUENCE: 818
cacucaagaa cugucaagua a                                              21
```

```
<210> SEQ ID NO 819
<211> LENGTH: 21
<212> TYPE: RNA
<213> ORGANISM: Artificial Sequence
<220> FEATURE:
<223> OTHER INFORMATION: target sequence

<400> SEQUENCE: 819
ucaguuggua gaaauaauca a                                              21

<210> SEQ ID NO 820
<211> LENGTH: 21
<212> TYPE: RNA
<213> ORGANISM: Artificial Sequence
<220> FEATURE:
<223> OTHER INFORMATION: target sequence

<400> SEQUENCE: 820
cacggauuua gucccacccu a                                              21

<210> SEQ ID NO 821
<211> LENGTH: 21
<212> TYPE: RNA
<213> ORGANISM: Artificial Sequence
<220> FEATURE:
<223> OTHER INFORMATION: target sequence

<400> SEQUENCE: 821
gaggagcgau gugaugaaua a                                              21

<210> SEQ ID NO 822
<211> LENGTH: 21
<212> TYPE: RNA
<213> ORGANISM: Artificial Sequence
<220> FEATURE:
<223> OTHER INFORMATION: target sequence

<400> SEQUENCE: 822
cccgcggauc uacgugggca a                                              21

<210> SEQ ID NO 823
<211> LENGTH: 21
<212> TYPE: RNA
<213> ORGANISM: Artificial Sequence
<220> FEATURE:
<223> OTHER INFORMATION: target sequence

<400> SEQUENCE: 823
ccguauuuac uuaacaagau u                                              21

<210> SEQ ID NO 824
<211> LENGTH: 21
<212> TYPE: RNA
<213> ORGANISM: Artificial Sequence
<220> FEATURE:
<223> OTHER INFORMATION: target sequence

<400> SEQUENCE: 824
cacaguuauu acugcaguga a                                              21

<210> SEQ ID NO 825
<211> LENGTH: 21
<212> TYPE: RNA
<213> ORGANISM: Artificial Sequence
<220> FEATURE:
<223> OTHER INFORMATION: target sequence
```

```
<400> SEQUENCE: 825
aagacagucu uuaaagugua a                                              21

<210> SEQ ID NO 826
<211> LENGTH: 21
<212> TYPE: RNA
<213> ORGANISM: Artificial Sequence
<220> FEATURE:
<223> OTHER INFORMATION: target sequence

<400> SEQUENCE: 826
cuggauugac uuugcuguca a                                              21

<210> SEQ ID NO 827
<211> LENGTH: 21
<212> TYPE: RNA
<213> ORGANISM: Artificial Sequence
<220> FEATURE:
<223> OTHER INFORMATION: target sequence

<400> SEQUENCE: 827
caagacagag auggaccgca a                                              21

<210> SEQ ID NO 828
<211> LENGTH: 21
<212> TYPE: RNA
<213> ORGANISM: Artificial Sequence
<220> FEATURE:
<223> OTHER INFORMATION: target sequence

<400> SEQUENCE: 828
uggguagaag ucacuauaua a                                              21

<210> SEQ ID NO 829
<211> LENGTH: 21
<212> TYPE: RNA
<213> ORGANISM: Artificial Sequence
<220> FEATURE:
<223> OTHER INFORMATION: target sequence

<400> SEQUENCE: 829 uugauuguu ucaacagccu a                                               21

<210> SEQ ID NO 830
<211> LENGTH: 21
<212> TYPE: RNA
<213> ORGANISM: Artificial Sequence
<220> FEATURE:
<223> OTHER INFORMATION: target sequence

<400> SEQUENCE: 830
uacugcauuc ucaauuagaa a                                              21

<210> SEQ ID NO 831
<211> LENGTH: 21
<212> TYPE: RNA
<213> ORGANISM: Artificial Sequence
<220> FEATURE:
<223> OTHER INFORMATION: target sequence

<400> SEQUENCE: 831
cugucuuuaa guagggauaa a                                              21

<210> SEQ ID NO 832
<211> LENGTH: 21
```

```
<212> TYPE: RNA
<213> ORGANISM: Artificial Sequence
<220> FEATURE:
<223> OTHER INFORMATION: target sequence

<400> SEQUENCE: 832
aaguagggau aaauuacucu a                                              21
```